US010766903B2

(12) United States Patent
O'Dowd et al.

(10) Patent No.: US 10,766,903 B2
(45) Date of Patent: Sep. 8, 2020

(54) PIPERIDINE DERIVATIVES AS INHIBITORS OF UBIQUITIN SPECIFIC PROTEASE 7

(71) Applicant: ALMAC DISCOVERY LIMITED, Craigavon (GB)

(72) Inventors: Colin O'Dowd, Craigavon (GB); Tim Harrison, Craigavon (GB); Peter Hewitt, Craigavon (GB); Shane Rountree, Craigavon (GB); Miel Hugues, Craigavon (GB); Frank Burkamp, Craigavon (GB); Linda Duncan Jordan, Craigavon (GB); Matthew Helm, Craigavon (GB); Fabio Broccatelli, Craigavon (GB); James John Crawford, Craigavon (GB); Lewis Gazzard, Craigavon (GB); Ingrid Wertz, Craigavon (GB); Wendy Lee, Craigavon (GB)

(73) Assignee: ALMAC DISCOVERY LIMITED, Craigavon, Armagh (GB)

( * ) Notice: Subject to any disclaimer, the term of this patent is extended or adjusted under 35 U.S.C. 154(b) by 0 days.

(21) Appl. No.: 16/343,917

(22) PCT Filed: Oct. 20, 2017

(86) PCT No.: PCT/GB2017/053175
§ 371 (c)(1),
(2) Date: Apr. 22, 2019

(87) PCT Pub. No.: WO2018/073602
PCT Pub. Date: Apr. 26, 2018

(65) Prior Publication Data
US 2019/0256518 A1 Aug. 22, 2019

(30) Foreign Application Priority Data
Oct. 20, 2016 (GB) .................................. 1617758.6

(51) Int. Cl.
| | | |
|---|---|---|
| *C07D 487/04* | (2006.01) | |
| *C07D 401/14* | (2006.01) | |
| *C07D 401/06* | (2006.01) | |
| *C07D 471/10* | (2006.01) | |
| *A61P 35/00* | (2006.01) | |
| *C07D 401/04* | (2006.01) | |
| *C07D 405/14* | (2006.01) | |
| *C07D 413/14* | (2006.01) | |
| *C07D 473/00* | (2006.01) | |
| *C07D 487/08* | (2006.01) | |
| *C07D 491/107* | (2006.01) | |
| *C07D 493/04* | (2006.01) | |
| *C07D 513/04* | (2006.01) | |
| *C07D 471/04* | (2006.01) | |
| *C07D 403/04* | (2006.01) | |
| *C07D 491/04* | (2006.01) | |
| *A61K 31/506* | (2006.01) | |

(52) U.S. Cl.
CPC .......... *C07D 487/04* (2013.01); *A61K 31/506* (2013.01); *A61P 35/00* (2018.01); *C07D 401/04* (2013.01); *C07D 401/06* (2013.01); *C07D 401/14* (2013.01); *C07D 403/04* (2013.01); *C07D 405/14* (2013.01); *C07D 413/14* (2013.01); *C07D 471/04* (2013.01); *C07D 471/10* (2013.01); *C07D 473/00* (2013.01); *C07D 487/08* (2013.01); *C07D 491/04* (2013.01); *C07D 491/107* (2013.01); *C07D 493/04* (2013.01); *C07D 513/04* (2013.01)

(58) Field of Classification Search
CPC .. C07D 487/04; C07D 401/14; C07D 401/06; C07D 471/10; A61P 35/00
USPC .......................................................... 546/199
See application file for complete search history.

(56) References Cited

U.S. PATENT DOCUMENTS

| | | | | |
|---|---|---|---|---|
| 9,546,150 B2 * | 1/2017 | Colland | ............... | C07D 401/06 |
| 9,840,491 B2 * | 12/2017 | Ioannidis | ............. | C07D 401/06 |
| 9,932,351 B2 * | 4/2018 | Ioannidis | ............. | C07D 495/04 |
| 10,377,773 B2 * | 8/2019 | Ioannidis | ............. | C07D 513/04 |
| 2011/0124626 A1 | 5/2011 | Pooni et al. | | |
| 2013/0090341 A1 | 4/2013 | Koike et al. | | |
| 2014/0288081 A1 | 9/2014 | Cianchetta et al. | | |
| 2014/0371247 A1 | 12/2014 | Colland et al. | | |
| 2016/0184318 A1 | 6/2016 | Beattie et al. | | |
| 2016/0185785 A1 | 6/2016 | Ioannidis et al. | | |
| 2016/0229833 A1 | 8/2016 | Ioannidis et al. | | |
| 2016/0229864 A1 | 8/2016 | Ioannidis et al. | | |
| 2016/0229872 A1 | 8/2016 | Ioannidis et al. | | |
| 2019/0202929 A1 * | 7/2019 | Buhrlage | ........... | A01K 67/0271 |

FOREIGN PATENT DOCUMENTS

| | | | |
|---|---|---|---|
| EP | 2 565 186 A1 | | 3/2013 |
| WO | 2013030218 | * | 3/2013 |
| WO | 2014045101 A1 | | 3/2014 |
| WO | 2016109515 A1 | | 7/2016 |

(Continued)

OTHER PUBLICATIONS

Database Reguistry, database accession No. 2125660-51-5, Sep. 6, 2017.

(Continued)

*Primary Examiner* — Niloofar Rahmani
(74) *Attorney, Agent, or Firm* — Brian C. Trinque; Lathrop GPM, LLP

(57) ABSTRACT

The present invention concerns the identification of inhibitors of ubiquitin specific protease 7 (USP7), and methods of use thereof.

22 Claims, 5 Drawing Sheets

(56) References Cited

FOREIGN PATENT DOCUMENTS

Figure 1:
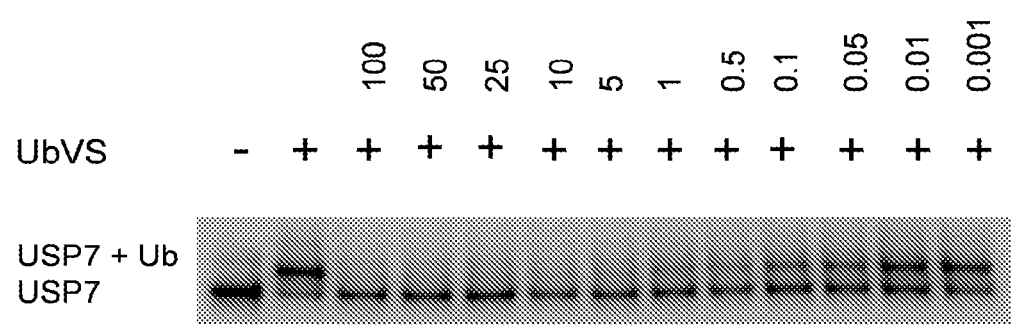

WO    2016126929 A1    8/2016
WO    2016126935 A1    8/2016

OTHER PUBLICATIONS

Gavory et al. (2017) "Discovery and characterization of highly potent and selective allosteric USP7 inhibitors," Nature Chemical Biology, 14:118-125.
International Preliminary Report on Patentability for International Application No. PCT/GB2017/053175, dated Apr. 23, 2019.

* cited by examiner

A

B

B

C

PIPERIDINE DERIVATIVES AS INHIBITORS OF UBIQUITIN SPECIFIC PROTEASE 7

RELATED APPLICATIONS

This application is a 35 U.S.C. § 371 filing of International Application No. PCT/GB2017/053175, filed Oct. 20, 2017, which claims the benefit of Great Britain Patent Application No. 1617758.6, filed Oct. 20, 2016. The entire contents of these applications are incorporated herein by reference in their entireties.

The present invention concerns the identification of inhibitors of ubiquitin specific protease 7 (USP7), and methods of use thereof.

BACKGROUND OF THE INVENTION

Over the past three decades, protein ubiquitination has emerged as an important post-translational modification with roles in a plethora of cellular processes including: proteolysis, gene expression, DNA repair, immune response, metabolism and cell-cycle regulation. Dysregulation of the ubiquitin proteasome system (UPS) has also been implicated in the pathogenesis of multiple human diseases including (but not limited to): cancer (Hoeller et al., Nat. Rev. Cancer (2006), 6, 776-788), viral infection (Gao et al., Can. J. Physiol. Pharmacol. (2006), 84, 5-14), metabolic or neurodegenerative disorders (Loosdregt et al., Immunity (2013), 39, 259-271; Rubinsztein et al., Nature (2006), 443, 780-786) as well as immune and inflammatory-related medical conditions (Wang et al., Cell Mol. Immunol. (2006), 3, 255-261; Corn J. et al., Nat. Struct. Mol. Biol. (2014), 21, 297-300; Nicholson et al., Cell Biochem. Biophys. (2011), 60, 61-68).

The approval and clinical success of the proteasome inhibitors Velcade® (bortezomib) and Kyprolis® (carfilzomib) for the treatment of mantle cell lymphoma and multiple myeloma (MM) have validated the UPS as a cancer target amenable for pharmacological intervention. Although effective, their clinical utility has however been severely limited due to poor selectivity and acute toxicity issues. By inhibiting the proteasome 26S subunit, the currently available proteasome inhibitors indiscriminately impair proteolysis in both cancer and normal cells and are therefore characterised by a low therapeutic index. To circumvent this issue, a promising alternative approach involves targeting the UPS upstream of the proteasome. Interfering with the ubiquitin (Ub) conjugation/deconjugation machinery, for instance, at the level of the ubiquitin specific protease (USP), should allow for the development of improved therapeutics with enhanced specificity and reduced toxicity profiles.

USPs are the largest sub-family of the deubiquitinating enzymes (DUBs) with over 60 family members reported to date (Komander et al., Nat. Rev. Mol. Cell Biol. (2009), 10, 550-563; Clague et al., Physiol. Rev. (2013), 93, 1289-1315). USPs are cysteine proteases that catalyse the removal of Ub from specific target substrates thus preventing their induced degradation by the proteasome, or regulating their activation and/or subcellular localization (Colland et al., Biochimie (2008), 90, 270-283; Nicholson et al., Cell Biochem. Biophys. (2011), 60, 61-68). It is now well established that USPs regulate the stability and activation of numerous proteins involved in the pathogenesis of human diseases including oncogenes and tumor suppressors. As such, USPs represent an emerging and attractive target class for pharmacological intervention.

Amongst all USPs, ubiquitin specific protease 7 (USP7—also known as herpes associated ubiquitin specific protease HAUSP) has attracted considerable attention due to implications in multiple oncogenic pathways (Nicholson et al., Cell Biochem. Biophys. (2011), 60, 61-68). USP7 plays a key role in regulating the ubiquitination and stability of the E3 ligase MDM2 (and human homolog MDM4) which in turn promotes the proteosomal degradation of the tumor suppressor p53 (Cummins, et al., Cell Cycle (2004), 3, 689-692; Cummins, et al. Nature (2004), 428, 486). Inhibition of USP7 reverses this process, restores p53 levels and ultimately results in anti-proliferative effects both in vitro and in vivo (Cheng et al., Cell Death and Disease (2013), 4, e867; Reverdy et al., Chem. Biol. (2012), 19, 467-477; Colland et al., Mol. Cancer Ther. (2009), 8, 2286-2295; Chauhan et al., Cancer Cell (2012), 22, 345-358). In addition to MDM2, USP7 has also been shown to mediate mono-deubiquitination of the tumor suppressor PTEN and transcription factor FOXO4, leading to their nuclear exclusion and respective inactivation (Song et al., Nature (2008), 455, 813-817; van der Horst et al., Nat. Cell Biol. (2006), 8, 1064-1073). Additional reported substrates of USP7 include (but are not restricted to): TSPYL5 (Epping et al. Nat. Cell Biol. (2011), 13, 102-108), the tumor suppressor p16 (Maertens et al., EMBO J. (2010), 29, 2553-2565), as well as various proteins involved in either genomic integrity or the DNA damage machinery such as: claspin, Tip60, UHRF1 or DNMT1 (Faustrup et al., J. Cell Biol. (2009), 184, 13-19; Dar et al., Mol Cell Biol. (2013), 33, 3309-3320; Qin et al., J. Cell Biochem. (2011), 112, 439-444; Du et al., Sci. Signal. (2010), 3, ra80; Nicholson et al., Cell Biochem. Biophys. (2011), 60, 61-68; Jackson et al., Nature Cell Biol. (2014), 16, 1016-1026). Finally, USP7 overexpression has been reported in multiple cancers including: prostate cancer, other haematological malignancies such as multiple myeloma, neuroblastomas and glioblastomas (Song, et al., Nature (2008), 455, 813-817; Cheng et al., Cell Death and Disease (2013), 4, e867; Chauhan et al., Cancer Cell (2012), 22, 345-358; Cheng et al., Oncology Reports (2013), 29, 1730-1736). Overexpression typically correlates with tumor aggressiveness and poor survival. USP7 inhibition may therefore have broad anticancer applications with potential use of small molecule inhibitors in mono- and/or combination treatment modalities. USP7 inhibitors may be particularly useful in disorders driven by overexpression of USP7, and/or in disorders driven by genetic (e.g. mutation, copy number variation) or epigenetic contexts.

In addition to cancer, USP7 has been shown to deubiquitinate and suppress the transcriptional activity of FOXO1 leading to suppression of gluconeogenesis in hepatocyte cell culture and animal studies (Hall et al., Mol. Endrocrinol. (2014), 28, 912-924). The involvement of USP7 in glucose metabolism may provide a strategy for clinical intervention in diabetes as well as in the treatment of other metabolic disorders including obesity. Furthermore, the connections and interactions of USP7 with viral proteins including for instance the EBNA1 protein of Epstein-Bar or the ICPO/VMW110 protein of herpes simplex type-1 viruses (Holowaty et al., J. Biol. Chem. (2003), 278, 29987-29994; Everett et al. J. Virol. (1999), 73, 417-426), strongly suggest that USP7 inhibitors may also be beneficial in the treatment of viral infections. Finally, the involvement of USP7 in regulatory T cell (Treg) function demonstrated in vitro and in vivo through modulation of the transcription factor FOXP3 stability (van Loosdregt et al., Immunity (2013), 39, 259-271), may open new therapeutic avenues for disorders characterised by inappropriate immune responses.

3

The established and growing connections between USP7 and numerous proteins involved in human disease indicate that small molecule inhibitors of USP7 may have broad therapeutic applications beneficial to human health. Small molecule USP7 inhibitors have been reported in the following patent applications: US 2008/0103149 A1, WO 2010/114881 A1, WO 2010/081783 A1, WO 2011/086178 A1, WO 2013/030218 A1, EP 2565186 A1, EP 1749822 A1, WO 2016/109515 A1, WO 2016/109480 A1, WO 2016/126929 A1, WO 2016/126926 A1, WO 2016/126935 A1, WO 2016/150800 A1, WO2017/158381, and WO2017/158388.

SUMMARY OF THE INVENTION

USP7 has been associated with a number of diseases and conditions including (but not limited to) cancer and neoplastic conditions, diabetes, and viral infections. For example, prostate cancer, haematological malignancies (e.g. mantle cell lymphoma, multiple myeloma), neuroblastomas, and glioblastomas have been associated with USP7.

The compounds described herein are able to selectively inhibit USP7 activity. The compounds provided herein may therefore be suitable for the treatment and prevention of cancer and neoplastic conditions such as prostate cancer, haematological malignancies (e.g. mantle cell lymphoma, multiple myeloma), neuroblastomas, and glioblastomas. The compounds may be used as monotherapy or as combination therapy with radiation and/or additional therapeutic agents.

Therefore, in a first aspect is provided a compound of formula (I):

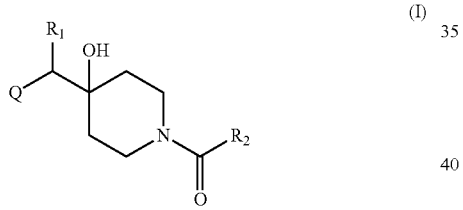

including a pharmaceutically acceptable salt, tautomer, stereoisomer or N-oxide derivative thereof, wherein:
$R_1$ is H, OH or an optionally substituted alkyl group;
$R_2$ is an optionally substituted C1-C6 alkyl, optionally substituted C2-C6 alkenyl, optionally substituted C2-C6 alkynyl, optionally substituted C3-C6 cycloalkyl, optionally substituted C4-C6 alkylcycloalkyl, optionally substituted C4-C6 aryl, optionally substituted C3-C6 heteroaryl, optionally substituted C4-C8 aryloxy, optionally substituted C7-C10 arylalkyl or optionally substituted C5-C10 heteroarylalkyl group; and
Q is an optionally substituted nitrogen containing heterocyclyl group.
In certain embodiments, Q is selected from:

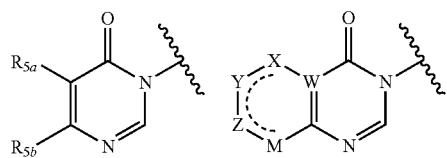

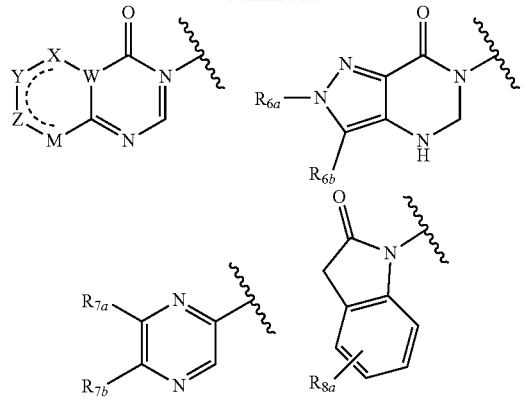

wherein:
W is N or C
X is S, O, N, or CH
Y is $CR_{6a}$, $CR_{9a}$, N, or $NR_{6a}$,
Z is $CR_{6b}$, N, $NR_{6b}$, $NR_{9b}$, or O
M is absent or $CR_8a$
  wherein if X is S, Z is N and M is absent; and wherein if M is $CR_{6a}$ Y is not N;
$R_{5a}$ is H, halo, optionally substituted C1-C6 alkyl, or optionally substituted amino;
$R_{5b}$ is H, halo, optionally substituted C1-C6 alkyl, optionally substituted C2-C6 alkynyl, benzyl, optionally monosubstituted C3-C6 heteroaryl, optionally substituted C3-C6 heterocycloalkyl, optionally substituted C1-C6 alkoxy, NR'R", or $R^aNR'R"$,
  wherein $R^a$ is C1-C6 alkyl or C2-C6 alkenyl; and
  wherein R' and R" are each independently selected from H, oxo-substituted C1-C6 alkyl, hydroxy-substituted C1-C6 alkyl, optionally substituted C1-C6 alkoxy, optionally substituted C3-C6 cycloalkyl, optionally substituted C1-C7 alkylamine, optionally substituted C2-C7 alkenylamine, optionally substituted C3-C10 heterocycloalkyl, optionally substituted C4-C10 aryl, optionally substituted C3-C10 heteroaryl, optionally substituted C5-C10 alkylaryl, optionally substituted C4-C10 alkylheterocycloalkyl, and C4-C6 alkylheteroaryl, or wherein R' and R" together form an optionally substituted C3-C8 heterocycloalkyl including the N to which they are attached;
$R_{6a}$ is H, optionally substituted C1-C6 alkyl, optionally substituted amino, optionally substituted C4-C6 aryl, optionally substituted C1-C6 sulfide, optionally substituted C1-C6 sulfonyl, or optionally substituted amino;
$R_{6b}$ is H, cyano, halo, optionally substituted C1-C6 alkyl, optionally substituted C2-C6 alkenyl, optionally substituted C2-C6 alkynyl, optionally substituted C3-C6 cycloalkyl, optionally substituted C4-C6 cycloalkenyl, optionally substituted C2-C6 ynol, optionally substituted C4-C6 aryl, optionally substituted C3-C6 heteroaryl, optionally substituted amino;
$R_{7a}$ is H;
$R_{7b}$ is H or optionally substituted C4-C6 aryl
  or wherein $R_{7a}$ and $R_{7b}$ together form an optionally substituted C1-C6 aryl group together with the carbons to which they are attached;
$R_{8a}$ is H or is optionally substituted C4-C6 aryl;
$R_{9a}$ is Cl, F, Br, I, or cyano;

R$_{9b}$ is H, optionally substituted C1-C6 alkyl, optionally substituted C4-C6 aryl, optionally substituted C3-C8 heteroaryl, C1-C6 alkoxy.

In a second aspect the present invention provides a pharmaceutical composition comprising a compound of formula (I) or pharmaceutically acceptable salt thereof according to the first aspect and at least one pharmaceutically acceptable excipient.

In a third aspect the present invention provides a compound of formula (I) according to the first aspect or a pharmaceutical composition comprising a compound of formula (I), according to the second aspect, for use in therapy.

In a fourth aspect, the present invention provides a method of treating or preventing cancer comprising administering to a subject a compound of formula (I) or pharmaceutical composition comprising a compound of formula (I).

In a fifth aspect, the present invention provides a use of a compound according to formula (I) in the manufacture of a medicament for treating or preventing cancer.

Other preferred embodiments of the compounds according to the invention appear throughout the specification and in particular in the examples. Particularly preferred are those named compounds having greater activity as tested. Compounds having higher activity are more preferred over those having lower activity.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

FIGURES

FIG. 1: Representative target engagement assay with Example 29. HCT116 cells were treated with vehicle (DMSO) or compound (as indicated in μM) for 2 h and subsequently lysed on ice and homogenised. The Ub-VS probe was then added to the cell lysate and incubated on ice for 10 min. Samples were analysed by western blotting probing for USP7. + and − signs represent the presence or absence of Ub-VS.

Figure 2:
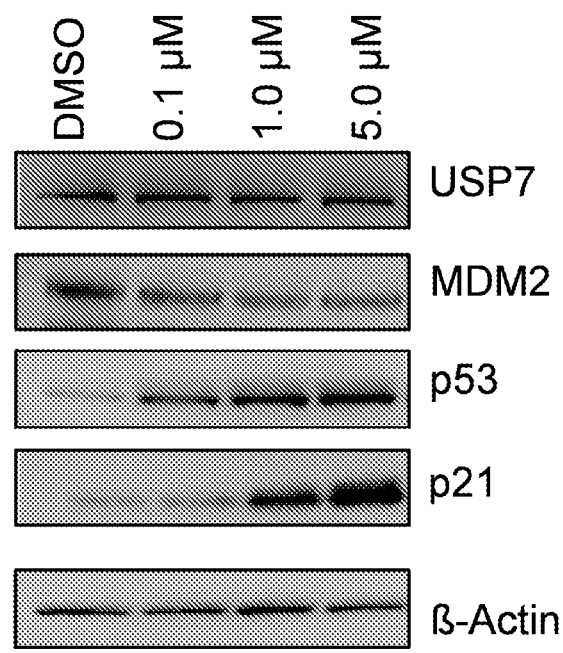
Figure 2:
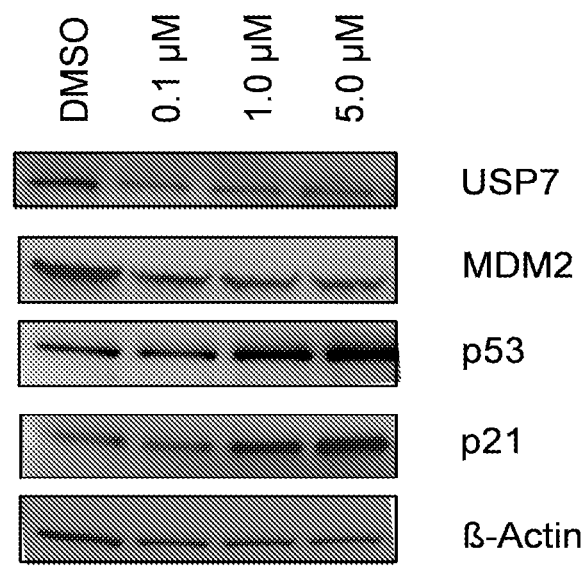

FIG. 2: (A) Effects of Example 29 on p53, p21 and MDM2 protein levels in HCT116. HCT116 cells were treated with vehicle (DMSO) or Example 29 (as indicated) for 24 h, lysed in RIPA buffer and samples subsequently analysed by western blotting probing for USP7, p53, p21 and MDM2 (as indicated). A dose-dependent p53 stabilisation, p21 induction and concomitant decrease in MDM2 levels was observed. (B) Effects of Example 29 on p53, p21 and MDM2 protein levels in SJSA-1. This osteosarcoma cell line with a known functional p53 pathway was used as a second model for these experiments. Cells were treated as described above and samples analysed by western blotting as indicated. Similar observations were made with stabilisation of p53, p21 induction and MDM2 decreased levels in a concentration dependent manner.

Figure 3A:
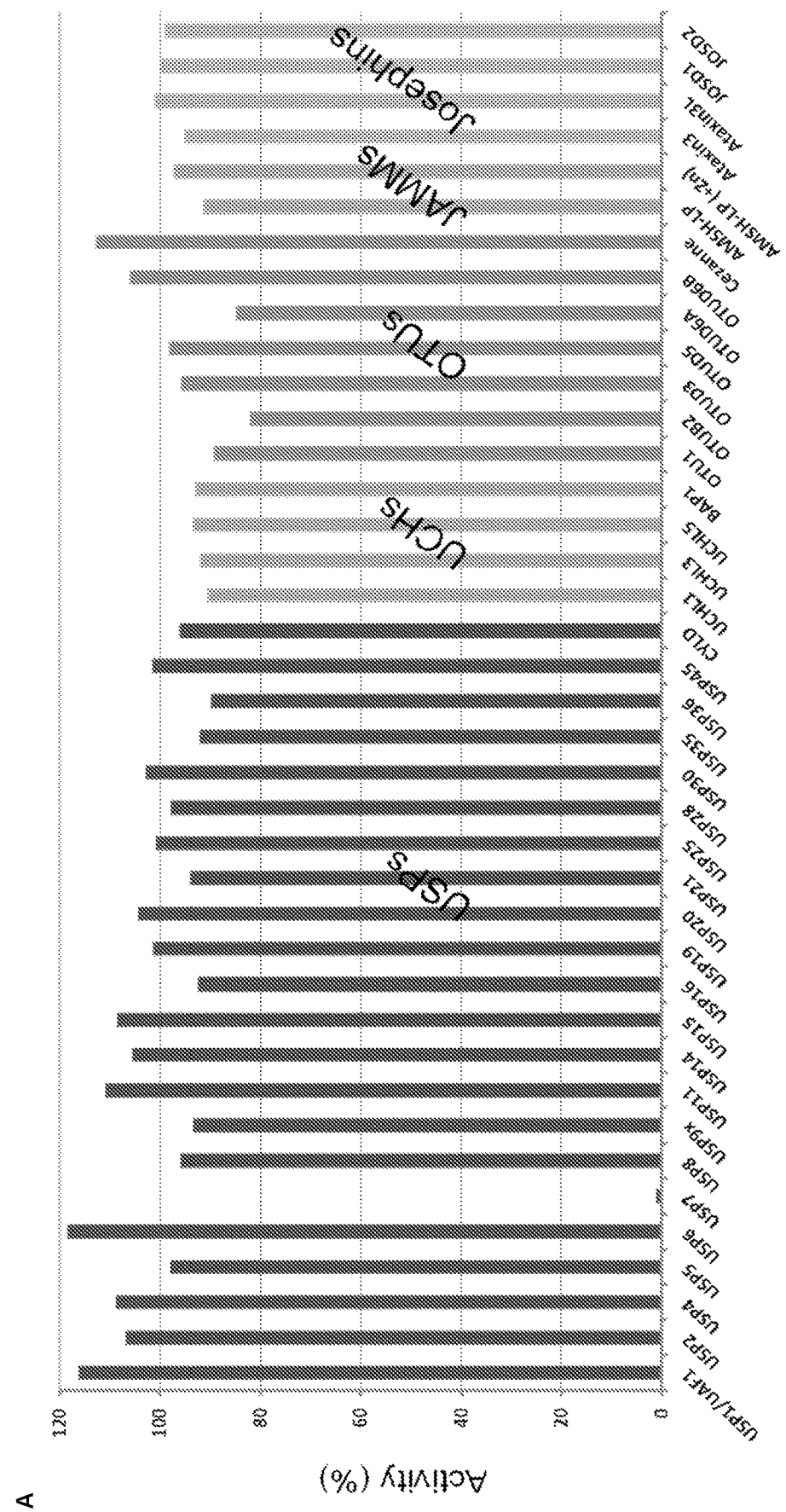
Figure 3:
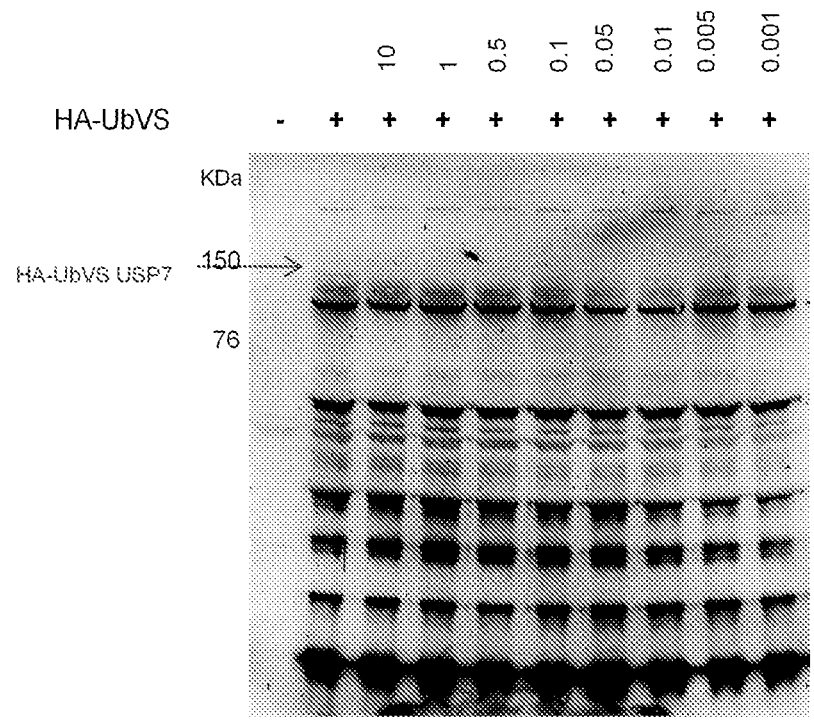
Figure 3:
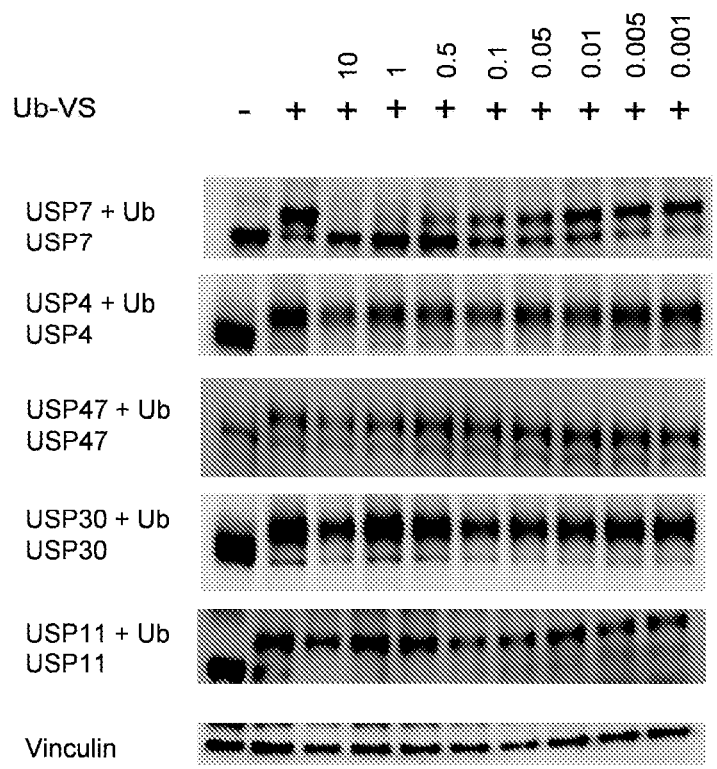

FIG. 3: (A) Biochemical DUB selectivity profile of Example 29. In vitro selectivity was assessed against a panel of 38 DUBs (DUBprofiler™, Ubiquigent, Dundee). Screening was performed at a fixed concentration of 100 μM and levels of activity determined and represented as a histogram. (B) Representative cellular overall DUB selectivity experiments of Example 29 as assessed by immunoblotting. HCT116 cells were treated with vehicle (DMSO) or compound (as indicated, in μM) for 2 h and subsequently lysed on ice and homogenised. The HA-UbVS probe was then added to the cell lysate and incubated on ice for 10 min. Samples were analysed by western blotting probing for HA. + and − signs represent the presence or absence of Ub-VS. Labelled HA-UbVS USP7 is indicated by the red arrow. (C) Representative selectivity experiments of Example 29 assessed on several specific USPs (as indicated). Experiments were performed as described above in FIG. 3B using Ub-VS and probing the samples for USP4, USP47, USP11 and USP30. Compound concentrations are shown in μM (as indicated). As the closest related DUB to USP7, USP47 was used as a stringent test for selectivity. USP4, USP11 and USP30 were used as general, non-relative representative members of the DUB family. + and − signs represent the presence or absence of Ub-VS.

Figure 4:
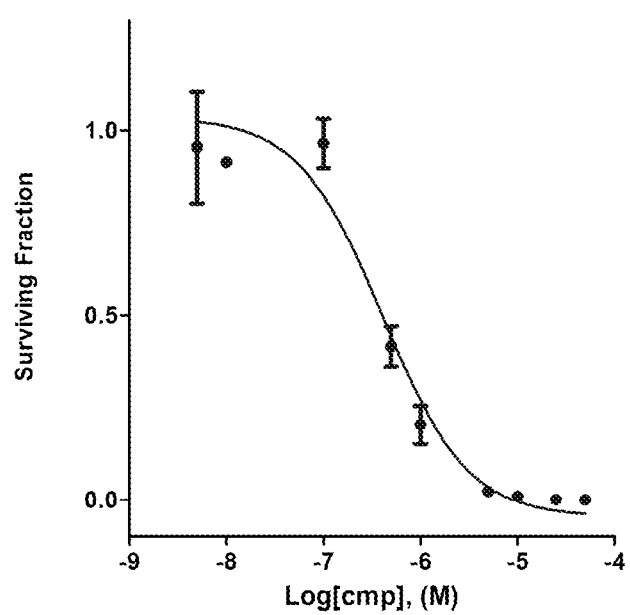

FIG. 4: Representative clonogenic assay with Example 29. HCT116 cell were treated with compound Example 29 in 6 well plates. Colonies were fixed and scored after 7 days and the surviving fractions determined and plotted against the compound concentration.

DETAILED DESCRIPTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

As used in the specification and the appended claims, unless specified to the contrary, the following terms have the meaning indicated:

The term "alkyl group" (alone or in combination with another term(s)) means a straight- or branched-chain saturated hydrocarbon substituent typically containing 1 to 15 carbon atoms, such as 1 to 10, 1 to 8, 1 to 6, or 1 to 4 carbon atoms. A "C$_n$ alkyl" group refers to an aliphatic group containing n carbon atoms. For example, a C$_1$-C$_{10}$ alkyl group contains 1, 2, 3, 4, 5, 6, 7, 8, 9 or 10 carbon atoms. Attachment to the alkyl group occurs through a carbon atom. Examples of such substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

The term "alkenyl group" (alone or in combination with another term(s)) means a straight- or branched-chain hydrocarbon substituent containing one or more double bonds and typically 2 to 15 carbon atoms; such as 2 to 10, 2 to 8, 2 to 6 or 2 to 4 carbon atoms. Examples of such substituents include ethenyl (vinyl), 1-propenyl, 3-propenyl, 1,4-pentadienyl, 1,4-butadienyl, 1-butenyl, 2-butenyl, 3-butenyl, pentenyl and hexenyl.

The term "alkynyl group" (alone or in combination with another term(s)) means a straight- or branched-chain hydrocarbon substituent containing one or more triple bonds and typically 2 to 15 carbon atoms; such as 2 to 10, 2 to 8, 2 to 6 or 2 to 4 carbon atoms. Examples of such substituents include ethynyl, 1-propynyl, 3-propynyl, 1-butynyl, 3-butynyl and 4-butynyl.

The term "carbocyclyl group" (alone or in combination with another term(s)) means a saturated cyclic (i.e. "cycloalkyl"), partially saturated cyclic (i.e. "cycloalkenyl"), or completely unsaturated (i.e. "aryl") hydrocarbon substituent containing from 3 to 14 carbon ring atoms ("ring atoms" are the atoms bound together to form the ring or rings of a cyclic substituent). A carbocyclyl may be a single-ring (monocyclic) or polycyclic ring structure.

The term "heteroalkyl group" (alone or in combination with another term(s)) means a straight- or branched-chain saturated hydrocarbyl substituent typically containing 1 to 15 atoms, such as 1 to 10, 1 to 8, 1 to 6, or 1 to 4 atoms, wherein at least one of the atoms is a heteroatom (i.e. oxygen, nitrogen, or sulfur), with the remaining atoms being carbon atoms, for example an alkyl group containing an ether linkage. A "$C_n$ heteroalkyl" group refers to an aliphatic group containing n carbon atoms and one or more heteroatoms, for example one heteroatom. For example, a $C_1$-$C_{10}$ heteroalkyl group contains 1, 2, 3, 4, 5, 6, 7, 8, 9 or 10 carbon atoms in addition to one or more heteroatoms, for example one heteroatom. Attachment to the heteroalkyl group occurs through a carbon atom or through a heteroatom.

The term "heteroalkenyl group" (alone or in combination with another term(s)) means a straight- or branched-chain hydrocarbon substituent containing one or more carbon-carbon double bonds and typically 2 to 15 atoms; such as 2 to 10, 2 to 8, 2 to 6 or 2 to 4 atoms, wherein at least one of the atoms is a heteroatom (i.e. oxygen, nitrogen, or sulfur), with the remaining atoms being carbon atoms. A "$C_n$ heteroalkenyl" group refers to an aliphatic group containing n carbon atoms and one or more heteroatoms, for example one heteroatom. For example, a $C_2$-$C_{10}$ heteroalkenyl group contains 2, 3, 4, 5, 6, 7, 8, 9 or 10 carbon atoms in addition to one or more heteroatoms, for example one heteroatom. Attachment to the heteroalkenyl group occurs through a carbon atom or through a heteroatom.

The term "heteroalkynyl group" (alone or in combination with another term(s)) means a straight- or branched-chain hydrocarbon substituent containing one or more carbon-carbon triple bonds and typically 2 to 15 carbon atoms; such as 2 to 10, 2 to 8, 2 to 6 or 2 to 4 carbon atoms, wherein at least one of the atoms is a heteroatom (i.e. oxygen, nitrogen, or sulfur), with the remaining atoms being carbon atoms. A "$C_n$ heteroalkynyl" group refers to an aliphatic group containing n carbon atoms and one or more heteroatoms, for example one heteroatom. For example, a $C_2$-$C_{10}$ heteroalkynyl group contains 1, 2, 3, 4, 5, 6, 7, 8, 9 or 10 carbon atoms in addition to one or more heteroatoms, for example one heteroatom. Attachment to the heteroalkynyl group occurs through a carbon atom or through a heteroatom.

A carbocyclyl may be a single ring structure, which typically contains 3 to 8 ring atoms, more typically 3 to 7 ring atoms, and more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl group" (alone or in combination with another term(s)) means a saturated cyclic hydrocarbon substituent containing 3 to 14 carbon ring atoms. A cycloalkyl may be a single carbon ring, which typically contains 3 to 8 carbon ring atoms and more typically 3 to 6 ring atoms. It is understood that attachment to a cycloalkyl group is via a ring atom of the cycloalkyl group. Examples of single-ring cycloalkyls include cyclopropyl, cyclobutyl, cyclopentyl, and cyclohexyl. A cycloalkyl may alternatively be polycyclic or contain more than one ring. Polycyclic cycloalkyls include bridged, fused, and spirocyclic cycloalkyls.

The term "alkylcycloalkyl" refers to a cycloalkyl substituent attached via an alkyl chain. Examples of an alkylcycloalkyl substituent include cyclohexylethane, where the cyclohexane is attached via an ethane linker. Other examples include cyclopropylethane, cyclobutylethane, cyclopentylethane, cycloheptylethane, cyclohexylmethane. In a "$C_n$" alkylcycloalkyl, $C_n$ includes the carbon atoms in the alkyl chain and in the cycloalkyl ring. For example, cyclohexylethane is a C8 alkylcycloalkyl. For the avoidance of doubt, a $C_n$ alkylcycloalkyl group may be substituted with a carbon-containing substitutent (e.g. a cycloalkyl group). In such embodiments, the carbons of the substituent are not included within the "n" carbons.

The term "aryl group" (alone or in combination with another term(s)) means an aromatic carbocyclyl containing from 5 to 14 carbon ring atoms, optionally 5 to 8, 5 to 7, optionally 5 to 6 carbon ring atoms. A "$C_n$ aryl" group refers to an aromatic group containing n carbon atoms. For example, a $C_3$-$C_{10}$ aryl group contains 3, 4, 5, 6, 7, 8, 9 or 10 carbon atoms. Attachment to the aryl group occurs through a carbon atom. An aryl group may be monocyclic or polycyclic (i.e. may contain more than one ring). In the case of polycyclic aromatic rings, only one ring in the polycyclic system is required to be unsaturated while the remaining ring(s) may be saturated, partially saturated or unsaturated. Attachment to the aryl group occurs through a carbon atom contained in the ring. Examples of aryl groups include phenyl, naphthyl, acridinyl, indenyl, indanyl, and tetrahydronaphthyl.

The term "arylalkyl" refers to an aryl substituent attached via an alkyl chain. Examples of an arylalkyl substituent include phenylethane/ethylbenzene, where the ethane chain links to a phenyl group to the point of attachment. In a "$C_n$" arylalkyl, $C_n$ includes the carbon atoms in the alkyl chain and in the aryl group. For example, ethylbenzene is a C8 arylalkyl.

The term "heterocyclyl group" (alone or in combination with another term(s)) means a saturated (i.e. "heterocycloalkyl"), partially saturated (i.e. "heterocycloalkenyl"), or completely unsaturated (i.e. "heteroaryl") ring structure containing a total of 3 to 14 ring atoms, wherein at least one of the ring atoms is a heteroatom (i.e. oxygen, nitrogen, or sulfur), with the remaining ring atoms being carbon atoms. A heterocyclyl group may, for example, contain one, two, three, four or five heteroatoms. Attachment to the heterocyclyl group may occur through a carbon atom and/or one or more heteroatoms that are contained in the ring. A heterocyclyl may be a single-ring (monocyclic) or polycyclic ring structure.

A heterocyclyl group may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl) or 1,3,4-oxadiazolyl), oxatriazolyl, dioxazolyl oxathiolyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl) or pyrazinyl (1,4-diazinyl)), piperazinyl, triazinyl (including 1,3,5-triazinyl, 1,2,4-triazinyl and 1,2,3-triazinyl)), oxazinyl (including 1,2-oxazinyl, 1,3-oxazinyl or 1,4-oxazinyl)), oxadiazinyl (including 1,2,3-oxadiazinyl, 1,2,4-oxadiazinyl, 1,4,2-oxadiazinyl or 1,3,5-oxadiazinyl)), morpholinyl, azepinyl, oxepinyl, thiepinyl, and diazepinyl.

A heterocyclyl group may alternatively be polycyclic (i.e. may contain more than one ring). Examples of polycyclic heterocyclyl groups include bridged, fused, and spirocyclic heterocyclyl groups. In a spirocyclic heterocyclyl group, one atom is common to two different rings. In a bridged heterocyclyl group, the rings share at least two common nonadjacent atoms. In a fused-ring heterocyclyl group, two or more rings may be fused together, such that two rings share one common bond. Examples of fused ring heterocyclyl groups containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyl groups include benzo-fused heterocyclyl groups, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), and benzisoxazinyl (including 1,2-benzisoxazinyl or 1,4-benzisoxazinyl).

The term "heterocycloalkyl group" (alone or in combination with another term(s)) means a saturated heterocyclyl. A "$C_n$ heterocycloalkyl" group refers to a cyclic aliphatic group containing n carbon atoms in addition to at least one heteroatom, for example nitrogen. For example, a $C_1$-$C_{10}$ heterocycloalkyl group contains 1, 2, 3, 4, 5, 6, 7, 8, 9 or 10 carbon ring atoms in addition to the at least one heteroatom. Attachment to the heterocycloalkyl group occurs through a carbon atom or one of the at least one heteroatoms.

The term "alkylheterocycloalkyl" refers to a heterocycloalkyl substituent attached via an alkyl chain. In a "$C_n$," alkylheterocycloalkyl, $C_n$ includes the carbon atoms in the alkyl chain and in the heterocycloalkyl ring. For example, ethylpiperidine is a C7 alkylheterocycloalkyl.

The term "nitrogen-containing heterocyclyl group" refers to a monocyclic or bicyclic heterocyclyl group containing at least one nitrogen ring atom, in which each ring comprises from 3 to 7 ring atoms and optionally contains, in addition to the nitrogen atom, zero or one or two or more, the same or different hetero atoms, but preferably zero or one additional heteroatom selected from the group consisting of an oxygen atom, a nitrogen atom and a sulfur atom; and the heterocyclyl group may be saturated (i.e. "heterocycloalkyl"), partially saturated (i.e. "heterocycloalkenyl"), or completely unsaturated (i.e. "heteroaryl"). The bicyclic heterocyclyl group may have a spiro structure of which the two rings share one and the same ring atom, or may have a bicyclo structure of which the rings share two or more ring atoms, for example bridged or fused rings. Examples of the nitrogen-containing heterocyclyl group include, for example, a pyrrolyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group, an azetidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a piperidinyl group, a piperazinyl group, a dihydropyridyl group, a morpholinyl group, a thiomorpholinyl group, a 2,6-diazaspiro[3.5]nonyl group, a 2,7-diazaspiro[3.5]nonyl group, a 2,7-diazaspiro[4.5]decyl group, a 2,7-diazabicyclo[3.3.0]octyl group, or a 3,6-diazabicyclo[3.3.0]octyl group.

The nitrogen-containing heterocyclyl group can be optionally substituted—i.e. can be an unsubstituted nitrogen-containing heterocyclyl group or a substituted nitrogen-containing heterocyclyl group. A substituted nitrogen-containing heterocyclyl group is substituted with one or more substituents which can be the same or different. Possible substituents are set out below.

The term "heteroaryl group" (alone or in combination with another term(s)) means an aromatic heterocyclyl containing from 5 to 14 ring atoms. A "$C_n$ heteroaryl" group refers to an aromatic group containing n carbon atoms and at least one heteroatom. For example, a $C_2$-$C_{10}$ aryl group contains 2, 3, 4, 5, 6, 7, 8, 9 or 10 carbon atoms in addition to at least one heteroatom. Attachment to the heteroaryl group occurs through a carbon atom or through a heteroatom. A heteroaryl group may be monocyclic or polycyclic. A heteroaryl may be a single ring or 2 or 3 fused rings. Examples of monocyclic heteroaryl groups include 6-membered rings such as pyridyl, pyrazinyl, pyrimidinyl, pyridazinyl, and 1,3,5-, 1,2,4- or 1,2,3-triazinyl; 5-membered rings such as imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl. Polycyclic heteroaryl groups may be 2 or 3 fused rings. Examples of polycyclic heteroaryl groups include 6/5-membered fused ring groups such as benzothiofuranyl, benzisoxazolyl, benzoxazolyl, and purinyl; and 6/6-membered fused ring groups such as benzopyranyl, quinolinyl, isoquinolinyl, cinnolinyl, quinazolinyl, and benzoxazinyl. In the case of polycyclic heteroaryl groups, only one ring in the polycyclic system is required to be unsaturated while the remaining ring(s) may be saturated, partially saturated or unsaturated.

A nitrogen-containing heteroaryl group is a heteroaryl group in which at least one of the one or more heteroatoms in the ring is nitrogen.

The term "heteroarylalkyl" refers to a heteroaryl substituent attached via an alkyl chain. Examples of a heteroarylalkyl substituent include ethylpyridine, where the ethane chain links a pyridine group to the point of attachment.

The term "amino group" refers to the —NR'R" group. The amino group can be optionally substituted. In an unsubstituted amino group, R' and R" are hydrogen. In a substituted amino group R' and R" each independently may be, but are not limited to, hydrogen, an alkyl, heteroalkyl, cycloalkyl, heterocycloalkyl, alkylcycloalkyl, alkylheterocycloalkyl, alkoxy, sulfonyl, alkenyl, alkanoyl, aryl, arylalkyl, or a heteroaryl group, provided R' and R" are not both hydrogen. In a substituted amino group R' and R" may cyclise to form a heterocyclic group including the nitrogen to which they are attached (e.g. a pyrrolidine group). The heterocyclic group formed by R' and R" may optionally include additional heteroatoms, for example nitrogen or oxygen (e.g. the NR'R" group may form morpholine or piperazine). The heterocyclic group formed by R' and R" may be monocyclic, polycyclic (e.g. bicyclic), spirocyclic or a bridged ring group (e.g. a diazabicyclo[3.2.1]octane group). Such a cyclic amino group may be optionally substituted, e.g. with an amino group, a methyl group, a hydroxyl group or an oxo group.

The term "aminoalkyl" or "alkylamine" group (the terms are used interchangeably herein) refers to the —$R^a$NR'R" group, wherein $R^a$ is an alkyl chain as defined above and NR'R" is an optionally substituted amino group as defined above. The alkyl chain $R^a$ may be straight chained or branched, or may be cyclic. Where alkyl chain $R^a$ is cyclic, the group is referred to as "cycloalkylamine" and the group is attached by a ring carbon to which the NR'R" group is also attached. "$C_n$ aminoalkyl" group refers to a group containing n carbon atoms. For example, a $C_1$-$C_{10}$ aminoalkyl group contains 1, 2, 3, 4, 5, 6, 7, 8, 9 or 10 carbon atoms. When the amino group of the aminoalkyl group is a substituted amino group, the number of carbon atoms includes any carbon atoms in the substituent groups. Attachment to the aminoalkyl group occurs through a carbon atom of the $R^a$ alkyl group. Examples of aminoalkyl substituents include methylamine, ethylamine, methylaminomethyl, dimethylaminomethyl, methylaminoethyl, dimethylaminoethyl, methylpyrrolidine, and ethylpyrrolidine.

The term "aminoalkenyl" or "alkenylamine" group (the terms are used interchangeably herein) refers to the $R^x$NR'R" group, where $R^x$ is an alkenyl chain as defined herein. The alkenyl chain $R^x$ may be straight chained or branched. "$C_n$ aminoalkenyl" group refers to a group containing n carbon atoms. For example, a $C_1$-$C_{10}$ aminoalkenyl group contains 1, 2, 3, 4, 5, 6, 7, 8, 9 or 10 carbon atoms. When the amino group of the aminoalkyl group is a substituted amino group, the number of carbon atoms includes any carbon atoms in the substituent groups. Attachment to the aminoalkyl group occurs through a carbon atom of the $R^x$ alkenyl group.

The term "amido group" refers to the —C(=O)—NR— group. Attachment may be through the carbon and/or nitrogen atom. For example, the amido group may be attached as a substituent via the carbon atom only, in which case the nitrogen atom has two R groups attached (—C(=O)—NR$_2$). The amido group may be attached by the nitrogen atom only, in which case the carbon atom has an R group attached (—NR—C(=O)R).

The term "alkoxy group" refers to an —O-alkyl group. The alkoxy group can refer to linear, branched, or cyclic, saturated or unsaturated oxy-hydrocarbon chains, including, for example, methoxyl, ethoxyl, propoxyl, isopropoxyl, butoxyl, t-butoxyl and pentoxyl. The alkoxy group can be optionally substituted (a "substituted alkoxy") with one or more alkoxy group substituents.

The term "aryloxy" refers to a —O-aryl group, for example a phenoxy group or benzyloxy group. A "Cn aryloxy" group refers to an aryloxy group having n carbons. The carbons may form the aryl ring (e.g. C6 aryloxy may be phenoxy) or part of a linking alkyl chain (e.g. C7 aryloxy may be benzyloxy).

The term "alkylester" refers to a —C(O)OR group, where R is an alkyl group as defined herein. An example of an alkylester is ethyl methanoate—i.e. R is an ethyl group.

The term "hydroxyl" refers to an —OH group.

The term "oxo group" refers to the (=O) group, i.e. a substituent oxygen atom connected to another atom by a double bond. For example, a carbonyl group (—C(=O)—) is a carbon atom connected by a double bond to an oxygen atom, i.e. an oxo group attached to a carbon atom.

The term "halo group" refers to a group selected from chlorine, fluorine, bromine and iodine. Preferably, the halo group is selected from chlorine and fluorine.

The term "optionally substituted" means the group may be substituted with one or more substituents, which can be the same or different, or the group may have no substituents. The term "optionally monosubstituted" means the group may have a single substituent or may be unsubstituted.

A substituent can be attached through a carbon atom and/or a heteroatom in the alkyl, alkenyl, alkynyl, carbocyclyl (including cycloalkyl, cycloalkenyl and aryl), heterocyclyl (including heterocycloalkyl, heterocycloalkenyl, heteroaryl, nitrogen-containing heterocyclyl, nitrogen-containing heteroaryl), amino, amido, ester, ether, alkoxy, or sulfonamide group. The term "substituent" (or "radical") includes but is not limited to alkyl, substituted alkyl, heteroalkyl, substituted heteroalkyl, aralkyl, substituted aralkyl, alkenyl, substituted alkenyl, alkynyl, substituted alkynyl, halo, hydroxyl, cyano, amino, amido, alkylamino, arylamino, carbocyclyl, cycloalkyl, substituted cycloalkyl, heterocycloalkyl, substituted heterocycloalkyl, cycloalkenyl, substituted cycloalkenyl, aryl, substituted aryl, heteroaryl, substituted heteroaryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl, arylsulfonyl and sulfoximinyl.

In certain aspects, the substituent is alkyl, substituted alkyl, heteroalkyl, substituted heteroalkyl, alkenyl, substituted alkenyl, alkynyl, substituted alkynyl, halo, hydroxyl, cyano, amino, amido, alkylamino, arylamino, carbocyclyl, cycloalkyl, substituted cycloalkyl, heterocycloalkyl, substituted heterocycloalkyl, cycloalkenyl, substituted cycloalkenyl, aryl, substituted aryl, heteroaryl, substituted heteroaryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl and arylsulfonyl.

In certain embodiments, each of the one or more substitutents of any optionally substituted group is independently selected from OH, F, Cl, Br, I, CN, C1-C6 alkyl, $CF_3$, $CHF_2$, $CH_2F$, $CH_2OH$, $C(O)CH_3$, $CH_2NHC(O)OCH_2CH_3$, C2-C6 alkenyl, C2-C6 alkynyl, C3-C6 cycloalkyl, C1-C6 alkoxy, amino, C1-C6 alkylamine, C5-C6 aryl, C3-C6 heteroaryl, benzyl, oxo and amide or two adjacent substituents may together constitute a ring, for example dioxolane.

If a group is substituted with a further optionally substituted group, it is understood that the first substituent may itself be either unsubstituted or substituted.

For completeness, it is also noted that certain chemical formulae used herein define delocalized systems. This definition is known in the art as a definition of aromaticity and may indicate the presence of, for example, a planar mono-, di- or tri-cyclic system that contains (4n+2) electrons where n is an integer. In other words, these systems may display Hückel aromaticity.

In whatever aspect, the compounds of the present invention may possess some aspect of stereochemistry. For example, the compounds may possess chiral centres and/or planes and/or axes of symmetry. As such, the compounds may be provided as single stereoisomers, single diastereomers, mixtures of stereoisomers or as racemic mixtures, unless otherwise specified. Stereoisomers are known in the art to be molecules that have the same molecular formula and sequence of bonded atoms, but which differ in their spatial orientations of their atoms and/or groups.

In addition, the compounds of the present invention may exhibit tautomerism. Each tautomeric form is intended to fall within the scope of the invention.

In addition, the compounds of the present invention may be provided as a pro-drug. Pro-drugs are transformed, generally in vivo, from one form to the active forms of the drugs described herein.

In addition, it will be understood that the elements described herein may be the common isotope or an isotope other than the common isotope. For example, a hydrogen atom may be $^1H$, $^2H$ (deuterium) or $^3H$ (tritium).

In addition, the compounds of the present invention may be provided in the form of their pharmaceutically acceptable salts or as co-crystals.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulfate, bisulfate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the handbook of pharmaceutical salts published by IUPAC.

In addition, the compounds of the present invention may sometimes exist as zwitterions, which are considered as part of the invention.

Accordingly, in a first aspect, the invention provides a compound of formula (I):

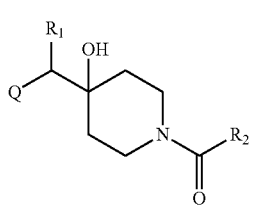

including a pharmaceutically acceptable salt, tautomer, stereoisomer or N-oxide derivative thereof, wherein:

$R_1$ is H, OH or an optionally substituted alkyl group;

$R_2$ is an optionally substituted C1-C6 alkyl, optionally substituted C2-C6 alkenyl, optionally substituted C2-C6 alkynyl, optionally substituted C3-C6 cycloalkyl, optionally substituted C4-C6 alkylcycloalkyl, optionally substituted C4-C6 aryl, optionally substituted C3-C6 heteroaryl, optionally substituted C4-C8 aryloxy, optionally substituted C7-C10 arylalkyl or optionally substituted C5-C10 heteroarylalkyl group; and Q is an optionally substituted nitrogen containing heterocyclyl group.

In certain embodiments, Q is selected from:

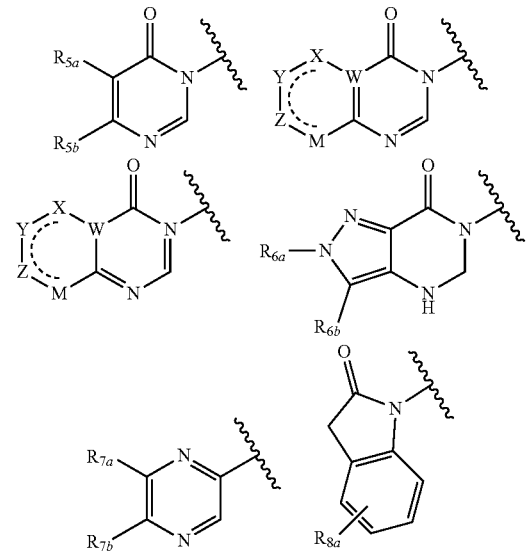

wherein:

W is N or C

X is S, O, N, or CH

Y is $CR_{6a}$, $CR_{9a}$, N, or $NR_{6a}$,

Z is $CR_{6b}$, N, $NR_{6b}$, $NR_{9b}$, or O

M is absent or $CR_8a$ wherein if X is S, Z is N and M is absent; and wherein if M is $CR_{8a}$ Y is not N;

$R_{5a}$ is H, halo, optionally substituted C1-C6 alkyl, or optionally substituted amino;

$R_{5b}$ is H, halo, optionally substituted C1-C6 alkyl, optionally substituted C2-C6 alkynyl, benzyl, optionally monosubstituted C3-C6 heteroaryl, optionally substituted C3-C6 heterocycloalkyl, optionally substituted C1-C6 alkoxy, NR'R", or $R^aNR'R"$, wherein $R^a$ is C1-C6 alkyl or C2-C6 alkenyl; and wherein R' and R" are each independently selected from H, oxo-substituted C1-C6 alkyl, hydroxy-substituted C1-C6 alkyl, optionally substituted C1-C6 alkoxy, optionally substituted C3-C6 cycloalkyl, optionally substituted C1-C7 alkylamine, optionally substituted C2-C7 alkenylamine, optionally substituted C3-C10 heterocycloalkyl, optionally substituted C4-C10 aryl, optionally substituted C3-C10 heteroaryl, optionally substituted C5-C10 alkylaryl, optionally substituted C4-C10 alkylheterocycloalkyl, and C4-C6 alkylheteroaryl, or wherein R' and R" together form an optionally substituted C3-C8 heterocycloalkyl including the N to which they are attached;

$R_{6a}$ is H, optionally substituted C1-C6 alkyl, optionally substituted amino, optionally substituted C4-C6 aryl, optionally substituted C1-C6 sulfide, optionally substituted C1-C6 sulfonyl, or optionally substituted amino;

$R_{6b}$ is H, cyano, halo, optionally substituted C1-C6 alkyl, optionally substituted C2-C6 alkenyl, optionally substituted C2-C6 alkynyl, optionally substituted C3-C6 cycloalkyl, optionally substituted C4-C6 cycloalkenyl, optionally substituted C2-C6 ynol, optionally substituted C4-C6 aryl, optionally substituted C3-C6 heteroaryl, optionally substituted amino;

$R_{7a}$ is H;

$R_{7b}$ is H or optionally substituted C4-C6 aryl
or wherein $R_{7a}$ and $R_{7b}$ together form an optionally substituted C1-C6 aryl group together with the carbons to which they are attached;

$R_{8a}$ is H or is optionally substituted C4-C6 aryl;

$R_{9a}$ is Cl, F, Br, I, or cyano;

$R_{9b}$ is H, optionally substituted C1-C6 alkyl, optionally substituted C4-C6 aryl, optionally substituted C3-C8 heteroaryl, C1-C6 alkoxy.

As will be appreciated by the skilled person, the dotted line notation within the fused ring structures indicates that all bonds between integers may be single bonds, or may form part of a delocalised system. That is, the ring may be fully saturated, partially saturated or fully unsaturated (i.e. aromatic).

In certain embodiments Q is selected from:

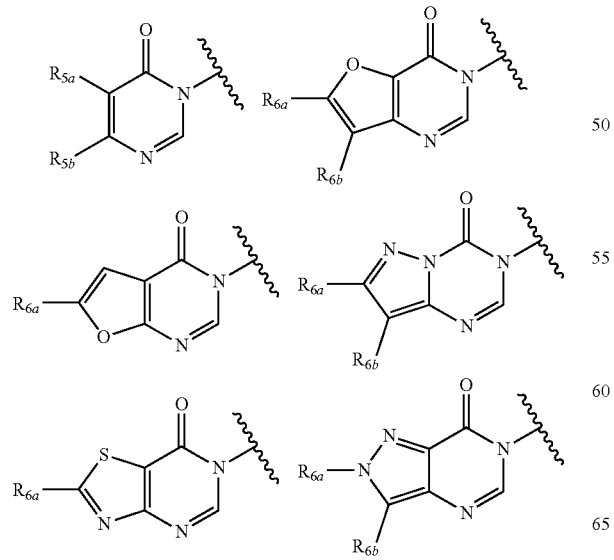

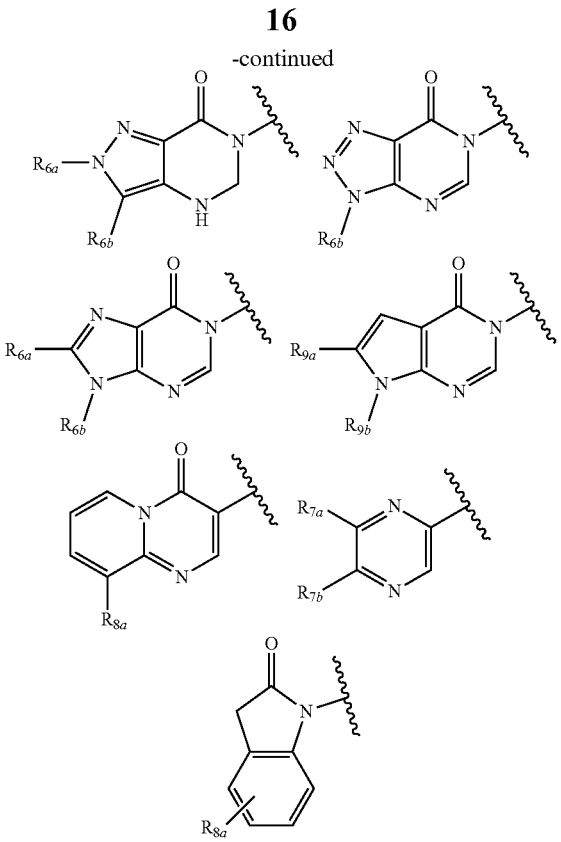

and $R_{5a}$ is H, halo, optionally substituted C1-C6 alkyl, or optionally substituted amino;

$R_{5b}$ is H, halo, optionally substituted C1-C6 alkyl, optionally substituted C2-C6 alkynyl, benzyl, optionally monosubstituted C3-C6 heteroaryl, optionally substituted C3-C6 heterocycloalkyl, optionally substituted C1-C6 alkoxy, NR'R", or $R^a$NR'R",
wherein $R^a$ is C1-C6 alkyl or C2-C6 alkenyl; and
wherein R' and R" are each independently selected from H, oxo-substituted C1-C6 alkyl, hydroxy-substituted C1-C6 alkyl, optionally substituted C1-C6 alkoxy, optionally substituted C3-C6 cycloalkyl, optionally substituted C1-C7 alkylamine, optionally substituted C2-C7 alkenylamine, optionally substituted C3-C10 heterocycloalkyl, optionally substituted C4-C10 aryl, optionally substituted C3-C10 heteroaryl, optionally substituted C5-C10 alkylaryl, optionally substituted C4-C10 alkylheterocycloalkyl, and C4-C6 alkylheteroaryl, or wherein R' and R" together form an optionally substituted C3-C8 heterocycloalkyl including the N to which they are attached;

$R_{6a}$ is H, optionally substituted C1-C6 alkyl, optionally substituted amino, optionally substituted C4-C6 aryl, optionally substituted C1-C6 sulfide, optionally substituted C1-C6 sulfonyl, or optionally substituted amino;

$R_{6b}$ is H, cyano, halo, optionally substituted C1-C6 alkyl, optionally substituted C2-C6 alkenyl, optionally substituted C2-C6 alkynyl, optionally substituted C3-C6 cycloalkyl, optionally substituted C4-C6 cycloalkenyl, optionally substituted C2-C6 ynol, optionally substituted C4-C6 aryl, optionally substituted C3-C6 heteroaryl, optionally substituted amino;

$R_{7a}$ is H;

R$_{7b}$ is H or optionally substituted C4-C6 aryl or wherein R$_{7a}$ and R$_{7b}$ together form an optionally substituted C1-C6 aryl group together with the carbons to which they are attached;

R$_{8a}$ is H or is optionally substituted C4-C6 aryl;

R$_{9a}$ is Cl, F, Br, I, or cyano;

R$_{9b}$ is H, optionally substituted C1-C6 alkyl, optionally substituted C4-C6 aryl, optionally substituted C3-C8 heteroaryl, C1-C6 alkoxy.

In certain of such embodiments, for any of the functional groups for which substituents are optional, the optional substituents are independently selected from OH, F, Cl, Br, I, CN, C1-C6 alkyl, CF$_3$, CHF$_2$, CH$_2$F, CH$_2$OH, COOH, C(O)CH$_3$, CH$_2$NHC(O)OCH$_2$CH$_3$, C2-C6 alkenyl, C2-C6 alkynyl, C3-C6 cycloalkyl, C1-C6 alkoxy, amino, C1-C6 alkylamine, C5-C6 aryl, C3-C6 heteroaryl, benzyl, oxo and amide.

In certain embodiments, Q is

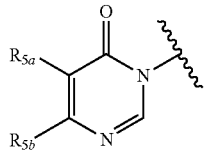

R$_{5a}$ is H,

R$_{5b}$ is selected from optionally methyl- or ethylamine-substituted pyrazole, and NR'R", wherein R' and R" are each independently selected from H, methyl, cyclohexylamine, optionally methyl-, fluoro-, or fluorophenyl-substituted C2-C7 ethylamine, optionally substituted phenyl or wherein R' and R" together form an optionally substituted C3-C8 heterocycloalkyl including the N to which they are attached. In certain preferred embodiments R' is H and R" is ethylpyrrolidine optionally substituted with methyl, fluoro, or fluorophenyl.

In preferred embodiments R$_{5b}$ is an aminopyrrolidinyl group, a dimethylaminopiperidine group, an optionally substituted C$_1$-C$_{08}$ aminoalkyl-substituted amino group, or a 3,6-diazabicyclo[3.2.1]octane of the type:

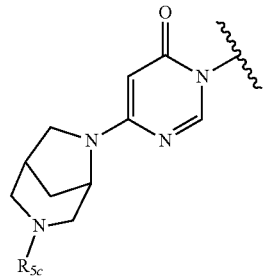

wherein R$_{5c}$ is hydrogen, or optionally substituted C$_1$-C$_6$ alkyl.

In certain embodiments Q is:

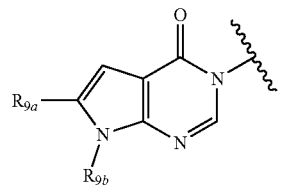

and

R$_{9a}$ is Cl, F, Br, I, or cyano;

R$_{9b}$ is H, optionally substituted C1-C6 alkyl, optionally substituted C4-C6 aryl;

wherein the optional substituents are selected from F, Cl, Br, methoxy, OH, CH2OH, C1-C6 alkylamine, cyclopropane, dioxolane, methylpyrazole.

In certain embodiments R$_{9a}$ is Cl, F, Br, I, or cyano and R$_{9b}$ is phenyl optionally substituted with F, Cl, Br, methoxy, OH, C1-C6 alkylamine, cyclopropane, dioxolane, methylpyrazole optionally substituted with F, and morpholine.

In preferred embodiments, R$_{9a}$ is Cl or F, preferably Cl. As shown in Table 1, compounds wherein R$_{9a}$ is Cl exhibit improved potency in both the USP7 biochemical assay and LNCaP anti-proliferative assay compared to their direct analogues in which R$_{9a}$=H. Also, compounds wherein R$_{9a}$ is Cl may exhibit improved potency compared to compounds wherein R$_{9a}$ is Br or I. In addition, compounds where R$_{9a}$=Cl may exhibit substantially increased solubility in the kinetic solubility assay compared to R$_{9a}$=H (Table 2).

TABLE 1

| Structure | USP7 IC$_{50}$ (µM) (Example Number) | | LNCaP EC$_{50}$ (µM) (Example Number) | |
|---|---|---|---|---|
| | R$_{9a}$ = H | R$_{9a}$ = Cl | R$_{9a}$ = H | R$_{9a}$ = Cl |
| [structure] | 0.42 (N/A) | 0.25 (202) | 0.14 (N/A) | 0.051 (202) |

TABLE 1-continued

| Structure | USP7 IC$_{50}$ (μM) (Example Number) | | LNCaP EC$_{50}$ (μM) (Example Number) | |
|---|---|---|---|---|
| | R$_{9a}$ = H | R$_{9a}$ = Cl | R$_{9a}$ = H | R$_{9a}$ = Cl |
| [pyrrolopyrimidinone with 4-chlorophenyl N-substituent and piperidine-methylcyclopropanecarbonyl] | 0.39 (N/A) | 0.22 (203) | 0.049 (N/A) | 0.022 (203) |
| [pyrrolopyrimidinone with 3-(1-methylpyrazol-4-yl)phenyl N-substituent and piperidine-methylcyclopropanecarbonyl] | 0.33 (N/A) | 0.14 (212) | 0.13 (N/A) | 0.055 (212) |

TABLE 2

| Structure | KSol (μM) (Example Number) | |
|---|---|---|
| | R = H | R = Cl |
| [pyrrolopyrimidinone with phenyl N-substituent and piperidine-methylcyclopropanecarbonyl] | 16 (N/A) | 173 (200) |

In certain embodiments Q is:

[pyrido[1,2-a]pyrimidin-4-one substituted with R$_{8a}$]

and

R$_{8a}$ is H or phenyl; and optionally wherein R1 is OH.

In certain embodiments Q is:

[purin-6-one substituted with R$_{6a}$ and R$_{6b}$]

and

R$_{6a}$ is H, or C1-C6 alkyl;

R$_{6b}$ is H, or optionally substituted C4-C6 aryl;

wherein the optional substituent is selected from C1-C6 alkylamine.

In certain such embodiments R$_{6a}$ is H, or methyl and R$_{6b}$ is H, or phenyl optionally substituted with CH2NH2 or CH(CH3)NH2.

In certain embodiments Q is:

[triazolopyridinone substituted with R$_{6b}$]

and

R$_{6b}$ is H, or C4-C6 aryl, optionally wherein R$_{6b}$ is phenyl.

In certain embodiments Q is:

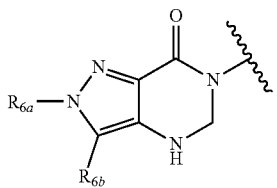

and
$R_{6a}$ is H or C1-C6 alkyl, optionally wherein $R_{6a}$ is methyl;
$R_{6b}$ is H, or C1-C6 alkyl, optionally wherein $R_{6b}$ is propyl.
In certain embodiments Q is:

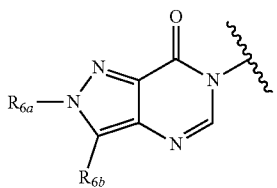

and
$R_{6a}$ is H or C1-C6 alkyl;
$R_{6b}$ is H, halo, optionally substituted C2-C6 alkenyl, optionally substituted C2-C6 alkynyl, optionally substituted C3-C6 cycloalkyl, optionally substituted C4-C6 aryl, optionally substituted C3-C6 heteroaryl;
wherein the optional substituents are independently selected from F, CN, OH, CH2OH, amide, NH2, C1-C6 alkylamine, C3-C6 cycloalkylamine, CF3, COOH, methylmorpholine, CH(CF3)NH2, CH(CHF2)NH2 and CH2NHC(O)OCH2CH3.

In certain such embodiments, $R_{6a}$ is H, methyl or ethyl; $R_{6b}$ is H, Br, optionally substituted propenyl, ethynyl, optionally substituted propynyl, optionally substituted pentynyl, optionally substituted cyclohexane, optionally substituted phenyl, pyrazole, pyridine;
wherein the optional substituents are independently selected from F, CN, OH, CH2OH, amide, NH2, C1-C6 alkylamine, C3-C6 cycloalkylamine, CF3, CH(CF3)NH2, CH(CHF2)NH2.

In certain such embodiments, $R_{6a}$ is methyl and $R_{6b}$ is phenyl optionally substituted with one or more of F, CN, OH, CH2OH, NH2, CH2NH2, CH2CH2NH2, CH(CH3)NH2, amide, cyclopropylamine, and cyclobutylamine.

In certain embodiments, Q is:

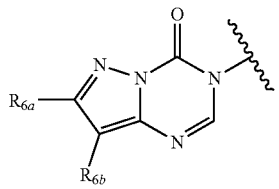

and $R_{6a}$ is H or C1-C6 alkyl, and $R_{6b}$ is C4-C6 aryl. In certain embodiments, $R_{6a}$ is phenyl.

In certain preferred embodiments, the substitutent at $R_2$ has the arrangement $CH2CR^bR^cR^d$ wherein no more than one of $R^b$, $R^c$ and $R^d$ are hydrogen. For the avoidance of doubt, while no more than one of the substituents at $R^b$, $R^c$ and $R^d$ is hydrogen, the substituents at $R^b$, $R^c$ and $R^d$ can otherwise be any functional group necessary to form the applicable options for $R_2$ described herein.

In certain embodiments $R_2$ is optionally substituted C3-C5 heteroaryl, optionally substituted C4-C6 alkylcycloalkyl, optionally substituted C5-C10 arylalkyl or optionally substituted C5-C10 heteroarylalkyl group, wherein each optional substituent is independently selected from OH, F, methyl, $CF_3$, $CHF_2$, $CH_2F$, $CH_2OH$, C1-C4 alkoxy, and C3-C4 cycloalkyl.

In certain embodiments, $R_2$ is optionally substituted ethylphenyl, wherein the ethyl group is optionally substituted with methyl, methoxymethyl, $CF_3$, $CHF_2$, or $CH_2F$ and the phenyl group is optionally substituted with F.

In certain alternative embodiments $R_2$ is oxazole optionally substituted with cyclopropane, or pyrazole optionally substituted with methyl.

It has been newly and surprisingly identified that compounds according to formula (I) in which $R_2$ is $CH2CR^aR^bR^c$ and wherein no more than one of $R^a$, $R^b$ and $R^c$ are hydrogen have a surprising and unexpected advantage: namely, a significant increase in potency for USP7 inhibition relative to compounds where more than one $R^a$, $R^b$ and $R^c$ are hydrogen, This surprising effect is clearly demonstrated in Table 3 below. Unexpected USP7 potency gains were achieved when no more than one of $R^a$, $R^b$ and $R^c$ are hydrogen (right-hand column) compared to more than one of $R^a$, $R^b$ and $R^c$ are hydrogen (centre column).

TABLE 3

TABLE 3-continued

| Structure | USP7 IC$_{50}$ (μM) (Example Number) | |
|---|---|---|
| [pyrazolo[4,3-d]pyrimidin-7(6H)-one core with 2-methyl, 3-CF$_3$, and N-CH$_2$-(4-hydroxypiperidine-1-carbonyl) substituent] | 14 (39) [3-phenylpropyl] | 0.6 (23) [(R)-3-phenylbutyl with Me] |

Preferably, the compound according to formula (I) is selected from:
(R)-6-Chloro-3-((4-hydroxy-1-(3-phenylbutanoyl)piperidin-4-yl)methyl)pyrimidin-4(3H)-one
(R)-3-((4-Hydroxy-1-(3-phenylbutanoyl)piperidin-4-yl)methyl)-6-(pyridin-4-yl)pyrimidin-4(3H)-one
(R)-3-((4-Hydroxy-1-(3-phenylbutanoyl)piperidin-4-yl)methyl)-6-(1H-pyrazol-5-yl)pyrimidin-4(3H)-one
(R)-3-((4-Hydroxy-1-(3-phenylbutanoyl)piperidin-4-yl)methyl)-6-(phenylamino)pyrimidin-4(3H)-one
(R)-6-Amino-3-((4-hydroxy-1-(3-phenylbutanoyl)piperidin-4-yl)methyl)pyrimidin-4(3H)-one
(R)-6-((2-(Dimethylamino)ethyl)amino)-3-((4-hydroxy-1-(3-phenylbutanoyl)piperidin-4-yl)methyl)pyrimidin-4(3H)-one
(R)-6-((2-(Dimethylamino)ethyl)(methyl)amino)-3-((4-hydroxy-1-(3-phenylbutanoyl)piperidin-4-yl)methyl)pyrimidin-4(3H)-one
(R)-3-((4-Hydroxy-1-(3-phenylbutanoyl)piperidin-4-yl)methyl)-6-(4-methylpiperazin-1-yl)pyrimidin-4(3H)-one
(R)-3-((4-Hydroxy-1-(3-phenylbutanoyl)piperidin-4-yl)methyl)-6-methoxypyrimidin-4(3H)-one
(R)-6-(2-(Dimethylamino)ethoxy)-3-((4-hydroxy-1-(3-phenylbutanoyl)piperidin-4-yl)methyl)pyrimidin-4(3H)-one
(R)-3-((4-Hydroxy-1-(3-phenylbutanoyl)piperidin-4-yl)methyl)-6-((2-(pyrrolidin-1-yl)ethyl)amino)pyrimidin-4(3H)-one
6-((S)-3-Aminopyrrolidin-1-yl)-3-((4-hydroxy-1-((R)-3-phenylbutanoyl)piperidin-4-yl)methyl)pyrimidin-4(3H)-one
(R)-6-(3-Aminoazetidin-1-yl)-3-((4-hydroxy-1-(3-phenylbutanoyl)piperidin-4-yl)methyl)pyrimidin-4(3H)-one
(R)-5-Amino-6-chloro-3-((4-hydroxy-1-(3-phenylbutanoyl)piperidin-4-yl)methyl)pyrimidin-4(3H)-one
(R)-1-((4-Hydroxy-1-(3-phenylbutanoyl)piperidin-4-yl)methyl)-9-methyl-1H-purin-6(9H)-one
(R)-1-((4-Hydroxy-1-(3-phenylbutanoyl)piperidin-4-yl)methyl)-9-methyl-8-phenyl-1H-purin-6(9H)-one
(R)-1-((4-Hydroxy-1-(3-phenylbutanoyl)piperidin-4-yl)methyl)-9-phenyl-1H-purin-6(9H)-one
(R)-3-((4-Hydroxy-1-(3-phenylbutanoyl)piperidin-4-yl)methyl)-4H-pyrido[1,2-a]pyrimidin-4-one
(R)-3-((4-Hydroxy-1-(3-phenylbutanoyl)piperidin-4-yl)methyl)-9-phenyl-4H-pyrido[1,2-a]pyrimidin-4-one
(R)-6-((4-Hydroxy-1-(3-phenylbutanoyl)piperidin-4-yl)methyl)-2-methyl-2H-pyrazolo[4,3-d]pyrimidin-7(6H)-one
(R)-3-Bromo-6-((4-hydroxy-1-(3-phenylbutanoyl)piperidin-4-yl)methyl)-2-methyl-2H-pyrazolo[4,3-d]pyrimidin-7(6H)-one
(R)-3-Ethynyl-6-((4-hydroxy-1-(3-phenylbutanoyl)piperidin-4-yl)methyl)-2-methyl-2H-pyrazolo[4,3-d]pyrimidin-7(6H)-one
(R)-6-((4-Hydroxy-1-(3-phenylbutanoyl)piperidin-4-yl)methyl)-2-methyl-3-(trifluoromethyl)-2H-pyrazolo[4,3-d]pyrimidin-7(6H)-one
(R)-6-((4-Hydroxy-1-(3-phenylbutanoyl)piperidin-4-yl)methyl)-3-(3-hydroxy-3-methylbut-1-yn-1-yl)-2-methyl-2H-pyrazolo[4,3-d]pyrimidin-7(6H)-one
(R)-6-((4-Hydroxy-1-(3-phenylbutanoyl)piperidin-4-yl)methyl)-2-methyl-3-(1H-pyrazol-5-yl)-2H-pyrazolo[4,3-d]pyrimidin-7(6H)-one
(R)-6-((4-Hydroxy-1-(3-phenylbutanoyl)piperidin-4-yl)methyl)-2-methyl-3-(pyridin-4-yl)-2H-pyrazolo[4,3-d]pyrimidin-7(6H)-one
(R)-6-((4-Hydroxy-1-(3-phenylbutanoyl)piperidin-4-yl)methyl)-2-methyl-3-phenyl-2H-pyrazolo[4,3-d]pyrimidin-7(6H)-one
(R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzamide
(R)-3-(3-Aminophenyl)-6-((4-hydroxy-1-(3-phenylbutanoyl)piperidin-4-yl)methyl)-2-methyl-2H-pyrazolo[4,3-d]pyrimidin-7(6H)-one
(R)-3-(4-(Aminomethyl)phenyl)-6-((4-hydroxy-1-(3-phenylbutanoyl)piperidin-4-yl)methyl)-2-methyl-2H-pyrazolo[4,3-d]pyrimidin-7(6H)-one
(R)-6-((4-Hydroxy-1-(3-phenylbutanoyl)piperidin-4-yl)methyl)-3-(3-hydroxyprop-1-yn-1-yl)-2-methyl-2H-pyrazolo[4,3-d]pyrimidin-7(6H)-one
(R)-6-((4-Hydroxy-1-(3-phenylbutanoyl)piperidin-4-yl)methyl)-2-methyl-3-(prop-1-en-2-yl)-2H-pyrazolo[4,3-d]pyrimidin-7(6H)-one
(R)-6-((4-Hydroxy-1-(3-phenylbutanoyl)piperidin-4-yl)methyl)-3-isopropyl-2-methyl-2H-pyrazolo[4,3-d]pyrimidin-7(6H)-one
(R)-6-((4-Hydroxy-1-(3-phenylbutanoyl)piperidin-4-yl)methyl)-3-isopropyl-2-methyl-5,6-dihydro-2H-pyrazolo[4,3-d]pyrimidin-7(4H)-one
(R)-6-((1-(3,4-Dimethylpent-4-enoyl)-4-hydroxypiperidin-4-yl)methyl)-2-methyl-3-phenyl-2H-pyrazolo[4,3-d]pyrimidin-7(6H)-one
(R)-6-((4-Hydroxy-1-(4-methyl-3-(trifluoromethyl)pent-4-enoyl)piperidin-4-yl)methyl)-2-methyl-3-phenyl-2H-pyrazolo[4,3-d]pyrimidin-7(6H)-one (R)-6-((4-Hydroxy-1-(4,4,4-trifluoro-3-phenylbutanoyl)piperidin-4-yl)methyl)-2-methyl-3-phenyl-2H-pyrazolo[4,3-d]pyrimidin-7(6H)-one
6-((4-Hydroxy-1-(3-phenylpropanoyl)piperidin-4-yl)methyl)-2-methyl-2H-pyrazolo[4,3-d]pyrimidin-7(6H)-one
6-((4-Hydroxy-1-(3-phenylpropanoyl)piperidin-4-yl)methyl)-2-methyl-3-(trifluoromethyl)-2H-pyrazolo[4,3-d]pyrimidin-7(6H)-one
(R)-3-((4-Hydroxy-1-(3-phenylbutanoyl)piperidin-4-yl)methyl)-6-(1-methyl-1H-pyrazol-4-yl)pyrimidin-4(3H)-one
(R)-3-((4-Hydroxy-1-(3-phenylbutanoyl)piperidin-4-yl)methyl)-6-(1-isobutyl-1H-pyrazol-4-yl)pyrimidin-4(3H)-one
3-((4-Hydroxy-1-((R)-3-phenylbutanoyl)piperidin-4-yl)methyl)-6-((1,2,3,4-tetrahydro-1,4-epiminonaphthalen-6-yl)amino)pyrimidin-4(3H)-one
(R)-6-((4-Hydroxy-1-(3-phenylbutanoyl)piperidin-4-yl)methyl)methyl-3-(phenylamino)-2H-pyrazolo[4,3-d]pyrimidin-7(6H)-one
(R)-6-Chloro-3-((4-hydroxy-1-(3-phenylbutanoyl)piperidin-4-yl)methyl)-5-methylpyrimidin-4(3H)-one
(R)-5-Bromo-3-((4-hydroxy-1-(3-phenylbutanoyl)piperidin-4-yl)methyl)-6-((2-(pyrrolidin-1-yl)ethyl)amino)pyrimidin-4(3H)-one
(R)-3-(4-(Aminomethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one
6-((S)-3-Aminopiperidin-1-yl)-3-((4-hydroxy-1-((R)-3-phenylbutanoyl)piperidin-4-yl)methyl)pyrimidin-4(3H)-one
(R)-6-(4-Aminopiperidin-1-yl)-3-((4-hydroxy-1-(3-phenylbutanoyl)piperidin-4-yl)methyl)pyrimidin-4(3H)-one
(R)-3-((4-Hydroxy-1-(3-phenylbutanoyl)piperidin-4-yl)methyl)-6-(2,8-diazaspiro[4.5]decan-8-yl)pyrimidin-4(3H)-one
6-((S)-3-(Dimethylamino)piperidin-1-yl)-3-((4-hydroxy-1-((R)-3-phenylbutanoyl)piperidin-4-yl)methyl)pyrimidin-4(3H)-one
(R,E)-3-((4-Hydroxy-1-(3-phenylbutanoyl)piperidin-4-yl)methyl)-6-(3-(pyrrolidin-1-yl)prop-1-en-1-yl)pyrimidin-4(3H)-one
(R)-3-((4-Hydroxy-1-(3-phenylbutanoyl)piperidin-4-yl)methyl)-6-((2-(piperidin-1-yl)ethyl)amino)pyrimidin-4(3H)-one
(R,S)-3-(4-(Aminomethyl)phenyl)-6-((4-hydroxy-1-(4-methoxy-3-phenylbutanoyl)piperidin-4-yl)methyl)-2-methyl-2H-pyrazolo[4,3-d]pyrimidin-7(6H)-one
(R)-6-(1-(2-(Dimethylamino)ethyl)-1H-pyrazol-4-yl)-3-((4-hydroxy-1-(3-phenylbutanoyl)piperidin-4-yl)methyl)pyrimidin-4(3H)-one
6-((E)-3-((R)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one
6-((E)-3-((S)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one
3-((4-Hydroxy-1-((R)-3-phenylbutanoyl)piperidin-4-yl)methyl)-6-(((S)-1-phenyl-3-(pyrrolidin-1-yl)propan-2-yl)amino)pyrimidin-4(3H)-one
3-((4-Hydroxy-1-((R)-3-phenylbutanoyl)piperidin-4-yl)methyl)-6-(((R)-2-(pyrrolidin-1-yl)propyl)amino)pyrimidin-4(3H)-one
3-((4-Hydroxy-1-((R)-3-phenylbutanoyl)piperidin-4-yl)methyl)-6-(((S)-2-(pyrrolidin-1-yl)propyl)amino)pyrimidin-4(3H)-one
3-((4-Hydroxy-1-((R)-3-phenylbutanoyl)piperidin-4-yl)methyl)-6-(((R)-1-(pyrrolidin-1-yl)propan-2-yl)amino)pyrimidin-4(3H)-one
3-((4-Hydroxy-1-((R)-3-phenylbutanoyl)piperidin-4-yl)methyl)-6-(((S)-1-(pyrrolidin-1-yl)propan-2-yl)amino)pyrimidin-4(3H)-one
6-((S)-3-(Dimethylamino)pyrrolidin-1-yl)-3-((4-hydroxy-1-((R)-3-phenylbutanoyl)piperidin-4-yl)methyl)pyrimidin-4(3H)-one
rac-6-(((±-trans-1,2)-2-Aminocyclohexyl)amino)-3-((4-hydroxy-1-((R)-3-phenylbutanoyl)piperidin-4-yl)methyl)pyrimidin-4(3H)-one
6-(((±-cis-1,2)-2-Aminocyclohexyl)amino)-3-((4-hydroxy-1-((R)-3-phenylbutanoyl)piperidin-4-yl)methyl)pyrimidin-4(3H)-one
3-((4-Hydroxy-1-((R)-3-phenylbutanoyl)piperidin-4-yl)methyl)-6-((((R)-1-methylpyrrolidin-2-yl)methyl)amino)pyrimidin-4(3H)-one
3-((4-Hydroxy-1-((R)-3-phenylbutanoyl)piperidin-4-yl)methyl)-6-((((S)-1-methylpyrrolidin-2-yl)methyl)amino)pyrimidin-4(3H)-one
(R)-3-((4-Hydroxy-1-(3-phenylbutanoyl)piperidin-4-yl)methyl)pyrimidin-4(3H)-one
(R)-9-(4-(Aminomethyl)phenyl)-1-((4-hydroxy-1-(3-phenylbutanoyl)piperidin-4-yl)methyl)-1H-purin-6(9H)-one
3-((4-Hydroxy-1-((R)-3-phenylbutanoyl)piperidin-4-yl)methyl)-6-((2-((S)-2-methylpyrrolidin-1-yl)ethyl)amino)pyrimidin-4(3H)-one
3-((4-Hydroxy-1-((R)-3-phenylbutanoyl)piperidin-4-yl)methyl)-6-((2-((R)-2-(methoxymethyl)pyrrolidin-1-yl)ethyl)amino)pyrimidin-4(3H)-one
3-((4-Hydroxy-1-((R)-3-phenylbutanoyl)piperidin-4-yl)methyl)-6-((2-((S)-3-methylpyrrolidin-1-yl)ethyl)amino)pyrimidin-4(3H)-one
(R)-9-(4-(Aminomethyl)phenyl)-1-((4-hydroxy-1-(3-phenylbutanoyl)piperidin-4-yl)methyl)-8-methyl-1H-purin-6(9H)-one
6-((2-((R)-3-Fluoropyrrolidin-1-yl)ethyl)amino)-3-((4-hydroxy-1-((R)-3-phenylbutanoyl)piperidin-4-yl)methyl)pyrimidin-4(3H)-one
6-((2-((S)-3-Fluoropyrrolidin-1-yl)ethyl)amino)-3-((4-hydroxy-1-((R)-3-phenylbutanoyl)piperidin-4-yl)methyl)pyrimidin-4(3H)-one
3-(4-((R)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one
3-(4-((S)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one
(R)-9-(4-(Aminomethyl)phenyl)-1-((4-hydroxy-1-(4,4,4-trifluoro-3-phenylbutanoyl)piperidin-4-yl)methyl)-1H-purin-6(9H)-one
(R)-9-(4-(Aminomethyl)phenyl)-1-((4-hydroxy-1-(4,4,4-trifluoro-3-phenylbutanoyl)piperidin-4-yl)methyl)-8-methyl-1H-purin-6(9H)-one
(R)-3-(4-((Dimethylamino)methyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one
(R)-3-(4-(Aminomethyl)phenyl)-6-((1-(4,4-difluoro-3-phenylbutanoyl)-4-hydroxypiperidin-4-yl)methyl)-2-methyl-2H-pyrazolo[4,3-d]pyrimidin-7(6H)-one
(R)-3-((4-Hydroxy-1-(3-phenylbutanoyl)piperidin-4-yl)methyl)-6-isopropylpyrimidin-4(3H)-one (R)-3-(4-(Aminomethyl)-3-fluorophenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-6-((4-Hydroxy-1-(4,4,4-trifluoro-3-phenylbutanoyl)piperidin-4-yl)methyl)-2-methyl-3-(4-((methylamino)methyl)phenyl)-2H-pyrazolo[4,3-d]pyrimidin-7(6H)-one (R)-3-(4-(Aminomethyl)phenyl)-6-((1-(3-(3,5-difluorophenyl)-4,4,4-trifluorobutanoyl)-4-hydroxypiperidin-4-yl)methyl)-2-methyl-2H-pyrazolo[4,3-d]pyrimidin-7(6H)-one (R)-3-(4-(Aminomethyl)phenyl)-6-((4-hydroxy-1-(4,4,4-trifluoro-3-(4-fluorophenyl)butanoyl)piperidin-4-yl)methyl)-2-methyl-2H-pyrazolo[4,3-d]pyrimidin-7(6H)-one (R)-6-((2-(4-Fluoroisoindolin-2-yl)ethyl)amino)-3-((4-hydroxy-1-(3-phenylbutanoyl)piperidin-4-yl)methyl)pyrimidin-4(3H)-one (R)-3-(4-(2-Aminoethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-(4-(1-Aminocyclobutyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-((1-(4,4-Difluoro-3-phenylbutanoyl)-4-hydroxypiperidin-4-yl)methyl)-6-((2-(pyrrolidin-1-yl)ethyl)amino)pyrimidin-4(3H)-one 6-((4-Hydroxy-1-(3-phenylpropanoyl)piperidin-4-yl)methyl)-2-(methylthio)thiazolo[4,5-d]pyrimidin-7(6H)-one 3-((4-Hydroxy-1-(3-phenylpropanoyl)piperidin-4-yl)methyl)furo[3,2-d]pyrimidin-4(3H)-one 6-((4-Hydroxy-1-(3-phenylpropanoyl)piperidin-4-yl)methyl)-2-(methyethysulfonyl)thiazol[4,5-d]pyrimidin-7(6H)-one 6-((4-Hydroxy-1-(3-phenylpropanoyl)piperidin-4-yl)methyl)-2-(methylamino)thiazolo[4,5-d]pyrimidin-7(6H)-one 3-((4-Hydroxy-1-(3-phenylpropanoyl)piperidin-4-yl)methyl)furo[2,3-d]pyrimidin-4(3H)-one 6-((4-Hydroxy-1-(3-phenylpropanoyl)piperidin-4-yl)methyl)-2-methyl-3-(trifluoromethyl)-2H-pyrazolo[4,3-d]pyrimidin-7(6H)-one (R)-1-((4-Hydroxy-1-(3-phenylbutanoyl)piperidin-4-yl)methyl)-9-methyl-8-(trifluoromethyl)-1H-purin-6(9H)-one 3-(2-Fluorophenyl)-6-((4-hydroxy-1-((R)-3-phenylbutanoyl)piperidin-4-yl)methyl)-2-methyl-2H-pyrazolo[4,3-d]pyrimidin-7(6H)-one (R)-3-(6-((4-Hydroxy-1-(3-phenylbutanoyl)piperidin-4-yl)-2-methyl-7-oxo-6,7-dihydro-2H-pyrazolo[4,3-d]pyrimidin-3-yl)benzonitrile 3-(2-Aminophenyl)-6-((4-hydroxy-1-((R)-3-phenylbutanoyl)piperidin-4-yl)methyl)-2-methyl-2H-pyrazolo[4,3-d]pyrimidin-7(6H)-one (R)-3-((4-Hydroxy-1-(3-phenylbutanoyl)piperidin-4-yl)methyl)-6-morpholinopyrimidin-4(3H)-one 3-(Hydroxy(4-hydroxy-1-((R)-3-phenylbutanoyl)piperidin-4-yl)methyl)-4H-pyrido[1,2-a]pyrimidin-4-one (R)-1-((4-Hydroxy-1-(3-phenylbutanoyl)piperidin-4-yl)methyl)-[4,5'-bipyrimidin]-6(1H)-one (R)-3-((4-Hydroxy-1-(3-phenylbutanoyl)piperidin-4-yl)methyl)-6-((2-hydroxyethyl)amino)pyrimidin-4(3H)-one (R)-6-((4-Hydroxy-1-(3-phenylbutanoyl)piperidin-4-yl)methyl)-3-(3-hydroxyphenyl)methyl-2H-pyrazolo[4,3-d]pyrimidin-7(6H)-one 3-(Hydroxy(4-hydroxy-1-((R)-3-phenylbutanoyl)piperidin-4-yl)methyl)-9-phenyl-4H-pyrido[1,2-a]pyrimidin-4-one (R)-4-(6-((4-Hydroxy-1-(3-phenylbutanoyl)piperidin-4-yl)-2-methyl-7-oxo-6,7-dihydro-2H-pyrazolo[4,3-d]pyrimidin-3-yl)benzamide (R)-6-((4-Hydroxy-1-(3-phenylbutanoyl)piperidin-4-yl)methyl)-3-(4-(hydroxymethyl)phenyl)-2-methyl-2H-pyrazolo[4,3-d]pyrimidin-7(6H)-one (R)-6-((4-Hydroxy-1-(3-phenylbutanoyl)piperidin-4-yl)methyl)-2-methyl-3-(3-(morpholinomethyl)phenyl)-2H-pyrazolo[4,3-d]pyrimidin-7(6H)-one (R)-3-((4-Hydroxy-1-(3-phenylbutanoyl)piperidin-4-yl)methyl)-6-((2-methoxyethyl)amino)pyrimidin-4(3H)-one 3-((4-Hydroxy-1-((R)-3-phenylbutanoyl)piperidin-4-yl)methyl)-6-(((R)-pyrrolidin-3-yl)amino)pyrimidin-4(3H)-one (R)-3-((4-Hydroxy-1-(3-phenylbutanoyl)piperidin-4-yl)methyl)-5-methyl-6-((2-(pyrrolidin-1-yl)ethyl)amino)pyrimidin-4(3H)-one Benzyl 4-((3-(4-(aminomethyl)phenyl)-2-methyl-7-oxo-2,7-dihydro-6H-pyrazolo[4,3-d]pyrimidin-6-yl)methyl)-4-hydroxypiperidine-1-carboxylate (R)—N-(1-((4-Hydroxy-1-(3-phenylbutanoyl)piperidin-4-yl)methyl)-6-oxo-1,6-dihydropyrimidin-4-yl)-N-(2-(pyrrolidin-1-yl)ethyl)acetamide 3-((4-Hydroxy-1-((R)-3-phenylbutanoyl)piperidin-4-yl)methyl)-6-((2-((R)-2-methylpyrrolidin-1-yl)ethyl)amino)pyrimidin-4(3H)-one (R)-1-(4-Hydroxy-4-((5-phenylpyrazin-2-yl)methyl)piperidin-1-yl)-3-phenylbutan-1-one (R)-3-((4-Hydroxy-1-(3-phenylbutanoyl)piperidin-4-yl)methyl)-6-(phenylethynyl)pyrimidin-4(3H)-one (R)-6-Benzyl-3-((4-hydroxy-1-(3-phenylbutanoyl)piperidin-4-yl)methyl)pyrimidin-4(3H)-one 3-(4-((R)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one 3-(4-((S)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one (R)-3-(4-(Aminomethyl)phenyl)-2-ethyl-6-((4-hydroxy-1-(3-phenylbutanoyl)piperidin-4-yl)methyl)-2H-pyrazolo[4,3-d]pyrimidin-7(6H)-one (R)-3-((4-Hydroxy-1-(3-phenylbutanoyl)piperidin-4-yl)methyl)-6-(phenyl(2-(pyrrolidin-1-yl)ethyl)amino)pyrimidin-4(3H)-one 3-(4-((S)-1-Amino-2,2-difluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one (R)-3-(4-(Aminomethyl)-3-(trifluoromethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-(4-(1-Aminocyclopropyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (S)-3-(4-(Aminomethyl)phenyl)-6-((4-hydroxy-1-(4,4,4-trifluoro-3-(5-methylthiophen-2-yl)butanoyl)piperidin-4-yl)methyl)-2-methyl-2H-pyrazolo[4,3-d]pyrimidin-7(6H)-one (R)-1-((4-Hydroxy-1-(3-phenylbutanoyl)piperidin-4-yl)methyl)indolin-2-one 3-(4-(Aminomethyl)phenyl)-6-((1-(3,3-dicyclopropylpropanoyl)-4-hydroxypiperidin-4-yl)methyl)-2-methyl-2H-pyrazolo[4,3-d]pyrimidin-7(6H)-one (R)-1-((4-Hydroxy-1-(4,4,4-trifluoro-3-phenylbutanoyl)piperidin-4-yl)methyl)-9-phenyl-1H-purin-6(9H)-one (R)-1-((1-(4,4-Difluoro-3-phenylbutanoyl)-4-hydroxypiperidin-4-yl)methyl)-9-phenyl-1H-purin-6(9H)-one (R)-6-((4-Hydroxy-1-(4,4,4-trifluoro-3-phenylbutanoyl)piperidin-4-yl)methyl)-2-methyl-3-(1-methyl-1,2,3,6-tetrahydropyridin-4-yl)-2H-pyrazolo[4,3-d]pyrimidin-7(6H)-one 6-((1-Acetyl-4-hydroxypiperidin-4-yl)methyl)-2-methyl-3-phenyl-2H-pyrazolo[4,3-d]pyrimidin-7(6H)-one 3-((1-Acetyl-4-hydroxypiperidin-4-yl)methyl)-6-((2-(pyrrolidin-1-yl)ethyl)amino)pyrimidin-4(3H)-one 3-((1-(3,3-Dicyclopropylpropanoyl)-4-hydroxypiperidin-4-yl)methyl)-6-((2-(pyrrolidin-1-yl)ethyl)amino)pyrimidin-4(3H)-one (R)-3-(Cyclohex-1-en-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-(3-(Dimethylamino)prop-1-yn-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-Cyclohexyl-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-6-((4-Hydroxy-1-(4,4,4-trifluoro-3-phenylbutanoyl)piperidin-4-yl)methyl)-2-methyl-3-(4-(morpholinomethyl)phenyl)-2H-pyrazolo[4,3-d]pyrimidin-7(6H)-one 3-(4-(Aminomethyl)phenyl)-6-((1-(3-cyclobutylpropanoyl)-4-hydroxypiperidin-4-yl)methyl)-2-methyl-2H-pyrazolo[4,3-d]pyrimidin-7(6H)-one (R)-3-((4-Hydroxy-1-(3-phenylbutanoyl)piperidin-4-yl)methyl)-8-phenylpyrazolo[1,5-a][1,3,5]triazin-4(3H)-one 3-((4-hydroxy-1-((R)-3-phenylbutanoyl)piperidin-4-yl)methyl)-6-((R)-2-(hydroxymethyl)pyrrolidin-1-yl)pyrimidin-4(3H)-one (R)-3-((4-hydroxy-1-(3-phenylbutanoyl)piperidin-4-yl)-6-(3-(methoxymethyl)azetidin-1-yl)pyrimidin-4(3H)-one (R)-3-((4-hydroxy-1-(3-phenylbutanoyl)piperidin-4-yl)methyl)-6-((2-(isopropylamino)ethyl)amino)pyrimidin-4(3H)-one (R)—N-(2-((1-((4-hydroxy-1-(3-phenylbutanoyl)piperidin-4-yl)methyl)-6-oxo-1,6-dihydropyrimidin-4-yl)amino)ethyl)acetamide (R)-3-((4-hydroxy-1-(3-phenylbutanoyl)piperidin-4-yl)methyl)-6-(4-hydroxypiperidin-1-yl)pyrimidin-4(3H)-one (R)-3-((4-hydroxy-1-(3-phenylbutanoyl)piperidin-4-yl)methyl)-6-((2-((4-(trifluoromethyl)pyrimidin-2-yl)amino)ethyl)amino)pyrimidin-4(3H)-one (R)-3-((4-hydroxy-1-(3-phenylbutanoyl)piperidin-4-yl)methyl)-6-((2-(phenylamino)ethyl)amino)pyrimidin-4(3H)-one tert-butyl ((1-(1-((4-hydroxy-1-((R)-3-phenylbutanoyl)piperidin-4-yl)methyl)-6-oxo-1,6-dihydropyrimidin-4-yl)pyrrolidin-2-yl)methyl)carbamate 4-(1-((4-hydroxy-1-((R)-3-phenylbutanoyl)piperidin-4-yl)methyl)-6-oxo-1,6-dihydropyrimidin-4-yl)-N,N,2-trimethylmorpholine-2-carboxamide 3-((4-hydroxy-1-((R)-3-phenylbutanoyl)piperidin-4-yl)methyl)-6-(3-morpholinopyrrolidin-1-yl)pyrimidin-4(3H)-one 3-((4-hydroxy-1-((R)-3-phenylbutanoyl)piperidin-4-yl)methyl)-6-(3-hydroxy-3-methylpyrrolidin-1-yl)pyrimidin-4(3H)-one 3-((4-hydroxy-1-((R)-3-phenylbutanoyl)piperidin-4-yl)methyl)-6-((tetrahydrofuran-3-yl)amino)pyrimidin-4(3H)-one 3-((4-hydroxy-1-((R)-3-phenylbutanoyl)piperidin-4-yl)methyl)-6-(2-oxa-7-azaspiro[4.4]nonan-7-yl)pyrimidin-4(3H)-one 3-((4-hydroxy-1-((R)-3-phenylbutanoyl)piperidin-4-yl)methyl)-6-(tetrahydro-2H-furo[2,3-c]pyrrol-5(3H)-yl)pyrimidin-4(3H)-one (R)-3-((4-hydroxy-1-(3-phenylbutanoyl)piperidin-4-yl)methyl)-6-(((1-methyl-1H-pyrazol-5-yl)methyl)amino)pyrimidin-4(3H)-one (R)-3-((4-hydroxy-1-(3-phenylbutanoyl)piperidin-4-yl)methyl)-6-((3-methyloxetan-3-yl)amino)pyrimidin-4(3H)-one (R)-6-(4-(1H-pyrazol-5-yl)piperidin-1-yl)-3-((4-hydroxy-1-(3-phenylbutanoyl)piperidin-4-yl)methyl)pyrimidin-4(3H)-one (R)-6-((4-chlorobenzyl)amino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(4-(pyridin-3-ylmethyl)piperazin-1-yl)pyrimidin-4(3H)-one (R)-3-((4-hydroxy-1-(3-phenylbutanoyl)piperidin-4-yl)methyl)-6-(4-(pyridin-2-ylmethyl)piperazin-1-yl)pyrimidin-4(3H)-one (R)-6-(4,4-difluoropiperidin-1-yl)-3-((4-hydroxy-1-(3-phenylbutanoyl)piperidin-4-yl)methyl)pyrimidin-4(3H)-one (R)-2-((1-((4-hydroxy-1-(3-phenylbutanoyl)piperidin-4-yl)methyl)-6-oxo-1,6-dihydropyrimidin-4-yl)amino)-N,N-dimethylacetamide (R)-6-(((2,3-dihydrobenzo[b][1,4]dioxin-6-yl)methyl)amino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(((tetrahydro-2H-pyran-4-yl)methyl)amino)pyrimidin-4(3H)-one (R)—N-(cyclopropylmethyl)-1-(1-((4-hydroxy-1-(3-phenylbutanoyl)piperidin-4-yl)methyl)-6-oxo-1,6-dihydropyrimidin-4-yl)azetidine-3-carboxamide (R)-6-(3-fluoroazetidin-1-yl)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-((2-hydroxyethyl)(methyl)amino)pyrimidin-4(3H)-one (R)-6-(cyclopentylamino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(4-methyl-3-oxopiperazin-1-yl)pyrimidin-4(3H)-one (R)-3-((4-hydroxy-1-(3-phenylbutanoyl)piperidin-4-yl)methyl)-6-(5-oxa-2-azaspiro[3.4]octan-2-yl)pyrimidin-4(3H)-one (R)-6-((1,3-dimethyl-1H-pyrazol-4-yl)amino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(8-methyl-5-oxa-2,8-diazaspiro[3.5]nonan-2-yl)pyrimidin-4(3H)-one (R)-6-(6-acetyl-2,6-diazaspiro[3.3]heptan-2-yl)-3-((4-hydroxy-1-(3-phenylbutanoyl)piperidin-4-yl)methyl)pyrimidin-4(3H)-one (R)-6-(5,5-difluoro-2-azaspiro[3.3]heptan-2-yl)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(7-oxa-2-azaspiro[3.5]nonan-2-yl)pyrimidin-4(3H)-one (R)-3-((4-hydroxy-1-(3-phenylbutanoyl)piperidin-4-yl)methyl)-6-(2-oxa-7-azaspiro[3.5]nonan-7-yl)pyrimidin-4(3H)-one (R)-3-((4-hydroxy-1-(3-phenylbutanoyl)piperidin-4-yl)methyl)-6-(6-oxa-2-azaspiro[3.4]octan-2-yl)pyrimidin-4(3H)-one (R)-3-((4-hydroxy-1-(3-phenylbutanoyl)piperidin-4-yl)methyl)-6-((2-hydroxyethyl)(pyridin-3-ylmethyl)amino)pyrimidin-4(3H)-one (R)-3-((4-hydroxy-1-(3-phenylbutanoyl)piperidin-4-yl)methyl)-6-(5-methyl-2,5-diazaspiro[3.4]octan-2-yl)pyrimidin-4(3H)-one (R)-3-((4-hydroxy-1-(3-phenylbutanoyl)piperidin-4-yl)methyl)-6-(2-oxa-6-azaspiro[3.4]octan-6-yl)pyrimidin-4(3H)-one 3-((4-hydroxy-1-((R)-3-phenylbutanoyl)piperidin-4-yl)methyl)-6-((1R,5S)-3-methyl-3,6-diazabicyclo[3.2.1]octan-6-yl)pyrimidin-4(3H)-one 3-((4-hydroxy-1-((R)-3-phenylbutanoyl)piperidin-4-yl)methyl)-6-((1S,5R)-3-methyl-3,6-diazabicyclo[3.2.1]octan-6-yl)pyrimidin-4(3H)-one (R)-3-(4-(1-Aminocyclobutyl)phenyl)-6-((4-hydroxy-1-(3-phenylbutanoyl)piperidin-4-yl)methyl)-2-methyl-2H-pyrazolo[4,3-d]pyrimidin-7(6H)-one 3-((1-(3-Cyclobutylpropanoyl)-4-hydroxypiperidin-4-yl)methyl)-6-((2-(pyrrolidin-1-yl)ethyl)amino)pyrimidin-4(3H)-one 3-((1-(2,2-Dicyclobutylacetyl)-4-hydroxypiperidin-4-yl)methyl)-6-((2-(pyrrolidin-1-yl)ethyl)amino)pyrimidin-4(3H)-one (R)-6-((4-Hydroxy-1-(3-phenylbutanoyl)piperidin-4-yl)methyl)-3-phenyl-3H-[1,2,3]triazolo[4,5-d]pyrimidin-7(6H)-one 6-((1-(3-Cyclobutylpropanoyl)-4-hydroxypiperidin-4-yl)methyl)-3-phenyl-3H-[1,2,3]triazolo[4,5-d]pyrimidin-7(6H)-one 6-((1-(3,3-Dicyclopropylpropanoyl)-4-hydroxypiperidin-4-yl)methyl)-3-phenyl-3H-[1,2,3]triazolo[4,5-d]pyrimidin-7(6H)-one (R)-1-((4-Hydroxy-1-(3-phenylbutanoyl)piperidin-4-yl)methyl)-8-methyl-9-phenyl-1H-purin-6(9H)-one (R)-1-((4-Hydroxy-1-(4,4,4-trifluoro-3-phenylbutanoyl)piperidin-4-yl)methyl)-8-methyl-9-phenyl-1H-purin-6(9H)-one 1-((1-(3,3-Dicyclopropylpropanoyl)-4-hydroxypiperidin-4-yl)methyl)-8-methyl-9-phenyl-1H-purin-6(9H)-one 6-((4-Hydroxy-1-(1-methylcyclopropanecarbonyl)piperidin-4-yl)methyl)-2-methyl-3-phenyl-2H-pyrazolo[4,3-d]pyrimidin-7(6H)-one 6-((4-Hydroxy-1-(oxazole-5-carbonyl)piperidin-4-yl)methyl)-2-methyl-3-phenyl-2H-pyrazolo[4,3-d]pyrimidin-7(6H)-one 6-((1-(3,3-Dicyclopropylpropanoyl)-4-hydroxypiperidin-4-yl)methyl)-2-methyl-3-phenyl-2H-pyrazolo[4,3-d]pyrimidin-7(6H)-one (R)-Ethyl 4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzylcarbamate 1-((1-(2-Cyclopropyloxazole-5-carbonyl)-4-hydroxypiperidin-4-yl)methyl)-8-methyl-9-phenyl-1H-purin-6(9H)-one 6-((1-(2-Cyclopropyloxazole-5-carbonyl)-4-hydroxypiperidin-4-yl)methyl)-2-methyl-3-phenyl-2H-pyrazolo[4,3-d]pyrimidin-7(6H)-one 6-((4-Hydroxy-1-(1-methylcyclopropanecarbonyl)piperidin-4-yl)methyl)-3-phenyl-3H-[1,2,3]triazolo[4,5-d]pyrimidin-7(6H)-one 6-((1-(2-Cyclopropyloxazole-5-carbonyl)-4-hydroxypiperidin-4-yl)methyl)-3-phenyl-3H-[1,2,3]triazolo[4,5-d]pyrimidin-7(6H)-one 7-Cyclopropyl-3-((4-hydroxy-1-(3-phenylpropanoyl)piperidin-4-yl)methyl)thieno[3,2-d]pyrimidin-4(3H)-one 6-Chloro-3-((4-hydroxy-1-(1-methylcyclopropanecarbonyl)piperidin-4-yl)methyl)-7-phenyl-3H-pyrrolo[2,3-d]pyrimidin-4(7H)-one 7-(Benzo[d][1,3]dioxol-5-yl)-6-chloro-3-((4-hydroxy-1-(1-methylcyclopropanecarbonyl)piperidin-4-yl)methyl)-3H-pyrrolo[2,3-d]pyrimidin-4(7H)-one 6-Chloro-7-(4-chlorophenyl)-3-((4-hydroxy-1-(1-methylcyclopropanecarbonyl)piperidin-4-yl)methyl)-3H-pyrrolo[2,3-d]pyrimidin-4(7H)-one 6-Chloro-7-(4-fluorophenyl)-3-((4-hydroxy-1-(1-methylcyclopropanecarbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-fluorophenyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-fluoro-3-methoxyphenyl)-3H-pyrrolo[2,3-d]pyrimidin-4(7H)-one 6-Chloro-7-(4-fluoro-3-methoxyphenyl)-3-((4-hydroxy-1-(1-methylcyclopropanecarbonyl)piperidin-4-yl)methyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-(1-methyl-1H-pyrazol-5-yl)phenyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-methyl-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(3-(1-methyl-1H-pyrazol-5-yl)phenyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(3-(1-methyl-1H-pyrazol-4-yl)phenyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-(1-methyl-1H-pyrazol-4-yl)phenyl)-3H-pyrrolo[2,3-d]pyrimidin-4(7H)-one 7-(3-Bromophenyl)-6-chloro-3-((1-(2-cyclopropyloxazole-5-carbonyl)-4-hydroxypiperidin-4-yl)methyl)-3H-pyrrolo[2,3-d]pyrimidin-4(7H)-one 7-(3-Bromophenyl)-6-chloro-3-((4-hydroxy-1-(1-methylcyclopropanecarbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-phenyl-3H-pyrrolo[2,3-d]pyrimidin-4(7H)-one 6-Chloro-3-((4-hydroxy-1-(1-methyl-1H-pyrazole-4-carbonyl)piperidin-4-yl)methyl)-7-phenyl-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(3-cyclopropylphenyl)-3H-pyrrolo[2,3-d]pyrimidin-4(7H)-one 6-Chloro-7-(3-cyclopropylphenyl)-3-((4-hydroxy-1-(1-methylcyclopropanecarbonyl)piperidin-4-yl)methyl)-3H-pyrrolo[2,3-d]pyrimidin-4(7H)-one 6-Chloro-7-(3-cyclopropylphenyl)-3-((4-hydroxy-1-(1-methyl-1H-pyrazole-4-carbonyl)piperidin-4-yl)methyl)-3H-pyrrolo[2,3-d]pyrimidin-4(7H)-one 6-Chloro-7-(4-cyclopropylphenyl)-3-((4-hydroxy-1-(1-methylcyclopropanecarbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-cyclopropylphenyl)-3H-pyrrolo[2,3-d]pyrimidin-4(7H)-one 6-Bromo-3-((1-(2-cyclopropyloxazole-5-carbonyl)-4-hydroxypiperidin-4-yl)methyl)-7-phenyl-3H-pyrrolo[2,3-d]pyrimidin-4(7H)-one 6-Bromo-3-((4-hydroxy-1-(1-methylcyclopropanecarbonyl)piperidin-4-yl)methyl)-7-phenyl-3H-pyrrolo[2,3-d]pyrimidin-4(7H)-one 3-((1-(2-Cyclopropyloxazole-5-carbonyl)-4-hydroxypiperidin-4-yl)methyl)-6-iodo-7-phenyl-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-(4-(trifluoromethyl)-1H-pyrazol-1-yl)phenyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-morpholinophenyl)-3H-pyrrolo[2,3-d]pyrimidin-4(7H)-one 6-Chloro-7-(3-(4-fluoro-1H-pyrazol-1-yl)phenyl)-3-((4-hydroxy-1-(1-methylcyclopropanecarbonyl)piperidin-4-yl)methyl)-3H-pyrrolo[2,3-d]pyrimidin-4(7H)-one 6-Chloro-7-(4-chlorophenyl)-3-((1-(2-cyclopropyloxazole-5-carbonyl)-4-hydroxypiperidin-4-yl)methyl)-3H-pyrrolo[2,3-d]pyrimidin-4(7H)-one 6-Chloro-7-(4-chlorophenyl)-3-((4-hydroxy-1-(1-methyl-1H-pyrazole-4-carbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-fluoro-3-(1-methyl-1H-pyrazol-5-yl)phenyl)-3H-pyrrolo[2,3-d]pyrimidin-4(7H)-one 3-((4-Hydroxy-1-(1-methylcyclopropanecarbonyl)piperidin-4-yl)methyl)-4-oxo-7-phenyl-4,7-dihydro-3H-pyrrolo[2,3-d]pyrimidine-6-carbonitrile, 7-(Benzo[d][1,3]dioxol-5-yl-2,2-d$_2$)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one 7-(Benzo[d][1,3]dioxol-5-yl-2,2-d$_2$)-6-chloro-3-((1-(2-cyclopropyloxazole-5-carbonyl)-4-hydroxypiperidin-4-yl)methyl)-3,7-dihydro-4H-pyrrolo[2,3-d]pyrimidin-4-one 3-(4-(Aminomethyl)phenyl)-6-((4-hydroxy-1-(1-methylcyclopropane-1-carbonyl)piperidin-4-yl)methyl)-2-methyl-2,6-dihydro-7H-pyrazolo[4,3-d]pyrimidin-7-one 3-(4-(Aminomethyl)phenyl)-6-((1-(2-cyclopropyloxazole-5-carbonyl)-4-hydroxypiperidin-4-yl)methyl)-2-methyl-2,6-dihydro-7H-pyrazolo[4,3-d]pyrimidin-7-one 6-Chloro-7-(3,4-dimethoxyphenyl)-3-((4-hydroxy-1-(1-methylcyclopropane-1-carbonyl)piperidin-4-yl)methyl)-3,7-dihydro-4H-pyrrolo[2,3-d]pyrimidin-4-one 6-Chloro-3-((1-(2-cyclopropyloxazole-5-carbonyl)-4-hydroxypiperidin-4-yl)methyl)-7-(3,4-dimethoxyphenyl)-3,7-dihydro-4H-pyrrolo[2,3-d]pyrimidin-4-one 7-(4-(Aminomethyl)phenyl)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one 7-(4-(Aminomethyl)phenyl)-6-chloro-3-((1-(2-cyclopropyloxazole-5-carbonyl)-4-hydroxypiperidin-4-yl)methyl)-3,7-dihydro-4H-pyrrolo[2,3-d]pyrimidin-4-one (R)-4-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic acid (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic acid 4-(6-((4-Hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzoic acid or a pharmaceutically acceptable salt, tautomer, isomer, or N-oxide derivative thereof.

In certain embodiments, compounds of the present invention have an $IC_{50}$ value for USP7 of about 1 nM to about 10,000 nM, more preferably from about 1 nM to about 1000 nM, or from about 100 nM to about 1000 nM, or from about 100 nM to about 500 nM, or from about 100 nM to about 300 nM, or from about 100 nM to about 250 nM. In certain preferred embodiments, the compounds of the invention have an $IC_{50}$ value for USP7 of less than 500 nM, most preferably less than 250 nM. A method for determining the $IC_{50}$ value of a compound for USP7 is described below (see examples).

In certain embodiments, there is provided the compound of formula (I) and at least one pharmaceutically acceptable excipient.

In a second aspect the present invention provides a pharmaceutical composition comprising a compound according to any embodiment of the first aspect and at least one pharmaceutically acceptable excipient.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

Suitable pharmaceutically acceptable excipients would be known by the person skilled in the art, for example: fats, water, physiological saline, alcohol (e.g. ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds of the present invention may be admixed with pharmaceutically inert, inorganic or organic excipients. Examples of suitable excipients include lactose, mize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose.

For injectable solutions, excipients include, for example, water, alcohols, polyols, glycerine and vegetable oil.

For suppositories and for local and percutaneous application, excipients include, for example, natural or hardened oils, waxes, fats and semi-solid or liquid polyols.

The pharmaceutical compositions may also contain preserving agents, solubilizing agents, stabilizing agents, wetting agents, emulsifiers, sweeteners, colorants, odorants, buffers, coating agents and/or antioxidants.

For combination therapies, the second drug may be provided in pharmaceutical composition with the present invention or may be provided separately.

Thus, a pharmaceutical formulation for oral administration may, for example, be granule, tablet, sugar-coated tablet, capsule, pill, suspension or emulsion. For parenteral injection for, for example, intravenous, intramuscular or subcutaneous use, a sterile aqueous solution may be provided that may contain other substances including, for example, salts and/or glucose to make the solution isotonic. The anti-cancer agent may also be administered in the form of a suppository or pessary, or may be applied topically in the form of a lotion, solution, cream, ointment or dusting powder.

In a third aspect the invention provides a compound or composition according to any embodiment of the first aspect or second aspect for use in therapy, preferably in the treatment and/or prevention of cancer. Cancers or neoplastic conditions suitable to be treated with the compounds or compositions according to the invention include, for example: prostate cancer, colon cancer, breast cancer, lung cancer, kidney cancer, CNS cancers (e.g. neuroblastomas, glioblastomas), osteosarcoma, haematological malignancies (e.g. leukemia, multiple myeloma and mantle cell lymphoma). In certain preferred embodiments the cancer is associated with p53 dysregulation. In certain preferred embodiments, the cancer is selected from a haematological malignancy (e.g. mantle cell lymphoma, multiple myeloma), prostate cancer, a neuroblastoma, or a glioblastoma.

The compound or composition of the invention may be used in monotherapy and/or a combination modality. Suitable agents to be used in such combination modalities with compounds or compositions according to the invention include one or more of anti-cancer agents, anti-inflammatory agents, immuno-modulatory agents, immuno-suppressive agents, neurological agents, anti-diabetic agents, anti-viral agents, anti-bacterial agents and/or radiation therapy.

Agents used in combination with the compounds of the present invention may target the same or a similar biological pathway to that targeted by the compounds of the present invention or may act on a different or unrelated pathway.

Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including *vinca* alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

In a fourth aspect the invention provides a method of treating or preventing cancer comprising administering to a subject a compound according to any embodiment of the first aspect of the invention or a composition according to any embodiment of the second aspect of the invention. Cancers or neoplastic conditions suitable to be treated or prevented according to these methods include, for example, prostate cancer, colon cancer, breast cancer, lung cancer, kidney cancer, CNS cancers (e.g. neuroblastomas, glioblastomas), osteosarcoma, haematological malignancies (e.g. leukemia, multiple myeloma and mantle cell lymphoma). In certain preferred embodiments the cancer is associated with p53 dysregulation. In certain preferred embodiments, the cancer is selected from a haematological malignancy (e.g. mantle cell lymphoma, multiple myeloma), prostate cancer, a neuroblastoma, or a glioblastoma.

As part of a method according to the fourth aspect, the compound or composition may be used in monotherapy and/or a combination modality. Suitable agents to be used in such combination modalities with compounds or compositions according to the invention include one or more of anti-cancer agents, anti-inflammatory agents, immuno-modulatory agents, immuno-suppressive agents, neurological agents, anti-diabetic agents, anti-viral agents, anti-bacterial agents and/or radiation therapy.

Agents used in combination with the compounds of the present invention may target the same or a similar biological pathway to that targeted by the compounds of the present invention or may act on a different or unrelated pathway.

Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including *vinca* alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

In a fifth aspect the invention provides a use of a compound according to any embodiment of the first aspect in the manufacture of a medicament for treating or preventing cancer. Cancers or neoplastic conditions suitable to be treated or prevented by such a medicament include, for example, prostate cancer, colon cancer, breast cancer, lung cancer, kidney cancer, CNS cancers (e.g. neuroblastomas, glioblastomas), osteosarcoma, haematological malignancies (e.g. leukemia, multiple myeloma and mantle cell lymphoma). In certain preferred embodiments the cancer is associated with p53 dysregulation. In certain preferred embodiments, the cancer is selected from a haematological malignancy (e.g. mantle cell lymphoma, multiple myeloma), prostate cancer, a neuroblastoma, or a glioblastoma.

In regard to aspects of the invention relating to therapeutic use of compounds according to the invention, the compounds may be administered to the subject in need of treatment in an "effective amount". The term "effective amount" refers to the amount or dose of a compound which, upon single or multiple dose administration to a subject, provides therapeutic efficacy in the treatment of disease. Therapeutically effective amounts of a compound according to the invention can comprise an amount in the range of from about 0.1 mg/kg to about 20 mg/kg per single dose. A therapeutic effective amount for any individual patient can be determined by the healthcare professional by methods understood by the skilled person. The amount of compound administered at any given time point may be varied so that optimal amounts of the compound, whether employed alone or in combination with any other therapeutic agent, are administered during the course of treatment. It is also contemplated to administer compounds according to the invention, or pharmaceutical compositions comprising such compounds, in combination with any other cancer treatment, as a combination therapy.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

The present invention will now be described in relation to several examples. The Examples indicated below were synthesised according to the methods described subsequently. $IC_{50}$ values were determined as described below and are represented in the following table.

TABLE 4

USP7 inhibition in the biochemical assay by exemplified compounds.

| Example Number | USP7 $IC_{50}$ |
|---|---|
| 1 | * |
| 2 | * |
| 3 | ** |
| 4 | * |
| 5 | * |
| 6 | *** |
| 7 | ** |
| 8 | * |
| 9 | * |
| 10 | * |
| 11 | *** |
| 12 | *** |
| 13 | ** |
| 14 | * |
| 15 | * |
| 16 | * |
| 17 | *** |
| 18 | * |
| 19 | * |
| 20 | * |
| 21 | ** |
| 22 | *** |
| 23 | ** |
| 24 | * |
| 25 | *** |
| 26 | ** |
| 27 | *** |
| 28 | *** |
| 29 | *** |
| 30 | *** |
| 31 | *** |
| 32 | ** |
| 33 | ** |
| 34 | * |
| 35 | ** |
| 36 | * |
| 37 | ** |
| 38 | * |
| 39 | * |
| 40 | ** |
| 41 | ** |
| 42 | ** |
| 43 | * |
| 44 | * |
| 45 | * |
| 46 | *** |
| 47 | ** |
| 48 | ** |
| 49 | ** |
| 50 | *** |
| 51 | * |
| 52 | *** |
| 53 | *** |
| 54 | ** |
| 55 | * |
| 56 | * |
| 57 | * |
| 58 | *** |
| 59 | *** |
| 60 | *** |
| 61 | ** |
| 62 | ** |
| 63 | ** |
| 64 | ** |
| 65 | ** |
| 66 | * |
| 67 | * |
| 68 | *** |
| 69 | *** |
| 70 | * |
| 71 | *** |
| 72 | *** |
| 73 | ** |
| 74 | ** |

TABLE 4-continued

USP7 inhibition in the biochemical assay by exemplified compounds.

| Example Number | USP7 IC$_{50}$ |
|---|---|
| 75 | *** |
| 76 | *** |
| 77 | *** |
| 78 | *** |
| 79 | *** |
| 80 | *** |
| 81 | * |
| 82 | *** |
| 83 | *** |
| 84 | * |
| 85 | *** |
| 86 | ** |
| 87 | *** |
| 88 | *** |
| 89 | ** |
| 90 | * |
| 91 | * |
| 92 | * |
| 93 | * |
| 94 | * |
| 95 | * |
| 96 | * |
| 97 | *** |
| 98 | *** |
| 99 | * |
| 100 | * |
| 101 | * |
| 102 | * |
| 103 | * |
| 104 | *** |
| 105 | * |
| 106 | *** |
| 107 | *** |
| 108 | ** |
| 109 | * |
| 110 | ** |
| 111 | * |
| 112 | * |
| 113 | * |
| 114 | *** |
| 115 | * |
| 116 | * |
| 117 | * |
| 118 | ** |
| 119 | *** |
| 120 | *** |
| 121 | * |
| 122 | *** |
| 123 | *** |
| 124 | *** |
| 125 | ** |
| 126 | * |
| 127 | *** |
| 128 | ** |
| 129 | *** |
| 130 | * |
| 131 | * |
| 132 | * |
| 133 | ** |
| 134 | *** |
| 135 | * |
| 136 | ** |
| 137 | *** |
| 138 | ** |
| 139 | *** |
| 140 | * |
| 141 | * |
| 142 | ** |
| 143 | * |
| 144 | * |
| 145 | * |
| 146 | * |
| 147 | * |
| 148 | * |
| 149 | * |
| 150 | * |
| 151 | * |
| 152 | * |
| 153 | * |
| 154 | * |
| 155 | * |
| 156 | * |
| 157 | * |
| 158 | * |
| 159 | * |
| 160 | * |
| 161 | * |
| 162 | * |
| 163 | * |
| 164 | * |
| 165 | * |
| 166 | * |
| 167 | ** |
| 168 | * |
| 169 | * |
| 170 | * |
| 171 | * |
| 172 | ** |
| 173 | * |
| 174 | ** |
| 175 | * |
| 176 | ** |
| 177 | * |
| 178 | ** |
| 179 | ** |
| 180 | *** |
| 181 | ** |
| 182 | *** |
| 183 | * |
| 184 | * |
| 185 | *** |
| 186 | * |
| 187 | ** |
| 188 | *** |
| 189 | ** |
| 190 | * |
| 191 | * |
| 192 | * |
| 193 | ** |
| 194 | *** |
| 195 | * |
| 196 | * |
| 197 | * |
| 198 | * |
| 199 | * |
| 200 | ** |
| 201 | *** |
| 202 | ** |
| 203 | *** |
| 204 | *** |
| 205 | *** |
| 206 | *** |
| 207 | ** |
| 208 | ** |
| 209 | * |
| 210 | ** |
| 211 | *** |
| 212 | *** |
| 213 | *** |
| 214 | ** |
| 215 | *** |
| 216 | ** |
| 217 | *** |
| 218 | *** |
| 219 | *** |
| 220 | *** |
| 221 | *** |
| 222 | *** |

TABLE 4-continued

USP7 inhibition in the biochemical assay by exemplified compounds.

| Example Number | USP7 IC$_{50}$ |
|---|---|
| 223 | *** |
| 224 | *** |
| 225 | * |
| 226 | *** |
| 227 | *** |
| 228 | *** |
| 229 | ** |
| 230 | ** |
| 231 | ** |
| 232 | *** |
| 233 | *** |
| 234 | *** |
| 235 | *** |
| 236 | *** |
| 237 | * |
| 238 | ** |
| 239 | *** |
| 240 | *** |
| 241 | *** |
| 242 | *** |
| 243 | * |
| 244 | * |
| 245 | * |

For representative examples in Table 4, USP7 inhibitory activities are classified as the following:

| | *** | ** | * |
|---|---|---|---|
| USP7 IC$_{50}$ [nM] | <250 | 250-999 | 1000-200000 |

Experimental Section

Abbreviations and Acronyms

Ac$_2$O: acetic anhydride; AcOH: acetic acid; aq: aqueous; dba: dibenzylideneacetone; Boc: tert-butyloxycarbonyl; DCM: dichloromethane; br: broad; d: doublet; DIPEA: diisopropylethylamine; DMAP: 4-(dimethylamino)pyridine; DME: dimethoxyethane; DMF: N,N-dimethylformamide; DMSO: dimethylsulfoxide; dppf: 1,1'-bis(diphenylphosphino)ferrocene; EDC: N-(3-dimethylaminopropyl)-N'-ethylcarbodiimide hydrochloride; equiv.: equivalents; EtOAc: ethyl acetate; EtOH: ethyl alcohol; ESI: electrospray ionisation; h: hour; HATU: N-[(dimethylamino)-1H-1,2,3-triazolo-[4,5-b]pyridin-1-ylmethylene]-N-methylmethanaminium hexafluorophosphate N-oxide; HPLC: high pressure liquid chromatography; IPA: isopropyl alcohol; LC: liquid chromatography; LCMS: liquid chromatography mass spectrometry; LDA: lithium diisopropylamide; M: molar; m/z: mass-to-charge ratio; mCPBA: 3-chloroperbenzoic acid; MeCN: acetonitrile; MeOH: methanol; min: minutes; Ms: methylsulfonyl; MS: mass spectrometry; m: multiplet (spectral); NBS: N-bromosuccinimide; NMO: N-morpholine oxide; NMP: N-methyl-2-pyrrolidone; NMR: nuclear magnetic resonance; OAc: acetate; PE: petroleum ether (40-60° C.); q: quartet; quint: quintet; R$_T$: retention time; RT: room temperature; RuPhos: 2-dicyclohexylphosphino-2',6'-diisopropoxybiphenyl; s: singlet; SEM: 2-trimethylsilylethoxymethyl; SM: starting material; sxt: sextet; t: triplet; tert-Butyl X-Phos: 2-di-tert-butylphosphino-2',4',6'-triisopropylbiphenyl; TFA: trifluoroacetic acid; THF: tetrahydrofuran; Ts: p-toluenesulfonyl; v/v: volume per unit volume; Walphos SL-W008-2:(S)-1-{(S$_p$)-2-[2-(dicyclohexylphosphino)phenyl]ferrocenyl}ethylbis[3,5-bis(trifluoromethyl)phenyl]phosphine; Xantphos: 4,5-bis(diphenylphosphino)-9,9-dimethylxanthene.

General Experimental Conditions

Solvents and Reagents

Common organic solvents that were used in reactions (e.g. THF, DMF, DCM, and methanol) were purchased anhydrous from Sigma-Aldrich® in Sure/Seal™ bottles and were handled appropriately under nitrogen. Water was deionised using an Elga PURELAB Option-Q. All other solvents used (i.e. for work-up procedures and purification) were generally HPLC grade and were used as supplied from various commercial sources. Unless otherwise stated, all starting materials used were purchased from commercial suppliers and used as supplied.

Microwave Synthesis

Microwave experiments were carried out using a Biotage Initiator™ Eight system, unless otherwise stated for cases in which a CEM Discover™/Explorer24™ system controlled by Synergy 1.5 software was used. Both machines give good reproducibility and control at temperature ranges from 60-250° C. and pressures of up to a maximum of 20 bar.

Flash Chromatography

Purification of compounds by flash chromatography was achieved using a Biotage Isolera Four system. Unless otherwise stated, Biotage KP-Sil SNAP cartridge columns (10-340 g) were used along with the stated solvent system and an appropriate solvent gradient depending on compound polarity. In the case of more polar and basic compounds, Biotage KP-NH SNAP cartridge columns (11 g) were used.

NMR Spectroscopy $^1$H NMR spectra were recorded at ambient temperature using a Bruker Avance (300 MHz), Bruker Avance III (400 MHz) or Bruker Ascend (500 MHz) spectrometer. All chemical shifts (δ) are expressed in ppm. Residual solvent signals were used as an internal standard and the characteristic solvent peaks were corrected to the reference data outlined in *J. Org. Chem.*, 1997, 62, p 7512-7515; in other cases, NMR solvents contained tetramethylsilane, which was used as an internal standard.

Liquid Chromatography Mass Spectrometry (LCMS)

Liquid Chromatography Mass Spectrometry (LCMS) experiments to determine retention times (R$_T$) and associated mass ions were performed using the following method:

Method A:

The system consisted of an Agilent Technologies 6130 quadrupole mass spectrometer linked to an Agilent Technologies 1290 Infinity LC system with UV diode array detector and autosampler. The spectrometer consisted of an electrospray ionization source operating in positive and negative ion mode. LCMS experiments were performed on each sample submitted using the following conditions: LC Column: Agilent Eclipse Plus C18 RRHD, 1.8 μm, 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 0.5 | 80 | 20 |
| 1.80 | 0.5 | 0 | 100 |
| 2.20 | 0.5 | 0 | 100 |

| Gradient Time (min) | Flow (mL/min) | % A | % B |
|---|---|---|---|
| 2.50 | 0.5 | 80 | 20 |
| 3.00 | 0.5 | 80 | 20 |

Method B:

The system consisted of an Agilent Technologies 6140 single quadrupole mass spectrometer linked to an Agilent Technologies 1290 Infinity LC system with UV diode array detector and autosampler. The spectrometer consisted of a multimode ionization source (electrospray and atmospheric pressure chemical ionizations) operating in positive and negative ion mode. LCMS experiments were performed on each sample submitted using the following conditions: LC Column: Zorbax Eclipse Plus C18 RRHD, 1.8 μm, 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Method C:

The system consisted of Agilent Technologies 6140 single quadrupole mass spectrometer linked to an Agilent Technologies 1290 Infinity LC system with UV diode array detector and autosampler. The spectrometer consisted of a multimode ionization source (electrospray and atmospheric pressure chemical ionizations) operating in positive and negative ion mode. LCMS experiments were performed on each sample submitted using the following conditions: LC Column: Phenomenex XB-C18, 1.7 μm, 50 mm×2.1 mm maintained at 40° C. The standardized gradient was 2-98% HPLC grade acetonitrile with 0.1% formic acid (solvent B) in HPLC grade water with 0.1% formic acid (solvent A) over 7 min, and hold at 98% B for 1.5 min following equilibration for 1.5 min.

Preparative High Pressure Liquid Chromatography

Method A:

This system consisted of an Agilent Technologies 6120 single quadrupole mass spectrometer linked to an Agilent Technologies 1200 Preparative LC system with multiple wavelength detector and autosampler. The mass spectrometer used a multimode ionization source (electrospray and atmospheric pressure chemical ionizations) operating in positive and negative ion mode. Fraction collection was mass-triggered (multimode positive and negative ion). Purification experiments, unless otherwise stated, were performed under basic conditions at an appropriate solvent gradient that was typically determined by the retention time found using the LCMS method. In cases where the basic conditions were unsuccessful, acidic conditions were employed.

Basic Conditions:

LC Column: Waters XBridge™ Prep C18 5 μm OBD™ 19×50 mm column at RT. Mobile phase: A) 0.1% (v/v) ammonium hydroxide in water; B) 0.1% (v/v) ammonium hydroxide in 95:5, acetonitrile/water. Total experiment time was ca. 10 min and an example method is given:

| Gradient Time (min) | Flow (mL/min) | % A | % B |
|---|---|---|---|
| 0.00 | 20.0 | 50 | 50 |
| 3.00 | 20.0 | 12 | 88 |
| 5.00 | 20.0 | 12 | 88 |
| 7.00 | 20.0 | 0 | 100 |
| 8.0 | 20.0 | 0 | 100 |
| 8.20 | 20.0 | 50 | 50 |

Acidic Conditions:

LC Column: Waters XBridge™ Prep C18 5 μm OBD™ 19×50 mm column at RT. Mobile phase: A) Water 0.1% (v/v) formic acid in water; B) 0.1% (v/v) formic acid in 95:5, acetonitrile/water. Total experiment time was ca. 10 min and an example method is given:

| Gradient Time (min) | Flow (mL/min) | % A | % B |
|---|---|---|---|
| 0.00 | 20.0 | 95 | 5 |
| 7.00 | 20.0 | 0 | 100 |
| 9.00 | 20.0 | 0 | 100 |
| 9.20 | 20.0 | 95 | 5 |

Method B:

This system consisted of a Waters Autopurification HPLC/MS, with a Gemini NX-C18 column from Phenomenex, 5 μm, 50 mm×30 mm i.d., running at a flow rate of 60 mL/min, 25° C. with UV diode array detection (210-400 nm) and mass-directed collection. A typical gradient was 5-50% HPLC grade acetonitrile (mobile phase B) in HPLC grade water+0.1% (v/v) ammonia solution (mobile phase A) over 10 min, or modified as necessary. The mass spectrometer used was a Waters Micromass ZQ2000 spectrometer, operating in positive or negative ion electrospray ionisation modes, with a molecular weight scan range of 150 to 1000.

The pure fractions were combined and concentrated using a Genevac EZ-2 Elite, unless stated otherwise.

Supercritical Fluid Chromatography (SFC)

Chiral separation was performed using SFC. Separations were performed using a PIC Solution Inc SFC-PICLab PREP 100, with a Chiralcel OX column from Daicel, 5 μm, 150 mm×21 mm i.d., running at a flow rate of 70 mL/min, 40° C. and 100 bar, fraction collected using UV diode array detection (210-400 nm). A typical separation used isocratic elution with 40% HPLC grade methanol containing 0.1% ammonium hydroxide (solvent B) in supercritical carbon dioxide (solvent A) and a run time of 6 min, or modified as necessary. Enantiomeric excess was determined using analytical SFC chromatography. Analyses were performed using a Waters UPC2 instrument, with a Chiralcel OX column from Daicel, 3 μm, 50 mm×4.6 mm i.d., running at a flow rate of 4.0 mL/min, 40° C. and 105 bar. A typical analysis used isocratic elution with 45% HPLC grade methanol containing 0.1% ammonium hydroxide (solvent B) in supercritical carbon dioxide (solvent A) and a run time of 2.5 min, or modified as necessary.

Mass Spectrometry (MS)

Mass spectra were collected using a Waters Micromass ZQ2000 spectrometer, operating in positive or negative ion electrospray ionisation (ESI) modes, with a molecular weight scan range of 150 to 1000.

Nomenclature

Unless otherwise indicated, the nomenclature of structures was determined using the 'Convert Structure to Name' function of ChemBioDraw Ultra 12.0.2 for Examples 1-234 or ChemDraw Professional 15.1.0 for Examples 235-245 (CambridgeSoft/PerkinElmer).

General Procedures

General Procedure 1: Epoxide Opening with a Pyrimidinone

A suspension of the pyrimidinone (1 equiv.), epoxide (1-3 equiv.) and $Cs_2CO_3$ (1-3 equiv.) in DMF were heated at 80° C. for 10-24 h. The reaction was then cooled to RT, saturated $NH_4Cl_{(aq)}$ was added and the mixture extracted with DCM (×3) using a Biotage phase separator. The combined organic phases were concentrated and the residue was purified by flash chromatography (Biotage KP-Sil and KP-NH, 0-100% EtOAc in cyclohexane or PE, then 0-30% MeOH in EtOAc) to give the product.

General Procedure 2: N-Boc Deprotection

A solution of the N-Boc piperidine in DCM/TFA was stirred for 1-24 h before being concentrated. The residue was then dissolved in triethylamine and DCM before being purified on a Biotage KP-NH column (0-100% EtOAc in cyclohexane or PE, then 0-30% MeOH in EtOAc or 0-100% DCM in cyclohexane or PE, then 0-30% MeOH in DCM) to give the product.

General Procedure 3: EDC Coupling

A solution of amine (1 equiv.), carboxylic acid (1 equiv.) and EDC (3 equiv.) was stirred in (DCM) for 1-24 h. The reaction was quenched by the addition of water and the resulting mixture was extracted with DCM (×3) using a Biotage phase separator. The combined organic phases were concentrated and the residue purified by flash chromatography (Biotage KP-Sil and KP-NH, 0-100% EtOAc in cyclohexane or PE, then 0-30% MeOH in EtOAc) to give the product.

General Procedure 4: HATU Coupling in DCM

To a suspension of the amine (1 equiv.), carboxylic acid (1.5 equiv.) and HATU (1.5 equiv.) in DCM was added DIPEA (4 equiv.). The reaction was stirred for 1-24 h before being quenched by the addition of saturated $NaHCO_{3(aq)}$ and the resulting mixture was extracted with DCM (×3) using a Biotage phase separator. The combined organic phases were concentrated and the residue purified by flash chromatography (Biotage KP-Sil and KP-NH, 0-100% EtOAc in cyclohexane or PE, then 0-30% MeOH in EtOAc) to give the product.

General Procedure 5: Suzuki Coupling

A reaction vial was charged with a mixture of the bromide (1 equiv.), the organoboron reagent (1-3 equiv.), a Pd catalyst (0.05-0.1 equiv.) and an inorganic base (2-5 equiv.) in 1,4-dioxane/water or DME/water and the $O_2$ was removed by evacuating and refilling with $N_2$ three times before the reaction tube was sealed. The reaction was heated under the indicated conditions for the indicated time before being cooled to RT and saturated $NH_4Cl_{(aq)}$ was added. The mixture was then extracted with DCM (×3) using a Biotage phase separator. The combined organic phases were concentrated and the residue purified by flash chromatography (Biotage KP-Sil and KP-NH, 0-100% EtOAc in cyclohexane or PE, then 0-30% MeOH in EtOAc) to give the product.

General Procedure 6: Sonagashira Coupling

A reaction tube was charged with the Bromide (1 equiv.), a Cu catalyst (0.2-0.4 equiv.) and a Pd catalyst (0.1-0.2 equiv.) and then evacuated and refilled with $N_2$ 3 times. To this was added toluene, triethylamine (20-40 equiv.) and then the alkyne (1-4 equiv.) before the mixture was again evacuated and refilled with $N_2$ 3 times. The reaction tube was sealed and the reaction was heated under the indicated conditions. The reaction was cooled to RT and quenched by the addition of saturated $NH_4Cl_{(aq)}$. The mixture was extracted with DCM (×3) using a Biotage phase separator, the combined organic phases were concentrated and the products were purified by flash chromatography (Biotage KP-Sil and KP-NH, 0-100% EtOAc in cyclohexane or PE, then 0-30% MeOH in EtOAc) to give the product.

General Procedure 7: N-Cbz Deprotection

A suspension of the N-Cbz compound (1 equiv.), 10% Pd on carbon (0.1 equiv.) and ammonium formate (10-30 equiv.) in EtOH was heated at reflux for the indicated time before the reaction mixture was cooled to RT, diluted with MeOH and filtered through Dicalite®. The solids were washed with MeOH (×3), the combined filtrates were then concentrated and the residue purified by flash chromatography (Biotage KP-NH, 0-100% DCM in cyclohexane, then 0-30% MeOH in DCM) to give the product.

General Procedure 8: $S_NAr$ Method A for Monocycle Library

A mixture of 6-chloro-3-[[4-hydroxy-1-[(3R)-3-phenylbutanoyl]-4-piperidyl]methyl]pyrimidin-4-one, Intermediate A (30.0 mg, 0.0769 mmol) and selected amine (10 equiv.) [e.g. for Example 140, D-prolinol (77.8 mg, 0.769 mmol)] in 1,4-dioxane (2.6 mL) was heated under microwave irradiation at 150° C. for 45 min. After cooling, the reaction mixture was concentrated in vacuo. The residue was purified by flash chromatography (e.g. for Example 140, 0-100% MeOH in isopropyl acetate), followed by preparative HPLC (Method B) to afford the product (e.g. for Example 140, 36% yield).

General Procedure 9: $S_NAr$ Method B for Monocycle Library

A mixture of 6-chloro-3-[[4-hydroxy-1-[(3R)-3-phenylbutanoyl]-4-piperidyl]methyl]pyrimidin-4-one, Intermediate A (33.3 mg, 0.0854 mmol) and selected amine (ca. 5 equiv.) [e.g. for Example 144, piperidin-4-ol (48.8 mg, 0.482 mmol) in 1,4-dioxane (2.0 mL) was heated in a sealed vessel to 100° C. for 14 h, allowed to cool and concentrated in vacuo. The crude residue was purified preparative HPLC (Method B) to afford the product (e.g. for Example 144, 54% yield).

General Procedure 10: $S_NAr$ Method C for Monocycle Library

A mixture of 6-chloro-3-[[4-hydroxy-1-[(3R)-3-phenylbutanoyl]-4-piperidyl]methyl]pyrimidin-4-one, Intermediate A (30 mg, 0.077 mmol), DIPEA (50 uL, 0.29 mmol)

and selected amine (2 equiv.) in 1,4-dioxane (0.8 mL) was heated in a sealed vessel to 100° C. for 16 h, allowed to cool and concentrated in vacuo. The crude residue was purified preparative HPLC (Method B) to afford the product.

General Procedure 11: HATU Coupling in DMF

To a suspension of the amine (1 equiv.), carboxylic acid (1.5 equiv.) and HATU (1.25 equiv.) in DMF was added DIPEA (3 equiv.). The reaction was stirred for 1-24 h before being quenched by the addition of saturated sodium bicarbonate (aq) solution and the resulting mixture was extracted with DCM (×3) using a Biotage phase separator. The combined organic phases were washed using brine, dried ($Na_2SO_4$), the solvents were removed in vacuo. The remaining residue was purified by preparative HPLC (Method B), followed by SFC using a reversed phase column, if required, to afford the product.

Epoxide 1: tert-Butyl 1-oxa-6-azaspiro[2.5]octane-6-carboxylate

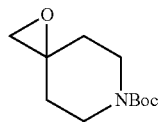 [SMILES: CC(C)(C)OC(=O)N1CCC2(CC1)CO2]

Commercially available or made according to a variation of a literature procedure (J. Med. Chem. 2008, 51, 2170): To a suspension of trimethylsulfoxonium iodide (22.5 g, 102 mmol) in DME (100 mL) in a 250 mL 3-necked round bottom flask under $N_2$ was added KOt-Bu (12.5 g, 111 mmol). After 30 min this suspension was cooled to 0° C. and a solution of tert-butyl 4-oxopiperidine-1-carboxylate (20 g, 100 mmol) in DME (20 mL) was added dropwise from a pressure-equalised dropping funnel over 45 min. The reaction was then allowed to warm to RT over 16 h before being quenched by the addition of water (150 mL). The mixture was extracted with $Et_2O$ (3×100 mL), the combined organic phases were washed with brine (100 mL), dried over $MgSO_4$ and the volatiles removed in vacuo. To the resulting oil was then added toluene (50 mL) and the volatiles removed in vacuo to give Epoxide 1 (16.5 g, 83% yield) as a colourless solid. $^1H$ NMR (300 MHz, $CDCl_3$): δ 3.81-3.58 (m, 2H), 3.40 (ddd, 2H), 2.67 (s, 2H), 1.78 (ddd, 2H), 1.56-1.30 (m, 2H), 1.45 (s, 9H).

Epoxide 2: (R)-3-Phenyl-1-(1-oxa-6-azaspiro[2.5]octan-6-yl)butan-1-one

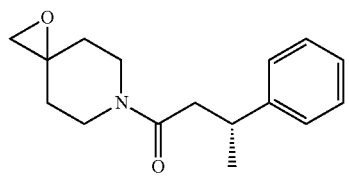 [SMILES: C[C@H](CC(=O)N1CCC2(CC1)CO2)c1ccccc1]

Step 1: (R)-1-(3-Phenylbutanoyl)piperidin-4-one

To freshly prepared piperidin-4-one hydrochloride (PCT Int. Appl., 2011084402, 14 Jul. 2011) (1.70 g, 12.6 mmol) was added EDC (2.89 g, 15.1 mmol), DMAP (153 mg, 1.26 mmol), DCM (15 mL) and DIPEA (11 mL, 62.7 mmol). After 10 min. a solution of (R)-3-phenylbutanoic acid (2.47 g, 15.1 mmol) in DCM (10 mL) was added. After 20 h EDC (2.89 g, 15.1 mmol) was added and the reaction stirred for a further 4 h before the reaction was quenched by the addition of saturated $NaHCO_{3(aq)}$ (150 mL). The mixture was then extracted with EtOAc (3×50 mL), the combined organic phases were washed with water (50 mL), then brine (50 mL), dried over $MgSO_4$, concentrated and the residue was purified by flash chromatography (Biotage 50 g KP-Sil, 0-60% EtOAc in PE) to give (R)-1-(3-phenylbutanoyl)piperidin-4-one (2.93 g, 95%) as a colourless oil. LCMS (Method A): $R_T$=1.07 min, m/z=246 [M+H]+. $^1H$ NMR (300 MHz, $CDCl_3$): δ 7.44-7.13 (m, 5H), 4.30-4.03 (m, 1H), 3.77-3.58 (m, 1H), 3.46 (tdd, 2H), 3.11-2.93 (m, 2H), 2.82-2.61 (m, 4H), 1.86 (m, 1H), 1.77-1.62 (m, 1H), 1.54-1.33 (m, 2H).

Step 2: (R)-3-Phenyl-1-(1-oxa-6-azaspiro[2.5]octan-6-yl)butan-1-one (Epoxide 2)

To a solution of trimethylsulfonium iodide (6.09 g, 29.9 mmol) in DMSO (30 mL) was added NaH (1.19 g, 29.9 mmol). The resulting mixture was stirred at RT for 1 h before a solution of (R)-1-(3-phenylbutanoyl)piperidin-4-one (2.93 g, 11.9 mmol) in DMSO (15 mL) was added. The reaction mixture was stirred at 50° C. for 2 h before it was cooled to RT and quenched by the addition of water (100 mL) and the mixture was extracted with $Et_2O$ (3×50 mL). The combined organic phases were washed with brine, dried over $Na_2SO_4$, concentrated and the residue purified by flash chromatography (Biotage KP-Sil, 0-70% EtOAc in PE) to give Epoxide 2 (2.68 g, 87%) as a colourless oil. LCMS (Method A): $R_T$=1.16 min, m/z=260 [M+H]+. $^1H$ NMR (300 MHz, $CDCl_3$): δ 7.43-7.14 (m, 5H), 4.30-3.95 (m, 1H), 3.69-3.18 (m, 4H), 2.84-2.47 (m, 4H), 1.87-1.66 (m, 2H), 1.51-1.31 (m, 2H), 1.37 (d, 3H).

Epoxide 3: 3-Phenyl-1-(1-oxa-6-azaspiro[2.5]octan-6-yl)propan-1-one

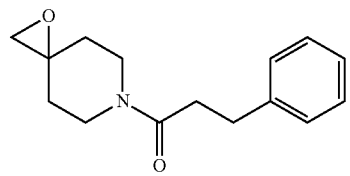 [SMILES: O=C(CCc1ccccc1)N1CCC2(CC1)CO2]

Step 1: 1-(3-Phenylpropanoyl)piperidin-4-one

To a solution of tert-butyl 4-oxopiperidine-1-carboxylate (5 g, 25.1 mmol) in DCM (25 mL) was added TFA (9.67 mL, 125 mmol). The resulting mixture was stirred at RT for 24 h before the solvent was removed in vacuo and the product was dried under high vacuum. To a stirred suspension of the TFA salt in dry DCM (125 mL) under $N_2$ was added DIPEA (13.2 mL, 75.0 mmol) dropwise over 5 min before 3-phenylpropanoic acid (4.52 g, 30.1 mmol), EDC (6.26 g, 32.6 mmol) and DMAP (0.307 g, 2.510 mmol) were added. The reaction mixture was stirred at RT for 18 h before it was diluted with DCM (150 mL) and washed with saturated $NaHCO_3$ (250 mL). The phases were separated and the aqueous layer was further extracted with DCM (75 mL). The combined organic phases were washed with 3% HCl$_{(aq)}$ (150 mL), then brine (150 mL) and dried using a Biotage phase separator. The resulting solution was then concentrated and purified by flash chromatography (Biotage KP-Sil 100 g, 0-100% EtOAc in PE) to give the product as colourless oil. $^1$H NMR (300 MHz, CDCl$_3$): δ 7.51-6.98 (m, 5H), 3.89 (t, 2H), 3.66 (t, 2H), 3.04 (t, 2H), 2.73 (t, 2H), 2.44 (t, 2H), 2.26 (t, 2H).

Step 2: 3-Phenyl-1-(1-oxa-6-azaspiro[2.5]octan-6-yl)propan-1-one (Epoxide 3)

To a solution of trimethylsulfonium iodide (4.59 g, 22.5 mmol) in dry DMSO (20 mL) was added NaH (0.899 g, 22.5 mmol). The resulting mixture was stirred at RT for 1 h before a solution of 1-(3-phenylpropanoyl)piperidin-4-one (2.08 g, 8.99 mmol) in dry DMSO (10 mL) was added. The reaction mixture was stirred at 50° C. for 2 h before it was cooled to RT and quenched by the addition of water (100 mL) and the mixture was extracted with Et$_2$O (3×50 mL). The combined organic phases were washed with brine, dried over Na$_2$SO$_4$, concentrated and the product purified by flash chromatography (Biotage 50 g KP-Sil, 0-60% EtOAc in PE) to give Epoxide 2 (1.41 g, 64%) as a colourless oil. LCMS (Method A): R$_T$=1.07 min, m/z=246 [M+H]+. $^1$H NMR (300 MHz, CDCl$_3$): δ 7.44-7.13 (m, 5H), 4.30-4.03 (m, 1H), 3.77-3.58 (m, 1H), 3.46 (tdd, 2H), 3.11-2.93 (m, 2H), 2.82-2.61 (m, 4H), 1.86 (m, 1H), 1.77-1.62 (m, 1H), 1.54-1.33 (m, 2H).

Epoxide 4: Benzyl 1-oxa-6-azaspiro[2.5]octane-6-carboxylate

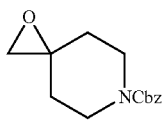

To a suspension of trimethylsulfoxonium iodide (11.7 g, 53.0 mmol) in DME (50 mL) under N$_2$ was added KOt-Bu (6.49 g, 57.8 mmol). After 30 min this suspension was cooled to 0° C. and a solution of benzyl 4-oxopiperidine-1-carboxylate (11.2 g, 48.2 mmol) in DME (20 mL) was added dropwise over 45 min. The reaction was allowed to warm to RT over 16 h before being quenched by the addition of water (150 mL). The mixture was then extracted with Et$_2$O (3×100 mL), the combined organic phases were washed with brine (100 mL), dried over MgSO$_4$ and the volatiles removed in vacuo. To the resulting oil was added toluene (50 mL) and the volatiles removed in vacuo to give benzyl 1-oxa-6-azaspiro[2.5]octane-6-carboxylate (9.00 g, 76%) as a yellow oil. $^1$H NMR (300 MHz, CDCl$_3$): δ 7.41-7.28 (m, 5H), 5.16 (s, 2H), 3.93-3.75 (m, 2H), 3.55-3.39 (m, 2H), 2.71 (s, 2H), 1.93-1.73 (m, 2H), 1.53-1.37 (m, 2H).

Example 1: (R)-6-Chloro-3-((4-hydroxy-1-(3-phenylbutanoyl)piperidin-4-yl)methyl)pyrimidin-4(3H)-one (Intermediate A)

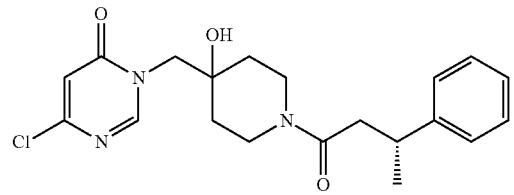 [SMILES: C[C@H](CC(=O)N1CCC(O)(Cn2cnc(Cl)cc2=O)CC1)c1ccccc1]

A suspension of 6-chloropyrimidin-4(3H)-one (U.S. Pat. Appl. Publ., 20090149466, 11 Jun. 2009) (200 mg, 1.53 mmol), Epoxide 2 (397 mg, 1.53 mmol) and DIPEA (401 µl, 2.30 mmol) in DMF (3 mL) was heated at 80° C. for 16 h. The reaction mixture was then allowed to cool to RT and was quenched by the addition of saturated NH$_4$Cl$_{(aq)}$ (20 mL). The mixture was extracted with EtOAc (3×20 mL), the combined organic extracts were dried over Na$_2$SO$_4$, concentrated, and the residue was purified by flash chromatography (Biotage 25 g KP-Sil, 0-100% EtOAc in PE then 0-30% MeOH in EtOAc) to give the title compound (350 mg, 59%) as a pale yellow solid. LCMS (Method A): R$_T$=1.11 min, m/z=390, 392 [M+H]+. $^1$H NMR (300 MHz, methanol-d$_4$, this molecule appears as two conformers A and B in a 2:3 ratio respectively): δ 8.28 (s, 0.4H (conformer A)), 8.24 (s, 0.6H (conformer B)), 7.38-7.13 (m, 5H), 6.58 (s, 1H), 4.27-4.09 (m, 1H), 4.00 (dd, 0.8H (conformer A)), 3.84 (dd, 1.2H (conformer B)), 3.74-3.57 (m, 1H), 3.39-2.86 (m, 3H), 2.86-2.67 (m, 1H), 2.66-2.43 (m, 1H), 1.66-1.20 (m, 7H), 0.93-0.79 (m, 0.6H (conformer B only)).

Example 2: (R)-3-((4-Hydroxy-1-(3-phenylbutanoyl)piperidin-4-yl)methyl)-6-(pyridin-4-yl)pyrimidin-4(3H)-one

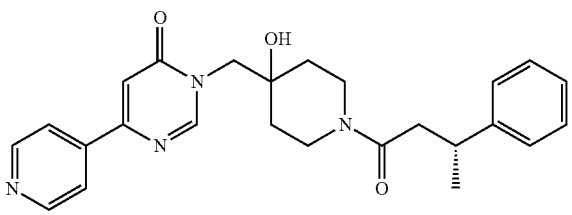 [SMILES: C[C@H](CC(=O)N1CCC(O)(Cn2cnc(-c3ccncc3)cc2=O)CC1)c1ccccc1]

General procedure 5 using Intermediate A (25 mg, 0.064 mmol), pyridin-4-ylboronic acid (12 mg, 0.096 mmol), Na$_2$CO$_3$ (14 mg, 0.128 mmol), Pd(PPh$_3$)$_4$ (3.7 mg, 3.21 µmol), 1,4-dioxane (0.4 mL) and water (0.16 mL) in a sealed tube under microwave heating at 150° C. for 10 min gave the title compound (24 mg, 86%) as a colourless solid. LCMS (Method A): R$_T$=0.81 min, m/z=433 [M+H]$^+$. $^1$H NMR (300 MHz, CDCl$_3$, this molecule appears as two conformers A and B in a 2:3 ratio respectively): δ 8.76-8.62 (m, 2H), 8.23 (s, 0.4H (conformer A)), 8.13 (s, 0.6H (conformer B)), 7.83-7.71 (m, 2H), 7.40-7.13 (m, 5H), 6.95 (s, 1H), 4.49-4.23 (m, 1H), 4.21-3.80 (m, 3H), 3.67-3.47 (m, 1H), 3.44-2.87 (m, 3H), 2.72-2.59 (m, 1H), 2.59-2.42 (m, 1H), 1.68-1.21 (m, 7H), 0.94-0.71 (m, 0.6H (conformer B only)).

Example 3: (R)-3-((4-Hydroxy-1-(3-phenylbutanoyl)piperidin-4-yl)methyl)-6-(1H-pyrazol-5-yl)pyrimidin-4(3H)-one

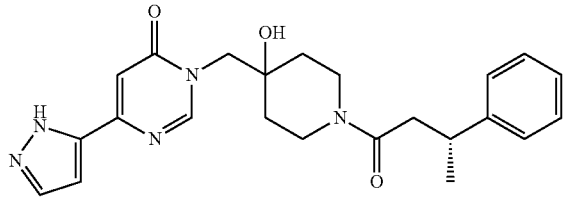 [SMILES: C[C@H](CC(=O)N1CCC(O)(Cn2cnc(-c3ccn[nH]3)cc2=O)CC1)c1ccccc1]

General procedure 5 using Intermediate A (25 mg, 0.064 mmol), (1H-pyrazol-5-yl)boronic acid (11 mg, 0.096 mmol), Na$_2$CO$_3$ (14 mg, 0.128 mmol), Pd(PPh$_3$)$_4$ (3.7 mg, 3.21 µmol), 1,4-dioxane (0.4 mL) and water (0.16 mL) in a sealed tube under microwave heating at 150° C. for 10 min gave the title compound (19 mg, 70%) as a colourless solid. LCMS (Method A): R$_T$=0.921 min, m/z=422 [M+H]$^+$. $^1$H NMR (300 MHz, CDCl$_3$, this molecule appears as two conformers A and B in a 2:3 ratio respectively): δ 8.28 (s, 0.4H (conformer A)), 8.18 (s, 0.6H (conformer B)), 7.65-7.56 (m, 1H), 7.37-7.14 (m, 5H), 7.05-6.92 (m, 1H), 6.81-6.71 (m, 1H), 4.44-4.20 (m, 1H), 4.21-3.79 (m, 2H), 3.65-2.86 (m, 4H), 2.71-2.57 (m, 1H), 2.57-2.41 (m, 1H), 1.63-1.21 (m, 7H), 0.90-0.73 (m, 0.6H (conformer B only)).

Example 4: (R)-3-((4-Hydroxy-1-(3-phenylbutanoyl)piperidin-4-yl)methyl)-6-(phenylamino)pyrimidin-4(3H)-one

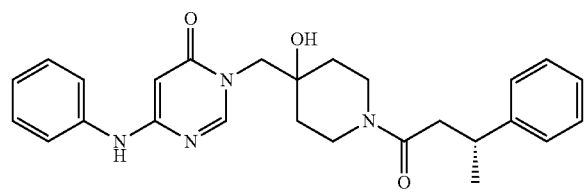 [SMILES: C[C@H](CC(=O)N1CCC(O)(Cn2cnc(Nc3ccccc3)cc2=O)CC1)c1ccccc1]

A solution of Intermediate A (30 mg, 0.08 mmol) in aniline (175 µL, 1.92 mmol) was heated under microwave conditions at 130° C. for 1 h and the reaction mixture was purified by flash chromatography (Biotage 11 g KP-NH, 0-100% EtOAc in PE then 0-30% MeOH in EtOAc) to give the title compound (22 mg, 64%) as a colourless solid. LCMS (Method A): R$_T$=1.20 min, m/z=447 [M+H]$^+$. $^1$H NMR (300 MHz, methanol-d$_4$, this molecule appears as two conformers A and B in a 2:3 ratio respectively): δ 8.23 (d, 0.4H (conformer A)), 8.08 (d, 0.6H (conformer B)), 7.43-6.92 (m, 10H), 6.56 (s, 0.4H (conformer A)), 5.65 (s, 0.6H (conformer B)), 4.26-3.51 (m, 4H), 3.35-2.85 (m, 3H), 2.85-2.65 (m, 1H), 2.64-2.41 (m, 1H), 1.63-1.20 (m, 7H), 0.95-0.73 (m, 0.6H (conformer B only)).

Example 5: (R)-6-Amino-3-((4-hydroxy-1-(3-phenylbutanoyl)piperidin-4-yl)methyl)pyrimidin-4(3H)-one

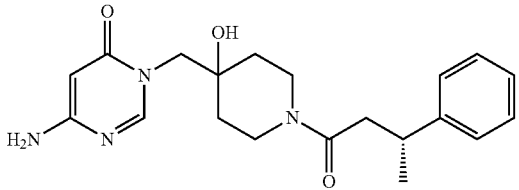 [SMILES: C[C@H](CC(=O)N1CCC(O)(Cn2cnc(N)cc2=O)CC1)c1ccccc1]

A solution of Intermediate A (25 mg, 0.064 mmol) in 6 M NH$_3$ in MeOH (0.5 mL, 3.00 mmol) was heated under microwave conditions at 120° C. for 20 min before the reaction mixture was concentrated and the residue purified by flash chromatography (Biotage 11 g KP-NH, 0-100% EtOAc in PE then 0-30% MeOH in EtOAc) to give the title compound (16 mg, 67%) as a colourless solid. LCMS (Method A): R$_T$=0.82 min, m/z=371 [M+H]$^+$. $^1$H NMR (300 MHz, CDCl$_3$, this molecule appears as two conformers A and B in a 2:3 ratio respectively): δ 7.77 (s, 0.4H (conformer A)), 7.66 (s, 0.6H (conformer B)), 7.37-7.16 (m, 5H), 5.48-5.42 (m, 1H), 4.80 (br s, 2H), 4.50-4.30 (m, 1H), 4.03-3.17 (m, 6H), 3.07-2.82 (m, 1H), 2.72-2.58 (m, 1H), 2.57-2.42 (m, 1H), 1.78-1.11 (m, 7H), 0.63-0.49 (m, 0.6H (conformer B only)).

Example 6: (R)-6-((2-(Dimethylamino)ethyl)amino)-3-((4-hydroxy-1-(3-phenylbutanoyl)piperidin-4-yl)methyl)pyrimidin-4(3H)-one

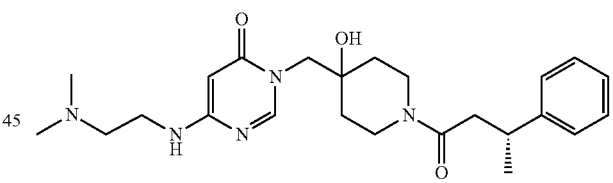

A mixture of Intermediate A (25 mg, 0.064 mmol), N,N-dimethylethylenediamine (85 mg, 0.962 mmol) and ethanol (0.5 mL) was heated under microwave conditions at 120° C. for 20 min and the reaction mixture was purified by flash chromatography (Biotage 11 g KP-NH, 0-100% EtOAc in PE then 0-30% MeOH in EtOAc) to give the title compound (22 mg, 78%) as a colourless solid. LCMS (Method A): R$_T$=0.60 min, m/z=442 [M+H]$^+$. $^1$H NMR (300 MHz, CDCl$_3$, this molecule appears as two conformers A and B in a 2:3 ratio respectively): δ 7.71 (s, 0.4H (conformer A)), 7.60 (s, 0.6H (conformer B)), 7.36-7.15 (m, 5H), 5.68-5.58 (m, 1H), 5.29-5.23 (m, 1H), 4.49-4.32 (m, 1H), 4.00-3.48 (m, 3H), 3.43-3.07 (m, 4H), 3.05-2.84 (m, 1H), 2.71-2.59 (m, 1H), 2.56-2.42 (m, 3H), 2.25 (s, 6H), 1.61-1.11 (m, 7H), 0.62-0.49 (m, 0.6H (conformer B only)).

Example 7: (R)-6-((2-(Dimethylamino)ethyl)(methyl)amino)-3-((4-hydroxy-1-(3-phenylbutanoyl)piperidin-4-yl)methyl)pyrimidin-4(3H)-one

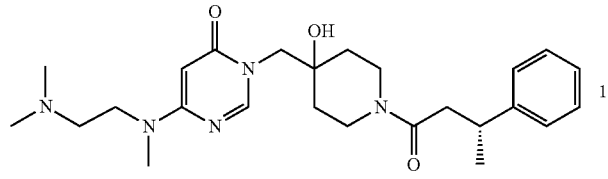

A mixture of Intermediate A (25 mg, 0.064 mmol), N,N,N'-trimethylethylenediamine (0.083 mL, 0.641 mmol) and 1,4-dioxane (0.5 mL) was heated under microwave conditions at 150° C. for 15 min and the reaction mixture was purified by flash chromatography (Biotage 11 g KP-NH, 0-100% EtOAc in PE then 0-30% MeOH in EtOAc) to give the title compound (24 mg, 82%) as a colourless solid. LCMS (Method A): $R_T$=0.64 min, m/z=456 [M+H]$^+$. $^1$H NMR (300 MHz, CDCl$_3$, this molecule appears as two conformers A and B in a 2:3 ratio respectively): δ 7.74 (s, 0.4H (conformer A)), 7.63 (s, 0.6H (conformer B)), 7.36-7.15 (m, 5H), 5.38-5.30 (m, 1H), 4.50-4.33 (m, 1H), 4.00-3.17 (m, 8H), 3.08-2.84 (m, 4H), 2.72-2.59 (m, 1H), 2.57-2.40 (m, 3H), 2.28 (d, 6H), 1.62-1.10 (m, 7H), 0.63-0.50 (m, 0.6H (conformer B)).

Example 8: (R)-3-((4-Hydroxy-1-(3-phenylbutanoyl)piperidin-4-yl)methyl)-6-(4-methylpiperazin-1-yl)pyrimidin-4(3H)-one

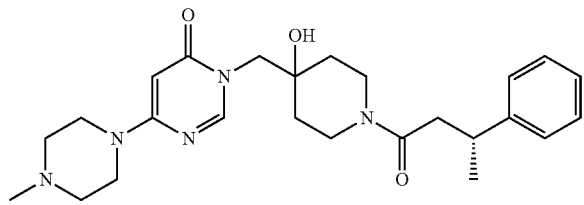 [SMILES: C[C@H](CC(=O)N1CCC(O)(Cn2cnc(N3CCN(C)CC3)cc2=O)CC1)c1ccccc1]

A mixture of Intermediate A (27 mg, 0.069 mmol), 1-methylpiperazine (77 μL, 0.693 mmol) and 1,4-dioxane (0.5 mL) was heated under microwave conditions at 150° C. for 15 min and the reaction mixture was purified by flash chromatography (Biotage 11 g KP-NH, 0-100% EtOAc in PE then 0-30% MeOH in EtOAc) to give the title compound (28 mg, 89%) as a colourless solid. LCMS (Method A): $R_T$=0.67 min, m/z=454 [M+H]$^+$. $^1$H NMR (300 MHz, CDCl$_3$, this molecule appears as two conformers A and B in a 2:3 ratio respectively): δ 7.78 (s, 0.4H (conformer A)), 7.67 (s, 0.6H (conformer B)), 7.37-7.14 (m, 5H), 5.50-5.40 (m, 1H), 5.00 (br s, 1H), 4.50-4.30 (m, 1H), 4.03-3.17 (m, 9H), 3.06-2.83 (m, 1H), 2.73-2.58 (m, 1H), 2.56-2.28 (m, 8H), 1.61-1.10 (m, 7H), 0.68-0.52 (m, 0.6H (conformer B)).

Example 9: (R)-3-((4-Hydroxy-1-(3-phenylbutanoyl)piperidin-4-yl)methyl)-6-methoxypyrimidin-4(3H)-one

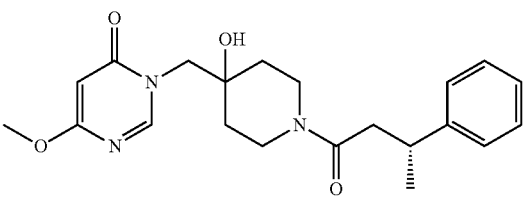 [SMILES: COc1cc(=O)n(CC2(O)CCN(C(=O)C[C@@H](C)c3ccccc3)CC2)cn1]

A mixture of Intermediate A (25 mg, 0.064 mmol) and sodium methoxide (35 mg, 0.641 mmol) in MeOH (0.5 mL) was heated under microwave conditions at 150° C. for 15 min and the reaction mixture was purified by flash chromatography (Biotage 11 g KP-NH, 0-100% EtOAc in PE then 0-30% MeOH in EtOAc) to give the title compound (14 mg, 56%) as a colourless solid. LCMS (Method A): $R_T$=0.96 min, m/z=386 [M+H]$^+$. $^1$H NMR (300 MHz, CDCl$_3$, this molecule appears as two conformers A and B in a 2:3 ratio respectively): δ 7.94 (s, 0.4H (conformer A)), 7.82 (s, 0.6H (conformer B)), 7.38-7.16 (m, 5H), 5.76 (s, 1H), 4.49-3.69 (m, 5H), 3.66-2.82 (m, 6H), 2.72-2.58 (m, 1H), 2.57-2.42 (m, 1H), 1.70-1.16 (m, 7H), 0.64-0.50 (m, 0.6H (conformer B)).

Example 10: (R)-6-(2-(Dimethylamino)ethoxy)-3-((4-hydroxy-1-(3-phenylbutanoyl)piperidin-4-yl)methyl)pyrimidin-4(3H)-one

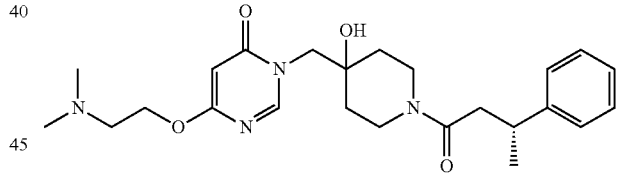

A mixture of Intermediate A (25 mg, 0.064 mmol) and 2-(dimethylamino)ethanol (200 μL, 1.99 mmol) was heated under microwave conditions at 150° C. for 15 min and the reaction mixture was purified by flash chromatography (Biotage 11 g KP-NH, 0-100% EtOAc in PE then 0-30% MeOH in EtOAc) to give the title compound (17 mg, 59%) as a colourless solid. LCMS (Method A): $R_T$=0.58 min, m/z=443 [M+H]$^+$. $^1$H NMR (300 MHz, CDCl$_3$, this molecule appears as two conformers A and B in a 2:3 ratio respectively): δ 7.95 (s, 0.4H (conformer A)), 7.83 (s, 0.6H (conformer B)), 7.37-7.16 (m, 5H), 5.78 (s, 1H), 4.47-4.23 (m, 3H), 4.11-4.02 (m, 0.6 (conformer B only), 3.90-3.69 (m, 1.4H (0.4H=conformer A)), 3.64-3.49 (m, 1H), 3.42-3.16 (m, 2H), 3.10-2.85 (m, 1H), 2.75-2.58 (m, 3H), 2.56-2.42 (m, 1H), 2.32 (d, 6H), 1.58-1.16 (m, 7H), 0.68-0.52 (m, 0.6H (conformer B)).

Example 11: (R)-3-((4-Hydroxy-1-(3-phenylbutanoyl)piperidin-4-yl)methyl)-6-((2-(pyrrolidin-1-yl)ethyl)amino)pyrimidin-4(3H)-one

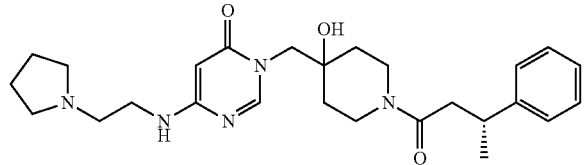 [SMILES: C[C@H](CC(=O)N1CCC(O)(Cn2cnc(NCCN3CCCC3)cc2=O)CC1)c1ccccc1]

A mixture of Intermediate A (25 mg, 0.064 mmol), 2-(pyrrolidin-1-yl)ethanamine (81 µL, 0.641 mmol) and 1,4-dioxane (0.5 mL) was heated under microwave conditions at 150° C. for 15 min and the reaction mixture was purified by flash chromatography (Biotage 11 g KP-NH, 0-100% EtOAc in PE then 0-30% MeOH in EtOAc) to give the title compound (22 mg, 73%) as a colourless solid. LCMS (Method A): $R_T$=0.61 min, m/z=468 [M+H]$^+$. $^1$H NMR (300 MHz, CDCl$_3$, this molecule appears as two conformers A and B in a 2:3 ratio respectively): δ 7.69 (s, 0.4H (conformer A)), 7.58 (s, 0.6H (conformer B)), 7.37-7.15 (m, 5H), 5.31-5.23 (m, 1H), 5.12 (s, 0.6H (conformer B)), 4.94 (s, 0.4H (conformer A)), 4.51-4.33 (m, 1H), 3.99-3.09 (m, 8H), 3.06-2.83 (m, 1H), 2.77-2.58 (m, 3H), 2.57-2.41 (m, 5H), 1.85-1.08 (m, 10H), 0.96-0.83 (m, 0.4H (conformer A)), 0.60-0.46 (m, 0.6H (conformer B)).

Example 12: 6-((S)-3-Aminopyrrolidin-1-yl)-3-((4-hydroxy-1-((R)-3-phenylbutanoyl)piperidin-4-yl)methyl)pyrimidin-4(3H)-one

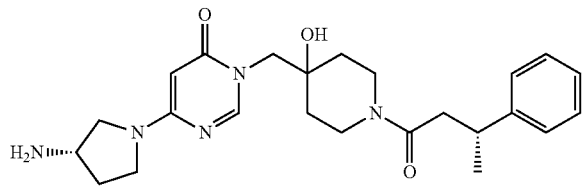 [SMILES: C[C@H](CC(=O)N1CCC(O)(Cn2cnc(N3CC[C@H](N)C3)cc2=O)CC1)c1ccccc1]

Step 1: tert-Butyl ((S)-1-(1-((4-hydroxy-1-((R)-3-phenylbutanoyl)piperidin-4-yl)methyl)-6-oxo-1,6-dihydropyrimidin-4-yl)pyrrolidin-3-yl)carbamate A mixture of Intermediate A (25 mg, 0.064 mmol), (S)-tert-butyl pyrrolidin-3-ylcarbamate (119 mg, 0.641 mmol) and 1,4-dioxane (0.5 mL) was heated under microwave conditions at 150° C. for 75 min and the reaction mixture was purified by flash chromatography (Biotage 11 g KP-NH, 0-100% EtOAc in PE then 0-30% MeOH in EtOAc) to give the title compound (24 mg, 69%) as a colourless solid. LCMS (Method A): $R_T$=1.23 min, m/z=540 [M+H]$^+$.

Step 2: 6-((S)-3-Aminopyrrolidin-1-yl)-3-((4-hydroxy-1-((R)-3-phenylbutanoyl)piperidin-4-yl)methyl)pyrimidin-4(3H)-one General procedure 2 using tert-butyl ((S)-1-(1-((4-hydroxy-1-((R)-3-phenylbutanoyl)piperidin-4-yl)methyl)-6-oxo-1,6-dihydropyrimidin-4-yl)pyrrolidin-3-yl)carbamate (24 mg, 0.048 mmol), TFA (0.5 mL) and DCM (0.5 mL) gave the title compound (19 mg, 90%) as a colourless solid. LCMS (Method A): $R_T$=0.60 min, m/z=440 [M+H]$^+$. $^1$H NMR (300 MHz, CDCl$_3$, this molecule appears as two conformers A and B in a 2:3 ratio respectively): δ 7.75 (s, 0.4H (conformer A)), 7.65 (s, 0.6H (conformer B)), 7.40-7.16 (m, 5H), 5.21 (s, 1H), 4.50-4.32 (m, 1H), 4.03-3.17 (m, 11H), 3.05-2.83 (m, 1H), 2.72-2.58 (m, 1H), 2.57-2.42 (m, 1H), 2.29-2.08 (m, 1H), 1.91-1.70 (m, 1H), 1.69-1.10 (m, 9H), 0.64-0.50 (m, 0.6H (conformer B)).

Example 13: (R)-6-(3-Aminoazetidin-1-yl)-3-((4-hydroxy-1-(3-phenylbutanoyl)piperidin-4-yl)methyl)pyrimidin-4(3H)-one

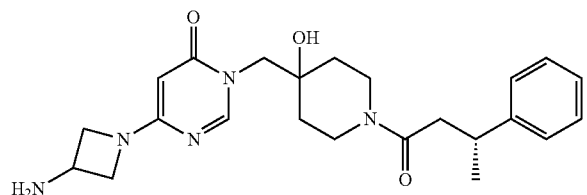

Step 1: (R)-tert-Butyl (1-(1-((4-hydroxy-1-(3-phenylbutanoyl)piperidin-4-yl)methyl)-6-oxo-1,6-dihydropyrimidin-4-yl)azetidin-3-yl)carbamate A mixture of Intermediate A (25 mg, 0.064 mmol), tert-butyl azetidin-3-ylcarbamate (110 mg, 0.641 mmol) and 1,4-dioxane (0.5 mL) was heated under microwave conditions at 150° C. for 15 min and the reaction mixture was purified by flash chromatography (Biotage 11 g KP-NH, 0-100% EtOAc in PE then 0-30% MeOH in EtOAc) to give the title compound (24 mg, 71%) as a colourless solid. LCMS (Method A): $R_T$=1.19 min, m/z=526 [M+H]$^+$.

Step 2: (R)-6-(3-Aminoazetidin-1-yl)-3-((4-hydroxy-1-(3-phenylbutanoyl)piperidin-4-yl)methyl)pyrimidin-4(3H)-one General procedure 2 using (R)-tert-butyl (1-(1-((4-hydroxy-1-(3-phenylbutanoyl)piperidin-4-yl)methyl)-6-oxo-1,6-dihydropyrimidin-4-yl)azetidin-3-yl)carbamate (21 mg, 0.040 mmol), TFA (0.5 mL) and DCM (0.5 mL) gave the title compound (14 mg, 82%) as a colourless solid. LCMS (Method A): $R_T$=0.56 min, m/z=426 [M+H]$^+$. $^1$H NMR (300 MHz, CDCl$_3$, this molecule appears as two conformers A and B in a 2:3 ratio respectively): δ 7.75 (s, 0.4H (conformer A)), 7.65 (s, 0.6H (conformer B)), 7.38-7.15 (m, 5H), 5.15-5.05 (m, 1H), 4.50-4.19 (m, 3H), 4.00-3.17 (m, 9H), 3.05-2.83 (m, 1H), 2.72-2.58 (m, 1H), 2.58-2.42 (m, 1H), 1.93-1.10 (m, 9H), 0.63-0.49 (m, 0.6H (conformer B)).

Example 14: (R)-5-Amino-6-chloro-3-((4-hydroxy-1-(3-phenylbutanoyl)piperidin-4-yl)methyl)pyrimidin-4(3H)-one

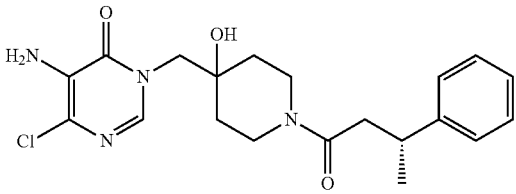 [SMILES: C[C@H](CC(=O)N1CCC(O)(Cn2cnc(Cl)c(N)c2=O)CC1)c1ccccc1]

General procedure 1 using Epoxide 2 (100 mg, 0.386 mmol), 5-amino-6-chloropyrimidin-4(3H)-one (56 mg, 0.386 mmol), DIPEA (101 μL, 0.578 mmol) and DMF (0.8 mL) gave the title compound (90 mg, 46%) as a colourless foam. LCMS (Method A): $R_T$=1.03 min, m/z=405, 407 [M+H]$^+$. $^1$H NMR (300 MHz, CDCl$_3$, this molecule appears as two conformers A and B in a 2:3 ratio respectively): δ 7.57 (s, 0.4H (conformer A)), 7.46 (s, 0.6H (conformer B)), 7.37-7.14 (m, 5H), 4.45-4.21 (m, 3H), 4.11-3.70 (m, 3H), 3.63-3.45 (m, 1H), 3.40-3.12 (m, 2H), 3.08-2.83 (m, 1H), 2.71-2.58 (m, 1H), 2.57-2.40 (m, 1H), 1.60-1.20 (m, 7H), 0.75-0.60 (m, 0.6H (conformer B)).

Example 15: (R)-1-((4-Hydroxy-1-(3-phenylbutanoyl)piperidin-4-yl)methyl)-9-methyl-1H-purin-6(9H)-one

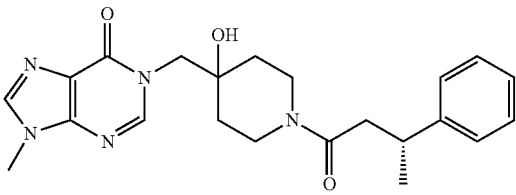 [SMILES: C[C@H](CC(=O)N1CCC(O)(Cn2cnc3c(ncn3C)c2=O)CC1)c1ccccc1]

General procedure 1 using Epoxide 2 (86 mg, 0.333 mmol), 9-methyl-1H-purin-6(9H)-one (*J. Am. Chem. Soc.* 1957, 79, 490) (50 mg, 0.333 mmol), Cs$_2$CO$_3$ (163 mg, 0.500 mmol) and DMF (0.7 mL) gave the title compound (63 mg, 46%) as a colourless solid. LCMS (Method A): $R_T$=0.85 min, m/z=410 [M+H]$^+$. $^1$H NMR (300 MHz, CDCl$_3$, this molecule appears as two conformers A and B in a 2:3 ratio respectively): δ 8.22 (s, 0.4H (conformer A)), 8.11 (s, 0.6H (conformer B)), 7.74 (s, 1H), 7.38-7.12 (m, 5H), 4.58-4.01 (m, 4H), 3.77 (s, 3H), 3.65-3.48 (m, 1H), 3.41-3.18 (m, 2H), 3.10-2.86 (m, 1H), 2.69-2.41 (m, 2H), 1.65-1.23 (m, 7H), 1.01-0.85 (m, 0.6H (conformer B only)).

Example 16: (R)-1-((4-Hydroxy-1-(3-phenylbutanoyl)piperidin-4-yl)methyl)-9-methyl-8-phenyl-1H-purin-6(9H)-one

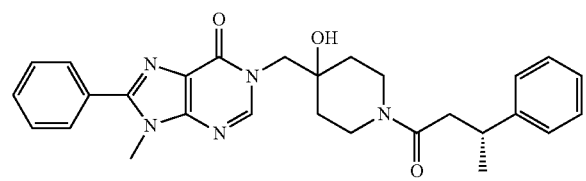 [SMILES: C[C@H](CC(=O)N1CCC(O)(Cn2cnc3c(nc(-c4ccccc4)n3C)c2=O)CC1)c1ccccc1]

Step 1: 8-Bromo-9-methyl-1H-purin-6(9H)-one

To a stirred suspension of 9-methyl-1H-purin-6(9H)-one (190 mg, 1.27 mmol) in AcOH (1.3 mL) in a reaction tube was dropwise added Br$_2$ (196 μL, 3.80 mmol). The reaction tube was then sealed and the mixture heated at 95° C. for 16 h before the reaction was cooled to RT. To this mixture was then added MeOH (7 mL) and Et$_2$O (7 mL). The resulting precipitate was collected by filtration, washed with Et$_2$O and dried in vacuo to give the title compound (246 mg, 85%) as beige solid. LCMS (Method A): $R_T$=0.38 min, m/z=229, 231 [M+H]$^+$.

Step 2: (R)-8-Bromo-1-((4-hydroxy-1-(3-phenylbutanoyl)piperidin-4-yl)methyl)-9-methyl-1H-purin-6(9H)-one General procedure 1 using Epoxide 2 (45 mg, 0.175 mmol), 8-bromo-9-methyl-1H-purin-6(9H)-one (40 mg, 0.175 mmol), Cs$_2$CO$_3$ (85 mg, 0.262 mmol) and DMF (0.35 mL) gave the title compound (55 mg, 64%) as a colourless solid. LCMS (Method A): $R_T$=1.02 min, m/z=488, 490 [M+H]$^+$.

Step 3: (R)-1-((4-Hydroxy-1-(3-phenylbutanoyl)piperidin-4-yl)methyl)-9-methyl-8-phenyl-1H-purin-6(9H)-one General procedure 5 using (R)-8-bromo-1-((4-hydroxy-1-(3-phenylbutanoyl)piperidin-4-yl)methyl)-9-methyl-1H-purin-6(9H)-one (57 mg, 0.117 mmol), phenylboronic acid (43 mg, 0.350 mmol), K$_3$PO$_4$ (74 mg, 0.350 mmol), Pd(PPh$_3$)$_4$(13.5 mg, 0.012 mmol), 1,4-dioxane (0.9 mL) and water (0.23 mL) in a microwave at 150° C. for 10 min gave the title compound (46 mg, 81%) as a colourless solid. LCMS (Method A): $R_T$=1.17 min, m/z=486 [M+H]$^+$. $^1$H NMR (300 MHz, CDCl$_3$, this molecule appears as two conformers A and B in a 2:3 ratio respectively): δ 8.14 (s, 0.4H (conformer A)), 8.01 (s, 0.6H (conformer B)), 7.86-7.73 (m, 2H), 7.61-7.45 (m, 3H), 7.41-7.12 (m, 5H), 4.42-3.94 (m, 3H), 3.85 (d, 3H), 3.66-2.84 (m, 5H), 2.71-2.40 (m, 2H), 1.65-1.24 (m, 7H), 0.97-0.78 (m, 0.6H (conformer B only)).

Example 17: (R)-1-((4-Hydroxy-1-(3-phenylbutanol)piperidin-4-yl)methyl)-9-phenyl-1H-purin-6(9H)-one

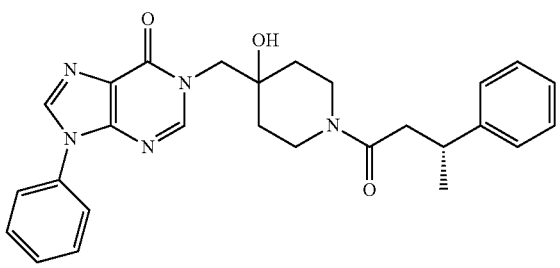 [SMILES: C[C@H](CC(=O)N1CCC(O)(Cn2cnc3c(ncn3-c3ccccc3)c2=O)CC1)c1ccccc1]

Step 1: 9-Phenyl-1H-purin-6(9H)-one

A solution of 6-chloro-N$^4$-phenylpyrimidine-4,5-diamine (*J. Combinatorial Chem.* 2003, 5, 653) (250 mg, 1.133 mmol) and formic acid (1.78 mL, 46.5 mmol) was refluxed for 8 h. The solution was then concentrated and NH₄OH was added to residue until pH=10 was reached. The crude product was collected and recrystallized from water to give the title compound as colourless needles (127 mg, 53%). LCMS (Method A): $R_T$=0.63 min, m/z=213 [M+H]⁺. ¹H NMR (300 MHz, DMSO-d₆): δ 8.48 (s, 1H), 8.10 (s, 1H), 7.82-7.73 (m, 2H), 7.65-7.54 (m, 2H), 7.53-7.44 (m, 1H).

Step 2: (R)-1-((4-Hydroxy-1-(3-phenylbutanoyl) piperidin-4-yl)methyl)-9-phenyl-1H-purin-6(9H)-one General procedure 1 using Epoxide 2 (61 mg, 0.236 mmol), 9-phenyl-1H-purin-6(9H)-one (50 mg, 0.236 mmol), Cs₂CO3 (115 mg, 0.353 mmol) and DMF (0.5 mL) gave the title compound (61 mg, 55%) as a colourless solid. LCMS (Method A): $R_T$=1.15 min, m/z=472 [M+H]⁺. ¹H NMR (300 MHz, CDCl₃, this molecule appears as two conformers A and B in a 2:3 ratio respectively): δ 8.20 (s, 0.4H (conformer A)), 8.09 (s, 0.6H (conformer B)), 8.00 (s, 1H), 7.63-7.41 (m, 5H), 7.36-7.12 (m, 5H), 4.41-3.95 (m, 3H), 3.64-3.50 (m, 1H), 3.39-2.89 (m, 3H), 2.69-2.40 (m, 2H), 1.68-1.24 (m, 7H), 1.01-0.83 (m, 0.6H (conformer B only)).

Example 18: (R)-3-((4-Hydroxy-1-(3-phenylbutanoyl)piperidin-4-yl)methyl)-4H-pyrido[1,2-a]pyrimidin-4-one

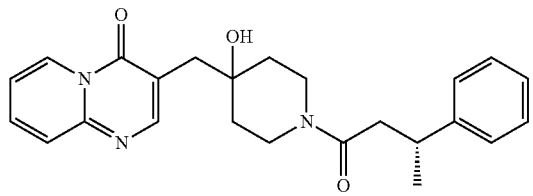 [SMILES: C[C@H](CC(=O)N1CCC(O)(Cc2cnc3ccccn3c2=O)CC1)c1ccccc1]

Step 1: (E)-tert-Butyl 3-((dimethylamino)methylene)-2-oxo-1-oxa-8-azaspiro[4.5]decane-8-carboxylate A solution of tert-butyl 2-oxo-1-oxa-8-azaspiro[4.5]decane-8-carboxylate (PCT Int. Appl., 2004058763, 15 Jul. 2004) (1 g, 3.92 mmol) and tert-butoxybis(dimethylamino) methane (1.21 mL, 5.88 mmol) in toluene (8 mL) were heated in a sealed tube at 90° C. for 24 h before the volatiles were removed in vacuo. The crude product was purified by crystallisation from DCM/MeOH to give (E)-tert-butyl 3-((dimethylamino)methylene)-2-oxo-1-oxa-8-azaspiro [4.5]decane-8-carboxylate (0.650 g, 53%) as a yellow solid. LCMS (Method A): $R_T$=1.14 min, m/z=311 [M+H]⁺. ¹H NMR (300 MHz, CDCl₃): δ 7.16 (t, 1H), 3.79 (d, 2H), 3.37-3.19 (m, 2H), 3.02 (s, 6H), 2.86 (s, 2H), 1.79 (d, 2H), 1.66-1.52 (m, 2H), 1.45 (s, 9H).

Step 2: (R)-3-((4-Hydroxy-1-(3-phenylbutanoyl) piperidin-4-yl)methyl)-4H-pyrido[1,2-a]pyrimidin-4-one A suspension of (E)-tert-butyl 3-((dimethylamino)methylene)-2-oxo-1-oxa-8-azaspiro[4.5]decane-8-carboxylate (120 mg, 0.387 mmol), pyridin-2-amine (36 mg, 0.387 mmol) and NaOAc (32 mg, 0.387 mmol) in AcOH (1.5 mL) was refluxed for 16 h. The reaction was cooled to RT then loaded onto a 5 g Biotage SCX-2 cartridge (pre-equilibriated with 20% MeOH in DCM) and the column was flushed under gravity with 20% MeOH in DCM (2×50 mL) and then with 20% 7 M NH₃ in MeOH in DCM (2×50 mL). The desired product was contained in the NH₃ washes which were concentrated and the residue purified by flash chromatography (11 g Biotage KP-NH, 0-100% DCM in PE then 0-30% MeOH in DCM) to give approximately 30% pure (3-((4-hydroxypiperidin-4-yl)methyl)-4H-pyrido[1,2-a]pyrimidin-4-one (11 mg). This material was used directly in General procedure 4 using (R)-3-phenylbutanoic acid (10.45 mg, 0.064 mmol), HATU (24 mg, 0.064 mmol), DIPEA (30 μl, 0.170 mmol) and DCM (1 ml) to give the title compound (2.8 mg, 1.8% (2 steps)) as a colourless solid. LCMS (Method A): $R_T$=0.99 min, m/z=406 [M+H]⁺. ¹H NMR (300 MHz, CDCl₃): δ 9.12-9.05 (m, 1H), 8.30-8.13 (m, 1H), 7.83-7.68 (m, 2H), 7.40-7.16 (m, 6H), 4.53-4.44 (m, 1H), 4.44-4.30 (m, 1H), 3.61-3.47 (m, 1H), 3.43-3.25 (m, 2H), 3.08-2.86 (m, 2H), 2.78-2.71 (m, 1H), 2.71-2.61 (m, 1H), 2.59-2.44 (m, 1H), 1.60-1.28 (m, 6H), 0.94-0.69 (m, 1H).

Example 19: (R)-3-((4-Hydroxy-1-(3-phenylbutanoyl)piperidin-4-yl)methyl)-9-phenyl-4H-pyrido[1,2-a]pyrimidin-4-one

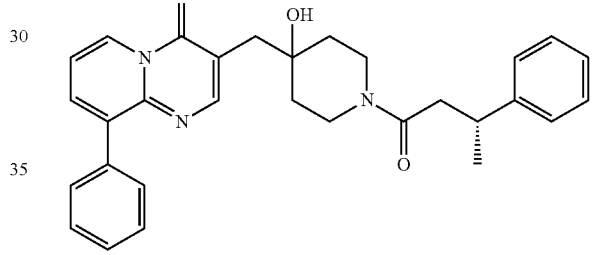

Step 1: 3-Bromo-9-phenyl-4H-pyrido[1,2-a]pyrimidin-4-one

To a solution of 9-phenyl-4H-pyrido[1,2-a]pyrimidin-4-one (*Org. Biomol. Chem.*, 2011, 9, p6559-6565) (454 mg, 2.04 mmol) in CCl₄ (20 mL) was added NBS (436 mg, 2.45 mmol) and the reaction was stirred at RT for 44 h before the reaction was quenched by the addition of saturated sodium thiosulfate$_{(aq)}$ (10 mL). The mixture was extracted with DCM (20 mL) and the organic layer was washed with saturated NaHCO$_{3(aq)}$ (20 mL). The organic layer was passed through a phase separator, concentrated and the crude product purified by flash chromatography (Biotage 50 g KP-Sil, 0-100% EtOAc in PE) to give the title compound (440 mg, 72%) as a colourless solid that darkened upon standing. LCMS (Method A): $R_T$=1.44 min, m/z=301, 303 [M+H]⁺. ¹H NMR (300 MHz, CDCl₃): δ 9.18 (dd, 1H), 8.60 (s, 1H), 7.81 (dd, 1H), 7.67-7.57 (m, 2H), 7.57-7.42 (m, 3H), 7.32 (t, 1H).

Step 2: tert-Butyl 4-((4-oxo-9-phenyl-4H-pyrido[1,2-a]pyrimidin-3-yl)methylene) piperidine-1-carboxylate General procedure 5 using 3-bromo-9-phenyl-4H-pyrido [1,2-a]pyrimidin-4-one (346 mg, 1.15 mmol), tert-butyl 4-((4,4,5,5-tetramethyl-1,3,2-dioxaborolan-2-yl)methylene)

piperidine-1-carboxylate (PCT Int. Appl., 2013027001, 28 Feb. 2013) (446 mg, 1.38 mmol), Pd(PPh$_3$)$_4$(66 mg, 0.057 mmol), Na$_2$CO$_3$ (487 mg, 4.60 mmol), DME (5 mL) and water (1 mL) at 100° C. for 3 days gave the title compound (354 mg, 74%) as a yellow solid. LCMS (Method A): R$_T$=1.84 min, m/z=418 [M+H]$^+$. $^1$H NMR (300 MHz, CDCl$_3$): δ 9.13 (dd, 1H), 8.26 (s, 1H), 7.69 (dd, 1H), 7.65-7.55 (m, 2H), 7.52-7.38 (m, 3H), 7.21 (t, 1H), 6.35 (s, 1H), 3.52 (t, 2H), 3.40 (t, 2H), 2.52-2.19 (m, 4H), 1.47 (s, 9H).

Step 3: tert-Butyl 2-(4-oxo-9-phenyl-4H-pyrido[1,2-a]pyrimidin-3-yl)-1-oxa-6-azaspiro[2.5]octane-6-carboxylate To a solution of tert-butyl 4-((4-oxo-9-phenyl-4H-pyrido[1,2-a]pyrimidin-3-yl)methylene)piperidine-1-carboxylate (150 mg, 0.359 mmol) in DCM (0.5 mL) was added 50-55% mCPBA (186 mg, 0.539 mmol). The reaction was stirred at RT for 2 h before being quenched by the addition of saturated sodium thiosulfate (aq.) (10 mL). The mixture was then extracted with DCM (2×10 mL) using a Biotage phase separator and the combined organic layers were washed with saturated NaHCO$_{3(aq)}$ (10 mL) using a phase separator. The organic phase was concentrated and the crude material purified by flash chromatography (25 g Biotage KP-Sil, 0-100% EtOAc in PE) to give the title compound (77 mg, 49%) as a yellow solid. LCMS (Method A): R$_T$=1.71 min, m/z=434 [M+H]$^+$. $^1$H NMR (300 MHz, CDCl$_3$): δ 9.11 (dd, 1H), 8.28 (d, 1H), 7.76 (dd, 1H), 7.66-7.56 (m, 2H), 7.53-7.39 (m, 3H), 7.28 (t, 1H), 4.11 (s, 1H), 3.67 (t, 2H), 3.55-3.29 (m, 2H), 1.96-1.71 (m, 2H), 1.56-1.35 (m, 2H), 1.41 (s, 9H).

Step 4: tert-Butyl 4-hydroxy-4-((4-oxo-9-phenyl-4H-pyrido[1,2-a]pyrimidin-3-yl)methyl)piperidine-1-carboxylate A suspension of tert-butyl 2-(4-oxo-9-phenyl-4H-pyrido[1,2-a]pyrimidin-3-yl)-1-oxa-6-azaspiro[2.5]octane-6-carboxylate (77 mg, 0.178 mmol), 10% Pd/C (19 mg, 0.018 mmol), Et$_3$N (248 µL, 1.776 mmol) and formic acid (68 µL, 1.776 mmol) in EtOAc (2 mL) was stirred at room temperature for 18 h before the reaction was filtered through Dicalite® speed plus and the filtrate partitioned between DCM (20 mL) and water (20 mL). The mixture was extracted with DCM (3×20 mL) using a Biotage phase separator and the combined organic phases were concentrated and the products purified by flash chromatography (10 g Biotage KP-Sil, 0-100% EtOAc in PE) to give the title compound (49 mg, 63%) as a colourless solid. LCMS (Method A): R$_T$=1.54 min, m/z=436 [M+H]$^+$. $^1$H NMR (300 MHz, CDCl$_3$): δ 9.14 (dd, 1H), 8.25 (s, 1H), 7.75 (dd, 1H), 7.67-7.59 (m, 2H), 7.56-7.42 (m, 3H), 7.28 (t, 1H), 4.41 (br s, 1H), 3.99-3.60 (m, 2H), 3.20 (t, 2H), 2.89 (s, 2H), 1.68-1.49 (m, 4H), 1.45 (s, 9H).

Step 5: 3-((4-Hydroxypiperidin-4-yl)methyl)-9-phenyl-4H-pyrido[1,2-a]pyrimidin-4-one General procedure 2 using tert-butyl 4-hydroxy-4-((4-oxo-9-phenyl-4H-pyrido[1,2-a]pyrimidin-3-yl)methyl)piperidine-1-carboxylate (49 mg, 0.113 mmol), TFA (1 mL) and DCM (1 mL) gave the title compound (31 mg, 81%) as a pale yellow solid. LCMS (Method A): R$_T$=0.65 min, m/z=336 [M+H]$^+$. $^1$H NMR (300 MHz, CDCl$_3$): δ 9.14 (dd, 1H), 8.26 (s, 1H), 7.74 (dd, 1H), 7.70-7.58 (m, 2H), 7.57-7.41 (m, 3H), 7.26 (t, 1H), 3.47 (s, 1H), 3.28-2.66 (m, 4H), 2.91 (s, 2H), 2.00-1.40 (m, 5H).

Step 6: (R)-3-((4-Hydroxy-1-(3-phenylbutanoyl)piperidin-4-yl)methyl)-9-phenyl-4H-pyrido[1,2-a]pyrimidin-4-one General procedure 4 using 3-((4-hydroxypiperidin-4-yl)methyl)-9-phenyl-4H-pyrido[1,2-a]pyrimidin-4-one (31 mg, 0.092 mmol), (R)-3-phenylbutanoic acid (23 mg, 0.139 mmol), HATU (53 mg, 0.139 mmol), DIPEA (65 µL, 0.370 mmol) and DCM (2 ml) to give the title compound (38 mg, 85%) as a colourless solid. LCMS (Method A): R$_T$=1.46 min, m/z=482 [M+H]$^+$. $^1$H NMR (300 MHz, CDCl$_3$): δ 9.16-8.98 (m, 1H), 8.32-8.03 (m, 1H), 7.75-7.64 (m, 1H), 7.62-7.51 (m, 2H), 7.50-7.33 (m, 3H), 7.30-7.06 (m, 6H), 4.57-4.39 (m, 1H), 4.37-4.18 (m, 1H), 3.58-3.11 (m, 3H), 3.05-2.34 (m, 5H), 1.60-1.20 (m, 6H), 0.84-0.64 (m, 1H).

Example 20: (R)-6-((4-Hydroxy-1-(3-phenylbutanoyl)piperidin-4-yl)methyl)-2-methyl-2H-pyrazolo[4,3-d]pyrimidin-7(6H)-one

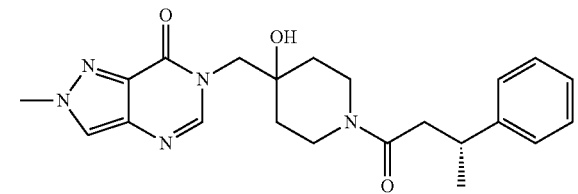 [SMILES: C[C@H](CC(=O)N1CCC(O)(Cn2cnc3cn(C)nc3c2=O)CC1)c1ccccc1]

Step 1: tert-Butyl 4-hydroxy-4-((2-methyl-7-oxo-2H-pyrazolo[4,3-d]pyrimidin-6(7H)-yl)methyl)piperidine-1-carboxylate General procedure 1 using Epoxide 1 (284 mg, 1.33 mmol), 2-methyl-2H-pyrazolo[4,3-d]pyrimidin-7(6H)-one (PCT Int. Appl., 2007013964, 1 Feb. 2007) (200 mg, 1.33 mmol), Cs$_2$CO$_3$ (1.30 mg, 4.00 mmol) and DMF (2.6 mL) gave the title compound (389 mg, 80%) as a colourless solid. LCMS (Method A): R$_T$=0.99 min, m/z=386 [M+Na]$^+$. $^1$H NMR (300 MHz, CDCl$_3$): δ 8.02 (s, 1H), 7.86 (s, 1H), 4.38-4.02 (m, 5H), 3.95-3.74 (m, 2H), 3.26-3.12 (m, 2H), 1.73-1.55 (m, 4H), 1.44 (s, 9H).

Step 2: 6-((4-Hydroxypiperidin-4-yl)methyl)-2-methyl-2H-pyrazolo[4,3-d]pyrimidin-7(6H)-one General procedure 2 using tert-butyl 4-hydroxy-4-((2-methyl-7-oxo-2H-pyrazolo[4,3-d]pyrimidin-6(7H)-yl)methyl)piperidine-1-carboxylate (120 mg, 0.330 mmol), TFA (2 mL) and DCM (2 mL) gave the title compound (82 mg, 94%) as a pale yellow solid. LCMS (Method A): R$_T$=0.23 min, m/z=264 [M+H]$^+$.

Step 3: (R)-6-((4-Hydroxy-1-(3-phenylbutanoyl)piperidin-4-yl)methyl)-2-methyl-2H-pyrazolo[4,3-d]pyrimidin-7(6H)-one General procedure 3 using 6-((4-hydroxypiperidin-4-yl)methyl)-2-methyl-2H-pyrazolo[4,3-d]pyrimidin-7(6H)-one (28 mg, 0.106), (R)-3-phenylbutanoic acid (18 mg, 0.106 mmol), EDC (61 mg, 0.319 mmol) and DCM (1 mL) gave the title compound (27 mg, 62%) as a colourless solid. LCMS (Method A): R$_T$=0.91 min, m/z=410 [M+H]$^+$. $^1$H NMR (300 MHz, CDCl$_3$, this molecule appears as two conformers A and B in a 2:3 ratio respectively): δ 7.91-7.74 (m, 2H), 7.36-7.16 (m, 5H), 4.38-3.88 (m, 6H), 3.60-2.90 (m, 5H), 2.69-2.43 (m, 2H), 1.67-1.24 (m, 7H), 0.92-0.78 (m, 0.6H (conformer B only)).

Example 21: (R)-3-Bromo-6-((4-hydroxy-1-(3-phenylbutanoyl)piperidin-4-yl)methyl)-2-methyl-2H-pyrazolo[4,3-d]pyrimidin-7(6H)-one (Intermediate B)

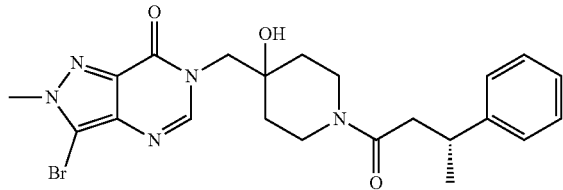 [SMILES: C[C@H](CC(=O)N1CCC(O)(Cn2cnc3c(Br)n(C)nc3c2=O)CC1)c1ccccc1]

Step 1: 3-Bromo-2-methyl-2H-pyrazolo[4,3-d]pyrimidin-7(6H)-one

To a stirred suspension of 2-methyl-2H-pyrazolo[4,3-d]pyrimidin-7(6H)-one (400 mg, 2.66 mmol) in AcOH (2.664 mL) in a 10 mL vial was added dropwise Br$_2$ (412 µL, 7.99 mmol). The vial was sealed and the mixture was heated at 95° C. for 16 h before cooling to room temperature. To this mixture was added MeOH (4 mL) and Et$_2$O (4 mL). The resulting precipitate was collected by filtration, washed with Et$_2$O and dried in vacuo to give the title compound (555 mg, 91%) as beige solid. LCMS (Method A): R$_T$=0.40 min, m/z=229, 231 [M+H]$^+$. $^1$H NMR (300 MHz, DMSO-d$_6$): δ 12.06 (br s, 1H), 7.85 (s, 1H), 4.07 (s, 3H).

Step 2: (R)-3-Bromo-6-((4-hydroxy-1-(3-phenylbutanoyl)piperidin-4-yl)methyl)-2-methyl-2H-pyrazolo[4,3-d]pyrimidin-7(6H)-one (Intermediate B)

General procedure 1 using Epoxide 2 (453 mg, 1.75 mmol), 3-bromo-2-methyl-2H-pyrazolo[4,3-d]pyrimidin-7(6H)-one (400 mg, 1.75 mmol) and Cs$_2$CO$_3$ (854 mg, 2.62 mmol) gave the title compound (529 mg, 62%) as a colourless solid. LCMS (Method A): R$_T$=1.06 min, m/z=488, 490 [M+H]$^+$. $^1$H NMR (300 MHz, CDCl$_3$, this molecule appears as two conformers A and B in a 2:3 ratio respectively): δ 7.89 (s, 0.4H (conformer A)), 7.77 (s, 0.6H (conformer B)), 7.38-7.16 (m, 5H), 4.45-4.38 (m, 1H), 4.14 (s, 3H), 4.00-3.84 (m, 2H), 3.62-2.86 (m, 5H), 2.71-2.42 (m, 2H), 1.74-1.23 (m, 7H), 0.80-0.68 (m, 0.6H (conformer B only)).

Example 22: (R)-3-Ethynyl-6-((4-hydroxy-1-(3-phenylbutanoyl)piperidin-4-yl)methyl)-2-methyl-2H-pyrazolo[4,3-d]pyrimidin-7(6H)-one

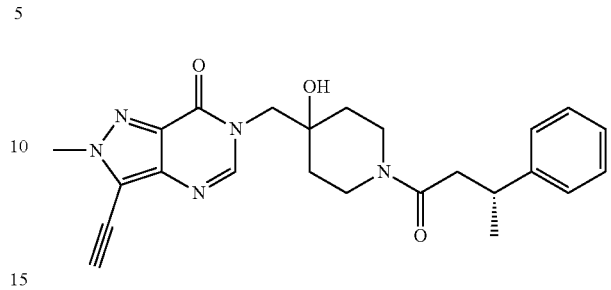

Step 1: tert-Butyl 4-((3-bromo-2-methyl-7-oxo-2H-pyrazolo[4,3-d]pyrimidin-6(7H)-yl)methyl)-4-hydroxypiperidine-1-carboxylate (Intermediate C)

General procedure 1 using Epoxide 1 (293 mg, 1.28 mmol), 3-bromo-2-methyl-2H-pyrazolo[4,3-d]pyrimidin-7(6H)-one (300 mg, 1.41 mmol) and Cs$_2$CO$_3$ (500 mg, 1.54 mmol) gave the title compound (223 mg, 39%) as a colourless solid. LCMS (Method A): R$_T$=1.06 min, m/z=464, 466 [M+Na]$^+$. $^1$H NMR (300 MHz, CDCl$_3$): δ 7.92 (s, 1H), 4.19-4.02 (m, 2H), 4.16 (s, 3H), 4.00-3.76 (m, 2H), 3.26-3.07 (m, 2H), 1.73-1.52 (m, 4H), 1.46 (s, 9H).

Step 2: tert-Butyl 4-hydroxy-4-((2-methyl-7-oxo-3-((trimethylsilyl)ethynyl)-2H-pyrazolo[4,3-d]pyrimidin-6(7H)-yl)methyl)piperidine-1-carboxylate General procedure 6 using Intermediate 1 (60 mg, 0.136 mmol), CuI (5.2 mg, 0.027 mmol), Pd(PPh$_3$)$_2$Cl$_2$ (9.5 mg, 0.014 mmol), triethylamine (0.378 mL, 2.71 mmol), ethynyltrimethylsilane (75 µL, 0.918 mmol) and toluene (1.4 mL) at 110° C. for 16 h gave the title compound (41 mg, 66%) as a yellow oil. LCMS (Method A): R$_T$=1.60 min, m/z=460 [M+H]$^+$. $^1$H NMR (300 MHz, CDCl$_3$): δ 7.94 (s, 1H), 4.27-4.00 (m, 5H), 4.00-3.77 (m, 2H), 3.27-3.06 (m, 3H), 1.75-1.39 (m, 13H), 0.31 (s, 9H).

Step 3: 3-Ethynyl-6-((4-hydroxypiperidin-4-yl)methyl)-2-methyl-2H-pyrazolo[4,3-d]pyrimidin-7(6H)-one General procedure 2 using tert-butyl 4-hydroxy-4-((2-methyl-7-oxo-3-((trimethylsilyl)ethynyl)-2H-pyrazolo[4,3-d]pyrimidin-6(7H)-yl)methyl)piperidine-1-carboxylate (32 mg, 0.070 mmol), TFA (1 mL) and DCM (1 mL) gave a mixture of the TMS and desilated alkyne. This material was treated with K$_2$CO$_3$ (29 mg, 0.209 mmol) in MeOH (1 mL) for 45 min before the reaction was purified directly by flash chromatography (Biotage 11 g KP-NH, 0-100% DCM in PE then 0-40% MeOH in DCM) affording the title compound (16 mg, 80% (2 steps)) as a colourless solid. LCMS (Method A): R$_T$=0.33 min, m/z=288 [M+H]$^+$.

Step 4: (R)-3-Ethynyl-6-((4-hydroxy-1-(3-phenylbutanoyl)piperidin-4-yl)methyl)-2-methyl-2H-pyrazolo[4,3-d]pyrimidin-7(6H)-one General procedure 3 using 3-ethynyl-6-((4-hydroxypiperidin-4-yl)methyl)-2-methyl-2H-pyrazolo[4,3-d]pyrimidin-7(6H)-one (12 mg, 0.042 mmol), (R)-3-phenylbutanoic acid (7 mg, 0.042 mmol), EDC (24 mg, 0.125 mmol) and DCM (0.4 mL) gave the title compound (9 mg, 50%) as a colourless solid. LCMS (Method A): $R_T$=1.06 min, m/z=434 [M+H]$^+$. $^1$H NMR (300 MHz, CDCl$_3$, this molecule appears as two conformers A and B in a 2:3 ratio respectively): δ 7.94 (s, 0.4H (conformer A)), 7.82 (s, 0.6H (conformer B)), 7.39-7.16 (m, 5H), 4.42-4.32 (m, 1H), 4.17 (s, 3H), 4.01-3.88 (m, 2H), 3.61-2.87 (m, 5H), 2.71-2.41 (m, 2H), 1.67-1.23 (m, 8H), 0.89-0.75 (m, 0.6H (conformer B only)).

Example 23: (R)-6-((4-Hydroxy-1-(3-phenylbutanoyl)piperidin-4-yl)methyl)-2-methyl-3-(trifluoromethyl)-2H-pyrazolo[4,3-d]pyrimidin-7(6H)-one

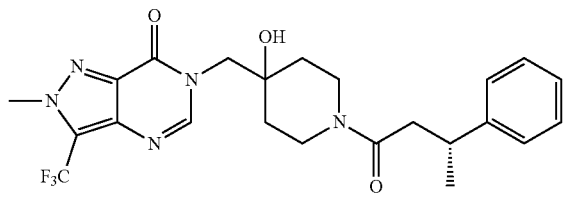 [SMILES: C[C@H](CC(=O)N1CCC(O)(Cn2cnc3c(C(F)(F)F)n(C)nc3c2=O)CC1)c1ccccc1]

Step 1: 2-Methyl-3-(trifluoromethyl)-2H-pyrazolo[4,3-d]pyrimidin-7(6H)-one

To a mixture of 2-methyl-2H-pyrazolo[4,3-d]pyrimidin-7(6H)-one (150 mg, 0.999 mmol) and sodium trifluoromethanesulfinate (468 mg, 3.00 mmol) in DCM (4 mL) and water (1.5 mL) was dropwise added t-BuOOH (484 μL, 5.00 mmol). The reaction showed incomplete conversion after 24 h therefore further sodium trifluoromethanesulfinate (468 mg, 3.00 mmol) and t-BuOOH (484 μL, 5.00 mmol) were added. After 24 h the reaction mixture was diluted with water (20 mL) and extracted with DCM (5×10 mL) using a Biotage phase separator. The combined organic layers were concentrated and then dried in vacuo to give the title compound (147 mg, 68%) as a beige solid. LCMS (Method A): $R_T$=0.61 min, m/z=219 [M+H]$^+$. $^1$H NMR (300 MHz, DMSO-d$_6$): δ 12.29 (br s, 1H), 7.96 (d, 1H), 4.21 (s, 3H).

Step 2: tert-Butyl 4-hydroxy-4-((2-methyl-7-oxo-3-(trifluoromethyl)-2H-pyrazolo[4,3-d]pyrimidin-6(7H)-yl)methyl)piperidine-1-carboxylate General procedure 1 using Epoxide 1 (207 mg, 0.972 mmol), 2-methyl-3-(trifluoromethyl)-2H-pyrazolo[4,3-d]pyrimidin-7(6H)-one (212 mg, 0.972 mmol), Cs$_2$CO3 (475 mg, 1.458 mmol) and DMF (2 mL) gave the title compound (243 mg, 58%) as a pale yellow solid. LCMS (Method A): $R_T$=1.22 min, m/z=432 [M+H]$^+$. $^1$H NMR (300 MHz, CDCl$_3$): δ 8.30 (s, 1H), 7.94 (s, 1H), 4.11-3.71 (m, 7H), 3.24-3.07 (m, 2H), 1.76-1.39 (m, 13H).

Step 3: 6-((4-Hydroxypiperidin-4-yl)methyl)-2-methyl-3-(trifluoromethyl)-2H-pyrazolo[4,3-d]pyrimidin-7(6H)-one General procedure 2 using tert-butyl 4-hydroxy-4-((2-methyl-7-oxo-3-(trifluoromethyl)-2H-pyrazolo[4,3-d]pyrimidin-6(7H)-yl)methyl)piperidine-1-carboxylate (124 mg, 0.287 mmol), TFA (2 mL) and DCM (2 mL) gave the title compound (85 mg, 89%) as a pale yellow solid. LCMS (Method A): $R_T$=0.37 min, m/z=332 [M+H]$^+$.

Step 4: (R)-6-((4-Hydroxy-1-(3-phenylbutanoyl)piperidin-4-yl)methyl)-2-methyl-3-(trifluoromethyl)-2H-pyrazolo[4,3-d]pyrimidin-7(6H)-one General procedure 3 using 6-((4-hydroxypiperidin-4-yl)methyl)-2-methyl-3-(trifluoromethyl)-2H-pyrazolo[4,3-d]pyrimidin-7(6H)-one (30 mg, 0.091 mmol), (R)-3-phenylbutanoic acid (15 mg, 0.091 mmol), EDC (52 mg, 0.272 mmol) and DCM (0.9 mL) gave the title compound (23 mg, 53%) as a colourless solid. LCMS (Method A): $R_T$=1.21 min, m/z=478 [M+H]$^+$. $^1$H NMR (300 MHz, CDCl$_3$, this molecule appears as two conformers A and B in a 2:3 ratio respectively): δ 8.01 (s, 0.4H (conformer A)), 7.90 (s, 0.6H (conformer B)), 7.38-7.16 (m, 5H), 4.41-3.86 (m, 6H), 3.63-3.49 (m, 1H), 3.39-2.86 (m, 4H), 2.71-2.41 (m, 2H), 1.67-1.22 (m, 7H), 0.89-0.75 (m, 0.6H (conformer B only)).

Example 24: (R)-6-((4-Hydroxy-1-(3-phenylbutanoyl)piperidin-4-yl)methyl)-3-(3-hydroxy-3-methylbut-1-yn-1-yl)-2-methyl-2H-pyrazolo[4,3-d]pyrimidin-7(6H)-one

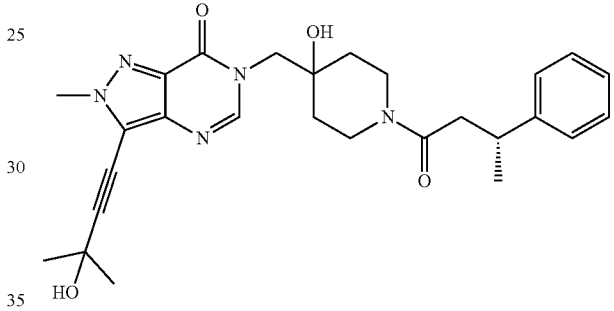

General procedure 6 using Intermediate B (40 mg, 0.061 mmol), CuBr.SMe$_2$ (0.7 mg, 3.28 μmol), Pd(PPh$_3$)$_4$(1.9 mg, 1.64 μmol), triethylamine (0.46 mL, 3.28 mmol) and 2-methylbut-3-yn-2-ol (8 mg, 0.090 mmol) at 70° C. for 1 h gave the title compound (27 mg, 68%) as a colourless solid. LCMS (Method A): $R_T$=1.06 min, m/z=492 [M+H]$^+$. $^1$H NMR (300 MHz, CDCl$_3$, this molecule appears as two conformers A and B in a 2:3 ratio respectively): δ 7.94 (s, 0.4H (conformer A)), 7.86 (s, 0.6H (conformer B)), 7.37-7.15 (m, 5H), 4.45-3.83 (m, 6H), 3.63-3.46 (m, 1H), 3.39-3.19 (m, 2H), 3.12-2.90 (m, 1H), 2.71-2.41 (m, 2H), 2.08 (br s, 2H), 1.76-1.21 (m, 13H), 1.01-0.82 (m, 0.6H (conformer B only)).

Example 25: (R)-6-((4-Hydroxy-1-(3-phenylbutanoyl)piperidin-4-yl)methyl)-2-methyl-3-(1H-pyrazol-5-yl)-2H-pyrazolo[4,3-d]pyrimidin-7(6H)-one

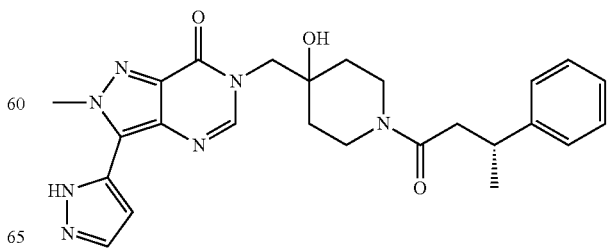

General procedure 5 using Intermediate B (40 mg, 0.082 mmol), (1H-pyrazol-5-yl)boronic acid (28 mg, 0.246 mmol), $K_3PO_4$ (52 mg, 0.246 mmol), $Pd(PPh_3)_4$ (9 mg, 8.19 μmol), 1,4-dioxane (0.65 mL) and water (0.16 mL) in a microwave at 150° C. for 10 min gave the title compound (26 mg, 67%) as a colourless solid. LCMS (Method A): $R_T$=0.97 min, m/z=476 [M+H]$^+$. $^1$H NMR (300 MHz, CDCl$_3$, this molecule appears as two conformers A and B in a 2:3 ratio respectively): δ 7.87 (s, 0.4H (conformer A)), 7.81-7.71 (m, 1.6H (+conformer B)), 7.39-7.15 (m, 6H), 6.95 (br s, 1H), 4.46-3.90 (m, 6H), 3.77-3.47 (m, 2H), 3.44-2.88 (m, 3H), 2.72-2.42 (m, 2H), 1.79-1.24 (m, 7H), 0.97-0.74 (m, 0.6H (conformer B only)).

Example 26: (R)-6-((4-Hydroxy-1-(3-phenylbutanoyl)piperidin-4-yl)methyl)-2-methyl-3-(pyridin-4-yl)-2H-pyrazolo[4,3-d]pyrimidin-7(6H)-one

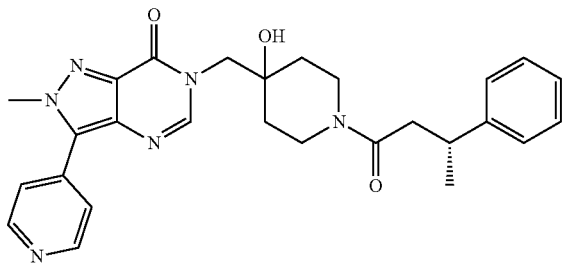 [SMILES: C[C@H](CC(=O)N1CCC(O)(Cn2cnc3c(-c4ccncc4)n(C)nc3c2=O)CC1)c1ccccc1]

General procedure 5 using Intermediate B (50 mg, 0.102 mmol), pyridin-4-ylboronic acid (38 mg, 0.307 mmol), $K_3PO_4$ (65 mg, 0.307 mmol), $Pd(PPh_3)_4$ (12 mg, 10.24 μmol), 1,4-dioxane (0.8 mL) and water (0.2 mL) in a microwave at 150° C. for 10 min gave the title compound (37 mg, 74%) as a colourless solid. LCMS (Method A): $R_T$=0.86 min, m/z=487 [M+H]$^+$. $^1$H NMR (300 MHz, CDCl$_3$, this molecule appears as two conformers A and B in a 2:3 ratio respectively): δ 8.87-8.75 (m, 2H), 7.93 (s, 0.4H (conformer A)), 7.82 (s, 0.6H (conformer B)), 7.58 (d, 2H), 7.40-7.14 (m, 5H), 4.43-3.91 (m, 6H), 3.71-3.49 (m, 2H), 3.41-2.87 (m, 3H), 2.72-2.41 (m, 2H), 1.68-1.24 (m, 7H), 0.98-0.79 (m, 0.6H (conformer B only)).

Example 27: (R)-6-((4-Hydroxy-1-(3-phenylbutanoyl)piperidin-4-yl)methyl)-2-methyl-3-phenyl-2H-pyrazolo[4,3-d]pyrimidin-7(6H)-one

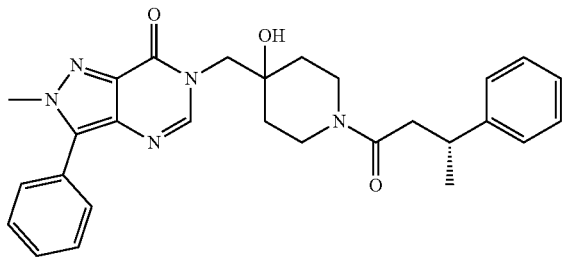 [SMILES: C[C@H](CC(=O)N1CCC(O)(Cn2cnc3c(-c4ccccc4)n(C)nc3c2=O)CC1)c1ccccc1]

General procedure 5 using Intermediate B (40 mg, 0.082 mmol), phenylboronic acid (30 mg, 0.246 mmol), $K_3PO_4$ (52 mg, 0.246 mmol), $Pd(PPh_3)_4$ (9.5 mg, 8.19 μmol), 1,4-dioxane (0.7 mL) and water (0.15 mL) in a microwave at 150° C. for 10 min gave the title compound (31 mg, 78%) as a colourless solid. LCMS (Method A): $R_T$=1.23 min, m/z=486 [M+H]$^+$. $^1$H NMR (300 MHz, CDCl$_3$, this molecule appears as two conformers A and B in a 2:3 ratio respectively): δ 7.84 (s, 0.4H (conformer A)), 7.73 (s, 0.6H (conformer B)), 7.65-7.44 (m, 5H), 7.39-7.14 (m, 5H), 4.43-3.88 (m, 6H), 3.68-3.44 (m, 2H), 3.40-2.85 (m, 3H), 2.71-2.41 (m, 2H), 1.66-1.23 (m, 7H), 0.93-0.73 (m, 0.6H (conformer B only)).

Example 28: (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzamide

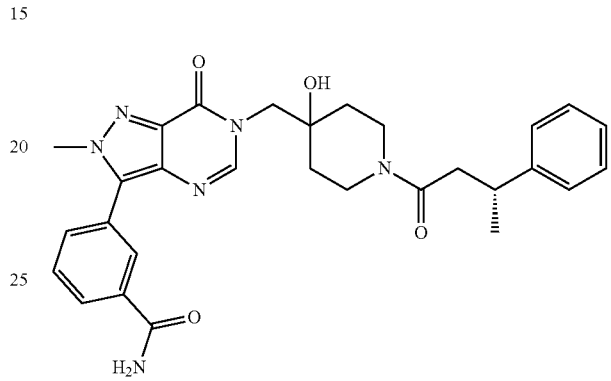

General procedure 5 using Intermediate B (40 mg, 0.082 mmol), (3-carbamoylphenyl)boronic acid (41 mg, 0.246 mmol), $K_3PO_4$ (52 mg, 0.246 mmol), $Pd(PPh_3)_4$ (9.5 mg, 8.19 μmol), 1,4-dioxane (0.65 mL) and water (0.16 mL) in a microwave at 150° C. for 10 min gave the title compound (29 mg, 67%) as a colourless solid. LCMS (Method A): $R_T$=0.96 min, m/z=529 [M+H]$^+$. $^1$H NMR (300 MHz, CDCl$_3$, this molecule appears as two conformers A and B in a 2:3 ratio respectively): δ 8.48-8.43 (m, 1H), 8.19 (s, 0.4H (conformer A)), 8.13-8.05 (m, 1.6H (+conformer B)), 7.99-7.93 (m, 1H), 7.63-7.54 (m, 1H), 7.39-7.17 (m, 5H), 6.97 (s, 1H), 4.51-3.79 (m, 3H), 3.66-3.48 (m, 1H), 3.45-2.81 (m, 3H), 2.75-2.44 (m, 2H), 1.75-1.24 (m, 9H), 0.76-0.60 (m, 0.6H (conformer B only)).

Example 29: (R)-3-(3-Aminophenyl)-6-((4-hydroxy-1-(3-phenylbutanoyl)piperidin-4-yl)methyl)-2-methyl-2H-pyrazolo[4,3-d]pyrimidin-7(6H)-one

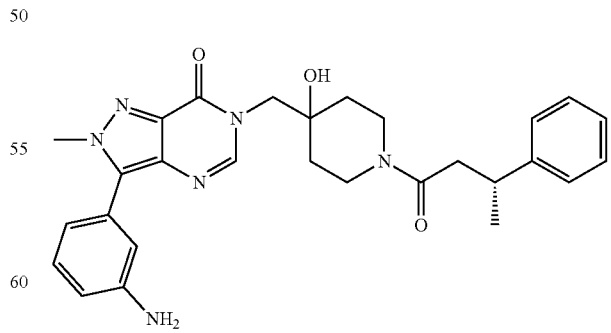

General procedure 5 using Intermediate B (40 mg, 0.082 mmol), (3-aminophenyl)boronic acid (34 mg, 0.246 mmol), $K_3PO_4$ (52 mg, 0.246 mmol), $Pd(PPh_3)_4$ (9.5 mg, 8.19 μmol), 1,4-dioxane (0.65 mL) and water (0.16 mL) in a microwave at 150° C. for 10 min gave the title compound (35 mg, 85%) as a colourless solid. LCMS (Method A): $R_T$=0.99 min, m/z=501 [M+H]$^+$. $^1$H NMR (300 MHz, CDCl$_3$, this molecule appears as two conformers A and B in a 2:3 ratio respectively): δ 7.83 (s, 0.4H (conformer A)), 7.73 (s, 0.6H (conformer B)), 7.38-7.15 (m, 6H), 6.87-6.71 (m, 3H), 4.42-3.71 (m, 8H), 3.59-3.43 (m, 1H), 3.42-3.11 (m, 2H), 3.09-2.82 (m, 1H), 2.71-2.40 (m, 2H), 1.93 (s, 1H), 1.63-1.23 (m, 7H), 0.96-0.73 (m, 0.6H (conformer B only)).

Example 30: (R)-3-(4-(Aminomethyl)phenyl)-6-((4-hydroxy-1-(3-phenylbutanoyl)piperidin-4-yl)methyl)-2-methyl-2H-pyrazolo[4,3-d]pyrimidin-7(6H)-one

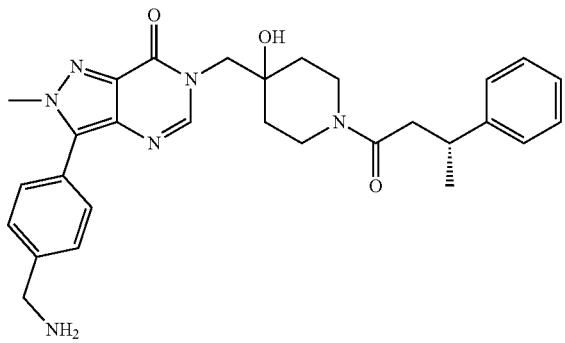 [SMILES: C[C@H](CC(=O)N1CCC(O)(Cn2cnc3c(-c4ccc(CN)cc4)n(C)nc3c2=O)CC1)c1ccccc1]

Step 1: (R)-tert-Butyl 4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzylcarbamate General procedure 5 using Intermediate B (25 mg, 0.051 mmol), tert-butyl 4-(4,4,5,5-tetramethyl-1,3,2-dioxaborolan-2-yl)benzylcarbamate (43 mg, 0.128 mmol), K$_3$PO$_4$ (33 mg, 0.154 mmol), Pd(PPh$_3$)$_4$(6 mg, 5.12 µmol), 1,4-dioxane (0.4 mL) and water (0.1 mL) in a microwave at 130° C. for 15 min gave the title compound (19 mg, 60%) as a colourless solid. LCMS (Method A): $R_T$=1.37 min, m/z=615 [M+H]$^+$.

Step 2: (R)-3-(4-(Aminomethyl)phenyl)-6-((4-hydroxy-1-(3-phenylbutanoyl)piperidin-4-yl)methyl)-2-methyl-2H-pyrazolo[4,3-d]pyrimidin-7(6H)-one General procedure 2 using (R)-tert-butyl 4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzylcarbamate (16 mg, 0.026 mmol), TFA (0.5 mL) and DCM (0.5 mL) gave the title compound (11 mg, 82%) as a colourless solid. LCMS (Method A): $R_T$=0.71 min, m/z=515 [M+H]$^+$. $^1$H NMR (300 MHz, CDCl$_3$, this molecule appears as two conformers A and B in a 2:3 ratio respectively): δ 7.74 (s, 0.4H (conformer A)), 7.63 (s, 0.6H (conformer B)), 7.51-7.41 (m, 4H), 7.30-7.08 (m, 5H), 4.37-4.27 (m, 0.6H (conformer B)), 4.26-4.15 (m, 0.4H (conformer A)), 4.15-3.78 (m, 7H), 3.56-3.41 (m, 1H), 3.34-3.07 (m, 2H), 3.04-2.75 (m, 1H), 2.64-2.50 (m, 1H), 2.50-2.35 (m, 1H), 1.54-1.14 (m, 9H), 0.77-0.63 (m, 0.6H (conformer B only)).

Example 31: (R)-6-((4-Hydroxy-1-(3-phenylbutanoyl)piperidin-4-yl)methyl)-3-(3-hydroxyprop-1-yn-1-yl)-2-methyl-2H-pyrazolo[4,3-d]pyrimidin-7(6H)-one

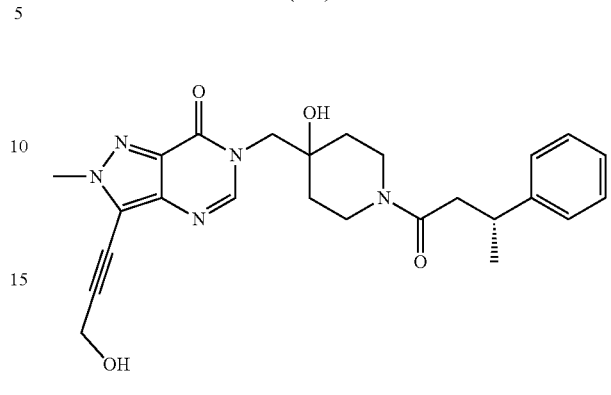

Step 1: 6-((4-Hydroxy-1-((R)-3-phenylbutanoyl)piperidin-4-yl)methyl)-2-methyl-3-(3-((tetrahydro-2H-pyran-2-yl)oxy)prop-1-yn-1-yl)-2H-pyrazolo[4,3-d]pyrimidin-7(6H)-one General procedure 6 using Intermediate B (30 mg, 0.061 mmol), CuI (2.3 mg, 0.012 mmol), Pd(PPh$_3$)$_2$Cl$_2$ (4.3 mg, 6.14 µmol), triethylamine (0.171 mL, 2.71 mmol), 2-(prop-2-yn-1-yloxy)tetrahydro-2H-pyran (34 mg, 0.246 mmol) and toluene (0.6 mL) at 110° C. for 16 h gave the title compound (15 mg, 45%) as a yellow oil. LCMS (Method A): $R_T$=1.31 min, m/z=548 [M+H]$^+$.

Step 2: (R)-6-((4-Hydroxy-1-(3-phenylbutanoyl)piperidin-4-yl)methyl)-3-(3-hydroxyprop-1-yn-1-yl)-2-methyl-2H-pyrazolo[4,3-d]pyrimidin-7(6H)-one To a solution of 6-((4-hydroxy-1-((R)-3-phenylbutanoyl)piperidin-4-yl)methyl)-2-methyl-3-(3-((tetrahydro-2H-pyran-2-yl)oxy)prop-1-yn-1-yl)-2H-pyrazolo[4,3-d]pyrimidin-7(6H)-one (12 mg, 0.022 mmol) in MeOH (0.2 mL) was added p-TsOH-H$_2$O (0.834 mg, 4.38 µmol) and the reaction mixture was stirred for 16 h before K$_2$CO$_3$ (0.606 mg, 4.38 µmol) was added and the resulting suspension was stirred for 30 min. The mixture was diluted with water (20 mL) and the mixture extracted with DCM (3×10 mL) using a Biotage phase separator. The combined organic phases were concentrated and the residue purified by flash chromatography (10 g Biotage KP-Sil, 0-100% EtOAc in PE then 0-30% MeOH in EtOAc) to give the title compound (8 mg, 79%) as a colourless solid. LCMS (Method A): $R_T$=0.95 min, m/z=464 [M+H]$^+$. $^1$H NMR (300 MHz, CDCl$_3$, this molecule appears as two conformers A and B in a 2:3 ratio respectively): δ 7.91 (s, 0.4H (conformer A)), 7.81 (s, 0.6H (conformer B)), 7.40-7.14 (m, 5H), 4.61 (s, 2H), 4.46-3.78 (m, 6H), 3.65-3.47 (m, 1H), 3.40-2.82 (m, 3H), 2.72-2.41 (m, 2H), 1.68-1.21 (m, 7H), 0.93-0.77 (m, 0.6H (conformer B only)).

Example 32: (R)-6-((4-Hydroxy-1-(3-phenylbutanoyl)piperidin-4-yl)methyl)-2-methyl-3-(prop-1-en-2-yl)-2H-pyrazolo[4,3-d]pyrimidin-7(6H)-one

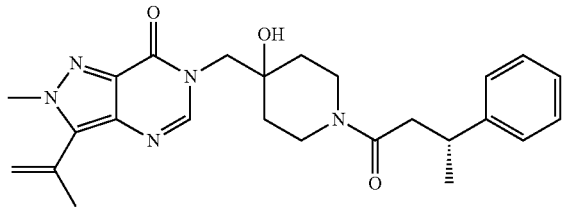 [SMILES: C=C(C)c1c2ncn(CC3(O)CCN(C(=O)C[C@@H](C)c4ccccc4)CC3)c(=O)c2nn1C]

General procedure 5 using Intermediate B (75 mg, 0.154 mmol), potassium isopropenyltrifluoroborate (68 mg, 0.461 mmol), $K_3PO_4$ (98 mg, 0.461 mmol), $Pd(PPh_3)_4$ (18 mg, 0.015 mmol), 1,4-dioxane (1.2 mL) and water (0.3 mL) in a microwave at 130° C. for 45 min gave the title compound (56 mg, 81%) as a colourless solid. LCMS (Method A): $R_T$=1.12 min, m/z=450 [M+H]$^+$. $^1$H NMR (300 MHz, $CDCl_3$, this molecule appears as two conformers A and B in a 2:3 ratio respectively): δ 7.85 (s, 0.4H (conformer A)), 7.74 (s, 0.6H (conformer B)), 7.37-7.13 (m, 5H), 5.66-5.55 (m, 1H), 5.32-5.25 (m, 1H), 4.44-3.88 (m, 6H), 3.77-3.46 (m, 2H), 3.40-3.14 (m, 2H), 3.11-2.85 (m, 1H), 2.71-2.57 (m, 1H), 2.57-2.41 (m, 1H), 2.27 (d, 3H), 1.66-1.21 (m, 7H), 0.93-0.74 (m, 0.6H (conformer B only)).

Example 33: (R)-6-((4-Hydroxy-1-(3-phenylbutanoyl)piperidin-4-yl)methyl)-3-isopropyl-2-methyl-2H-pyrazolo[4,3-d]pyrimidin-7(6H)-one

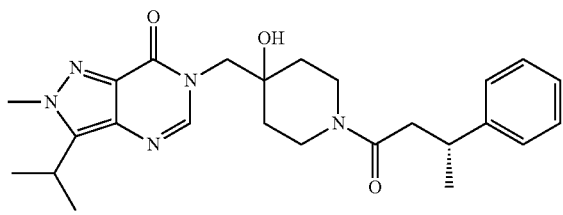 [SMILES: CC(C)c1c2ncn(CC3(O)CCN(C(=O)C[C@@H](C)c4ccccc4)CC3)c(=O)c2nn1C]

A solution (R)-6-((4-hydroxy-1-(3-phenylbutanoyl)piperidin-4-yl)methyl)-2-methyl-3-(prop-1-en-2-yl)-2H-pyrazolo[4,3-d]pyrimidin-7(6H)-one (50 mg, 0.111 mmol) in MeOH (10 mL) was hydrogenated in an H-Cube® (10% Pd/C CatCart®, 1 mLmin$^{-1}$, 50° C., 60 bar $H_2$). The resulting solution was concentrated and the residue purified by flash chromatography (Biotage 10 g KP-Sil, 0-100% EtOAc in PE then 0-30% MeOH in EtOAc) to give the title compound (20 mg, 40%) as a colourless solid. LCMS (Method A): $R_T$=1.02 min, m/z=452 [M+H]$^+$. $^1$H NMR (300 MHz, $CDCl_3$, this molecule appears as two conformers A and B in a 2:3 ratio respectively): δ 7.70 (s, 0.4H (conformer A)), 7.59 (s, 0.6H (conformer B)), 7.38-7.15 (m, 5H), 4.48-4.26 (m, 1H), 4.19-3.83 (m, 5H), 3.65-2.84 (m, 6H), 2.72-2.58 (m, 1H), 2.58-2.42 (m, 1H), 1.64-1.21 (m, 13H), 0.79-0.63 (m, 0.6H (conformer B only)).

Example 34: (R)-6-((4-Hydroxy-1-(3-phenylbutanoyl)piperidin-4-yl)methyl)-3-isopropyl-2-methyl-5,6-dihydro-2H-pyrazolo[4,3-d]pyrimidin-7(4H)-one

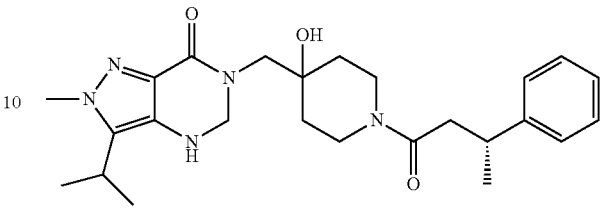

Isolated during preparation of Example 33. (R)-6-((4-hydroxy-1-(3-phenylbutanoyl)piperidin-4-yl)methyl)-3-isopropyl-2-methyl-5,6-dihydro-2H-pyrazolo[4,3-d]pyrimidin-7(4H)-one (22 mg, 43%) as a colourless solid. LCMS (Method A): $R_T$=1.05 min, m/z=454 [M+H]$^+$. $^1$H NMR (300 MHz, $CDCl_3$, this molecule appears as two conformers A and B in a 2:3 ratio respectively): δ 7.35-7.15 (m, 5H), 4.57-4.23 (m, 3H), 4.15-4.06 (m, 0.6H (conformer B only), 3.86 (s, 3H), 3.69-3.17 (m, 6.4H), 3.11-2.89 (m, 2H), 2.71-2.58 (m, 1H), 2.56-2.43 (m, 1H), 1.74-1.17 (m, 13H), 0.78-0.64 (m, 0.6H (conformer B)).

Example 35: (R)-6-((1-(3,4-Dimethylpent-4-enoyl)-4-hydroxypiperidin-4-yl)methyl)-2-methyl-3-phenyl-2H-pyrazolo[4,3-d]pyrimidin-7(6H)-one

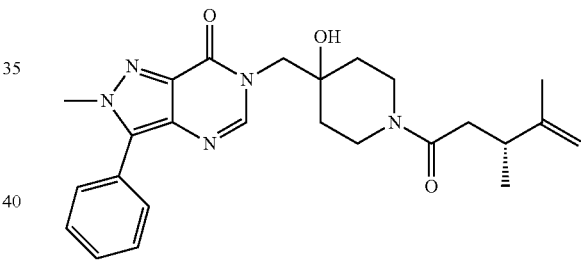

Step 1: (R)-3,4-Dimethylpent-4-enoic Acid

LiOH (88 mg, 3.67 mmol) was added to a solution of (S)-3-((R)-3,4-dimethylpent-4-enoyl)-4-phenyloxazolidin-2-one (*Tetrahedron Lett.* 1998, 39, 8593) (501 mg, 1.83 mmol) in THF (9 mL) and water (9 mL) and the reaction was vigorously stirred for 18 h before water (10 mL) was added. The mixture was then extracted with DCM (3×5 mL) to remove the auxiliary and the aqueous phase was acidified to pH 3-4 by the dropwise addition of 3 M $HCl_{(aq)}$. The acidified aqueous phase was extracted with DCM (5×5 mL) using a Biotage phase separator and carefully concentrated to give the title compound (114 mg, 49%) as a colourless oil. $^1$H NMR (300 MHz, $CDCl_3$): δ 4.80-4.69 (m, 2H), 2.68 (sxt, 1H), 2.58-2.45 (m, 1H), 2.39-2.25 (m, 1H), 1.74 (s, 3H), 1.11 (d, 3H).

Step 2: tert-Butyl 4-hydroxy-4-((2-methyl-7-oxo-3-phenyl-2H-pyrazolo[4,3-d]pyrimidin-6(7H)-yl)methyl)piperidine-1-carboxylate General procedure 5 using Intermediate C (223 mg, 0.504 mmol), phenylboronic acid (184 mg, 1.51 mmol), $PdCl_2$ (dppf) (9 mg, 0.013 mmol), K$_3$PO$_4$ (642 mg, 3.03 mmol), 1,4-dioxane (4 mL) and water (0.8 mL) at 90° C. for 16 h gave the title compound (161 mg, 73%) as a pale yellow solid. LCMS (Method A): R$_T$=1.26 min, m/z=440 [M+H]$^+$. $^1$H NMR (300 MHz, CDCl$_3$): δ 7.86 (s, 1H), 7.60-7.41 (m, 5H), 4.08 (s, 3H), 4.22-3.94 (m, 2H), 3.92-3.70 (m, 2H), 3.62-3.41 (m, 1H), 3.23-2.98 (m, 1H), 1.67-1.47 (m, 4H), 1.43 (s, 9H).

Step 3: 6-((4-Hydroxypiperidin-4-yl)methyl)-2-methyl-3-phenyl-2H-pyrazolo[4,3-d]pyrimidin-7(6H)-one, Intermediate D General procedure 2 using tert-butyl 4-hydroxy-4-((2-methyl-7-oxo-3-phenyl-2H-pyrazolo[4,3-d]pyrimidin-6(7H)-yl)methyl)piperidine-1-carboxylate (161 mg, 0.366 mmol), TFA (3 mL) and DCM (3 mL) gave the title compound (89 mg, 72%) as a pale yellow solid. LCMS (Method A): R$_T$=0.49 min, m/z=340 [M+H]$^+$. $^1$H NMR (300 MHz, CDCl$_3$): δ 7.91 (s, 1H), 7.66-7.44 (m, 5H), 4.16 (s, 3H), 4.12 (s, 2H), 3.07-2.60 (m, 6H), 1.78-1.50 (m, 4H).

Step 4: (R)-6-((1-(3,4-Dimethylpent-4-enoyl)-4-hydroxypiperidin-4-yl)methyl)-2-methyl-3-phenyl-2H-pyrazolo[4,3-d]pyrimidin-7(6H)-one General procedure 4 using Intermediate D (15 mg, 0.044 mmol), (R)-3,4-dimethylpent-4-enoic acid (8.5 mg, 0.066 mmol), HATU (25 mg, 0.066 mmol), DIPEA (31 μL, 0.177 mmol) and DCM (2 mL) gave the title compound (19 mg, 96%) as a colourless solid. LCMS (Method A): R$_T$=1.17 min, m/z=450 [M+H]$^+$. $^1$H NMR (300 MHz, CDCl$_3$): δ 7.84 (m, 1H), 7.62-7.44 (m, 5H), 4.71 (s, 2H), 4.44-4.29 (m, 1H), 4.21 (dd, 1H), 4.12 (s, 3H), 3.98 (d, 1H), 3.69 (d, 1H), 3.59 (d, 1H), 3.49-3.31 (m, 1H), 3.12-2.96 (m, 1H), 2.74-2.55 (m, 1H), 2.53-2.40 (m, 1H), 2.33-2.18 (m, 1H), 1.73 (s, 3H), 1.68-1.49 (m, 4H), 1.07 (d, 3H).

Example 36: (R)-6-((4-Hydroxy-1-(4-methyl-3-(trifluoromethyl)pent-4-enoyl)piperidin-4-yl)methyl)-2-methyl-3-phenyl-2H-pyrazolo[4,3-d]pyrimidin-7(6H)-one

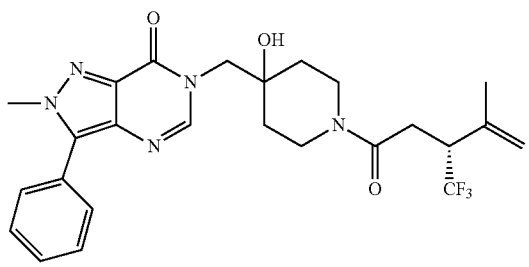 [SMILES: C=C(C)[C@@H](CC(=O)N1CCC(O)(Cn2cnc3c(-c4ccccc4)n(C)nc3c2=O)CC1)C(F)(F)F]

Step 1: (S,E)-4-Phenyl-3-(4,4,4-trifluorobut-2-enoyl)oxazolidin-2-one

To a solution of (E)-4,4,4-trifluorobut-2-enoic acid (2.06 g, 14.7 mmol) in DCM (10 mL) at 0° C. was added oxalyl chloride (1.07 mL, 12.3 mmol). After 5 min, DMF (50 μL, 0.646 mmol) was added and the mixture was allowed to stir at RT for 2 h. In a separate vessel NaH (60% disp., 735 mg, 18.4 mmol) was added to a solution of (S)-4-phenyloxazolidin-2-one (2 g, 12.3 mmol) in THF (20 mL) at RT and the mixture was stirred for 2 h. The DMF solution of the acid chloride was then added to the sodiated (S)-4-phenyloxazolidin-2-one solution via syringe. After stirring for 18 h the mixture was diluted with water (50 mL) and the mixture extracted with DCM (3×20 mL) using a Biotage phase separator. The combined organic layers were concentrated and the residue purified by flash chromatography (50 g Biotage KP-Sil, 0-100% EtOAc in PE) to give the title compound (1.07 g, 30% yield) as a colourless solid. LCMS (Method A): R$_T$=1.33 min, m/z=286 [M+H]$^+$. $^1$H NMR (300 MHz, CDCl$_3$): δ 7.93 (dq, 1H), 7.49-7.22 (m, 5H), 6.80 (dq, 1H), 5.50 (dd, 1H), 4.77 (t, 1H), 4.36 (dd, 1H).

Step 2: (S)-3-((R)-4-Methyl-3-(trifluoromethyl)pent-4-enoyl)-4-phenyloxazolidin-2-one A 0.392 M solution of prop-1-en-2-yl magnesium bromide in THF (6.71 ml, 2.63 mmol) was added to a suspension of CuBr.SMe$_2$ (541 mg, 2.63 mmol) in THF (12 mL) at −60° C. After 1 h a solution of (S,E)-4-phenyl-3-(4,4,4-trifluorobut-2-enoyl)oxazolidin-2-one (500 mg, 1.75 mmol) in THF (6 mL) was added and the reaction stirred for 3 h at −60° C. before being allowed to warm to −20° C. over 18 h. The reaction was then quenched by the addition of saturated NH$_4$Cl$_{(aq)}$ (50 mL) and the mixture extracted with ethyl acetate (3×30 mL). The combined organic phases were washed with brine, dried over Na$_2$SO$_4$, concentrated and the residue was purified by flash chromatography (50 g Biotage KP-Sil, 0-40% EtOAc in PE) to give the title compound (356 mg, 62% yield) as a colourless oil. LCMS (Method A): R$_T$=1.68 min, m/z=328 [M+H]$^+$. $^1$H NMR (300 MHz, CDCl$_3$): δ 7.50-7.00 (m, 5H), 5.35 (dd, 1H), 4.87 (d, 2H), 4.63 (t, 1H), 4.20 (dd, 1H), 3.56-3.27 (m, 2H), 3.19 (dd, 1H), 1.66 (s, 3H).

Step 3: (R)-4-Methyl-3-(trifluoromethyl)pent-4-enoic Acid

LiOH (48 mg, 2.02 mmol) was added to a solution of (S)-3-((R)-4-methyl-3-(trifluoromethyl)pent-4-enoyl)-4-phenyloxazolidin-2-one (331 mg, 1.01 mmol) in THF (5 mL) and water (5 mL) and the reaction was vigorously stirred for 18 h before water (10 mL) was added. The mixture was then extracted with DCM (3×5 mL) to remove the auxiliary and the aqueous phase was acidified to pH 3-4 by the dropwise addition of 3 M HCl$_{(aq)}$. The acidified aqueous phase was extracted with DCM (5×5 mL), the combined DCM washes were dried using a Biotage phase separator and carefully concentrated to give the title compound (116 mg, 63% yield) as a colourless oil. $^1$H NMR (300 MHz, CDCl$_3$): δ 5.13 (s, 1H), 5.05 (s, 1H), 3.33 (quint 1H), 2.87-2.65 (m, 2H), 1.86 (s, 3H).

Step 4: (R)-6-((4-Hydroxy-1-(4-methyl-3-(trifluoromethyl)pent-4-enoyl)piperidin-4-yl)methyl)-2-methyl-3-phenyl-2H-pyrazolo[4,3-d]pyrimidin-7(6H)-one General procedure 4 using Intermediate D (16 mg, 0.047 mmol), (R)-4-methyl-3-(trifluoromethyl)pent-4-enoic acid (13 mg, 0.071 mmol), HATU (27 mg, 0.071 mmol), DIPEA (33 μL, 0.189 mmol) and DCM (2 mL) gave the title compound (17 mg, 72%) as a colourless solid. LCMS (Method A): R$_T$=1.29 min, m/z=504 [M+H]$^+$. $^1$H NMR (400 MHz, CDCl$_3$, this molecule appears as two conformers A and B in a 1:1 ratio): δ 7.91-7.70 (m, 1H), 7.62-7.40 (m, 5H), 5.14-5.06 (m, 1H), 5.04-4.95 (m, 1H), 4.43-4.28 (m, 1H), 4.27-4.08 (m, 1H), 4.13 (s, 3H), 4.04-3.90 (m, 1H), 3.81-3.33 (m, 4H), 3.15-3.00 (m, 1H), 2.82-2.61 (m, 2H), 1.91-1.83 (m, 3H), 1.80-1.49 (m, 4H).

Example 37: (R)-6-((4-Hydroxy-1-(4,4,4-trifluoro-3-phenylbutanoyl)piperidin-4-yl)methyl)-2-methyl-3-phenyl-2H-pyrazolo[4,3-d]pyrimidin-7(6H)-one

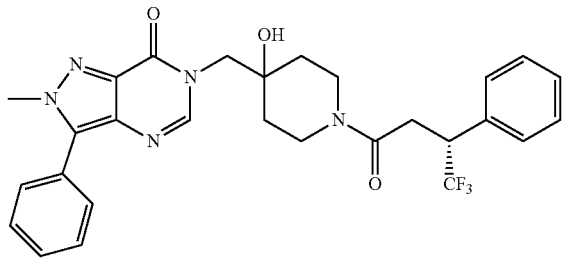 [SMILES: Cn1nc2c(=O)n(CC3(O)CCN(C(=O)C[C@H](c4ccccc4)C(F)(F)F)CC3)cnc2c1-c1ccccc1]

Step 1: (E)-4,4,4-Trifluoro-3-phenylbut-2-enoic Acid

LiOH (132 mg, 5.5 mmol) was added to solution of (E)-ethyl 4,4,4-trifluoro-3-phenylbut-2-enoate (J. Fluorine Chem. 2013, 152, 56.) (1.22 g, 5 mmol) in THF (10 mL) and water (5 mL) at RT. After 1 h the pH of the reaction mixture was adjusted to pH 4 by the addition of 1 M HCl$_{(aq)}$ and the mixture was extracted with DCM (3×10 mL) using a Biotage phase separator. The combined organic phases were concentrated and the product dried in vacuo to give the title compound (1.06 g, 98%) as a colourless solid. LCMS (Method A): R$_T$=1.27 min, m/z=215 [M−H]$^−$. $^1$H NMR (300 MHz, DMSO-d$_6$): δ 13.22 (br s, 1H), 7.54-7.38 (m, 3H), 7.36-7.22 (m, 2H), 6.84 (s, 1H).

Step 2: (R)-4,4,4-Trifluoro-3-phenylbutanoic Acid

A suspension of bis(norbornadiene)rhodium(I) tetrafluoroborate (3.46 mg, 9.25 μmol) and Walphos SL-W008-2 (8.72 mg, 9.25 μmol) in MeOH (6 mL) was degassed with N$_2$. After 30 min a solution was obtained and (E)-4,4,4-trifluoro-3-phenylbut-2-enoic acid (200 mg, 0.925 mmol) was added. The reaction was then shaken in a Parr® Shaker apparatus at 3.5-4 bar H$_2$ for 22 h. Since there was no conversion, further bis(norbornadiene)rhodium(I) tetrafluoroborate (3.46 mg, 9.25 μmol) and Walphos SL-W008-2 (8.72 mg, 9.25 μmol) were added and the reaction was shaken in a Parr® Shaker apparatus at 5 bar H$_2$ for 24 h. The mixture was concentrated and the residue purified by flash chromatography (10 g Biotage KP-Sil, 0-20% MeOH in DCM) to give the title compound (100 mg, 49%) as a colourless solid. LCMS (Method A): R$_T$=1.24 min, m/z=217 [M−H]$^−$. $^1$H NMR (300 MHz, CDCl$_3$): δ 10.67 (br s, 1H), 7.49-7.21 (m, 5H), 3.89 (m, 1H), 3.20-2.82 (m, 2H).

Step 3: (R)-6-((4-Hydroxy-1-(4,4,4-trifluoro-3-phenylbutanoyl)piperidin-4-yl)methyl)-2-methyl-3-phenyl-2H-pyrazolo[4,3-d]pyrimidin-7(6H)-one General procedure 4 using Intermediate D (16 mg, 0.047 mmol), (R)-4,4,4-trifluoro-3-phenylbutanoic acid (15 mg, 0.071 mmol), HATU (27 mg, 0.071 mmol), DIPEA (33 μL, 0.189 mmol) and DCM (2 mL) gave the title compound (21 mg, 84%) as a colourless solid. LCMS (Method A): R$_T$=1.35 min, m/z=540 [M+H]$^+$. $^1$H NMR (400 MHz, CDCl$_3$, this molecule appears as two conformers A and B in a 1:1 ratio): δ 7.79-7.71 (m, 1H), 7.61-7.45 (m, 5H), 7.43-7.28 (m, 5H), 4.33-4.21 (m, 1H), 4.17-3.83 (m, 6H), 3.73-3.28 (m, 3H), 3.04-2.84 (m, 3H), 1.66-1.45 (m, 3H), 1.30-1.08 (m, 1H).

Example 38: 6-((4-Hydroxy-1-(3-phenylpropanoyl)piperidin-4-yl)methyl)-2-methyl-2H-pyrazolo[4,3-d]pyrimidin-7(6H)-one

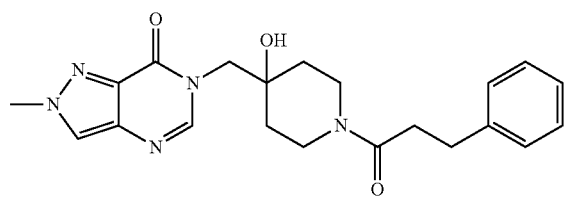 [SMILES: Cn1cc2ncn(CC3(O)CCN(C(=O)CCc4ccccc4)CC3)c(=O)c2n1]

General procedure 1 using Epoxide 3 (65 mg, 0.266 mmol), 2-methyl-2H-pyrazolo[4,3-d]pyrimidin-7(6H)-one (PCT Int. Appl., 2007013964, 1 Feb. 2007) (40 mg, 0.266 mmol) and Cs$_2$CO$_3$ (260 mg, 0.799 mmol) gave the title compound (54 mg, 51%) as a colourless solid. LCMS (Method A): R$_T$=0.85 min, m/z=396 [M+H]$^+$. $^1$H NMR (300 MHz, CDCl$_3$): δ 7.91 (s, 1H), 7.78 (s, 1H), 7.31-7.18 (m, 5H), 4.32 (d, 1H), 4.21-3.95 (m, 5H), 3.60 (d, 1H), 3.38-3.30 (m, 1H), 3.10-3.01 (m, 1H), 2.92 (t, 2H), 2.66-2.55 (m, 2H), 1.62-1.37 (m, 4H).

Example 39: 6-((4-Hydroxy-1-(3-phenylpropanoyl)piperidin-4-yl)methyl)-2-methyl-3-(trifluoromethyl)-2H-pyrazolo[4,3-d]pyrimidin-7(6H)-one

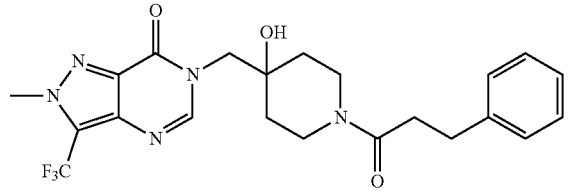 [SMILES: Cn1nc2c(=O)n(CC3(O)CCN(C(=O)CCc4ccccc4)CC3)cnc2c1C(F)(F)F]

General procedure 1 using Epoxide 3 (34 mg, 0.138 mmol), 2-methyl-3-(trifluoromethyl)-2H-pyrazolo[4,3-d]pyrimidin-7(6H)-one (30 mg, 0.138 mmol), Cs$_2$CO$_3$ (54 mg, 0.165 mmol) and DMF (0.3 mL) gave the title compound (27 mg, 42%) as a colourless solid. LCMS (Method A): R$_T$=1.16 min, m/z=464 [M+H]$^+$. $^1$H NMR (300 MHz, CDCl$_3$): δ 7.95 (s, 1H), 7.38-7.19 (m, 5H), 4.44-4.24 (m, 4H), 4.13-3.95 (m, 2H), 3.66-3.54 (m, 1H), 3.37-3.30 (m, 1H), 3.20-2.91 (m, 4H), 2.70-2.56 (m, 2H), 1.63-1.22 (m, 4H).

Example 40: (R)-3-((4-Hydroxy-1-(3-phenylbutanoyl)piperidin-4-yl)methyl)-6-(1-methyl-1H-pyrazol-4-yl)pyrimidin-4(3H)-one

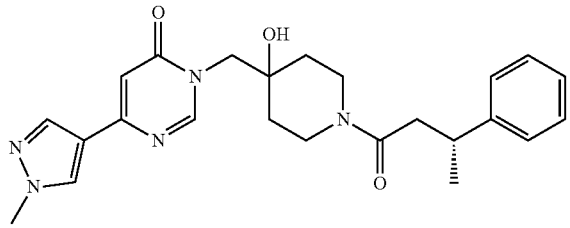 [SMILES: C[C@H](CC(=O)N1CCC(O)(Cn2cnc(-c3cnn(C)c3)cc2=O)CC1)c1ccccc1]

General procedure 5 using Intermediate A (20 mg, 0.051 mmol), 1-methyl-4-(4,4,5,5-tetramethyl-1,3,2-dioxaborolan-2-yl)-1H-pyrazole (16 mg, 0.077 mmol), Na$_2$CO$_3$ (11 mg, 0.103 mmol), Pd(PPh$_3$)$_4$(3.0 mg, 2.56 µmol), 1,4-dioxane (0.5 mL) and water (0.2 mL) in a microwave at 150° C. for 10 min gave the title compound (12 mg, 54%) as an off-white solid. LCMS (Method B): R$_T$=0.89 min, m/z=436 [M+H]$^+$. $^1$H NMR (400 MHz, methanol-d$_4$, this molecule appears as two conformers A and B in a 2:3 ratio respectively): δ 8.36 (s, 0.4H (conformer A)), 8.33 (s, 0.6H (conformer B)), 8.02 (s, 1H), 7.35-7.17 (m, 5H), 6.67 (s, 1H), 4.25-4.13 (m, 1H), 4.03 (dd, 1H), 3.96 (s, 3H), 3.88 (dd, 1H), 3.72-3.65 (m, 1H), 3.28-3.22 (m, 1H), 3.09-2.92 (m, 1H), 2.84-2.73 (m, 1H), 2.64-2.49 (m, 1H), 1.65-1.26 (m, 7H), 0.96-0.89 (m, 0.6H (conformer B)).

Example 41: (R)-3-((4-Hydroxy-1-(3-phenylbutanoyl)piperidin-4-yl)methyl)-6-(1-isobutyl-1H-pyrazol-4-yl)pyrimidin-4(3H)-one

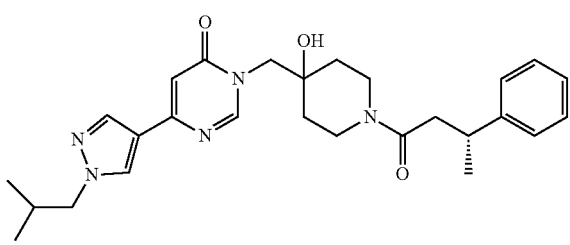 [SMILES: CC(C)Cn1cc(-c2cc(=O)n(CC3(O)CCN(C(=O)C[C@@H](C)c4ccccc4)CC3)cn2)cn1]

General procedure 5 using Intermediate A (20 mg, 0.051 mmol), 1-isobutyl-4-(4,4,5,5-tetramethyl-1,3,2-dioxaborolan-2-yl)-1H-pyrazole (19 mg, 0.077 mmol), Na$_2$CO$_3$ (11 mg, 0.103 mmol), Pd(PPh$_3$)$_4$(3.0 mg, 2.56 µmol), 1,4-dioxane (0.5 mL) and water (0.2 mL) in a microwave at 150° C. for 10 min gave the title compound (22 mg, 91%) as an off-white solid. LCMS (Method B): R$_T$=1.10 min, m/z=478 [M+H]$^+$. $^1$H NMR (400 MHz, methanol-d$_4$, this molecule appears as two conformers A and B in a 2:3 ratio respectively): δ 8.33 (s, 0.4H (conformer A)), 8.29 (s, 0.6H (conformer B)), 8.24 (s, 1H), 8.05 (s, 1H), 7.35-7.16 (m, 5H), 6.68 (s, 1H), 4.25-4.13 (m, 1H), 4.03 (dd, 1H), 4.01 (d, 2H), 3.89 (dd, 1H), 3.72-3.65 (m, 1H), 3.26-3.15 (m, 1H), 3.09-2.92 (m, 1H), 2.84-2.73 (m, 1H), 2.64-2.49 (m, 1H), 2.23 (septet, 1H), 1.66-1.31 (m, 7H), 0.99-0.89 (m, 0.6H (conformer B)), 0.94 (d, 6H).

Example 42: 3-((4-Hydroxy-1-((R)-3-phenylbutanoyl)piperidin-4-yl)methyl)-6-((1,2,3,4-tetrahydro-1,4-epiminonaphthalen-6-yl)amino)pyrimidin-4(3H)-one hydrochloride

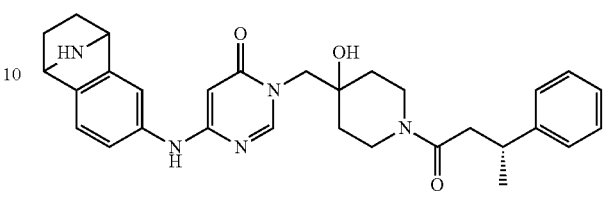

A mixture of Intermediate A (20 mg, 0.051 mmol), tert-butyl 6-amino-1,2,3,4-tetrahydro-1,4-epiminonaphthalene-9-carboxylate (20 mg, 0.077 mmol), Xantphos (4.45 mg, 7.69 µmol) and Cs$_2$CO$_3$ (33 mg, 0.103 mmol) in 1,4-dioxane (1 mL) was de-gassed by bubbling N$_2$ through the mixture for 5 min. Pd$_2$(dba)$_3$ (2.3 mg, 2.56 µmol) was added and the reaction mixture heated at 125° C. in the microwave for 30 min. After dilution with DCM, the mixture was filtered through Celite® and purified by flash chromatography (Biotage 10 g KP-Sil, 0-100% EtOAc in cyclohexane, then 0-20% MeOH in EtOAc). The resultant material was dissolved in DCM (0.5 mL) and 4 M HCl in 1,4-dioxane (0.5 mL) was added. After stirring for 2 h, Et$_2$O (2 mL) was added and the resulting suspension was stirred for 10 min. The supernatant was removed, further Et$_2$O (2 mL) was added to the remainder and the suspension stirred for 10 min. After the removal of the supernatant the resulting solid was lyophilised to give the title compound (11 mg, 41%) as a pale brown solid. LCMS (Method B): R$_T$=0.71 min, m/z=514 [M+H]$^+$. $^1$H NMR (400 MHz, methanol-d$_4$, this molecule appears as two conformers A and B in a 2:3 ratio respectively): δ 8.22 (s, 0.4H (conformer A)), 8.18 (s, 0.6H (conformer B)), 7.66 (s, 1H), 7.47 (d, 1H), 7.38-7.17 (m, 5H), 5.25 (m, 2H), 4.25-4.13 (m, 1H), 4.00 (s, 1H), 3.86 (dd, 1H), 3.75-3.64 (m, 2H), 3.30-3.17 (m, 2H), 3.09-2.94 (m, 1H), 2.85-2.74 (m, 1H), 2.65-2.50 (m, 1H), 2.40-2.30 (m, 2H), 1.71-1.31 (m, 9H), 0.94-0.86 (m, 0.6H (conformer B)).

Example 43: (R)-6-((4-Hydroxy-1-(3-phenylbutanoyl)piperidin-4-yl)methyl)-2-methyl-3-(phenylamino)-2H-pyrazolo[4,3-d]pyrimidin-7(6H)-one

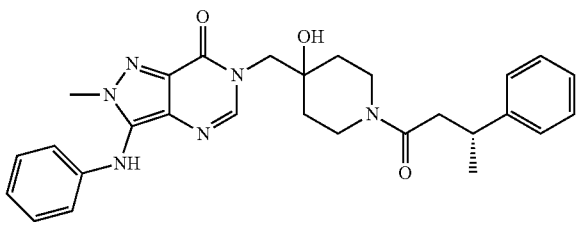 [SMILES: C[C@H](CC(=O)N1CCC(O)(Cn2cnc3c(Nc4ccccc4)n(C)nc3c2=O)CC1)c1ccccc1]

Intermediate B (30 mg, 0.061 mmol) was dissolved in 1,4-dioxane (1 mL) and Cs$_2$CO3 (28 mg, 0.086 mmol) was added, followed by aniline (5.61 µL, 0.061 mmol). The mixture was degassed with N$_2$. Pd(OAc)$_2$ (1.379 mg, 6.14 µmol) was added followed by Xantphos (5.33 mg, 9.21 µmol) and the tube was sealed. The mixture was heated at 100° C. for 1 h. A further 2 µL aniline was added and the mixture was heated at 100° C. for 16 h. The mixture was cooled to RT, concentrated and the residue purified by flash chromatography (GraceResolv 4 g Silica, eluted 0-100% EtOAc/c-hex then 0-30% MeOH/EtOAc; then Biotage 11 g KP-NH, eluted 0-100% EtOAc/c-hex then 0-30% MeOH/EtOAc) to give the title compound as a foam (11 mg, 36%). LCMS (Method A): $R_T$=1.20 min, m/z=501 [M+H]$^+$. $^1$H NMR (300 MHz, DMSO-d$_6$): δ 8.35 (s, 1H), 7.85 (d, 1H), 7.26 (m, 4H), 7.15 (m, 3H), 6.77 (t, 1H), 6.69 (d, 2H), 4.88 (d, 1H), 3.90 (m, 6H), 3.65 (m, 1H), 3.18 (m, 2H), 2.86 (m, 1H), 2.57 (m, 2H), 1.30 (m, 4H), 1.21 (d, 3H).

Example 44: (R)-6-Chloro-3-((4-hydroxy-1-(3-phenylbutanoyl)piperidin-4-yl)methyl)-5-methylpyrimidin-4(3H)-one

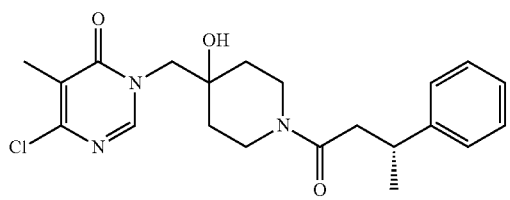 [SMILES: Cc1c(Cl)ncn(CC2(O)CCN(C(=O)C[C@@H](C)c3ccccc3)CC2)c1=O]

Step 1: tert-Butyl 4-((4-chloro-5-methyl-6-oxopyrimidin-1(6H)-yl)methyl)-4-hydroxypiperidine-1-carboxylate A solution of 6-chloro-5-methylpyrimidin-4(3H)-one (300 mg, 2.075 mmol), Epoxide 1 (443 mg, 2.075 mmol) and DIPEA (0.54 mL, 3.11 mmol) in DMF (2.5 mL) was heated at 80° C. for 16 h. The mixture was allowed to cool to RT, before the reaction was quenched by the addition of saturated NH$_4$Cl$_{(aq)}$ (20 mL) and the mixture was extracted with EtOAc. The combined organic extracts were dried over Na$_2$SO$_4$, concentrated and the residue purified by flash chromatography (24 g GraceResolv silica, 0-100% EtOAc in cyclohexane) to give the title compound (148 mg, 20%) as an off-white solid. $^1$H NMR (400 MHz, CDCl$_3$): δ 7.93 (s, 1H), 4.10-3.80 (br m, 4H), 3.20-3.10 (br m, 3H), 2.20 (s, 3H), 1.63-1.50 (br m, 4H), 1.45 (s, 9H).

Step 2: 6-Chloro-3-((4-hydroxypiperidin-4-yl)methyl)-5-methylpyrimidin-4(3H)-one. TFA A solution of tert-butyl 4-((4-chloro-5-methyl-6-oxopyrimidin-1(6H)-yl)methyl)-4-hydroxypiperidine-1-carboxylate (150 mg, 0.419 mmol) and TFA (0.5 mL, 6.49 mmol) in DCM (1 mL) was stirred at RT for 1 h and subsequently concentrated in vacuo. Excess TFA was removed by thrice adding DCM followed by concentration in vacuo. The resultant solid was triturated with Et$_2$O (×2) and dried in vacuo to give the title compound (145 mg, 93%) as a white solid which was used without purification. LCMS (Method B): $R_T$=0.39 min, m/z=258.

Step 3: (R)-6-Chloro-3-((4-hydroxy-1-(3-phenylbutanoyl)piperidin-4-yl)methyl)-5-methylpyrimidin-4(3H)-one General procedure 4 using 6-chloro-3-((4-hydroxypiperidin-4-yl)methyl)-5-methylpyrimidin-4(3H)-one. TFA (145 mg, 0.390 mmol), (R)-3-phenylbutanoic acid (96 mg, 0.585 mmol), HATU (201 mg, 1.56 mmol) and DIPEA (0.273 mL, 1.560 mmol) in DCM (1 mL) gave the title compound (63 mg, 40%) as an off-white solid. LCMS (Method B): $R_T$=1.08 min, m/z=404 [M+H]$^+$. $^1$H NMR (400 MHz, methanol-d$_4$, this molecule appears as two conformers A and B in a 2:3 ratio respectively): δ 8.16 (s, 0.4H (conformer A)), 8.11 (s, 0.6H (conformer B)), 7.36-7.17 (m, 5H), 4.24-4.12 (m, 1H), 4.02 (dd, 1H), 3.87 (dd, 1H), 3.71-3.64 (m, 1H), 3.28-3.16 (m, 1H), 3.06-2.90 (m, 1H), 2.84-2.72 (m, 1H), 2.63-2.49 (m, 1H), 2.17 (s, 1.8H (conformer B)), 2.17 (s, 1.2H (conformer A)), 1.63-1.27 (m, 7H), 0.93-0.85 (m, 0.6H (conformer B)).

Example 45: (R)-5-Bromo-3-((4-hydroxy-1-(3-phenylbutanoyl)piperidin-4-yl)methyl)-6-((2-(pyrrolidin-1-yl)ethyl)amino)pyrimidin-4(3H)-one

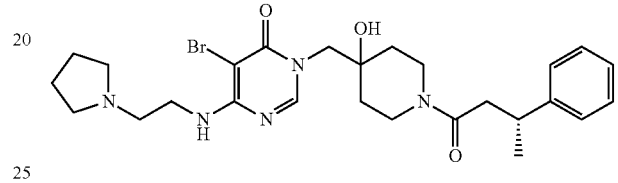

(R)-3-((4-Hydroxy-1-(3-phenylbutanoyl)piperidin-4-yl)methyl)-6-((2-(pyrrolidin-1-yl)ethyl)amino)pyrimidin-4(3H)-one (50 mg, 0.107 mmol) and NBS (19.0 mg, 0.107 mmol) in DMF (1.5 mL) was stirred at RT for 3 days. Further NBS (9 mg, 0.051 mmol) was added, and reaction stirred for 3 h. The reaction mixture was partitioned between EtOAc and water. The aqueous layer was extracted with EtOAc. The combined organic extracts were dried over MgSO$_4$, concentrated and the residue was purified by flash chromatography (Biotage 11 g KP-NH, 0-100% EtOAc in cyclohexane then 0-20% MeOH in EtOAc) to give the title compound (13 mg, 23%) as a pale brown solid. LCMS (Method B): $R_T$=0.69 min, m/z=546/548 [M+H]$^+$. $^1$H NMR (400 MHz, methanol-d$_4$, this molecule appears as two conformers A and B in a 2:3 ratio respectively): δ 8.07 (s, 0.4H (conformer A)), 8.03 (s, 0.6H (conformer B)), 7.35-7.17 (m, 5H), 4.23-4.11 (m, 1H), 4.11-3.79 (m, 3H), 3.70-3.66 (m, 3H), 3.27-3.16 (m, 2H), 3.08-2.93 (m, 1H), 2.87-2.49 (m, 7H), 1.96-1.84 (m, 3H), 1.61-1.24 (m, 7H), 0.96-0.89 (m, 0.6H (conformer B)).

Example 46: (R)-3-(4-(Aminomethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

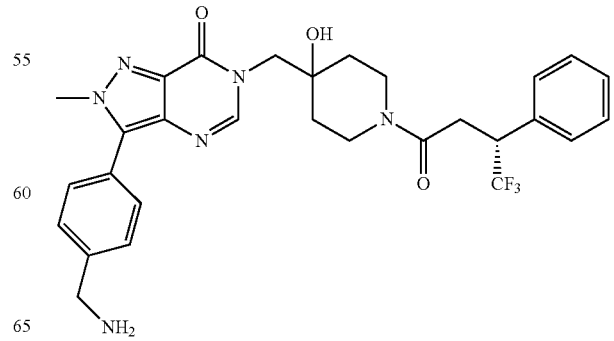

Step 1: Benzyl 4-((3-bromo-2-methyl-7-oxo-2H-pyrazolo[4,3-d]pyrimidin-6(7H)-yl)methyl)-4-hydroxypiperidine-1-carboxylate General procedure 1 using Epoxide 4 (3.24 g, 13.1 mmol), 3-bromo-2-methyl-2H-pyrazolo[4,3-d]pyrimidin-7(6H)-one (2.00 g, 8.73 mmol), Cs$_2$CO3 (4.27 g, 13.10 mmol) and DMF (40 mL) gave the title compound (4.16 g, quant.) as a beige solid. LCMS (Method A): R$_T$=1.13 min, m/z=476, 478 [M+H]$^+$. $^1$H NMR (300 MHz, CDCl$_3$): δ 7.88 (s, 1H), 7.41-7.28 (m, 5H), 5.13 (s, 2H), 4.15 (s, 3H), 4.25-3.87 (m, 4H), 3.31-3.10 (m, 2H), 2.88 (s, 1H), 1.75-1.48 (m, 4H).

Step 2: Benzyl 4-((3-(4-(((tert-butoxycarbonyl)amino)methyl)phenyl)-2-methyl-7-oxo-2H-pyrazolo[4,3-d]pyrimidin-6(7H)-yl)methyl)-4-hydroxypiperidine-1-carboxylate General procedure 5 using benzyl 4-((3-bromo-2-methyl-7-oxo-2H-pyrazolo[4,3-d]pyrimidin-6(7H)-yl)methyl)-4-hydroxypiperidine-1-carboxylate (476 mg, 1.00 mmol), tert-butyl 4-(4,4,5,5-tetramethyl-1,3,2-dioxaborolan-2-yl)benzylcarbamate (1.00 g, 3.00 mmol), Pd(PPh$_3$)$_4$ (58 mg, 50.0 µmol), K$_3$PO$_4$ (1.27 g, 6.00 mmol), 1,4-dioxane (7.5 mL) and water (2.5 mL) at 130° C. for 30 min in the microwave gave the title compound (448 mg, 74%) as a colourless foam. LCMS (Method A): R$_T$=1.44 min, m/z=603 [M+H]$^+$. $^1$H NMR (300 MHz, CDCl$_3$): δ 7.80 (s, 1H), 7.52 (d, 2H), 7.46 (d, 2H), 7.39-7.28 (m, 5H), 5.12 (s, 2H), 4.39 (d, 2H), 4.11 (s, 3H), 4.08 (s, 2H), 4.00-3.81 (m, 2H), 3.40 (s, 1H), 3.30-3.06 (m, 2H), 1.65-1.51 (m, 4H), 1.48 (s, 9H).

Step 3: tert-Butyl 4-(6-((4-hydroxypiperidin-4-yl)methyl)-2-methyl-7-oxo-6,7-dihydro-2H-pyrazolo[4,3-d]pyrimidin-3-yl)benzylcarbamate General procedure 7 using benzyl 4-((3-(4-(((tert-butoxycarbonyl)amino)methyl)phenyl)-2-methyl-7-oxo-2H-pyrazolo[4,3-d]pyrimidin-6(7H)-yl)methyl)-4-hydroxypiperidine-1-carboxylate (448 mg, 0.743 mmol), 10% Pd on carbon (79 mg, 0.074 mmol), ammonium formate (1.41 g, 22.3 mmol) and EtOH (7.4 mL) after 45 min gave the title compound (260 mg, 74%) as a colourless solid. $^1$H NMR (400 MHz, CDCl$_3$): δ 7.88 (s, 1H), 7.56 (d, 2H), 7.48 (d, 2H), 5.02 (br. s, 1H), 4.40 (d, 2H), 4.15 (s, 3H), 4.11 (s, 2H), 3.01-2.82 (m, 4H), 1.75-1.50 (m, 4H), 1.48 (s, 9H).

Step 4: (R)-3-(4-(Aminomethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one General procedure 4 using tert-butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (80 mg, 0.171 mmol), (R)-4,4,4-trifluoro-3-phenylbutanoic acid (56 mg, 0.256 mmol), HATU (97 mg, 0.256 mmol), DIPEA (0.119 mL, 0.683 mmol) and DCM (3.4 mL) and then general procedure 2 using TFA (1.5 mL) and DCM (1.5 mL) gave the title compound (79 mg, 81% (2 steps)) as a colourless solid. LCMS (Method B): R$_T$=0.81 min, m/z 569 [M+H]$^+$. $^1$H NMR (300 MHz, DMSO-d$_6$): δ 8.02-7.90 (m, 1H), 7.65 (d, 2H), 7.54 (d, 2H), 7.44-7.22 (m, 5H), 4.91 (s, 1H), 4.11 (s, 3H), 4.16-3.69 (m, 7H), 3.26-3.09 (m, 2H), 3.03-2.69 (m, 2H), 2.04 (br. s, 2H), 1.67-1.14 (m, 4H).

Example 47: 6-((S)-3-Aminopiperidin-1-yl)-3-((4-hydroxy-1-((R)-3-phenylbutanoyl)piperidin-4-yl)methyl)pyrimidin-4(3H)-one hydrochloride

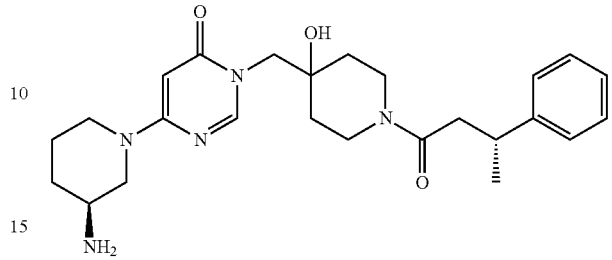

A mixture of Intermediate A (25 mg, 0.064 mmol), (S)-tert-butyl piperidin-3-ylcarbamate (64 mg, 0.321 mmol) and 1,4-dioxane (1 mL) was heated in the microwave at 150° C. for 30 min. The reaction mixture was partitioned between EtOAc and water and the aqueous layer was extracted with EtOAc. The combined organic extracts were dried over MgSO$_4$, concentrated and the residue was purified by flash chromatography (Biotage 11 g KP-NH, 0-100% EtOAc in cyclohexane, then 0-10% MeOH in EtOAc). The resultant material was dissolved in DCM (0.5 mL) and 4 M HCl/1,4-dioxane (0.5 mL) was added. After stirring for 2 h, Et$_2$O (2 mL) was added, and the suspension triturated for 10 min. The supernatant was removed, and further Et$_2$O (2 mL) was added, and the suspension triturated for 10 min. The supernatant was removed, and the solid was lyophilised to give the title compound (19 mg, 60%) as a white solid. LCMS (Method B): R$_T$=0.66 min, m/z=454 [M+H]$^+$. $^1$H NMR (400 MHz, methanol-d$_4$, this molecule appears as two conformers A and B in a 2:3 ratio respectively): δ 8.06 (s, 0.4H (conformer A)), 8.01 (s, 0.6H (conformer B)), 7.35-7.17 (m, 5H), 5.51 (s, 1H), 4.61 (br s, 1H), 4.23-4.09 (m, 2H), 4.02-3.87 (m, 1H), 3.78 (dd, 1H), 3.70-3.64 (m, 1H), 3.52-3.43 (m, 1H), 3.28-2.94 (m, 4H), 2.85-2.72 (m, 1H), 2.63-2.49 (m, 1H), 2.20-1.95 (m, 1H), 1.85-1.75 (m, 1H), 1.61-1.24 (m, 10H), 0.96-0.90 (m, 0.6H (conformer B)).

Example 48: (R)-6-(4-Aminopiperidin-1-yl)-3-((4-hydroxy-1-(3-phenylbutanoyl)piperidin-4-yl)methyl)pyrimidin-4(3H)-one hydrochloride

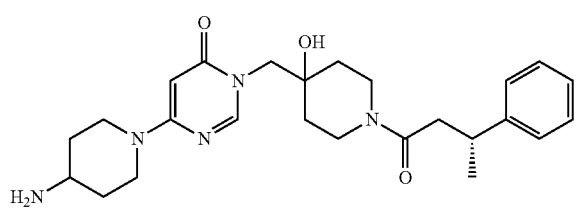 [SMILES: C[C@H](CC(=O)N1CCC(O)(Cn2cnc(N3CCC(N)CC3)cc2=O)CC1)c1ccccc1]

A mixture of Intermediate A (25 mg, 0.064 mmol), tert-butyl piperidin-4-ylcarbamate (64 mg, 0.321 mmol) and 1,4-dioxane (1 mL) was heated in the microwave at 150° C. for 30 min. The reaction mixture was partitioned between EtOAc and water. The aqueous layer was extracted with EtOAc. The combined organic extracts were dried over MgSO$_4$, concentrated and the residue was purified by flash chromatography (Biotage 11 g KP-NH, 0-100% EtOAc in cyclohexane, then 0-10% MeOH in EtOAc). The resultant material was dissolved in DCM (0.5 mL) and 4 M HCl/1,4-dioxane (0.5 mL) was added. After stirring for 2 h, Et$_2$O (2 mL) was added and the suspension triturated for 10 min. The supernatant was removed, and further Et$_2$O (2 mL) was added, and the suspension triturated for 10 min. The supernatant was removed, and the solid was lyophilised to give the title compound (29 mg, 92%) as a white solid. LCMS (Method B): R$_T$=0.66 min, m/z=454 [M+H]$^+$. $^1$H NMR (400 MHz, methanol-d$_4$, this molecule appears as two conformers A and B in a 2:3 ratio respectively): δ 8.17 (s, 0.4H (conformer A)), 8.13 (s, 0.6H (conformer B)), 7.35-7.19 (m, 5H), 4.89 (s, 1H), 4.49 (br s, 2H), 4.25-4.13 (m, 1H), 3.87 (dd, 1H), 3.73-3.65 (m, 1H), 3.57-3.42 (m, 2H), 3.28-2.95 (m, 4H), 2.84-2.74 (m, 1H), 2.64-2.50 (m, 1H), 2.31-2.26 (m, 1H), 2.13-2.10 (m, 1H), 1.95-1.85 (m, 1H), 1.63-1.28 (m, 6H), 0.92-0.86 (m, 0.6H (conformer B)).

Example 49: (R)-3-((4-Hydroxy-1-(3-phenylbutanoyl)piperidin-4-yl)methyl)-6-(2,8-diazaspiro[4.5]decan-8-yl)pyrimidin-4(3H)-one hydrochloride

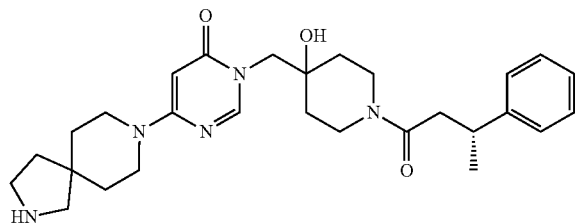 [SMILES: C[C@H](CC(=O)N1CCC(O)(Cn2cnc(N3CCC4(CCNC4)CC3)cc2=O)CC1)c1ccccc1]

A mixture of Intermediate A (20 mg, 0.051 mmol), tert-butyl 2,8-diazaspiro[4.5]decane-2-carboxylate (62 mg, 0.256 mmol) and 1,4-dioxane (1 mL) was heated in the microwave at 150° C. for 30 min. The reaction mixture was partitioned between EtOAc and water. The aqueous layer was extracted with EtOAc. The combined organic extracts were dried over MgSO$_4$, concentrated and the residue was purified by flash chromatography (Biotage 11 g KP-NH, 0-100% EtOAc in cyclohexane, then 0-10% MeOH in EtOAc). The resultant material was dissolved in DCM (0.5 mL) and 4 M HCl/1,4-dioxane (0.5 mL) was added. After stirring for 2 h Et$_2$O (2 mL) was added and the suspension was triturated for 10 min. The supernatant was removed, further Et$_2$O (2 mL) was added, and the suspension triturated for 10 min. The supernatant was removed and the solid was lyophilised to give the title compound (6 mg, 24%) as an off-white solid. LCMS (Method B): R$_T$=0.70 min, m/z=494 [M+H]$^+$. $^1$H NMR (400 MHz, methanol-d$_4$, this molecule appears as two conformers A and B in a 2:3 ratio respectively): δ 8.13 (s, 0.4H (conformer A)), 8.09 (s, 0.6H (conformer B)), 7.29-7.17 (m, 5H), 4.89 (s, 1H), 4.24-4.12 (m, 1H), 3.95-3.94 (m, 1H), 3.89-3.60 (m, 5H), 3.46-3.42 (m, 1H), 3.32-3.14 (m, 4H), 3.10-2.89 (m, 2H), 2.84-2.73 (m, 2H), 2.62-2.50 (m, 1H), 2.06-2.02 (m, 2H), 1.73-1.28 (m, 10H), 0.92-0.86 (m, 0.6H (conformer B)).

Example 50: 6-((S)-3-(Dimethylamino)piperidin-1-yl)-3-((4-hydroxy-1-((R)-3-phenylbutanoyl)piperidin-4-yl)methyl)pyrimidin-4(3H)-one

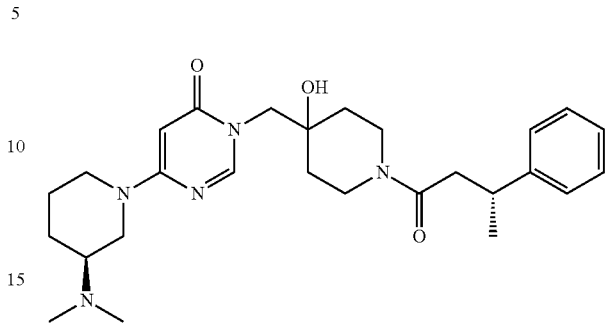

To a mixture of 6-((S)-3-aminopiperidin-1-yl)-3-((4-hydroxy-1-((R)-3-phenylbutanoyl)piperidin-4-yl)methyl)pyrimidin-4(3H)-one hydrochloride (12 mg, 0.024 mmol) and formaldehyde (37% in water) (12 μL, 0.163 mmol) in methanol (1 mL) was added sodium triacetoxyborohydride (86 mg, 0.408 mmol), and the mixture was stirred for 30 min. After concentration in vacuo, the residue was dissolved in DCM, washed (aq. NaHCO$_3$), dried (Biotage phase separator) and re-concentrated. Lyophilisation gave the title compound (8 mg, 70%) as an off-white solid. LCMS (Method B): R$_T$=0.67 min, m/z=482 [M+H]$^+$. $^1$H NMR (400 MHz, methanol-d$_4$, this molecule appears as two conformers A and B in a 2:3 ratio respectively): δ 8.07 (s, 0.4H (conformer A)), 8.02 (s, 0.6H (conformer B)), 7.35-7.17 (m, 5H), 5.49 (s, 1H), 4.53-4.50 (m, 1H), 4.23-4.05 (m, 2H), 3.89 (dd, 1H), 3.79 (dd, 1H), 3.71-3.63 (m, 1H), 3.28-3.15 (m, 2H), 3.07-2.90 (m, 3H), 2.83-2.72 (m, 1H), 2.63-2.49 (m, 1H), 2.4 (s, 6H), 2.12-2.05 (m, 1H), 1.89-1.82 (m, 1H), 1.61-1.28 (m, 9H), 0.96-0.89 (m, 0.6H (conformer B)).

Example 51: (R,E)-3-((4-Hydroxy-1-(3-phenylbutanoyl)piperidin-4-yl)methyl)-6-(3-(pyrrolidin-1-yl)prop-1-en-1-yl)pyrimidin-4(3H)-one

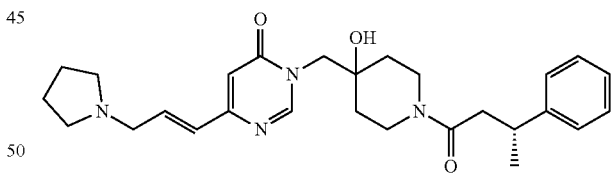

A mixture of Intermediate A (50 mg, 0.128 mmol), (E)-(3-chloroprop-1-en-1-yl)boronic acid (15. mg, 0.128 mmol), pyrrolidine (0.021 mL, 0.256 mmol) and K$_2$CO$_3$ (44 mg, 0.321 mmol) in 1,4-dioxane (2 mL)-Water (0.4 mL) was degassed by bubbling N$_2$ through the mixture and Pd(Ph$_3$P)$_4$ (7.41 mg, 6.41 μmol) was added. The reaction was heated to 160° C. in the microwave for 20 min, then diluted with EtOAc and filtered through Celite®. The filtrate was partitioned between EtOAc and water. The aqueous layer was extracted with EtOAc. The combined organic extracts were washed (water), dried over MgSO$_4$, concentrated and the residue was purified by flash chromatography (Biotage 11 g KP-NH column, 0-100% EtOAc/c-hex, then 0-20% MeOH/EtOAc). Further purification by preparative HPLC (Method A) gave the title compound (13 mg, 22%) as an off-white solid. LCMS (Method B): $R_T$=0.70 min, m/z=465 [M+H]$^+$. $^1$H NMR (400 MHz, methanol-d$_4$, this molecule appears as two conformers A and B in a 2:3 ratio respectively): δ 8.28 (s, 0.4H (conformer A)), 8.23 (s, 0.6H (conformer B)), 7.31-7.17 (m, 5H), 7.03 (dt, 1H), 6.50 (d, 1H), 6.35 (s, 1H), 4.24-4.12 (m, 1H), 4.01 (dd, 1H), 3.86 (dd, 1H), 3.71-3.64 (m, 1H), 3.28-3.15 (m, 2H), 3.08-2.91 (m, 2H), 2.84-2.72 (m, 1H), 2.66-2.60 (m, 4H), 2.53-2.48 (m, 1H), 1.87-1.84 (m, 4H), 1.63-1.28 (m, 7H), 0.94-0.86 (m, 0.6H (conformer B)).

Example 52: (R)-3-((4-Hydroxy-1-(3-phenylbutanoyl)piperidin-4-yl)methyl)-6-((2-(piperidin-1-yl)ethyl)amino)pyrimidin-4(3H)-one

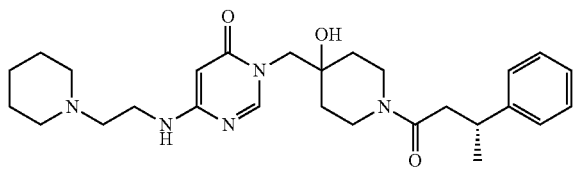 [SMILES: C[C@H](CC(=O)N1CCC(O)(Cn2cnc(NCCN3CCCCC3)cc2=O)CC1)c1ccccc1]

A mixture of Intermediate A (25 mg, 0.064 mmol), 2-(piperidin-1-yl)ethanamine (41 mg, 0.321 mmol) and 1,4-dioxane (1 mL) was heated in the microwave at 150° C. for 30 min. The reaction mixture was concentrated and the residue was purified by preparative HPLC (Method A) to give the title compound (14 mg, 44%) as a colourless gum. LCMS (Method B): $R_T$=0.68 min, m/z=482 [M+H]$^+$. $^1$H NMR (400 MHz, methanol-d$_4$, this molecule appears as two conformers A and B in a 2:3 ratio respectively): δ 8.03 (s, 0.4H (conformer A)), 7.98 (s, 0.6H (conformer B)), 7.35-7.17 (m, 5H), 5.29 (s, 1H), 4.24-4.12 (m, 1H), 3.97-3.64 (m, 3H), 3.40-3.35 (m, 2H), 3.28-3.15 (m, 2H), 3.07-2.92 (m, 1H), 2.83-2.72 (m, 1H), 2.63-2.49 (m, 7H), 1.67-1.28 (m, 12H), 0.94-0.86 (m, 0.6H (conformer B)).

Example 53: (R,S)-3-(4-(Aminomethyl)phenyl)-6-((4-hydroxy-1-(4-methoxy-3-phenylbutanoyl)piperidin-4-yl)methyl)-2-methyl-2H-pyrazolo[4,3-d]pyrimidin-7(6H)-one

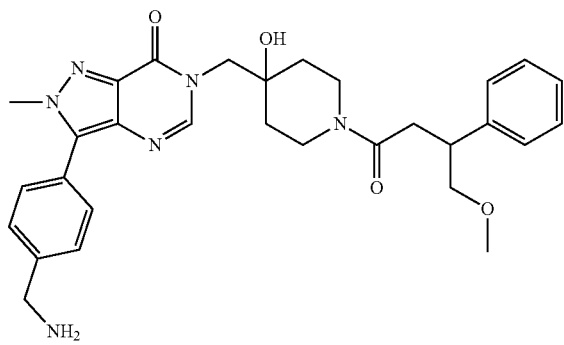 [SMILES: COCC(CC(=O)N1CCC(O)(Cn2cnc3c(-c4ccc(CN)cc4)n(C)nc3c2=O)CC1)c1ccccc1]

Step 1: (rac)-Ethyl 4-methoxy-3-phenylbutanoate

Triethylphosphonoacetate (0.859 mL, 4.33 mmol) was dissolved in THF (10 mL) and the solution was cooled to −78° C. Butyllithium (2.5 M in hexanes, 1.86 mL, 4.66 mmol) was added dropwise and the resulting mixture was stirred for 15 min. 2-methoxy-1-phenylethanone (0.459 mL, 3.33 mmol) was added as a solution in THF (10 mL). The mixture was stirred for 10 min then allowed to return to RT and stirred a further 90 min. The mixture was concentrated in vacuo. The reaction was quenched by the addition of dilute HCl and mixture was then extracted with dichloromethane (×3). The combined organic extracts were washed sequentially with dilute NaHCO$_3$ and brine, then dried over MgSO$_4$ and concentrated in vacuo. The residue was purified by flash chromatography (Grace Resolv 12 g Si; eluted 0-20% EtOAc/c-hex) to give a colourless oil. This was hydrogenated in an H-Cube® (10% Pd/C CatCart®, 1 mL/min, 50 bar, rt) and the resulting solution was concentrated to give the title compound as a colourless oil (510 mg, 69%). LCMS (Method A): $R_T$=1.50 min, m/z=223 [M+H]$^+$. $^1$H NMR (300 MHz, CDCl$_3$): δ 7.27 (m, 5H), 4.06 (m, 2H), 3.50 (m, 3H), 3.33 (s, 3H), 2.80 (dd, 1H), 2.56 (dd, 1H), 1.13 (t, 3H).

Step 2: (rac)-4-Methoxy-3-phenylbutanoic Acid (rac)-Ethyl 4-methoxy-3-phenylbutanoate (505 mg, 2.272 mmol) was dissolved in ethanol (10 mL) and a solution of sodium hydroxide (182 mg, 4.54 mmol) in water (10 mL) was added. The resulting mixture was stirred at 50° C. for 2 h. The volatile components were removed in vacuo then the mixture was acidified with dilute HCl until the pH was approximately 1. The mixture was extracted with ethyl acetate (×2). The combined organic extracts were dried over MgSO$_4$ and concentrated to give the title compound as a colourless oil (290 mg, 66%). LCMS (Method A): $R_T$=1.00 min, m/z=195 [M+H]$^+$.

Step 3: (rac)-3-(4-(Aminomethyl)phenyl)-6-((4-hydroxy-1-(4-methoxy-3-phenylbutanoyl)piperidin-4-yl)methyl)-2-methyl-2H-pyrazolo[4,3-d]pyrimidin-7(6H)-one General procedure 4 using (rac)-4-methoxy-3-phenylbutanoic acid (8.3 mg, 0.043 mmol), tert-butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (20 mg, 0.043 mmol), HATU (24 mg, 0.064 mmol), DIPEA (0.030 mL, 0.171 mmol) and DCM (1 mL) gave the Boc-protected compound as a colourless glass. This was dissolved in DCM (1 mL) and TFA (1 mL) and stirred for 1 h, then concentrated in vacuo. The residue was taken up in methanol and added to a 2 g SCX-2 cartridge. The column was flushed with MeOH then eluted with 2 M NH$_3$ in MeOH. The NH$_3$ fractions were concentrated to give a glass which was purified by chromatography (Biotage 11 g KP-NH; eluted 50-100% EtOAc/c-hex then 0-40% MeOH/EtOAc) to give a glass which was azeotroped with ether then water to give the title compound (13 mg, 56%) as a waxy solid. LCMS (Method A): $R_T$=0.68 min, m/z=545 [M+H]$^+$. $^1$H NMR (300 MHz, DMSO-d$_6$): δ 7.97 (d, 1H), 7.64 (d, 2H), 7.54 (d, 2H), 7.25 (m, 4H), 7.15 (m, 1H), 4.87 (d, 1H), 4.10 (s, 2H), 3.97 (m, 3H), 3.80 (m, 2H), 3.65 (m, 1H), 3.45 (m, 2H), 3.20 (d, 3H), 2.60-2.85 (m, 2H), 2.63 (m, 2H), 2.20 (m, 2H), 1.50 (m, 1H), 1.30 (m, 4H).

Example 54: (R)-6-(1-(2-(Dimethylamino)ethyl)-1H-pyrazol-4-yl)-3-((4-hydroxy-1-(3-phenylbutanoyl)piperidin-4-yl)methyl)pyrimidin-4(3H)-one, Formic Acid

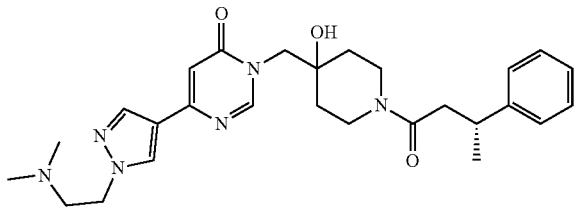 [SMILES: C[C@H](CC(=O)N1CCC(O)(Cn2cnc(-c3cnn(CCN(C)C)c3)cc2=O)CC1)c1ccccc1]

Step 1: N,N-Dimethyl-2-(4-(4,4,5,5-tetramethyl-1,3,2-dioxaborolan-2-yl)-1H-pyrazol-1-yl)ethanamine A mixture of 4-(4,4,5,5-tetramethyl-1,3,2-dioxaborolan-2-yl)-1H-pyrazole (100 mg, 0.515 mmol), 2-chloro-N,N-dimethylethanamine hydrochloride (82 mg, 0.567 mmol), and $Cs_2CO_3$ (504 mg, 1.546 mmol) in acetonitrile (2 mL) was heated at 90° C. for 3 d. After cooling to RT, the reaction mixture was partitioned between DCM and water. The aqueous layer was extracted with DCM and the combined extracts were washed (water), dried ($MgSO_4$), and concentrated in vacuo to give the title compound (76 mg, 56%) as a colourless oil. LCMS (Method B): $R_T$=0.61 min, m/z=266 [M+H]$^+$.

Step 2: (R)-6-(1-(2-(Dimethylamino)ethyl)-1H-pyrazol-4-yl)-3-((4-hydroxy-1-(3-phenylbutanoyl)piperidin-4-yl)methyl)pyrimidin-4(3H)-one, Formic Acid A mixture of Intermediate A (50 mg, 0.128 mmol), N,N-dimethyl-2-(4-(4,4,5,5-tetramethyl-1,3,2-dioxaborolan-2-yl)-1H-pyrazol-1-yl)ethanamine (34 mg, 0.128 mmol) and $Na_2CO_3$ (27 mg, 0.256 mmol) in 1,4-dioxane (0.5 mL) and water (0.2 mL) was degassed by bubbling $N_2$ through the mixture for 5 min. Pd(PPh$_3$)$_4$(7.4 mg, 6.4 µmol) was added and the reaction heated in the microwave at 150° C. for 10 min. The reaction mixture was loaded directly onto a 2 g SCX-2 cartridge. After standing for 5 min, the cartridge was washed with DCM:MeOH (4:1). The product was then eluted with DCM:2 M $NH_3$ in MeOH (4:1). Purification by preparative HPLC (Method A, acidic conditions) gave the title compound (12 mg, 17%) as an off-white solid. LCMS (Method B): $R_T$=0.69 min, m/z=493 [M+H]$^+$. $^1$H NMR (400 MHz, methanol-d$_4$, this molecule appears as two conformers A and B in a 2:3 ratio respectively): δ 8.46 (s, 1H), 8.34 (s, 0.4H (conformer A)), 8.31 (s, 1H), 8.29 (s, 0.6H (conformer B)), 7.35-7.17 (m, 5H), 6.68 (s, 1H), 4.45 (t, 2H), 4.24-4.12 (m, 1H), 4.01 (dd, 1H), 3.89 (dd, 1H), 3.74-3.65 (m, 1H), 3.28-2.92 (m, 3H), 3.14 (t, 2H), 2.84-2.71 (m, 1H), 2.64-2.49 (m, 1H), 2.54 (s, 6H), 1.66-1.24 (m, 7H), 0.96-0.89 (m, 0.6H (conformer B)).

Example 55: 6-((E)-3-((R)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one, Formic Acid

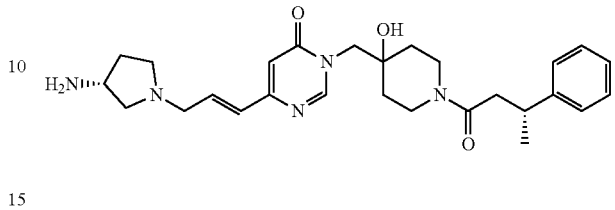

Step 1: (R,E)-tert-Butyl (1-(3-(4,4,5,5-tetramethyl-1,3,2-dioxaborolan-2-yl)allyl)pyrrolidin-3-yl)carbamate A mixture of (E)-2-(3-chloroprop-1-en-1-yl)-4,4,5,5-tetramethyl-1,3,2-dioxaborolane (50 mg, 0.247 mmol), (R)-tert-butyl pyrrolidin-3-ylcarbamate (92 mg, 0.494 mmol), and $K_2CO_3$ (68.3 mg, 0.494 mmol) in MeCN (1 mL) was stirred at RT for 18 h. The reaction mixture was partitioned between EtOAc and water. The aqueous layer was extracted with EtOAc. The combined organic extracts were dried over $MgSO_4$ and concentrated to give crude the title compound (80 mg) as a yellow oil which was used as such without purification. LCMS (Method B): $R_T$=0.81 min, m/z=353 [M+H]$^+$.

Step 2: 6-((E)-3-((R)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one.HCO$_2$H A mixture of Intermediate A (50 mg, 0.128 mmol), (R,E)-tert-butyl (1-(3-(4,4,5,5-tetramethyl-1,3,2-dioxaborolan-2-yl)allyl)pyrrolidin-3-yl)carbamate (54 mg, 0.154 mmol), and $Na_2CO_3$ (27 mg, 0.256 mmol) in 1,4-dioxane (0.5 mL) and water (0.2 mL) was degassed by bubbling $N_2$ through the mixture for 5 min. Pd(PPh$_3$)$_4$(7.4 mg, 6.4 µmol) was added and the reaction heated in the microwave at 150° C. for 10 min. The reaction mixture concentrated in vacuo. The crude residue was dissolved in DCM (0.5 mL) and 4M HCl/1,4-dioxane (0.5 mL) was added. After stirring for 30 min, the solution was loaded directly onto a 2 g SCX-2 cartridge. After standing for 5 min, the cartridge was washed with DCM:MeOH (4:1). The product was then eluted with DCM-2 M $NH_3$ in MeOH (4:1). Purification by preparative HPLC (Method A, acidic conditions) gave the title compound (9 mg, 13%) as a yellow gum. LCMS (Method B): $R_T$=0.57 min, m/z=480 [M+H]$^+$. $^1$H NMR (400 MHz, methanol-d$_4$, this molecule appears as two conformers A and B in a 2:3 ratio respectively): δ 8.38 (s, 1H), 8.32 (s, 0.4H (conformer A)), 8.29 (s, 0.6H (conformer B)), 7.34-7.19 (m, 5H), 6.99 (dt, 1H), 6.54 (d, 1H), 6.41 (s, 1H), 4.23-4.11 (m, 1H), 4.02-3.64 (m, 4H), 3.56-3.35 (m, 1H), 3.28-2.90 (m, 6H), 2.85-2.46 (m, 3H), 2.39-2.23 (m, 1H), 2.19-2.12 (m, 1H), 1.87-1.81 (m, 1H), 1.64-1.29 (m, 6H), 0.95-0.86 (m, 0.6H (conformer B)).

Example 56: 6-((E)-3-((S)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one, Formic Acid

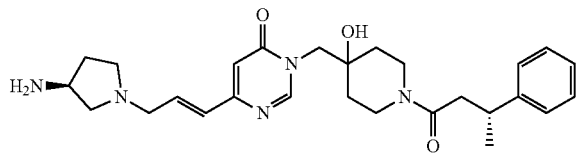 [SMILES: C[C@H](CC(=O)N1CCC(O)(Cn2cnc(/C=C/CN3CC[C@H](N)C3)cc2=O)CC1)c1ccccc1]

Step 1: (S,E)-tert-Butyl (1-(3-(4,4,5,5-tetramethyl-1,3,2-dioxaborolan-2-yl)allyl)pyrrolidin-3-yl)carbamate A mixture of (E)-2-(3-chloroprop-1-en-1-yl)-4,4,5,5-tetramethyl-1,3,2-dioxaborolane (50 mg, 0.247 mmol), (S)-tert-butyl pyrrolidin-3-ylcarbamate (92 mg, 0.494 mmol), and $K_2CO_3$ (68 mg, 0.494 mmol) in MeCN (1 mL) was stirred at RT for 18 h. The reaction mixture was partitioned between EtOAc and water. The aqueous layer was extracted with EtOAc. The combined organic extracts were dried over $MgSO_4$ and concentrated to give crude the title compound (60 mg) as a yellow oil which was used without purification. LCMS (Method B): $R_T$=0.83 min, m/z=353 [M+H]⁺.

Step 2: 6-((E)-3-((S)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one.HCO₂H A mixture of Intermediate A (50 mg, 0.128 mmol), (S,E)-tert-butyl (1-(3-(4,4,5,5-tetramethyl-1,3,2-dioxaborolan-2-yl)allyl)pyrrolidin-3-yl)carbamate (54 mg, 0.154 mmol), and $Na_2CO_3$ (27 mg, 0.256 mmol) in 1,4-dioxane (0.5 mL) and water (0.2 mL) was degassed by bubbling $N_2$ through the mixture for 5 min. Pd(PPh₃)₄(7.4 mg, 6.4 μmol) was added and the reaction heated in the microwave at 150° C. for 10 min. The reaction mixture concentrated in vacuo. The crude residue was dissolved in DCM (0.5 mL) and 4M HCl/1,4-dioxane (0.5 mL) was added. After stirring for 30 min, the solution was loaded directly onto a 2 g SCX-2 cartridge. After standing for 5 min, the cartridge was washed with DCM-MeOH (4:1). The product was then eluted with DCM-2 M $NH_3$ in MeOH (4:1). Purification by preparative HPLC (Method A, acidic conditions) gave the title compound (12 mg, 18%) as a yellow gum. LCMS (Method B): $R_T$=0.57 min, m/z=480 [M+H]⁺. ¹H NMR (400 MHz, methanol-d₄, this molecule appears as two conformers A and B in a 2:3 ratio respectively): δ 8.43 (s, 1H), 8.32 (s, 0.4H (conformer A)), 8.28 (s, 0.6H (conformer B)), 7.36-7.19 (m, 5H), 6.99 (dt, 1H), 6.54 (d, 1H), 6.40 (s, 1H), 4.23-4.11 (m, 1H), 4.02-3.64 (m, 4H), 3.56-3.35 (m, 1H), 3.28-2.90 (m, 6H), 2.84-2.48 (m, 3H), 2.39-2.23 (m, 1H), 2.19-2.12 (m, 1H), 1.87-1.81 (m, 1H), 1.65-1.24 (m, 6H), 0.96-0.86 (m, 0.6H (conformer B)).

Example 57: 3-((4-Hydroxy-1-((R)-3-phenylbutanoyl)piperidin-4-yl)methyl)-6-(((S)-1-phenyl-3-(pyrrolidin-1-yl)propan-2-yl)amino)pyrimidin-4(3H)-one, Formic Acid

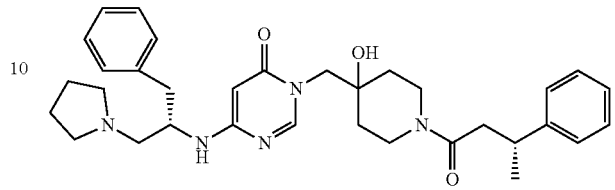

A mixture of Intermediate A (25 mg, 0.064 mmol), (S)-1-phenyl-3-(pyrrolidin-1-yl)propan-2-amine (66 mg, 0.321 mmol) and 1,4-dioxane (1 mL) was heated in the microwave at 150° C. for 30 min. The reaction mixture was concentrated and the residue was purified by preparative HPLC (Method A, acidic conditions) to give the title compound (8 mg, 20%) as a pale yellow solid. LCMS (Method B): $R_T$=0.83 min, m/z=558 [M+H]⁺. ¹H NMR (400 MHz, methanol-d₄, this molecule appears as two conformers A and B in a 2:3 ratio respectively): δ 8.56 (s, 1H), 7.99 (s, 0.4H (conformer A)), 7.95 (s, 0.6H (conformer B)), 7.35-7.17 (m, 10H), 5.29 (s, 1H), 4.22-4.11 (m, 1H), 3.94-3.62 (m, 3H), 3.32-2.50 (m, 13H), 1.99-1.85 (br m, 4H), 1.58-1.22 (m, 7H), 0.92-0.86 (m, 0.6H (conformer B)).

Example 58: 3-((4-Hydroxy-1-((R)-3-phenylbutanoyl)piperidin-4-yl)methyl)-6-(((R)-2-(pyrrolidin-1-yl)propyl)amino)pyrimidin-4(3H)-one

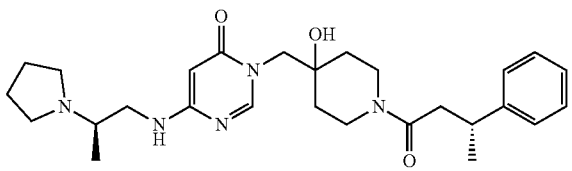 [SMILES: C[C@H](CC(=O)N1CCC(O)(Cn2cnc(NC[C@@H](C)N3CCCC3)cc2=O)CC1)c1ccccc1]

Step 1: (R)-2-(Pyrrolidin-1-yl)propanamide

To a mixture of (R)-2-aminopropanamide hydrochloride (685 mg, 5.50 mmol), $K_2CO_3$ (760 mg, 5.50 mmol), and KI (2.74 mg, 0.016 mmol) in acetonitrile (17 mL) was added 1,4-dibromobutane (0.657 mL, 5.50 mmol). After heating to 80° C. for 18 h, the reaction was cooled to RT and 2N HCl (15 mL) and DCM (20 mL) were added. The aqueous layer was basified with aq NaOH, and extracted sequentially with DCM, EtOAc and CHCl₃—IPA (4:1). The combined organic extracts were dried ($Na_2SO_4$) and concentrated in vacuo to give the title compound (362 mg, 46%) as a white solid. ¹H NMR (400 MHz, CDCl₃): δ 6.85 (br s, 1H), 5.25 (br s, 1H), 2.90 (br m, 1H), 2.50-2.70 (br m, 4H), 1.40-1.60 (br m, 4H), 1.35 (d, 3H).

Step 2: (R)-2-(Pyrrolidin-1-yl)propan-1-amine

A solution of (R)-2-(pyrrolidin-1-yl)propanamide (360 mg, 2.53 mmol) in THF (15 mL) was cooled to 0° C. LiAlH₄ (384 mg, 10.13 mmol) was added, and the mixture was heated at 50° C. for 18 h. Further LiAlH₄ (384 mg, 10.13 mmol) was added, and heating continued at 50° C. for 3 days. The reaction was quenched with a small amount of 40% aq KOH, and stirred for 30 min. The resultant suspension was filtered through Celite® and concentrated in vacuo to give the title compound (>100%) as a yellow oil which was used without purification. $^1$H NMR (400 MHz, CDCl$_3$): δ 3.76-3.72 (m, 4H), 2.73 (d, 2H), 2.34-2.26 (m, 1H), 1.89-1.84 (m, 4H), 1.10 (d, 3H).

Step 3: 3-((4-Hydroxy-1-((R)-3-phenylbutanoyl)piperidin-4-yl)methyl)-6-(((R)-2-(pyrrolidin-1-yl)propyl)amino)pyrimidin-4(3H)-one.HCO$_2$H A mixture of Intermediate A (50 mg, 0.128 mmol), ((R)-2-(pyrrolidin-1-yl)propan-1-amine (82 mg, 0.641 mmol) and 1,4-dioxane (1.5 mL) was heated in the microwave at 175° C. for 30 min. The reaction mixture was concentrated and the residue was purified by preparative HPLC (Method A, acidic conditions) to give the title compound (27 mg, 40%) as a pale orange solid. LCMS (Method B): R$_T$=0.69 min, m/z=482 [M+H]$^+$. $^1$H NMR (400 MHz, methanol-d$_4$, this molecule appears as two conformers A and B in a 2:3 ratio respectively): δ 8.52 (s, 1H), 8.12 (s, 0.4H (conformer A)), 8.08 (s, 0.6H (conformer B)), 7.35-7.17 (m, 5H), 5.42 (s, 1H), 4.22-4.10 (m, 1H), 3.99-3.55 (m, 5H), 3.51-2.93 (m, 10H), 2.83-2.73 (m, 1H), 2.63-2.50 (m, 1H), 2.11-2.02 (m, 4H), 1.62-1.28 (m, 7H), 0.96-0.89 (m, 0.6H (conformer B)).

Example 59: 3-((4-Hydroxy-1-((R)-3-phenylbutanoyl)piperidin-4-yl)methyl)-6-(((S)-2-(pyrrolidin-1-yl)propyl)amino)pyrimidin-4(3H)-one, Formic Acid

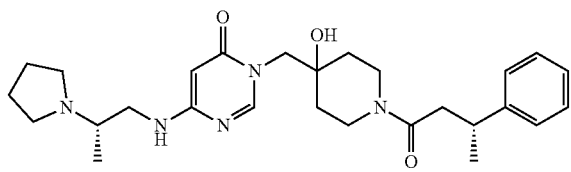 [SMILES: C[C@H](CC(=O)N1CCC(O)(Cn2cnc(NC[C@H](C)N3CCCC3)cc2=O)CC1)c1ccccc1]

A mixture of Intermediate A (50 mg, 0.128 mmol), ((S)-2-(pyrrolidin-1-yl)propan-1-amine (82 mg, 0.641 mmol) (prepared in the same manner as the (R)-enantiomer above) and 1,4-dioxane (1.5 mL) was heated in the microwave at 175° C. for 30 min. The reaction mixture was concentrated and the residue was purified by preparative HPLC (Method A, acidic conditions) to give the title compound (15 mg, 22%) as a pale orange solid. LCMS (Method B): R$_T$=0.66 min, m/z=482 [M+H]$^+$. $^1$H NMR (400 MHz, methanol-d$_4$, this molecule appears as two conformers A and B in a 2:3 ratio respectively): δ 8.53 (s, 1H), 8.12 (s, 0.4H (conformer A)), 8.08 (s, 0.6H (conformer B)), 7.35-7.17 (m, 5H), 5.42 (s, 1H), 4.22-4.11 (m, 1H), 3.98-3.55 (m, 5H), 3.51-2.93 (m, 10H), 2.83-2.73 (m, 1H), 2.63-2.50 (m, 1H), 2.10-2.00 (m, 4H), 1.62-1.28 (m, 7H), 0.97-0.90 (m, 0.6H (conformer B)).

Example 60: 3-((4-Hydroxy-1-((R)-3-phenylbutanoyl)piperidin-4-yl)methyl)-6-(((R)-1-(pyrrolidin-1-yl)propan-2-yl)amino)pyrimidin-4(3H)-one, Formic Acid

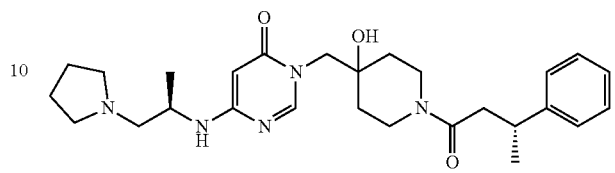

Step 1: (R)-tert-Butyl (1-hydroxypropan-2-yl)carbamate

A solution of (R)-2-aminopropan-1-ol (1 mL, 12.85 mmol) in THF (10 mL) was cooled to 0° C. and Na$_2$CO$_3$ (1.634 g, 15.42 mmol) followed by water (2 mL) were added. A solution of Boc$_2$O (3.04 mL, 13.10 mmol) in THF (4 mL) was added slowly over 15 min and the reaction was stirred at 0° C. for a further 1.5 h. The reaction mixture was concentrated in vacuo. The residue was partitioned between EtOAc and water. The aqueous layer was extracted with EtOAc. The combined organic extracts were dried over MgSO$_4$ and concentrated in vacuo to give the title compound (2.35 g, 104%) as a colourless oil which was used as such without further purification. $^1$H NMR (400 MHz, CDCl$_3$): δ 4.65 (br s, 1H), 3.77 (br s, 1H), 3.60-3.70 (m, 1H), 3.48-3.53 (m, 1H), 2.61 (br s, 1H), 1.45 (s, 9H), 1.14 (d, 3H).

Step 2: (R)-2-((tert-Butoxycarbonyl)amino)propyl Methanesulfonate

A solution of (R)-tert-butyl (1-hydroxypropan-2-yl)carbamate (2.25 g, 12.84 mmol) and Et$_3$N (3.58 mL, 25.7 mmol) in DCM (20 mL) was cooled to 0° C., and MsCl (1.20 mL, 15.41 mmol) was added. After stirring at RT for 30 min, the reaction was quenched with dilute aq NaHCO$_3$. The aqueous layer was extracted with DCM, and the combined organic extracts were dried (Biotage phase separator) and concentrated in vacuo to give the title compound (3.19 g, 98%) as a pale yellow solid. $^1$H NMR (400 MHz, CDCl$_3$): δ 4.61 (br s, 1H), 4.28-4.20 (br m, 1H), 4.17-4.14 (dd, 1H), 4.05-3.95 (br m, 1H), 3.04 (s, 3H), 1.45 (s, 9H), 1.24 (d, 3H).

Step 3: (R)-tert-Butyl (1-(pyrrolidin-1-yl)propan-2-yl)carbamate

A solution of (R)-2-((tert-butoxycarbonyl)amino)propyl methanesulfonate (500 mg, 1.97 mmol) and pyrrolidine (1.632 mL, 19.74 mmol) in THF (5 mL) was heated at 70° C. for 18 h. The mixture was partitioned between EtOAc and water. The aqueous layer was extracted with EtOAc. The combined organic extracts were washed (brine), dried over MgSO$_4$ and concentrated in vacuo to give the title compound (389 mg, 86%). $^1$H NMR (400 MHz, CDCl$_3$): δ 4.61 (br s, 1H), 3.67 (br m, 1H), 2.60-2.45 (m, 5H), 2.33 (dd, 1H), 1.80-1.72 (m, 4H), 1.45 (s, 9H), 1.17 (d, 3H).

Step 4: (R)-1-(Pyrrolidin-1-yl)propan-2-amine

A solution of (R)-tert-butyl (1-(pyrrolidin-1-yl)propan-2-yl)carbamate (389 mg, 1.704 mmol) and TFA (1.5 mL, 19.47 mmol) in DCM (2.5 mL) was stirred for 1 h. The reaction mixture was concentrated in vacuo and loaded onto a 5 g SCX-2 cartridge. After standing for 30 min, the cartridge was washed with DCM:MeOH (4:1). Elution with DCM-2 M NH₃ in MeOH (4:1), followed by concentration in vacuo gave the title compound (178 mg, 81%) as a pale brown oil which was used as such without further purification. ¹H NMR (400 MHz, CDCl₃): δ 3.09-3.02 (m, 1H), 2.65-2.61 (m, 1H), 2.51-2.35 (br m, 6H), 2.25 (dd, 1H), 1.88-1.74 (m, 4H), 1.08 (d, 3H).

Step 5: 3-((4-Hydroxy-1-((R)-3-phenylbutanoyl)piperidin-4-yl)methyl)-6-(((R)-1-(pyrrolidin-1-yl)propan-2-yl)amino)pyrimidin-4(3H)-one, Formic Acid A mixture of Intermediate A (50 mg, 0.128 mmol), (R)-1-(pyrrolidin-1-yl)propan-2-amine (82 mg, 0.641 mmol) and 1,4-dioxane (1.5 mL) was heated in the microwave at 175° C. for 30 min. The reaction mixture was concentrated and the residue was purified by preparative HPLC (Method A, acidic conditions) to give the title compound (23 mg, 35%) as a pale orange solid. LCMS (Method B): R$_T$=0.66 min, m/z=482 [M+H]⁺. ¹H NMR (400 MHz, methanol-d₄, this molecule appears as two conformers A and B in a 2:3 ratio respectively): δ 8.52 (s, 1H), 8.12 (s, 0.4H (conformer A)), 8.08 (s, 0.6H (conformer B)), 7.35-7.17 (m, 5H), 5.42 (s, 1H), 4.45 (br s, 1H), 4.22-4.10 (m, 1H), 3.94-3.61 (m, 3H), 3.51-2.94 (m, 10H), 2.83-2.73 (m, 1H), 2.63-2.50 (m, 1H), 2.10-2.00 (m, 4H), 1.62-1.26 (m, 9H), 0.98-0.91 (m, 0.6H (conformer B)).

Example 61: 3-((4-Hydroxy-1-((R)-3-phenylbutanoyl)piperidin-4-yl)methyl)-6-(((S)-1-(pyrrolidin-1-yl)propan-2-yl)amino)pyrimidin-4(3H)-one, Formic Acid

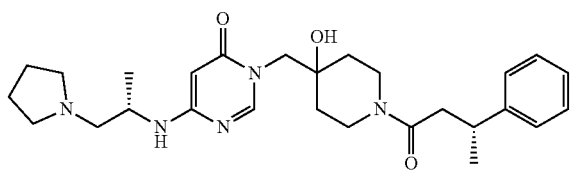 [SMILES: C[C@H](CC(=O)N1CCC(O)(Cn2cnc(N[C@@H](C)CN3CCCC3)cc2=O)CC1)c1ccccc1]

A mixture of Intermediate A (50 mg, 0.128 mmol), (S)-1-(pyrrolidin-1-yl)propan-2-amine (82 mg, 0.641 mmol) (prepared as (R)-enantiomer above) and 1,4-dioxane (1.5 mL) was heated in the microwave at 175° C. for 30 min. The reaction mixture was concentrated and the residue was purified by preparative HPLC (Method A, acidic conditions) to give the title compound (15 mg, 22%) as a pale orange solid. LCMS (Method B): R$_T$=0.69 min, m/z=482 [M+H]⁺. ¹H NMR (400 MHz, methanol-d₄, this molecule appears as two conformers A and B in a 2:3 ratio respectively): δ 8.54 (s, 1H), 8.11 (s, 0.4H (conformer A)), 8.07 (s, 0.6H (conformer B)), 7.35-7.17 (m, 5H), 5.41 (s, 1H), 4.45 (br s, 1H), 4.23-4.11 (m, 1H), 4.00-3.65 (m, 3H), 3.51-2.93 (m, 10H), 2.83-2.73 (m, 1H), 2.63-2.50 (m, 1H), 2.10-2.00 (m, 4H), 1.62-1.26 (m, 9H), 0.95-0.88 (m, 0.6H (conformer B)).

Example 62: 6-((S)-3-(Dimethylamino)pyrrolidin-1-yl)-3-((4-hydroxy-1-((R)-3-phenylbutanoyl)piperidin-4-yl)methyl)pyrimidin-4(3H)-one

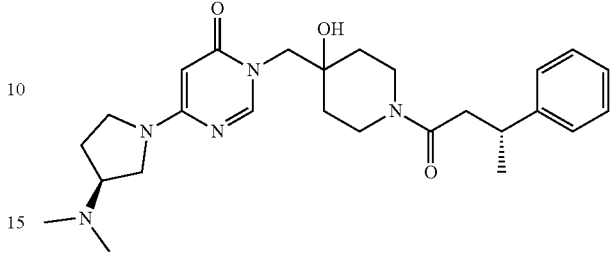

To a mixture of 6-((S)-3-aminopyrrolidin-1-yl)-3-((4-hydroxy-1-((R)-3-phenylbutanoyl)piperidin-4-yl)methyl)pyrimidin-4(3H)-one. HCO₂H (50 mg, 0.103 mmol) and formaldehyde (37% in water) (31 μL, 0.412 mmol) in methanol (2 mL) was added sodium triacetoxyborohydride (218 mg, 1.03 mmol), and the mixture was stirred for 30 min. After concentration in vacuo, the residue was dissolved in DCM, washed (aq NaHCO₃), dried (Biotage phase separator) and re-concentrated. Lyophilisation gave the title compound (28 mg, 59%) as an off-white solid. LCMS (Method B): R$_T$=0.63 min, m/z=468 [M+H]⁺. ¹H NMR (400 MHz, methanol-d₄, this molecule appears as two conformers A and B in a 2:3 ratio respectively): δ 8.08 (s, 0.4H (conformer A)), 8.01 (s, 0.6H (conformer B)), 7.35-7.17 (m, 5H), 5.22 (s, 1H), 4.23-4.11 (m, 1H), 4.02-3.64 (m, 5H), 3.30-3.15 (m, 3H), 3.08-2.92 (m, 2H), 2.83-2.72 (m, 1H), 2.63-2.49 (m, 1H), 2.39 (s, 6H), 2.42-2.27 (m, 1H), 2.00-1.85 (m, 1H), 1.62-1.27 (m, 7H), 0.95-0.88 (m, 0.6H (conformer B)).

Example 63: rac-6-(((±-trans-1,2)-2-Aminocyclohexyl)amino)-3-((4-hydroxy-1-((R)-3-phenylbutanoyl)piperidin-4-yl)methyl)pyrimidin-4(3H)-one, Formic Acid

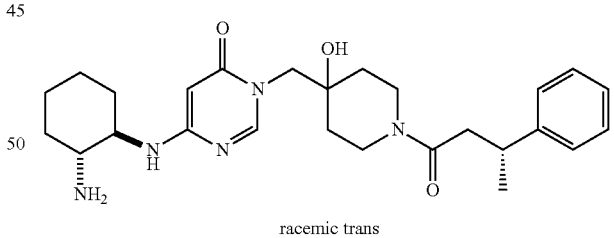

racemic trans

A mixture of Intermediate A (50 mg, 0.128 mmol), (rac)-trans-1,2-diaminocyclohexane (77 μl, 0.641 mmol) and 1,4-dioxane (1.5 mL) was heated in the microwave at 175° C. for 30 min. The reaction mixture was concentrated and the residue was purified by preparative HPLC (Method A, acidic conditions) to give the title compound (14 mg, 21%) as a pale yellow solid. LCMS (Method B): R$_T$=0.69 min, m/z=468 [M+H]⁺. ¹H NMR (400 MHz, methanol-d₄, this molecule appears as two conformers A and B in a 2:3 ratio respectively): δ 8.53 (s, 1H), 8.10 (s, 0.4H (conformer A)), 8.06 (s, 0.6H (conformer B)), 7.35-7.17 (m, 5H), 5.41 (s, 1H), 4.22-4.10 (m, 1H), 3.99-3.61 (m, 4H), 3.29-2.93 (m, 4H), 2.83-2.73 (m, 1H), 2.63-2.50 (m, 1H), 2.18-1.98 (m, 2H), 1.90-1.80 (m, 2H), 1.63-1.29 (m, 10H), 0.99-0.88 (m, 0.6H (conformer B)).

Example 64: 6-(((±-cis-1,2)-2-Aminocyclohexyl)amino)-3-((4-hydroxy-1-((R)-3-phenylbutanoyl)piperidin-4-yl)methyl)pyrimidin-4(3H)-one, Formic Acid

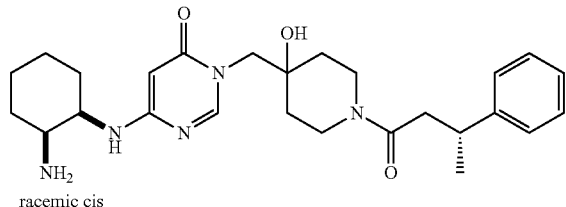 [SMILES: C[C@H](CC(=O)N1CCC(O)(Cn2cnc(N[C@@H]3CCCC[C@@H]3N)cc2=O)CC1)c1ccccc1]

racemic cis

A mixture of Intermediate A (50 mg, 0.128 mmol), cis-1,2-diaminocyclohexane (77 µL, 0.641 mmol) and 1,4-dioxane (1.5 mL) was heated in the microwave at 175° C. for 30 min. The reaction mixture was concentrated and the residue was purified by preparative HPLC (Method A, acidic conditions) to give the title compound (22 mg, 33%) as a pale yellow solid. LCMS (Method B): $R_T$=0.69 min, m/z=468 [M+H]$^+$. $^1$H NMR (400 MHz, methanol-d$_4$, this molecule appears as two conformers A and B in a 2:3 ratio respectively): δ 8.53 (s, 1H), 8.12 (s, 0.4H (conformer A)), 8.08 (s, 0.6H (conformer B)), 7.35-7.17 (m, 5H), 5.55 (s, 1H), 4.40 (br s, 1H), 4.22-4.10 (m, 1H), 4.00-3.61 (m, 3H), 3.50-3.43 (m, 1H), 3.29-2.96 (m, 3H), 2.83-2.73 (m, 1H), 2.63-2.50 (m, 1H), 1.90-1.29 (m, 15H), 0.98-0.88 (m, 0.6H (conformer B)).

Example 65: 3-((4-Hydroxy-1-((R)-3-phenylbutanoyl)piperidin-4-yl)methyl)-6-((((R)-1-methylpyrrolidin-2-yl)methyl)amino)pyrimidin-4(3H)-one, Formic Acid

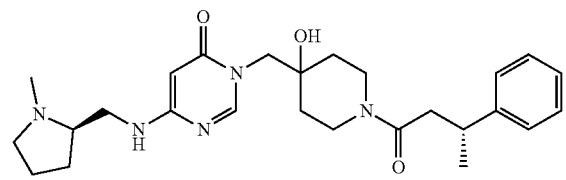 [SMILES: C[C@H](CC(=O)N1CCC(O)(Cn2cnc(NC[C@H]3CCCN3C)cc2=O)CC1)c1ccccc1]

A mixture of Intermediate A (50 mg, 0.128 mmol), (R)-(1-methylpyrrolidin-2-yl)methanamine (73 mg, 0.641 mmol) and 1,4-dioxane (1.5 mL) was heated in the microwave at 150° C. for 30 min. The reaction mixture was concentrated and the residue was purified by preparative HPLC (Method A, acidic conditions) to give the title compound (24 mg, 37%) as a pale yellow solid. LCMS (Method B): $R_T$=0.71 min, m/z=468 [M+H]$^+$. $^1$H NMR (400 MHz, methanol-d$_4$, this molecule appears as two conformers A and B in a 2:3 ratio respectively): δ 8.43 (s, 1H), 8.15 (s, 0.4H (conformer A)), 8.11 (s, 0.6H (conformer B)), 7.36-7.17 (m, 5H), 5.34 (s, 1H), 4.55 (br s, 1H), 4.21-4.08 (m, 1H), 4.01-3.61 (m, 3H), 3.51-3.43 (m, 1H), 3.32-2.97 (m, 6H), 2.74 (s, 3H), 2.63-2.50 (m, 1H), 2.25-1.91 (m, 4H), 1.62-1.31 (m, 7H), 1.02-0.92 (m, 0.6H (conformer B)).

Example 66: 3-((4-Hydroxy-1-((R)-3-phenylbutanoyl)piperidin-4-yl)methyl)-6-((((S)-1-methylpyrrolidin-2-yl)methyl)amino)pyrimidin-4(3H)-one, Formic Acid

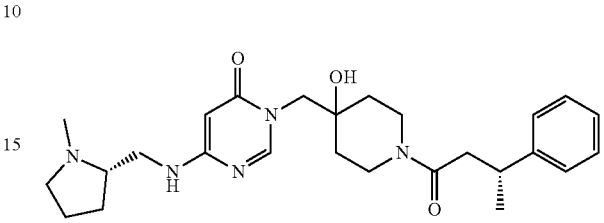

A mixture of Intermediate A (50 mg, 0.128 mmol), (S)-(1-methylpyrrolidin-2-yl)methanamine (73 mg, 0.641 mmol) and 1,4-dioxane (1.5 mL) was heated in the microwave at 150° C. for 30 min. The reaction mixture was concentrated and the residue was purified by preparative HPLC (Method A, acidic conditions) to give the title compound (26 mg, 39%) as a pale yellow solid. LCMS (Method B): $R_T$=0.72 min, m/z=468 [M+H]$^+$. $^1$H NMR (400 MHz, methanol-d$_4$, this molecule appears as two conformers A and B in a 2:3 ratio respectively): δ 8.44 (s, 1H), 8.15 (s, 0.4H (conformer A)), 8.11 (s, 0.6H (conformer B)), 7.36-7.17 (m, 5H), 5.34 (s, 1H), 4.55 (br s, 1H), 4.21-3.61 (m, 4H), 3.50-3.40 (m, 1H), 3.32-2.97 (m, 6H), 2.73 (s, 3H), 2.63-2.50 (m, 1H), 2.25-1.91 (m, 4H), 1.62-1.31 (m, 7H), 0.99-0.88 (m, 0.6H (conformer B)).

Example 67: (R)-3-((4-Hydroxy-1-(3-phenylbutanoyl)piperidin-4-yl)methyl)pyrimidin-4(3H)-one

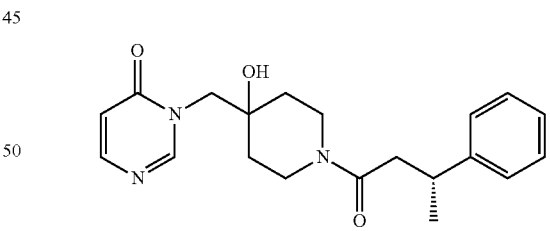

General procedure A using pyrimidin-4(3H)-one (22 mg, 0.23 mmol), Cs$_2$CO$_3$ (94 mg, 0.29 mmol), Epoxide 2 (50 mg, 0.19 mmol) and DMF (1 mL) gave the title compound (27 mg, 39%) as a white solid. LCMS (Method A): $R_T$=0.88 min, m/z=356 [M+H]$^+$. $^1$H NMR (300 MHz, CDCl$_3$): δ 7.92-8.10 (m, 2H), 7.25 (m, partially obscured by solvent, presumed 5H), 6.52 (d, 1H), 4.25-4.50 (m, 1H), 3.48-4.06 (m, 4H), 2.80-3.46 (m, 3H), 2.70 (m, 1H), 2.51 (m, 1H), 1.50 (m, 2H), 1.28 (m, 4H), 0.70 (m, 1H).

Example 68: (R)-9-(4-(Aminomethyl)phenyl)-1-((4-hydroxy-1-(3-phenylbutanoyl)piperidin-4-yl)methyl)-1H-purin-6(9H)-one

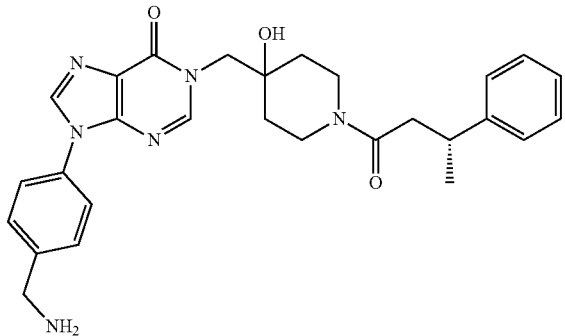 [SMILES: C[C@H](CC(=O)N1CCC(O)(Cn2cnc3c(ncn3-c3ccc(CN)cc3)c2=O)CC1)c1ccccc1]

Step 1: tert-Butyl 4-((6-chloro-5-nitropyrimidin-4-yl)amino)benzylcarbamate A solution of tert-butyl 4-aminobenzylcarbamate (2.36 g, 10.6 mmol) (PCT Int. Appl., 9905096, 4 Feb. 1999) in THF (21 mL) was slowly added to a solution of 4,6-dichloro-5-nitropyrimidine (2.06 g, 10.6 mmol) and NEt$_3$ (1.78 mL, 12.7 mmol) in THF (21 mL) using a pressure equalising dropping funnel. After 16 h the reaction was quenched by the addition of saturated NaHCO$_{3(aq)}$ (150 mL) and the mixture was extracted with EtOAc (3×50 mL). The combined organic phases had a fine precipitate so DCM (200 mL) was added to give a homogeneous solution which was passed through a Biotage phase separator before being concentrated. The mixture was slurried in a mixture of MeOH and DCM (1:1~75 mL) and the precipitate filtered off. The filtrate was concentrated and the residue dried in vacuo to give the title compound (2.58 g, 64%) as a yellow solid. This compound was used without further purification. LCMS (Method A): R$_T$=1.57 min, m/z=380, 382 [M+H]$^+$. $^1$H NMR (300 MHz, DMSO-d$_6$): δ 8.48 (s, 1H), 7.41 (d, 2H), 7.23 (d, 2H), 4.10 (s, 2H), 1.39 (s, 9H).

Step 2: tert-Butyl 4-((5-amino-6-chloropyrimidin-4-yl)amino)benzylcarbamate A suspension of tert-butyl 4-((6-chloro-5-nitropyrimidin-4-yl)amino)benzylcarbamate (2.58 g, 6.79 mmol) and Fe (3.79 g, 67.9 mmol) in AcOH (68 mL) were heated at 80° C. for 1 h before being cooled to RT and the reaction mixture filtered to remove the unreacted Fe. The filtrate was concentrated, saturated NaHCO$_{3(aq)}$ (500 mL) added and the mixture extracted with DCM (3×200 mL) using a Biotage phase separator. The combined organic phases were concentrated and the residue purified by flash chromatography (120 g GraceResolv™ silica, 0-100% EtOAc in cyclohexane) to give the title compound (900 mg, 38%) as a pale yellow foam. LCMS (Method A): R$_T$=1.28 min, m/z=350, 352 [M+H]$^+$. $^1$H NMR (300 MHz, CDCl$_3$): δ 8.10 (s, 1H), 7.47-7.30 (m, 2H), 7.20-7.00 (m, 2H), 5.03 (br. s, 1H), 4.23 (d, 2H), 3.90 (br. s, 2H), 1.47 (s, 9H).

Step 3: tert-Butyl 4-(6-chloro-9H-purin-9-yl)benzylcarbamate

A solution of tert-butyl 4-((5-amino-6-chloropyrimidin-4-yl)amino)benzylcarbamate (245 mg, 0.700 mmol), triethyl orthoformate (0.583 mL, 3.50 mmol) and NEt$_3$ (98 μL, 0.700 mmol) in MeCN (2.80 mL) were heated in a microwave at 140° C. for 1 h. Further triethyl orthoformate (0.583 mL, 3.50 mmol) was added and the reaction was heated at 140° C. for 5 h. The reaction mixture was concentrated and the residue purified by flash chromatography (40 g GraceResolv™ silica, 0-70% EtOAc in cyclohexane) to give the title compound (228 mg, 90%) as a pale yellow solid. LCMS (Method A): R$_T$=1.34 min, m/z=360, 362 [M+H]$^+$. $^1$H NMR (300 MHz, CDCl$_3$): δ 8.82 (s, 1H), 8.39 (s, 1H), 7.68 (d, 2H), 7.53 (d, 2H), 4.99 (br. s, 1H), 4.42 (d, 2H), 1.48 (s, 9H).

Step 4: tert-Butyl 4-(6-oxo-1H-purin-9(6H)-yl)benzylcarbamate

A mixture of tert-butyl 4-(6-chloro-9H-purin-9-yl)benzylcarbamate (201 mg, 0.559 mmol), 1 M NaOH$_{(aq)}$ (2.24 mL, 2.235 mmol) and MeOH (2.24 mL) was heated at 80° C. for 17 h before the reaction was allowed to cooled to room temperature. The pH was adjusted to pH 4 by the addition of AcOH and the precipitate was isolated by filtration. The precipitate was washed with water (3×5 mL) and then dried under high vacuum at 50° C. to give the title compound (89 mg, 46%) as a pinkish beige solid. The combined filtrate and aqueous washes were then extracted with DCM (3×20 mL) using a Biotage phase separator. The combined organic phases were then concentrated and the residue purified by flash chromatography (12 g GraceResolv™ silica, 0-40% MeOH in DCM) to give the title compound (52 mg, 27%) as a yellow solid. LCMS (Method A): R$_T$=0.94 min, m/z=342 [M+H]$^+$. $^1$H NMR (300 MHz, DMSO-d$_6$): δ 12.42 (br. s, 1H), 8.45 (s, 1H), 8.09 (s, 1H), 7.71 (d, 2H), 7.52 (t, 1H), 7.42 (d, 2H), 4.19 (d, 2H), 1.40 (s, 9H).

Step 5: Benzyl 4-((9-(4-(((tert-butoxycarbonyl)amino)methyl)phenyl)-6-oxo-6,9-dihydro-1H-purin-1-yl)methyl)-4-hydroxypiperidine-1-carboxylate General procedure 1 using Epoxide 4 (120 mg, 0.486 mmol), tert-butyl 4-(6-oxo-1H-purin-9(6H)-yl)benzylcarbamate (83 mg, 0.243 mmol), Cs$_2$CO$_3$ (87 mg, 0.267 mmol) and DMF (0.8 mL) gave the title compound (94 mg, 65%) as a cloudy yellow gum. LCMS (Method A): R$_T$=1.36 min, m/z=589 [M+H]$^+$. $^1$H NMR (300 MHz, CDCl$_3$): δ 8.03 (s, 1H), 8.02 (s, 1H), 7.58 (d, 2H), 7.50 (d, 2H), 7.39-7.30 (m, 5H), 5.31 (s, 1H), 5.13 (s, 2H), 4.98 (br. s, 1H), 4.41 (d, 2H), 4.08-3.89 (br. m, 2H), 3.34-3.17 (br. m, 2H), 1.6-1.54 (br. m, 4H), 1.48 (s, 9H).

Step 6: tert-Butyl 4-(1-((4-hydroxypiperidin-4-yl)methyl)-6-oxo-1H-purin-9(6H)-yl)benzylcarbamate General procedure 7 using benzyl 4-((9-(4-(((tert-butoxycarbonyl)amino)methyl)phenyl)-6-oxo-6,9-dihydro-1H-purin-1-yl)methyl)-4-hydroxypiperidine-1-carboxylate (90 mg, 0.153 mmol), 10% Pd on carbon (16 mg, 0.015 mmol), ammonium formate (289 mg, 4.59 mmol) and EtOH (1.5 mL) after 50 min gave the title compound (54 mg, 78%) as a colourless solid. LCMS (Method A): R$_T$=0.71 min, m/z=455 [M+H]$^+$. $^1$H NMR (300 MHz, CDCl$_3$): δ 8.13 (s, 1H), 7.99 (s, 1H), 7.56 (d, 2H), 7.48 (d, 2H), 4.39 (d, 2H), 4.18 (s, 2H), 2.96-2.85 (m, 4H), 1.75-1.50 (m, 4H), 1.47 (s, 9H).

Step 7: (R)-9-(4-(Aminomethyl)phenyl)-1-((4-hydroxy-1-(3-phenylbutanoyl)piperidin-4-yl)methyl)-1H-purin-6(9H)-one General procedure 4 using tert-butyl 4-(1-((4-hydroxypiperidin-4-yl)methyl)-6-oxo-1H-purin-9(6H)-yl)benzylcarbamate (29 mg, 0.064 mmol), (R)-3-phenylbutanoic acid (16 mg, 0.096 mmol), HATU (36 mg, 0.096 mmol), DIPEA (45 μL, 0.255 mmol) and DCM (1.3 mL) and then general procedure 2 using TFA (1 mL) and DCM (1 mL) gave the title compound (24 mg, 65% (2 steps)) as a colourless solid. LCMS (Method A): $R_T$=0.66 min, m/z=501 [M+H]$^+$. $^1$H NMR (300 MHz, DMSO-d$_6$): δ 8.47 (s, 1H), 8.29-8.22 (m, 1H), 7.70 (d, 2H), 7.54 (d, 2H), 7.29-7.21 (m, 4H), 7.20-7.11 (m, 1H), 4.91 (d, 1H), 4.25-3.84 (m, 3H), 3.84-3.48 (m, 3H), 3.30-3.08 (m, 2H), 2.99-2.52 (m, 3H), 1.61 (m, 4H), 1.20 (d, 3H).

Example 69: 3-((4-Hydroxy-1-((R)-3-phenylbutanoyl)piperidin-4-yl)methyl)-6-((2-((S)-2-methylpyrrolidin-1-yl)ethyl)amino)pyrimidin-4(3H)-one, Formic Acid

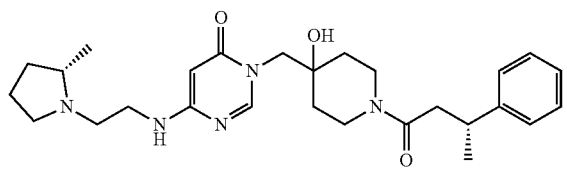 [SMILES: C[C@H](CC(=O)N1CCC(O)(Cn2cnc(NCCN3CCC[C@@H]3C)cc2=O)CC1)c1ccccc1]

Step 1: 2-((tert-Butoxycarbonyl)amino)ethyl methanesulfonate

A solution of tert-butyl (2-hydroxyethyl)carbamate (1.5 mL, 9.70 mmol) and Et$_3$N (3.38 mL, 24.24 mmol) in DCM (15 mL) was cooled to 0° C., and methanesulfonyl chloride (0.907 mL, 11.64 mmol) was added slowly. After stirring at RT for 30 min, the reaction was quenched with aq NaHCO$_3$. The aqueous layer was extracted with DCM. The combined extracts were dried (Biotage phase separator) and concentrated to give the title compound (2.54 g, 109%) as a colourless oil which was used without purification. $^1$H NMR (400 MHz, CDCl$_3$): δ 4.92 (br s, 1H), 4.29 (t, 2H), 3.50-3.46 (m, 2H), 3.04 (s, 3H), 1.45 (s, 9H).

Step 2: (S)-tert-Butyl (2-(2-methylpyrrolidin-1-yl)ethyl)carbamate

A solution of 2-((tert-butoxycarbonyl)amino)ethyl methanesulfonate (200 mg, 0.836 mmol) and (S)-2-methylpyrrolidine (0.211 mL, 2.09 mmol) in THF (2 mL) was heated to 70° C. for 3 h. The reaction mixture was partitioned between EtOAc and water. The aqueous layer was extracted with EtOAc. The combined organic extracts were dried over MgSO$_4$ and concentrated to give crude the title compound (181 mg, <95%) as a yellow oil which was used without purification. LCMS (Method B): $R_T$=0.56 min, m/z=229 [M+H]$^+$.

Step 3: 3-((4-Hydroxy-1-((R)-3-phenylbutanoyl)piperidin-4-yl)methyl)-6-((2-((S)-2-methylpyrrolidin-1-yl)ethyl)amino)pyrimidin-4(3H)-one, Formic Acid A solution of (S)-tert-butyl (2-(2-methylpyrrolidin-1-yl)ethyl)carbamate (181 mg, 0.793 mmol) and TFA (0.5 mL, 6.49 mmol) in DCM (2 mL) was stirred for 30 min. The reaction mixture was concentrated in vacuo, and then loaded onto a 2 g SCX-2 cartridge. After standing for 30 min, the cartridge was washed with DCM-MeOH (4:1). Elution with DCM-2 M NH$_3$ in MeOH (4:1), followed by concentration in vacuo gave crude (S)-2-(2-methylpyrrolidin-1-yl)ethanamine which was combined with Intermediate A (40 mg, 0.103 mmol) and 1,4-dioxane (1.5 mL), and heated in the microwave at 175° C. for 30 min. The reaction mixture was concentrated and the residue was purified by preparative HPLC (Method A, acidic conditions) to give the title compound (11 mg, 21%) as a pale orange solid. LCMS (Method B): $R_T$=0.68 min, m/z=482 [M+H]$^+$. $^1$H NMR (400 MHz, methanol-d$_4$, this molecule appears as two conformers A and B in a 2:3 ratio respectively): δ 8.53 (s, 1H), 8.11 (s, 0.4H (conformer A)), 8.06 (s, 0.6H (conformer B)), 7.35-7.17 (m, 5H), 5.38 (s, 1H), 4.23-4.11 (m, 1H), 3.94 (dd, 1H), 3.80 (dd, 1H), 3.77-3.55 (m, 3H), 3.51-3.38 (m, 1H), 3.29-3.15 (m, 2H), 3.09-2.93 (m, 3H), 2.83-2.72 (m, 1H), 2.63-2.49 (m, 1H), 2.30-2.21 (m, 1H), 2.10-1.98 (m, 4H), 1.74-1.26 (m, 10H), 0.96-0.89 (m, 0.6H (conformer B)).

Example 70: 3-((4-Hydroxy-1-((R)-3-phenylbutanoyl)piperidin-4-yl)methyl)-6-((2-((R)-2-(methoxymethyl)pyrrolidin-1-yl)ethyl)amino)pyrimidin-4(3H)-one

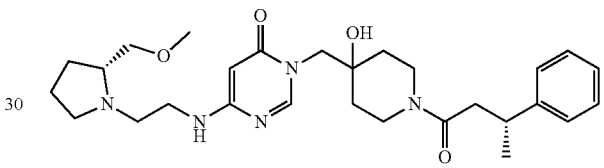

Step 1: (R)-tert-Butyl (2-(2-(methoxymethyl)pyrrolidin-1-yl)ethyl)carbamate

Following the procedure for (S)-tert-butyl (2-(2-methylpyrrolidin-1-yl)ethyl)carbamate, (R)-2-(methoxymethyl)pyrrolidine (0.26 mL, 2.09 mmol) was reacted to give crude (R)-tert-butyl (2-(2-(methoxymethyl)pyrrolidin-1-yl)ethyl)carbamate (187 mg, <87%) which was used without purification. LCMS (Method B): $R_T$=0.60 min, m/z=259 [M+H]$^+$.

Step 2: 3-((4-Hydroxy-1-((R)-3-phenylbutanoyl)piperidin-4-yl)methyl)-6-((2-((R)-2-(methoxymethyl)pyrrolidin-1-yl)ethyl)amino)pyrimidin-4(3H)-one Following the procedure for 3-((4-hydroxy-1-((R)-3-phenylbutanoyl)piperidin-4-yl)methyl)-6-((2-((S)-2-methylpyrrolidin-1-yl)ethyl)amino)pyrimidin-4(3H)-one, formic acid, (R)-tert-butyl (2-(2-(methoxymethyl)pyrrolidin-1-yl)ethyl)carbamate (187 mg, 0.724 mmol) and Intermediate A (40 mg, 0.103 mmol) were reacted and the mixture was purified by preparative HPLC (Method A, acidic conditions) to give the title compound (30 mg, 57%) as a pale orange solid. LCMS (Method B): $R_T$=0.82 min, m/z=512 [M+H]$^+$. $^1$H NMR (400 MHz, methanol-d$_4$, this molecule appears as two conformers A and B in a 2:3 ratio respectively): δ 8.03 (s, 0.4H (conformer A)), 7.98 (s, 0.6H (conformer B)), 7.35-7.17 (m, 5H), 5.29 (s, 1H), 4.24-4.12 (m, 1H), 3.99-3.64 (m, 4H), 3.43-2.92 (m, 7H), 2.83-2.72 (m, 2H), 2.63-2.49 (m, 2H), 2.40-2.33 (m, 1H), 2.05 (s, 3H), 2.00-1.91 (m, 1H), 1.83-1.72 (m, 2H), 1.63-1.28 (m, 8H), 0.95-0.87 (m, 0.6H (conformer B)).

Example 71: 3-((4-Hydroxy-1-((R)-3-phenylbutanoyl)piperidin-4-yl)methyl)-6-((2-((S)-3-methylpyrrolidin-1-yl)ethyl)amino)pyrimidin-4(3H)-one, Formic Acid

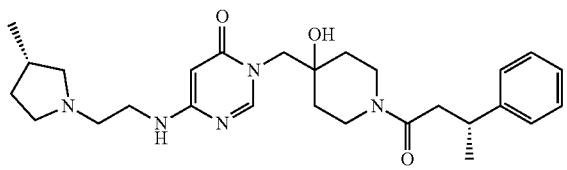 [SMILES: C[C@H]1CCN(CCNc2cc(=O)n(CC3(O)CCN(C(=O)C[C@@H](C)c4ccccc4)CC3)cn2)C1]

Step 1: (S)-2-Methylbutane-1,4-diyl Dimethanesulfonate

A solution of (S)-2-methylbutane-1,4-diol (0.5 mL, 4.76 mmol) and Et₃N (3.32 mL, 23.81 mmol) in DCM (10 mL) was cooled to 0° C., and methanesulfonyl chloride (0.891 mL, 11.43 mmol) was added slowly. After stirring at RT for 30 min, the reaction was quenched with aq NaHCO₃. The aqueous layer was extracted with DCM. The combined extracts were dried (Biotage phase separator) and concentrated to give the title compound (crude, 1.39 g) as an orange oil which was used without purification. ¹H NMR (400 MHz, CDCl₃): δ 4.37-4.27 (m, 2H), 4.12 (ddd, 2H), 3.03 (s, 6H), 2.18-2.08 (m, 1H), 2.00-1.91 (m, 1H), 1.70-1.61 (m, 1H), 1.07 (d, 3H).

Step 2: (S)-tert-Butyl (2-(3-methylpyrrolidin-1-yl)ethyl)carbamate

A mixture of (S)-2-methylbutane-1,4-diyl dimethanesulfonate (300 mg, 1.152 mmol) and tert-butyl (2-aminoethyl)carbamate (0.9 mL, 5.76 mmol) was heated to 100° C. under microwave conditions for 10 mins. The reaction mixture was partitioned between DCM and aq NaHCO₃. The aqueous layer was extracted with DCM. The combined extracts were washed (aq NaHCO₃), dried (Biotage phase separator) and concentrated to give the title compound (crude, 374 mg) as an orange oil which was used without purification. LCMS (Method B): $R_T$=0.50 min, m/z=229 [M+H]⁺.

Step 3: (S)-2-(3-Methylpyrrolidin-1-yl)ethanamine

A solution of (S)-tert-butyl (2-(3-methylpyrrolidin-1-yl)ethyl)carbamate (263 mg, 1.152 mmol) and TFA (1.0 mL, 12.98 mmol) in DCM (2 mL) was stirred for 1 h. The reaction mixture was concentrated in vacuo, and then loaded onto a 5 g SCX-2 cartridge. After standing for 30 min, the cartridge was washed with DCM-MeOH (4:1). Elution with DCM-2 M NH₃ in MeOH (4:1), followed by concentration in vacuo gave the title compound (crude, 135 mg) as an orange oil which was used without purification. ¹H NMR (400 MHz, CDCl₃): δ 6.67 (br s, 2H), 3.04-2.99 (m, 2H), 2.91-2.63 (m, 5H), 2.36-2.27 (m, 1H), 2.21 (dd, 1H), 2.11-2.03 (m, 1H), 1.47-1.38 (m, 1H), 1.06 (d, 3H).

Step 4: 3-((4-Hydroxy-1-((R)-3-phenylbutanoyl)piperidin-4-yl)methyl)-6-((2-((S)-3-methylpyrrolidin-1-yl)ethyl)amino)pyrimidin-4(3H)-one, Formic Acid A mixture of Intermediate A (40 mg, 0.103 mmol), (S)-2-(3-methylpyrrolidin-1-yl)ethanamine (66 mg, 0.513 mmol) and 1,4-dioxane (1.5 mL) was heated in the microwave at 175° C. for 30 min. The reaction mixture was concentrated and the residue was purified by preparative HPLC (Method A, acidic conditions) to give the title compound (10 mg, 19%) as a pale orange solid. LCMS (Method B): $R_T$=0.84 min, m/z=482 [M+H]⁺. ¹H NMR (400 MHz, methanol-d₄, this molecule appears as two conformers A and B in a 2:3 ratio respectively): δ 8.52 (s, 1H), 8.11 (s, 0.4H (conformer A)), 8.07 (s, 0.6H (conformer B)), 7.35-7.17 (m, 5H), 5.38 (s, 1H), 4.22-4.10 (m, 1H), 3.99-3.44 (m, 6H), 3.29-2.93 (m, 6H), 2.83-2.72 (m, 2H), 2.63-2.44 (m, 2H), 2.28-2.19 (m, 1H), 1.70-1.28 (m, 8H), 1.16 (d, 3H), 0.96-0.89 (m, 0.6H (conformer B)).

Example 72: (R)-9-(4-(Aminomethyl)phenyl)-1-((4-hydroxy-1-(3-phenylbutanoyl)piperidin-4-yl)methyl)-8-methyl-1H-purin-6(9H)-one

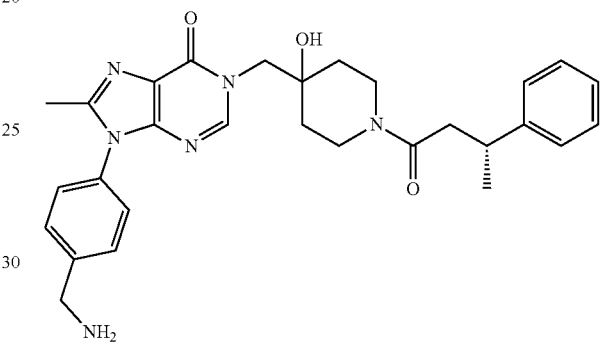

Step 1: tert-Butyl 4-(6-chloro-8-methyl-9H-purin-9-yl)benzylcarbamate

A solution of tert-butyl 4-((5-amino-6-chloropyrimidin-4-yl)amino)benzylcarbamate (264 mg, 0.755 mmol), trimethyl orthoacetate (0.480 mL, 3.77 mmol) and NEt₃ (0.105 mL, 0.755 mmol) in MeCN (3 mL) were heated in a microwave at 140° C. for 1 h. Further trimethyl orthoacetate (0.480 mL, 3.77 mmol) was added and the reaction was heated at 140° C. for 15 h. The reaction mixture was concentrated and the residue purified by flash chromatography (40 g GraceResolv™ silica, 0-70% EtOAc in cyclohexane) to give the title compound (200 mg, 71%) as a pale yellow solid. LCMS (Method A): $R_T$=1.30 min, m/z=374, 376 [M+H]⁺. ¹H NMR (300 MHz, CDCl₃): δ 8.67 (s, 1H), 7.56 (d, 2H), 7.37 (d, 2H), 4.99 (br. s, 1H), 4.45 (d, 2H), 2.62 (s, 3H), 1.49 (s, 9H).

Step 2: tert-Butyl 4-(8-methyl-6-oxo-1H-purin-9(6H)-yl)benzylcarbamate Acetate A mixture of tert-butyl 4-(6-chloro-8-methyl-9H-purin-9-yl)benzylcarbamate (223 mg, 0.597 mmol), 1 M NaOH$_{(aq)}$ (2.39 mL, 2.39 mmol) and MeOH (2.39 mL) was heated at 80° C. for 24 h. Further 1 M NaOH$_{(aq)}$ (1 mL) was added and the reaction was heated at 80° C. for a further 16 h. The reaction was allowed to cool to RT and AcOH was added to adjust the pH to ~pH 4. The mixture was diluted with water (15 mL) and then extracted with DCM (3×25 mL) using a Biotage phase separator. The combined organic phases were concentrated and the residue dried in vacuo to give the title compound (175 mg, 70%) as a pale yellow solid. LCMS (Method A): $R_T$=0.94 min, 356 [M+H]$^+$. $^1$H NMR (300 MHz, DMSO-d$_6$): δ 12.31 (br. s, 1H), 11.95 (br. s, 1H), 7.91 (s, 1H), 7.53 (t, 1H), 7.49-7.39 (m, 4H), 4.23 (d, 2H), 2.33 (s, 3H), 1.91 (s, 3H), 1.41 (s, 9H).

Step 3: Benzyl 4-((9-(4-(((tert-butoxycarbonyl)amino)methyl)phenyl)-8-methyl-6-oxo-6,9-dihydro-1H-purin-1-yl)methyl-4-hydroxypiperidine-1-carboxylate General procedure 1 using Epoxide 4 (119 mg, 0.481 mmol), tert-butyl 4-(8-methyl-6-oxo-1H-purin-9(6H)-yl)benzylcarbamate (100 mg, 0.241 mmol), Cs$_2$CO$_3$ (165 mg, 0.505 mmol) and DMF (0.8 mL) gave the title compound (100 mg, 69%) as a colourless solid. LCMS (Method A): 1.35 min, m/z=603 [M+H]$^+$. $^1$H NMR (300 MHz, CDCl$_3$): δ 7.96 (s, 1H), 7.47 (d, 2H), 7.41-7.23 (m, 7H), 5.20 (t, 1H), 5.11 (s, 2H), 4.41 (d, 2H), 4.25-3.83 (m, 5H), 3.33-3.09 (m, 2H), 2.42 (s, 3H), 1.69-1.50 (m, 4H), 1.48 (s, 9H).

Step 4: tert-Butyl 4-(1-((4-hydroxypiperidin-4-yl)methyl)-8-methyl-6-oxo-1H-purin-9(6H)-yl)benzylcarbamate General procedure 7 using benzyl 4-((9-(4-(((tert-butoxycarbonyl)amino)methyl)phenyl)-8-methyl-6-oxo-6,9-dihydro-1H-purin-1-yl)methyl)-4-hydroxypiperidine-1-carboxylate (100 mg, 0.166 mmol), 10% Pd on carbon (18 mg, 0.017 mmol), ammonium formate (314 mg, 4.98 mmol) and EtOH (1.7 mL) after 2 h gave the title compound (56 mg, 72%) as a colourless solid. LCMS (Method A): $R_T$=0.71 min, m/z=469 [M+H]$^+$. $^1$H NMR (300 MHz, CDCl$_3$): δ 8.04 (s, 1H), 7.49 (d, 2H), 7.31 (d, 2H), 5.20 (br. s, 1H), 4.41 (d, 2H), 4.16 (s, 2H), 3.02-2.66 (m, 4H), 2.44 (s, 3H) 1.74-1.50 (m, 4H), 1.48 (s, 9H).

Step 6: (R)-9-(4-(Aminomethyl)phenyl)-1-((4-hydroxy-1-(3-phenylbutanoyl)piperidin-4-yl)methyl)-8-methyl-1H-purin-6(9H)-one General procedure 4 using tert-butyl 4-(1-((4-hydroxypiperidin-4-yl)methyl)-8-methyl-6-oxo-1H-purin-9(6H)-yl)benzylcarbamate (30 mg, 0.065 mmol), (R)-3-phenylbutanoic acid (16 mg, 0.097 mmol), HATU (37 mg, 0.097 mmol), DIPEA (45 µL, 0.260 mmol) and DCM (1.3 mL) and then general procedure 2 using TFA (1 mL) and DCM (1 mL) gave the title compound (24 mg, 73% (2 steps)) as a colourless solid. LCMS (Method A): $R_T$=0.66 min, m/z=515 [M+H]$^+$. $^1$H NMR (300 MHz, DMSO-d$_6$): δ 8.15-8.09 (m 1H), 7.55 (d, 2H), 7.42 (d, 2H), 7.32-7.22 (m, 4H), 7.20-7.11 (m, 1H), 4.90 (s, 1H), 4.14-3.84 (m, 2H), 3.82 (s, 2H), 3.73-3.58 (m, 1H), 3.26-3.05 (m, 3H), 2.94-2.54 (m, 4H), 2.34 (s, 3H), 1.59-1.25 (m, 4H), 1.21 (d, 3H).

Example 73: 6-((2-((R)-3-Fluoropyrrolidin-1-yl)ethyl)amino)-3-((4-hydroxy-1-((R)-3-phenylbutanoyl)piperidin-4-yl)methyl)pyrimidin-4(3H)-one, Formic Acid

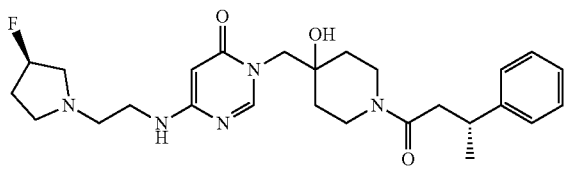 [SMILES: C[C@H](CC(=O)N1CCC(O)(Cn2cnc(NCCN3CC[C@@H](F)C3)cc2=O)CC1)c1ccccc1]

A solution of 2-((tert-butoxycarbonyl)amino)ethyl methanesulfonate (200 mg, 0.836 mmol), Et$_3$N (0.47 mL, 3.34 mmol) and (R)-3-fluoropyrrolidine hydrochloride (210 mg, 1.672 mmol) was heated at 70° C. for 3 h. The reaction mixture was partitioned between EtOAc and water. The aqueous layer was extracted with EtOAc. The combined organic extracts were dried over MgSO$_4$ and concentrated. The residue was dissolved in 4M HCl in 1,4-dioxane (2 mL) and stirred for 18 h, before concentration to dryness. The resulting solid was combined with Intermediate A (40 mg, 0.103 mmol), Et$_3$N (0.1 mL, 0.717 mmol) and 1,4-dioxane (1.5 mL), and heated in the microwave at 175° C. for 60 min. The reaction mixture was concentrated in vacuo and the resulting residue was purified by preparative HPLC (Method A, acidic conditions) to give the title compound (3.0 mg, 6%) as a pale orange solid. LCMS (Method B): $R_T$=0.67 min, m/z=486 [M+H]$^+$. $^1$H NMR (400 MHz, methanol-d$_4$, this molecule appears as two conformers A and B in a 2:3 ratio respectively): δ 8.42 (s, 1H), 8.06 (s, 0.4H (conformer A)), 8.01 (s, 0.6H (conformer B)), 7.35-7.19 (m, 5H), 5.32 (s, 1H), 4.23-4.12 (m, 1H), 3.92 (dd, 1H), 3.79 (dd, 1H), 3.72-3.38 (m, 4H), 3.28-2.72 (m, 8H), 2.63-2.49 (m, 1H), 2.40-2.03 (m, 2H), 1.63-1.28 (m, 8H), 0.95-0.87 (m, 0.6H (conformer B)).

Example 74: 6-((2-((S)-3-Fluoropyrrolidin-1-yl)ethyl)amino)-3-((4-hydroxy-1-((R)-3-phenylbutanoyl)piperidin-4-yl)methyl)pyrimidin-4(3H)-one, Formic Acid

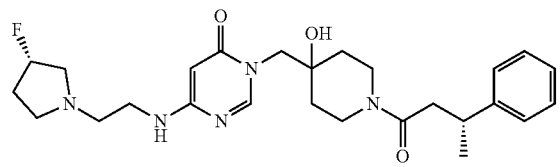 [SMILES: C[C@H](CC(=O)N1CCC(O)(Cn2cnc(NCCN3CC[C@H](F)C3)cc2=O)CC1)c1ccccc1]

Following the procedure for Example 73, (S)-3-fluoropyrrolidine hydrochloride (210 mg, 1.672 mmol) was reacted to give the title compound (4.1 mg, 8%) as a pale orange solid. LCMS (Method B): $R_T$=0.67 min, m/z=486 [M+H]$^+$. $^1$H NMR (400 MHz, methanol-d$_4$, this molecule appears as two conformers A and B in a 2:3 ratio respectively): δ 8.40 (s, 1H), 8.06 (s, 0.4H (conformer A)), 8.01 (s, 0.6H (conformer B)), 7.35-7.17 (m, 5H), 5.33 (s, 1H), 4.23-4.11 (m, 1H), 3.92 (dd, 1H), 3.79 (dd, 1H), 3.72-3.38 (m, 4H), 3.28-2.72 (m, 8H), 2.63-2.49 (m, 1H), 2.38-2.03 (m, 2H), 1.63-1.28 (m, 8H), 0.95-0.87 (m, 0.6H (conformer B)).

Example 75: 3-(4-((R)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one

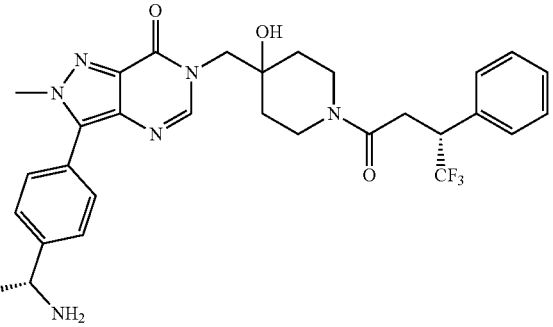

Step 1: (R)-(4-(1-((tert-Butoxycarbonyl)amino)ethyl)phenyl)boronic Acid

NaIO₄ (5.99 g, 28.0 mmol) and NH₄Cl (2.16 g, 28.0 mmol) were added to a suspension of (R)-tert-butyl (1-(4-(4,4,5,5-tetramethyl-1,3,2-dioxaborolan-2-yl)phenyl)ethyl) carbamate (3.24 g, 9.33 mmol) (PCT Int. Appl., 2011123419, 6 Oct. 2011) in acetone (93 ml) and water (93 ml) and the reaction was stirred at RT for 16 h before the mixture was concentrated to remove most of the acetone. The resulting aqueous suspension which had an initial pH of pH 6-7 was diluted with water (50 mL) and DCM (50 mL) and then the pH was adjusted to pH 5 by the addition of 1 M HCl$_{(aq)}$. The phases were then separated using a Biotage phase separator and the aqueous phase was further extracted with DCM (2×50 mL). The combined organic phases were concentrated and the product purified by flash chromatography (80 g GraceResolv™ silica, 0-15% MeOH in DCM) to give the title compound (1.09 g, 44%) as a colourless solid. ¹H NMR (300 MHz, DMSO-d₆): δ 7.97 (s, 1H), 7.70 (t, 2H), 7.38 (d, 1H), 7.25 (d, 2H), 4.60 (m, 1H), 3.61 (s, 1H), 1.36 (s, 9H), 1.29 (d, 3H) and boroxine signals.

Step 2: (R)-3-Bromo-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (Intermediate E)

General procedure 4 using 3-bromo-6-((4-hydroxypiperidin-4-yl)methyl)-2-methyl-2H-pyrazolo[4,3-d]pyrimidin-7(6H)-one (132 mg, 0.385 mmol), (R)-4,4,4-trifluoro-3-phenylbutanoic acid (70 mg, 0.32 mmol), HATU (122 mg, 0.32 mmol), DIPEA (0.224 mL, 1.283 mmol) and DCM (20 mL) and gave the title compound (142 mg, 82%) as a white solid. LCMS (Method B): R$_T$=1.19 min, m/z 542, 544 [M+H]⁺.

Step 3: 3-(4-((R)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one General procedure 5 using Intermediate E (30 mg, 0.055 mmol), (R)-(4-(1-((tert-butoxycarbonyl)amino)ethyl)phenyl)boronic acid (29 mg, 0.111 mmol), Pd(PPh₃)₄(6.4 mg, 5.53 μmol), K₃PO₄ (47 mg, 0.221 mmol), 1,4-dioxane (0.415 mL) and water (0.138 mL) at 130° C. for 1 h in the microwave then general procedure 2 using TFA (0.7 mL) and DCM (0.7 mL) gave the title compound (12 mg, 35% (2 steps)) as a colourless solid. LCMS (Method A): R$_T$=0.89 min, m/z=583 [M+H]⁺. ¹H NMR (300 MHz, DMSO-d₆): δ 8.02-7.93 (m, 1H), 7.70-7.49 (m, 4H), 7.45-7.23 (m, 5H), 4.90 (s, 1H), 4.26-3.64 (m, 7H), 3.56-2.76 (m, 8H), 1.65-0.94 (m, 7H).

Example 76: 3-(4-((S)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one

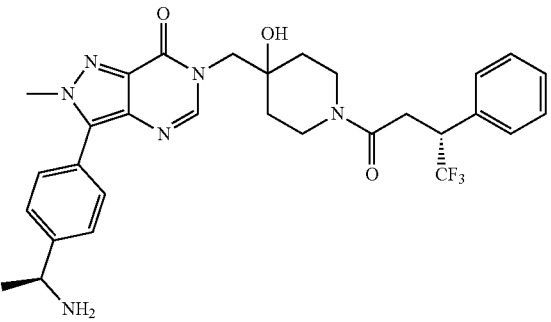 [SMILES: C[C@H](N)c1ccc(-c2c3ncn(CC4(O)CCN(C(=O)C[C@H](c5ccccc5)C(F)(F)F)CC4)c(=O)c3nn2C)cc1]

Step 1: (S)-(4-(1-((tert-Butoxycarbonyl)amino)ethyl)phenyl)boronic Acid

NaIO₄ (5.53 g, 25.8 mmol) and NH₄Cl (1.99 g, 25.8 mmol) were added to a suspension of (S)-tert-butyl (1-(4-(4,4,5,5-tetramethyl-1,3,2-dioxaborolan-2-yl)phenyl)ethyl) carbamate (2.99 g, 8.61 mmol) (PCT Int. Appl., 2011123419, 6 Oct. 2011) in acetone (86 ml) and water (86 ml) and the reaction was stirred at RT for 16 h before the mixture was concentrated to remove most of the acetone. The resulting aqueous suspension which had an initial pH of pH 6-7 was diluted with water (50 mL) and DCM (50 mL) before the the pH was adjusted to pH 5 by the addition of 1 M HCl$_{(aq)}$. The phases were then separated using a Biotage phase separator and the aqueous phase was further extracted with DCM (2×50 mL). The combined organic phases were concentrated and the product purified by flash chromatography (80 g GraceResolv™ silica, 0-15% MeOH in DCM) to give the title compound (928 mg, 40%) as a colourless solid. ¹H NMR (300 MHz, DMSO-d₆): δ 7.97 (s, 1H), 7.70 (t, 2H), 7.38 (d, 1H), 7.25 (d, 2H), 4.60 (m, 1H), 3.61 (s, 1H), 1.36 (s, 9H), 1.29 (d, 3H) and boroxine signals.

Steps 2 and 3: 3-(4-((S)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one General procedure 5 using Intermediate E (30 mg, 0.055 mmol), (S)-(4-(1-((tert-butoxycarbonyl)amino)ethyl)phenyl)boronic acid (29 mg, 0.111 mmol), Pd(PPh₃)₄(6.4 mg, 5.53 μmol), K₃PO₄ (47 mg, 0.221 mmol), 1,4-dioxane (0.415 mL) and water (0.138 mL) at 130° C. for 1 h in the microwave then general procedure 2 using TFA (0.7 mL) and DCM (0.7 mL) gave the title compound (11 mg, 34% (2 steps)). LCMS (Method A): R$_T$=0.89 min, m/z=583 [M+H]⁺. ¹H NMR (300 MHz, DMSO-d₆): δ 8.00-7.93 (m, 1H), 7.64 (d, 2H), 7.57 (d, 2H), 7.44-7.25 (m, 5H), 4.90 (s, 1H), 4.16-3.71 (m, 7H), 3.54-2.70 (8H), 1.72-0.96 (m, 7H).

Example 77: (R)-9-(4-(Aminomethyl)phenyl)-1-((4-hydroxy-1-(4,4,4-trifluoro-3-phenylbutanoyl)piperidin-4-yl)methyl)-1H-purin-6(9H)-one

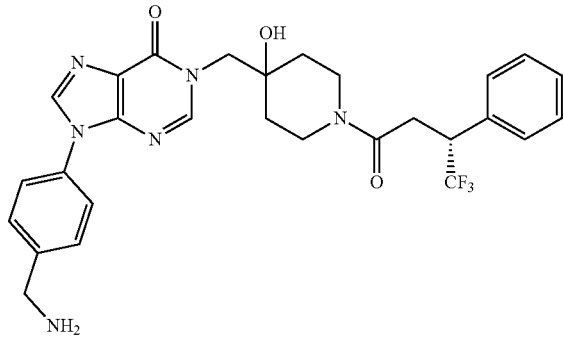 [SMILES: NCc1ccc(-n2cnc3c(=O)n(CC4(O)CCN(C(=O)C[C@H](c5ccccc5)C(F)(F)F)CC4)cnc32)cc1]

General procedure 4 using tert-butyl 4-(1-((4-hydroxypiperidin-4-yl)methyl)-6-oxo-1H-purin-9(6H)-yl)benzylcarbamate (25 mg, 0.055 mmol), (R)-4,4,4-trifluoro-3-phenylbutanoic acid (18 mg, 0.083 mmol), HATU (31 mg, 0.083 mmol), DIPEA (0.038 mL, 0.220 mmol) and DCM (1.1 mL) and then general procedure 2 using TFA (0.7 mL) and DCM (0.7 mL) gave the title compound (21 mg, 68%) as a colourless solid. LCMS (Method A): $R_T$=0.82 min, m/z=555 [M+H]$^+$. $^1$H NMR (300 MHz, DMSO-d$_6$): δ 8.47 (s, 1H), 8.29-8.20 (m, 1H), 7.70 (d, 2H), 7.55 (d, 2H), 7.46-7.26 (m, 5H), 4.93 (s, 1H), 4.21-3.72 (m, 7H), 3.47-2.76 (m, 4H), 1.72-0.98 (m, 4H).

Example 78: (R)-9-(4-(Aminomethyl)phenyl)-1-((4-hydroxy-1-(4,4,4-trifluoro-3-phenylbutanoyl)piperidin-4-yl)methyl)-8-methyl-1H-purin-6(9H)-one

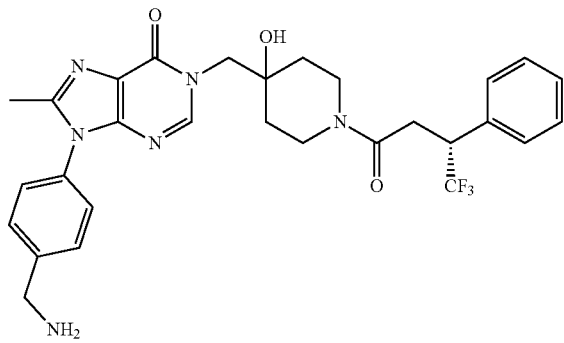

General procedure 4 using tert-butyl 4-(1-((4-hydroxypiperidin-4-yl)methyl)-8-methyl-6-oxo-1H-purin-9(6H)-yl)benzylcarbamate (27 mg, 0.058 mmol), (R)-4,4,4-trifluoro-3-phenylbutanoic acid (19 mg, 0.086 mmol), HATU (33 mg, 0.086 mmol), DIPEA (0.040 mL, 0.230 mmol) and DCM (1.2 mL) and then general procedure 2 using TFA (0.7 mL) and DCM (0.7 mL) gave the title compound (24 mg, 73% (2 steps)) as a colourless solid. LCMS (Method A): $R_T$=0.80 min, m/z=569 [M+H]$^+$. $^1$H NMR (300 MHz, DMSO-d$_6$): δ 8.15-8.07 (m, 1H), 7.55 (d, 2H), 7.47-7.22 (m, 7H), 4.91 (s, 1H), 4.24-3.68 (m, 7H), 3.30-3.06 (m, 2H), 3.01-2.73 (m, 2H), 2.34 (s, 3H), 2.16 (br. s, 2H), 1.66-0.97 (m, 4H).

Example 79: (R)-3-(4-((Dimethylamino)methyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

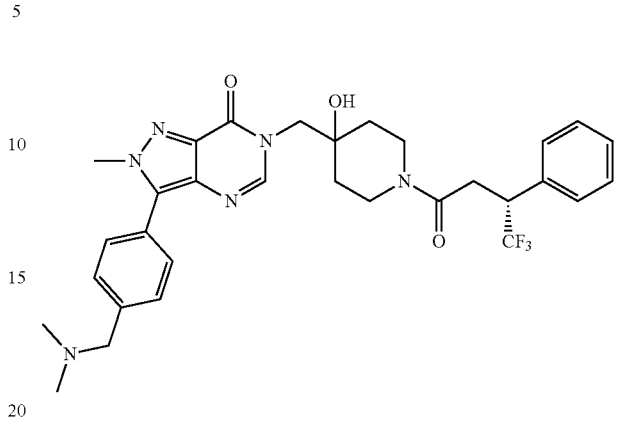

To a solution of (R)-3-(4-(aminomethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (25 mg, 0.044 mmol) and formaldehyde (37% solution in water, 8 μL, 0.110 mmol) in a mixture of THF (2 mL) and methanol (2 mL) was added sodium cyanoborohydride (7 mg, 0.110 mmol). The mixture was stirred at RT for 5 h. Further formaldehyde (37% solution in water, 8 μL, 0.110 mmol) and sodium cyanoborohydride (7 mg, 0.110 mmol) were added and the mixture stirred at RT overnight. The reaction mixture was loaded onto a prewashed 2 g Biotage Isolute SCX-2 cartridge, allowed to bind for 10 min, washed with 80:20 DCM:methanol before the product was eluted with 80:20 DCM:2M ammonia in methanol. The resulting solution was concentrated to dryness under reduced pressure, slurried in diethyl ether, purified by flash chromatography (GraceResolv™ silica 4 g cartridge, DCM:2M ammonia in methanol, gradient elution from 100:0 to 90:10) followed by flash chromatography (Biotage KP-NH 11 g cartridge, DCM:methanol, gradient elution from 100:0 to 90:10) and freeze-dried to give the title compound (6 mg, 90%) as a colourless solid. LCMS (Method A): $R_T$=0.85 min, m/z=597 [M+H]$^+$. $^1$H NMR (300 MHz, DMSO-d$_6$): δ 7.98 (d, 1H), 7.68 (d, 2H), 7.50 (d, 2H), 7.39-7.45 (m, 2H), 7.28-7.39 (m, 3H), 4.90 (s, 1H), 4.04-4.19 (m, 4H), 3.85-4.03 (m, 3H), 3.71-3.83 (m, 1H), 3.48 (s, 2H), 3.11-3.32 (m, 2H), 2.78-3.03 (m, 2H), 2.20 (s, 6H), 1.15-1.68 (m, 4H).

Example 80: (R)-3-(4-(Aminomethyl)phenyl)-6-((1-(4,4-difluoro-3-phenylbutanoyl)-4-hydroxypiperidin-4-yl)methyl)-2-methyl-2H-pyrazolo[4,3-d]pyrimidin-7(6H)-one

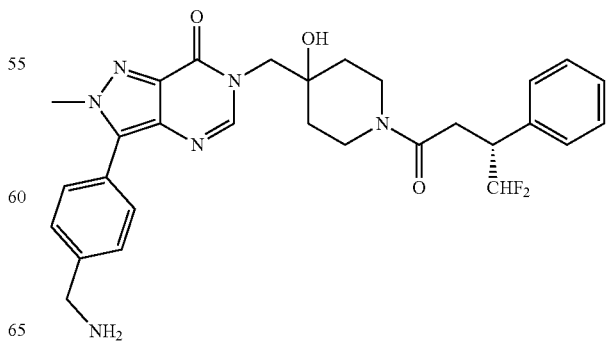

Step 1: Ethyl 4,4-difluoro-3-phenylbut-2-enoate

A suspension of sodium hydride (60% in mineral oil, 1.54 g, 38.4 mmol) in anhydrous THF (100 mL) was cooled to 0° C. before triethyl phosphonoacetate (7.05 mL, 35.2 mmol) was added dropwise. After stirring at 0° C. for 30 min 2,2-difluoro-1-phenylethanone (5.0 g, 32.0 mmol) dropwise and the reaction mixture stirred at 0° C. for a further 60 min. The reaction mixture was quenched by the addition of water (100 mL) and extracted into EtOAc (3×50 mL). The combined organic phases were washed with brine (50 mL), dried over $Na_2SO_4$, filtered, concentrated to dryness under reduced pressure and purified by Flash chromatography (GraceResolv™ silica 120 g cartridge, cyclohexane:ethyl acetate, gradient elution from 95:5 to 60:40) to give the title compound (3.38 g, 47%) as a colourless oil.

Step 2: Ethyl 4,4-difluoro-3-phenylbutanoate

A solution of ethyl 4,4-difluoro-3-phenylbut-2-enoate (1.00 g, 4.42 mmol) in methanol (88 mL) was hydrogenated by H-Cube® (10% Pd/C cartridge, 60 bar $H_2$, 60° C., 1 mL/min). The reaction mixture was concentrated to dryness under reduced pressure and purified by Flash chromatography (GraceResolv™ silica 80 g cartridge, cyclohexane:ethyl acetate, gradient elution from 100:0 to 80:20) to give the title compound (975 mg, 97%) as a colourless oil. LCMS (Method A): $R_T$=1.55 min, m/z=229 [M+H]$^+$. $^1$H NMR (300 MHz, $CDCl_3$): δ 7.23-7.39 (m, 5H), 5.94 (td, 1H), 3.98-4.15 (m, 2H), 3.51-3.74 (m, 1H), 2.96 (dd, 1H), 2.78 (dd, 1H), 1.15 (t, 3H).

Step 3: 4,4-Difluoro-3-phenylbutanoic Acid

To a solution of ethyl 4,4-difluoro-3-phenylbutanoate (975 mg, 4.27 mmol) in 1,4-dioxane (8.5 mL) was added a 1 M sodium hydroxide solution (8.5 mL, 8.54 mmol) and the reaction was stirred at RT for 60 min. The reaction mixture was acidified to pH 4 by the addition of 2M $HCl_{(aq)}$, followed by extraction into EtOAc (3×30 mL). The combined organic phases were washed with brine (30 mL), dried over $Na_2SO_4$, filtered, concentrated to dryness under reduced pressure and slurried in cyclohexane (20 mL) to give the title compound (682 mg, 80%) as a colourless solid. LCMS (Method A): $R_T$=1.10 min, m/z=199 [M−H]$^-$. $^1$H NMR (300 MHz, $CDCl_3$): 7.20-7.40 (m, 5H), 5.92 (td, 1H), 3.48-3.72 (m, 1H), 3.02 (dd, 1H), 2.83 (dd, 1H).

Step 4: (S)-4-Benzyl-3-((R)-4,4-difluoro-3-phenylbutanoyl)oxazolidin-2-one

A solution of 4,4-difluoro-3-phenylbutanoic acid (2.00 g, 10.0 mmol), (S)-4-benzyloxazolidin-2-one (1.95 g, 11.0 mmol) and lithium chloride (850 mg, 20.0 mmol) in anhydrous THF (25 mL) was cooled to −20° C. followed by the dropwise addition of pivaloyl chloride (3.07 mL, 25.0 mmol) then triethylamine (3.62 mL, 26.0 mmol). The resulting mixture was stirred at −20° C. for 30 min, then allowed to warm to RT, diluted with saturated ammonium chloride solution (30 mL) and extracted into EtOAc (3×20 mL). The combined organic phases were dried over $Na_2SO_4$, filtered, concentrated to dryness under reduced pressure and purified by flash chromatography (GraceResolv™ silica 330 g cartridge, cyclohexane:ethyl acetate, gradient elution from 95:5 to 60:40, later running diastereoisomer isolated) to give the title compound (1.42 g, 40%) as a colourless solid. LCMS (Method A): $R_T$=1.67 min, m/z=360 [M+H]$^+$. $^1$H NMR (300 MHz, $CDCl_3$): δ 7.19-7.43 (m, 8H), 6.96-7.06 (m, 2H), 5.99 (td, 1H), 4.59-4.69 (m, 1H), 4.20 (ddd, 1H), 4.14 (dd, 1H), 3.76-3.90 (m, 1H), 3.69 (dd, 1H), 3.44 (dd, 1H), 3.02 (dd, 1H), 2.62 (dd, 1H).

Step 5: (R)-4,4-Difluoro-3-phenylbutanoic Acid

A solution of (S)-4-benzyl-3-((R)-4,4-difluoro-3-phenylbutanoyl)oxazolidin-2-one (1.42 g, 3.95 mmol) in a mixture of THF (28 mL) and water (5.6 mL) was cooled to 0° C. before a 30% aqueous hydrogen peroxide solution (1.01 mL, 9.88 mmol) and then a solution of lithium hydroxide (237 mg, 9.88 mmol) in water (5.6 mL) were added dropwise. The reaction mixture was stirred at 0° C. for 90 min then quenched by the addition of 2M sodium thiosulfate$_{(aq)}$ (19.8 mL, 39.5 mmol), diluted with water (20 mL) and washed with EtOAc (3×20 mL). The organic phase was extracted into saturated sodium bicarbonate solution (3×20 mL) and the aqueous phases combined with that from above. The combined aqueous phases were adjusted to ~pH4 by the addition of 2 M HCl solution, followed by extraction into EtOAc (3×20 mL). The combined organic phases were dried over $Na_2SO_4$, filtered, concentrated to dryness under reduced pressure and slurried in cyclohexane (15 mL) to give the title compound (683 mg, 86%) as a colourless solid. LCMS (Method A): $R_T$=1.11 min, m/z=199 [M−H]$^-$. $^1$H NMR (300 MHz, $CDCl_3$): δ 7.23-7.40 (m, 5H), 5.92 (td, 1H), 3.49-3.70 (m, 1H), 3.02 (dd, 1H), 2.82 (dd, 1H).

Step 6: (R)-3-(4-(Aminomethyl)phenyl)-6-((1-(4,4-difluoro-3-phenylbutanoyl)-4-hydroxypiperidin-4-yl)methyl)-2-methyl-2H-pyrazolo[4,3-d]pyrimidin-7(6H)-one General procedure 4 using tert-butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (50 mg, 0.171 mmol), (R)-4,4-difluoro-3-phenylbutanoic acid (21 mg, 0.107 mmol), HATU (60.9 mg, 0.160 mmol), DIPEA (0.075 mL, 0.427 mmol) and DCM (3.4 mL) and then general procedure 2 using TFA (1.5 mL) and DCM (1.5 mL) gave the title compound as a white solid. LCMS (Method B): $R_T$=0.74 min, m/z 551 [M+H]$^+$. $^1$H NMR (300 MHz, DMSO-$d_6$): δ 7.97 (d, 1H), 7.64 (d, 2H), 7.55 (d, 2H), 7.30 (m, 5H), 6.23 (td, 1H), 4.90 (s, 1H), 3.50-4.15 (m, 9H), 2.75-3.25 (m, 4H), 2.30-1.95 (m, 2H), 1.65-1.15 (m, 5H).

Example 81: (R)-3-((4-Hydroxy-1-(3-phenylbutanoyl)piperidin-4-yl)methyl)-6-isopropylpyrimidin-4(3H)-one

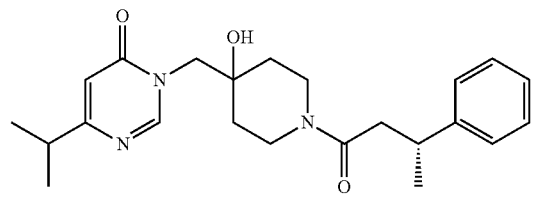 [SMILES: CC(C)c1cc(=O)n(CC2(O)CCN(C(=O)C[C@@H](C)c3ccccc3)CC2)cn1]

Step 1: tert-Butyl 4-((4-chloro-6-oxopyrimidin-1(6H)-yl)methyl)-4-hydroxypiperidine-1-carboxylate A solution of 6-chloropyrimidin-4(3H)-one (3.72 g, 28.5 mmol), Epoxide 1 (6.08 g, 28.5 mmol) and DIPEA (7.47 mL, 42.7 mmol) in DMF (35 mL) was heated at 80° C. for 16 h. The reaction mixture was allowed to cool to RT before it was quenched by the addition of saturated NH$_4$Cl$_{(aq)}$ (20 mL) and the resulting mixture was extracted with EtOAc. The combined organic extracts were dried over MgSO$_4$, concentrated and the residue was purified by chromatography (Grace 120 g Resolv, 0-100% EtOAc in cyclohexane) to give tert-butyl 4-((4-chloro-6-oxopyrimidin-1 (6H)-yl)methyl)-4-hydroxypiperidine-1-carboxylate (5.87 g, 60%) as an off-white solid. LCMS (Method B): R$_T$=0.99 min, m/z=342 [M+H]$^+$.

Step 2: 3-((4-Hydroxypiperidin-4-yl)methyl)-6-(prop-1-en-2-yl)pyrimidin-4(3H)-one General procedure 5 using tert-butyl 4-((4-chloro-6-oxopyrimidin-1(6H)-yl)methyl)-4-hydroxypiperidine-1-carboxylate (100 mg, 0.29 mmol), 4,4,5,5-tetramethyl-2-(prop-1-en-2-yl)-1,3,2-dioxaborolane (73.3 mg, 0.44 mmol), dioxane (2 mL), sodium carbonate (61.7 mg, 0.58 mmol), water (1 mL), and Pd(PPh$_3$)$_4$(16.8 mg, 0.015 mmol) at 150° C. for 15 min (microwave) gave a glassy solid. This was dissolved in DCM (1 mL) and TFA (1 mL) and stirred 15 min, then concentrated. The residue was dissolved in MeOH and added to a 2 g SCX-2 cartridge. The column was washed with MeOH then eluted with 2 M NH$_3$/MeOH to give the title compound (61 mg, 84%) as a white solid. $^1$H NMR (CDCl$_3$, 300 MHz): δ 8.08 (s, 1H), 6.51 (s, 1H), 6.24 (br s, 1H), 5.44 (br s, 1H), 4.00 (s, 2H), 2.92 (m, 4H), 2.06 (s, 3H), 1.56 (m, 4H), 1.43 (s, 1H).

Step 3: (R)-3-((4-Hydroxy-1-(3-phenylbutanoyl) piperidin-4-yl)methyl)-6-(prop-1-en-2-yl)pyrimidin-4(3H)-one General procedure 4 using (R)-3-phenylbutanoic acid (39.5 mg, 0.241 mmol), 3-((4-hydroxypiperidin-4-yl) methyl)-6-(prop-1-en-2-yl)pyrimidin-4(3H)-one (60 mg, 0.241 mmol), DIPEA (0.050 mL, 0.289 mmol), DCM (2 mL) and HATU (101 mg, 0.265 mmol) gave the title compound (69 mg, 73%) as a white foam. LCMS (Method A): R$_T$=1.12 min, m/z=396 [M+H]$^+$. $^1$H NMR (300 MHz, DMSO-d$_6$): δ 8.24 (d, 1H), 7.25 (m, 4H), 7.17 (m, 1H), 6.41 (s, 1H), 6.17 (s, 1H), 5.42 (s, 1H), 4.95 (s, 1H), 4.00 (m, 1H), 3.89 (d, 1H), 3.82 (m, 1H), 3.63 (m, 1H), 3.15 (m, 2H), 2.87 (m, 1H), 2.60 (m, 2H), 2.02 (s, 3H), 1.25-1.55 (m, 4H), 1.20 (d, 3H).

Step 3: (R)-3-((4-Hydroxy-1-(3-phenylbutanoyl) piperidin-4-yl)methyl)-6-isopropylpyrimidin-4(3H)-one (R)-3-((4-Hydroxy-1-(3-phenylbutanoyl)piperidin-4-yl) methyl)-6-(prop-1-en-2-yl)pyrimidin-4(3H)-one (49 mg, 0.124 mmol) was dissolved in ethanol (2 mL) and ammonium formate (78 mg, 1.24 mmol) was added, followed by 10% palladium on carbon (13 mg, 0.012 mmol). The mixture was heated at reflux for 1 h, then cooled, filtered through Celite® and concentrated. The residue was taken up in water and extracted with DCM; the layers were separated using a phase separator cartridge then the organic layer was concentrated. The residue was purified by chromatography (Grace 12 g column; 20-100% EtOAc in cyclohexane, then 0-15% MeOH in EtOAc) and the resulting glass was azeotroped with water to give the title compound (18 mg, 37%) as a glassy solid. LCMS (Method A): R$_T$=1.15 min, m/z=398 [M+H]$^+$. $^1$H NMR (300 MHz, DMSO-d$_6$): δ 8.23 (d, 1H), 7.26 (m, 4H), 7.21 (m, 1H), 6.20 (m, 1H), 4.94 (m, 1H), 3.99 (m, 1H), 3.86 (m, 2H), 3.63 (m, 1H), 3.15 (m, 2H), 2.88 (m, 1H), 2.68 (m, 3H), 1.10-1.55 (m, 13H).

Example 82: (R)-3-(4-(Aminomethyl)-3-fluorophenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

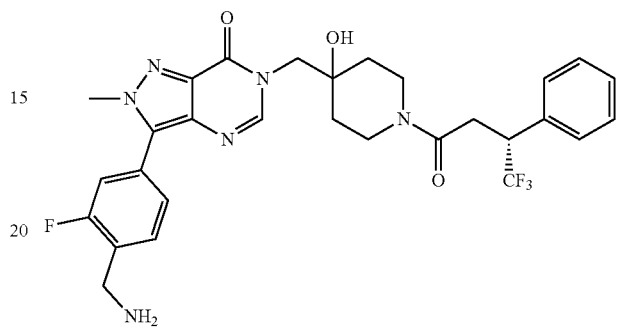

General procedure 5 using Intermediate E (24 mg, 0.045 mmol), 2-fluoro-4-(4,4,5,5-tetramethyl-1,3,2-dioxaborolan-2-yl)benzylcarbamate (47 mg, 0.134 mmol) (PCT Int. Appl., 2013134219, 12 Sep. 2013), Pd(PPh$_3$)$_4$(5.15 mg, 4.46 μmol), K$_3$PO$_4$ (57 mg, 0.268 mmol), 1,4-dioxane (0.45 mL) and water (0.15 mL) at 130° C. for 30 min in the microwave then general procedure 2 using TFA (0.7 mL) and DCM (0.7 mL) gave the title compound (10 mg, 39%) as a colourless solid. LCMS (Method A): R$_T$=0.86 min, m/z=587 [M+H]$^+$. $^1$H NMR (300 MHz, DMSO-d$_6$): δ 8.02-7.96 (m, 1H), 7.74-7.66 (m, 1H), 7.57-7.50 (m, 2H), 7.44-7.26 (m, 5H), 4.91 (s, 1H), 4.13 (s, 3H), 4.16-3.88 (m, 4H), 3.85-3.70 (m, 3H), 3.30-3.10 (m, 2H), 3.02-2.74 (m, 2H), 2.20 (br. s, 2H), 1.66-1.18 (m, 4H).

Example 83: (R)-6-((4-Hydroxy-1-(4,4,4-trifluoro-3-phenylbutanoyl)piperidin-4-yl)methyl)-2-methyl-3-(4-((methylamino)methyl)phenyl)-2H-pyrazolo[4,3-d]pyrimidin-7(6H)-one

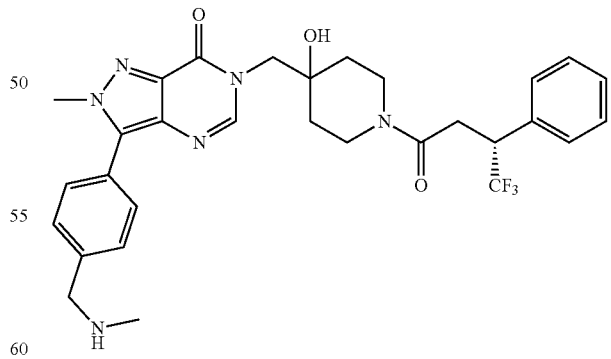

Step 1: tert-Butyl methyl(4-(4,4,5,5-tetramethyl-1,3,2-dioxaborolan-2-yl)benzyl)carbamate A solution of tert-butyl 4-bromobenzyl(methyl)carbamate (150 mg, 0.50 mmol), bis(pinacolato)diboron (190 mg, 0.75 mmol) and potassium acetate (147 mg, 1.50 mmol) in anhydrous 1,4-dioxane (2 mL) was degassed by bubbling nitrogen through the solution for 10 min, followed by the addition of PdCl$_2$(dppf)-DCM adduct (20 mg, 0.025 mmol). The reaction mixture was heated to 95° C. under a nitrogen atmosphere overnight, allowed to cool to RT, diluted with water (5 mL) and extracted into EtOAc (3×5 mL). The combined organic phases were dried over Na$_2$SO$_4$, filtered, concentrated to dryness under reduced pressure, purified by flash chromatography (GraceResolv™ silica 12 g cartridge, cyclohexane:ethyl acetate, gradient elution from 95:5 to 70:30) to give the title compound (72 mg, 42%) as a colourless solid. LCMS (Method A): R$_T$=2.02 min, m/z=292 [M-butene+H]$^+$. $^1$H NMR (300 MHz, CDCl$_3$): δ 7.77 (d, 2H), 7.20 (br d, 2H), 4.43 (br s, 2H), 2.68-2.89 (m, 3H), 1.39-1.53 (m, 9H), 1.33 (s, 12H).

Step 2: (R)-tert-Butyl 4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)benzyl(methyl)carbamate General procedure 5 using Intermediate E (42 mg, 0.077 mmol), tert-butyl methyl(4-(4,4,5,5-tetramethyl-1,3,2-dioxaborolan-2-yl)benzyl)carbamate (40 mg, 0.116 mmol), K$_3$PO$_4$ (41 mg, 0.232 mmol), PdCl$_2$(dppf)-DCM adduct (3.2 mg, 3.87 μmol), 1,4-dioxane (1.7 mL) and water (0.4 mL) in a microwave at 150° C. for 15 min gave the title compound (24 mg, 45%) as a colourless oil. LCMS (Method A): R$_T$=1.38 min, m/z=683 [M+H]$^+$. $^1$H NMR (400 MHz, CDCl$_3$): δ 7.74 (d, 1H), 7.55 (d, 2H), 7.42 (d, 2H), 7.29-7.39 (m, 5H), 4.51 (br s, 2H), 4.22-4.35 (m, 1H), 3.85-4.22 (m, 6H), 3.58-3.73 (m, 1H), 3.27-3.45 (m, 2H), 2.79-3.03 (m, 6H), 1.44-1.64 (m, 11H), 1.23-1.32 (m, 1H), 1.01-1.10 (m, 1H).

Step 3: (R)-6-((4-Hydroxy-1-(4,4,4-trifluoro-3-phenylbutanoyl)piperidin-4-yl)methyl)-2-methyl-3-(4-((methylamino)methyl)phenyl)-2H-pyrazolo[4,3-d]pyrimidin-7(6H)-one To a solution of (R)-tert-butyl 4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)benzyl(methyl)carbamate (24 mg, 0.035 mmol) in DCM (1 mL) was added TFA (1 mL) and the resulting mixture stirred at RT for 30 min. The reaction mixture was loaded onto a prewashed 5 g Biotage Isolute SCX-2 cartridge, allowed to bind for 10 min, washed with 80:20 DCM:methanol before the product was eluted with 80:20 DCM:2M ammonia in methanol. The resulting solution was concentrated to dryness under reduced pressure, slurried in diethyl ether and freeze-dried to give the title compound (13 mg, 64%) as a colourless solid. LCMS (Method A): R$_T$=0.80 min, m/z=583 [M+H]$^+$. $^1$H NMR (400 MHz, DMSO-d$_6$): δ 7.97 (d, 1H), 7.67 (d, 2H), 7.53 (d, 2H), 7.38-7.44 (m, 2H), 7.27-7.38 (m, 3H), 4.89 (s, 1H), 4.03-4.19 (m, 4H), 3.86-4.03 (m, 3H), 3.70-3.83 (m, 3H), 3.09-3.30 (m, 2H), 2.77-3.03 (m, 2H), 2.32 (s, 3H), 1.13-1.67 (m, 4H).

Example 84: (R)-3-(4-(Aminomethyl)phenyl)-6-((1-(3-(3,5-difluorophenyl)-4,4,4-trifluorobutanoyl)-4-hydroxypiperidin-4-yl)methyl)-2-methyl-2H-pyrazolo[4,3-d]pyrimidin-7(6H)-one

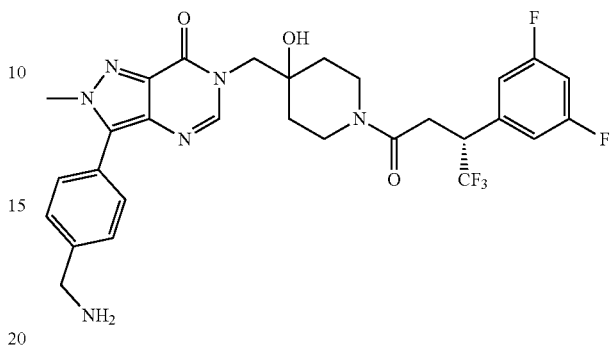

Step 1: (E)-3-(3,5-Difluorophenyl)-4,4,4-trifluorobut-2-enoic Acid

A suspension of 1-(3,5-difluorophenyl)-2,2,2-trifluoroethanone (860 mg, 4.09 mmol), ethyl 2-(diethoxyphosphoryl)acetate (0.893 mL, 4.50 mmol) and K$_3$PO$_4$ (2.17 g, 10.2 mmol) in EtOH (8 mL) was stirred at RT for 2.5 h before the temperature was increased to 30° C. and the mixture stirred for a further 21 h. The mixture was diluted with water (16 mL) and concentrated using the rotary evaporator. 3 M HCl$_{(aq)}$ was added to the residue and the resulting precipitate was isolated by filtration. The product was washed with water (3×10 mL) and dried under high vacuum at 65° C. to give the title compound (800 mg, 78% (9:1 E/Z)) as colourless solid. LCMS (Method A): R$_T$=1.36 min, m/z=251 [M−H]$^-$. $^1$H NMR (300 MHz, CDCl$_3$): δ 8.44 (br. s, 1H), 6.91 (tt, 1H), 6.86-6.77 (m, 2H), 6.64 (d, 1H).

Step 2: 3-(3,5-Difluorophenyl)-4,4,4-trifluorobutanoic Acid

A solution of (E)-3-(3,5-difluorophenyl)-4,4,4-trifluorobut-2-enoic acid (766 mg, 3.04 mmol) in MeOH (30 mL) was reduced using the H-Cube® (10% Pd/C CatCart®, 1 mLmin$^{-1}$, 50° C., 50 bar H$_2$ then 1 mLmin$^{-1}$, 60° C., 60 bar). The solution was concentrated and the product dried in vacuo to give the title compound (660 mg, 85%) as a colourless solid. LCMS (Method A): R$_T$=1.33 min, m/z=253 [M−H]$^-$. $^1$H NMR (400 MHz, CDCl$_3$): δ 7.98 (br. s, 1H), 6.93-6.76 (m, 3H), 3.87 (m, 1H), 3.07 (dd, 1H), 2.88 (dd, 1H).

Step 3: (R)-4-Benzyl-3-((R)-3-(3,5-difluorophenyl)-4,4,4-trifluorobutanoyl) oxazolidin-2-one Trimethylacetyl chloride (0.781 mL, 6.34 mmol) and then NEt$_3$ (0.920 mL, 6.60 mmol) were added to a suspension of 3-(3,5-difluorophenyl)-4,4,4-trifluorobutanoic acid (645 mg, 2.54 mmol), (R)-4-benzyloxazolidin-2-one (495 mg, 2.79 mmol) and LiCl (215 mg, 5.08 mmol) in THF (6 mL) at −20° C. After 30 min the reaction was allowed to warm to RT before being quenched by the addition of saturated NH$_4$Cl$_{(aq)}$ (50 mL). The mixture was extracted with EtOAc (3×30 mL), the combined organic layers were washed with brine (30 mL) and dried over MgSO$_4$. The mixture was concentrated and the residue purified by flash chromatography (120 g GraceResolv™ silica, 0-40% EtOAc in cyclohexane) to give the title compound (433 mg, 41%) as a colourless solid. LCMS (Method A): $R_T$=1.81 min, m/z=414 [M+H]⁺. ¹H NMR (300 MHz, CDCl₃): δ 7.40-7.24 (m, 3H), 7.23-7.12 (m, 2H), 7.01-6.88 (m, 2H), 6.81 (tt, 1H), 4.64-4.52 (m, 1H), 4.20 (d, 2H), 4.19-4.03 (m, 1H), 3.68 (dd, 1H), 3.58 (dd, 1H), 3.27 (dd, 1H), 2.75 (dd, 1H). The NMR of (R)-4-benzyl-3-((R)-3-(3,5-difluorophenyl)-4,4,4-trifluorobutanoyl)oxazolidin-2-one is consistent with that reported for (S)-4-benzyl-3-((S)-3-(3,5-difluorophenyl)-4,4,4-trifluorobutanoyl)oxazolidin-2-one in Org. Process Rev. Dev. 2009, 13, 1161-1168.

Step 4:
(R)-3-(3,5-Difluorophenyl)-4,4,4-trifluorobutanoic Acid

LiOH (12 mg, 0.484 mmol) was added to a solution of (R)-4-benzyl-3-((R)-3-(3,5-difluorophenyl)-4,4,4-trifluorobutanoyl)oxazolidin-2-one (100 mg, 0.242 mmol) and H₂O₂(30% aqueous solution) (0.099 mL, 0.968 mmol) in THF (1.2 mL) and water (1.2 mL) at 0° C. After 1 h the reaction mixture was concentrated on the rotory evaporator without heat to remove the THF. The mixture was diluted with water (3 mL) and extracted with DCM (2×5 mL) using a Biotage phase separator to remove the chiral auxiliary. The H₂O₂ in the aqueous phase was quenched by the addition of saturated sodium thiosulfate$_{(aq)}$ (0.2 mL), the pH was adjusted to ~pH 1-2 by the addition of 3 M HCl$_{(aq)}$ and the aqueous phase was extracted with DCM (3×5 mL) using a Biotage phase separator. The combined organic phases from the acidic extractions were concentrated and the residue dried in vacuo to give the title compound (42 mg, 67%) as a colourless solid. ¹H NMR (400 MHz, CDCl₃): δ 6.93-6.76 (m, 3H), 3.87 (m, 1H), 3.07 (dd, 1H), 2.88 (dd, 1H).

Step 5: (R)-3-(4-(Aminomethyl)phenyl)-6-((1-(3-(3,5-difluorophenyl)-4,4,4-trifluorobutanoyl)-4-hydroxypiperidin-4-yl)methyl)-2-methyl-2H-pyrazolo[4,3-d]pyrimidin-7(6H)-one General procedure 4 using tert-butyl 4-(6-((4-hydroxypiperidin-4-yl)methyl)-2-methyl-7-oxo-6,7-dihydro-2H-pyrazolo[4,3-d]pyrazol-3-yl)benzylcarbamate (33 mg, 0.071 mmol), (R)-3-(3,5-difluorophenyl)-4,4,4-trifluorobutanoic acid (27 mg, 0.106 mmol), HATU (40 mg, 0.106 mmol), DIPEA (49 µL, 0.683 mmol) and DCM (1.4 mL) and then general procedure 2 using TFA (0.7 mL) and DCM (0.7 mL) gave the title compound (29 mg, 68% (2 steps)) as a colourless solid. LCMS (Method B): $R_T$=0.85 min, m/z=605 [M+H]⁺. ¹H NMR (300 MHz, DMSO-d₆): δ 8.00-7.94 (m, 1H), 7.64 (d, 2H), 7.53 (d, 2H), 7.34-7.14 (m, 3H), 4.92 (s, 1H), 4.29-4.14 (m, 1H), 4.10 (s, 3H), 4.03-3.86 (m, 3H), 3.80 (s, 2H), 3.78-3.68 (m, 1H), 3.33-3.17 (m, 2H), 3.05-2.78 (m, 2H), 2.16 (br. s, 2H), 1.70-1.19 (m, 4H).

Example 85: (R)-3-(4-(Aminomethyl)phenyl)-6-((4-hydroxy-1-(4,4,4-trifluoro-3-(4-fluorophenyl)butanoyl)piperidin-4-yl)methyl)-2-methyl-2H-pyrazolo[4,3-d]pyrimidin-7(6H)-one

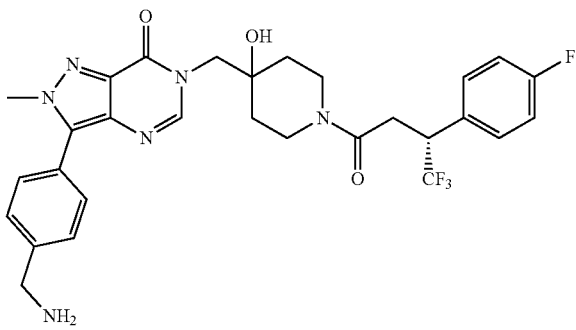 [SMILES: Cn1nc2c(=O)n(CC3(O)CCN(C(=O)C[C@H](c4ccc(F)cc4)C(F)(F)F)CC3)cnc2c1-c1ccc(CN)cc1]

Step 1: (E)-4,4,4-Trifluoro-3-(4-fluorophenyl)but-2-enoic Acid

A mixture 2,2,2-trifluoro-1-(4-fluorophenyl)ethanone (961 mg, 5 mmol), NaOAc (820 mg, 10.0 mmol) and Ac₂O (10 mL, 106 mmol) were heated in a sealed tube at 130° C. for 20 h before the reaction was allowed to cool to RT. The mixture was diluted with water (40 mL) and extracted with EtOAc (3×30 mL). The combined organic layers were dried over Na₂SO₄, concentrated and the residue purified by flash chromatography (40 g GraceResolv™ silica, 0-70% EtOAc in cyclohexane) to give the title compound (470 mg, 40% (4:1 E/Z)) as a yellow solid. LCMS (Method A): $R_T$=1.31 min, m/z=233 [M–H]⁻. ¹H NMR (300 MHz, CDCl₃): δ 7.31-7.20 (m, 2H), 7.14-7.03 (m, 2H), 6.59 (d, 1H).

Step 2: 4,4,4-Trifluoro-3-(4-fluorophenyl)butanoic Acid

A solution of (E)-4,4,4-trifluoro-3-(4-fluorophenyl)but-2-enoic acid (450 mg, 1.92 mmol) in MeOH (30 mL) was reduced using the H-Cube® (10% Pd/C CatCart®, 1 mLmin⁻¹, 50° C.; 50 bar H₂). The solution was concentrated and the product dried in vacuo to give the title compound (380 mg, 84%) as a colourless solid. LCMS (Method A): $R_T$=1.27 min, m/z=235 [M–H]⁻. ¹H NMR (400 MHz, CDCl₃): δ 7.36-7.20 (m, 2H), 7.11-6.97 (m, 2H), 3.86 (m, 1H), 3.07 (dd, 1H), 2.90 (dd, 1H).

Step 3: (R)-4-Benzyl-3-((R)-4,4,4-trifluoro-3-(4-fluorophenyl)butanoyl) oxazolidin-2-one Trimethylacetyl chloride (0.490 mL, 3.98 mmol) and then NEt₃ (0.577 mL, 4.14 mmol) were added to a suspension of 4,4,4-trifluoro-3-(4-fluorophenyl)butanoic acid (376 mg, 1.59 mmol), (R)-4-benzyloxazolidin-2-one (310 mg, 2.79 mmol) and LiCl (135 mg, 3.18 mmol) in THF (4 mL) at −20° C. After 30 min the reaction was allowed to warm to RT before being quenched by the addition of saturated NH₄Cl$_{(aq)}$ (30 mL) and the mixture was extracted with EtOAc (3×20 mL). The combined organic layers were washed with brine (30 mL), dried over MgSO₄, concentrated and the residue purified by flash chromatography (80 g GraceResolv™ silica, 0-40% EtOAc in cyclohexane) to give the title compound (291 mg, 46%) as a colourless viscous oil. LCMS (Method A): $R_T$=1.78 min, m/z=396 [M+H]$^+$. $^1$H NMR (300 MHz, CDCl$_3$): δ 7.43-7.24 (m, 5H), 7.22-7.14 (m, 2H), 7.12-7.01 (m, 2H), 4.56 (ddt, 1H), 4.21-4.04 (m, 3H), 3.72 (dd, 1H), 3.57 (dd, 1H), 3.25 (dd, 1H), 2.73 (dd, 1H).

Step 4:
(R)-4,4,4-Trifluoro-3-(4-fluorophenyl)butanoic Acid

LiOH (20 mg, 0.814 mmol) was added to a solution of (R)-4-benzyl-3-((R)-4,4,4-trifluoro-3-(4-fluorophenyl)butanoyl)oxazolidin-2-one (161 mg, 0.407 mmol) and H$_2$O$_2$ (30% aqueous solution) (0.166 mL, 1.63 mmol) in THF (2 mL) and water (2 mL) at 0° C. After 1 h the reaction mixture was concentrated on the rotary evaporator without heat to remove the THF. The mixture was diluted with water (3 mL) and extracted with DCM (2×5 mL) using a Biotage phase separator to remove the chiral auxiliary. The H$_2$O$_2$ in the aqueous phase was quenched by the addition of saturated sodium thiosulfate$_{(aq)}$ (0.3 mL), the pH was adjusted to ~pH 1-2 by the addition of 3 M HCl$_{(aq)}$ and the aqueous phase was extracted with DCM (3×5 mL) using a Biotage phase separator. The combined organic phases from the acidic extractions were concentrated and the residue dried in vacuo to give the title compound (76 mg, 79%) as a colourless solid. $^1$H NMR (400 MHz, CDCl$_3$): δ 7.35-7.25 (m, 2H), 7.11-7.01 (m, 2H), 3.87 (m, 1H), 3.08 (dd, 1H), 2.90 (dd, 1H).

Step 5: (R)-3-(4-(Aminomethyl)phenyl)-6-((4-hydroxy-1-(4,4,4-trifluoro-3-(4-fluorophenyl)butanoyl)piperidin-4-yl)methyl)-2-methyl-2H-pyrazolo[4,3-d]pyrimidin-7(6H)-one General procedure 4 using tert-butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (36 mg, 0.076 mmol), (R)-4,4,4-trifluoro-3-(4-fluorophenyl)butanoic acid (27 mg, 0.114 mmol), HATU (43 mg, 0.114 mmol), DIPEA (53 μL, 0.305 mmol) and DCM (1.5 mL) and then general procedure 2 using TFA (0.7 mL) and DCM (0.7 mL) gave the title compound (33 mg, 74% (2 steps)) as a colourless solid. LCMS (Method B): $R_T$=0.80 min, m/z=587 [M+H]$^+$. $^1$H NMR (300 MHz, DMSO-d$_6$): δ 8.01-7.93 (m, 1H), 7.64 (d, 2H), 7.57-7.41 (m, 4H), 7.24-7.12 (m, 2H), 4.91 (s, 1H), 4.26-4.11 (m, 1H), 4.10 (s, 3H), 4.02-3.86 (m, 3H), 3.81 (s, 2H), 3.78-3.68 (m, 1H), 3.29-3.11 (m, 2H), 3.04-2.75 (m, 2H), 1.64-1.16 (m, 4H).

Example 86: (R)-6-((2-(4-Fluoroisoindolin-2-yl)ethyl)amino)-3-((4-hydroxy-1-(3-phenylbutanoyl)piperidin-4-yl)methyl)pyrimidin-4(3H)-one, Formic Acid

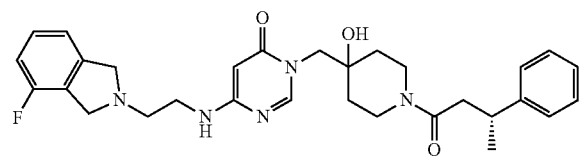 [SMILES: C[C@H](CC(=O)N1CCC(O)(Cn2cnc(NCCN3Cc4cccc(F)c4C3)cc2=O)CC1)c1ccccc1]

Step 1: tert-Butyl (2-(4-Fluoroisoindolin-2-yl)ethyl)carbamate

A mixture of 2-((tert-butoxycarbonyl)amino)ethyl methanesulfonate (200 mg, 0.836 mmol), 4-fluoroisoindoline.HCl (218 mg, 1.254 mmol) and Et$_3$N (0.349 mL, 2.51 mmol) in THF (2 mL) was heated at 70° C. for 18 h. The mixture was partitioned between EtOAc and water. The aqueous layer was extracted with EtOAc and the combined organic extracts were washed (brine), dried over MgSO$_4$ and concentrated in vacuo. The residue was purified by flash chromatography (Biotage 11 g KP-NH, 0-100% EtOAc in cyclohexane) to give the title compound (52 mg, 22%) as a yellow oil. $^1$H NMR (400 MHz, CDCl$_3$): δ 7.21-7.16 (m, 1H), 6.99 (d, 1H), 6.91-6.86 (m, 1H), 5.09 (br s, 1H), 4.01 (s, 2H), 3.97 (s, 2H), 3.34-3.30 (m, 2H), 2.87 (t, 2H), 1.45 (s, 9H).

Step 2: (R)-6-((2-(4-Fluoroisoindolin-2-yl)ethyl)amino)-3-((4-hydroxy-1-(3-phenylbutanoyl)piperidin-4-yl)methyl)pyrimidin-4(3H)-one, Formic Acid A solution of tert-butyl (2-(4-Fluoroisoindolin-2-yl)ethyl)carbamate (53.9 mg, 0.192 mmol) and HCl (4M in 1,4-dioxane) (1 mL, 32.9 mmol) in DCM (0.5 mL) was stirred for 30 min. Et$_2$O (2 mL) was added, and the suspension was stirred for 10 min. The supernatant was removed, and further Et$_2$O (2 mL) was added, and the suspension was stirred for 10 min. After the removal of the supernatant the resulting solid was dried in vacuo for 5 min and combined with Intermediate A (30 mg, 0.077 mmol) and Et$_3$N (0.054 mL, 0.385 mmol) in NMP (0.5 mL). The mixture was heated in the microwave at 175° C. for 30 min and the reaction mixture was purified by preparative HPLC (Method A, acidic conditions) to give the title compound (12.7 mg, 28%) as a pale yellow solid. LCMS (Method B): $R_T$=0.77 min, m/z=534 [M+H]$^+$. $^1$H NMR (400 MHz, methanol-d$_4$, this molecule appears as two conformers A and B in a 2:3 ratio respectively): δ 8.35 (s, 1H), 8.06 (s, 0.4H (conformer A)), 8.01 (s, 0.6H (conformer B)), 7.35-7.17 (m, 6H), 7.09 (d, 1H), 6.96 (dd, 1H), 5.35 (s, 1H), 4.23-4.10 (m, 1H), 4.12 (s, 2H), 4.10 (s, 2H), 4.00-3.65 (m, 3H), 3.60-3.40 (m, 1H), 3.28-3.15 (m, 2H), 3.10-2.92 (m, 3H), 2.85-2.72 (m, 1H), 2.63-2.46 (m, 1H), 1.63-1.28 (m, 7H), 0.95-0.87 (m, 0.6H (conformer B)).

Example 87: (R)-3-(4-(2-Aminoethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

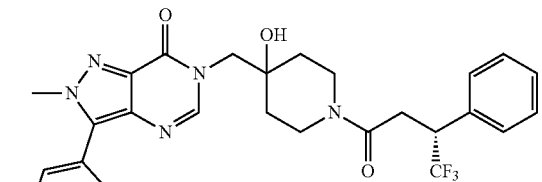

Step 1: (R)-tert-Butyl 4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenethylcarbamate General procedure 5 using Intermediate E (30 mg, 0.055 mmol), tert-butyl 4-(4,4,5,5-tetramethyl-1,3,2-dioxaborolan-2-yl)phenethylcarbamate (PCT Int. Appl., 2011123419, 6 Oct. 2011) (29 mg, 0.083 mmol), $K_3PO_4$ (30 mg, 0.166 mmol), $PdCl_2(dppf)$-DCM adduct (2.3 mg, 2.77 μmol), 1,4-dioxane (1.2 mL) and water (0.3 mL) in a microwave at 150° C. for 15 min gave the title compound (23 mg, 61%) as a yellow oil. LCMS (Method A): $R_T$=1.33 min, m/z=683 $[M+H]^+$. $^1H$ NMR (300 MHz, $CDCl_3$): δ 7.73 (d, 1H), 7.27-7.61 (m, 9H), 5.30 (s, 1H), 4.55-4.72 (m, 2H), 3.80-4.36 (m, 7H), 3.65 (t, 1H), 3.24-3.49 (m, 3H), 2.77-3.04 (m, 4H), 1.35-1.67 (m, 11H), 1.16-1.35 (m, 1H), 0.96-1.17 (m, 1H).

Step 2: (R)-3-(4-(2-Aminoethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one To a solution of (R)-tert-butyl 4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenethylcarbamate (24 mg, 0.035 mmol) in DCM (1 mL) was added TFA (1 mL) and the resulting mixture stirred at RT for 30 min. The reaction mixture was loaded onto a prewashed 5 g Biotage Isolute SCX-2 cartridge, allowed to bind for 10 min, washed with 80:20 DCM:methanol before the product was eluted with 80:20 DCM:2M ammonia in methanol. The resulting solution was concentrated to dryness under reduced pressure, slurried in diethyl ether and freeze-dried to give the title compound (16 mg, 78%) as a colourless solid. LCMS (Method A): $R_T$=0.79 min, m/z=583 $[M+H]^+$. $^1H$ NMR (400 MHz, DMSO-$d_6$): δ 7.97 (d, 1H), 7.62 (d, 2H), 7.38-7.45 (m, 4H), 7.27-7.38 (m, 3H), 4.89 (s, 1H), 4.03-4.17 (m, 4H), 3.84-4.03 (m, 3H), 3.71-3.82 (m, 1H), 3.12-3.30 (m, 2H), 2.77-3.03 (m, 4H), 2.73 (t, 2H), 1.11-1.82 (m, 6H).

Example 88: (R)-3-(4-(1-Aminocyclobutyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

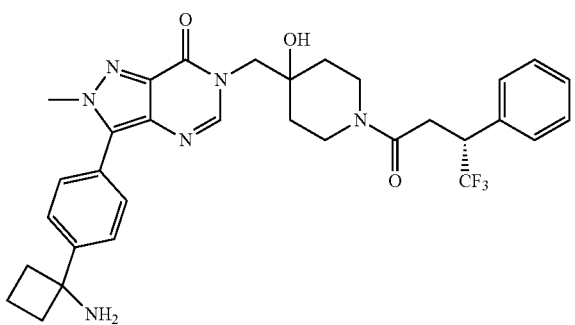 [SMILES: Cn1nc2c(=O)n(CC3(O)CCN(C(=O)C[C@H](c4ccccc4)C(F)(F)F)CC3)cnc2c1-c1ccc(C2(N)CCC2)cc1]

General procedure 5 using Intermediate E (80 mg, 0.148 mmol), (4-(1-((tert-butoxycarbonyl)amino)cyclobutyl)phenyl)boronic acid (86 mg, 0.295 mmol), $Pd(PPh_3)_4$ (17 mg, 15.2 μmol), $K_3PO_4$ (56 mg, 0.490 mmol), 1,4-dioxane (3 mL) and water (1 mL) at 130° C. for 1 hour in the microwave then general procedure 2 using TFA (1 mL) and DCM (1 mL) gave the title compound (51 mg, 35% (2 steps)) as a white solid. LCMS (Method A): $R_T$=0.87 min, m/z=609 $[M+H]^+$. $^1H$ NMR (300 MHz, DMSO-$d_6$): δ 7.99 (d, 1H), 7.7-7.6 (m, 4H), 7.45-7.25 (m, 5H), 4.91 (s, 1H), 4.12 (s, 3H), 4.0-3.4 (m, 7H), 3.2-3.1 (m, 2H), 3-2.8 (m, 2H), 2.16 (m, 2H), 2.07 (m, 1H), 1.8-1.6 (m, 2H), 1.4-1.2 (4H).

Example 89: (R)-3-((1-(4,4-Difluoro-3-phenylbutanoyl)-4-hydroxypiperidin-4-yl)methyl)-6-((2-(pyrrolidin-1-yl)ethyl)amino)pyrimidin-4(3H)-one, Formic Acid

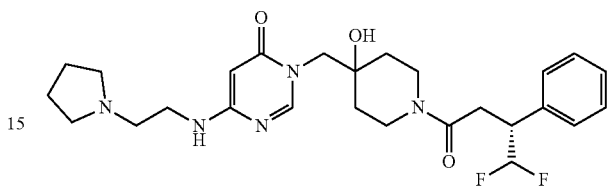

Step 1: 6-Chloro-3-((4-hydroxypiperidin-4-yl)methyl)pyrimidin-4(3H)-one

A solution of tert-butyl 4-((4-chloro-6-oxopyrimidin-1(6H)-yl)methyl)-4-hydroxypiperidine-1-carboxylate (5.87 g, 17.1 mmol) and TFA (20 mL, 260 mmol) in DCM (40 mL) was stirred at RT for 30 min and subsequently concentrated in vacuo. Excess TFA was removed by thrice dissolving in DCM followed by removal of the solvent in vacuo. The residue was dissolved in 4:1 $CHCl_3$/IPA and basified with aq $NaHCO_3$. The layers were separated and the aqueous was extracted with 10% MeOH/EtOAc. The combined organic extracts were dried ($MgSO_4$) and concentrated to give the title compound (3.09 g, 74%) as a white solid which was used without purification. LCMS (Method B): $R_T$=0.15 min, m/z=244 $[M+H]^+$.

Step 2: (R)-6-Chloro-3-((1-(4,4-difluoro-3-phenylbutanoyl)-4-hydroxypiperidin-4-yl)methyl)pyrimidin-4(3H)-one General procedure 4 using 6-chloro-3-((4-hydroxypiperidin-4-yl)methyl)pyrimidin-4(3H)-one (80 mg, 0.328 mmol), (R)-4,4-difluoro-3-phenylbutanoic acid (99 mg, 0.492 mmol), DIPEA (0.229 mL, 1.313 mmol), HATU (187 mg, 0.492 mmol) and DCM (1 mL) gave the title compound (68 mg, 48%) as a colourless oil. LCMS (Method B): $R_T$=1.01 min, m/z=426 $[M+H]^+$.

Step 3: (R)-3-((1-(4,4-Difluoro-3-phenylbutanoyl)-4-hydroxypiperidin-4-yl)methyl)-6-((2-(pyrrolidin-1-yl)ethyl)amino)pyrimidin-4(3H)-one, Formic Acid A solution of (R)-6-chloro-3-((1-(4,4-difluoro-3-phenylbutanoyl)-4-hydroxypiperidin-4-yl)methyl)pyrimidin-4(3H)-one (60 mg, 0.141 mmol), 2-(pyrrolidin-1-yl)ethanamine (0.089 mL, 0.704 mmol) and $Et_3N$ (0.098 mL, 0.704 mmol) in NMP (1 mL) was was heated in the microwave at 175° C. for 30 min. The reaction mixture was purified by preparative HPLC (Method A, acidic conditions) to give the title compound (22.4 mg, 31%) as a pale brown solid. LCMS (Method B): $R_T$=0.67 min, m/z=504 $[M+H]^+$. $^1H$ NMR (400 MHz, methanol-$d_4$, this molecule appears as two conformers A and B in a 2:3 ratio respectively): δ 8.51 (s, 1H), 8.12 (s, 0.4H (conformer A)), 8.08 (s, 0.6H (conformer B)), 7.40-7.29 (m, 5H), 6.11 (tt, 1H), 5.39 (s, 0.4H (conformer A)), 5.38 (s, 0.6H (conformer B)), 4.16-4.08 (m, 1H), 3.95 (dd, 1H), 3.86-3.55 (m, 6H), 3.07-2.91 (m, 3H), 2.87-2.82 (m, 1H), 2.12-2.02 (m, 7H), 1.66-1.31 (m, 5H), 1.19-1.11 (m, 0.6H (conformer B)).

Example 90: 6-((4-Hydroxy-1-(3-phenylpropanoyl) piperidin-4-yl)methyl)-2-(methylthio)thiazolo[4,5-d] pyrimidin-7(6H)-one

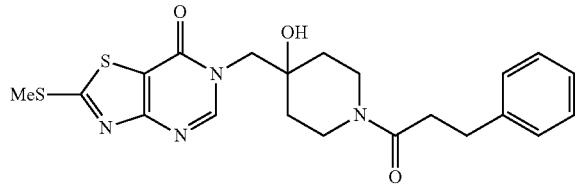 [SMILES: CSc1nc2ncn(CC3(O)CCN(C(=O)CCc4ccccc4)CC3)c(=O)c2s1]

General procedure 1 using Epoxide 3 (55 mg, 0.224 mmol), 2-(methylthio)thiazolo[4,5-d]pyrimidin-7(6H)-one (Prepared according to *Liebigs Annalen der Chemie*, 1989, p409-411) (41 mg, 0.204 mmol), Cs$_2$CO$_3$ (80 mg, 0.245 mmol) and DMF (1.5 mL) gave the title compound (36 mg, 40%) as a colourless foam. LCMS (Method A): R$_T$=1.12 min, m/z=445 [M+H]$^+$. $^1$H NMR (300 MHz, CDCl$_3$): δ 8.20 (s, 1H), 7.47-7.06 (m, 5H), 4.69-4.28 (m, 2H), 4.17-3.90 (m, 2H), 3.62 (d, 1H), 3.49-3.26 (m, 1H), 3.19-2.87 (m, 3H), 2.74 (s, 3H), 2.69-2.50 (m, 2H), 1.87-1.32 (m, 4H).

Example 91: 3-((4-Hydroxy-1-(3-phenylpropanoyl) piperidin-4-yl)methyl)furo[3,2-d]pyrimidin-4(3H)-one

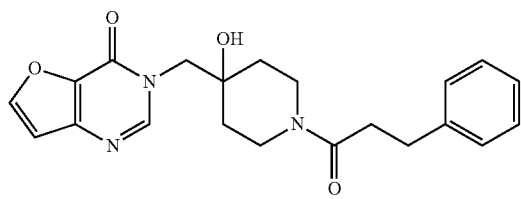 [SMILES: O=C(CCc1ccccc1)N1CCC(O)(Cn2cnc3ccoc3c2=O)CC1]

General procedure 1 using Epoxide 3 (81 mg, 0.331 mmol), furo[3,2-d]pyrimidin-4(3H)-one (Prepared according to WO2010014930, p39, Compound 23) (45 mg, 0.331 mmol), Cs$_2$CO$_3$ (323 mg, 0.992 mmol) and DMF (0.6 mL) gave the title compound (100 mg, 79%) as a colourless solid. LCMS (Method A): R$_T$=0.94 min, m/z=382 [M+H]$^+$. $^1$H NMR (300 MHz, CDCl$_3$): δ 8.10 (s, 1H), 7.81 (d, 1H), 7.32-7.19 (m, 5H), 6.80 (d, 1H), 4.35 (d, 1H), 4.17-4.00 (m, 2H), 3.92 (s, 1H), 3.60 (d, 1H), 3.33 (t, 1H), 3.09-2.92 (m, 3H), 2.65-2.58 (m, 2H), 1.61-1.26 (m, 4H).

Example 92: 6-((4-Hydroxy-1-(3-phenylpropanol) piperidin-4-yl)methyl)-2-(methylsulfonyl)thiazolo[4, 5-d]pyrimidin-7(6H)-one

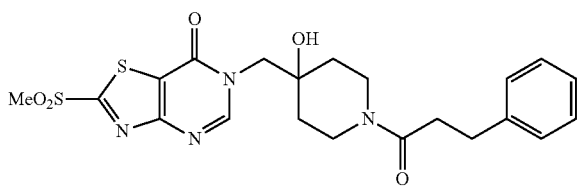 [SMILES: CS(=O)(=O)c1nc2ncn(CC3(O)CCN(C(=O)CCc4ccccc4)CC3)c(=O)c2s1]

A solution of OXONE® (763 mg, 1.24 mmol) in water (3 mL) was added to a solution of 6-((4-hydroxy-1-(3-phenyl-propanoyl)piperidin-4-yl)methyl)-2-(methylthio)thiazolo[4, 5-d]pyrimidin-7(6H)-one (138 mg, 0.310 mmol) in MeOH (3 mL) and THF (3 mL). The reaction was stirred for 30 min at RT, before increasing the temperature to 50° C. After 4.5 h, the reaction was allowed to cool to RT before it was poured in to saturated NaHCO$_{3(aq)}$ (50 mL) and the mixture was extracted with EtOAc (3×30 mL). The combined organic phases were dried over Na$_2$SO$_4$, concentrated and the residue was purified by flash chromatography (25 g Biotage KP-Sil, 0-100% EtOAc in PE then 0-30% MeOH in EtOAc) to give the title compound (77 mg, 52%) as a colourless solid. LCMS (Method A): R$_T$=1.07 min, m/z=477 [M+H]$^+$. $^1$H NMR (300 MHz, CDCl$_3$): δ 8.45 (s, 1H), 7.63-6.91 (m, 5H), 4.51-3.81 (m, 4H), 3.58 (d, 1H), 3.41 (s, 3H), 3.36-3.19 (m, 1H), 3.06-2.79 (m, 3H), 2.74-2.44 (m, 2H), 1.75-1.32 (m, 4H).

Example 93: 6-((4-Hydroxy-1-(3-phenylpropanoyl) piperidin-4-yl)methyl)-2-(methylamino)thiazolo[4,5-d]pyrimidin-7(6H)-one

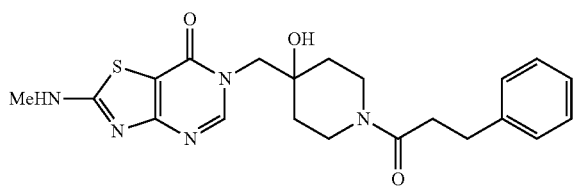 [SMILES: CNc1nc2ncn(CC3(O)CCN(C(=O)CCc4ccccc4)CC3)c(=O)c2s1]

A mixture of 6-((4-hydroxy-1-(3-phenylpropanoyl)piperidin-4-yl)methyl)-2-(methylsulfonyl)thiazolo[4,5-d]pyrimidin-7(6H)-one (20 mg, 0.042 mmol) and 2 M MeNH$_2$ in MeOH (0.525 mL, 1.05 mmol) was heated in the microwave at 100° C. for 30 min. The reaction was concentrated and the residue was purified by flash chromatography (11 g Biotage KP-NH, 0-100% EtOAc in PE; then 0-40% MeOH in EtOAc) to give the title compound (11 mg, 62%) as a colourless solid. LCMS (Method A): R$_T$=0.88 min, m/z=428 [M+H]$^+$. $^1$H NMR (300 MHz, CDCl$_3$): δ 8.02 (s, 1H), 7.59-7.19 (m, 5H), 6.52 (br. S, 1H), 4.45 (d, 1H), 4.24-3.94 (m, 3H), 3.62 (d, 1H), 3.43-3.27 (m, 1H), 3.11 (s, 3H), 3.06-2.90 (m, 2H), 2.73-2.51 (m, 2H), 1.56-1.33 (m, 4H).

Example 94: 3-((4-Hydroxy-1-(3-phenylpropanoyl) piperidin-4-yl)methyl)furo[2,3-d]pyrimidin-4(3H)-one

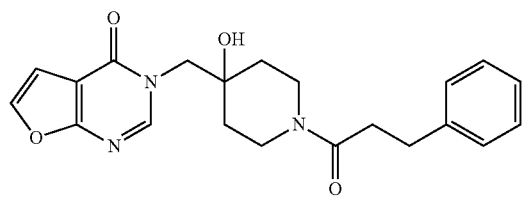 [SMILES: O=C(CCc1ccccc1)N1CCC(O)(Cn2cnc3occc3c2=O)CC1]

Step 1: tert-Butyl 4-hydroxy-4-((2-iodofuran-3-carboxamido)methyl) piperidine-1-carboxylate General procedure 3 using tert-butyl 4-(aminomethyl)-4-hydroxypiperidine-1-carboxylate (Prepared according to Bioorg. Med. Chem. Lett., 2010, 20, p7458) (100 mg, 0.434 mmol), 2-iodofuran-3-carboxylic acid (103 mg, 0.434 mmol), EDC (166 mg, 0.868 mmol) and DCM (5.4 mL) gave the title compound (123 mg, 63%) as a yellow solid. LCMS (Method A): $R_T$=1.22 min, m/z=473 [M+Na]$^+$.

Step 2: tert-Butyl 4-hydroxy-4-((4-oxofuro[2,3-d] pyrimidin-3(4H)-yl)methyl) piperidine-1-carboxylate A suspension of tert-butyl 4-hydroxy-4-((2-iodofuran-3-carboxamido)methyl)piperidine-1-carboxylate (400 mg, 0.888 mmol), formamidine hydrochloride (358 mg, 4.44 mmol), CuI (17 mg, 0.089 mmol) and $K_2CO_3$ (368 mg, 2.67 mmol) in DMF (6 mL) was heated in a microwave at 150° C. for 8 h. The mixture was partitioned between 1:1 brine/water (40 mL) and EtOAc (10 mL) and the mixture was filtered through a plug of Celite®. The aqueous layer was separated and extracted using EtOAc (3×10 mL). The combined organic layers were washed with 1:1 brine/water (40 mL), dried over $Na_2SO_4$, concentrated and the residue purified by flash chromatography (50 g Biotage KP-Sil, 0-100% EtOAc in PE) to give the title compound (34 mg, 11%) as a pale yellow solid. LCMS (Method A): $R_T$=1.17 min, m/z=372 [M+Na]$^+$.

Step 3: 3-((4-Hydroxypiperidin-4-yl)methyl)furo[2,3-d]pyrimidin-4(3H)-one

General procedure 2 using tert-butyl 4-hydroxy-4-((4-oxofuro[2,3-d]pyrimidin-3(4H)-yl)methyl)piperidine-1-carboxylate (34 mg, 0.097 mmol), TFA (0.6 mL) and DCM (0.6 mL) gave the title compound (23 mg, 95%) as a pale yellow solid. LCMS (Method A): $R_T$=0.23 min, m/z=250 [M+H]$^+$.

Step 4: 3-((4-Hydroxy-1-(3-phenylpropanoyl)piperidin-4-yl)methyl)furo[2,3-d]pyrimidin-4(3H)-one General procedure 3 using 3-((4-hydroxypiperidin-4-yl) methyl)furo[2,3-d]pyrimidin-4(3H)-one (23 mg, 0.092 mmol), 3-phenylpropanoic acid (14 mg, 0.092 mmol), EDC (53 mg, 0.277 mmol) and DCM (0.9 mL) gave the title compound (13 mg, 37%) as a colourless solid. LCMS (Method A): $R_T$=0.91 min, m/z=382 [M+H]$^+$. $^1$H NMR (300 MHz, CDCl$_3$): δ 7.99 (s, 1H), 7.49 (d, 1H), 7.33-7.21 (m, 5H), 6.92 (d, 1H), 4.41 (d, 1H), 4.16-4.00 (m, 2H), 3.56 (d, 1H), 3.32 (t, 1H), 3.08-2.94 (m, 4H), 2.66-2.60 (m, 2H), 1.65-1.27 (m, 4H).

Example 95: 6-((4-Hydroxy-1-(3-phenylpropanoyl) piperidin-4-yl)methyl)-2-methyl-3-(trifluoromethyl)-2H-pyrazolo[4,3-d]pyrimidin-7(6H)-one

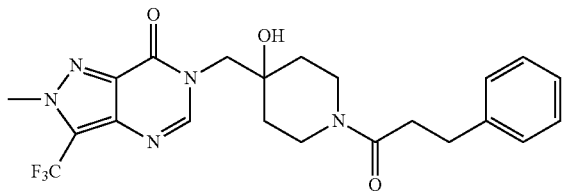 [SMILES: Cn1nc2c(=O)n(CC3(O)CCN(C(=O)CCc4ccccc4)CC3)cnc2c1C(F)(F)F]

General procedure 1 using Epoxide 3 (34 mg, 0.138 mmol), 2-methyl-3-(trifluoromethyl)-2H-pyrazolo[4,3-d] pyrimidin-7(6H)-one (30 mg, 0.138 mmol), $Cs_2CO_3$ (54 mg, 0.165 mmol) and DMF (0.3 mL) gave the title compound (27 mg, 42%) as a colourless solid. LCMS (Method A): $R_T$=1.16 min, m/z=464 [M+H]$^+$. $^1$H NMR (300 MHz, CDCl$_3$): δ 7.95 (s, 1H), 7.38-7.19 (m, 5H), 4.44-4.24 (m, 4H), 4.13-3.95 (m, 2H), 3.66-3.54 (m, 1H), 3.37-3.30 (m, 1H), 3.20-2.91 (m, 4H), 2.70-2.56 (m, 2H), 1.63-1.22 (m, 4H).

Example 96: (R)-1-((4-Hydroxy-1-(3-phenylbutanoyl)piperidin-4-yl)methyl)-9-methyl-8-(trifluoromethyl)-1H-purin-6(9H)-one

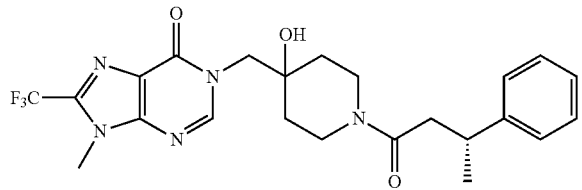 [SMILES: C[C@H](CC(=O)N1CCC(O)(Cn2cnc3c(nc(C(F)(F)F)n3C)c2=O)CC1)c1ccccc1]

Step 1: 9-Methyl-8-(trifluoromethyl)-1H-purin-6(9H)-one

To a mixture of 9-methyl-1H-purin-6(9H)-one (100 mg, 0.666 mmol) and sodium trifluoromethanesulfinate (312 mg, 2.00 mmol) in DCM (2 mL) and water (0.75 mL) was dropwise added t-BuOOH (323 µL, 3.33 mmol). The reaction showed incomplete conversion after 24 h so sodium trifluoromethanesulfinate (312 mg, 2.00 mmol) and t-BuOOH (323 µL, 3.33 mmol) were added. After 24 h the reaction mixture was diluted with water (20 mL) and extracted with DCM (5×10 mL) using a Biotage phase separator. The combined organic layers were concentrated and then dried in vacuo to give the title compound (110 mg, 76%) as a beige solid. LCMS (Method A): $R_T$=0.58 min, m/z=219 [M+H]$^+$.

Step 2: (R)-1-((4-Hydroxy-1-(3-phenylbutanoyl) piperidin-4-yl)methyl)-9-methyl-8-(trifluoromethyl)-1H-purin-6(9H)-one General procedure 1 using Epoxide 2 (149 mg, 0.573 mmol), 9-methyl-8-(trifluoromethyl)-1H-purin-6(9H)-one (125 mg, 0.573 mmol), $Cs_2CO_3$ (280 mg, 0.860 mmol) and DMF (1.1 mL) gave the title compound (76 mg, 28%) as a colourless solid. LCMS (Method A): $R_T$=1.19 min, m/z=478 [M+H]$^+$. $^1$H NMR (300 MHz, CDCl$_3$, this molecule appears as two conformers A and B in a 2:3 ratio respectively): δ 8.27 (s, 0.4H (conformer A)), 8.16 (s, 0.6H (conformer B)), 7.35-7.15 (m, 5H), 4.39-3.93 (m, 4H), 3.89 (s, 3H), 3.63-3.49 (m, 1H), 3.40-2.87 (m, 3H), 2.70-2.41 (m, 2H), 1.68-1.23 (m, 7H), 0.99-0.83 (m, 0.6H (conformer B only)).

Example 97: 3-(2-Fluorophenyl)-6-((4-hydroxy-1-((R)-3-phenylbutanoyl)piperidin-4-yl)methyl)-2-methyl-2H-pyrazolo[4,3-d]pyrimidin-7(6H)-one

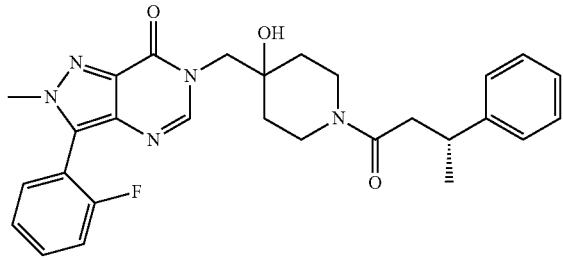 [SMILES: C[C@H](CC(=O)N1CCC(O)(Cn2cnc3c(-c4ccccc4F)n(C)nc3c2=O)CC1)c1ccccc1]

General procedure 5 using Intermediate B (33 mg, 0.068 mmol), (2-fluorophenyl)boronic acid (28 mg, 0.203 mmol), $K_3PO_4$ (43 mg, 0.203 mmol), $Pd(PPh_3)_4$ (7.8 mg, 6.76 μmol), 1,4-dioxane (0.5 mL) and water (0.13 mL) in a microwave at 150° C. for 10 min gave the title compound (24 mg, 71%) as a colourless solid. LCMS (Method A): $R_T$=1.23 min, m/z=504 [M+H]$^+$. $^1$H NMR (300 MHz, CDCl$_3$, this molecule appears as two conformers A and B in a 2:3 ratio respectively): δ 7.86 (s, 0.4H (conformer A)), 7.74 (s, 0.6H (conformer B)), 7.61-7.44 (m, 2H), 7.41-7.15 (m, 7H), 4.44-3.89 (m, 6H), 3.62-2.86 (m, 5H), 2.70-2.41 (m, 2H), 1.63-1.23 (m, 7H), 0.98-0.71 (m, 0.6H (conformer B only)).

Example 98: (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzonitrile

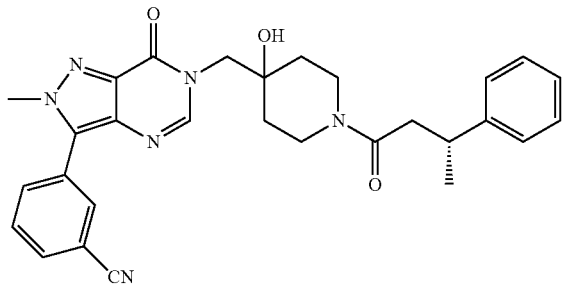 [SMILES: C[C@H](CC(=O)N1CCC(O)(Cn2cnc3c(-c4cccc(C#N)c4)n(C)nc3c2=O)CC1)c1ccccc1]

General procedure 5 using Intermediate B (33 mg, 0.068 mmol), (3-cyanophenyl)boronic acid (30 mg, 0.203 mmol), $K_3PO_4$ (43 mg, 0.203 mmol), $Pd(PPh_3)_4$ (7.8 mg, 6.76 μmol), 1,4-dioxane (0.5 mL) and water (0.13 mL) in a microwave at 150° C. for 10 min gave the title compound (24 mg, 70%) as a colourless solid. LCMS (Method A): $R_T$=1.20 min, m/z=511 [M+H]$^+$. $^1$H NMR (300 MHz, CDCl$_3$, this molecule appears as two conformers A and B in a 2:3 ratio respectively): δ 7.92-7.67 (m, 5H), 7.33-7.18 (m, 5H), 4.43-3.90 (m, 6H), 3.65-2.86 (m, 5H), 2.72-2.41 (m, 2H), 1.66-1.23 (m, 7H), 0.92-0.77 (m, 0.6H (conformer B only)).

Example 99: 3-(2-Aminophenyl)-6-((4-hydroxy-1-((R)-3-phenylbutanoyl)piperidin-4-yl)methyl)-2-methyl-2H-pyrazolo[4,3-d]pyrimidin-7(6H)-one

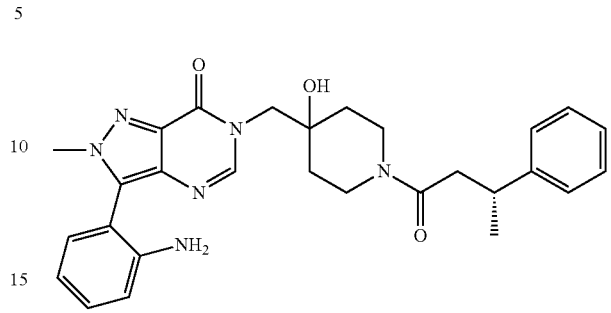

General procedure 5 using Intermediate B (40 mg, 0.082 mmol), 2-aminophenylboronic acid hydrochloride (36 mg, 0.205 mmol), $K_3PO_4$ (70 mg, 0.328 mmol), $Pd(PPh_3)_4$ (9.5 mg, 8.19 μmol), 1,4-dioxane (0.7 mL) and water (0.16 mL) in a microwave at 150° C. for 10 min gave the title compound (33 mg, 80%) as a colourless solid. LCMS (Method A): $R_T$=1.14 min, m/z=501 [M+H]$^+$. $^1$H NMR (300 MHz, CDCl$_3$, this molecule appears as two conformers A and B in a 2:3 ratio respectively): δ 7.82 (s, 0.4H (conformer A)), 7.72 (s, 0.6H (conformer B)), 7.39-7.13 (m, 5H), 7.13-7.05 (m, 1H), 6.93-6.57 (m, 3H), 4.40-3.84 (m, 6H), 3.62-2.84 (m, 5H), 2.70-2.41 (m, 2H), 1.64-1.24 (m, 7H), 0.92-0.77 (m, 0.6H (conformer B only)).

Example 100: (R)-3-((4-Hydroxy-1-(3-phenylbutanoyl)piperidin-4-yl)methyl)-6-morpholinopyrimidin-4(3H)-one

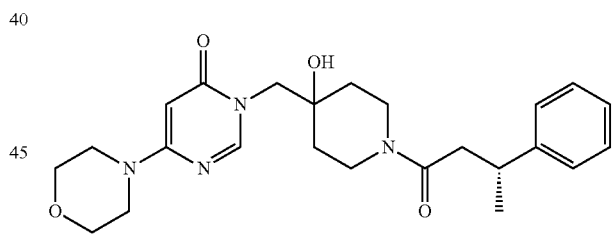

A mixture Intermediate A (30 mg, 0.077 mmol), morpholine (67 μL, 0.769 mmol) and 1,4-dioxane (0.5 mL) was heated in the microwave at 150° C. for 15 min. The reaction mixture was purified directly by flash chromatography (11 g Biotage KP-NH, 0-100% EtOAc in PE then 0-30% MeOH in EtOAc) to give the title compound (31 mg, 91%) as a colourless solid. LCMS (Method A): $R_T$=1.00 min, m/z=441 [M+H]$^+$. $^1$H NMR (300 MHz, CDCl$_3$, this molecule appears as two conformers A and B in a 2:3 ratio respectively): δ 7.78 (s, 0.4H (conformer A)), 7.67 (s, 0.6H (conformer B)), 7.37-7.14 (m, 5H), 5.49-5.40 (m, 1H), 5.02 (s, 0.6H (conformer B)), 4.84 (s, 0.4H (conformer A)), 4.51-4.31 (m, 1H), 4.16-3.43 (m, 11H), 3.43-3.17 (m, 2H), 3.07-2.84 (m, 1H), 2.71-2.42 (m, 2H), 1.65-1.11 (m, 7H), 0.68-0.52 (m, 0.6H (conformer B only)).

Example 101: 3-(Hydroxy(4-hydroxy-1-((R)-3-phenylbutanoyl)piperidin-4-yl)methyl)-4H-pyrido[1,2-a]pyrimidin-4-one

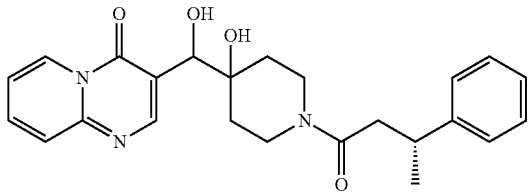 [SMILES: C[C@H](CC(=O)N1CCC(O)(C(O)c2cnc3ccccn3c2=O)CC1)c1ccccc1]

Step 1: tert-Butyl 4-((4-oxo-4H-pyrido[1,2-a]pyrimidin-3-yl)methylene) piperidine-1-carboxylate General procedure 5 using 3-bromo-4H-pyrido[1,2-a]pyrimidin-4-one (Prepared according to Heterocycles, 2009, 78, p2477) (200 mg, 0.889 mmol), tert-butyl 4-((4,4,5,5-tetramethyl-1,3,2-dioxaborolan-2-yl)methylene)piperidine-1-carboxylate (Prepared according to WO2013027001) (345 mg, 1.07 mmol), Pd(PPh$_3$)$_4$(51 mg, 0.044 mmol), Na$_2$CO$_3$ (376 mg, 6.27 mmol), DME (4 mL) and water (0.8 mL) after 3 days at 80° C. gave the title compound (216 mg, 71%) as a yellow solid. LCMS (Method A): R$_T$=1.29 min, m/z=342 [M+H]$^+$.

Step 2: tert-Butyl 4-hydroxy-4-(hydroxy(4-oxo-4H-pyrido[1,2-a]pyrimidin-3-yl)methyl)piperidine-1-carboxylate Water (0.25 mL) was added to a vigorously stirred mixture of tert-butyl 4-((4-oxo-4H-pyrido[1,2-a]pyrimidin-3-yl)methylene)piperidine-1-carboxylate (35 mg, 0.103 mmol), K$_2$OsO$_4$.2H$_2$O (3.8 mg, 10.3 µmol) and NMO (14 mg, 0.123 mmol) in DCM (0.75 mL). After 24 h the mixture was diluted by the addition of water (10 mL) and then extracted with DCM (3×10 mL) using a Biotage phase separator. The combined organic phases were concentrated and the products purified by flash chromatography (10 g Biotage KP-Sil, 0-40% MeOH in DCM) to give the title compound (14 mg, 36%) as a yellow oil. $^1$H NMR (300 MHz, CDCl$_3$): δ 9.09 (d, 1H), 8.34 (s, 1H), 7.89-7.69 (m, 2H), 7.33-7.20 (m, 1H), 4.48 (br. s., 1H), 4.32-3.73 (m, 3H), 3.24-2.99 (m, 2H), 1.94 (dd, 1H), 1.18-1.69 (m, 3H), 1.44 (s, 9H).

Step 3: 3-(Hydroxy(4-hydroxypiperidin-4-yl)methyl)-4H-pyrido[1,2-a]pyrimidin-4-one General procedure 2 using tert-butyl 4-hydroxy-4-(hydroxy(4-oxo-4H-pyrido[1,2-a]pyrimidin-3-yl)methyl)piperidine-1-carboxylate (14 mg, 0.037 mmol), DCM (1 mL) and TFA (1 mL) gave the title compound (9 mg, 88%) as a pale yellow solid. $^1$H NMR (300 MHz, methanol-d$_4$): δ 9.17-8.90 (m, 1H), 8.61-8.28 (m, 1H), 8.02-7.83 (m, 1H), 7.75-7.51 (m, 1H), 7.44-7.13 (m, 1H), 3.42-3.07 (m, 4H), 3.00-2.54 (m, 4H), 2.10-0.71 (m, 4H).

Step 4: 3-(Hydroxy(4-hydroxy-1-((R)-3-phenylbutanoyl)piperidin-4-yl)methyl)-4H-pyrido[1,2-a]pyrimidin-4-one General procedure 4 using 3-(hydroxy(4-hydroxypiperidin-4-yl)methyl)-4H-pyrido[1,2-a]pyrimidin-4-one (9 mg, 0.033 mmol), (R)-3-phenylbutanoic acid (8 mg, 0.049 mmol), HATU (19 mg, 0.049 mmol), DIPEA (23 µL, 0.131 mmol) and DCM (1 mL) gave the title compound (10 mg, 73%) as a colourless solid. LCMS (Method A): R$_T$=0.86 and 0.85 min (2 diastereoisomers), m/z=422 [M+H]$^+$. $^1$H NMR (300 MHz, CDCl$_3$): δ 9.08 (d, 1H), 8.41-8.24 (m, 1H), 7.90-7.71 (m, 2H), 7.34-7.09 (m, 6H), 4.58-4.33 (m, 2H), 4.27 (d, 1H), 3.73-3.44 (m, 1H), 3.41-3.14 (m, 2H), 2.98-2.82 (m, 1H), 2.72-2.37 (m, 2H), 1.98-1.71 (m, 2H), 1.61-1.09 (m, 5H), 1.05-0.62 (m, 1H).

Example 102: (R)-1-((4-Hydroxy-1-(3-phenylbutanoyl)piperidin-4-yl)methyl)piperidin-4-yl)methyl)-[4,5'-bipyrimidin]-6(1H)-one

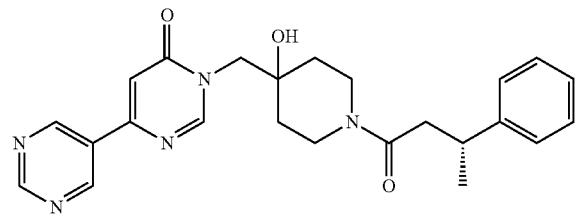 [SMILES: C[C@H](CC(=O)N1CCC(O)(Cn2cnc(-c3cncnc3)cc2=O)CC1)c1ccccc1]

General procedure 5 using Intermediate A (25 mg, 0.064 mmol), (pyrimidin-5-yl)boronic acid (12 mg, 0.096 mmol), Na$_2$CO$_3$ (14 mg, 0.128 mmol), Pd(PPh$_3$)$_4$(3.7 mg, 3.21 µmol), 1,4-dioxane (0.4 mL) and water (0.16 mL) in a microwave at 150° C. for 10 min gave the title compound (24 mg, 86%) as a colourless solid. LCMS (Method A): R$_T$=0.93 min, m/z=434 [M+H]$^+$. $^1$H NMR (300 MHz, CDCl$_3$, this molecule appears as two conformers A and B in a 2:3 ratio respectively): δ 9.37-9.21 (m, 3H), 8.28 (s, 0.4H (conformer A)), 8.17 (s, 0.6H (conformer B)), 7.41-7.14 (m, 5H), 6.96 (s, 1H), 4.48-4.35 (m, 0.6H (conformer B)), 4.35-4.22 (m, 0.4H (conformer A)), 4.22-3.82 (m, 2H), 3.67-2.86 (m, 5H), 2.74-2.58 (m, 1H), 2.58-2.42 (m, 1H), 1.64-1.24 (m, 7H), 0.84-0.67 (m, 0.6H (conformer B only)).

Example 103: (R)-3-((4-Hydroxy-1-(3-phenylbutanoyl)piperidin-4-yl)methyl)-6-((2-hydroxyethyl)amino)pyrimidin-4(3H)-one

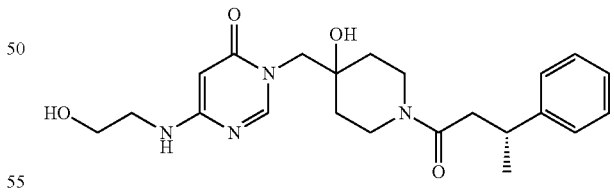

A mixture of Intermediate A (25 mg, 0.064 mmol), 2-aminoethanol (59 mg, 0.962 mmol) and ethanol (0.5 mL) was heated in the microwave at 120° C. for 20 min. The reaction mixture was purified by flash chromatography (11 g Biotage KP-NH, 0-100% EtOAc in PE then 0-30% MeOH in EtOAc) to give the title compound (20 mg, 75%) as a colourless solid. LCMS (Method A): R$_T$=0.81 min, m/z=415 [M+H]$^+$. $^1$H NMR (300 MHz, CDCl$_3$, this molecule appears as two conformers A and B in a 2:3 ratio respectively): δ 7.83 (s, 0.4H (conformer A)), 7.74 (s, 0.6H (conformer B)), 7.37-7.15 (m, 5H), 6.08-5.94 (m, 1H), 5.26 (s, 1H), 5.07-

4.84 (m, 1H), 4.42-4.23 (m, 1H), 4.02-3.47 (m, 6H), 3.40-3.15 (m, 4H), 3.07-2.82 (m, 1H), 2.72-2.57 (m, 1H), 2.57-2.43 (m, 1H), 1.54-1.22 (m, 6H), 0.92-0.80 (m, 0.4H (conformer A)), 0.80-0.65 (m, 0.6H (conformer B)).

Example 104: (R)-6-((4-Hydroxy-1-(3-phenylbutanoyl)piperidin-4-yl)methyl)-3-(3-hydroxyphenyl)-2-methyl-2H-pyrazolo[4,3-d]pyrimidin-7(6H)-one

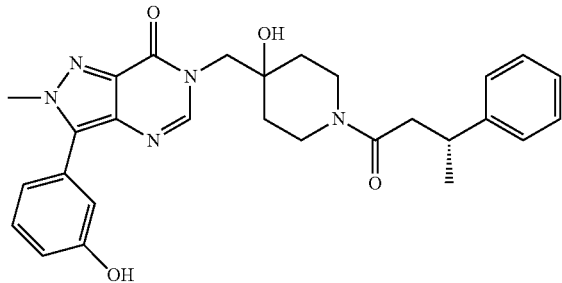

General procedure 5 using Intermediate B (32 mg, 0.066 mmol), (3-hydroxyphenyl)boronic acid (27 mg, 0.197 mmol), $K_3PO_4$ (42 mg, 0.197 mmol), $Pd(PPh_3)_4$ (7.6 mg, 6.55 μmol), 1,4-dioxane (0.5 mL) and water (0.13 mL) in a microwave at 150° C. for 10 min gave the title compound (21 mg, 64%) as a colourless solid. LCMS (Method A): $R_T$=1.09 min, m/z=502 [M+H]$^+$. $^1$H NMR (300 MHz, methanol-$d_4$, this molecule appears as two conformers A and B in a 2:3 ratio respectively): δ 7.89 (s, 0.4H (conformer A)), 7.83 (s, 0.6H (conformer B)), 7.34-7.01 (m, 6H), 7.00-6.89 (m, 2H), 6.89-6.78 (m, 1H), 4.19-3.70 (m, 6H), 3.66-3.47 (m, 1H), 3.26-2.31 (m, 5H), 1.60-1.08 (m, 7H), 0.85-0.69 (m, 0.6H (conformer B only)).

Example 105: 3-(Hydroxy(4-hydroxy-1-((R)-3-phenylbutanoyl)piperidin-4-yl)methyl)-9-phenyl-4H-pyrido[1,2-a]pyrimidin-4-one

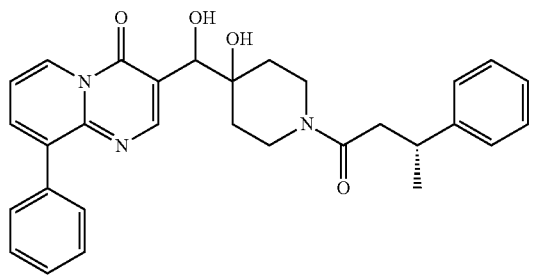 [SMILES: C[C@H](CC(=O)N1CCC(O)(C(O)c2cnc3c(-c4ccccc4)cccn3c2=O)CC1)c1ccccc1]

Step 1: tert-Butyl 4-hydroxy-4-(hydroxy(4-oxo-9-phenyl-4H-pyrido[1,2-a]pyrimidin-3-yl)methyl)piperidine-1-carboxylate Water (0.500 ml) was added to a vigorously stirred mixture of tert-butyl 4-((4-oxo-9-phenyl-4H-pyrido[1,2-a]pyrimidin-3-yl)methylene)piperidine-1-carboxylate (100 mg, 0.240 mmol), $K_2OsO_4\cdot2H_2O$ (2.2 mg, 5.99 μmol) and NMO (34 mg, 0.287 mmol) in DCM (1.5 mL). After 24 h, further t-BuOH (0.5 mL) was added. After 4 days, $K_2OsO_4\cdot2H_2O$ (2.2 mg, 5.99 μmol) was added and the reaction was stirred for a further 24 h. The mixture was diluted with water (10 mL) and extracted with DCM (3×10 mL) using a Biotage phase separator. The combined organic phases were concentrated and the residue purified by flash chromatography (Biotage 10 g KP-Sil, 0-40% MeOH in DCM) to give the title compound (93 mg, 86%) as a yellow foam. LCMS (Method A): $R_T$=1.32 min, m/z=452 [M+H]$^+$.

Step 2: 3-(Hydroxy(4-hydroxypiperidin-4-yl)methyl)-9-phenyl-4H-pyrido[1,2-a]pyrimidin-4-one General procedure 2 using tert-butyl 4-hydroxy-4-(hydroxy(4-oxo-9-phenyl-4H-pyrido[1,2-a]pyrimidin-3-yl)methyl)piperidine-1-carboxylate (93 mg, 0.206 mmol), TFA (2 mL) and DCM (2 mL) gave the title compound (65 mg, 90%) as a pale yellow solid. LCMS (Method A): $R_T$=0.46 min, m/z=352 [M+H]$^+$.

Step 3: 3-(Hydroxy(4-hydroxy-1-((R)-3-phenylbutanoyl)piperidin-4-yl)methyl)-9-phenyl-4H-pyrido[1,2-a]pyrimidin-4-one General procedure 4 using 3-(hydroxy(4-hydroxypiperidin-4-yl)methyl)-9-phenyl-4H-pyrido[1,2-a]pyrimidin-4-one (37 mg, 0.105 mmol), (R)-3-phenylbutanoic acid (26 mg, 0.158 mmol), HATU (60 mg, 0.158 mmol), DIPEA (74 μL, 0.421 mmol) and DCM (2 mL) gave the title compound (37 mg, 71%) as a colourless solid. LCMS (Method A): $R_T$=1.28 and 1.27 min (2 diastereoisomers), m/z=498 [M+H]$^+$. $^1$H NMR (300 MHz, CDCl$_3$): δ 9.15-9.08 (m, 1H), 8.39-8.22 (m, 1H), 7.85-7.76 (m, 1H), 7.68-7.57 (m, 2H), 7.56-7.44 (m, 3H), 7.37-7.07 (m, 6H), 4.57-4.18 (m, 3H), 3.69-3.44 (m, 1H), 3.41-3.11 (m, 2H), 2.99-2.81 (m, 1H), 2.72-2.38 (m, 2H), 1.97-1.74 (m, 1H), 1.62-1.29 (m, 5H), 0.98-0.73 (m, 1H).

Example 106: (R)-4-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzamide

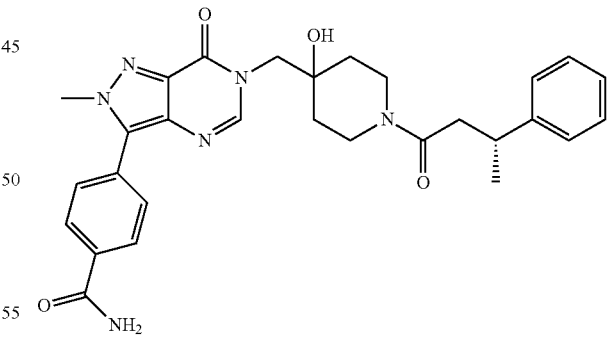

General procedure 5 using Intermediate B (25 mg, 0.051 mmol), (4-carbamoylphenyl)boronic acid (21 mg, 0.128 mmol), $K_3PO_4$ (33 mg, 0.154 mmol), $Pd(PPh_3)_4$ (6 mg, 5.12 μmol), 1,4-dioxane (0.4 mL) and water (0.1 mL) in a microwave at 130° C. for 15 min gave the title compound (22 mg, 81%) as a colourless solid. LCMS (Method A): $R_T$=0.94 min, m/z=529 [M+H]$^+$. $^1$H NMR (500 MHz, DMSO-$d_6$): δ 8.11 (s, 1H), 8.06 (d, J=8.2 Hz, 2H), 8.01 (d, J=12.4 Hz, 1H), 7.82 (d, J=8.2 Hz, 2H), 7.49 (s, 1H), 7.30-7.21 (m, 4H), 7.19-7.13 (m, 1H), 4.87 (d, J=5.7 Hz, 1H), 4.15 (s, 3H), 4.05-3.89 (m, 3H), 3.69-3.61 (m, 1H), 3.28-3.12 (m, 3H), 2.90-2.84 (m, 1H), 2.62-2.56 (m, 1H), 1.55-1.29 (m, 4H), 1.21 (d, J=6.9 Hz, 3H).

Example 107: (R)-6-((4-Hydroxy-1-(3-phenylbutanoyl)piperidin-4-yl)methyl)-3-(4-(hydroxymethyl)phenyl)-2-methyl-2H-pyrazolo[4,3-d]pyrimidin-7(6H)-one

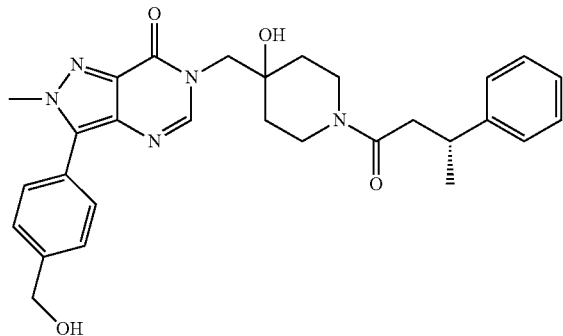 [SMILES: C[C@H](CC(=O)N1CCC(O)(Cn2cnc3c(-c4ccc(CO)cc4)n(C)nc3c2=O)CC1)c1ccccc1]

General procedure 5 using Intermediate B (25 mg, 0.051 mmol), (4-(hydroxymethyl)phenyl)boronic acid (19 mg, 0.128 mmol), K$_3$PO$_4$ (33 mg, 0.154 mmol), Pd(PPh$_3$)$_4$(6 mg, 5.12 µmol), 1,4-dioxane (0.4 mL) and water (0.1 mL) in a microwave at 130° C. for 15 min gave the title compound (19 mg, 72%) as a colourless solid. LCMS (Method A): R$_T$=1.01 min, m/z=516 [M+H]$^+$. $^1$H NMR (500 MHz, DMSO-d$_6$): δ 7.98 (d, J=12.6 Hz, 1H), 7.69-7.65 (m, 2H), 7.54-7.49 (m, 2H), 7.29-7.23 (m, 4H), 7.17-7.14 (m, 1H), 5.32 (t, J=5.7 Hz, 1H), 4.86 (d, J=5.9 Hz, 1H), 4.60 (d, J=5.7 Hz, 2H), 4.10 (s, 3H), 4.07-3.87 (m, 3H), 3.69-3.61 (m, 1H), 3.27-3.13 (m, 2H), 2.92-2.83 (m, 1H), 2.66-2.55 (m, 2H), 1.57-1.28 (m, 4H), 1.21 (d, J=6.9 Hz, 3H).

Example 108: (R)-6-((4-Hydroxy-1-(3-phenylbutanoyl)piperidin-4-yl)methyl)-2-methyl-3-(3-(morpholinomethyl)phenyl)-2H-pyrazolo[4,3-d]pyrimidin-7(6H)-one

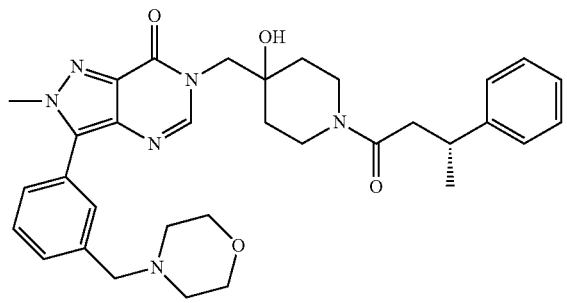 [SMILES: C[C@H](CC(=O)N1CCC(O)(Cn2cnc3c(-c4cccc(CN5CCOCC5)c4)n(C)nc3c2=O)CC1)c1ccccc1]

General procedure 5 using Intermediate B (25 mg, 0.051 mmol), 4-(3-(4,4,5,5-tetramethyl-1,3,2-dioxaborolan-2-yl)benzyl)morpholine (39 mg, 0.128 mmol), K$_3$PO$_4$ (33 mg, 0.154 mmol), Pd(PPh$_3$)$_4$(6 mg, 5.12 µmol), 1,4-dioxane (0.4 mL) and water (0.1 mL) in a microwave at 130° C. for 15 min gave the title compound (19 mg, 63%) as a colourless solid. LCMS (Method B): R$_T$=0.76 min, m/z=585 [M+H]$^+$. $^1$H NMR (500 MHz, DMSO-d$_6$): δ 7.99 (d, J=12.7 Hz, 1H), 7.64 (s, 1H), 7.60 (d, J=7.7 Hz, 1H), 7.54 (t, J=7.6 Hz, 1H), 7.46 (d, J=7.5 Hz, 1H), 7.26 (t, J=6.4 Hz, 4H), 7.18-7.12 (m, 1H), 4.88 (d, J=5.9 Hz, 1H), 4.11 (s, 3H), 4.14-3.86 (m, 4H), 3.70-3.53 (m, 6H), 3.27-3.13 (m, 2H), 2.92-2.83 (m, 1H), 2.66-2.55 (m, 2H), 2.44-2.35 (m, 4H), 1.58-1.25 (m, 4H), 1.21 (d, J=6.9 Hz, 3H).

Example 109: (R)-3-((4-Hydroxy-1-(3-phenylbutanoyl)piperidin-4-yl)methyl)-6-((2-methoxyethyl)amino)pyrimidin-4(3H)-one

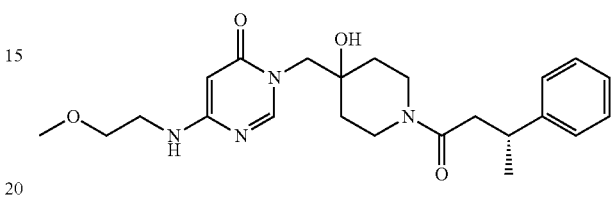

A mixture of Intermediate A (25 mg, 0.064 mmol), 2-methoxyethanamine (0.056 mL, 0.641 mmol) and 1,4-dioxane (0.5 mL) was heated for 15 min at 150° C. in the microwave. The reaction mixture was diluted with brine (15 mL) and extracted with DCM (10 mL) using a Biotage phase separator. The organic layer was concentrated and the residue purified by flash chromatography to afford the title compound (17 mg, 62%) as colourless solid. LCMS (Method A): R$_T$=0.85 min, m/z=429 [M+H]$^+$. $^1$H NMR (500 MHz, DMSO-d$_6$): δ 7.97 (d, J=13.6 Hz, 1H), 7.31-7.21 (m, 4H), 7.20-7.12 (m, 1H), 6.95 (s, 1H), 5.09 (s, 1H), 4.99 (d, J=3.3 Hz, 1H), 4.03-3.94 (m, 1H), 3.84-3.58 (m, 4H), 3.42 (t, J=5.6 Hz, 2H), 3.25 (s, 3H), 3.28-3.12 (m, 3H), 2.93-2.86 (m, 1H), 2.62-2.53 (m, 2H), 1.48-1.22 (m, 4H), 1.20 (d, J=6.8 Hz, 3H).

Example 110: 3-((4-Hydroxy-1-((R)-3-phenylbutanoyl)piperidin-4-yl)methyl)-6-(((R)-pyrrolidin-3-yl)amino)pyrimidin-4(3H)-one

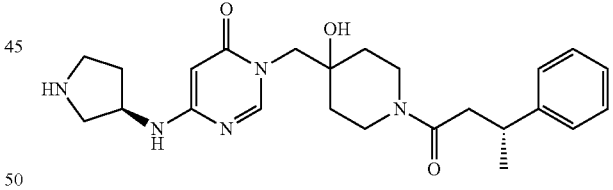

A mixture of Intermediate A (25 mg, 0.064 mmol), (R)-tert-butyl 3-aminopyrrolidine-1-carboxylate (0.109 mL, 0.641 mmol) and 1,4-dioxane (0.5 mL) was heated for 75 min at 150° C. in the microwave. The reaction mixture was diluted with brine (15 mL) and extracted with DCM (10 mL) using a Biotage phase separator. The organic layer was concentrated and the residue purified by flash chromatography to afford (R)-tert-butyl 3-((1-((4-hydroxy-1-((R)-3-phenylbutanoyl)piperidin-4-yl)methyl)-6-oxo-1,6-dihydropyrimidin-4-yl)amino)pyrrolidine-1-carboxylate. This material was stirred in DCM (0.2 mL) and TFA (0.2 mL) for 2 h before being concentrated. The residue was dissolved in DCM (1 mL) and NEt$_3$ (1 mL) and the mixture purified directly by flash chromatography (11 g Biotage KP-NH, 0-100% EtOAc in PE then 0-20% MeOH in EtOAc) to afford the title compound (13 mg, 89%) as a pale yellow solid. LCMS (Method B): $R_T$=0.64 min, m/z=440 [M+H]$^+$. $^1$H NMR (500 MHz, DMSO-d$_6$): δ 7.97 (d, J=13.6 Hz, 1H), 7.32-7.19 (m, 4H), 7.19-7.13 (m, 1H), 7.03 (d, J=6.5 Hz, 1H), 5.03 (s, 1H), 4.98 (s, 1H), 4.03-3.93 (m, 1H), 3.87-3.57 (m, 4H), 3.23-3.09 (m, 2H), 2.99-2.83 (m, 3H), 2.79-2.71 (m, 1H), 2.64-2.53 (m, 2H), 2.00-1.90 (m, 1H), 1.64-1.54 (m, 1H), 1.49-1.22 (m, 5H), 1.20 (d, J=6.9 Hz, 3H).

Example 111: (R)-3-((4-Hydroxy-1-(3-phenylbutanoyl)piperidin-4-yl)methyl)-5-methyl-6-((2-(pyrrolidin-1-yl)ethyl)amino)pyrimidin-4(3H)-one

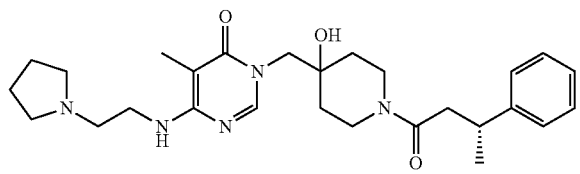 [SMILES: Cc1c(NCCN2CCCC2)ncn(CC2(O)CCN(C(=O)C[C@@H](C)c3ccccc3)CC2)c1=O]

In a 10 mL vial was charged (R)-6-chloro-3-((4-hydroxy-1-(3-phenylbutanoyl)piperidin-4-yl)methyl)-5-methylpyrimidin-4(3H)-one (40 mg, 0.099 mmol) (Example 44) and 2-(pyrrolidin-1-yl)ethanamine (0.126 mL, 0.990 mmol) in 1,4-dioxane (1.0 mL) to give a pale yellow solution. The vessel was sealed and heated to 150° C. for 15 min (Biotage microwave). Due to incomplete reaction, the reaction was heated to 175° C. for 1 h (Biotage microwave). The reaction mixture was partitioned between EtOAc and water, the resultant biphasic mixture was separated, the aqueous phase was extracted using EtOAc (×2), the combined organic phase was dried (MgSO$_4$), the solvents were removed in vacuo and the remaining residue was purified by flash chromatography (11 g KP-NH column, 0-100% EtOAc/cyclohexane, then 0-20% MeOH/EtOAc) to give the title compound (12 mg, 25%) as an off-white solid. LCMS (Method B): $R_T$=0.70 min, m/z=482 [M+H]$^+$. $^1$H NMR (400 MHz, methanol-d$_4$): δ 7.99 (m, 1H), 7.35-7.14 (m, 5H), 4.25-4.10 (m, 1H), 4.02-3.59 (m, 5H), 3.28-3.12 (m, 2H, overlapping solvent), 3.05-2.88 (m, 1H), 2.83-2.45 (m, 8H), 1.90-1.77 (m, 6H), 1.62-0.85 (m, 8H).

Example 112: Benzyl 4-((3-(4-(aminomethyl)phenyl)-2-methyl-7-oxo-2,7-dihydro-6H-pyrazolo[4,3-d]pyrimidin-6-yl)methyl)-4-hydroxypiperidine-1-carboxylate

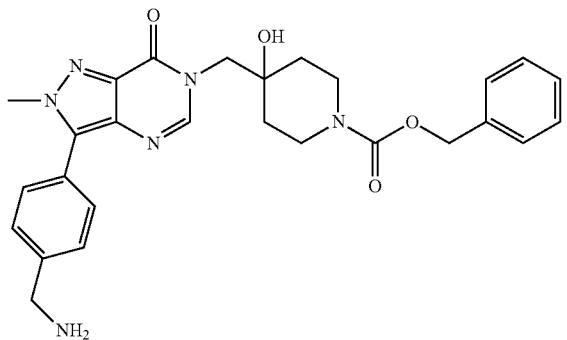 [SMILES: Cn1nc2c(=O)n(CC3(O)CCN(C(=O)OCc4ccccc4)CC3)cnc2c1-c1ccc(CN)cc1]

tert-Butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (20 mg, 0.043 mmol) was dissolved in DCM (1 mL) and DIPEA (0.022 mL, 0.13 mmol) was added, followed by benzyl chloroformate (6.7 μL, 0.047 mmol). The mixture was stirred at RT for 10 min, then TFA (1 mL) was added. The mixture was stirred at RT for a further 10 min then concentrated. The residue was taken up in methanol and added to a 2 g SCX-2 cartridge. The column was flushed with MeOH then eluted with 2 M NH$_3$ in MeOH. The NH$_3$ fractions were concentrated to give a glass which was purified by flash chromatography (Biotage 11 g KP-NH; eluted 50-100% EtOAc in cyclohexane then 0-35% MeOH in EtOAc) to give the title compound (14 mg, 65%) as a white solid. LCMS (Method A): $R_T$=0.77 min, m/z=503 [M+H]$^+$. $^1$H NMR (300 MHz, DMSO-d$_6$): δ 7.99 (s, 1H), 7.63 (d, 2H), 7.53 (d, 2H), 7.35 (m, 5H), 5.07 (s, 2H), 4.92 (s, 1H), 4.10 (s, 3H), 3.99 (s, 2H), 3.81 (m, 4H), 3.14 (m, 2H), 2.13 (m, 2H), 1.50 (m, 2H), 1.42 (m, 2H).

Example 113: (R)—N-(1-((4-Hydroxy-1-(3-phenylbutanoyl)piperidin-4-yl)methyl)-6-oxo-1,6-dihydropyrimidin-4-yl)-N-(2-(pyrrolidin-1-yl)ethyl)acetamide, Formic Acid

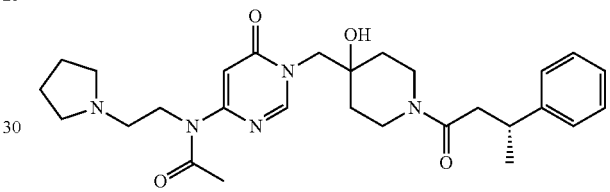

DIPEA (0.045 mL, 0.257 mmol) and Ac$_2$O (0.022 mL, 0.235 mmol) were added to a stirred solution of Intermediate A (100 mg, 0.214 mmol) in THF (1 mL) at RT in a sealed vial. After 1 h, further DIPEA (0.045 mL, 0.257 mmol) and Ac$_2$O (0.022 mL, 0.235 mmol) were added. After a further 1 h, further DIPEA (0.045 mL, 0.257 mmol) and Ac$_2$O (0.022 mL, 0.235 mmol) were added. After a further hour, the solvents were removed in vacuo and the remaining residue was purified by preparative HPLC (Method A, acidic conditions) to give the title compound (6.9 mg, 6%) as a pale orange solid. LCMS (Method B): $R_T$=0.72 min, m/z=510 [M+H]$^+$. $^1$H NMR (400 MHz, methanol-d$_4$): δ 8.48 (br s, 1H), 8.39-8.28 (m, 1H), 7.38-7.14 (m, 5H), 6.50 (s, 1H), 4.28-3.98 (m, 4H), 3.96-3.77 (m, 1H), 3.75-3.58 (m, 1H), 3.20-2.43 (m, 8H, overlapping solvent), 2.25 (s, 3H), 2.15-1.88 (m, 5H), 1.67-0.78 (m, 9H).

Example 114: 3-((4-Hydroxy-1-((R)-3-phenylbutanoyl)piperidin-4-yl)methyl)-6-((2-((R)-2-methylpyrrolidin-1-yl)ethyl)amino)pyrimidin-4(3H)-one, Formic Acid

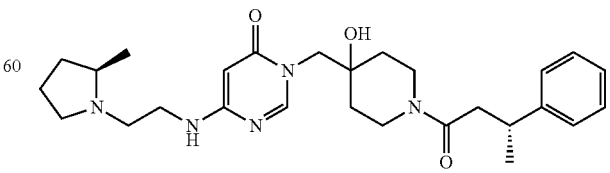

In a microwave reactor tube was Intermediate A (40 mg, 0.103 mmol) and (R)-2-(2-methylpyrrolidin-1-yl)ethanamine (65.8 mg, 0.513 mmol) in 1,4-dioxane (1.5 mL) to give a pale yellow solution. The reaction mixture was heated to 150° C. for 30 min using microwave irradiation. Due to incomplete reaction, the reaction mixture was heated to 175° C. for 30 min using microwave irradiation. Due to incomplete reaction, the reaction mixture was heated to 175° C. for 1 h using microwave irradiation. The reaction mixture was purified directly by preparative HPLC (Method A, acidic conditions) to give the title compound (8.8 mg, 16%). LCMS (Method B): $R_T$=0.73 min, m/z=482 [M+H]$^+$. $^1$H NMR (400 MHz, methanol-d$_4$): δ 8.50 (s, 1H), 8.12-8.01 (m, 1H), 7.35-7.14 (m, 5H), 5.37 (s, 1H), 4.15 (ddt, 1H), 3.98-3.52 (m, 3H), 3.50-3.38 (m, 1H), 3.28-3.15 (m, 1H, overlapping solvent), 3.11-2.88 (m, 3H), 2.84-2.69 (m, 1H), 2.66 (s, 1H), 2.54 (ddd, 1H), 2.30-2.19 (m, 1H), 2.11-1.94 (m, 5H), 1.77-0.84 (m, 12H).

Example 115: (R)-1-(4-Hydroxy-4-((5-phenylpyrazin-2-yl)methyl) piperidin-1-yl)-3-phenylbutan-1-one

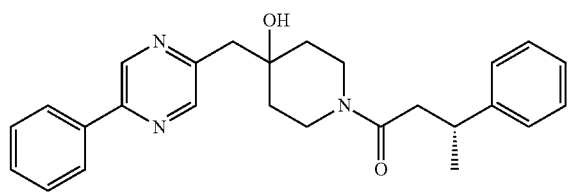 [SMILES: C[C@H](CC(=O)N1CCC(O)(Cc2cnc(-c3ccccc3)cn2)CC1)c1ccccc1]

Step 1: tert-Butyl 4-hydroxy-4-((5-phenylpyrazin-2-yl)methyl)piperidine-1-carboxylate 2-methyl-5-phenylpyrazine (200 mg, 1.18 mmol) (commercially available) was dissolved in THF (3 mL) and the solution was cooled to −78° C. under N$_2$. LDA (2 M in THF/heptane/ethylbenzene, 1.18 mL, 2.36 mmol) was added and the mixture was stirred for 1 h. tert-Butyl 4-oxopiperidine-1-carboxylate (351 mg, 1.76 mmol) was added as a solution in THF (3 mL) and the mixture was stirred for 30 min at −78° C., then allowed to return to RT with stirring for 3 h. Saturated ammonium chloride (aq) solution was added and the mixture was extracted into ethyl acetate (×3). The combined organic phases were washed with brine, dried over MgSO$_4$ and concentrated. The residue was purified by flash chromatography (GraceResolv™ 12 g; eluted 0-50% EtOAc in cyclohexane) to give tert-butyl 4-hydroxy-4-((5-phenylpyrazin-2-yl)methyl)piperidine-1-carboxylate (102 mg, 24%) as a glass. LCMS (Method A): $R_T$=1.55 min, m/z=370 [M+H]$^+$.

Step 2: 4-((5-Phenylpyrazin-2-yl)methyl)piperidin-4-ol tert-Butyl 4-hydroxy-4-((5-phenylpyrazin-2-yl)methyl) piperidine-1-carboxylate (102 mg, 0.28 mmol) was dissolved in DCM (2 mL) and TFA (2 mL) was added. The mixture was stirred at RT for 15 min then concentrated. The residue was taken up in methanol and added to a 2 g SCX-2 cartridge. The column was flushed with MeOH then eluted with 2 M NH$_3$ in MeOH. The NH$_3$ fractions were concentrated to give a glass which was purified by flash chromatography (Biotage 11 g KP-NH; eluted 30-100% EtOAc in cyclohexane) to give 4-((5-phenylpyrazin-2-yl)methyl)piperidin-4-ol (38 mg, 51%) as a greasy solid. LCMS (Method A): $R_T$=0.59 min, m/z=270 [M+H]$^+$.

Step 3: (R)-1-(4-Hydroxy-4-((5-phenylpyrazin-2-yl)methyl)piperidin-1-yl)-3-phenylbutan-1-one General procedure 4 using 4-((5-phenylpyrazin-2-yl)methyl)piperidin-4-ol (35 mg, 0.13 mmol), HATU (54 mg, 0.14 mmol), (R)-3-phenylbutanoic acid (24 mg, 0.14 mmol), DIPEA (0.030 mL, 0.17 mmol) and DCM (2 mL) gave the title compound (39 mg, 72%) as a colourless glass. LCMS (Method A): $R_T$=1.46 min, m/z=416 [M+H]$^+$. $^1$H NMR (300 MHz, DMSO-d$_6$): δ 9.15 (s, 1H), 8.58 (d, 1H), 8.12 (d, 2H), 7.51 (m, 3H), 7.24 (m, 4H), 7.14 (m, 1H), 4.71 (d, 1H), 4.02 (m, 1H), 3.62 (m, 1H), 3.15 (m, 2H), 2.85 (m, 3H), 2.60 (m, 2H), 1.05-1.50 (m, 7H).

Example 116: (R)-3-((4-Hydroxy-1-(3-phenylbutanoyl)piperidin-4-yl)methyl)-6-(phenylethynyl)pyrimidin-4(3H)-one

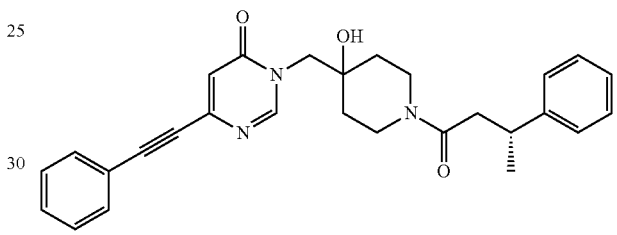

Step 1: tert-Butyl 4-((4-chloro-6-oxopyrimidin-1 (6H)-yl)methyl)-4-hydroxypiperidine-1-carboxylate General procedure 1 using Epoxide 1 (6.08 g, 28.5 mmol), 6-chloropyrimidin-4(3H)-one (3.72 g, 28.5 mmol), DIPEA (7.47 mL, 42.7 mmol) and DMF (35 mL) gave the title compound (5.87 g, 60%) as an off-white solid. LCMS (Method B): $R_T$=0.99 min, m/z=224 [M+H-Boc]$^+$.

Step 2: 3-((4-Hydroxypiperidin-4-yl)methyl)-6-(phenylethynyl)pyrimidin-4(3H)-one tert-Butyl 4-((4-chloro-6-oxopyrimidin-1(6H)-yl) methyl)-4-hydroxypiperidine-1-carboxylate (100 mg, 0.29 mmol) and trimethylamine (0.24 mL, 1.75 mmol) were dissolved in DMF (1 mL) and phenylacetylene (0.07 mL, 0.64 mmol) was added. The mixture was evacuated and refilled with N$_2$ three times. Triphenylphosphinegold(I) chloride (7.2 mg, 0.015 mmol) was added and the tube was sealed. The mixture was heated at 60° C. for 16 h, then cooled to RT. The mixture was diluted with water then extracted with ethyl acetate (×3). The combined organic phases were washed with brine, dried (MgSO$_4$) and concentrated. The residue was purified by flash chromatography (GraceResolv 12 g; eluted 0-100% EtOAc in cyclohexane) to give an orange syrup. This was dissolved in DCM (1 mL) and TFA (1 mL) and stirred for 5 min then concentrated. The residue was dissolved in methanol and added to a 2 g SCX-2 cartridge. The column was flushed with methanol then eluted with 2 M NH$_3$ in methanol. The NH$_3$ fractions were concentrated to give the title compound (60 mg, 67%). LCMS (Method A): $R_T$=0.73 min, m/z=310 [M+H]$^+$.

Step 3: (R)-3-((4-Hydroxy-1-(3-phenylbutanoyl) piperidin-4-yl)methyl)-6-(phenylethynyl)pyrimidin-4 (3H)-one General procedure 4 using 3-((4-hydroxypiperidin-4-yl) methyl)-6-(phenylethynyl)pyrimidin-4(3H)-one (58 mg, 0.19 mmol), (R)-3-phenylbutanoic acid (33.9 mg, 0.21 mmol), DIPEA (0.043 mL, 0.24 mmol), HATU (82 mg, 0.22 mmol) and DCM (2 mL) gave the title compound (9 mg, 11%) as a colourless glass. LCMS (Method B): $R_T$=1.25 min, m/z=456 [M+H]$^+$. $^1$H NMR (300 MHz, DMSO-d$_6$): δ 8.28 (d, 1H), 7.60 (d, 2H), 7.50 (m, 3H), 7.26 (m, 4H), 7.22 (m, 1H), 6.68 (m, 1H), 4.96 (m, 1H), 4.00 (m, 1H), 3.94 (m, 2H), 3.71 (m, 1H), 3.21 (m, 2H), 2.90 (m, 1H), 2.55 (m, 2H), 1.05-1.55 (m, 7H).

Example 117: (R)-6-Benzyl-3-((4-hydroxy-1-(3-phenylbutanoyl)piperidin-4-yl)methyl)pyrimidin-4 (3H)-one

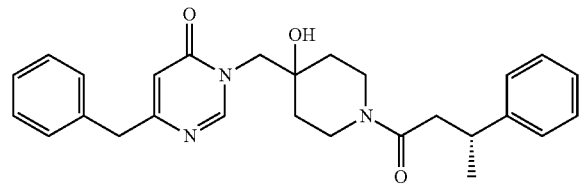 [SMILES: C[C@H](CC(=O)N1CCC(O)(Cn2cnc(Cc3ccccc3)cc2=O)CC1)c1ccccc1]

Step 1: 6-Benzyl-3-((4-hydroxypiperidin-4-yl) methyl)pyrimidin-4(3H)-one tert-Butyl 4-((4-chloro-6-oxopyrimidin-1 (6H)-yl) methyl)-4-hydroxypiperidine-1-carboxylate (60 mg, 0.18 mmol) and benzyltrifluoroborate (31 mg, 0.19 mmol) were dissolved in toluene (2 mL). Triethylamine (0.036 mL, 0.26 mmol) was added, followed by water (0.2 mL). The mixture was evacuated and refilled with N$_2$ three times, then PdCl$_2$ (dppf) (12.8 mg, 0.017 mmol) was added. The tube was sealed and the mixture was heated at 110° C. for 16 h. The mixture was cooled and diluted with water then extracted into ethyl acetate (×3). The combined organic phases were washed with brine then dried (MgSO$_4$) and concentrated. The residue was purified by flash chromatography (GraceResolv 12 g; eluted 10-100% EtOAc in cyclohexane then 0-15% MeOH in EtOAc) to give a colourless glass. This was dissolved in DCM (1 mL) and TFA (1 mL) and stirred for 10 min then concentrated. The residue was dissolved in methanol and added to a 2 g SCX-2 cartridge. The column was flushed with methanol then eluted with 2 M NH$_3$ in methanol. The NH$_3$ fractions were concentrated to give the title compound (11 mg, 21%) as a colourless glass. LCMS (Method A): $R_T$=0.55 min, m/z=300 [M+H]$^+$.

Step 2: (R)-6-Benzyl-3-((4-hydroxy-1-(3-phenylbutanoyl)piperidin-4-yl)methyl)pyrimidin-4(3H)-one General procedure 4 using 6-benzyl-3-((4-hydroxypiperidin-4-yl)methyl)pyrimidin-4(3H)-one (11 mg, 0.037 mmol), (R)-3-phenylbutanoic acid (6.6 mg, 0.04 mmol), HATU (15.4 mg, 0.040 mmol), DIPEA (7.7 μL, 0.044 mmol) and DCM (1 mL) gave the title compound (11 mg, 67%) as a white solid. LCMS (Method B): $R_T$=1.14 min, m/z=446 [M+H]$^+$. $^1$H NMR (300 MHz, DMSO-d$_6$): δ 8.20 (d, 1H), 7.27 (m, 9H), 7.22 (m, 1H), 6.21 (m, 1H), 4.92 (m, 1H), 3.86 (m, 2H), 3.76 (s, 3H), 3.60 (m, 1H), 3.14 (m, 2H), 2.80 (m, 1H), 2.55 (m, 2H), 1.10-1.50 (m, 7H).

Example 118: 3-(4-((R)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one

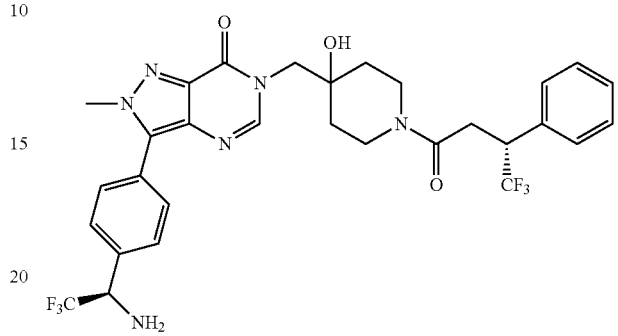

Step 1: (S,Z)—N-(4-Bromobenzylidene)-2-methyl-propane-2-sulfinamide

In a 250 mL round-bottomed flask was added 4-bromobenzaldehyde (10 g, 54.0 mmol) in toluene (43.2 ml) to give a colourless solution. To this was added (S)-2-methylpropane-2-sulfinamide (6.55 g, 54.0 mmol) portionwise followed by stirring at RT for 15 min. To the resulting mixture was added sodium hydroxide (2.16 g, 54.0 mmol). After 16 h, sodium sulfate (2.5 g) and Celite® (2.5 g) were added. After 15 min, the solids were removed by filtration and the filtrate was concentrated in vacuo, followed by purification by flash chromatography (GraceResolv silica 330 g cartridge, 5-30% EtOAc/cyclohexane) to give the title compound (13.5 g, 87%) as a yellow oil that solidifed upon standing. LCMS (Method A): $R_T$=1.57 min, m/z=288, 290 [M+H]$^+$.

Step 2: (S)—N—((R)-1-(4-Bromophenyl)-2,2,2-trifluoroethyl)-2-methylpropane-2-sulfinamide In a 40 mL reaction tube was added (S,Z)—N-(4-bromobenzylidene)-2-methylpropane-2-sulfinamide (1.00 g, 3.47 mmol) and tetrabutylammonium acetate (1.03 g, 3.47 mmol) in DMF (10 mL) to give a colourless solution. The reaction mixture was stirred and cooled to 0° C. followed by the dropwise addition of trimethyl(trifluoromethyl)silane (1.28 mL, 8.67 mmol). After 90 min, the reaction mixture was diluted with saturated ammonium chloride (aq) solution (50 mL) and extracted into ethyl acetate (3×25 mL). The combined organic phases were washed with 1:1 water/brine (3×25 mL), dried over Na$_2$SO$_4$, filtered, concentrated to dryness under reduced pressure. The resultant solid material was slurried using cyclohexane (30 mL) and collected to give the title compound (878 mg, 71%) as a tan solid. LCMS (Method A): $R_T$=1.57 min, m/z=358, 360 [M+H]$^+$.

Step 3: (S)-2-Methy-N—((R)-2,2,2-trifluoro-1-(4-(4,4,5,5-tetramethyl-1,3,2-dioxaborolan-2-yl)phenyl) ethyl)propane-2-sulfinamide In a 40 mL reaction tube was added (S)—N—((R)-1-(4-bromophenyl)-2,2,2-trifluoroethyl)-2-methylpropane-2-sulfinamide (500 mg, 1.40 mmol), bis(pinacolato)diboron (532 mg, 2.09 mmol) and potassium acetate (411 mg, 4.19 mmol) in anhydrous 1,4-dioxane (5.6 mL). The resultant colourless solution was degassed (bubbling nitrogen) for 10 min, followed by the addition of PdCl$_2$(dppf).DCM (57.0 mg, 0.070 mmol) and the temperature was increased to 95° C. under a nitrogen atmosphere overnight. The reaction mixture was allowed to cool to RT, diluted with water (10 mL) and extracted into ethyl acetate (3×10 mL). The combined organic phases were dried (Na$_2$SO$_4$), filtered and concentrated to dryness under reduced pressure. The residue was purified by flash chromatography (Grace 80 g cartridge, 5-60%, EtOAc in cyclohexane) to give the title compound (333 mg, 59%) as an off-white solid. LCMS (Method A): R$_T$=1.78 min, m/z=406 [M+H]$^+$. $^1$H NMR (300 MHz, CDCl$_3$): δ 7.84 (d, 2H), 7.42 (d, 2H), 4.83 (quin, 1H), 3.63 (d, 1H), 1.34 (s, 12H), 1.25 (s, 9H).

Step 4: (S)-2-Methyl-N—((R)-2,2,2-trifluoro-1-(4-(6-((4-hydroxy-1-((R)-4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)ethyl)propane-2-sulfinamide In a 10 mL microwave tube was added Intermediate E (30 mg, 0.055 mmol), (S)-2-methyl-N—((R)-2,2,2-trifluoro-1-(4-(4,4,5,5-tetramethyl-1,3,2-dioxaborolan-2-yl)phenyl)ethyl)propane-2-sulfinamide (33.6 mg, 0.083 mmol) and potassium phosphate, tribasic (28.9 mg, 0.166 mmol) in a mixture of 1,4-dioxane (1.2 mL) and water (0.3 mL) to give a yellow solution. This was degassed by bubbling nitrogen for 10 min, followed by the addition of PdCl$_2$(dppf).DCM (2.3 mg, 2.77 μmol) and heating to 120° C. under microwave irradiation for 15 min. The reaction mixture was diluted with water (10 mL) and extracted into ethyl acetate (3×10 mL). The combined organic phases were washed with brine (10 mL), dried over Na$_2$SO$_4$, filtered and concentrated to dryness under reduced pressure. The residue was purified by flash chromatography (KP-NH 28 g cartridge, 10-100% EtOAc/cyclohexane; then 0-20% MeOH/EtOAc) to give the title compound (20 mg, 49) as a yellow solid. LCMS (Method B): R$_T$=1.31 min, m/z=685 [M-butene+H]$^+$.

Step 5: 3-(4-((R)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one In a 25 mL round-bottomed flask was added (S)-2-methyl-N—((R)-2,2,2-trifluoro-1-(4-(6-((4-hydroxy-1-((R)-4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)ethyl)propane-2-sulfinamide (20 mg, 0.027 mmol) in methanol (1 mL) to give a yellow solution. To this was added hydrochloric acid, 4M in 1,4-dioxane (0.027 mL, 0.108 mmol) and the resulting mixture stirred at RT for 1 h. The reaction mixture was loaded onto a pre-equilibrated 2 g SCX-2 cartridge. After 10 min, the cartridge was washed using 20% MeOH/DCM, before elution using 20% 2M ammonia in methanol/DCM. The resulting solution was concentrated to dryness under reduced pressure, triturated using diethyl ether and freeze-dried to give the title compound (12 mg, 70%) as a white solid. LCMS (Method B): R$_T$=0.98 min, m/z=637 [M+H]$^+$. $^1$H NMR (400 MHz, DMSO-d$_e$): δ 7.98 (d, 1H), 7.67-7.77 (m, 4H), 7.27-7.44 (m, 5H), 4.89 (s, 1H), 4.61 (sex, 1H), 4.04-4.19 (m, 4H), 3.86-4.02 (m, 3H), 3.71-3.82 (m, 1H), 3.10-3.29 (m, 2H), 2.78-3.02 (m, 2H), 2.61 (d, 2H), 1.12-1.68 (m, 4H).

Example 119: 3-(4-((S)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one

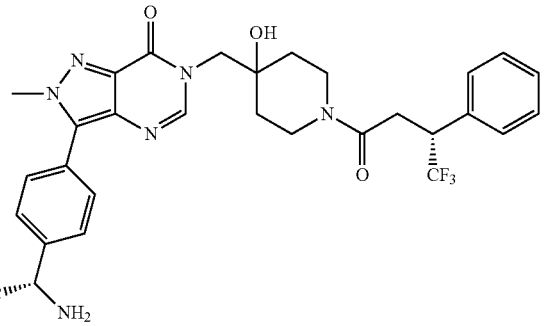

Step 1: (R,Z)—N-(4-Bromobenzylidene)-2-methylpropane-2-sulfinamide

In a 100 mL round-bottomed flask was added 4-bromobenzaldehyde (5 g, 27.0 mmol) in toluene (22 mL) to give a colourless solution. To this was added (R)-2-methylpropane-2-sulfinamide (3.28 g, 27.0 mmol) portionwise followed by stirring at RT for 15 min. To the resulting mixture was added sodium hydroxide (1.08 g, 27.0 mmol) followed by stirring at RT. After a further 16 h, solid sodium sulfate (1.3 g) and Celite® (1.3 g) were added and the resulting suspension was stirred for 15 min. The solids were removed by filtration and the filtrates were concentrated to dryness under reduced pressure followed by purification by flash chromatography (GraceResolv silica 120 g cartridge, 5-30% EtOAc/cyclohexane) to give the title compound (5.10 g, 66%) as a yellow oil that solidifed upon standing. LCMS (Method B): R$_T$=1.45 min, m/z=288, 290 [M+H]$^+$.

Step 2: (R)—N—((S)-1-(4-Bromophenyl)-2,2,2-trifluoroethyl)-2-methylpropane-2-sulfinamide In a 40 mL reaction tube was added (R,Z)—N-(4-bromobenzylidene)-2-methylpropane-2-sulfinamide (1.00 g, 3.47 mmol) and tetrabutylammonium acetate (1.03 g, 3.47 mmol) in DMF (10 mL) to give a colourless solution. This was cooled to 0° C. followed by the dropwise addition of trimethyl(trifluoromethyl)silane (1.28 mL, 8.67 mmol) and stirring at 0° C. for 90 min. The reaction mixture was diluted with saturated ammonium chloride (aq) solution (50 mL) and extracted into ethyl acetate (3×25 mL). The combined organic phases were washed with 1:1 water/brine (3×25 mL), dried over Na$_2$SO$_4$, filtered, concentrated to dryness under reduced pressure, and slurried in diethyl ether (20 mL) to give the title compound (336 mg, 27%) as a tan solid. LCMS (Method B): R$_T$=1.35 min, m/z=358, 360 [M+H]$^+$.

Step 3: (R)-2-Methyl-N—((S)-2,2,2-trifluoro-1-(4-(4,4,5,5-tetramethyl-1,3,2-dioxaborolan-2-yl)phenyl)ethyl)propane-2-sulfinamide In a 15 mL reaction tube was added (R)—N—((S)-1-(4-bromophenyl)-2,2,2-trifluoroethyl)-2-methylpropane-2-sulfinamide (336 mg, 0.938 mmol), bis(pinacolato)diboron (357 mg, 1.41 mmol) and potassium acetate (276 mg, 2.81 mmol) in anhydrous 1,4-dioxane (3.7 mL) to give a colourless solution. This was degassed by bubbling nitrogen through the solution for 10 min, followed by the addition of PdCl$_2$(dppf).DCM (38.3 mg, 0.047 mmol) and heating to 95° C. under nitrogen. After 16 h, the reaction mixture was cooled to RT, diluted with water (10 mL) and extracted into ethyl acetate (3×10 mL). The combined organic phases were dried over Na$_2$SO$_4$, filtered and concentrated to dryness under reduced pressure. The residue was purified by flash chromatography (GraceResolv silica 80 g cartridge, 5-60% EtOAc/cyclohexane) to give the title compound (184 mg, 48%) as an off-white solid. LCMS (Method B): R$_T$=1.52 min, m/z=406 [M+H]$^+$. $^1$H NMR (300 MHz, CDCl$_3$): δ 7.84 (d, 2H), 7.42 (d, 2H), 4.83 (quin, 1H), 3.63 (d, 1H), 1.34 (s, 12H), 1.25 (s, 9H).

Step 4: (R)-2-Methyl-N—((S)-2,2,2-trifluoro-1-(4-(6-((4-hydroxy-1-((R)-4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)ethyl)propane-2-sulfinamide In a 10 mL microwave tube was added Intermediate E (30 mg, 0.055 mmol), (R)-2-methyl-N—((S)-2,2,2-trifluoro-1-(4-(4,4,5,5-tetramethyl-1,3,2-dioxaborolan-2-yl)phenyl)ethyl)propane-2-sulfinamide (33.6 mg, 0.083 mmol) and potassium phosphate, tribasic (28.9 mg, 0.166 mmol) in a mixture of 1,4-dioxane (1.2 mL) and water (0.3 ml) to give a yellow solution. This was degassed by bubbling nitrogen for 10 min, followed by the addition of PdCl$_2$(dppf).DCM (2.3 mg, 2.77 μmol) and heating to 120° C. under microwave irradiation for 20 min. The reaction mixture was diluted with water (10 mL) and extracted into ethyl acetate (3×10 mL). The combined organic phases were washed with brine (10 mL), dried over Na$_2$SO$_4$, filtered and concentrated to dryness under reduced pressure. The residue was purified by flash chromatography (KP-NH 28 g cartridge, 10-100% EtOAc/cyclohexane; 0-20% MeOH/EtOAc) to give the title compound (30 mg, 73%) as a yellow solid. LCMS (Method B): R$_T$=1.31 min, m/z=685 [M-butene+H]$^+$.

Step 5: 3-(4-((S)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one In a 25 mL round-bottomed flask was added (R)-2-methyl-N—((S)-2,2,2-trifluoro-1-(4-(6-((4-hydroxy-1-((R)-4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)ethyl)propane-2-sulfinamide (30 mg, 0.040 mmol) in methanol (1 mL) to give a yellow solution. To this was added hydrochloric acid, 4M in 1,4-dioxane (0.040 mL, 0.162 mmol) and the resulting mixture was stirred at RT for 1 h. The reaction mixture was loaded onto a pre-equilibrated 2 g SCX-2 cartridge, allowed to bind for 10 min, washed using 20% MeOH/DCM, before elution using 20% 2M ammonia in methanol/DCM. The resulting solution was concentrated to dryness under reduced pressure, slurried in diethyl ether and freeze-dried to give the title compound (19 mg, 74%) as a white solid. LCMS (Method B): R$_T$=0.99 min, m/z=637 [M+H]$^+$. $^1$H NMR (400 MHz, DMSO-d$_6$): δ 7.98 (d, 1H), 7.67-7.77 (m, 4H), 7.27-7.44 (m, 5H), 4.89 (s, 1H), 4.61 (sex, 1H), 4.04-4.19 (m, 4H), 3.86-4.02 (m, 3H), 3.71-3.82 (m, 1H), 3.10-3.29 (m, 2H), 2.78-3.02 (m, 2H), 2.61 (d, 2H), 1.12-1.68 (m, 4H).

Example 120: (R)-3-(4-(Aminomethyl)phenyl)-2-ethyl-6-((4-hydroxy-1-(3-phenylbutanoyl)piperidin-4-yl)methyl)-2H-pyrazolo[4,3-d]pyrimidin-7(6H)-one

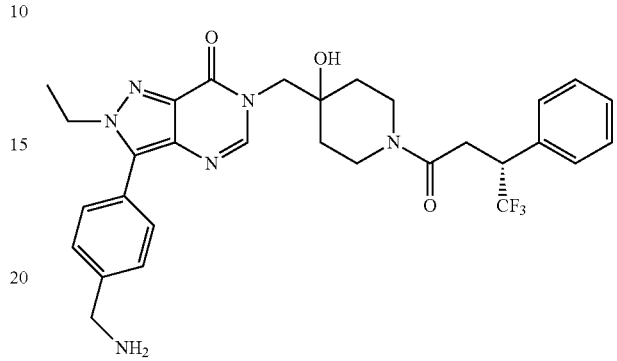

Step 1: Methyl 1-ethyl-4-nitro-1H-pyrazole-3-carboxylate

A 60% dispersion of sodium hydride in mineral oil (720 mg, 18 mmol) was added to a suspension of methyl 4-nitro-1H-pyrazole-3-carboxylate (2.57 g, 15 mmol) in THF (30 mL) at 0° C. After 1 h, iodoethane (1.46 mL, 18 mmol) was added and the reaction was allowed to warm to RT before being heated at 60° C. for 16 h. The reaction was cooled to RT, diluted with water (60 mL) and the mixture extracted with DCM (3×60 mL) using a Biotage phase separator. The combined organic phases were concentrated and the residue purified by flash chromatography (120 g GraceResolv silica, 0-70% EtOAc in cyclohexane) to give the title compound (1.76 g, 59%) as a colourless solid. LCMS (Method A): R$_T$=0.97 min, m/z=200 [M+H]$^+$.

Step 2: Methyl 4-amino-1-ethyl-1H-pyrazole-3-carboxylate

A solution of methyl 1-ethyl-4-nitro-1H-pyrazole-3-carboxylate (1.75 g, 8.79 mmol) in MeOH (88 mL) was reduced in the H-Cube® (10% Pd/C CatCart® 1 mLmin$^{-1}$, RT, 20 bar H$_2$; then 1 mLmin$^{-1}$, 40° C., 40 bar H$_2$; then 1.5 mLmin$^{-1}$, 50° C., 50 bar H$_2$). The resulting solution was concentrated to give the title compound (1.45 g, 98%) as a purple oil. LCMS (Method A): R$_T$=0.35 min, m/z=170 [M+H]$^+$.

Step 3: 2-Ethyl-2H-pyrazolo[4,3-d]pyrimidin-7(6H)-one

A suspension of methyl 4-amino-1-ethyl-1H-pyrazole-3-carboxylate (1.45 g, 8.57 mmol) and formamidine acetate (0.982 g, 9.43 mmol) in DIPEA (8 mL, 45.8 mmol) and EtOH (8 mL) was heated in the microwave at 110° C. for 1 h. The reaction was left overnight and the precipitate isolated by filtration. The precipitate was washed with Et$_2$O (30 mL) and then dried under high vacuum at 75° C. to give the title compound (1.15 g, 82%) as a colourless solid. $^1$H NMR (400 MHz, DMSO-d$_6$): δ 11.82 (s, 1H), 8.36 (s, 1H), 7.76 (s, 1H), 4.35 (q, J=7.3 Hz, 2H), 1.45 (t, J=7.3 Hz, 3H).

Step 4: 3-Bromo-2-ethyl-2H-pyrazolo[4,3-d]pyrimidin-7(6H)-one

Br$_2$ (1.06 mL, 20.7 mmol) was added to a suspension of 2-ethyl-2H-pyrazolo[4,3-d]pyrimidin-7(6H)-one (1.13 g, 6.88 mmol) in AcOH (7 mL) in a reaction tube. The tube was sealed and the mixture heated at 95° C. for 18 h before being cooled to RT and 1:1 EtOH/Et$_2$O (50 mL) added. The resulting precipitate was then isolated by filtration and washed with Et$_2$O (2×30 mL). The precipitate was then suspended in saturated sodium thiosulfate$_{(aq)}$ (50 mL) and stirred vigorously for 30 min before the solids were isolated by filtration. The product was then washed with water (3×30 mL) and dried under hi-vacuum at 80° C. to give the title compound (1.47 g, 88%) as a colourless solid. $^1$H NMR (300 MHz, DMSO-d$_6$): δ 12.04 (s, 1H), 7.85 (d, J=3.6 Hz, 1H), 4.41 (q, J=7.1 Hz, 2H), 1.42 (t, J=7.1 Hz, 3H).

Step 5: tert-Butyl 4-((3-bromo-2-ethyl-7-oxo-2H-pyrazolo[4,3-d]pyrimidin-6(7H)-yl)methyl)-4-hydroxypiperidine-1-carboxylate General procedure 1 using Epoxide 1 (427 mg, 2.00 mmol), 3-bromo-2-ethyl-2H-pyrazolo[4,3-d]pyrimidin-7(6H)-one (243 mg, 1 mmol), Cs$_2$CO$_3$ (358 mg, 1.10 mmol) and DMF (3.3 mL) gave the title compound (430 mg, 94%) as a colourless solid. $^1$H NMR (300 MHz, CDCl$_3$): δ 7.91 (s, 1H), 4.47 (q, J=7.3 Hz, 2H), 4.24-3.98 (m, 2H), 3.98-3.73 (m, 2H), 3.27-3.03 (m, 2H), 1.77-1.47 (m, 7H), 1.44 (s, 9H).

Step 6: 3-Bromo-2-ethyl-6-((4-hydroxypiperidin-4-yl)methy)-2H-pyrazolo[4,3-d]pyrimidin-7(6H)-one A solution of tert-butyl 4-((3-bromo-2-ethyl-7-oxo-2H-pyrazolo[4,3-d]pyrimidin-6(7H)-yl)methyl)-4-hydroxypiperidine-1-carboxylate (430 mg, 0.942 mmol) in DCM (5 mL) and TFA (5 mL) was stirred for 20 min before the reaction was purified using 3×10 g Biotage SCX-2 cartridges in parallel (10% MeOH in DCM then 20% 7 M in NH$_3$ in MeOH in DCM) the basic phases were concentrated to give the title compound (326 mg, 97%) as a colourless solid. $^1$H NMR (300 MHz, DMSO-d$_6$): δ 8.05 (s, 1H), 4.69 (s, 1H), 4.41 (q, J=7.2 Hz, 2H), 3.93 (s, 2H), 2.90-2.56 (m, 4H), 1.51-1.22 (m, 7H).

Step 7: (R)-3-Bromo-2-ethyl-6-((4-hydroxy-1-(4,4,4-trifluoro-3-phenylbutanoyl)piperidin-4-yl)methyl)-2H-pyrazolo[4,3-d]pyrimidin-7(6H)-one General procedure 4 using 3-bromo-2-ethyl-6-((4-hydroxypiperidin-4-yl)methyl)-2H-pyrazolo[4,3-d]pyrimidin-7(6H)-one (47 mg, 0.131 mmol), (R)-4,4,4-trifluoro-3-phenylbutanoic acid (43 mg, 0.197 mmol), HATU (75 mg, 0.197 mmol), DIPEA (92 μL, 0.526 mmol) and DCM (2.6 mL) gave the title compound (59 mg, 81%) as a beige foam. $^1$H NMR (300 MHz, CDCl$_3$): δ 7.93-7.69 (m, 1H), 7.44-7.27 (m, 5H), 4.48 (q, J=7.3 Hz, 2H), 4.35-3.83 (m, 4H), 3.75-3.56 (m, 1H), 3.43-3.26 (m, 1H), 3.10-2.81 (m, 4H), 1.66-0.96 (m, 7H).

Step 8: (R)-3-(4-(Aminomethyl)phenyl)-2-ethyl-6-((4-hydroxy-1-(4,4,4-trifluoro-3-phenylbutanoyl)piperidin-4-yl)methyl)-2H-pyrazolo[4,3-d]pyrimidin-7(6H)-one General procedure 5 using (R)-3-bromo-2-ethyl-6-((4-hydroxy-1-(4,4,4-trifluoro-3-phenylbutanoyl)piperidin-4-yl)methyl)-2H-pyrazolo[4,3-d]pyrimidin-7(6H)-one (59 mg, 0.106 mmol), (4-(((tert-butoxycarbonyl)amino)methyl)phenyl)boronic acid (80 mg, 0.318 mmol), K$_3$PO$_4$ (135 mg, 0.636 mmol), Pd(PPh$_3$)$_4$(6 mg, 5.30 μmol), 1,4-dioxane (0.9 mL) and water (0.3 mL) in a microwave at 130° C. for 1 h gave (R)-tert-butyl 4-(2-ethyl-6-((4-hydroxy-1-(3-phenylbutanoyl)piperidin-4-yl)methyl)-7-oxo-6,7-dihydro-2H-pyrazolo[4,3-d]pyrimidin-3-yl)benzylcarbamate as a colourless solid. This material was stirred in DCM (2 mL) and TFA (2 mL) for 10 min before being concentrated. The residue was dissolved in DCM (2 mL) and NEt$_3$ (2 mL) and purified directly by flash chromatography (28 g Biotage KP-NH, 0-100% DCM in cyclohexane then 0-30% MeOH in DCM) to afford the title compound (327 mg, 53%) as a colourless solid after lyophilisation. LCMS (Method B): R$_T$=0.81 min, m/z=583 [M+H]$^+$. $^1$H NMR (300 MHz, DMSO-d$_6$): δ 7.99-7.91 (m, 1H), 7.59-7.48 (m, 4H), 7.46-7.24 (m, 5H), 4.89 (s, 1H), 4.38 (q, J=7.2 Hz, 2H), 4.16-4.03 (m, 1H), 4.02-3.86 (m, 3H), 3.81 (s, 3H), 3.29-3.11 (m, 2H), 3.03-2.79 (m, 2H), 2.04 (s, 2H), 1.39 (q, J=8.0, 7.6 Hz, 7H).

Example 121: (R)-3-((4-Hydroxy-1-(3-phenylbutanoyl)piperidin-4-yl)methyl)-6-(phenyl(2-(pyrrolidin-1-yl)ethyl)amino)pyrimidin-4(3H)-one, Formic Acid

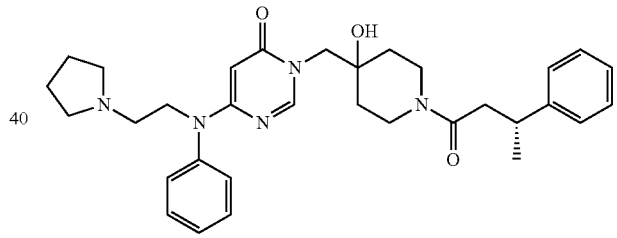

Pd$_2$(dba)$_3$ (5.9 mg, 6.41 μmol) was added to a stirred suspension of Intermediate A (50 mg, 0.128 mmol), N-(2-(pyrrolidin-1-yl)ethyl)aniline (36.6 mg, 0.192 mmol), Xantphos (11.1 mg, 0.019 mmol), and Cs$_2$CO$_3$ (84 mg, 0.256 mmol) in 1,4-dioxane (1.0 mL) in a reaction tube. The vessel was sealed and temperature was increased to 80° C. After 16 h, the reaction mixture was diluted with DCM, filtered and the solvents were removed in vacuo. The remaining residue was purified by preparative HPLC (Method A, acidic conditions) to give the title compound (3.3 mg, 4%) as a pale yellow solid. LCMS (Method B): R$_T$=0.83 min, m/z=544 [M+H]$^+$. $^1$H NMR (400 MHz, methanol-d$_4$): δ 8.53 (br s, 1H), 8.21-8.12 (m, 1H), 7.54 (t, 2H), 7.43 (t, 1H), 7.36-7.14 (m, 7H), 7.01 (t, 1H), 4.26-3.59 (m, 6H), 3.25-2.46 (m, 8H, overlapping solvent), 2.09-1.86 (m, 5H), 1.63-0.78 (m, 9H).

Example 122: 3-(4-((S)-1-Amino-2,2-difluoroethyl) phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one

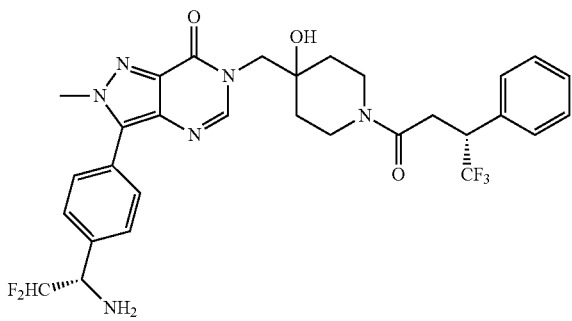 [SMILES: Cn1nc2c(=O)n(CC3(O)CCN(C(=O)C[C@H](c4ccccc4)C(F)(F)F)CC3)cnc2c1-c1ccc([C@H](N)C(F)F)cc1]

Step 1: (R)—N—((S)-1-(4-Bromophenyl)-2,2-difluoroethyl)-2-methylpropane-2-sulfinamide In a 100 mL round-bottomed flask was added (R,Z)—N-(4-bromobenzylidene)-2-methylpropane-2-sulfinamide (1.00 g, 3.47 mmol) and (difluoromethyl)trimethylsilane (1.08 g, 8.67 mmol) in anhydrous THF (20 mL) to give a colourless solution. This was stirred and cooled to −78° C., followed by the addition of a solution of potassium tert-butoxide (0.973 g, 8.67 mmol) in anhydrous THF (15 mL). After 15 min, the temperature was allowed to warm to room temperature. The reaction mixture was quenched with water (30 mL) and extracted using ethyl acetate (3×30 mL). The combined organic phase was dried (Na$_2$SO$_4$), filtered and the solvents were removed in vacuo. The residue was purified by flash chromatography (Grace 120 g, 10-60%, EtOAc in cyclohexane) to give the title compound (750 mg, 64%) as a white solid. LCMS (Method B): R$_T$=1.24 min, m/z=340, 342 [M+H]$^+$.

Step 2: (R)—N—((S)-2,2-Difluoro-1-(4-(4,4,5,5-tetramethyl-1,3,2-dioxaborolan-2-yl)phenyl)ethyl)-2-methylpropane-2-sulfinamide In a 100 mL round-bottomed flask was added (R)—N—((S)-1-(4-bromophenyl)-2,2-difluoroethyl)-2-methylpropane-2-sulfinamide (750 mg, 2.20 mmol), bis(pinacolato)diboron (840 mg, 3.31 mmol) and potassium acetate (649 mg, 6.61 mmol) in anhydrous 1,4-dioxane (8.8 mL). The resultant colourless solution was degassed (bubbling nitrogen) for 10 min. PdCl$_2$(dppf).DCM (90 mg, 0.110 mmol) was added and the temperature was increased to 95° C. and the reaction mixture was stirred under nitrogen. After 16 h, the reaction mixture was allowed to cool to RT and was diluted with water (30 mL) and extracted using EtOAc (3×30 mL). The combined organic phases were dried (Na$_2$SO$_4$), filtered and the solvents were removed in vacuo. The remaining residue was purified by flash chromatography (Grace 80 g, 5-60%, EtOAc in cyclohexane) to give the title compound (640 mg, 75%) as a tan solid. LCMS (Method B): R$_T$=1.40 min, m/z=388 [M+H]$^+$. $^1$H NMR (300 MHz, CDCl$_3$): δ 7.84 (dt, 2H), 7.38 (dt, 2H), 5.96 (td, 1H), 4.66 (tdd, 1H), 3.66 (d, 1H), 1.34 (s, 12H), 1.23 (s, 9H).

Step 3: (R)—N—((S)-2,2-Difluoro-1-(4-(6-((4-hydroxy-1-((R)-4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)ethyl)-2-methylpropane-2-sulfinamide In a 10 mL microwave tube was added Intermediate E (30 mg, 0.055 mmol), (R)—N—((S)-2,2-difluoro-1-(4-(4,4,5,5-tetramethyl-1,3,2-dioxaborolan-2-yl)phenyl)ethyl)-2-methylpropane-2-sulfinamide (32.1 mg, 0.083 mmol) and potassium phosphate, tribasic (28.9 mg, 0.166 mmol) in a mixture of 1,4-dioxane (1.2 mL) and water (0.3 mL). The resultant yellow solution was degassed (bubbling nitrogen) for 10 min. PdCl$_2$(dppf).DCM (2.3 mg, 2.77 μmol) was added and the reaction mixture was heated to 120° C. under microwave irradiation for 20 min. The reaction mixture was diluted with water (10 mL) and extracted using EtOAc (3×10 mL). The combined organic phase was washed with brine (10 mL), dried (Na$_2$SO$_4$), filtered, and the solvents were removed in vacuo. The remaining residue was purified by flash chromatography (KP-NH 28 g cartridge, 10-100%, EtOAc in cyclohexane; then 0-20% MeOH in EtOAc) to give the title compound (28 mg, 70%) as a pale brown solid. LCMS (Method B): R$_T$=1.23 min, m/z=667 [M-butene+H]$^+$.

Step 4: 3-(4-((S)-1-Amino-2,2-difluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one In a 25 mL round-bottomed flask was added (R)—N—((S)-2,2-difluoro-1-(4-(6-((4-hydroxy-1-((R)-4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)ethyl)-2-methylpropane-2-sulfinamide (28 mg, 0.039 mmol) in methanol (1 mL) to give a yellow solution. To this was added hydrochloric acid, 4M in 1,4-dioxane (0.039 mL, 0.155 mmol) and the resulting mixture stirred at RT for 60 min. The reaction mixture was loaded onto a pre-equilibrated 2 g SCX-2 cartridge. After 10 min, the cartridge was washed with 4:1 DCM/methanol before the product was eluted with 4:1 DCM/2M ammonia in methanol. The resulting solution was concentrated to dryness under reduced pressure, slurried in diethyl ether and freeze-dried to give a white solid that was purified by flash chromatography (Grace 4 g cartridge, 0-25% 2M ammonia in methanol/DCM) and freeze-dried to give the title compound (5 mg, 21%) as a white solid. LCMS (Method B): R$_T$=0.84 min, m/z=619 [M+H]$^+$. $^1$H NMR (400 MHz, DMSO-d$_6$): δ 7.98 (d, 1H), 7.71 (d, 2H), 7.63 (d, 2H), 7.38-7.44 (m, 2H), 7.27-7.38 (m, 3H), 6.06 (td, 1H), 4.90 (s, 1H), 4.03-4.26 (m, 5H), 3.85-4.02 (m, 3H), 3.71-3.82 (m, 1H), 3.11-3.32 (m, 2H), 2.77-3.02 (m, 2H), 2.25 (br s, 2H), 1.12-1.67 (m, 4H).

Example 123: (R)-3-(4-(Aminomethyl)-3-(trifluoromethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

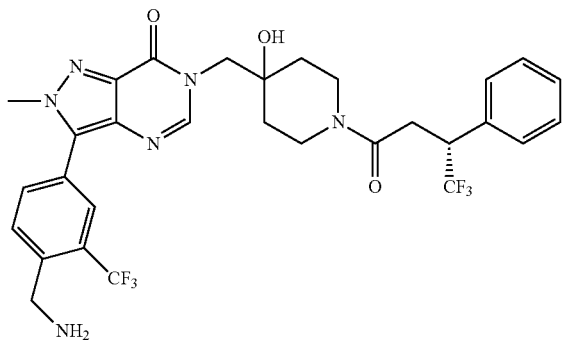 [SMILES: Cn1nc2c(=O)n(CC3(O)CCN(C(=O)C[C@H](c4ccccc4)C(F)(F)F)CC3)cnc2c1-c1ccc(CN)c(C(F)(F)F)c1]

Step 1: tert-Butyl 4-bromo-2-(trifluoromethyl)benzylcarbamate

In a 50 mL round-bottomed flask was added (4-bromo-2-(trifluoromethyl)phenyl)methanamine (872 mg, 3.43 mmol) (commercially available) in THF (10 mL) to give a colourless solution. This was cooled to 0° C. before the dropwise addition of a solution of sodium hydroxide (549 mg, 13.7 mmol) in water (5 mL) followed by a solution of di-tert-butyl dicarbonate (1.59 mL, 6.86 mmol) in THF (5 mL). The reaction mixture was stirred at 0° C. for 60 min. The reaction mixture was allowed to warm to RT and was extracted using ethyl acetate (3×10 mL). The combined organic phase was dried ($Na_2SO_4$), filtered, concentrated to dryness under reduced pressure, and purified by flash chromatography (Grace 40 g cartridge, 0-30%, EtOAc in cyclohexane) to give the title compound (1.02 g, 84%) as a colourless oil. LCMS (Method A): $R_T$=1.86 min, m/z=298 [M-butene+H]$^+$.

Step 2: tert-Butyl 4-(4,4,5,5-tetramethyl-1,3,2-dioxaborolan-2-yl)-2-(trifluoromethyl)benzylcarbamate In a 40 mL reaction tube was added tert-butyl 4-bromo-2-(trifluoromethyl)benzylcarbamate (1.00 g, 2.82 mmol), bis(pinacolato)diboron (1.08 g, 4.24 mmol) and potassium acetate (0.831 g, 8.47 mmol) in anhydrous 1,4-dioxane (11.3 mL). The resultant colourless solution was stirred and degassed (bubbling nitrogen) for 10 min. $PdCl_2$(dppf).DCM (0.115 g, 0.141 mmol) was added and the temperature was increased to 95° C. under nitrogen. After 16 h, the reaction mixture was allowed to cool to RT, diluted with water (20 mL) and extracted using EtOAc (3×10 mL). The combined organic phases were dried ($Na_2SO_4$), filtered and concentrated to dryness under reduced pressure. The remaining residue was purified by flash chromatography (Grace 80 g cartridge, 0-30%, EtOAc in cyclohexane) to give the title compound (884 mg, 78%) as an off-white solid. LCMS (Method A): $R_T$=2.04 min, m/z=346 [M-butene+H]$^+$. $^1$H NMR (300 MHz, CDCl$_3$): δ 8.05 (s, 1H), 7.94 (d, 1H), 7.56 (d, 1H), 4.91 (t, 1H), 4.51 (d, 2H), 4.44 (s, 9H), 1.34 (s, 12H).

Step 3: (R)-tert-Butyl 4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)-2-(trifluoromethyl)benzylcarbamate In a 10 mL microwave tube was added Intermediate E (30 mg, 0.055 mmol), tert-butyl 4-(4,4,5,5-tetramethyl-1,3,2-dioxaborolan-2-yl)-2-(trifluoromethyl)benzylcarbamate (33.3 mg, 0.083 mmol) and potassium phosphate, tribasic (28.9 mg, 0.166 mmol) in a mixture of 1,4-dioxane (1.2 mL) and water (0.3 mL). The resultant yellow solution was stirred and degassed (bubbling nitrogen) for 10 min. $PdCl_2$(dppf).DCM (2.3 mg, 2.77 μmol) and the reaction mixture was heated to 150° C. under microwave irradiation for 15 min. The reaction mixture was diluted with water (10 mL) and extracted using ethyl acetate (3×10 mL). The combined organic phase was washed with brine (10 mL), dried ($Na_2SO_4$), filtered, and concentrated to dryness under reduced pressure. The remaining residue was purified by flash chromatography (KP-NH 28 g cartridge, 10-100%, EtOAc in cyclohexane; then 0-20%, MeOH in EtOAc) and further flash chromatography (Grace 12 g cartridge, 0-10% 2M ammonia in methanol/DCM) to give the title compound (17 mg, 42%) as a pale brown solid. LCMS (Method A): $R_T$=1.63 min, m/z=737 [M+H]$^+$.

Step 4: (R)-3-(4-(Aminomethyl)-3-(trifluoromethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one In a 25 mL round-bottomed flask was added (R)-tert-butyl 4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)-2-(trifluoromethyl)benzylcarbamate (17 mg, 0.023 mmol) in DCM (1 mL) to give a colourless solution. To this was added trifluoroacetic acid (1.0 mL, 13.0 mmol) and the resulting mixture stirred at RT for 30 min. The reaction mixture was loaded onto a pre-equilibrated 2 g SCX-2 cartridge. After 10 min, the cartridge was washed using 4:1 DCM/methanol, before eluting with 4:1 DCM/2M ammonia in methanol. The resulting solution was concentrated to dryness under reduced pressure, slurried in diethyl ether and freeze-dried to give the title compound (10 mg, 68%) as a white solid. LCMS (Method A): $R_T$=0.91 min, m/z=637 [M+H]$^+$. $^1$H NMR (400 MHz, DMSO-d$_6$): δ 7.96-8.08 (m, 4H), 7.27-7.45 (m, 5H), 4.91 (s, 1H), 4.03-4.18 (m, 4H), 3.85-4.03 (m, 5H), 3.71-3.83 (m, 1H), 3.11-3.31 (m, 2H), 2.77-3.02 (m, 2H), 1.13-1.68 (m, 4H).

Example 124: (R)-3-(4-(1-Aminocyclopropyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

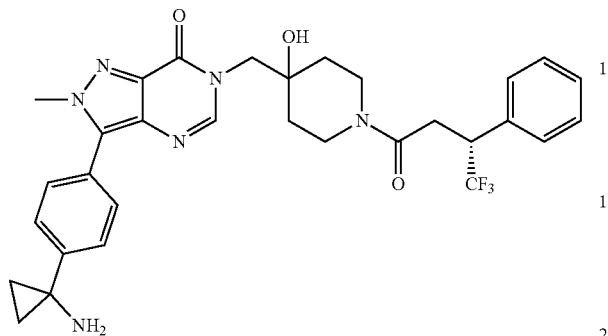

Step 1: (R)-tert-Butyl (1-(4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)cyclopropyl)carbamate In a 10 mL microwave tube was added Intermediate E (30 mg, 0.055 mmol), tert-butyl (1-(4-(4,4,5,5-tetramethyl-1,3,2-dioxaborolan-2-yl)phenyl)cyclopropyl)carbamate (29.8 mg, 0.083 mmol) (commercially available) and potassium phosphate, tribasic (28.9 mg, 0.166 mmol) in a mixture of 1,4-dioxane (1.2 mL) and water (0.3 mL). The resultant yellow solution was stirred and degassed (bubbling nitrogen) for 10 min. PdCl$_2$(dppf).DCM (2.3 mg, 2.77 µmol) was added and the reaction mixture was heated to 150° C. under microwave irradiation for 15 min. The reaction mixture was diluted with water (10 mL) and extracted using ethyl acetate (3×10 mL). The combined organic phase was washed with brine (10 mL), dried (Na$_2$SO$_4$), filtered, and concentrated to dryness under reduced pressure. The residue was purified by flash chromatography (KP-NH 28 g cartridge, 10-100%, EtOAc in cyclohexane; then 0-20% methanol in EtOAc) and further flash chromatography (Grace 12 g cartridge, 0-10%, 2M ammonia in methanol/DCM) to give the title compound (16 mg, 42%) as a pale brown solid. LCMS (Method A): R$_T$=1.54 min, m/z=695 [M+H]$^+$.

Step 2: (R)-3-(4-(1-Aminocyclopropyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one In a 25 mL round-bottomed flask was added (R)-tert-butyl (1-(4-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)phenyl)cyclopropyl)carbamate (16 mg, 0.023 mmol) in DCM (1 mL) to give a colourless solution. To this was added trifluoroacetic acid (1 mL, 13.0 mmol) and the resulting mixture stirred at RT for 30 min. The reaction mixture was loaded onto a pre-equilibrated 2 g SCX-2 cartridge. After 10 min, the cartridge was washed using 4:1 DCM/methanol before the product was eluted with 4:1 DCM/2M ammonia in methanol. The resulting solution was concentrated to dryness under reduced pressure, slurried in diethyl ether and freeze-dried to give the title compound (8 mg, 58%) as a white solid. LCMS (Method A): R$_T$=0.87 min, m/z=595 [M+H]$^+$. $^1$H NMR (400 MHz, DMSO-d$_6$): δ 7.96 (d, 1H), 7.61 (d, 2H), 7.49 (d, 2H), 7.38-7.44 (m, 2H), 7.27-7.38 (m, 3H), 4.90 (s, 1H), 4.03-4.19 (m, 4H), 3.82-4.03 (m, 3H), 3.69-3.82 (m, 1H), 3.10-3.32 (m, 2H), 2.76-3.03 (m, 2H), 2.69 (br s, 2H), 1.12-1.70 (m, 4H), 0.95-1.12 (m, 4H).

Example 125: (S)-3-(4-(Aminomethyl)phenyl)-6-((4-hydroxy-1-(4,4,4-trifluoro-3-(5-methylthiophen-2-yl)butanoyl)piperidin-4-yl)methyl)-2-methyl-2H-pyrazolo[4,3-d]pyrimidin-7(6H)-one

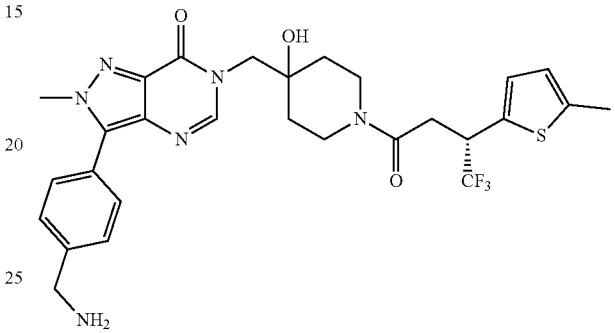

Step 1: (Z)-Ethyl 4,4,4-trifluoro-3-(5-methylthiophen-2-yl)but-2-enoate

To a suspension of a 60% dispersion of NaH in mineral oil (205 mg, 5.13 mmol) in THF (7 mL) at 0° C. was added triethyl phosphonoacetate (0.685 mL, 3.42 mmol). The mixture was stirred for 30 min to give a yellow solution to which was added 2,2,2-trifluoro-1-(5-methylthiophen-2-yl)ethanone (664 mg, 3.42 mmol). The mixture was stirred for a further 16 h at RT before the reaction was quenched by the addition of water (30 mL). The mixture was extracted with DCM (3×30 mL) using a Biotage phase separator, the combined organic phases were concentrated and the residue purified by flash chromatography (40 g Grace column, 0-50% EtOAc in cyclohexane) to give the title compound (537 mg, 59%) (E/Z=1:8) as a pale yellow oil. LCMS (Method A): R$_T$=1.82 min, m/z=265 [M+H]$^+$.

Step 2: Ethyl 4,4,4-trifluoro-3-(5-methylthiophen-2-yl)butanoate

A solution of (Z)-ethyl 4,4,4-trifluoro-3-(5-methylthiophen-2-yl)but-2-enoate (524 mg, 1.98 mmol) in MeOH (20 mL) was reduced using an H-Cube® (10% Pd/C CatCart® RT, 1 mLmin$^{-1}$, 60° C.; 60 bar H$_2$ (run repeated to get full conversion)) and the resulting solution was concentrated give the title compound (450 mg, 85%) as a yellow oil. LCMS (Method A): R$_T$=1.76 min, m/z=266 [M−H]$^−$.

Step 3: 4,4,4-Trifluoro-3-(5-methylthiophen-2-yl)butanoic Acid

To a solution of ethyl 4,4,4-trifluoro-3-(5-methylthiophen-2-yl)butanoate (450 mg, 1.69 mmol) in 1,4-dioxane (3.4 mL) was added 1 M NaOH$_{(aq)}$ (3.4 mL, 3.4 mmol) and after stirring at RT for 2 h the pH was adjusted to ~pH 2 by the addition of 3 M HCl$_{(aq)}$. The mixture was diluted with water (10 mL) and extracted with DCM (3×15 mL) using a Biotage phase separator. The combined organic phases were concentrated give the title compound (391 mg, 97%) as a pale yellow solid. LCMS (Method A): $R_T$=1.34 min, m/z=237 [M–H]⁻.

Step 4: (R)-4-Benzyl-3-((S)-4,4,4-trifluoro-3-(5-methylthiophen-2-yl) butanoyl) oxazolidin-2-one PivCl (0.491 mL, 3.99 mmol) and then NEt₃ (0.578 mL, 4.15 mmol) were added to a suspension of 4,4,4-trifluoro-3-(5-methylthiophen-2-yl)butanoic acid (380 mg, 1.60 mmol), (R)-4-benzyloxazolidin-2-one (311 mg, 1.76 mmol) and LiCl (135 mg, 3.19 mmol) in THF (4 mL) at −20° C. After 30 min the reaction was allowed to warm to RT before being quenched by the addition of saturated NH₄Cl$_{(aq)}$ (30 mL). The mixture was extracted with DCM (3×20 mL) using a Biotage phase separator, the combined organic phases were concentrated and the residue purified by flash chromatography (80 g GraceResolv Silica, 0-40% EtOAc in cyclohexane) to give the title compound (276 mg, 43%) as a pale yellow solid and (R)-4-benzyl-3-((R)-4,4,4-trifluoro-3-(5-methylthiophen-2-yl)butanoyl)oxazolidin-2-one (303 mg, 47%) as a yellow oil. (R)-4-benzyl-3-((S)-4,4,4-trifluoro-3-(5-methylthiophen-2-yl)butanoyl)oxazolidin-2-one: LCMS (Method A): $R_T$=1.86 min, m/z=398 [M+H]⁺. (R)-4-benzyl-3-((R)-4,4,4-trifluoro-3-(5-methylthiophen-2-yl)butanoyl)oxazolidin-2-one: LCMS (Method A): $R_T$=1.82 min, m/z=398 [M+H]⁺.

Step 5: (S)-4,4,4-Trifluoro-3-(5-methylthiophen-2-yl)butanoic Acid

LiOH (0.033 g, 1.389 mmol) was added to a solution of (R)-4-benzyl-3-((S)-4,4,4-trifluoro-3-(5-methylthiophen-2-yl)butanoyl)oxazolidin-2-one (276 mg, 0.694 mmol) and hydrogen peroxide (30% wt aqueous solution) (0.284 mL, 2.78 mmol) in THF (3.5 mL) and water (3.5 mL) at 0° C. After 10 min saturated sodium thiosulfate$_{(aq)}$ (0.5 mL) was added and the mixture was allowed to warm to RT. The mixture was diluted with water (30 mL) and extracted with DCM (3×20 mL). The aqueous phase was then acidified by the addition of 3 M HCl$_{(aq)}$ to ~pH 2 and the mixture was extracted with DCM (3×20 mL). The combined organic phases from the acidic extractions were passed through a Biotage phase separator, concentrated and the residue dried in vacuo to give the title compound (161 mg, 97%) as a colourless solid. LCMS (Method A): $R_T$=1.37 min, m/z=237 [M–H]⁻.

Step 6: (S)-3-(4-(Aminomethyl)phenyl)-6-((4-hydroxy-1-(4,4,4-trifluoro-3-(5-methylthiophen-2-yl)butanoyl)piperidin-4-yl)methyl)-2-methyl-2H-pyrazolo[4,3-d]pyrimidin-7(6H)-one General procedure 4 using tert-butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (17 mg, 0.036 mmol), (S)-4,4,4-trifluoro-3-(5-methylthiophen-2-yl)butanoic acid (13 mg, 0.054 mmol), HATU (21 mg, 0.054 mmol), DIPEA (0.025 mL, 0.145 mmol) and DCM (0.7 mL) gave (S)-tert-butyl 4-(6-((4-hydroxy-1-(4,4,4-trifluoro-3-(5-methylthiophen-2-yl)butanoyl) piperidin-4-yl)methyl)-2-methyl-7-oxo-6,7-dihydro-2H-pyrazolo[4,3-d]pyrimidin-3-yl)benzylcarbamate as a colourless foam. This material was then stirred in DCM (0.7 mL) and TFA (0.7 mL) for 10 min before the reaction was concentrated. The residue was dissolved in Et₃N (1 mL) and DCM (1 mL) and purified by flash chromatography (11 g Biotage KP-NH, 0-100% DCM in cyclohexane the 0-30% MeOH in DCM) to give the title compound (14 mg, 67%) as a colourless solid after lyophilisation. LCMS (Method A): $R_T$=0.89 min, m/z=589 [M+H]⁺. ¹H NMR (300 MHz, DMSO-d₆): δ 8.01-7.94 (m, 1H), 7.68-7.61 (m, 2H), 7.57-7.41 (m, 2H), 6.96-6.88 (m, 1H), 6.71-6.64 (m, 1H), 4.92 (s, 1H), 4.37-4.24 (m, 1H), 4.10 (s, 3H), 4.06-3.90 (m, 3H), 3.80 (s, 2H), 3.78-3.67 (m, 1H), 3.30-3.17 (m, 1H), 3.16-2.77 (m, 3H), 2.44-2.34 (m, 3H), 2.11 (s, 2H), 1.72-1.27 (m, 4H).

Example 126: (R)-1-((4-Hydroxy-1-(3-phenylbutanoyl)piperidin-4-yl)methyl)indolin-2-one

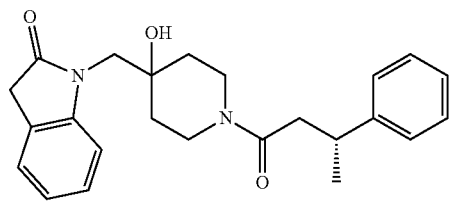 [SMILES: C[C@H](CC(=O)N1CCC(O)(CN2C(=O)Cc3ccccc32)CC1)c1ccccc1]

In a small capped vial was added indolin-2-one (25.7 mg, 0.193 mmol) and Epoxide 2 (50 mg, 0.193 mmol) in DMF (1.0 mL) to give a colourless solution. NaH, 60% in mineral oil (8.5 mg, 0.212 mmol) was added and the reaction mixture was stirred at 80° C. After 4 h, the reaction mixture was partitioned between EtOAc and water, the resultant biphasic mixture was separated, and the aqueous phase was extracted (EtOAc×3). The combined organic phase was washed using water, dried (MgSO₄), and the solvents were removed in vacuo. The remaining residue was purified by flash chromatography (Grace 4 g column, 0-100% EtOAc/cyclohexane; then 0-10% MeOH/EtOAc) to give the title compound (28.4 mg, 38%) as a pale brown solid. LCMS (Method B): $R_T$=1.11 min, m/z=393 [M+H]⁺. 1H NMR (400 MHz, methanol-d₄): δ 7.33-7.01 (m, 9H), 4.31-4.16 (m, 1H), 3.75-3.50 (m, 5H), 3.28-3.10 (m, 2H, overlapping solvent), 2.97-2.68 (m, 2H), 2.62-2.43 (m, 1H), 1.67-0.85 (m, 7H).

Example 127: 3-(4-(Aminomethyl)phenyl)-6-((1-(3,3-dicyclopropylpropanoyl)-4-hydroxypiperidin-4-yl)methyl)-2-methyl-2H-pyrazolo[4,3-d]pyrimidin-7(6H)-one

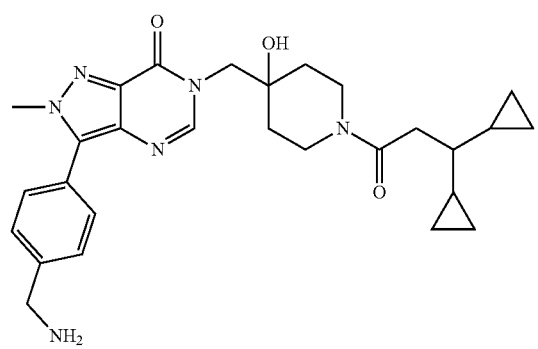 [SMILES: Cn1nc2c(=O)n(CC3(O)CCN(C(=O)CC(C4CC4)C4CC4)CC3)cnc2c1-c1ccc(CN)cc1]

Step 1: tert-Butyl 4-(6-((1-(3,3-dicyclopropylpropanoyl)-4-hydroxypiperidin-4-yl)methyl)-2-methyl-7-oxo-6,7-dihydro-2H-pyrazolo[4,3-d]pyrimidin-3-yl)benzylcarbamate In a 25 mL round-bottomed flask was added tert-butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (30 mg, 0.064 mmol), 3,3-dicyclopropylpropanoic acid (9.9 mg, 0.064 mmol) and HATU (29.2 mg, 0.077 mmol) in anhydrous DCM (3.2 mL). DIPEA (22.37 µL, 0.128 mmol) was added to the stirred solution at RT. After 2 h, the reaction mixture was diluted with saturated sodium bicarbonate (aq) solution (10 mL) and extracted into DCM (3×5 mL). The combined organic phase was dried ($Na_2SO_4$), filtered, the solvents were removed in vacuo, and the remaining residue was purified by flash chromatography (KP-NH 28 g cartridge, 5-100%, EtOAc/cyclohexane; then 0-20% MeOH/EtOAc) to give the title compound (34 mg, 88%) as an off-white solid. LCMS (Method A): $R_T$=1.34 min, m/z=605 [M+H]$^+$.

Step 2: 3-(4-(Aminomethyl)phenyl)-6-((1-(3,3-dicyclopropylpropanoyl)-4-hydroxypiperidin-4-yl)methyl)-2-methyl-2H-pyrazolo[4,3-d]pyrimidin-7(6H)-one In a 25 mL round-bottomed flask was added tert-butyl 4-(6-((1-(3,3-dicyclopropylpropanoyl)-4-hydroxypiperidin-4-yl)methyl)-2-methyl-7-oxo-6,7-dihydro-2H-pyrazolo[4,3-d]pyrimidin-3-yl)benzylcarbamate (17 mg, 0.028 mmol) in DCM (3 mL). The resultant colourless solution was stirred and cooled to 0° C., followed by the addition of trifluoroacetic acid (1 mL, 13.0 mmol). After 10 min, the temperature was allowed to increase to RT. After a further 30 min, the reaction mixture was loaded onto a pre-equilibrated 5 g SCX-2 cartridge. After 10 min, the cartridge was washed with 4:1 DCM/methanol before elution using 4:1 DCM/2M ammonia in methanol. The resulting solution was concentrated to dryness under reduced pressure and was purified by flash chromatography (KP-NH 11 g cartridge, 0-20% MeOH/DCM) and freeze-dried to give the title compound (9 mg, 63%) as a white solid. LCMS (Method A): $R_T$=0.72 min, m/z=505 [M+H]$^+$. $^1$H NMR (400 MHz, DMSO-$d_6$) δ 8.00 (s, 1H), 7.65 (dt, 2H), 7.54 (dt, 2H), 4.91 (s, 1H), 3.94-4.12 (m, 6H), 3.81 (s, 2H), 3.74 (dt, 1H), 2.94 (ddd, 1H), 2.49-2.54 (m, 1H), 2.38-2.43 (m, 2H), 2.24 (br s, 2H), 1.54 (ddd, 1H), 1.35-1.49 (m, 3H), 0.57-0.75 (m, 3H), 0.32-0.42 (m, 2H), 0.23-0.32 (m, 2H), 0.13-0.22 (m, 2H), 0.00-0.10 (m, 2H).

Example 128: (R)-1-((4-Hydroxy-1-(4,4,4-trifluoro-3-phenylbutanoyl)piperidin-4-yl)methyl)-9-phenyl-1H-purin-6(9H)-one

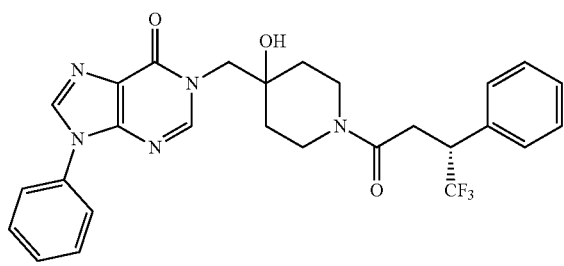 [SMILES: O=C(C[C@H](c1ccccc1)C(F)(F)F)N1CCC(O)(Cn2cnc3c(ncn3-c3ccccc3)c2=O)CC1]

Step 1: tert-Butyl 4-hydroxy-4-((6-oxo-9-phenyl-6,9-dihydro-1H-purin-1-yl)methyl)piperidine-1-carboxylate General procedure 1 using Epoxide 1 (121 mg, 0.565 mmol), 9-phenyl-1H-purin-6(9H)-one (60 mg, 0.283 mmol), $Cs_2CO_3$ (101 mg, 0.311 mmol) and DMF (0.9 mL) gave the title compound (107 mg, 89%) as a beige foam. LCMS (Method A): $R_T$=1.16 min, m/z=426 [M+H]$^+$.

Step 2: 1-((4-Hydroxypiperidin-4-yl)methyl)-9-phenyl-1H-purin-6(9H)-one

General procedure 2 using tert-butyl 4-hydroxy-4-((6-oxo-9-phenyl-6,9-dihydro-1H-purin-1-yl)methyl)piperidine-1-carboxylate (107 mg, 0.251 mmol), DCM (1 mL) and TFA (1 mL) gave the title compound (80 mg, 98%) as a colourless foam. LCMS (Method A): $R_T$=0.40 min, m/z=326 [M+H]$^+$.

Step 3: (R)-1-((4-Hydroxy-1-(4,4,4-trifluoro-3-phenylbutanoyl)piperidin-4-yl)methyl)-9-phenyl-1H-purin-6(9H)-one General procedure 4 using 1-((4-hydroxypiperidin-4-yl)methyl)-9-phenyl-1H-purin-6(9H)-one (35 mg, 0.108 mmol), (R)-4,4,4-trifluoro-3-phenylbutanoic acid (35 mg, 0.161 mmol), HATU (61 mg, 0.161 mmol), DIPEA (75 µL, 0.430 mmol) and DCM (2 mL) gave the title compound (38 mg, 67%) as a colourless solid after lyophilisation. LCMS (Method A): $R_T$=1.27 min, m/z=526 [M+H]$^+$. $^1$H NMR (300 MHz, DMSO-$d_6$): δ 8.51 (s, 1H), 8.26 (d, J=6.0 Hz, 1H), 7.83-7.75 (m, 2H), 7.66-7.55 (m, 2H), 7.54-7.46 (m, 1H), 7.45-7.26 (m, 5H), 4.92 (s, 1H), 4.19-3.88 (m, 4H), 3.85-3.71 (m, 1H), 3.30-3.11 (m, 2H), 3.04-2.75 (m, 2H), 1.68-1.27 (m, 4H).

Example 129: (R)-1-((1-(4,4-Difluoro-3-phenylbutanoyl)-4-hydroxypiperidin-4-yl)methyl)-9-phenyl-1H-purin-6(9H)-one

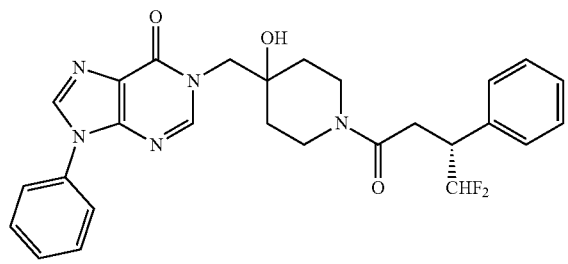 [SMILES: O=C(C[C@H](c1ccccc1)C(F)F)N1CCC(O)(Cn2cnc3c(ncn3-c3ccccc3)c2=O)CC1]

General procedure 4 using 1-((4-hydroxypiperidin-4-yl)methyl)-9-phenyl-1H-purin-6(9H)-one (32 mg, 0.098 mmol), (R)-4,4-difluoro-3-phenylbutanoic acid (30 mg, 0.148 mmol), HATU (56 mg, 0.148 mmol), DIPEA (69 µL, 0.393 mmol) and DCM (2 mL) gave the title compound (39 mg, 78%) as a colourless solid after lyophilisation. LCMS (Method A): $R_T$=1.17 min, m/z=508 [M+H]$^+$. $^1$H NMR (300 MHz, DMSO-$d_6$): δ 8.51 (s, 1H), 8.26 (d, J=6.2 Hz, 1H), 7.83-7.72 (m, 2H), 7.68-7.56 (m, 2H), 7.56-7.45 (m, 1H), 7.38-7.18 (m, 5H), 6.24 (td, J=56.5, 3.1 Hz, 1H), 4.92 (s, 1H), 4.15-3.90 (m, 3H), 3.80-3.51 (m, 2H), 3.30-3.14 (m, 1H), 3.01-2.73 (m, 3H), 1.63-1.20 (m, 4H).

Example 130: (R)-6-((4-Hydroxy-1-(4,4,4-trifluoro-3-phenylbutanoyl)piperidin-4-yl)methyl)-2-methyl-3-(1-methyl-1,2,3,6-tetrahydropyridin-4-yl)-2H-pyrazolo[4,3-d]pyrimidin-7(6H)-one

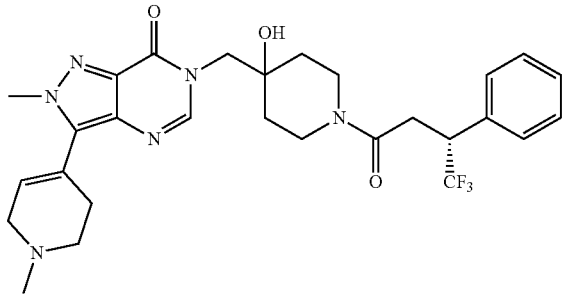 [SMILES: CN1CC=C(c2c3ncn(CC4(O)CCN(C(=O)C[C@H](c5ccccc5)C(F)(F)F)CC4)c(=O)c3nn2C)CC1]

In a 10 mL microwave tube was added Intermediate E (70 mg, 0.129 mmol), 1-methyl-4-(4,4,5,5-tetramethyl-1,3,2-dioxaborolan-2-yl)-1,2,3,6-tetrahydropyridine (43.2 mg, 0.194 mmol) and potassium phosphate, tribasic (67.4 mg, 0.387 mmol) in a mixture of 1,4-dioxane (2.8 mL) and water (0.7 mL). The resultant yellow solution was stirred and degassed (bubbling nitrogen) for 10 min. PdCl$_2$(dppf).DCM (5.3 mg, 6.45 μmol) was added and the reaction mixture was heated to 150° C. under microwave irradiation for 15 min. The reaction mixture was diluted with water (10 mL) and extracted using EtOAc (3×10 mL). The combined organic phase was washed with brine (10 mL), dried (Na$_2$SO$_4$), filtered, and concentrated to dryness under reduced pressure. The resultant yellow oil was purified by flash chromatography (KP-NH 28 g cartridge, 10-100% EtOAc/cyclohexane; then 0-20% MeOH/EtOAc) and further flash chromatography (Grace 24 g cartridge, 0-30% 2M ammonia in methanol/DCM) to give a colourless solid that was slurried in diethyl ether (3 mL) and freeze-dried to yield the title compound (18 mg, 25%) as a white solid. LCMS (Method A): R$_T$=0.78 min, m/z=559 [M+H]$^+$. $^1$H NMR (400 MHz, DMSO-d$_6$): δ 7.93 (d, 1H), 7.38-7.43 (m, 2H), 7.27-7.38 (m, 3H), 6.12 (t, 1H), 4.88 (s, 1H), 4.03-4.17 (m, 1H), 4.04 (s, 3H), 3.82-4.00 (m, 3H), 3.69-3.81 (m, 1H), 3.08-3.30 (m, 4H), 2.75-3.04 (m, 2H), 2.59-2.72 (m, 4H), 2.30-2.40 (m, 3H), 1.11-1.65 (m, 4H).

Example 131: 6-((1-Acetyl-4-hydroxypiperidin-4-yl)methyl)-2-methyl-3-phenyl-2H-pyrazolo[4,3-d]pyrimidin-7(6H)-one

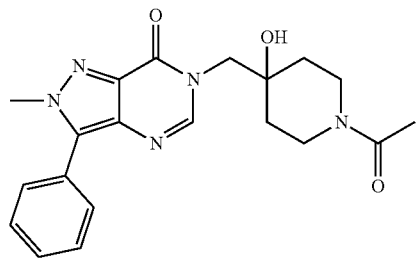 [SMILES: CC(=O)N1CCC(O)(Cn2cnc3c(-c4ccccc4)n(C)nc3c2=O)CC1]

Step 1: 3-Bromo-6-((4-hydroxypiperidin-4-yl)methy)-2-methyl-2H-pyrazolo[4,3-d]pyrimidin-7(6H)-one tert-Butyl 4-((3-bromo-2-methyl-7-oxo-2H-pyrazolo[4,3-d]pyrimidin-6(7H)-yl)methyl)-4-hydroxypiperidine-1-carboxylate (0.8 g, 1.81 mmol) was stirred in dichloromethane (8 mL) and trifluoroacetic acid (8 mL) for 20 min before the reaction was concentrated in vacuo. The residue was purified using 4×10 g SCX-2 cartridges in parallel (10% methanol in dichloromethane; then 10% 7M ammonia in methanol in dichloromethane) to afford the title compound (0.333 g, 54%) as a colourless solid. $^1$H NMR (300 MHz, CDCl$_3$): δ 7.96 (s, 1H), 4.14 (s, 3H), 4.09 (s, 2H), 2.95-2.83 (m, 4H), 1.95-1.46 (m, 4H).

Step 2: 6-((1-Acetyl-4-hydroxypiperidin-4-yl)methyl)-3-bromo-2-methyl-2H-pyrazolo[4,3-d]pyrimidin-7(6H)-one In a small capped vial was added 3-bromo-6-((4-hydroxypiperidin-4-yl)methyl)-2-methyl-2H-pyrazolo[4,3-d]pyrimidin-7(6H)-one (50 mg, 0.146 mmol), acetic anhydride (0.028 mL, 0.292 mmol) and triethylamine (0.061 mL, 0.438 mmol) in dichloromethane (1 mL). After 2 h, the mixture was partitioned between ethyl acetate and saturated sodium bicarbonate (aq) solution. Solid precipitate was collected by filtration. The phases were separated, the organic phase was dried (phase separator) and the solvents were removed in vacuo. The solid was combined with the precipitate to afford the title compound (41.0 mg, 73%) which was used without further purification. LCMS (Method A): R$_T$=0.27 min, m/z=384 [M+H]$^+$.

Step 3: 6-((1-Acetyl-4-hydroxypiperidin-4-yl)methyl)-2-methyl-3-phenyl-2H-pyrazolo[4,3-d]pyrimidin-7(6H)-one A stirring suspension of 6-((1-acetyl-4-hydroxypiperidin-4-yl)methyl)-3-bromo-2-methyl-2H-pyrazolo[4,3-d]pyrimidin-7(6H)-one (41 mg, 0.107 mmol), phenylboronic acid (39 mg, 0.320 mmol) and potassium phosphate, tribasic (136 mg, 0.640 mmol) in 1,4-dioxane (1.5 mL) and water (0.3 mL) was de-gassed with nitrogen for 5 min. PdCl$_2$(dppf).DCM (2.2 mg, 2.67 μmol) was then added and the reaction mixture de-gassed with nitrogen for 5 mins before heating to 90° C. and stirring for 16 h. After cooling, the solvents were removed in vacuo and the remaining mixture partitioned between saturated ammonium chloride (aq) solution (5 mL) and dichloromethane (10 mL). The layers were separated and the aqueous phase extracted with dichloromethane (3×5 mL). The combined organic phases were dried (phase separator), filtered and concentrated in vacuo. The resulting residue was purified by flash chromatography (gradient 0-100% EtOAc in cyclohexane; then 0-50% methanol in EtOAc). The residue was suspended in methanol (1 mL) and water (10 mL) and freeze-dried to afford the title compound (32.7 mg, 80%). LCMS (Method A): R$_T$=0.79 min, m/z=382 [M+H]$^+$. $^1$H NMR (400 MHz, DMSO-d$_6$): δ 8.01 (s, 1H), 7.72 (d, 2H), 7.59 (t, 2H), 7.48-7.55 (m, 1H), 4.90 (s, 1H), 4.11 (s, 3H), 3.94-4.07 (m, 3H), 3.58 (d, 1H), 3.28 (t, 1H), 2.92 (td, 1H), 1.98 (s, 3H), 1.57 (td, 1H), 1.34-1.50 (m, 3H).

Example 132: 3-((1-Acetyl-4-hydroxypiperidin-4-yl)methyl)-6-((2-(pyrrolidin-1-yl)ethyl)amino)pyrimidin-4(3H)-one

Example 133: 3-((1-(3,3-Dicyclopropylpropanoyl)-4-hydroxypiperidin-4-yl)methyl)-6-((2-(pyrrolidin-1-yl)ethyl)amino)pyrimidin-4(3H)-one

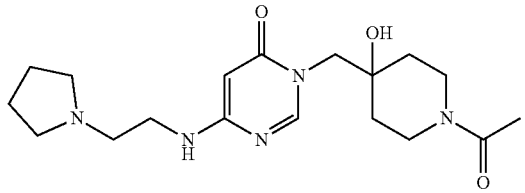 [SMILES: CC(=O)N1CCC(O)(Cn2cnc(NCCN3CCCC3)cc2=O)CC1]

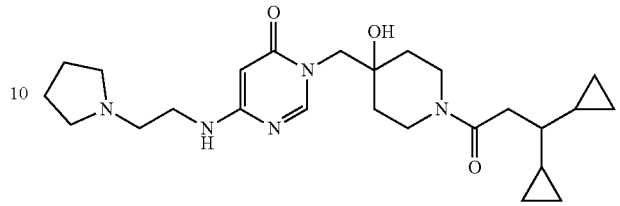

Step 1: 6-Chloro-3-((4-hydroxypiperidin-4-yl)methyl)pyrimidin-4(3H)-one, HCl In a 25 mL round-bottomed flask was tert-butyl 4-((4-chloro-6-oxopyrimidin-1 (6H)-yl)methyl)-4-hydroxypiperidine-1-carboxylate (257 mg, 0.748 mmol) and 4M HCl in 1,4-dioxane (2 mL, 8.00 mmol) in DCM (2 mL). The resultant pale yellow solution was stirred at RT. After 2 h, the solvents were removed in vacuo and the residue was slurried using Et$_2$O (×2). The residual solvents were removed in vacuo to give the title compound (crude, 201 mg) as a white solid that was using in the next step without further purification.

Step 2: 3-((1-Acetyl-4-hydroxypiperidin-4-yl)methyl)-6-chloropyrimidin-4(3H)-one A reaction vial was charged with 6-chloro-3-((4-hydroxypiperidin-4-yl)methyl)pyrimidin-4(3H)-one, HCl (crude, 100 mg, assumed 0.357 mmol), Ac$_2$O (0.067 mL, 0.714 mmol) and Et$_3$N (0.149 mL, 1.07 mmol) in DCM (1 mL). The reaction mixture was stirred at RT. After 2 h, the solvents were removed in vacuo to give the title compound (crude, 100 mg) that was used in next step without purification.

Step 3: 3-((1-Acetyl-4-hydroxypiperidin-4-yl)methyl)-6-((2-(pyrrolidin-1-yl)ethyl)amino)pyrimidin-4(3H)-one A 10 mL vial was charged with 3-((1-acetyl-4-hydroxypiperidin-4-yl)methyl)-6-chloropyrimidin-4(3H)-one (crude, 100 mg, assumed 0.350 mmol), 2-(pyrrolidin-1-yl)ethanamine (0.222 mL, 1.75 mmol) and 1,4-dioxane (2.0 mL). The vessel was sealed and the resultant pale yellow solution was heated to 150° C. using microwave irradiation for 30 min. The solvents were removed in vacuo and the remaining residue was purified by flash chromatography (11 g KP-NH column, 0-100% EtOAc/cyclohexane; then 0-20% MeOH/EtOAc) and freeze-dried to give the title compound (70.4 mg, 55%) as a pale yellow solid that appeared to be hygroscopic (turned into an oil, on standing). LCMS (Method A): R$_T$=0.78 min, m/z=559 [M+H]$^+$. $^1$H NMR (400 MHz, DMSO-d$_6$): δ 8.05 (s, 1H), 6.90 (br s, 1H), 5.11 (br s, 2H), 4.05 (dt, 1H), 3.85 (q, 2H), 3.62 (dt, 1H), 3.33 (ddd, 1H), 2.99 (ddd, 1H), 2.67 (t, 1H), 2.61 (apparent br d, 1H), 2.54-2.41 (m, 6H, overlapping solvent), 2.03 (s, 3H), 1.79-1.28 (m, 8H).

Step 1: 6-Chloro-3-((1-(3,3-dicyclopropylpropanoyl)-4-hydroxypiperidin-4-yl)methyl)pyrimidin-4 (3H)-one In a small capped vial was charged 6-chloro-3-((4-hydroxypiperidin-4-yl)methyl)pyrimidin-4(3H)-one, HCl (50 mg, 0.178 mmol), 3,3-dicyclopropylpropanoic acid (41.3 mg, 0.268 mmol) and DIPEA (0.125 mL, 0.714 mmol) in DCM (1 mL). The reaction mixture was stirred and HATU (102 mg, 0.268 mmol) was added. After 1 h, water was added, the resulting biphasic mixture was separated, the organic phase was dried (phase separator), the solvents were removed in vacuo, and the remaining residue was purified by flash chromatography (KP-NH 11 g column, 0-100% EtOAc/cyclohexane; then 0-10% MeOH/EtOAc) to give the title compound (46 mg, 68%) as a colourless oil. LCMS (Method A): R$_T$=1.12 min, m/z=380 [M+H]$^+$.

Step 2: 3-((1-(3,3-Dicyclopropylpropanoyl)-4-hydroxypiperidin-4-yl)methy)-6-((2-(pyrrolidin-1-yl)ethyl)amino)pyrimidin-4(3H)-one In a microwave reactor tube was charged 6-chloro-3-((1-(3,3-dicyclopropylpropanoyl)-4-hydroxypiperidin-4-yl)methyl)pyrimidin-4(3H)-one (45 mg, 0.118 mmol) and 2-(pyrrolidin-1-yl)ethanamine (0.075 mL, 0.592 mmol) in 1,4-dioxane (2 mL). The resultant pale yellow solution was heated to 150° C. using microwave irradiation for 30 min. The solvents were removed in vacuo and the remaining residue was purified by flash chromatography (Grace 4 g column, 0-100% EtOAc/cyclohexane; then 0-30% MeOH/EtOAc) and further flash chromatography (KP-NH 11 g column, 0-100% EtOAc/cyclohexane, then 0-20% MeOH/EtOAc) and freeze-dried to give the title compound (25.6 mg, 47%) as an off-white solid. LCMS (Method A): R$_T$=0.66 min, m/z=458 [M+H]$^+$. 1H NMR (400 MHz, DMSO-d$_6$): δ 7.99 (s, 1H), 6.82 (br s, 1H), 5.10-4.96 (m, 2H), 4.03 (br dt, 1H), 3.86-3.67 (m, 3H), 3.30-3.06 (m, 3H, overlapping solvent), 2.95 (ddd, 1H), 2.57-2.36 (m, 8H), 1.72-1.62 (m, 4H), 1.51-1.20 (m, 4H), 0.74-0.57 (m, 3H), 0.41-0.01 (m, 8H).

Example 134: (R)-3-(Cyclohex-1-en-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

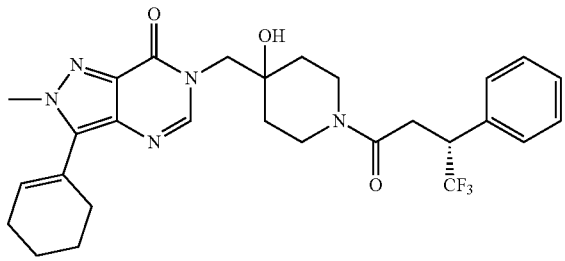 [SMILES: Cn1nc2c(=O)n(CC3(O)CCN(C(=O)C[C@H](c4ccccc4)C(F)(F)F)CC3)cnc2c1C1=CCCCC1]

A suspension of Intermediate E (50 mg, 0.092 mmol), cyclohex-1-en-1-ylboronic acid (11.6 mg, 0.092 mmol) and potassium phosphate, tribasic (78 mg, 0.369 mmol) in 1,4-dioxane (1.5 mL) and water (0.5 mL) in a reaction tube. The reaction mixture was pre-degassed (bubbling nitrogen) for 20 min. Pd(PPh$_3$)$_4$ (10.7 mg, 9.22 μmol) was added and the vessel was sealed. The reaction mixture was heated at 130° C. under microwave irradiation for 30 min. The vessel was cooled to RT and the reaction was quenched by the addition of saturated NH$_4$Cl$_{(aq)}$ solution. The resulting biphasic mixture was extracted using DCM (×3) (Phase Separator). The solvents were removed in vacuo and the remaining residue was purified by flash chromatography using a KP-NH column (0-100%, EtOAc in cyclohexane) to give the title compound (44.5 mg, 88%) as a white solid. LCMS (Method A): R$_T$=1.45 min, m/z=544 [M+H]$^+$. $^1$H NMR (400 MHz, CDCl$_3$): δ 7.67 (d, 1H), 7.42-27 (m, 5H), 6.09-6.02 (m, 1H), 4.30 (t, 1H), 4.20-4.04 (m, 4H), 4.03-3.83 (m, 1H), 3.72-3.57 (m, 1H), 3.44-3.28 (m, 2H), 3.03-2.82 (m, 3H), 2.50-2.39 (m, 2H), 2.36-2.25 (m, 2H), 1.90-1.70 (m, 4H), 1.65-1.43 (m, 2H), 1.33-1.17 (m, 3H), 1.07-0.81 (m, 1H).

Example 135: (R)-3-(3-(Dimethylamino)prop-1-yn-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

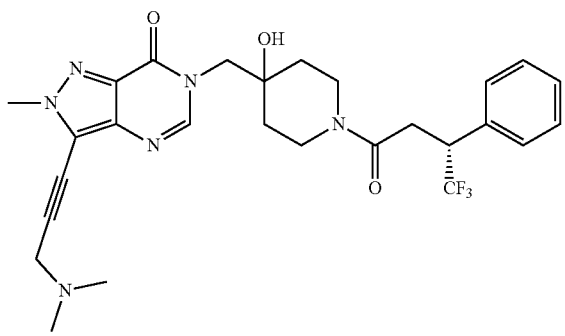 [SMILES: CN(C)CC#Cc1c2ncn(CC3(O)CCN(C(=O)C[C@H](c4ccccc4)C(F)(F)F)CC3)c(=O)c2nn1C]

Step 1: (R)-tert-Butyl (3-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)prop-2-yn-1-yl)carbamate Copper(I) iodide (0.4 mg, 2.31 μmol) and bis(triphenylphosphine)palladium(II) chloride (3.2 mg, 4.61 μmol) were added to a pre-degassed solution of Intermediate E (50.0 mg, 0.092 mmol), tert-butyl prop-2-yn-1-ylcarbamate (28.6 mg, 0.184 mmol) and tetrabutylammonium iodide (68.1 mg, 0.184 mmol) in triethylamine (0.2 mL, 1.44 mmol)/DMF (1.0 mL) in a microwave vial. The reaction vessel was sealed and the reaction mixture was heated using microwave irradiation at 100° C. (80 W ceiling) for 15 min. The reaction mixture was partitioned between diethyl ether and 1:1 water/brine, separated, extracted (diethyl ether×3), dried (Phase Separator), the solvents were removed in vacuo, and the remaining residue was purified by flash chromatography (0-100%, EtOAc in cyclohexane; then 0-10% MeOH in EtOAc) to give the title compound (41.4 mg, 73%) as a pale yellow solid. LCMS (Method A): R$_T$=1.41 min, m/z=617 [M+H]$^+$.

Step 2: (R)-3-(3-Aminoprop-1-yn-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one Trifluoroacetic acid (1.0 mL, 13.0 mmol) was added to a stirred solution of (R)-tert-butyl (3-(6-((4-hydroxy-1-(4,4,4-trifluoro-3-phenylbutanoyl)piperidin-4-yl)methyl)-2-methyl-7-oxo-6,7-dihydro-2H-pyrazolo[4,3-d]pyrimidin-3-yl)prop-2-yn-1-yl)carbamate (41.4 mg, 0.067 mmol) in DCM (2.0 mL) at RT under nitrogen. After 30 min, the reaction mixture was loaded directly onto a pre-equilibrated 5 g SCX-2 cartridge, washed with methanol, and the product was eluted with 2M ammonia in MeOH. The solvents were removed in vacuo and the remaining residue was purified by flash chromatography (0-100%, EtOAc in cyclohexane; then 0-10% MeOH in EtOAc) to give the title compound (13.0 mg, 38%) as an off-white solid. LCMS (Method A): R$_T$=0.86 min, m/z=517 [M+H]$^+$.

Step 3: (R)-3-(3-(Dimethylamino)prop-1-yn-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one Sodium triacetoxyborohydride (26.7 mg, 0.126 mmol) was added to a stirred solution of (R)-3-(3-aminoprop-1-yn-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (13.0 mg, 0.025 mmol) and formaldehyde (37% in water) (6 μL, 0.076 mmol) in methanol (1.0 mL) at RT under nitrogen. After 1 h, the temperature was increased to 50° C. After 18 h, the reaction mixture was cooled to RT and further formaldehyde (37% in water) (5.6 μL, 0.076 mmol) and a catalytic amount of acetic acid (3 drops) were added. After 30 min, sodium cyanoborohydride (7.9 mg, 0.126 mmol) was added. After a further 1 h, the reaction mixture was loaded directly onto a pre-equilibrated 2 g SCX-2 cartridge, washed with methanol, the product was eluted using 2M ammonia in MeOH. The solvents were removed in vacuo and the remaining residue was purified by flash chromatography using a KP-NH column (0-100%, EtOAc in cyclohexane; then 0-10% MeOH in EtOAc) and further flash chromatography using a Grace 12 g column (0-100%, EtOAc in cyclohexane; then 0-25% MeOH in EtOAc) and freeze-dried to give the title compound (5.8 mg, 40%) as an off-white solid. LCMS (Method A): R$_T$=0.88 min, m/z=545 [M+H]$^+$. $^1$H NMR (400 MHz, DMSO-d$_6$): δ 8.01 (d, 1H), 7.43-7.22 (m, 5H), 4.89 (s, 1H), 4.17-4.03 (m, 4H), 4.01-3.82 (m, 3H), 3.80-3.70 (m, 1H), 3.66 (s, 2H), 3.29-3.10 (m, 2H), 3.00-2.71 (m, 2H), 2.28 (s, 6H), 1.63-0.85 (m, 4H).

Example 136: (R)-3-Cyclohexyl-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one

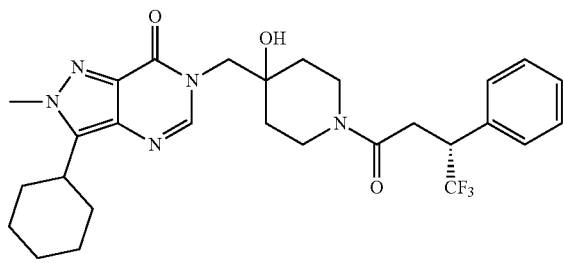 [SMILES: Cn1nc2c(=O)n(CC3(O)CCN(C(=O)C[C@H](c4ccccc4)C(F)(F)F)CC3)cnc2c1C1CCCCC1]

A solution of (R)-3-(cyclohex-1-en-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (39.4 mg, 0.072 mmol) (Example 134) in methanol (10 mL) was passed through an H-Cube® apparatus fitted with a 10% Pd—C cartridge under the following settings: 1.0 mL/min flow, RT, hydrogen (full $H_2$ mode). The solvents were removed in vacuo and the remaining residue was purified by flash chromatography using a Grace 12 g column (0-100%, EtOAc in cyclohexane) to give the title compound (18.2 mg, 46%) as a white solid. LCMS (Method A): $R_T$=1.52 min, m/z=546 [M+H]$^+$. $^1$H NMR (400 MHz, DMSO-$d_6$): δ 7.87 (d, 1H), 7.45-7.25 (m, 5H), 4.87 (s, 1H), 4.16-4.04 (m, 1H), 4.02 (s, 3H), 3.99-3.80 (m, 3H), 3.79-3.70 (m, 1H), 3.28-3.10 (m, 2H), 3.05-2.77 (m, 3H), 2.02-1.68 (m, 6H), 1.62-1.12 (m, 8H).

Example 137: (R)-6-((4-Hydroxy-1-(4,4,4-trifluoro-3-phenylbutanoyl)piperidin-4-yl)methyl)-2-methyl-3-(4-(morpholinomethyl)phenyl)-2H-pyrazolo[4,3-d]pyrimidin-7(6H)-one

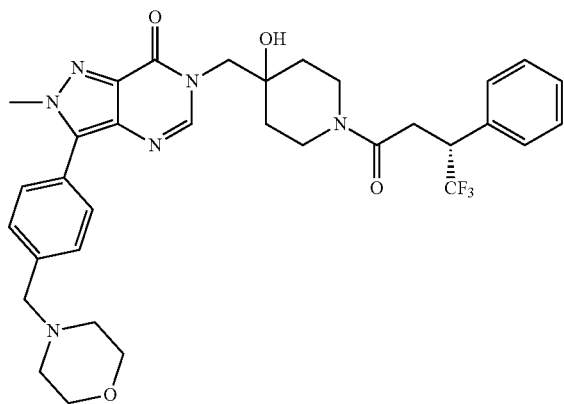 [SMILES: Cn1nc2c(=O)n(CC3(O)CCN(C(=O)C[C@H](c4ccccc4)C(F)(F)F)CC3)cnc2c1-c1ccc(CN2CCOCC2)cc1]

A suspension of Intermediate E (50 mg, 0.092 mmol), (4-(morpholinomethyl)phenyl)boronic acid (40.8 mg, 0.184 mmol) and tripotassium phosphate (78 mg, 0.369 mmol) in 1,4-dioxane (1.5 mL) and water (0.5 mL) in a reaction tube was pre-degassed (bubbling nitrogen) for 20 min. Pd(Ph$_3$P)$_4$ (10.7 mg, 9.22 μmol) was added and the reaction vessel was sealed. The reaction mixture was heated at 130° C. using microwave irradiation for 30 min. The vessel was cooled to RT and quenched by the addition of saturated ammonium chloride (aq) solution and the mixture was extracted using DCM (×3) and dried (phase separator). The solvents were removed in vacuo and the remaining residue was purified by flash chromatography using a KP-NH cartridge (0-100%, EtOAc in cyclohexane; 0-10%, MeOH in EtOAc) to give the title compound (48.0 mg, 82%) as a white fluffy solid. LCMS (Method A): $R_T$=0.90 min, m/z=639 [M+H]$^+$. $^1$H NMR (400 MHz, DMSO-$d_6$): δ 7.97 (d, 1H), 7.67 (d, 2H), 7.51 (d, 2H), 7.44-7.27 (m, 5H), 4.88 (s, 1H), 4.18-4.03 (m, 4H), 4.02-3.84 (m, 3H), 3.82-3.70 (m, 1H), 3.60 (t, 4H), 3.55 (s, 2H), 3.30-3.10 (m, 2H), 3.02-2.78 (m, 2H), 2.40 (t, 4H), 1.66-1.14 (m, 4H).

Example 138: 3-(4-(Aminomethyl)phenyl)-6-((1-(3-cyclobutylpropanoyl)-4-hydroxypiperidin-4-yl)methyl)-2-methyl-2H-pyrazolo[4,3-d]pyrimidin-7(6H)-one

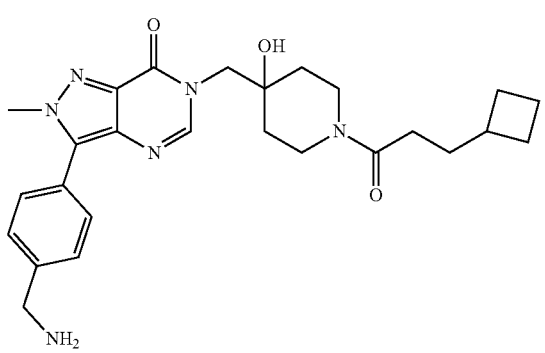 [SMILES: Cn1nc2c(=O)n(CC3(O)CCN(C(=O)CCC4CCC4)CC3)cnc2c1-c1ccc(CN)cc1]

Step 1: tert-Butyl 4-(6-((1-(3-cyclobutylpropanoyl)-4-hydroxypiperidin-4-yl)methyl)-2-methyl-7-oxo-6,7-dihydro-2H-pyrazolo[4,3-d]pyrimidin-3-yl)benzylcarbamate DIPEA (0.023 mL, 0.132 mmol) was added to a stirred solution of tert-butyl 4-(6-((4-hydroxypiperidin-4-yl)methyl)-2-methyl-7-oxo-6,7-dihydro-2H-pyrazolo[4,3-d]pyrimidin-3-yl)benzylcarbamate (31 mg, 0.066 mmol), 3-cyclobutylpropanoic acid (9.33 mg, 0.073 mmol) and HATU (30.2 mg, 0.079 mmol) in anhydrous DCM (5.0 mL) at RT under nitrogen. After 2 h, LCMS showed complete reaction. The reaction mixture was diluted with saturated sodium bicarbonate (aq) solution and extracted into DCM (×3). The combined organic phase was dried (Phase Separator), the solvents were removed in vacuo and the remaining residue was purified by flash chromatography using a KP-NH column (0-100%, EtOAc in cyclohexane; then 0-10% MeOH in EtOAc) to give the title compound (34.5 mg, 90%) as a white solid. LCMS (Method A): $R_T$=1.39 min, m/z=579 [M+H]$^+$.

Step 2: 3-(4-(Aminomethyl)phenyl)-6-((1-(3-cyclobutylpropanoyl)-4-hydroxypiperidin-4-yl)methyl)-2-methyl-2H-pyrazolo[4,3-d]pyrimidin-7(6H)-one Trifluoroacetic acid (1.0 mL, 13.0 mmol) was added to a stirred solution of tert-butyl 4-(6-((1-(3-cyclobutylpropanoyl)-4-hydroxypiperidin-4-yl)methyl)-2-methyl-7-oxo-6,7-dihydro-2H-pyrazolo[4,3-d]pyrimidin-3-yl)benzylcarbamate (34.5 mg, 0.060 mmol) in DCM (2.0 mL) at RT under nitrogen. After 30 min, LCMS showed complete reaction. The reaction mixture was loaded directly onto a pre-equilibrated 5 g SCX-2 cartridge, washed with methanol, the product was eluted with 2M ammonia in MeOH. The solvents were removed in vacuo and the remaining residue was purified by flash chromatography using a KP-NH column (0-100%, EtOAc in cyclohexane; then 0-10% MeOH in EtOAc). The pure fractions were concentrated and freeze-dried to give the title compound (20.5 mg, 71%) as a white fluffly solid. LCMS (Method A): $R_T$=0.75 min, m/z=479 [M+H]$^+$. $^1$H NMR (400 MHz, DMSO-d$_6$): δ 8.00 (s, 1H), 7.65 (d, 2H), 7.54 (d, 2H), 4.92 (s, 1H), 4.14-3.92 (m, 6H), 3.81 (s, 2H), 3.61 (br d, 1H), 3.31-3.20 (m, 1H), 2.97-2.86 (m, 1H), 2.30-2.06 (m, 4H), 2.04-1.93 (m, 2H), 1.86-1.70 (m, 2H), 1.62-1.18 (m, 9H).

Example 139: (R)-3-((4-Hydroxy-1-(3-phenylbutanoyl)piperidin-4-yl)methyl)-8-phenylpyrazolo[1,5-a][1,3,5]triazin-4(3H)-one

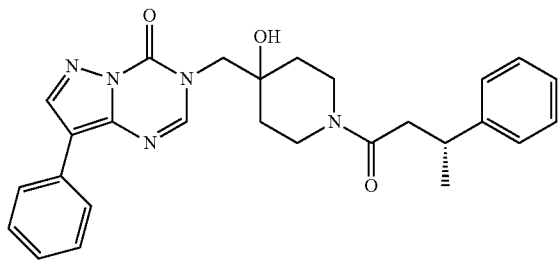 [SMILES: C[C@H](CC(=O)N1CCC(O)(Cn2cnc3c(-c4ccccc4)cnn3c2=O)CC1)c1ccccc1]

Step 1: tert-Butyl 4-hydroxy-4-((8-iodo-4-oxopyrazolo[1,5-a][1,3,5]triazin-3(4H)-yl)methyl)piperidine-1-carboxylate A mixture of 8-iodopyrazolo[1,5-a][1,3,5]triazin-4(3H)-one (300 mg, 1.14 mmol) (commercially available), Epoxide 1 (244 mg, 1.14 mmol) and DIPEA in anhydrous DMF (3 mL) was stirred at 80° C. for 23 h and allowed to cool. The mixture was diluted with isopropyl acetate, and the separated organic phase was washed using 1:1 water/brine, followed by brine. The combined organic phase was dried (Na$_2$SO$_4$), filtered and concentrated in vacuo. The residue was triturated with DCM and the solid was collected by filtration and dried under high vacuum to afford the title compound as a white solid (315 mg). The filtrate was concentrated and purified by flash chromatography (10-100% isopropyl acetate in heptane) to obtain a further quantity (110 mg) of the title compound (425 mg, 78%). $^1$H NMR (400 MHz, DMSO-d$_6$): δ 8.17 (s, 1H), 8.16 (s, 1H), 4.90 (s, 1H), 3.95 (s, 2H), 3.75-3.65 (m, 2H), 3.15-2.9 (br s, 2H), 1.56-1.39 (m, 4H), 1.39 (s, 9H). MS (ESI): m/z=420 [M-butene+H]$^+$.

Step 2: tert-Butyl 4-hydroxy-4-((4-oxo-8-phenylpyrazolo[1,5-a][1,3,5]triazin-3(4H)-yl)methyl)piperidine-1-carboxylate tert-Butyl 4-hydroxy-4-((8-iodo-4-oxopyrazolo[1,5-a][1,3,5]triazin-3(4H)-yl)methyl)piperidine-1-carboxylate (166 mg 0.35 mmol), phenylboronic acid (63.7 mg, 0.52 mmol), potassium acetate (61.5 mg, 0.63 mmol), sodium carbonate (62.7 mg, 0.59 mmol) and PdCl$_2$(dppf).DCM (23.2 mg, 0.028 mmol) were suspended together in degassed acetonitrile (3.5 mL) and water (0.7 mL). The mixture was vacuum-purged and backed-filled with nitrogen three times, and heated under microwave irradiation at 100° C. for 30 min. The cooled mixture was filtered through a pad of Celite®, which was rinsed with isopropyl acetate, and the filtrate was diluted with isopropyl acetate. The separated organic phase was washed with water and brine, dried (Na$_2$SO$_4$), filtered and concentrated in vacuo. The residue was purified by flash chromatography (50-100% isopropyl acetate in heptane) to afford the title compound (78.5 mg, 53%). $^1$H NMR (400 MHz, CDCl$_3$): δ 8.27 (s, 1H), 7.94 (s, 1H), 7.85 (dd, J=7.5, 1.9 Hz, 2H), 7.43 (t, J=7.7 Hz, 2H), 7.34-7.28 (m, 1H), 4.08 (s, 2H), 3.87 (s, 2H), 3.25-3.12 (m, 2H), 2.44 (s, 1H), 1.79-1.52 (m, 4H), 1.45 (s, 9H). MS (ESI): m/z=370 [M-butene+H]$^+$.

Step 3: 3-((4-Hydroxypiperidin-4-yl)methyl)-8-phenylpyrazolo[1,5-a][1,3,5]triazin-4(3H)-one To a solution of tert-butyl 4-hydroxy-4-((4-oxo-8-phenylpyrazolo[1,5-a][1,3,5]triazin-3(4H)-yl)methyl)piperidine-1-carboxylate (78.5 mg, 0.18 mmol) in DCM (0.6 mL) and MeOH (0.6 mL) was added 4M HCl 1,4-dioxane (0.46 mL), and the mixture was heated at 40° C. for 5 h. The solvents were removed in vacuo and the residue was made free of salts by passage through an ion-exchange cartridge (Strata X-C 33 μm polymeric strong cation resin) to afford the title compound (56.4 mg, 94%) as a white solid. $^1$H NMR (400 MHz, methanol-d$_4$): δ 8.45 (s, 1H), 8.12 (s, 1H), 8.01-7.95 (m, 2H), 7.45-7.38 (m, 2H), 7.32-7.25 (m, 1H), 4.08 (s, 2H), 3.60 (s, 1H), 3.01-2.84 (m, 4H), 1.81-1.68 (m, 2H), 1.64-1.52 (m, 2H). MS (ESI): m/z=326 [M+H]$^+$.

Step 4: (R)-3-((4-Hydroxy-1-(3-phenylbutanoyl)piperidin-4-yl)methyl)-8-phenylpyrazolo[1,5-a][1,3,5]triazin-4(3H)-one A solution of 3-((4-hydroxypiperidin-4-yl)methyl)-8-phenylpyrazolo[1,5-a][1,3,5]triazin-4(3H)-one (55.0 mg, 0.17 mmol) and (R)-3-phenylbutanoic acid (41.6 mg, 0.25 mmol) in DCM (3.4 mL) was treated at RT with DIPEA (0.12 mL, 0.68 mmol) and HATU (105 mg, 0.27 mmol). The mixture was stirred at 40° C. for 0.5 h, followed by RT for 18 h, quenched with saturated sodium bicarbonate (aq) solution, and extracted using DCM (×3). The combined organic phases were dried (Na$_2$SO$_4$), filtered, and concentrated in vacuo. The residue was purified by flash chromatography (0-50% methanol in isopropyl acetate), followed by preparative HPLC (Method B) to afford the title compound (32.0 mg, 36%) as a white solid. $^1$H NMR (400 MHz, DMSO-d$_6$): δ 8.63 (s, 1H), 8.16 (d, 1H), 8.03 (dd, 1H), 8.02 (dd, 1H), 7.47-7.41 (m, 2H), 7.35-7.20 (m, 5H), 7.19-7.12 (m, 1H), 4.95 (s, 1H), 4.14-4.03 (m, 2H), 3.99 (q, 1H), 3.90 (s, 1H), 3.73-3.63 (m, 1H), 3.23-3.13 (m, 2H), 2.85 (t, 1H), 2.66-2.52 (m, 3H), 1.51-1.37 (m, 3H), 1.21 (d, 3H). MS (ESI): m/z=472 [M+H]$^+$.

The following Examples were prepared according to the General Procedures (Gen. Proc.) shown in the table. Examples 180 and 181 were prepared by chiral separation of the corresponding racemic mixture (that was prepared using General Procedure 9) by SFC to yield Example 180 (first eluted) and Example 181 (second eluted) as the single unknown stereoisomers.

| Ex. | Structure | Name | Gen. Proc. | LCMS R$_T$, [M + H]$^+$ | $^1$H NMR (ppm) |
|---|---|---|---|---|---|
| 140 | 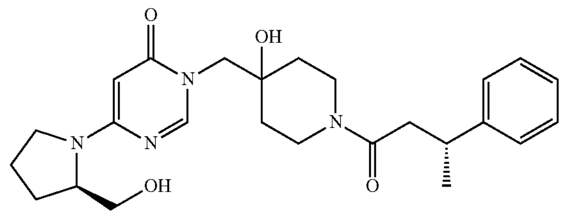 [SMILES: C[C@H](CC(=O)N1CCC(O)(Cn2cnc(N3CCC[C@@H]3CO)cc2=O)CC1)c1ccccc1] | 3-((4-hydroxy-1-((R)-3-phenylbutanoyl)piperidin-4-yl)methyl)-6-((R)-2-(hydroxymethyl)pyrrolidin-1-yl)pyrimidin-4(3H)-one | 8 | 3.73 min, m/z = 455 | $^1$H NMR (400 MHz, DMSO-d$_6$): δ 8.05-7.99 (m, 1H), 7.31-7.21 (m, 4H), 7.20-7.13 (m, 1H), 5.05 (s, 1H), 4.99 (s, 1H), 4.77 (t, J = 5.7 Hz, 1H), 3.98 (d, J = 12.7 Hz, 1H), 3.80 (s, 1H), 3.74 (s, 1H), 3.62 (s, 1H), 3.52 (d, J = 7.5 Hz, 1H), 3.29-3.21 (m, 3H), 3.20-3.10 (m, 2H), 2.89 (t, J = 10.7 Hz, 1H), 2.60-2.48 (m, 3H), 2.06-1.78 (m, 4H), 1.50-1.22 (m, 4H), 1.20 (d, J = 6.9 Hz, 3H). |
| 141 | 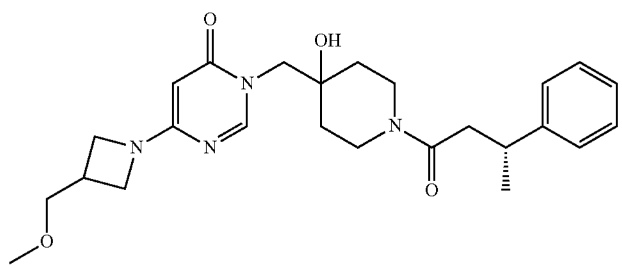 [SMILES: COCC1CN(c2cc(=O)n(CC3(O)CCN(C(=O)C[C@@H](C)c4ccccc4)CC3)cn2)C1] | (R)-3-((4-hydroxy-1-(3-phenylbutanoyl)piperidin-4-yl)methyl)-6-(3-(methoxymethyl)azetidin-1-yl)pyrimidin-4(3H)-one | 8 | 3.90 min, m/z = 455 | $^1$H NMR (400 MHz, DMSO-d$_6$): δ 8.01 (d, J = 10.0 Hz, 1H), 7.31-7.22 (m, 4H), 7.20-7.13 (m, 1H), 4.95 (d, J = 2.6 Hz, 1H), 4.88 (d, J = 2.5 Hz, 1H), 3.97 (t, J = 8.4 Hz, 3H), 3.87-3.71 (m, 2H), 3.65 (dd, J = 8.8, 5.5 Hz, 3H), 3.49 (d, J = 6.4 Hz, 2H), 3.28 (s, 3H), 3.21-3.11 (m, 2H), 2.94-2.84 (m, 2H), 2.62-2.51 (m, 3H), 1.38-1.22 (m, 3H), 1.22-1.17 (m, 3H). |
| 142 | 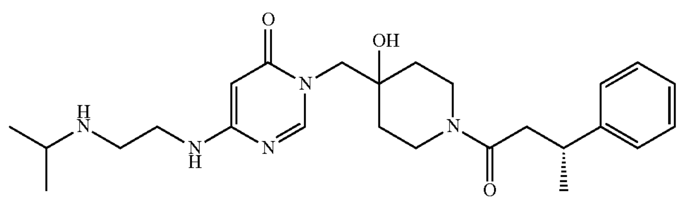 [SMILES: CC(C)NCCNc1cc(=O)n(CC2(O)CCN(C(=O)C[C@@H](C)c3ccccc3)CC2)cn1] | (R)-3-(4-hydroxy-1-(3-phenylbutanoyl)piperidin-4-yl)methyl)-6-((2-(isopropylamino)ethyl)amino)pyrimidin-4(3H)-one | 9 | 2.86 min, m/z = 456 | $^1$H NMR (400 MHz, DMSO-d$_6$): δ 7.96 (d, J = 11.0 Hz, 1H), 7.32-7.22 (m, 4H), 7.22-7.12 (m, 1H), 6.94-6.80 (m, 1H), 5.05 (d, J = 2.1 Hz, 1H), 4.99 (d, J = 2.5 Hz, 1H), 4.03-3.94 (m, 1H), 3.85-3.69 (m, 2H), 3.69-3.57 (m, 1H), 3.30-3.02 (m, 4H), 2.95-2.83 (m, 1H), 2.78-2.52 (m, 6H), 1.50-1.11 (m, 4H), 1.20 (d, J = 7.0 Hz, 3H), 0.96 (d, J = 6.2 Hz, 6H). |
| 143 | 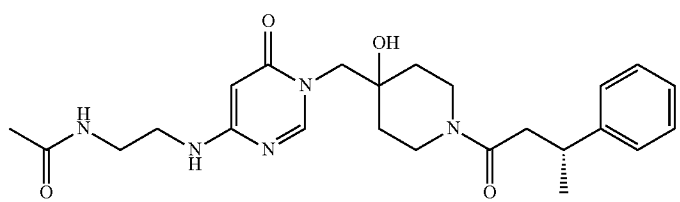 | (R)-N-(2-((1-((4-hydroxy-1-(3-phenylbutanoyl)piperidin-4-yl)methyl)-6-oxo-1,6-dihydropyrimidin-4-yl)amino)ethyl)acetamide | 9 | 3.35 min, m/z = 456 | $^1$H NMR (400 MHz, DMSO-d$_6$): δ 8.00-7.89 (m, 2H), 7.31-7.21 (m, 4H), 7.21-7.12 (m, 1H), 6.99-6.87 (m, 1H), 5.09 (d, J = 2.5 Hz, 1H), 4.98 (d, J = 2.4 Hz, 1H), 3.98 (d, J = 12.5 Hz, 1H), 3.86-3.69 (m, 2H), 3.68-3.56 (s, 1H), 3.44-3.19 (obscured, 2H), 3.22-3.03 (m, 5H), 2.95-2.84 (m, 1H), 2.64-2.51 (m, 2H), 1.80 (s, 3H), 1.50-1.23 (m, 3H), 1.20 (d, J = 6.9 Hz, 3H). |

| Ex. | Structure | Name | Gen. Proc. | LCMS R_T, [M + H]+ | 1H NMR (ppm) |
|---|---|---|---|---|---|
| 144 | 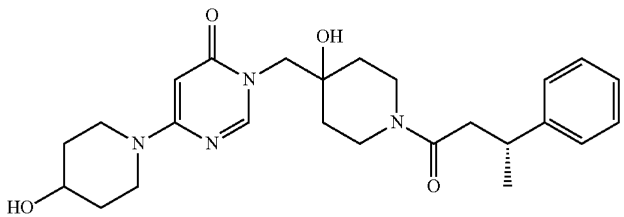 [SMILES: C[C@H](CC(=O)N1CCC(O)(Cn2cnc(N3CCC(O)CC3)cc2=O)CC1)c1ccccc1] | (R)-3-((4-hydroxy-1-(3-phenylbutanoyl)piperidin-4-yl)methyl)-6-(4-hydroxypiperidin-1-yl)pyrimidin-4(3H)-one | 9 | 3.63 min, m/z = 455 | 1H NMR (400 MHz, DMSO-d6): δ 8.24-7.92 (m, 1H), 7.34-7.11 (m, 5H), 5.36 (d, J = 2.3 Hz, 1H), 4.98 (d, J = 2.8 Hz, 1H), 4.73 (d, J = 4.1 Hz, 1H), 4.02-3.57 (m, 7H), 3.24-3.06 (m, 4H), 2.95-2.52 (m, 4H), 1.80-1.68 (m, 2H), 1.53-1.21 (m, 5H), 1.20 (d, J = 6.8 Hz, 3H). |
| 145 | 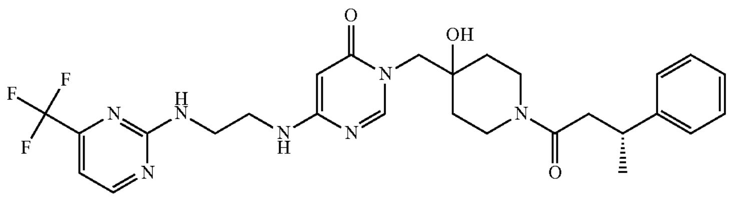 [SMILES: C[C@H](CC(=O)N1CCC(O)(Cn2cnc(NCCNc3nccc(C(F)(F)F)n3)cc2=O)CC1)c1ccccc1] | (R)-3-((4-hydroxy-1-(3-phenylbutanoyl)piperidin-4-yl)methyl)-6-((2-(4-(trifluoromethyl)pyrimidin-2-yl)amino)ethyl)amino)pyrimidin-4(3H)-one | 9 | 4.62 min, m/z = 560 | 1H NMR (400 MHz, DMSO-d6): δ 8.62 (s, 1H), 7.96 (d, J = 10.6 Hz, 1H), 7.90 (s, 1H), 7.32-7.12 (m, 5H), 7.05-6.95 (m, 2H), 5.13 (d, J = 2.2 Hz, 1H), 4.98 (s, 1H), 3.98 (d, J = 11.5 Hz, 1H), 3.86-3.69 (m, 2H), 3.62 (s, 1H), 3.44 (s, 2H), 3.40-3.11 (m, 5H), 2.91 (d, J = 11.1 Hz, 1H), 2.65-2.50 (m, 2H), 1.31 (s, 2H), 1.26 (s, 2H), 1.20 (d, J = 6.9 Hz, 3H). |
| 146 | 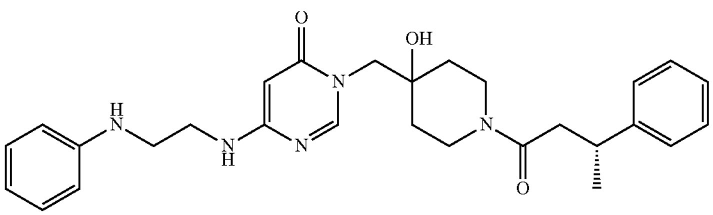 [SMILES: C[C@H](CC(=O)N1CCC(O)(Cn2cnc(NCCNc3ccccc3)cc2=O)CC1)c1ccccc1] | (R)-3-((4-hydroxy-1-(3-phenylbutanoyl)piperidin-4-yl)methyl)-6-((2-(phenylamino)ethyl)amino)pyrimidin-4(3H)-one | 9 | 4.30 min, m/z = 490 | 1H NMR (400 MHz, DMSO-d6): δ 7.99 (d, J = 10.5 Hz, 1H), 7.32-7.21 (m, 4H), 7.21-7.12 (m, 1H), 7.07 (dd, J = 8.6, 7.2 Hz, 2H), 7.06-6.95 (m, 1H), 6.57 (dd, J = 8.5, 1.2 Hz, 2H), 6.53 (tt, J = 7.2, 1.1 Hz, 1H), 5.61 (t, J = 5.6 Hz, 1H), 5.09 (d, J = 2.4 Hz, 1H), 4.98 (s, 1H), 4.03-3.93 (m, 1H), 3.87-3.69 (m, 2H), 3.68-3.57 (m, 1H), 3.28-3.11 (m, 6H), 2.95-2.84 (m, 1H), 2.62-2.52 (m, 2H), 1.50-1.21 (m, 4H), 1.20 (d, J = 6.9 Hz, 3H). |
| 147 | 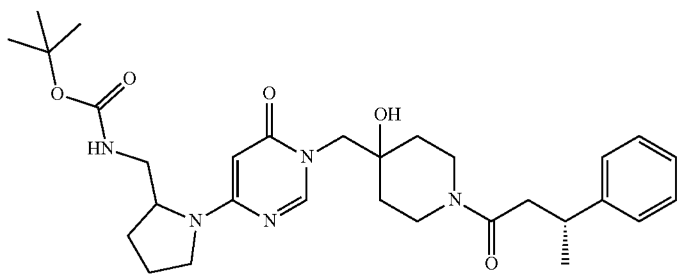 [SMILES: C[C@H](CC(=O)N1CCC(O)(Cn2cnc(N3CCCC3CNC(=O)OC(C)(C)C)cc2=O)CC1)c1ccccc1] | tert-butyl (((1-(1-((4-hydroxy-1-((R)-3-phenylbutanoyl)piperidin-4-yl)methyl)-6-oxo-1,6-dihydropyrimidin-4-yl)pyrrolidin-2-yl)methyl)carbamate (mixture of diastereomers) | 10 | 4.92 min, m/z = 554 | 1H NMR (400 MHz, DMSO-d6): δ 8.02 (d, J = 10.3 Hz, 1H), 7.32-7.21 (m, 4H), 7.17 (ddt, J = 6.8, 4.7, 2.4 Hz, 1H), 7.01 (s, 1H), 4.99 (d, J = 3.3 Hz, 1H), 3.98 (d, J = 12.0 Hz, 1H), 3.83-3.70 (m, 1H), 3.63 (s, 1H), 3.32-3.22 (m, 1H), 3.21-3.13 (m, 4H), 2.89 (d, J = 9.4 Hz, 1H), 2.63-2.51 (m, 2H), 1.90 (s, 3H), 1.80 (s, 1H), 1.38 (s, 9H), 1.36-1.24 (m, 4H), 1.20 (d, J = 6.9 Hz, 3H). |

| Ex. | Structure | Name | Gen. Proc. | LCMS R_T, [M + H]+ | 1H NMR (ppm) |
|---|---|---|---|---|---|
| 148 | 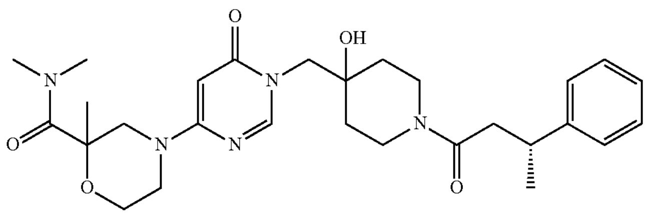 [SMILES: C[C@H](CC(=O)N1CCC(O)(Cn2cnc(N3CCOC(C)(C(=O)N(C)C)C3)cc2=O)CC1)c1ccccc1] | 4-(1-(4-hydroxy-1-((R)-3-phenylbutanoyl)piperidin-4-yl)methyl)-6-oxo-1,6-dihydropyrimidin-4-yl)-N,N,2-trimethyl-morpholine-2-carboxamide (mixture of diastereomers) | 10 | 4.12 min, m/z = 526 | 1H NMR (400 MHz, DMSO-d6): δ 8.04 (d, J = 10.1 Hz, 1H), 7.33-7.21 (m, 4H), 7.17 (t, J = 6.5 Hz, 1H), 5.37 (d, J = 2.4 Hz, 1H), 4.99 (d, J = 2.9 Hz, 1H), 4.46 (d, J = 12.8 Hz, 1H), 3.98 (s, 2H), 3.89-3.71 (m, 3H), 3.62 (s, 1H), 3.46-3.37 (m, 1H), 3.27-3.07 (m, 5H), 3.05-2.76 (m, 4H), 2.72 (d, J = 12.7 Hz, 1H), 2.62-2.54 (m, 2H), 1.33 (s, 6H), 1.20 (d, J = 6.9 Hz, 3H). |
| 149 | 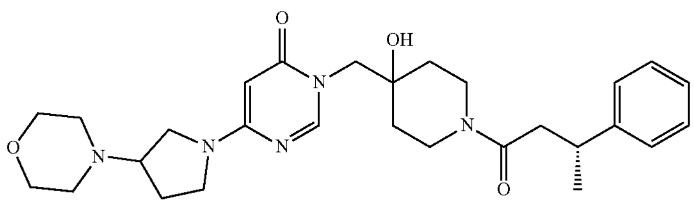 [SMILES: C[C@H](CC(=O)N1CCC(O)(Cn2cnc(N3CCC(N4CCOCC4)C3)cc2=O)CC1)c1ccccc1] | 3-(4-hydroxy-1-((R)-3-phenylbutanoyl)piperidin-4-yl)methyl)-6-(3-morpholinopyrrolidin-1-yl)pyrimidin-4(3H)-one (mixture of diastereomers) | 10 | 2.87 min, m/z = 510 | 1H NMR (400 MHz, DMSO-d6): δ 8.24 (s, 0.3H), 8.03 (d, J = 10.2 Hz, 1H), 7.95 (s, 0.1 H), 7.32-7.21 (m, 4H), 7.21-7.12 (m, 1H), 6.60 (s, 0.6H), 5.02 (s, 1H), 4.98 (s, 1H), 4.02-3.93 (m, 1H), 3.88-3.69 (m, 2H), 3.70-3.53 (m, 4H), 3.26-3.11 (m, 4H), 2.96-2.64 (m, 3H), 2.64-2.52 (m, 3H), 2.48-2.36 (m, 4H), 2.19-2.07 (m, 1H), 1.84-1.68 (m, 1H), 1.50-1.16 (m, 4H), 1.20 (d, J = 6.9 Hz, 3H). |
| 150 | 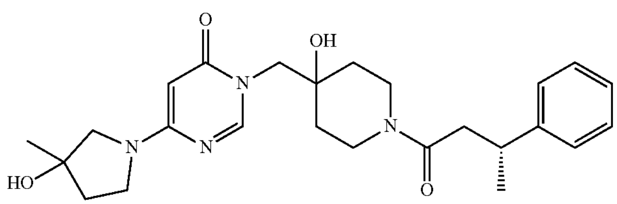 [SMILES: C[C@H](CC(=O)N1CCC(O)(Cn2cnc(N3CCC(C)(O)C3)cc2=O)CC1)c1ccccc1] | 3-((4-hydroxy-1-((R)-3-phenylbutanoyl)piperidin-4-yl)methyl)-6-(3-hydroxy-3-methylpyrrolidin-1-yl)pyrimidin-4(3H)-one (mixture of diastereomers) | 10 | 3.71 min, m/z = 455 | 1H NMR (400 MHz, DMSO-d6): δ 8.02 (d, J = 10.4 Hz, 1H), 7.32-7.21 (m, 4H), 7.21-7.12 (m, 1H), 4.99 (d, J = 1.9 Hz, 1H), 4.95 (s, 1H), 4.81 (s, 1H), 4.02-3.93 (m, 1H), 3.88-3.45 (m, 2H), 3.62 (dd, J = 14.1, 7.9 Hz, 2H), 3.26-3.03 (m, 3H), 2.97-2.84 (m, 1H), 2.75-2.42 (m, 4H), 1.94-1.58 (s, 3H), 1.57-1.22 (m, 6H), 1.20 (d, J = 6.8 Hz, 3H). |
| 151 | 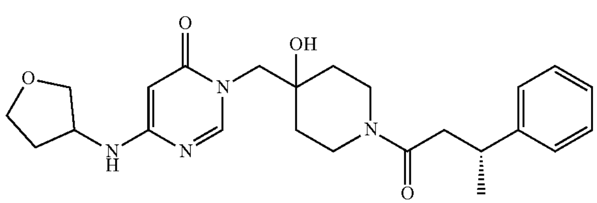 [SMILES: C[C@H](CC(=O)N1CCC(O)(Cn2cnc(NC3CCOC3)cc2=O)CC1)c1ccccc1] | 3-(4-hydroxy-1-((R)-3-phenylbutanoyl)piperidin-4-yl)methyl)-6-((tetrahydrofuran-3-yl)amino)pyrimidin-4(3H)-one (mixture of diastereomers) | 10 | 3.69 min, m/z = 441 | 1H NMR (400 MHz, DMSO-d6): δ 7.99 (d, J = 10.6 Hz, 1H), 7.32-7.12 (m, 6H), 5.07 (d, J = 2.1 Hz, 1H), 4.97 (d, J = 2.6 Hz, 1H), 4.09 (s, 1H), 4.03-3.94 (m, 1H), 3.86-3.57 (m, 7H), 3.53 (dd, J = 9.0, 3.7 Hz, 1H), 3.20 (dddd, J = 27.9, 13.9, 7.4, 3.0 Hz, 2H), 2.94-2.84 (m, 1H), 2.65-2.50 (m, 2H), 2.13 (dq, J = 12.6, 7.5 Hz, 1H), 1.86-1.74 (m, 1H), 1.37-1.16 (m, 7H). |

| Ex. | Structure | Name | Gen. Proc. | LCMS R_T, [M + H]+ | 1H NMR (ppm) |
|---|---|---|---|---|---|
| 152 | 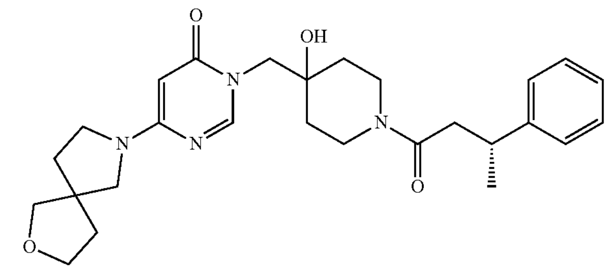 [SMILES: C[C@H](CC(=O)N1CCC(O)(Cn2cnc(N3CCC4(CCOC4)C3)cc2=O)CC1)c1ccccc1] | 3-(4-hydroxy-1-((R)-3-phenylbutanoyl)piperidin-4-yl)methyl)-6-(2-oxa-7-azaspiro[4.4]nonan-7-yl)pyrimidin-4(3H)-one (mixture of diastereomers) | 10 | 4.06 min, m/z = 481 | 1H NMR (400 MHz, DMSO-d6): δ 8.03 (d, J = 10.3 Hz, 1H), 7.31-7.21 (m, 4H), 7.21-7.11 (m, 1H), 4.99 (dd, J = 6.5, 2.4 Hz, 2H), 4.11-3.91 (m, 1H), 3.88-3.72 (m, 4H), 3.61 (s, 1H), 3.55 (s, 2H), 3.16 (dd, J = 14.3, 8.4 Hz, 1H), 2.89 (s, 1H), 2.62-2.54 (m, 2H), 2.01-1.79 (m, 4H), 1.29 (d, J = 18.9 Hz, 3H), 1.20 (d, J = 6.9 Hz, 3H). |
| 153 | 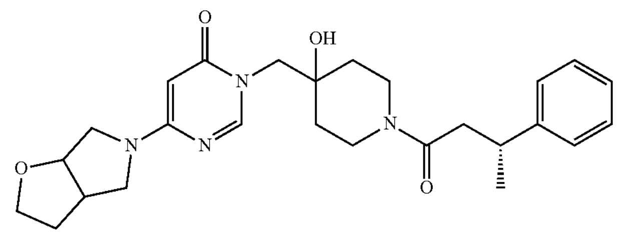 [SMILES: C[C@H](CC(=O)N1CCC(O)(Cn2cnc(N3CC4CCOC4C3)cc2=O)CC1)c1ccccc1] | 3-(4-hydroxy-1-((R)-3-phenylbutanoyl)piperidin-4-yl)methyl)-6-(tetrahydro-2H-furo[2,3-c]pyrrol-5(3H)-yl)pyrimidin-4(3H)-one (mixture of diastereomers) | 10 | 3.98 min, m/z = 467 | 1H NMR (400 MHz, DMSO-d6): δ 8.03 (d, J = 10.2 Hz, 1H), 7.32-7.12 (m, 5H), 5.03 (d, J = 2.4 Hz, 1H), 4.97 (d, J = 2.4 Hz, 1H), 4.48 (t, J = 5.3 Hz, 1H), 3.97 (dd, J = 12.9, 4.5 Hz, 1H), 3.90-3.68 (m, 4H), 3.67-3.56 (m, 3H), 3.44 (s, 1H), 3.20 (ddd, J = 22.6, 18.6, 9.9 Hz, 3H), 2.95 (dd, J = 27.5, 11.4 Hz, 2H), 2.65-2.50 (m, 2H), 2.07 (dq, J = 12.4, 7.8 Hz, 1H), 1.87-1.75 (m, 1H), 1.37-1.16 (m, 6H). |
| 154 | 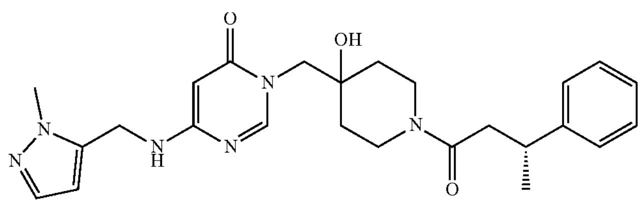 [SMILES: C[C@H](CC(=O)N1CCC(O)(Cn2cnc(NCc3ccnn3C)cc2=O)CC1)c1ccccc1] | (R)-3-((4-hydroxy-1-(3-phenylbutanoyl)piperidin-4-yl)methyl)-6-(((1-methyl-1H-pyrazol-5-yl)methyl)amino)pyrimidin-4(3H)-one | 10 | 3.73 min, m/z = 465 | 1H NMR (400 MHz, DMSO-d6): δ 8.00 (d, J = 10.5 Hz, 1H), 7.45 (t, J = 6.0 Hz, 1H), 7.36-7.22 (m, 5H), 7.22-7.10 (m, 1H), 6.55 (s, 1H), 6.16 (d, J = 1.8 Hz, 1H), 5.15 (d, J = 2.2 Hz, 1H), 4.96 (d, J = 4.5 Hz, 1H), 4.38 (s, 2H), 3.97 (d, J = 13.0 Hz, 1H), 3.78 (s, 3H), 3.61 (d, J = 6.2 Hz, 1H), 3.16 (d, J = 5.7 Hz, 1H), 2.95-2.82 (m, 1H), 2.57 (s, 1H), 1.36-1.23 (m, 4H), 1.24-1.15 (m, 3H). |
| 155 | 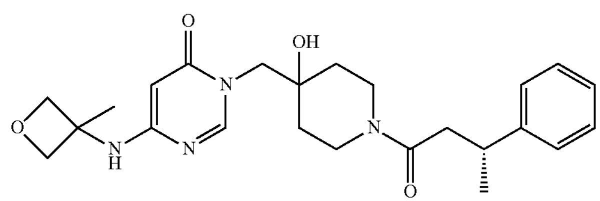 [SMILES: C[C@H](CC(=O)N1CCC(O)(Cn2cnc(NC3(C)COC3)cc2=O)CC1)c1ccccc1] | (R)-3-((4-hydroxy-1-(3-phenylbutanoyl)piperidin-4-yl)methyl)-6-((3-methyloxetan-3-yl)amino)pyrimidin-4(3H)-one | 10 | 3.93 min, m/z = 441 | 1H NMR (400 MHz, DMSO-d6): δ 8.06 (d, J = 9.8 Hz, 1H), 7.36-7.22 (m, 4H), 7.17 (td, J = 5.5, 4.6, 2.4 Hz, 1H), 5.37 (dd, J = 2.5 Hz, 1H), 4.95 (d, J = 3.1 Hz, 1H), 3.97 (dd, J = 13.1, 4.3 Hz, 1H), 3.81 (d, J = 11.5 Hz, 3H), 3.63 (dd, J = 5.8, 3.9 Hz, 5H), 3.45 (t, J = 4.8 Hz, 4H), 3.22-3.10 (m, 1H), 2.95-2.84 (m, 1H), 2.56 (dd, J = 6.9, 2.9 Hz, 1H), 1.29 (dd, J = 17.8, 4.1 Hz, 3H), 1.20 (d, J = 6.9 Hz, 3H). |

| Ex. | Structure | Name | Gen. Proc. | LCMS R_T, [M + H]+ | 1H NMR (ppm) |
|---|---|---|---|---|---|
| 156 | 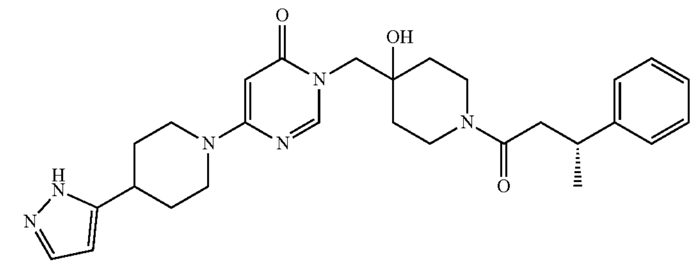 [SMILES: C[C@H](CC(=O)N1CCC(O)(Cn2cnc(N3CCC(c4ccn[nH]4)CC3)cc2=O)CC1)c1ccccc1] | (R)-6-(4-(1H-pyrazol-5-yl)piperidin-1-yl)-3-((4-hydroxy-1-(3-phenylbutanoyl)piperidin-4-yl)methyl)pyrimidin-4(3H)-one | 10 | 4.06 min, m/z = 505 | 1H NMR (400 MHz, DMSO-d6): δ 12.49 (s, 1H), 8.05 (d, J = 10.3 Hz, 1H), 7.48 (s, 1H), 7.32-7.12 (m, 5H), 6.06 (s, 1H), 5.39 (d, J = 2.3 Hz, 1H), 4.99 (d, J = 2.8 Hz, 1H), 4.26 (d, J = 13.0 Hz, 2H), 4.03-3.93 (m, 1H), 3.88-3.71 (m, 2H), 3.63 (dd, J = 14.6, 8.6 Hz, 1H), 3.30-3.11 (m, 2H), 3.02-2.85 (m, 4H), 2.65-2.50 (m, 2H), 1.93 (dd, J = 13.1, 3.7 Hz, 2H), 1.52 (qt, J = 10.4, 5.2 Hz, 2H), 1.41-1.17 (m, 6H). |
| 157 | 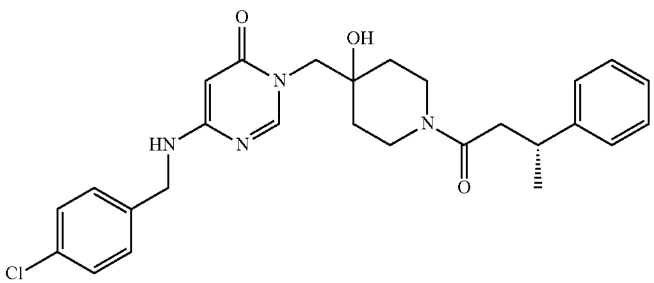 [SMILES: C[C@H](CC(=O)N1CCC(O)(Cn2cnc(NCc3ccc(Cl)cc3)cc2=O)CC1)c1ccccc1] | (R)-6-((4-chlorobenzyl)amino)-3-((4-hydroxy-1-(3-phenylbutanoyl)piperidin-4-yl)methyl)pyrimidin-4(3H)-one | 10 | 4.93 min, m/z = 495 | 1H NMR (400 MHz, DMSO-d6): δ 7.98 (d, J = 10.6 Hz, 1H), 7.62-7.54 (m, 1H), 7.43-7.20 (m, 8H), 7.11 (m, 1H), 5.02-4.92 (m, 2H), 4.31 (s, 2H), 3.92 (m, 1H), 3.84-3.67 (m, 2H), 3.60 (q, J = 9.3, 6.1 Hz, 1H), 3.28-3.10 (m, 2H), 2.88 (t, J = 10.2 Hz, 1H), 2.64-2.51 (m, 2H), 1.36-1.15 (m, 6H). |
| 158 | 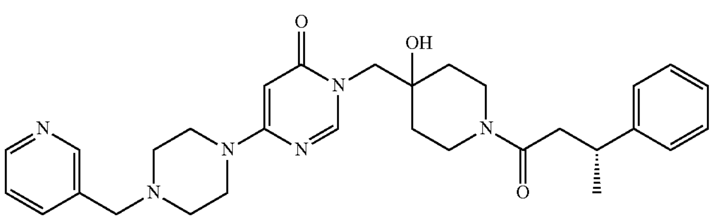 [SMILES: C[C@H](CC(=O)N1CCC(O)(Cn2cnc(N3CCN(Cc4cccnc4)CC3)cc2=O)CC1)c1ccccc1] | (R)-3-((4-hydroxy-1-(3-phenylbutanoyl)piperidin-4-yl)methyl)-6-(4-(pyridin-3-ylmethyl)piperazin-1-yl)pyrimidin-4(3H)-one | 10 | 2.88 min, m/z = 531 | 1H NMR (400 MHz, DMSO-d6): δ 8.51 (d, J = 2.1 Hz, 1H), 8.48 (dd, J = 4.8, 1.7 Hz, 1H), 8.04 (d, J = 10.0 Hz, 1H), 7.73 (dt, J = 7.9, 2.0 Hz, 1H), 7.41-7.32 (m, 1H), 7.26 (dd, J = 6.5, 3.4 Hz, 4H), 7.21-7.07 (m, 1H), 5.35 (d, J = 2.5 Hz, 1H), 5.00-4.90 (m, 1H), 3.96 (s, 1H), 3.86-3.70 (m, 2H), 3.62 (s, 0H), 3.54 (s, 2H), 3.48 (t, J = 4.9 Hz, 4H), 3.21-3.11 (m, 1H), 2.88 (d, J = 10.3 Hz, 1H), 2.55 (d, J = 12.0 Hz, 2H), 2.41 (dd, J = 6.0, 3.9 Hz, 4H), 1.28 (d, J = 20.3 Hz, 4H), 1.23-1.14 (m, 3H). |
| 159 | 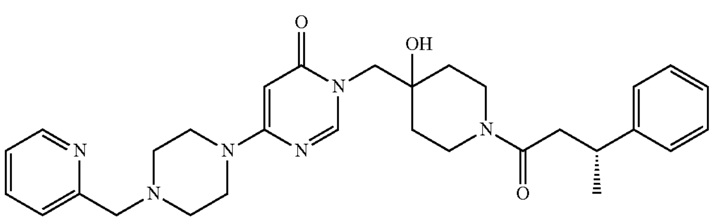 [SMILES: C[C@H](CC(=O)N1CCC(O)(Cn2cnc(N3CCN(Cc4ccccn4)CC3)cc2=O)CC1)c1ccccc1] | (R)-3-((4-hydroxy-1-(3-phenylbutanoyl)piperidin-4-yl)methyl)-6-(4-(pyridin-2-ylmethyl)piperazin-1-yl)pyrimidin-4(3H)-one | 10 | 3.09 min, m/z = 531 | 1H NMR (400 MHz, DMSO-d6): δ 8.62-8.45 (m, 1H), 8.04 (d, J = 10.0 Hz, 1H), 7.82-7.72 (m, 1H), 7.47 (d, J = 7.8 Hz, 1H), 7.26 (t, J = 4.7 Hz, 5H), 7.17 (s, 1H), 6.71 (s, 1H), 5.36 (d, J = 2.5 Hz, 1H), 4.97 (s, 1H), 3.97 (s, 1H), 3.90-3.72 (m, 1H), 3.63 (s, 2H), 3.49 (s, 4H), 2.90 (s, 1H), 1.29 (d, J = 20.4 Hz, 4H), 1.20 (d, J = 6.9 Hz, 3H). |

| Ex. | Structure | Name | Gen. Proc. | LCMS R$_T$, [M + H]$^+$ m/z | $^1$H NMR (ppm) |
|---|---|---|---|---|---|
| 160 | 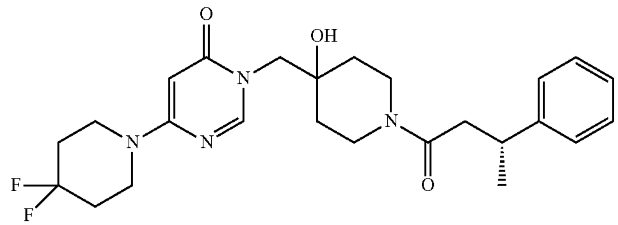 [SMILES: C[C@H](CC(=O)N1CCC(O)(Cn2cnc(N3CCC(F)(F)CC3)cc2=O)CC1)c1ccccc1] | (R)-6-(4,4-difluoropiperidin-1-yl)-3-((4-hydroxy-1-(3-phenylbutanoyl)piperidin-4-yl)methyl)pyrimidin-4(3H)-one | 10 | 4.67 min, m/z = 475 | $^1$H NMR (400 MHz, DMSO-d$_6$): δ 8.08 (d, J = 9.6 Hz, 1H), 7.33-7.21 (m, 4H), 7.17 (t, J = 6.9 Hz, 1H), 5.52 (d, J = 2.5 Hz, 1H), 4.95 (d, J = 2.9 Hz, 1H), 3.97 (d, J = 12.4 Hz, 1H), 3.89-3.72 (m, 2H), 3.65 (t, J = 5.9 Hz, 5H), 3.26-3.07 (m, 1H), 2.91 (d, J = 9.4 Hz, 1H), 2.56 (d, J = 8.6 Hz, 2H), 2.06-1.83 (m, 4H), 1.29 (d, J = 20.0 Hz, 3H), 1.20 (d, J = 6.9 Hz, 3H). |
| 161 | 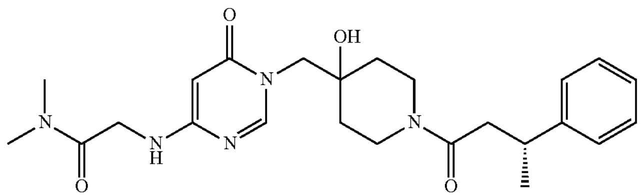 [SMILES: C[C@H](CC(=O)N1CCC(O)(Cn2cnc(NCC(=O)N(C)C)cc2=O)CC1)c1ccccc1] | (R)-2-(1-((4-hydroxy-1-(3-phenylbutanoyl)piperidin-4-yl)methyl)-6-oxo-1,6-dihydropyrimidin-4-yl)amino)-N,N-dimethylacetamide | 10 | 3.57 min, m/z = 456 | $^1$H NMR (400 MHz, DMSO-d$_6$): δ 7.99 (d, J = 10.4 Hz, 1H), 7.36-7.22 (m, 4H), 7.17 (s, 1H), 5.16 (s, 1H), 4.99 (d, J = 2.6 Hz, 1H), 3.98 (s, 3H), 3.88-3.69 (m, 2H), 3.62 (s, 1H), 3.16 (d, J = 7.0 Hz, 1H), 2.98 (s, 3H), 2.85 (s, 4H), 2.56 (d, J = 12.9 Hz, 2H), 1.28 (d, J = 20.7 Hz, 4H), 1.20 (d, J = 6.9 Hz, 3H). |
| 162 | 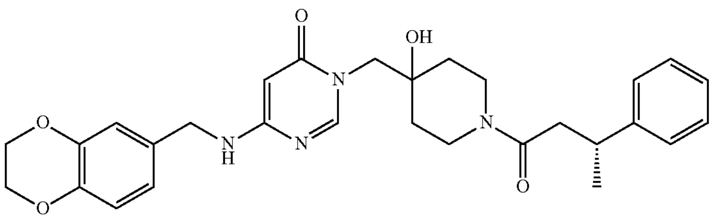 [SMILES: C[C@H](CC(=O)N1CCC(O)(Cn2cnc(NCc3ccc4c(c3)OCCO4)cc2=O)CC1)c1ccccc1] | (R)-6-(((2,3-dihydrobenzo[b][1,4]dioxin-6-yl)methyl)amino)-3-((4-hydroxy-1-(3-phenylbutanoyl)piperidin-4-yl)methyl)pyrimidin-4(3H)-one | 10 | 4.50 min, m/z = 519 | $^1$H NMR (400 MHz, DMSO-d$_6$): δ 7.97 (d, J = 10.8 Hz, 1H), 7.50 (d, J = 6.8 Hz, 1H), 7.33-7.23 (m, 4H), 7.20-7.09 (m, 1H), 6.78 (td, J = 9.3, 8.8, 5.9 Hz, 3H), 4.96 (d, J = 2.9 Hz, 2H), 4.20 (s, 4H), 3.97 (d, J = 12.8 Hz, 1H), 3.81-3.67 (m, 2H), 3.61 (s, 1H), 3.24-3.08 (m, 2H), 2.88 (s, 1H), 2.59-2.53 (m, 2H), 1.27 (d, J = 22.1 Hz, 4H), 1.19 (dd, J = 7.0, 1.9 Hz, 3H). |
| 163 | 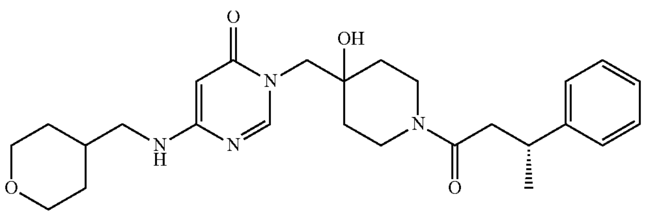 [SMILES: C[C@H](CC(=O)N1CCC(O)(Cn2cnc(NCC3CCOCC3)cc2=O)CC1)c1ccccc1] | (R)-3-((4-hydroxy-1-(3-phenylbutanoyl)piperidin-4-yl)methyl)-6-(((tetrahydro-2H-pyran-4-yl)methyl)amino)pyrimidin-4(3H)-one | 10 | 3.89 min, m/z = 469 | $^1$H NMR (400 MHz, DMSO-d$_6$): δ 7.96 (d, J = 10.9 Hz, 1H), 7.32-7.11 (m, 5H), 7.07 (s, 1H), 5.06 (s, 1H), 4.99 (d, J = 2.1 Hz, 1H), 4.02-3.94 (m, 1H), 3.88-3.69 (m, 4H), 3.62 (s, 1H), 3.32-3.11 (m, 4H), 2.93 (s, 3H), 2.65-2.50 (m, 2H), 1.74 (s, 1H), 1.60 (dd, J = 12.3, 3.2 Hz, 2H), 1.37-1.23 (m, 3H), 1.23-1.09 (m, 5H). |

| Ex. | Structure | Name | Gen. Proc. | LCMS R$_T$, [M + H]$^+$ m/z | $^1$H NMR (ppm) |
|---|---|---|---|---|---|
| 164 | 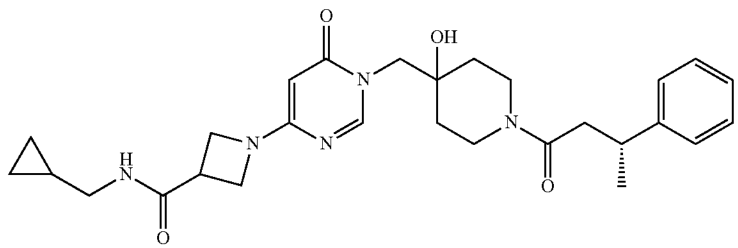 [SMILES: C[C@H](CC(=O)N1CCC(O)(Cn2cnc(N3CC(C(=O)NCC4CC4)C3)cc2=O)CC1)c1ccccc1] | (R)-N-(cyclopropylmethyl)-1-(1-((4-hydroxy-1-(3-phenylbutanoyl)piperidin-4-yl)methyl)-6-oxo-1,6-dihydropyrimidin-4-yl)azetidine-3-carboxamide | 10 | 3.97 min, m/z = 508 | $^1$H NMR (400 MHz, DMSO-d$_6$): δ 7.98 (t, J = 5.7 Hz, 1H), 7.89 (d, J = 9.9 Hz, 1H), 7.20-7.07 (m, 4H), 7.07-6.98 (m, 1H), 4.80 (dd, J = 9.5, 2.8 Hz, 2H), 3.84 (dt, J = 46.3, 8.0 Hz, 5H), 3.73-3.54 (m, 2H), 3.49 (s, 0H), 3.35-3.25 (m, 1H), 3.10-2.95 (m, 2H), 2.83 (dd, J = 6.8, 5.6 Hz, 2H), 2.75 (s, 1H), 2.49-2.39 (m, 2H), 1.14 (d, J = 20.5 Hz, 4H), 1.06 (d, J = 6.8 Hz, 3H), 0.83-0.69 (m, 1H), 0.35-0.19 (m, 2H), 0.06--0.02 (m, 2H). |
| 165 | 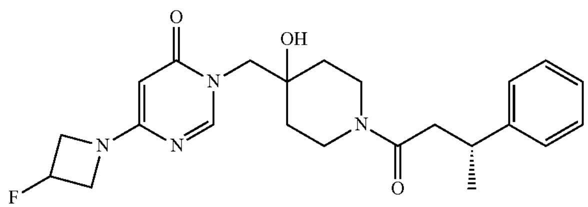 [SMILES: C[C@H](CC(=O)N1CCC(O)(Cn2cnc(N3CC(F)C3)cc2=O)CC1)c1ccccc1] | (R)-6-(3-fluoroazetidin-1-yl)-3-((4-hydroxy-1-(3-phenylbutanoyl)piperidin-4-yl)methyl)pyrimidin-4(3H)-one | 10 | 3.94 min, m/z = 429 | $^1$H NMR (400 MHz, DMSO-d$_6$): δ 8.05 (d, J = 9.6 Hz, 1H), 7.32-7.11 (m, 5H), 5.01 (d, J = 2.6 Hz, 1H), 4.93 (d, J = 2.9 Hz, 1H), 4.34-4.19 (m, 2H), 4.07-3.93 (m, 3H), 3.89-3.68 (m, 2H), 3.67-3.57 (m, 1H), 3.30-3.11 (m, 2H), 2.96-2.84 (m, 1H), 2.65-2.50 (m, 2H), 1.37-1.16 (m, 6H). |
| 166 | 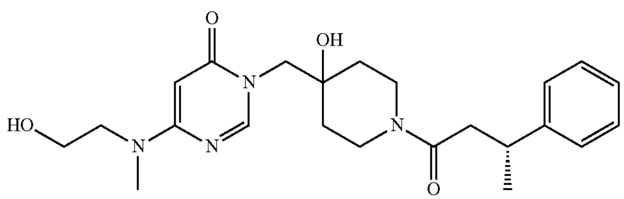 [SMILES: C[C@H](CC(=O)N1CCC(O)(Cn2cnc(N(C)CCO)cc2=O)CC1)c1ccccc1] | (R)-3-((4-hydroxy-1-(3-phenylbutanoyl)piperidin-4-yl)methyl)-6-((2-hydroxyethyl)(methyl)amino)pyrimidin-4(3H)-one | 10 | 3.57 min, m/z = 429 | $^1$H NMR (400 MHz, DMSO-d$_6$): δ 8.02 (d, J = 10.3 Hz, 1H), 7.32-7.12 (m, 5H), 5.17-5.12 (m, 1H), 5.00 (d, J = 2.0 Hz, 1H), 4.73-4.66 (m, 1H), 3.98 (dd, J = 13.3, 4.6 Hz, 1H), 3.88-3.71 (m, 2H), 3.64 (d, J = 12.9 Hz, 1H), 3.52 (d, J = 3.3 Hz, 4H), 3.27-3.11 (m, 2H), 2.99-2.84 (m, 4H), 2.65-2.50 (m, 2H), 1.38-1.16 (m, 6H). |
| 167 | 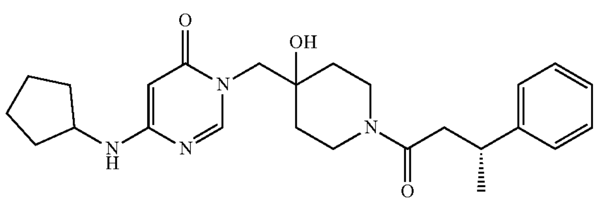 [SMILES: C[C@H](CC(=O)N1CCC(O)(Cn2cnc(NC3CCCC3)cc2=O)CC1)c1ccccc1] | (R)-6-(cyclopentylamino)-3-((4-hydroxy-1-(3-phenylbutanoyl)piperidin-4-yl)methyl)pyrimidin-4(3H)-one | 10 | 4.52 min, m/z = 439 | $^1$H NMR (400 MHz, DMSO-d$_6$): δ 7.95 (d, J = 11.0 Hz, 1H), 7.32-7.12 (m, 5H), 7.02-6.95 (m, 1H), 5.00 (dd, J = 7.1, 2.0 Hz, 2H), 3.98 (dd, J = 12.7, 4.5 Hz, 1H), 3.86-3.68 (m, 2H), 3.63 (s, 1H), 3.41-3.11 (m, 3H), 2.89 (s, 1H), 2.65-2.50 (m, 2H), 1.86 (dq, J = 12.1, 7.0 Hz, 2H), 1.70-1.43 (m, 6H), 1.37-1.23 (m, 3H), 1.20 (d, J = 6.9 Hz, 3H). |

-continued

| Ex. | Structure | Name | Gen. Proc. | LCMS R$_T$, [M + H]$^+$ | $^1$H NMR (ppm) |
|---|---|---|---|---|---|
| 168 | 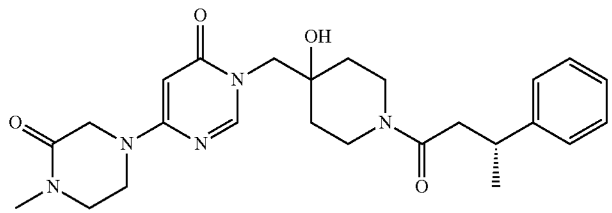 [SMILES: C[C@H](CC(=O)N1CCC(O)(Cn2cnc(N3CCN(C)C(=O)C3)cc2=O)CC1)c1ccccc1] | (R)-3-((4-hydroxy-1-(3-phenylbutanoyl)piperidin-4-yl)methyl)-6-(4-methyl-3-oxopiperazin-1-yl)pyrimidin-4(3H)-one | 10 | 3.63 min, m/z = 468 | $^1$H NMR (400 MHz, DMSO-d$_6$): δ 8.09 (d, J = 9.5 Hz, 1H), 7.32-7.22 (m, 4H), 7.16 (d, J = 7.1 Hz, 1H), 5.45-5.29 (m, 1H), 4.94 (d, J = 3.0 Hz, 1H), 4.01 (s, 3H), 3.83-3.72 (m, 3H), 3.62 (s, 1H), 3.38 (t, J = 5.4 Hz, 2H), 3.16 (q, J = 8.6, 7.8 Hz, 2H), 2.88 (s, 4H), 2.61-2.54 (m, 1H), 1.44 (d, J = 10.4 Hz, 0H), 1.29 (d, J = 19.2 Hz, 3H), 1.20 (d, J = 6.9 Hz, 3H). |
| 169 | 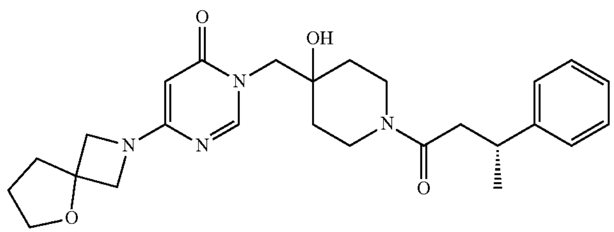 [SMILES: C[C@H](CC(=O)N1CCC(O)(Cn2cnc(N3CC4(CCCO4)C3)cc2=O)CC1)c1ccccc1] | (R)-3-((4-hydroxy-1-(3-phenylbutanoyl)piperidin-4-yl)methyl)-6-(5-oxa-2-azaspiro[3.4]octan-2-yl)pyrimidin-4(3H)-one | 10 | 4.11 min, m/z = 467 | $^1$H NMR (400 MHz, DMSO-d$_6$): δ 8.03 (d, J = 9.8 Hz, 1H), 7.33-7.23 (m, 4H), 7.21-7.12 (m, 1H), 4.94 (d, J = 2.6 Hz, 2H), 3.96 (d, J = 9.3 Hz, 3H), 3.88 (d, J = 8.9 Hz, 2H), 3.83-3.66 (m, 4H), 3.71-3.55 (m, 1H), 3.22-3.10 (m, 2H), 2.90 (d, J = 9.7 Hz, 1H), 2.59-2.54 (m, 2H), 2.08 (dd, J = 8.0, 6.5 Hz, 2H), 1.86 (p, J = 7.0 Hz, 2H), 1.28 (d, J = 20.2 Hz, 3H), 1.20 (d, J = 6.8 Hz, 3H). |
| 170 | 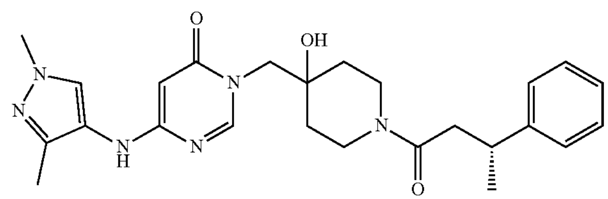 [SMILES: Cc1nn(C)cc1Nc1cc(=O)n(CC2(O)CCN(C(=O)C[C@@H](C)c3ccccc3)CC2)cn1] | (R)-6-((1,3-dimethyl-1H-pyrazol-4-yl)amino)-3-((4-hydroxy-1-(3-phenylbutanoyl)piperidin-4-yl)methyl)pyrimidin-4(3H)-one | 10 | 3.71 min, m/z = 465 | $^1$H NMR (400 MHz, DMSO-d$_6$): δ 8.29 (s, 1H), 8.03 (d, J = 10.4 Hz, 1H), 7.66 (s, 1H), 7.32-7.21 (m, 4H), 7.16 (td, J = 6.2, 5.7, 3.4 Hz, 1H), 5.03-4.93 (m, 2H), 3.98 (d, J = 12.4 Hz, 1H), 3.73 (s, 5H), 3.63 (t, J = 11.6 Hz, 1H), 3.19-3.11 (m, 2H), 2.89 (t, J = 10.0 Hz, 1H), 2.65-2.50 (m, 2H), 2.02 (s, 3H), 1.34 (d, J = 13.9 Hz, 2H), 1.27 (s, 2H), 1.20 (dd, J = 7.0, 1.5 Hz, 4H). |
| 171 | 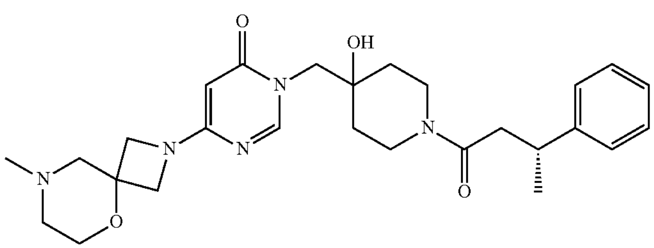 [SMILES: C[C@H](CC(=O)N1CCC(O)(Cn2cnc(N3CC4(CN(C)CCO4)C3)cc2=O)CC1)c1ccccc1] | (R)-3-((4-hydroxy-1-(3-phenylbutanoyl)piperidin-4-yl)methyl)-6-(8-methyl-5-oxa-2,8-diazaspiro[3.5]nonan-2-yl)pyrimidin-4(3H)-one | 10 | 2.94 min, m/z = 496 | $^1$H NMR (400 MHz, DMSO-d$_6$): δ 8.03 (d, J = 9.7 Hz, 1H), 7.32-7.21 (m, 4H), 7.21-7.12 (m, 1H), 4.96 (dd, J = 13.3, 2.5 Hz, 2H), 3.97 (dd, J = 12.6, 4.8 Hz, 1H), 3.88-3.71 (m, 6H), 3.61 (t, J = 4.8 Hz, 3H), 3.26-3.11 (m, 2H), 2.90 (d, J = 10.3 Hz, 2H), 2.65-2.50 (m, 2H), 2.46 (s, 2H), 2.27 (t, J = 4.6 Hz, 2H), 2.19 (s, 3H), 1.30 (s, 1H), 1.28-1.16 (m, 5H). |

-continued

| Ex. | Structure | Name | Gen. Proc. | LCMS R$_T$, m/z [M + H]$^+$ | $^1$H NMR (ppm) |
|---|---|---|---|---|---|
| 172 | 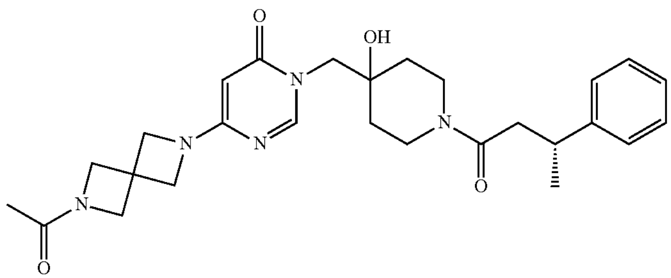 [SMILES: CC(=O)N1CC2(C1)CN(c1cc(=O)n(CC3(O)CCN(C(=O)C[C@@H](C)c4ccccc4)CC3)cn1)C2] | (R)-6-(6-acetyl-2,6-diazaspiro[3.3]heptan-2-yl)-3-((4-hydroxy-1-(3-phenylbutanoyl)piperidin-4-yl)methyl)pyrimidin-4(3H)-one | 10 | 3.57 min, m/z = 494 | $^1$H NMR (400 MHz, DMSO-d$_6$): δ 8.03 (d, J = 9.7 Hz, 1H), 7.31-7.22 (m, 4H), 7.20-7.13 (m, 1H), 4.92 (t, J = 2.0 Hz, 2H), 4.27 (s, 2H), 4.08 (s, 4H), 3.99 (s, 2H), 3.87-3.71 (m, 2H), 3.61 (d, J = 11.9 Hz, 1H), 3.23-3.10 (m, 2H), 2.89 (s, 1H), 2.56 (t, J = 5.8 Hz, 2H), 1.73 (s, 3H), 1.25 (s, 3H), 1.20 (d, J = 6.9 Hz, 3H). |
| 173 | 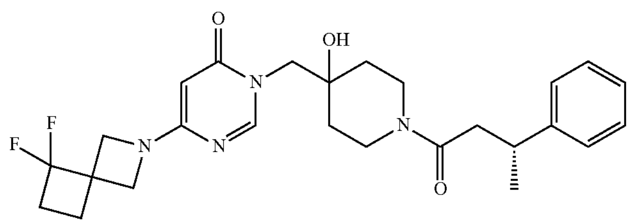 [SMILES: C[C@H](CC(=O)N1CCC(O)(Cn2cnc(N3CC4(CCC4(F)F)C3)cc2=O)CC1)c1ccccc1] | (R)-6-(5,5-difluoro-2-azaspiro[3.3]heptan-2-yl)-3-((4-hydroxy-1-(3-phenylbutanoyl)piperidin-4-yl)methyl)pyrimidin-4(3H)-one | 10 | 4.62 min, m/z = 487 | $^1$H NMR (400 MHz, DMSO-d$_6$): δ 8.05 (d, J = 9.6 Hz, 1H), 7.32-7.22 (m, 4H), 7.17 (t, J = 5.7 Hz, 1H), 5.01 (d, J = 2.5 Hz, 1H), 4.92 (d, J = 3.0 Hz, 1H), 4.20-4.07 (m, 2H), 4.05-3.94 (m, 1H), 3.90 (d, J = 9.5 Hz, 2H), 3.85-3.71 (m, 2H), 3.62 (s, 1H), 3.21-3.08 (m, 2H), 2.90 (d, J = 11.1 Hz, 1H), 2.56 (dt, J = 6.8, 3.2 Hz, 2H), 2.06 (t, J = 8.6 Hz, 2H), 1.28 (d, J = 21.1 Hz, 4H), 1.20 (d, J = 6.9 Hz, 3H). |
| 174 | 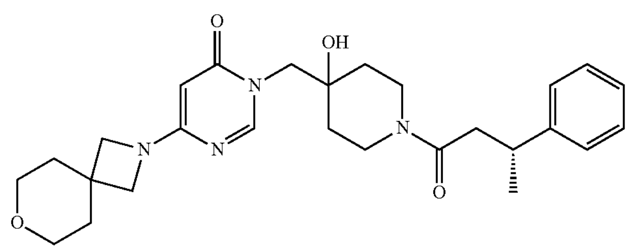 [SMILES: C[C@H](CC(=O)N1CCC(O)(Cn2cnc(N3CC4(CCOCC4)C3)cc2=O)CC1)c1ccccc1] | (R)-3-((4-hydroxy-1-(3-phenylbutanoyl)piperidin-4-yl)methyl)-6-(7-oxa-2-azaspiro[3.5]nonan-2-yl)pyrimidin-4(3H)-one | 10 | 4.01 min, m/z = 481 | $^1$H NMR (400 MHz, DMSO-d$_6$): δ 8.02 (d, J = 10.0 Hz, 1H), 7.33-7.22 (m, 4H), 7.20-7.11 (m, 1H), 4.92 (dd, J = 17.4, 2.6 Hz, 2H), 3.97 (d, J = 12.6 Hz, 1H), 3.86-3.57 (m, 7H), 3.53 (t, J = 5.2 Hz, 4H), 3.22-3.09 (m, 2H), 2.89 (s, 1H), 2.61-2.53 (m, 2H), 1.81-1.63 (m, 4H), 1.28 (d, J = 20.3 Hz, 3H), 1.20 (d, J = 6.9 Hz, 3H). |
| 175 | 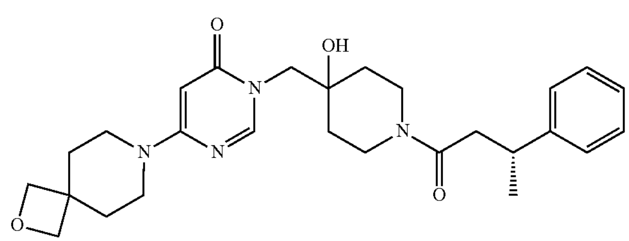 [SMILES: C[C@H](CC(=O)N1CCC(O)(Cn2cnc(N3CCC4(CC3)COC4)cc2=O)CC1)c1ccccc1] | (R)-3-((4-hydroxy-1-(3-phenylbutanoyl)piperidin-4-yl)methyl)-6-(2-oxa-7-azaspiro[3.5]nonan-7-yl)pyrimidin-4(3H)-one | 10 | 4.06 min, m/z = 481 | $^1$H NMR (400 MHz, DMSO-d$_6$): δ 8.03 (d, J = 10.1 Hz, 1H), 7.33-7.22 (m, 4H), 7.17 (td, J = 6.4, 5.7, 2.6 Hz, 1H), 5.46-5.33 (m, 1H), 4.97 (d, J = 2.8 Hz, 1H), 4.33 (s, 4H), 3.97 (d, J = 12.9 Hz, 1H), 3.88-3.69 (m, 2H), 3.62 (s, 1H), 3.51-3.40 (m, 4H), 3.22-3.09 (m, 1H), 2.90 (d, J = 9.6 Hz, 1H), 2.56 (dd, J = 6.7, 3.4 Hz, 2H), 1.88-1.71 (m, 4H), 1.28 (d, J = 20.1 Hz, 4H), 1.20 (d, J = 6.8 Hz, 3H). |

| Ex. | Structure | Name | Gen. Proc. | LCMS R$_T$, [M + H]$^+$ | $^1$H NMR (ppm) |
|---|---|---|---|---|---|
| 176 | 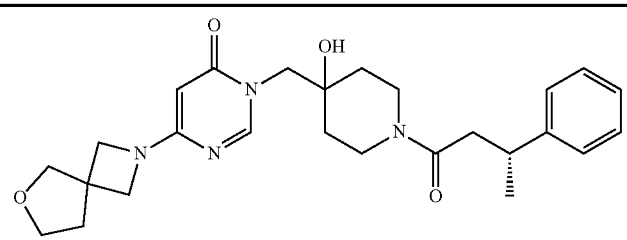 | (R)-3-((4-hydroxy-1-(3-phenylbutanoyl)piperidin-4-yl)methyl)-6-(6-oxa-2-azaspiro[3.4]octan-2-yl)pyrimidin-4(3H)-one | 10 | 3.88 min, m/z = 467 | $^1$H NMR (400 MHz, DMSO-d$_6$): δ 8.03 (d, J = 9.7 Hz, 1H), 7.32-7.21 (m, 4H), 7.21-7.13 (m, 1H), 4.93 (t, J = 2.7 Hz, 2H), 3.97 (dd, J = 12.9, 4.5 Hz, 1H), 3.91 (s, 3H), 3.84-3.68 (m, 6H), 3.31 (s, 28H), 3.23-3.11 (m, 2H), 2.89 (s, 1H), 2.56 (td, J = 5.7, 2.1 Hz, 2H), 2.13 (t, J = 7.0 Hz, 2H), 1.33-1.22 (m, 3H), 1.20 (d, J = 6.9 Hz, 4H). |
| 177 | 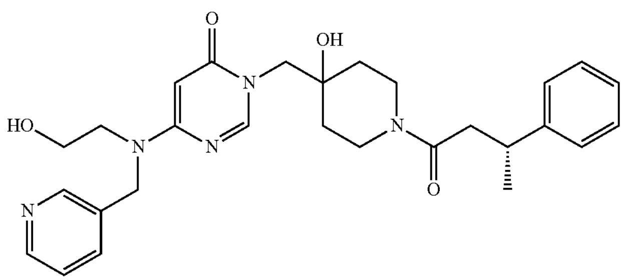 [SMILES: C[C@H](CC(=O)N1CCC(O)(Cn2cnc(N(CCO)Cc3cccnc3)cc2=O)CC1)c1ccccc1] | (R)-3-(3-phenylbutanoyl)piperidin-4-yl)methyl)-6-((2-hydroxyethyl)(pyridin-3-ylmethyl)amino)pyrimidin-4(3H)-one | 10 | 2.97 min, m/z = 506 | $^1$H NMR (400 MHz, DMSO-d$_6$): δ 8.54-8.37 (m, 2H), 8.06 (d, J = 9.9 Hz, 1H), 7.61 (dt, J = 8.0, 1.9 Hz, 1H), 7.40-7.31 (m, 1H), 7.26 (dd, J = 6.1, 3.0 Hz, 4H), 7.20-7.12 (m, 1H), 5.25 (m, 1H), 4.98 (s, 1H), 4.78 (s, 3H), 3.98 (d, J = 12.9 Hz, 1H), 3.88-3.69 (m, 2H), 3.69-3.44 (m, 3H), 3.16 (q, J = 8.6, 7.2 Hz, 1H), 2.96-2.83 (m, 1H), 2.56 (dd, J = 9.3, 3.6 Hz, 2H), 1.29 (d, J = 20.5 Hz, 4H), 1.23-1.16 (m, 3H). |
| 178 | 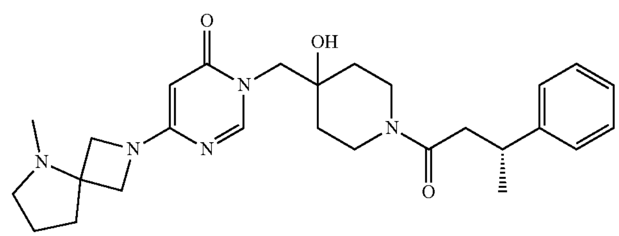 [SMILES: C[C@H](CC(=O)N1CCC(O)(Cn2cnc(N3CC4(CCCN4C)C3)cc2=O)CC1)c1ccccc1] | (R)-3-(3-phenylbutanoyl)piperidin-4-yl)methyl)-6-(5-methyl-2,5-diazaspiro[3.4]octan-2-yl)pyrimidin-4(3H)-one | 10 | 2.90 min, m/z = 480 | $^1$H NMR (400 MHz, DMSO-d$_6$): δ 8.02 (d, J = 10.0 Hz, 1H), 7.33-7.22 (m, 4H), 7.21-7.12 (m, 1H), 4.94 (dd, J = 7.9, 2.8 Hz, 2H), 4.09-3.92 (m, 3H), 3.90-3.56 (m, 5H), 3.24-3.09 (m, 2H), 2.89 (s, 1H), 2.62 (t, J = 7.1 Hz, 2H), 2.60-2.54 (m, 2H), 2.32 (s, 3H), 2.02 (dd, J = 9.2, 6.4 Hz, 2H), 1.75-1.59 (m, 2H), 1.28 (d, J = 20.3 Hz, 4H), 1.23-1.15 (m, 3H). |
| 179 | 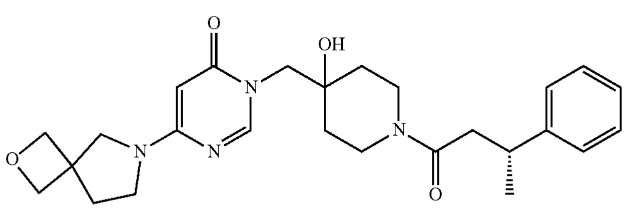 [SMILES: C[C@H](CC(=O)N1CCC(O)(Cn2cnc(N3CCC4(COC4)C3)cc2=O)CC1)c1ccccc1] | (R)-3-((4-hydroxy-1-(3-phenylbutanoyl)piperidin-4-yl)methyl)-6-(2-oxa-6-azaspiro[3.4]octan-6-yl)pyrimidin-4(3H)-one | 10 | 3.90 min, m/z = 467 | $^1$H NMR (400 MHz, DMSO-d$_6$): δ 8.03 (d, J = 10.2 Hz, 1H), 7.29-7.23 (m, 3H), 7.20-7.12 (m, 1H), 4.98 (dd, J = 14.9, 2.3 Hz, 2H), 4.56 (d, J = 6.0 Hz, 2H), 4.49 (d, J = 6.0 Hz, 2H), 3.97 (dd, J = 12.7, 4.5 Hz, 1H), 3.74 (d, J = 3.1 Hz, 1H), 3.68-3.57 (m, 2H), 3.16 (ddddt, J = 4.5, 2.0, 1.6, 1.0, 0.5 Hz, 1H), 2.89 (t, J = 10.9 Hz, 1H), 2.60-2.53 (m, 2H), 2.21 (t, J = 6.9 Hz, 2H), 1.28 (d, J = 19.7 Hz, 3H), 1.20 (d, J = 6.9 Hz, 3H). |

| Ex. | Structure | Name | Gen. Proc. | LCMS $R_T$, $[M+H]^+$ | $^1$H NMR (ppm) |
|---|---|---|---|---|---|
| 180 | 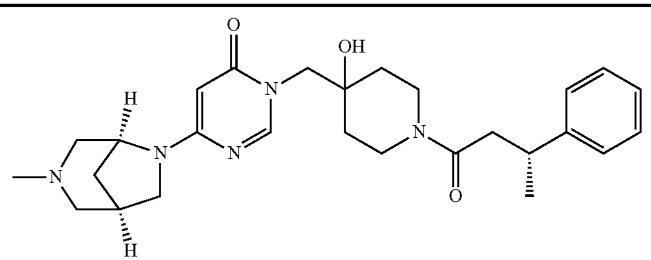 | 3-(4-hydroxy-1-((R)-3-phenylbutanoyl)piperidin-4-yl)methyl)-6-((1R,5S)-3-methyl-3,6-diazabicyclo[3.2.1]octan-6-yl)pyrimidin-4(3H)-one [first eluted by analytical SFC: $R_T$ = 1.14 min; single unknown stereoisomer] | 9 | 3.01 min, m/z = 480 | $^1$H NMR (400 MHz, DMSO-$d_6$): δ 8.01 (t, J = 10.5 Hz, 2H), 7.26 (dd, J = 6.2, 4.1 Hz, 6H), 7.16 (tdd, J = 6.6, 5.0, 2.5 Hz, 1H), 5.04 (d, J = 12.1 Hz, 2H), 4.92 (d, J = 2.5 Hz, 1H), 4.44 (s, 1H), 4.03-3.90 (m, 2H), 3.85-3.69 (m, 3H), 3.63 (t, J = 10.8 Hz, 2H), 3.45 (s, 2H), 3.39 (s, 2H), 3.29-3.11 (m, 4H), 3.07 (d, J = 9.8 Hz, 1H), 2.89 (dd, J = 14.0, 9.6 Hz, 3H), 2.75 (s, 2H), 2.65-2.51 (m, 4H), 2.15 (s, 7H), 1.98 (d, J = 10.8 Hz, 1H), 1.82 (s, 2H), 1.50 (dt, J = 36.1, 10.3 Hz, 2H), 1.28 (d, J = 17.4 Hz, 6H), 1.20 (d, J = 6.9 Hz, 5H). |
| 181 | 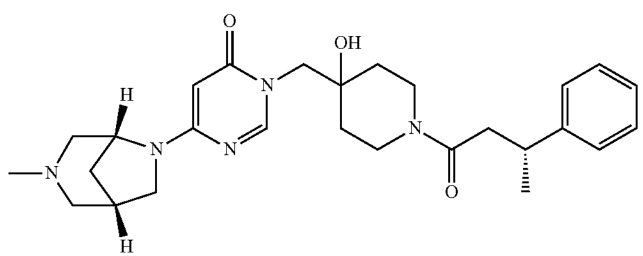 [SMILES: C[C@H](CC(=O)N1CCC(O)(Cn2cnc(N3C[C@H]4C[C@@H]3CN(C)C4)cc2=O)CC1)c1ccccc1] | 3-(4-hydroxy-1-((R)-3-phenylbutanoyl)piperidin-4-yl)methyl)-6-((1S,5R)-3-methyl-3,6-diazabicyclo[3.2.1]octan-6-yl)pyrimidin-4(3H)-one [second eluted by analytical SFC: $R_T$ = 1.56 min; single unknown stereoisomer] | 9 | 3.01 min, m/z = 480 | $^1$H NMR (400 MHz, DMSO-$d_6$): δ 8.01 (t, J = 10.8 Hz, 2H), 7.32-7.22 (m, 6H), 7.17 (ddt, J = 7.8, 5.5, 2.6 Hz, 2H), 5.09-4.99 (m, 2H), 4.93 (s, 1H), 4.44 (s, 1H), 4.03-3.58 (m, 6H), 3.45 (s, 3H), 3.39 (s, 6H), 3.24-3.10 (m, 4H), 3.07 (d, J = 9.9 Hz, 1H), 2.91 (q, J = 15.2, 10.5 Hz, 3H), 2.76 (d, J = 11.2 Hz, 1H), 2.65-2.51 (m, 7H), 2.15 (d, J = 8.4 Hz, 7H), 2.02-1.91 (m, 2H), 1.82 (s, 2H), 1.53 (d, J = 11.1 Hz, 2H), 1.24 (dd, J = 37.9, 13.4 Hz, 12H). |

Example 182: (R)-3-(4-(1-Aminocyclobutyl)phenyl)-6-((4-hydroxy-1-(3-phenylbutanoyl)piperidin-4-yl)methyl)-2-methyl-2H-pyrazolo[4,3-d]pyrimidin-7(6H)-one

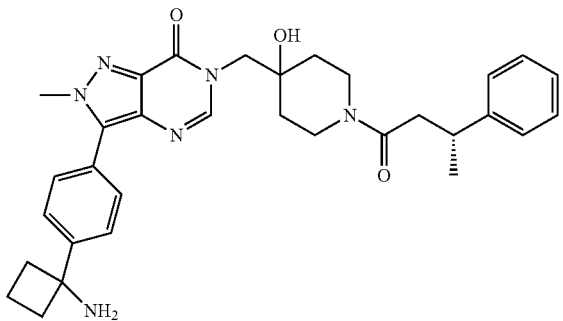 [SMILES: C[C@H](CC(=O)N1CCC(O)(Cn2cnc3c(-c4ccc(C5(N)CCC5)cc4)n(C)nc3c2=O)CC1)c1ccccc1]

Step 1: Benzyl 4-((3-(4-(1-((tert-butoxycarbonyl)amino)cyclobutyl)phenyl)-2-methyl-7-oxo-2H-pyrazolo[4,3-d]pyrimidin-6(7H)-yl)methyl)-4-hydroxypiperidine-1-carboxylate A stirred suspension of benzyl 4-((3-bromo-2-methyl-7-oxo-2H-pyrazolo[4,3-d]pyrimidin-6(7H)-yl)methyl)-4-hydroxypiperidine-1-carboxylate (200 mg, 0.420 mmol), (4-(1-((tert-butoxycarbonyl)amino)cyclobutyl)phenyl)boronic acid (367 mg, 1.26 mmol) and potassium phosphate, tribasic (535 mg, 2.52 mmol) in 1,4-dioxane (6 mL) and water (1.2 mL) was de-gassed with nitrogen for 5 min. PdCl$_2$(dppf).DCM (8.6 mg, 10.50 μmol) was added and the reaction mixture de-gassed with nitrogen for 5 min before heating to 90° C. and stirring for 2 h. After cooling, the solvents were removed in vacuo and the remaining mixture was partitioned between saturated ammonium chloride (aq) solution (20 mL) and dichloromethane (40 mL). The layers were separated and the aqueous phase extracted with dichloromethane (3×20 mL). The combined organic phases were dried (phase separator), filtered and concentrated in vacuo. The resulting residue was purified by flash chromatography (0-100% EtOAc in cyclohexane) to afford the title compound (110 mg, 41%). LCMS (Method A): R$_T$=1.66 min, m/z=643 [M+H]$^+$.

Step 2 tert-Butyl (1-(4-(6-((4-hydroxypiperidin-4-yl)methyl)-2-methyl-7-oxo-6,7-dihydro-2H-pyrazolo[4,3-d]pyrimidin-3-yl)phenyl)cyclobutyl)carbamate A stirred solution of benzyl 4-((3-(4-(1-((tert-butoxycarbonyl)amino)cyclobutyl)phenyl)-2-methyl-7-oxo-2H-pyrazol[4,3-d]pyrimidin-6(7H)-yl)methyl)-4-hydroxypiperidine-1-carboxylate (110 mg, 0.172 mmol) in ethanol (2 mL) was heated to reflux. 10% w/w palladium on carbon (18.3 mg, 0.017 mmol) was added followed by portionwise addition of ammonium formate (325 mg, 5.15 mmol) and the suspension was stirred for 1 h. The suspension was filtered through Celite® washing with hot methanol (4×20 mL). The organic solvent was removed in vacuo. The resulting residue was purified by flash chromatography using a KP-NH column (compound was loaded using ca. 3 mL of 1:1 DCM/triethylamine, 0-100% DCM in cyclohexane; then 0-30% methanol in DCM) to afford the title compound (85.5 mg, 98%). LCMS (Method A): R$_T$=0.96 min, m/z=509 [M+H]$^+$.

Step 3: (R)-tert-Butyl (1-(4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)phenyl)cyclobutyl) carbamate To a stirred solution of tert-butyl (1-(4-(6-((4-hydroxypiperidin-4-yl)methyl)-2-methyl-7-oxo-6,7-dihydro-2H-pyrazolo[4,3-d]pyrimidin-3-yl)phenyl)cyclobutyl)carbamate (85.5 mg, 0.168 mmol) and diisopropylethylamine (0.060 mL, 0.336 mmol) in anhydrous DCM (4 mL) was added (R)-3-phenylbutanoic acid (27.6 mg, 0.168 mmol) then HATU (77 mg, 0.202 mmol) and the solution stirred for 3 h at RT. The mixture was washed with saturated sodium bicarbonate (aq) solution (10 mL). The aqueous phase was separated and extracted with dichloromethane (3×7 mL). The combined organic phase was dried (phase separator) and concentrated in vacuo. The resulting residue was purified by flash chromatography (0-100% EtOAc in cyclohexane; then 0-5% methanol in EtOAc) to afford the title compound (45.7 mg, 42%). LCMS (Method A): R$_T$=1.60 min, m/z=655 [M+H]$^+$.

Step 4: (R)-3-(4-(1-Aminocyclobutyl)phenyl)-6-((4-hydroxy-1-(3-phenylbutanoyl)piperidin-4-yl)methyl)-2-methyl-2H-pyrazolo[4,3-d]pyrimidin-7(6H)-one To a stirring solution of (R)-tert-butyl (1-(4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)phenyl)cyclobutyl)carbamate (45.7 mg, 0.070 mmol) in anhydrous DCM (2 ml) was added trifluoroacetic acid (0.5 mL, 0.070 mmol) and the solution stirred for 10 min. An SCX-2 cartridge (5 g) was pretreated with 20% v/v methanol in dichloromethane (50 ml). The reaction mixture was loaded directly, using DCM (3×1 mL) to load residual material from the reaction flask. After 5 min, the column was flushed with 20% v/v methanol in dichloromethane (50 mL), followed by 20% v/v (7M ammonia in methanol) in dichloromethane (50 mL). The ammonia containing fraction was reduced in vacuo. The residue was dissolved in methanol (1 mL) and water (8 mL) and freeze-dried to afford the title compound (36.8 mg, 95%). LCMS (Method A): R$_T$=0.89 min, m/z=555 [M+H]$^+$. $^1$H NMR (400 MHz, DMSO-d$_6$): δ 7.98 (d, 1H), 7.62-7.71 (m, 4H), 7.21-7.31 (m, 4H), 7.12-7.20 (m, 1H), 4.87 (d, 1H), 4.11 (s, 3H), 3.85-4.08 (m, 3H), 3.59-3.71 (m, 1H), 3.12-3.28 (m, 2H), 2.81-2.94 (m, 1H), 2.52-2.80 (m, 4H), 2.40-2.47 (m, 2H), 2.09-2.23 (m, 2H), 1.95-2.09 (m, 1H), 1.64-1.78 (m, 1H), 1.25-1.59 (m, 4H), 1.21 (d, 3H).

Example 183: 3-((1-(3-Cyclobutylpropanoyl)-4-hydroxypiperidin-4-yl)methyl)-6-((2-(pyrrolidin-1-yl)ethyl)amino)pyrimidin-4(3H)-one

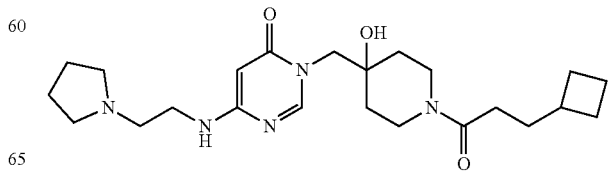

Step 1: 3-((4-Hydroxypiperidin-4-yl)methyl)-6-((2-(pyrrolidin-1-yl)ethyl)amino)pyrimidin-4(3H)-one A solution of tert-butyl 4-((4-chloro-6-oxopyrimidin-1(6H)-yl)methyl)-4-hydroxypiperidine-1-carboxylate (2.83 g, 8.23 mmol) and 1-(2-aminoethyl)pyrrolidine (5.22 mL, 41.2 mmol) in 1,4-dioxane (10 mL) were heated at 140° C. using microwave irradiation for 1 h. The reaction mixture was diluted with saturated sodium bicarbonate$_{(aq)}$ (200 mL) and the mixture was extracted using DCM (3×60 mL). The combined organic phases were dried (phase separator), concentrated in vacuo and the remaining residue was stirred in 1:1 DCM/TFA (20 mL). After 5 min, the mixture was concentrated in vacuo and the remaining residue was purified using 2 pre-equilibrated 10 g Biotage SCX-2 cartridges in parallel (10% MeOH in DCM; then 4:1 DCM/7 N NH$_3$ in MeOH). The basic washes were concentrated in vacuo to give the title compound (1.52 g, 57%) as an orange foam. LCMS (Method A): R$_T$=0.27 min, m/z=322 [M+H]$^+$.

Step 2: 3-((1-(3-Cyclobutylpropanoyl)-4-hydroxypiperidin-4-yl)methyl)-6-((2-(pyrrolidin-1-yl)ethyl)amino)pyrimidin-4(3H)-one General procedure 4 using 3-((4-hydroxypiperidin-4-yl)methyl)-6-((2-(pyrrolidin-1-yl)ethyl)amino)pyrimidin-4(3H)-one (50 mg, 0.156 mmol), 3-cyclobutylpropanoic acid (24 mg, 0.187 mmol), HATU (71 mg, 0.187 mmol), DIPEA (109 µL, 0.622 mmol) and DCM (3 mL) gave the title compound (46 mg, 68%) as a colourless solid after freeze-drying. LCMS (Method A): R$_T$=0.67 min, m/z=432 [M+H]$^+$. $^1$H NMR (400 MHz, DMSO-d$_6$): δ 7.98 (s, 1H), 6.80 (br. s, 1H), 5.05 (s, 1H), 5.02 (s, 1H), 3.99 (ddd, 1H), 3.78 (dd, 2H), 3.58 (ddd, 1H), 3.29-3.06 (m, 3H), 2.93 (ddd, 1H), 2.54 (t, 2H), 2.48-2.40 (m, 4H), 2.23 (dd, 1H), 2.16 (t, 2H), 2.03-1.93 (m, 2H), 2.84-1.71 (m, 2H), 1.71-1.61 (m, 4H), 1.61-1.25 (m, 8H).

Example 184: 3-((1-(2,2-Dicyclobutylacetyl)-4-hydroxypiperidin-4-yl)methyl)-6-((2-(pyrrolidin-1-yl)ethyl)amino)pyrimidin-4(3H)-one

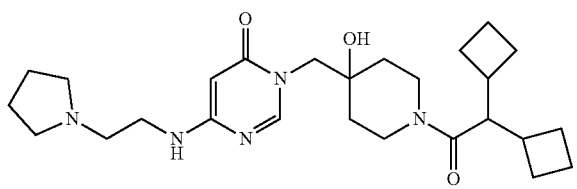 [SMILES: O=C(C(C1CCC1)C1CCC1)N1CCC(O)(Cn2cnc(NCCN3CCCC3)cc2=O)CC1]

General procedure 4 using 3-((4-hydroxypiperidin-4-yl)methyl)-6-((2-(pyrrolidin-1-yl)ethyl)amino)pyrimidin-4(3H)-one (50 mg, 0.156 mmol), 2,2-dicyclobutylacetic acid (31 mg, 0.187 mmol), HATU (71 mg, 0.187 mmol), DIPEA (109 µL, 0.622 mmol) and DCM (3 mL) gave the title compound (51 mg, 69%) as a colourless solid after freeze-drying. LCMS (Method A): R$_T$=0.85 min, m/z=472 [M+H]$^+$. $^1$H NMR (400 MHz, DMSO-d$_6$): δ 7.99 (s, 1H), 6.80 (br. s, 1H), 5.05 (s, 1H), 5.02 (s, 1H), 4.01 (ddd, 1H), 3.84 (ddd, 1H), 3.79 (dd, 2H), 3.37-3.27 (m, 1H signal partially obscured by HDO)), 3.17 (br. s, 2H), 3.02-2.93 (m, 1H), 2.85 (t, 1H), 2.58-2.31 (m, 9H (signals partially obscured by DMSO)), 1.94-1.21 (m, 19H).

Example 185: (R)-6-((4-Hydroxy-1-(3-phenylbutanoyl)piperidin-4-yl)methyl)-3-phenyl-3H-[1,2,3]triazolo[4,5-d]pyrimidin-7(6H)-one

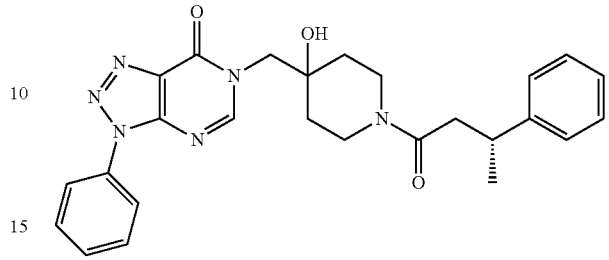

Step 1: tert-Butyl 4-hydroxy-4-((7-oxo-3-phenyl-3H-[1,2,3]triazolo[4,5-d]pyrimidin-6(7H)-yl)methyl)piperidine-1-carboxylate A solution of 3-phenyl-3H-[1,2,3]triazolo[4,5-d]pyrimidin-7(6H)-one (1.00 g, 4.71 mmol) (commercially available) and Epoxide 1 (1.01 g, 4.72 mmol) in DMF (10 mL) was treated with DIPEA (1.24 mL, 7.08 mmol) and heated to 80° C. After 16 h, the reaction mixture was allowed to cool to RT, treated with a second portion of Epoxide 1 (502 mg, 2.35 mmol) and heated to 80° C. After 3 days, the cooled mixture was diluted with water and extracted twice into ethyl acetate. The combined organic phases were washed with water and brine, dried (Na$_2$SO$_4$), filtered through a Celite® pad and concentrated in vacuo to afford a beige solid (2.25 g). The residue was absorbed onto silica gel and purified by flash chromatography (1-20% MeOH in DCM) to afford a white solid (1.82 g). This was recrystallized from hot ethanol to afford the title compound (1.38 g, 69%) as a white crystalline solid. $^1$H NMR (400 MHz, DMSO-d$_6$): δ 8.48 (s, 1H), 8.08-7.99 (m, 2H), 7.68 (dd, J=8.5, 7.1 Hz, 2H), 7.63-7.54 (m, 1H), 4.91 (s, 1H), 4.09 (s, 2H), 3.68 (d, J=13.2 Hz, 2H), 3.05 (s, 2H), 1.51 (ddd, J=13.3, 11.2, 4.6 Hz, 2H), 1.40 (s, 9H), 1.43-1.36 (m, 2H). MS (ESI): m/z=427 [M+H]$^+$.

Step 2: 6-((4-Hydroxypiperidin-4-yl)methyl)-3-phenyl-3H-[1,2,3]triazolo[4,5-d]pyrimidin-7(6H)-one A suspension of tert-butyl 4-hydroxy-4-((7-oxo-3-phenyl-3H-[1,2,3]triazolo[4,5-d]pyrimidin-6(7H)-yl)methyl)piperidine-1-carboxylate (1.11 g, 2.60 mmol) in DCM (30 mL) was treated with TFA (6 mL, 80 mmol) and the resulting solution was stirred at RT. After 30 min, the solvents were removed in vacuo to a give white foam. The residue was dissolved in water, treated with saturated sodium bicarbonate (aq) solution and filtered to recover the material as the free base that was dried under high vacuum to afford the title compound (703 mg, 83%) as a white solid. $^1$H NMR (400 MHz, DMSO-d$_6$): δ 8.49 (s, 1H), 8.08-7.99 (m, 2H), 7.73-7.63 (m, 2H), 7.63-7.54 (m, 1H), 4.92 (s, 1H), 4.10 (s, 2H), 2.95-2.79 (m, 4H), 1.61 (ddd, J=14.7, 10.5, 4.7 Hz, 2H), 1.45 (d, J=13.6 Hz, 2H). MS (ESI) m/z: 327 [MH+].

Step 3: (R)-6-((4-Hydroxy-1-(3-phenylbutanoyl)piperidin-4-yl)methyl)-3-phenyl-3H-[1,2,3]triazolo[4,5-d]pyrimidin-7(6H)-one General procedure 11 using 6-((4-hydroxypiperidin-4-yl)methyl)-3-phenyl-3H-[1,2,3]triazolo[4,5-d]pyrimidin-7

(6H)-one (61.7 mg, 0.189 mmol), (R)-3-phenylbutanoic acid (45.1 mg, 0.275 mmol), HATU (91.5 mg, 0.238 mmol), DIPEA (100 µL, 0.570 mmol) and DMF (1.0 mL), followed by purification using preparative HPLC (Method B) and SFC to give the title compound (18.9 mg, 21%) as a white solid. $^1$H NMR (400 MHz, DMSO-d$_6$): δ 8.47 (d, J=8.4 Hz, 1H), 8.04 (d, J=7.3 Hz, 2H), 7.68 (t, J=7.9 Hz, 2H), 7.58 (t, J=7.4 Hz, 1H), 7.33-7.22 (m, 4H), 7.20-7.12 (m, 1H), 4.92 (s, 1H), 4.17-3.99 (m, 3H), 3.67 (s, 1H), 3.32-3.10 (m, 2H), 2.87 (t, J=11.4 Hz, 1H), 2.68-2.52 (m, 2H), 1.61-1.23 (m, 4H), 1.21 (d, J=6.9 Hz, 3H). MS (ESI): m/z=473 [M+H]$^+$.

Example 186: 6-((1-(3-Cyclobutylpropanoyl)-4-hydroxypiperidin-4-yl)methyl)-3-phenyl-3H-[1,2,3]triazolo[4,5-d]pyrimidin-7(6H)-one

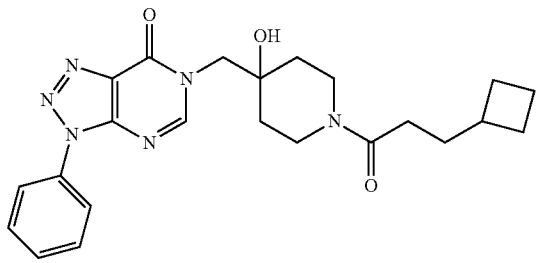 [SMILES: O=C(CCC1CCC1)N1CCC(O)(Cn2cnc3c(nnn3-c3ccccc3)c2=O)CC1]

General procedure 11 using 6-((4-hydroxypiperidin-4-yl)methyl)-3-phenyl-3H-[1,2,3]triazolo[4,5-d]pyrimidin-7(6H)-one and 3-cyclobutylpropanoic acid was performed similarly to the procedure outlined in Example 185 to give the title compound (16% yield). $^1$H NMR (400 MHz, DMSO-d$_6$): δ 8.49 (s, 1H), 8.04 (d, J=7.3 Hz, 2H), 7.68 (t, J=7.8 Hz, 2H), 7.58 (t, J=7.4 Hz, 1H), 4.95 (s, 1H), 4.10 (m, 3H), 3.63 (d, J=13.7 Hz, 1H), 3.29-3.19 (m, 1H), 2.91 (t, J=10.6 Hz, 1H), 2.30-2.14 (m, 3H), 2.04-1.93 (m, 2H), 1.86-1.70 (m, 2H), 1.63-1.37 (m, 8H). MS (ESI): m/z=437 [M+H]$^+$.

Example 187: 6-((1-(3,3-Dicyclopropylpropanoyl)-4-hydroxypiperidin-4-yl)methyl)-3-phenyl-3H-[1,2,3]triazolo[4,5-d]pyrimidin-7(6H)-one

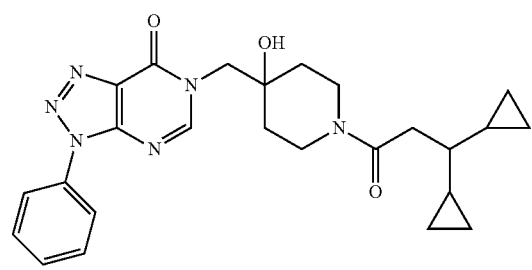 [SMILES: O=C(CC(C1CC1)C1CC1)N1CCC(O)(Cn2cnc3c(nnn3-c3ccccc3)c2=O)CC1]

General procedure 11 using 6-((4-hydroxypiperidin-4-yl)methyl)-3-phenyl-3H-[1,2,3]triazolo[4,5-d]pyrimidin-7(6H)-one and 3,3-dicyclopropylpropanoic acid was performed similarly to the procedure outlined in Example 185 to give the title compound (30% yield). $^1$H NMR (400 MHz, DMSO-d$_6$): δ 8.49 (s, 1H), 8.04 (d, J=7.4 Hz, 2H), 7.68 (t, J=7.8 Hz, 2H), 7.59 (t, J=7.4 Hz, 1H), 4.96 (s, 1H), 4.18-4.03 (m, 3H), 3.76 (br d, J=13.5 Hz, 1H), 3.38-3.24 (m, 1H), 2.99-2.87 (m, 1H), 2.41 (d, J=6.1 Hz, 2H), 1.65-1.38 (m, 4H), 0.76-0.59 (m, 3H), 0.42-0.23 (m, 4H), 0.23-0.13 (m, 2H), 0.12-0.02 (m, 2H). MS (ESI): m/z=463 [M+H]$^+$.

Example 188: (R)-1-((4-Hydroxy-1-(3-phenylbutanoyl)piperidin-4-yl)methyl)-8-methyl-9-phenyl-1H-purin-6(9H)-one

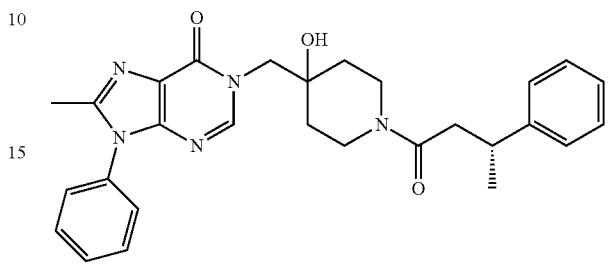

Step 1: 6-Chloro-8-methyl-9-phenyl-9H-purine

A mixture of 6-chloro-N$^4$-phenylpyrimidine-4,5-diamine (400 mg, 1.81 mmol), trimethyl orthoacetate (0.461 mL, 3.63 mmol), 3 M HCl$_{(aq)}$ (10 µL, 0.030 mmol) and EtOH (3.6 mL) were heated at 150° C. using microwave irradiation for 20 min, followed by 175° C. for 5 min. Further trimethyl orthoacetate (0.461 mL, 3.63 mmol) and 3 M HCl$_{(aq)}$ (10 µL, 0.030 mmol) were added and the reaction was further heated at 175° C. for 2 h, followed by 200° C. for 40 min using microwave irradiation. The reaction mixture was concentrated in vacuo and the residue was dissolved in DCM (30 mL) before being washed with saturated NaHCO$_{3(aq)}$ (40 mL), the aqueous phase was extracted with DCM (2×30 mL), the combined organic phases were dried (phase separator), concentrated in vacuo, and the residue purified by flash chromatography (80 g Grace silica, 0-100% EtOAc in cyclohexane) to give the title compound (230 mg, 51%) as an orange solid. LCMS (Method A): R$_T$=1.05 min, m/z=245, 247 [M+H]$^+$.

Step 2: 8-Methyl-9-phenyl-1H-purin-6(9H)-one Hydrochloride

A solution of 6-chloro-8-methyl-9-phenyl-9H-purine (230 mg, 0.940 mmol) in 3 M HCl$_{(aq)}$ (1 mL, 32.9 mmol) and 1,4-dioxane (3 mL) was heated at 120° C. using microwave irradiation for 30 min. The reaction mixture was concentrated in vacuo, the residue was azeotroped using MeOH and the material was dried at 100° C. under high vacuum to give title compound (232 mg, 94%) as a light beige solid. LCMS (Method A): R$_T$=1.05 min, m/z=227 [M+H]$^+$.

Step 3: tert-Butyl 4-hydroxy-4-((8-methyl-6-oxo-9-phenyl-6,9-dihydro-1H-purin-1-yl)methyl)piperidine-1-carboxylate General procedure 1 using Epoxide 1 (375 mg, 1.76 mmol), 8-methyl-9-phenyl-1H-purin-6(9H)-one hydrochloride (231 mg, 0.879 mmol), Cs$_2$CO$_3$ (602 mg, 1.847 mmol) and DMF (2.9 mL) gave the title compound (329 mg, 85%) as pale yellow solid. LCMS (Method A): R$_T$=1.38 min, m/z=440 [M+H]$^+$.

Step 4: 1-((4-Hydroxypiperidin-4-yl)methyl)-8-methyl-9-phenyl-1H-purin-6(9H)-one A solution of tert-butyl 4-hydroxy-4-((8-methyl-6-oxo-9-phenyl-6,9-dihydro-1H-purin-1-yl)methyl)piperidine-1-carboxylate (323 mg, 0.735 mmol) in DCM (2 mL) and TFA (2 mL) was stirred for 10 min before the reaction was purified using a 5 g SCX-2 cartridge (10% MeOH in DCM; then 20% 7 M in $NH_3$ in MeOH in DCM). The basic phases were combined and concentrated to give the title compound (230 mg, 92%) as a pale yellow solid. LCMS (Method A): $R_T$=0.55 min, m/z=340 $[M+H]^+$.

Step 5: (R)-1-((4-Hydroxy-1-(3-phenylbutanoyl)piperidin-4-yl)methyl)-8-methyl-9-phenyl-1H-purin-6(9H)-one General procedure 4 using 1-((4-hydroxypiperidin-4-yl)methyl)-8-methyl-9-phenyl-1H-purin-6(9H)-one (50 mg, 0.147 mmol), (R)-3-phenylbutanoic acid (29 mg, 0.177 mmol), HATU (67 mg, 0.177 mmol), DIPEA (103 µL, 0.589 mmol) and DCM (3 mL) gave the title compound (63 mg, 88%) as a colourless solid after freeze-drying. LCMS (Method A): $R_T$=1.18 min, m/z=486 $[M+H]^+$. $^1$H NMR (400 MHz, DMSO-$d_6$): δ 8.15-8.09 (m, 1H), 7.65-7.48 (m, 5H), 7.31-7.23 (m, 4H), 7.20-7.12 (m, 1H), 4.88-4.84 (m, 1H), 4.11-3.89 (m, 3H), 3.72-3.58 (m, 1H), 3.29-3.10 (m, 2H), 2.93-2.82 (m, 1H), 2.69-2.50 (m, 2H), 2.35 (s, 3H), 1.58-1.23 (m, 4H), 1.21 (d, 3H).

Example 189: (R)-1-((4-Hydroxy-1-(4,4,4-trifluoro-3-phenylbutanoyl)piperidin-4-yl)methyl)-8-methyl-9-phenyl-1H-purin-6(9H)-one

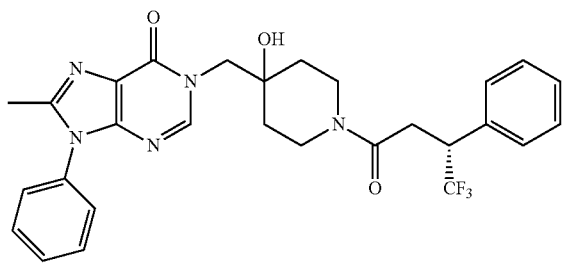 [SMILES: Cc1nc2c(=O)n(CC3(O)CCN(C(=O)C[C@H](c4ccccc4)C(F)(F)F)CC3)cnc2n1-c1ccccc1]

General procedure 4 using 1-((4-hydroxypiperidin-4-yl)methyl)-8-methyl-9-phenyl-1H-purin-6(9H)-one (50 mg, 0.147 mmol), (R)-4,4,4-trifluoro-3-phenylbutanoic acid (39 mg, 0.177 mmol), HATU (67 mg, 0.177 mmol), DIPEA (103 µL, 0.589 mmol) and DCM (3 mL) gave the title compound (39 mg, 48%) as a colourless solid after freeze-drying. LCMS (Method A): $R_T$=1.29 min, m/z=540 $[M+H]^+$. $^1$H NMR (400 MHz, DMSO-$d_6$): δ 8.15-8.09 (m, 1H), 7.65-7.48 (m, 5H), 7.45-7.28 (m, 5H), 4.89 (s, 1H), 4.17-3.88 (m, 4H), 3.83-3.70 (m, 1H), 3.30-3.10 (m, 2H), 3.02-2.78 (m, 2H), 2.35 (s, 3H), 1.66-1.20 (m, 4H).

Example 190: 1-((1-(3,3-Dicyclopropylpropanoyl)-4-hydroxypiperidin-4-yl)methyl)-8-methyl-9-phenyl-1H-purin-6(9H)-one

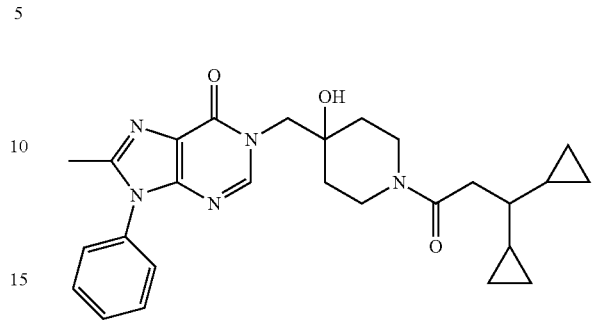

General procedure 4 using 1-((4-hydroxypiperidin-4-yl)methyl)-8-methyl-9-phenyl-1H-purin-6(9H)-one (50 mg, 0.147 mmol), 3,3-dicyclopropylpropanoic acid (27 mg, 0.177 mmol), HATU (67 mg, 0.177 mmol), DIPEA (103 µL, 0.589 mmol) and DCM (3 mL) gave the title compound (59 mg, 83%) as a colourless solid after freeze-drying. LCMS (Method A): $R_T$=1.18 min, m/z=476 $[M+H]^+$. $^1$H NMR (400 MHz, DMSO-$d_6$): δ 8.15 (s, 1H), 7.65-7.48 (m, 5H), 4.91 (s, 1H), 4.13-3.98 (m, 3H), 3.79-3.68 (m, 1H), 3.35-3.24 (m, 1H signal obscured by HDO)), 3.00-2.89 (m, 1H), 2.46-2.37 (m, 2H), 2.35 (s, 3H), 1.60-1.31 (m, 4H), 0.75-0.59 (m, 3H), 0.42-0.33 (m, 2H), 0.32-0.24 (m, 2H), 0.23-0.14 (m, 2H), 0.10-0.01 (m, 2H).

Example 191: 6-((4-Hydroxy-1-(1-methylcyclopropanecarbonyl)piperidin-4-yl)methyl)-2-methyl-3-phenyl-2H-pyrazolo[4,3-d]pyrimidin-7(6H)-one

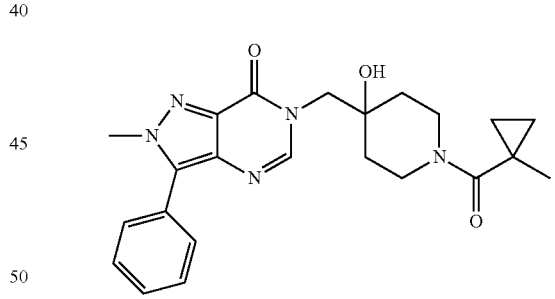

General procedure 4 using 6-((4-hydroxypiperidin-4-yl)methyl)-2-methyl-3-phenyl-2H-pyrazolo[4,3-d]pyrimidin-7(6H)-one (50 mg, 0.147 mmol), 1-methylcyclopropanecarboxylic acid (22 mg, 0.221 mmol), HATU (84 mg, 0.221 mmol), DIPEA (103 µL, 0.589 mmol) and DCM (3 mL) gave the title compound (53 mg, 85%) as a colourless solid after freeze-drying. LCMS (Method A): $R_T$=0.95 min, m/z=422 $[M+H]^+$. $^1$H NMR (400 MHz, DMSO-$d_6$): δ 8.01 (s, 1H), 7.74-7.69 (m, 2H), 7.62-7.56 (m, 2H), 7.55-7.49 (m, 1H), 4.91 (s, 1H), 4.11 (s, 3H), 4.01 (s, 2H), 4.00-3.96 (m, 1H), 3.96-3.91 (m, 1H), 3.28-3.03 (br. m, 2H), 1.60-1.38 (m, 4H), 1.21 (s, 3H), 0.77 (dd, 2H), 0.52 (dd, 2H).

Example 192: 6-((4-Hydroxy-1-(oxazole-5-carbonyl)piperidin-4-yl)methyl)-2-methyl-3-phenyl-2H-pyrazolo[4,3-d]pyrimidin-7(6H)-one

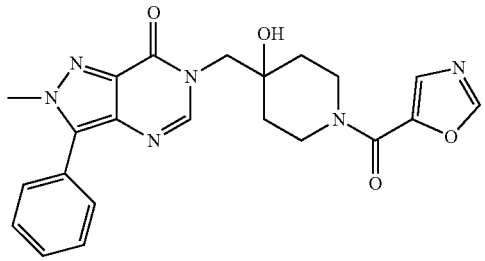 [SMILES: Cn1nc2c(=O)n(CC3(O)CCN(C(=O)c4cnco4)CC3)cnc2c1-c1ccccc1]

General procedure 4 using 6-((4-hydroxypiperidin-4-yl)methyl)-2-methyl-3-phenyl-2H-pyrazolo[4,3-d]pyrimidin-7(6H)-one (50 mg, 0.147 mmol), oxazole-5-carboxylic acid (25 mg, 0.221 mmol), HATU (84 mg, 0.221 mmol), DIPEA (103 μL, 0.589 mmol) and DCM (3 mL) gave the title compound (40 mg, 62%) as a colourless solid after freeze-drying. LCMS (Method A): $R_T$=0.81 min, m/z=435 [M+H]$^+$. $^1$H NMR (400 MHz, DMSO-d$_6$): δ 8.53 (s, 1H), 8.02 (s, 1H), 7.74-7.70 (m, 2H), 7.67 (s, 1H), 7.62-7.75 (m, 2H), 7.55-7.49 (m, 1H), 5.01 (s, 1H), 4.21-3.84 (br. m, 2H), 4.11 (s, 3H), 4.04 (s, 2H), 3.45 (br. s, 1H), 3.17 (br. s, 1H), 1.71-1.56 (m, 2H), 1.54-1.44 (m, 2H).

Example 193: 6-((1-(3,3-Dicyclopropylpropanoyl)-4-hydroxypiperidin-4-yl)methyl)-2-methyl-3-phenyl-2H-pyrazolo[4,3-d]pyrimidin-7(6H)-one

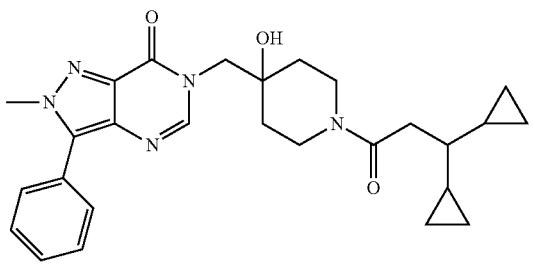 [SMILES: Cn1nc2c(=O)n(CC3(O)CCN(C(=O)CC(C4CC4)C4CC4)CC3)cnc2c1-c1ccccc1]

General procedure 4 using 6-((4-hydroxypiperidin-4-yl)methyl)-2-methyl-3-phenyl-2H-pyrazolo[4,3-d]pyrimidin-7(6H)-one (50 mg, 0.147 mmol), 3,3-dicyclopropylpropanoic acid (34 mg, 0.221 mmol), HATU (84 mg, 0.221 mmol), DIPEA (103 μL, 0.589 mmol) and DCM (3 mL) gave the title compound (55 mg, 78%) as a colourless solid after freeze-drying. LCMS (Method A): $R_T$=1.24 min, m/z=476 [M+H]$^+$. $^1$H NMR (400 MHz, DMSO-d$_6$): δ 8.01 (s, 1H), 7.76-7.67 (m, 2H), 7.62-7.56 (m, 2H), 7.55-7.49 (m, 1H), 4.91 (s, 1H), 4.15-4.04 (m, 1H), 4.11 (s, 3H), 4.00 (dd, 2H), 3.74 (ddd, 1H), 3.37-3.25 (m, 1H (signal obscured by HDO)), 2.94 (ddd, 1H), 2.46-2.34 (m, 2H), 1.60-1.36 (m, 4H), 0.76-0.58 (m, 3H), 0.42-0.23 (m, 4H), 0.22-0.14 (m, 2H), 0.11-0.01 (m, 2H).

Example 194: (R)-Ethyl 4-(6-((4-hydroxy-1-(3-phenyl butanoyl)piperidin-4-yl)methyl)-2-methyl-7-oxo-6,7-dihydro-2H-pyrazolo[4,3-d]pyrimidin-3-yl)benzylcarbamate

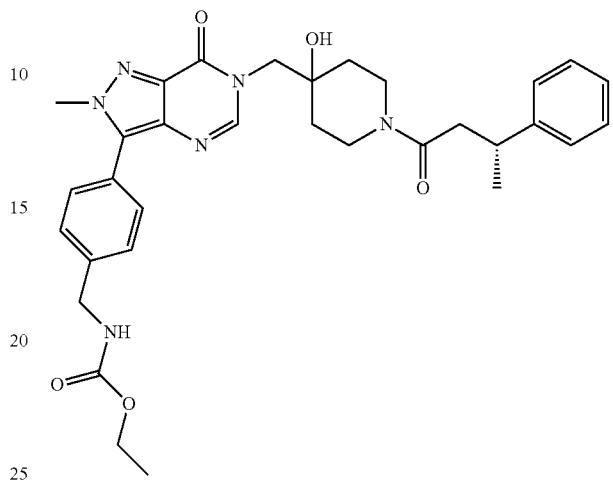

To stirred solution of (R)-3-(4-(aminomethyl)phenyl)-6-((4-hydroxy-1-(3-phenylbutanoyl)piperidin-4-yl)methyl)-2-methyl-2H-pyrazolo[4,3-d]pyrimidin-7(6H)-one (50 mg, 0.097 mmol) in DCM (1 mL) were added NEt$_3$ (27 μL, 0.194 mmol) and ethyl chloroformate (18 μL, 0.194 mmol). After 30 min, the reaction was quenched by the addition of saturated NaHCO$_{3(aq)}$ (15 mL) and the mixture extracted with DCM (3×10 mL) using a phase separator. The combined organic phases were concentrated and the residue was purified by flash chromatography (12 g GraceResolv silica, 0-20% MeOH in DCM) to give the title compound (45 mg, 80%) as a colourless solid after lyophilisation. LCMS (Method A): $R_T$=1.22 min, m/z=587 [M+H]$^+$. $^1$H NMR (400 MHz, DMSO-d$_6$): δ 7.97 (d, 1H), 7.75 (t, 1H), 7.66 (d, 2H), 7.45 (d, 2H), 7.30-7.22 (m, 4H), 7.19-7.11 (m, 1H), 4.87 (d, 1H), 4.27 (d, 2H), 4.10 (s, 3H), 4.02 (q, 2H), 4.07-3.85 (m, 3H), 3.74-3.58 (m, 1H), 3.29-3.10 (m, 2H), 2.94-2.81 (m, 1H), 2.69-2.51 (m, 2H), 1.61-1.24 (m, 4H), 1.21 (d, 3H), 1.18 (t, 3H).

Example 195: 1-((1-(2-Cyclopropyloxazole-5-carbonyl)-4-hydroxypiperidin-4-yl)methyl)-8-methyl-9-phenyl-1H-purin-6(9H)-one

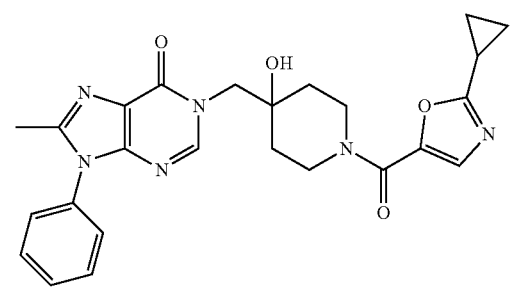 [SMILES: Cc1nc2c(=O)n(CC3(O)CCN(C(=O)c4cnc(C5CC5)o4)CC3)cnc2n1-c1ccccc1]

General procedure 4 using 1-((4-hydroxypiperidin-4-yl)methyl)-8-methyl-9-phenyl-1H-purin-6(9H)-one (41.2 mg, 0.121 mmol), 2-cyclopropyloxazole-5-carboxylic acid (22.3 mg, 0.146 mmol), HATU (55.4 mg, 0.146), DIPEA (42 µL, 0.243 mmol), and DCM (2 mL) gave the title compound (49.1 mg, 85%) as a colourless solid. LCMS (Method B): RT=0.81 min, m/z=475 [M+H]+. 1H NMR (500 MHz, DMSO-d6): δ 8.15 (s, 1H), 7.49-7.64 (m, 6H), 5.01 (s, 1H), 3.90-4.11 (m, 4H), 2.33-2.37 (m, 3H), 2.14-2.20 (m, 1H), 1.55-1.65 (m, 2H), 1.42-1.49 (m, 2H), 1.22-1.28 (m, 2H), 1.06-1.12 (m, 2H), 0.95-1.01 (m, 2H).

Example 196: 6-((1-(2-Cyclopropyloxazole-5-carbonyl)-4-hydroxypiperidin-4-yl)methyl)-2-methyl-3-phenyl-2H-pyrazolo[4,3-d]pyrimidin-7(6H)-one

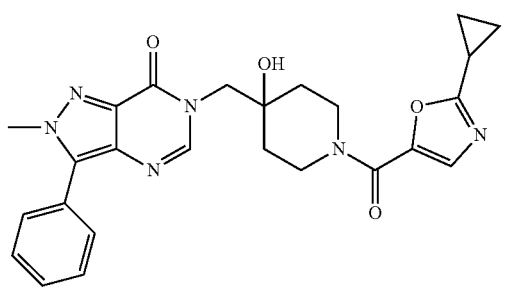 [SMILES: Cn1nc2c(=O)n(CC3(O)CCN(C(=O)c4cnc(C5CC5)o4)CC3)cnc2c1-c1ccccc1]

General procedure 4 using 6-((4-hydroxypiperidin-4-yl)methyl)-2-methyl-3-phenyl-2H-pyrazolo[4,3-d]pyrimidin-7(6H)-one (50 mg, 0.147 mmol), 2-cyclopropyloxazole-5-carboxylic acid (27.1 mg, 0.177 mmol), HATU (67.2 mg, 0.177 mmol), DIPEA (51 µL, 0.295 mmol), and DCM (2 mL) gave the title compound (69.4 mg, 99%) as a colourless solid. LCMS (Method B): R$_T$=0.88 min, m/z=475 [M+H]+. 1H NMR (500 MHz, DMSO-d6): δ 8.01 (s, 1H), 7.74-7.70 (m, 2H), 7.59 (t, 2H), 7.55-7.49 (m, 2H), 5.00 (s, 1H), 4.11 (s, 3H), 4.07-3.91 (m, 4H), 2.20-2.14 (m, 1H), 1.65-1.55 (m, 2H), 1.51-1.46 (m, 2H), 1.29-1.20 (m, 2H), 1.12-1.06 (m, 2H), 1.01-0.96 (m, 2H).

Example 197: 6-((4-Hydroxy-1-(1-methylcyclopropanecarbonyl)piperidin-4-yl)methyl)-3-phenyl-3H-[1,2,3]triazolo[4,5-d]pyrimidin-7(6H)-one

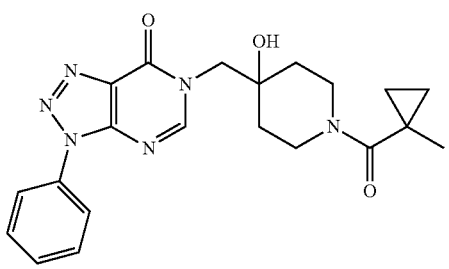 [SMILES: CC1(C(=O)N2CCC(O)(Cn3cnc4c(nnn4-c4ccccc4)c3=O)CC2)CC1]

General procedure 11 using 6-((4-hydroxypiperidin-4-yl)methyl)-3-phenyl-3H-[1,2,3]triazolo[4,5-d]pyrimidin-7(6H)-one and 1-methylcyclopropanecarboxylic acid was performed similarly to the procedure outlined in Example 185 to give the title compound (59% yield). 1H NMR (400 MHz, DMSO-d6): δ 8.49 (s, 1H), 8.04 (d, J=7.3 Hz, 2H), 7.69 (t, J=7.8 Hz, 2H), 7.59 (t, J=7.4 Hz, 1H), 4.96 (s, 1H), 4.11 (s, 2H), 3.98 (dt, J=13.3, 4.0 Hz, 2H), 3.21-3.05 (m, 2H), 1.62-1.51 (m, 2H), 1.45 (d, J=13.2 Hz, 2H), 1.22 (s, 3H), 0.78 (q, J=4.0 Hz, 2H), 0.52 (q, J=4.2 Hz, 2H). MS (ESI): m/z=409 [M+H]+.

Example 198: 6-((1-(2-Cyclopropyloxazole-5-carbonyl)-4-hydroxypiperidin-4-yl)methyl)-3-phenyl-3H-[1,2,3]triazolo[4,5-d]pyrimidin-7(6H)-one

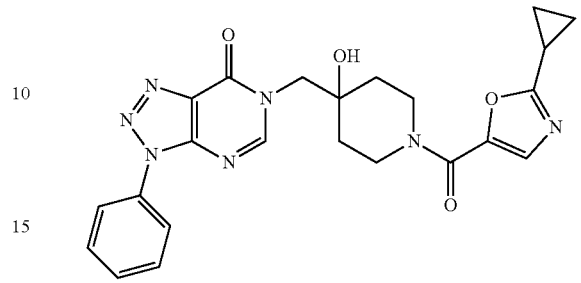

General procedure 11 using 6-((4-hydroxypiperidin-4-yl)methyl)-3-phenyl-3H-[1,2,3]triazolo[4,5-d]pyrimidin-7(6H)-one and 2-cyclopropyloxazole-5-carboxylic acid was performed similarly to the procedure outlined in Example 185 to give the title compound (32% yield). 1H NMR (400 MHz, DMSO-d6): δ 8.50 (s, 1H), 8.04 (d, J=8.3 Hz, 2H), 7.69 (t, J=7.8 Hz, 2H), 7.59 (t, J=7.5 Hz, 1H), 7.50 (s, 1H), 5.05 (s, 1H), 4.13 (s, 2H), 4.10-3.93 (m, 2H), 3.5-3.0 (br m, 2H), 2.17 (ddd, J=8.3, 4.9, 3.5 Hz, 1H), 1.71-1.59 (m, 2H), 1.55-1.47 (m, 2H), 1.14-1.05 (m, 2H), 1.03-0.94 (m, 2H). MS (ESI): m/z=462 [M+H]+.

Example 199: 6-Chloro-3-((4-hydroxy-1-(1-methylcyclopropanecarbonyl)piperidin-4-yl)methyl)-3H-pyrrolo[2,3d]pyrimidin-4(7H)-one (Intermediate F)

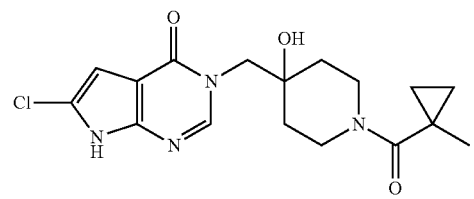 [SMILES: CC1(C(=O)N2CCC(O)(Cn3cnc4[nH]c(Cl)cc4c3=O)CC2)CC1]

Step 1: 4,6-Dichloro-7-((2-(trimethylsilyl)ethoxy)methyl)-7H-pyrrolo[2,3-d]pyrimidine A 60% dispersion of NaH in mineral oil (255 mg, 6.38 mmol) was added to a solution of 4,6-dichloro-7H-pyrrolo[2,3-d]pyrimidine (1 g, 5.32 mmol) in DMF (21 mL) at 0° C. After 1 h, SEM-Cl (1.13 mL, 6.38 mmol) was slowly added and the reaction was stirred at 0° C. for 2 h 15 min before being quenched by the addition of water (400 mL). The mixture was extracted with DCM (3×100 mL) using a phase separator, the combined organic phases were concentrated and the residue was purified by flash chromatography (120 g GraceResolv silica, 0-30% EtOAc in cyclohexane) to give the title compound (1.13 g, 66%) as a colourless oil. LCMS (Method A): R$_T$=2.14 min, m/z=318, 320 [M+H]+.

Step 2: 6-Chloro-7-((2-(trimethylsilyl)ethoxy)methyl)-7H-pyrrolo[2,3-d]pyrimidin-4(7H)-one A mixture of 4,6-dichloro-7-((2-(trimethylsilyl)ethoxy)methyl)-7H-pyrrolo[2,3-d]pyrimidine (1.13 g, 3.55 mmol), 5 M NaOH$_{(aq)}$ (14.2 mL, 71.0 mmol) and 1,4-dioxane (7.1 mL) was heated at reflux for 18 h. The reaction was allowed to cool to RT and was partitioned with water (150 mL) and DCM (150 mL). The pH was adjusted to pH 4-5 by the addition of AcOH and the phases were separated using a phase separator. The aqueous phase was extracted with DCM (2×75 mL), the combined organic phases were concentrated in vacuo and the product was dried in a vacuum oven at 50° C. to give the title compound (790 mg, 74%) as a beige solid. LCMS (Method A): R$_T$=1.51 min, m/z=300, 302 [M+H]$^+$.

Step 3: tert-Butyl 4-((6-chloro-4-oxo-7-((2-(trimethylsilyl)ethoxy)methyl)-4,7-dihydro-3H-pyrrolo[2,3-d]pyrimidin-3-yl)methyl)-4-hydroxypiperidine-1-carboxylate General procedure 1 using Epoxide 1 (1.12 g, 5.27 mmol), 6-chloro-7-((2-(trimethylsilyl)ethoxy)methyl)-3H-pyrrolo[2,3-d]pyrimidin-4(7H)-one (790 mg, 2.63 mmol), Cs$_2$CO$_3$ (944 mg, 2.90 mmol) and DMF (9 mL) gave the title compound (993 mg, 73%) as an orange foam. LCMS (Method A): R$_T$=1.94 min, m/z=513, 515 [M+H]$^+$.

Step 4: 6-Chloro-3-((4-hydroxypiperidin-4-yl)methy)-7-((2-(trimethylsily)ethoxy)methyl)-3H-pyrrolo[2,3-d]pyrimidin-4(7H)-one To a solution of tert-butyl 4-((6-chloro-4-oxo-7-((2-(trimethylsilyl)ethoxy)methyl)-4,7-dihydro-3H-pyrrolo[2,3-d]pyrimidin-3-yl)methyl)-4-hydroxypiperidine-1-carboxylate (988 mg, 1.93 mmol) in DCM (10 mL) at 0° C. was added TFA (2 mL). After 3 h, the reaction was quenched by the addition of 1 M NaOH$_{(aq)}$ (60 mL), diluted with water (60 mL) and extracted with DCM (3×100 mL) using a phase separator. The combined organic phases were concentrated in vacuo and the product was dried in a vacuum oven at 50° C. to give the title compound (699 mg, 88%) as an orange foam. LCMS (Method A): R$_T$=0.95 min, m/z=413, 415 [M+H]$^+$.

Step 5: 6-Chloro-3-((4-hydroxy-1-(1-methylcyclopropanecarbonyl)piperidin-4-yl)methyl)-7-((2-(trimethylsilyl)ethoxy)methyl)-3H-pyrrolo[2,3-d]pyrimidin-4(7H)-one General procedure 4 using 6-chloro-3-((4-hydroxypiperidin-4-yl)methyl)-7-((2-(trimethylsilyl)ethoxy)methyl)-3H-pyrrolo[2,3-d]pyrimidin-4(7H)-one (694 mg, 1.68 mmol), 1-methylcyclopropanecarboxylic acid (185 mg, 1.85 mmol), HATU (703 mg, 1.85 mmol), DIPEA (1.17 mL, 6.72 mmol) and DCM (34 mL) gave the title compound (717 mg, 86%) as a colourless foam. LCMS (Method A): R$_T$=1.59 min, m/z=495, 497 [M+H]$^+$.

Step 6: 6-Chloro-3-((4-hydroxy-1-(1-methylcyclopropanecarbonyl)piperidin-4-yl)methyl)-3H-pyrrolo[2,3-d]pyrimidin-4(7H)-one (Intermediate F)

A solution of 6-chloro-3-((4-hydroxy-1-(1-methylcyclopropanecarbonyl)piperidin-4-yl)methyl)-7-((2-(trimethylsilyl)ethoxy)methyl)-3H-pyrrolo[2,3-d]pyrimidin-4(7H)-one (717 mg, 1.448 mmol) in TFA (1.67 mL, 21.7 mmol) was stirred at RT for 1 h before the mixture was concentrated. The residue was stirred in NH$_4$OH (1.41 mL, 36.2 mmol) for 16 h before the mixture was diluted with DCM (10 mL) to give a precipitate. The fluids were decanted off and the residue washed with DCM (2×10 mL) by decanting off the fluids. The residue was purified by flash chromatography (100 g Biotage KP-Sil, 0-100% EtOAc in cyclohexane; then 0-30% MeOH in EtOAc) to give the title compound (202 mg, 38%) as a colourless solid. LCMS (Method A): R$_T$=0.74 min, m/z=365, 367 [M+H]$^+$. $^1$H NMR (400 MHz, DMSO-d$_6$): δ 12.7 (br. s, 1H), 8.06 (s, 1H), 6.46 (s, 1H), 4.91 (s, 1H), 3.98 (s, 2H), 3.98-3.89 (m, 2H), 3.25-3.03 (br. m, 2H), 1.55-1.44 (m, 2H), 1.42-1.32 (m, 2H), 1.20 (s, 3H), 0.79-0.72 (m, 2H), 0.54-0.46 (m, 2H).

Example 200: 6-Chloro-3-((4-hydroxy-1-(1-methylcyclopropanecarbonyl)piperidin-4-yl)methyl)-7-phenyl-3H-pyrrolo[2,3-d]pyrimidin-4(7H)-one

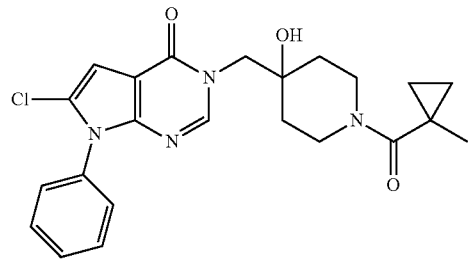 [SMILES: CC1(C(=O)N2CCC(O)(Cn3cnc4c(cc(Cl)n4-c4ccccc4)c3=O)CC2)CC1]

A suspension of Intermediate F (30 mg, 0.082 mmol), PhB(OH)$_2$ (20 mg, 0.164 mmol), Cu(OAc)$_2$ (15 mg, 0.082 mmol) and pyridine (53 μL, 0.658 mmol) in DMF (0.8 mL) was heated at 80° C. for 16 h. The reaction was cooled to RT, diluted with saturated NH$_4$Cl$_{(aq)}$ (60 mL) and the mixture was extracted with EtOAc (3×20 mL). The combined organic phases were passed through a phase separator, concentrated and the residue was purified by flash chromatography (12 g GraceResolv, 0-100% EtOAc in cyclohexane then 0-20% MeOH in EtOAc; 11 g Biotage KP-NH, 0-100% EtOAc in cyclohexane; then 0-20% MeOH in EtOAc; then 12 g GraceResolv silica, 0-20% MeOH in DCM) to give the title compound (7 mg, 19%) as a colourless solid after lyophilisation. LCMS (Method A): R$_T$=1.37 min, m/z=441, 443 [M+H]$^+$. $^1$H NMR (400 MHz, DMSO-d$_6$): δ 8.08 (s, 1H), 7.64-7.40 (m, 5H), 6.82 (s, 1H), 4.91 (s, 1H), 4.01 (s, 2H), 3.99-3.88 (m, 2H), 3.15 (br. s, 2H), 1.58-1.46 (m, 2H), 1.45-1.34 (m, 2H), 1.21 (s, 3H), 0.81-0.72 (m, 2H), 0.56-0.47 (m, 2H).

Example 201: 6-Chloro-3-((4-hydroxy-1-(1-methylcyclopropanecarbonyl)piperidin-4-yl)methyl)-7-(5-(hydroxymethyl)thiophen-3-yl)-3H-pyrrolo[2,3-d]pyrimidin-4(7H)-one

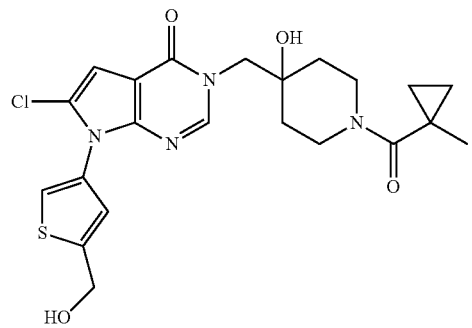 [SMILES: CC1(C(=O)N2CCC(O)(Cn3cnc4c(cc(Cl)n4-c4csc(CO)c4)c3=O)CC2)CC1]

A suspension of Intermediate F (50 mg, 0.137 mmol), Cu(OAc)$_2$ (50 mg, 0.274 mmol) and 1,10-phenanthroline (49 mg, 0.274 mmol) was stirred in DMF (0.7 mL) for 1 h before a solution of (5-(hydroxymethyl)thiophen-3-yl)boronic acid (65 mg, 0.411 mmol) in DMF (2.1 mL) was added dropwise in three portions (~0.7 mL) in 40 min intervals. The reaction was flushed with O$_2$ and stirred for 4 days. Due to poor conversion, further DIPEA (0.120 mL, 0.685 mmol) was added. After 3 h 25 min, there was no apparent change and therefore, the reaction was diluted with NH$_4$OH (30 mL) and the mixture extracted with EtOAc (3×15 mL). The combined organic phases were washed with water (3×15 mL) and brine (15 mL), before being passed through a phase separator and concentrated in vacuo. The residue was purified by flash chromatography (11 g Biotage KP-NH, 0-100% EtOAc in cyclohexane; then 0-20% MeOH in EtOAc; then 12 g GraceResolv silica, 0-20% MeOH in DCM) to give the title compound (7.2 mg, 11%) as a colourless solid after lyophilisation. LCMS (Method A): R$_T$=1.35 min, m/z=477, 479 [M+H]$^+$. $^1$H NMR (400 MHz, DMSO-d$_6$): δ 8.10 (s, 1H), 7.69 (d, 1H), 7.10-7.06 (m, 1H), 6.79 (s, 1H), 5.66 (t, 1H), 4.92 (s, 1H), 4.68 (d, 2H), 4.01 (s, 2H), 3.99-3.90 (m, 2H), 3.15 (br. s, 2H), 1.56-1.46 (m, 2H), 1.42-1.35 (m, 2H), 1.20 (s, 3H), 0.80-0.72 (m, 2H), 0.55-0.48 (m, 2H).

Example 202: 7-(Benzo[d][1,3]dioxol-5-yl)-6-chloro-3-((4-hydroxy-1-(1-methylcyclopropanecarbonyl)piperidin-4-yl)methyl)-3H-pyrrolo[2,3-d]pyrimidin-4(7H)-one

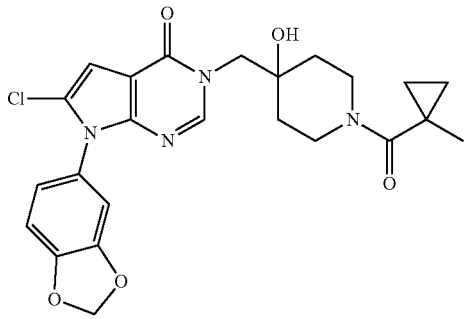 [SMILES: CC1(C(=O)N2CCC(O)(Cn3cnc4c(cc(Cl)n4-c4ccc5c(c4)OCO5)c3=O)CC2)CC1]

A solution of Intermediate F (52 mg, 0.143 mmol), benzo[d][1,3]dioxol-5-ylboronic acid (71 mg, 0.428 mmol), Cu(OAc)$_2$ (52 mg, 0.285 mmol) and 1,10-phenanthroline (51 mg, 0.285 mmol) in DMF (1.4 mL) was stirred at RT for 22 h. The temperature was increased to 50° C. After 42 h, the reaction mixture was allowed to cool to RT, diluted with NH$_4$OH (45 mL) and the mixture was extracted with EtOAc (3×30 mL). The combined organic phases were washed with water (3×15 mL) and brine (15 mL) before being passed through a phase separator and concentrated. The residue was purified by flash chromatography (11 g Biotage KP-NH, 0-100% EtOAc in cyclohexane, then 0-20% MeOH in EtOAc; then 12 g GraceResolv silica, 0-20% MeOH in DCM) to give the title compound (14 mg, 20%) as a colourless solid after lyophilisation. LCMS (Method B): R$_T$=1.09 min, m/z=485, 487 [M+H]$^+$. $^1$H NMR (400 MHz, DMSO-d$_6$): δ 8.08 (s, 1H), 7.11-7.06 (m, 2H), 6.93-6.86 (m, 1H), 6.77 (s, 1H), 6.16 (s, 2H), 4.92 (s, 1H), 4.00 (s, 2H), 3.99-3.89 (m, 2H), 3.15 (br. s, 2H), 1.57-1.45 (m, 2H), 1.43-1.33 (m, 2H), 1.20 (s, 3H), 0.80-0.71 (m, 2H), 0.58-0.46 (m, 2H).

Example 203: 6-Chloro-7-(4-chlorophenyl)-3-((4-hydroxy-1-(1-methylcyclopropanecarbonyl)piperidin-4-yl)methyl)-3H-pyrrolo[2,3-d]pyrimidin-4(7H)-one

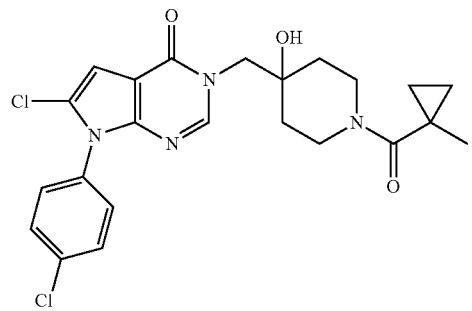 [SMILES: CC1(C(=O)N2CCC(O)(Cn3cnc4c(cc(Cl)n4-c4ccc(Cl)cc4)c3=O)CC2)CC1]

A mixture of Intermediate F (100 mg, 0.274 mmol), (4-chlorophenyl)boronic acid (129 mg, 0.822 mmol), Cu(OAc)$_2$ (100 mg, 0.548 mmol) and 1,10-phenanthroline (99 mg, 0.548 mmol) in DMF (2.7 mL) was heated at 50° C. for 18 h. The reaction was allowed to cool to RT, diluted with NH$_4$OH (45 mL) and the mixture was extracted with EtOAc (3×30 mL). The combined organic phases were washed with water (3×15 mL) and brine (15 mL) before being passed through a phase separator and concentrated in vacuo. The residue was purified by flash chromatography (11 g Biotage KP-NH, 0-100% EtOAc in cyclohexane the 0-20% MeOH in EtOAc; then 12 g GraceResolv silica, 0-15% MeOH in DCM) to give the title compound (10 mg, 7%). LCMS (Method A): R$_T$=1.36 min, m/z=475, 477 [M+H]$^+$. $^1$H NMR (400 MHz, DMSO-d$_6$) δ 8.10 (s, 1H), 7.72-7.63 (m, 2H), 7.57-7.48 (m, 2H), 6.84 (s, 1H), 4.92 (s, 1H), 4.01 (s, 2H), 3.95 (dt, J=13.3, 4.1 Hz, 2H), 3.14 (s, 2H), 1.53-1.45 (m, 2H), 1.43-1.34 (m, 2H), 1.20 (s, 3H), 0.80-0.72 (m, 2H), 0.57-0.47 (m, 2H).

Example 204: 6-Chloro-7-(4-fluorophenyl)-3-((4-hydroxy-1-(1-methylcyclopropanecarbonyl)piperidin-4-yl)methyl)-3H-pyrrolo[2,3-d]pyrimidin-4(7H)-one

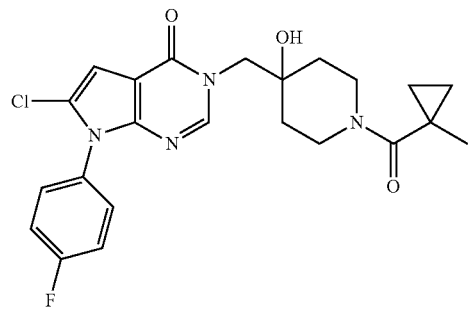 [SMILES: CC1(C(=O)N2CCC(O)(Cn3cnc4c(cc(Cl)n4-c4ccc(F)cc4)c3=O)CC2)CC1]

Step 1: 4,6-Dichloro-7-(4-fluorophenyl)-7H-pyrrolo[2,3-d]pyrimidine

A mixture of 4,6-dichloro-7H-pyrrolo[2,3-d]pyrimidine (188 mg, 1 mmol), (4-fluorophenyl)boronic acid (420 mg, 3 mmol), Cu(OAc)$_2$ (363 mg, 2 mmol) and 1,10-phenanthroline (360 mg, 2 mmol) was stirred in DMF (20 mL) for 22 h before the reaction was quenched by the addition of saturated NH$_4$Cl$_{(aq)}$ (200 mL) and water (200 mL). The resulting mixture was extracted with EtOAc (3×50 mL), the combined organic phases were passed through a phase separator, concentrated in vacuo and the residue purified by flash chromatography (24 g GraceResolv silica, 0-100% EtOAc in cyclohexane) to give the title compound (126 mg, 44%) as pale beige solid. LCMS (Method A): R$_T$=1.68 min, m/z=282, 284 [M+H]$^+$.

Step 2: 6-Chloro-7-(4-fluorophenyl)-3H-pyrrolo[2,3-d]pyrimidin-4(7H)-one 4,6-Dichloro-7-(4-fluorophenyl)-7H-pyrrolo[2,3-d]pyrimidine (126 mg, 0.447 mmol) and 1 M HCl$_{(aq)}$ (0.893 mL, 0.893 mmol) were heated in a microwave at 120° C. for 1.5 h. The reaction was diluted with water (5 mL) and the precipitate isolated by filtration. The precipitate was dried overnight in a vacuum oven at 50° C. to give the title compound (103 mg, 87%) as a light pink solid. LCMS (Method A): R$_T$=1.07 min, m/z=264, 266 [M+H]$^+$.

Step 3: tert-Butyl 4-((6-chloro-7-(4-fluorophenyl)-4-oxo-4,7-dihydro-3H-pyrrolo[2,3-d]pyrimidin-3-yl)methyl)-4-hydroxypiperidine-1-carboxylate General procedure 1 using Epoxide 1 (162 mg, 0.759 mmol), 6-chloro-7-(4-fluorophenyl)-3H-pyrrolo[2,3-d]pyrimidin-4(7H)-one (100 mg, 0.379 mmol), Cs$_2$CO$_3$ (136 mg, 0.417 mmol) and DMF (2.5 mL) gave the title compound (183 mg, 101%) as beige solid. LCMS (Method A): R$_T$=1.55 min, m/z=477, 479 [M+H]$^+$.

Step 4: 6-Chloro-7-(4-fluorophenyl)-3-((4-hydroxypiperidin-4-yl)methyl)-3H-pyrrolo[2,3-d]pyrimidin-4(7H)-one tert-Butyl 4-((6-chloro-7-(4-fluorophenyl)-4-oxo-4,7-dihydro-3H-pyrrolo[2,3-d]pyrimidin-3-yl)methyl)-4-hydroxypiperidine-1-carboxylate (178 mg, 0.373 mmol) was stirred in DCM (2 mL) and TFA (1 mL) for 15 min before the reaction was purified using a 5 g Biotage SCX-2 cartridge (pre-equilibrated with, then washed with 1:1 DCM/MeOH, eluted using 1:1 DCM/7 M in NH$_3$ in MeOH). The basic phases were combined, concentrated in vacuo and the residue was purified by flash chromatography (11 g Biotage KP-NH, 0-100% DCM in cyclohexane, then 0-20% MeOH in DCM) to give the title compound (124 mg, 88%) as light beige solid. LCMS (Method A): R$_T$=0.76 min, m/z=377, 379 [M+H]$^+$.

Step 5: 6-Chloro-7-(4-fluorophenyl)-3-((4-hydroxy-1-(1-methylcyclopropanecarbonyl)piperidin-4-yl)methyl)-3H-pyrrolo[2,3-d]pyrimidin-4(7H)-one General procedure 4 using 6-chloro-7-(4-fluorophenyl)-3-((4-hydroxypiperidin-4-yl)methyl)-3H-pyrrolo[2,3-d]pyrimidin-4(7H)-one (73 mg, 0.194 mmol), 1-methylcyclopropanecarboxylic acid (21 mg, 0.213 mmol), HATU (81 mg, 0.213 mmol), DIPEA (135 µL, 0.775 mmol) and DCM (3.9 mL) gave the title compound (57 mg, 64%) as a colourless solid after lyophilisation. LCMS (Method A): R$_T$=1.23 min, m/z=459, 461 [M+H]$^+$. $^1$H NMR (400 MHz, DMSO-d$_6$) δ 8.09 (s, 1H), 7.59-7.49 (m, 2H), 7.49-7.38 (m, 2H), 6.82 (s, 1H), 4.93 (s, 1H), 4.01 (s, 2H), 3.99-3.90 (m, 2H), 3.15 (s, 2H), 1.63-1.45 (m, 2H), 1.43-1.35 (m, 2H), 1.20 (s, 3H), 0.80-0.71 (m, 2H), 0.55-0.47 (m, 2H).

Example 205: 6-Chloro-3-((1-(2-cyclopropyloxazole-5-carbonyl)-4-hydroxypiperidin-4-yl)methyl)-7-(4-fluorophenyl)-3H-pyrrolo[2,3-d]pyrimidin-4(7H)-one

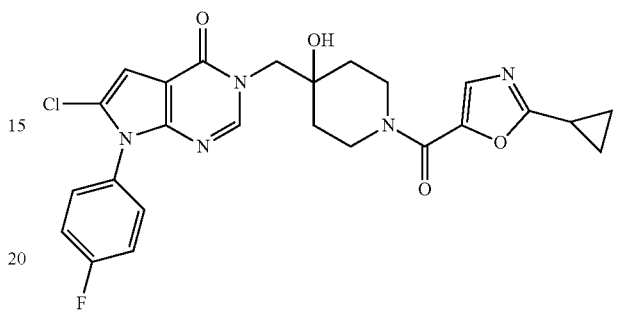

General procedure 4 using 6-chloro-7-(4-fluorophenyl)-3-((4-hydroxypiperidin-4-yl)methyl)-3H-pyrrolo[2,3-d]pyrimidin-4(7H)-one (51 mg, 0.135 mmol), 2-cyclopropyloxazole-5-carboxylic acid (23 mg, 0.149 mmol), HATU (57 mg, 0.149 mmol), DIPEA (95 µL, 0.541 mmol) and DCM (2.7 mL) gave the title compound (45 mg, 65%) as a colourless solid after lyophilisation. LCMS (Method A): R$_T$=1.23 min, m/z=512, 514 [M+H]$^+$. $^1$H NMR (400 MHz, DMSO-d$_6$): δ 8.10 (s, 1H), 7.54 (ddt, J=8.3, 5.6, 2.8 Hz, 2H), 7.50 (s, 1H), 7.48-7.39 (m, 2H), 6.82 (s, 1H), 5.01 (s, 1H), 4.18-3.83 (m, 4H), 3.56-3.00 (br. s, 2H (signal overlaps with HDO)), 2.17 (tt, J=8.3, 4.9 Hz, 1H), 1.68-1.54 (m, 2H), 1.49-1.40 (m, 2H), 1.14-1.04 (m, 2H), 1.02-0.93 (m, 2H).

Example 206: 6-Chloro-3-((1-(2-cyclopropyloxazole-5-carbonyl)-4-hydroxypiperidin-4-yl)methyl)-7-(4-fluoro-3-methoxyphenyl)-3H-pyrrolo[2,3-d]pyrimidin-4(7H)-one

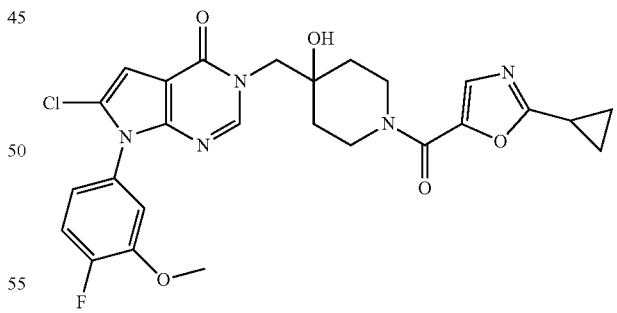

Step 1: 4,6-Dichloro-7-(4-fluoro-3-methoxyphenyl)-7H-pyrrolo[2,3-d]pyrimidine

A mixture of 4,6-dichloro-7H-pyrrolo[2,3-d]pyrimidine (188 mg, 1 mmol), (4-fluoro-3-methoxyphenyl)boronic acid (510 mg, 3 mmol), Cu(OAc)$_2$ (363 mg, 2 mmol) and 1,10-phenanthroline (360 mg, 2 mmol) was stirred in DMF (20 mL) for 18 h before the reaction was quenched by the addition of saturated NH$_4$Cl$_{(aq)}$ (200 mL) and water (200 mL). The resulting mixture was extracted with EtOAc (3×50 mL), the combined organic phases were washed with water (50 mL), then brine (50 mL) and passed through a phase separator. The organic phases were concentrated and the residue was purified by flash chromatography (40 g GraceResolv silica, 0-60% EtOAc in cyclohexane) to give the title compound (81 mg, 26%) as colourless solid. LCMS (Method B): $R_T$=1.40 min, m/z=312, 314 [M+H]$^+$.

Step 2: 6-Chloro-7-(4-fluoro-3-methoxyphenyl)-3H-pyrrolo[2,3-d]pyrimidin-4(7H)-one A mixture of 4,6-dichloro-7-(4-fluoro-3-methoxyphenyl)-7H-pyrrolo[2,3-d]pyrimidine (81 mg, 0.260 mmol), 1 M HCl$_{(aq)}$ (0.5 mL, 0.5 mmol) and 1,4-dioxane (1 mL) were heated in a microwave at 120° C. for 1.5 h. The product was isolated by filtration and dried in a vacuum oven at 50° C. for 1 h to give the title compound (52 mg, 68%) as a colourless solid. LCMS (Method B): $R_T$=0.96 min, m/z=294, 296 [M+H]$^+$.

Step 3: tert-Butyl 4-((6-chloro-7-(4-fluoro-3-methoxyphenyl)-4-oxo-4,7-dihydro-3H-pyrrolo[2,3-d]pyrimidin-3-yl)methyl)-4-hydroxypiperidine-1-carboxylate General procedure 1 using Epoxide 1 (76 mg, 0.354 mmol), 6-chloro-7-(4-fluoro-3-methoxyphenyl)-3H-pyrrolo[2,3-d]pyrimidin-4(7H)-one (52 mg, 0.177 mmol), Cs$_2$CO$_3$ (63 mg, 0.195 mmol) and DMF (1.2 mL) gave the title compound (86 mg, 96%) as beige solid. LCMS (Method A): $R_T$=1.55 min, m/z=507, 509 [M+H]$^+$.

Step 4: 6-Chloro-7-(4-fluoro-3-methoxyphenyl)-3-((4-hydroxypiperidin-4-yl)methyl)-3H-pyrrolo[2,3-d]pyrimidin-4(7H)-one A solution of tert-butyl 4-((6-chloro-7-(4-fluoro-3-methoxyphenyl)-4-oxo-4,7-dihydro-3H-pyrrolo[2,3-d]pyrimidin-3-yl)methyl)-4-hydroxypiperidine-1-carboxylate (86 mg, 0.170 mmol) in DCM (1 mL) and TFA (0.5 mL) was stirred for 15 min before the reaction was purified using a 2 g SCX-2 cartridge (pre-equilibrated with, then washed using 1:1 DCM/MeOH, eluted using 1:1 DCM/7 M in NH$_3$ in MeOH). The basic phases were combined, concentrated in vacuo and the residue was purified by flash chromatography (11 g Biotage KP-NH, 0-100% DCM in cyclohexane, then 0-20% MeOH in DCM) to give the title compound (60 mg, 87%) as colourless foam. LCMS (Method A): $R_T$=0.76 min, m/z=407, 409 [M+H]$^+$.

Step 5: 6-Chloro-3-((1-(2-cyclopropyloxazole-5-carbonyl)-4-hydroxypiperidin-4-yl)methy)-7-(4-fluoro-3-methoxyphenyl)-3H-pyrrolo[2,3-d]pyrimidin-4(7H)-one General procedure 4 using 6-chloro-7-(4-fluoro-3-methoxyphenyl)-3-((4-hydroxypiperidin-4-yl)methyl)-3H-pyrrolo[2,3-d]pyrimidin-4(7H)-one (37 mg, 0.0909 mmol), 2-cyclopropyloxazole-5-carboxylic acid (15 mg, 0.100 mmol), HATU (38 mg, 0.100 mmol), DIPEA (63 µL, 0.364 mmol) and DCM (1.8 mL) gave the title compound (38 mg, 78%) as a colourless solid after lyophilisation. LCMS (Method A): $R_T$=1.24 min, m/z=542, 544 [M+H]$^+$. $^1$H NMR (500 MHz, DMSO-d$_6$): δ 8.10 (s, 1H), 7.50 (s, 1H), 7.43 (dd, J=11.2, 8.6 Hz, 1H), 7.33 (dd, J=7.7, 2.5 Hz, 1H), 7.04 (ddd, J=8.6, 3.9, 2.5 Hz, 1H), 6.81 (s, 1H), 5.01 (s, 1H), 4.04 (s, 2H), 4.11-3.89 (m, 2H), 3.86 (s, 3H), 3.53-3.00 (m, 2H (broad signal that overlaps with HDO signal)), 2.17 (tt, J=8.3, 4.9 Hz, 1H), 1.66-1.52 (m, 2H), 1.50-1.38 (m, 2H), 1.13-1.05 (m, 2H), 1.01-0.94 (m, 2H).

Example 207: 6-Chloro-7-(4-fluoro-3-methoxyphenyl)-3-((4-hydroxy-1-(1-methylcyclopropanecarbonyl)piperidin-4-yl)methyl)-3H-pyrrolo[2,3-d]pyrimidin-4(7H)-one

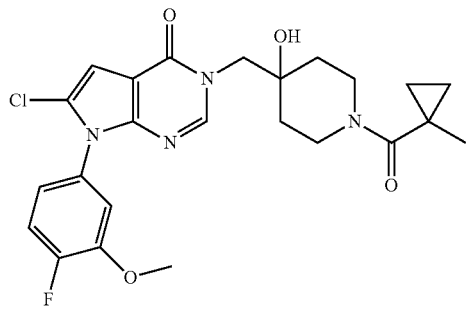 [SMILES: COc1cc(-n2c(Cl)cc3c(=O)n(CC4(O)CCN(C(=O)C5(C)CC5)CC4)cnc32)ccc1F]

General procedure 4 using 6-chloro-7-(4-fluoro-3-methoxyphenyl)-3-((4-hydroxypiperidin-4-yl)methyl)-3H-pyrrolo[2,3-d]pyrimidin-4(7H)-one (32 mg, 0.0787 mmol), 1-methylcyclopropanecarboxylic acid (9 mg, 0.0865 mmol), HATU (33 mg, 0.0865 mmol), DIPEA (54 µL, 0.315 mmol) and DCM (1.8 mL) gave the title compound (28.5 mg, 74%) as a colourless solid after lyophilisation. LCMS (Method A): $R_T$=1.25 min, m/z=489, 491 [M+H]$^+$. $^1$H NMR (500 MHz, DMSO-d$_6$): δ 8.10 (s, 1H), 7.43 (dd, J=11.2, 8.6 Hz, 1H), 7.33 (dd, J=7.7, 2.5 Hz, 1H), 7.04 (ddd, J=8.6, 3.9, 2.5 Hz, 1H), 6.81 (s, 1H), 4.93 (s, 1H), 4.02 (s, 2H), 3.95 (dt, J=13.2, 4.3 Hz, 2H), 3.86 (s, 3H), 3.16 (s, 2H), 1.60-1.47 (m, 2H), 1.42-1.36 (m, 2H), 1.21 (s, 3H), 0.80-0.74 (m, 2H), 0.55-0.49 (m, 2H).

Example 208: 6-Chloro-3-((4-hydroxy-1-(1-methylcyclopropanecarbonyl)piperidin-4-yl)methyl)-7-(3-(1-methyl-1H-pyrazol-5-yl)phenyl)-3H-pyrrolo[2,3-d]pyrimidin-4(7H)-one

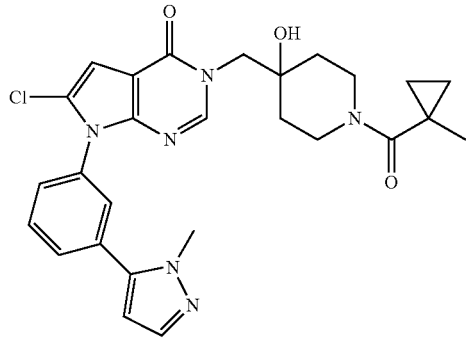 [SMILES: Cn1nccc1-c1cccc(-n2c(Cl)cc3c(=O)n(CC4(O)CCN(C(=O)C5(C)CC5)CC4)cnc32)c1]

Step 1: 7-(3-Bromophenyl)-4-chloro-5H-pyrrolo[2,3-d]pyrimidin-6(7H)-one

A mixture of methyl 2-(4,6-dichloropyrimidin-5-yl)acetate (884 mg, 4 mmol) and 3-bromoaniline (688 mg, 4 mmol) in EtOH (8 mL) was heated at 120° C. for 2 h in the microwave. The reaction mixture was concentrated and saturated NaHCO$_{3(aq)}$ (75 mL) was added to the residue. The resulting mixture was extracted with DCM (3×50 mL) using a phase separator, the combined organic phases were concentrated in vacuo and the residue was purified by flash chromatography (80 g GraceResolv silica, 0-40% EtOAc in cyclohexane) to give ethyl 2-(4-((3-bromophenyl)amino)-6-chloropyrimidin-5-yl)acetate (384 mg, 26%) as a colourless solid (LCMS (Method B): R$_T$=1.40 min, m/z=370, 372, 374 [M+H]$^+$) and the title compound (464 mg, 36%) as a beige solid (LCMS (Method B): R$_T$=1.18 min, m/z=324, 326, 328 [M+H]$^+$). A solution of ethyl 2-(4-((3-bromophenyl)amino)-6-chloropyrimidin-5-yl)acetate (348 mg, 0.939 mmol) and p-TSA (36 mg, 0.188 mmol) in toluene (7.5 mL) was heated at reflux for 1 h, the reaction mixture was concentrated and the residue purified by flash chromatography (40 g GraceResolv silica, 0-30% EtOAc in cyclohexane) to give the title compound (276 mg, 82%) as a colourless solid. LCMS (Method B): R$_T$=1.18 min, m/z=324, 326, 328 [M+H]$^+$.

Step 2: 7-(3-Bromophenyl)-4,6-dichloro-7H-pyrrolo[2,3-d]pyrimidine

Water (123 μL, 6.84 mmol) was added to a mixture of 7-(3-bromophenyl)-4-chloro-5H-pyrrolo[2,3-d]pyrimidin-6(7H)-one (740 mg, 2.28 mmol), POCl$_3$ (1.3 mL, 13.7 mmol) and PhNEt$_2$ (544 μL, 3.42 mmol) in a reaction vial. Once the effervescence had subsided, the vial was capped and the mixture was heated at 115° C. for 1.5 h. After cooling to RT, the reaction mixture was diluted with DCM (~2 mL) and then poured on to ice (~5 g). Once the ice had melted, saturated NaHCO$_{3(aq)}$ (75 mL) and DCM (200 mL) were added and the mixture was stirred for 1 h. The resulting mixture was extracted with DCM (3×50 mL) and the combined organic phases were passed through a phase separator. The resulting solution was concentrated and the residue was purified by flash chromatography (80 g GraceResolv silica, 0-40% EtOAc in cyclohexane) to give the title compound (419 mg, 53%) as a colourless solid. LCMS (Method B): R$_T$=1.55 min, m/z=342, 344, 346 [M+H]$^+$.

Step 3: 7-(3-Bromophenyl)-6-chloro-3H-pyrrolo[2,3-d]pyrimidin-4(7H)-one

A suspension of 7-(3-bromophenyl)-4,6-dichloro-7H-pyrrolo[2,3-d]pyrimidine (402 mg, 1.17 mmol) in 2 M HCl$_{(aq)}$ (2.34 mL, 4.68 mmol) and 1,4-dioxane (2.34 mL) was heated at 120° C. for 3 h in the microwave. The reaction mixture was concentrated and the residue was dried in a vacuum oven at 50° C. to give the title compound (370 mg, 97%) as a beige solid. LCMS (Method B): R$_T$=1.08 min, m/z=324, 326, 328 [M+H]$^+$.

Step 4: tert-Butyl 4-((7-(3-bromophenyl)-6-chloro-4-oxo-4,7-dihydro-3H-pyrrolo[2,3-d]pyrimidin-3-yl)methyl)-4-hydroxypiperidine-1-carboxylate General procedure 1 using Epoxide 1 (484 mg, 2.67 mmol), 7-(3-bromophenyl)-6-chloro-3H-pyrrolo[2,3-d]pyrimidin-4(7H)-one (368 mg, 1.13 mmol), Cs$_2$CO$_3$ (406 mg, 1.25 mmol) and DMF (3.8 mL) gave the title compound (572 mg, 93%) as a beige foam. LCMS (Method B): R$_T$=1.45 min, m/z=481, 483, 485 [M-butene+H]$^+$.

Step 5: tert-Butyl 4-((6-chloro-7-(3-(1-methyl-1H-pyrazol-5-yl)phenyl)-4-oxo-4,7-dihydro-3H-pyrrolo[2,3-d]pyrimidin-3-yl)methyl)-4-hydroxypiperidine-1-carboxylate General procedure 5 using tert-butyl 4-((7-(3-bromophenyl)-6-chloro-4-oxo-4,7-dihydro-3H-pyrrolo[2,3-d]pyrimidin-3-yl)methyl)-4-hydroxypiperidine-1-carboxylate (125 mg, 0.232 mmol), 1-methyl-5-(4,4,5,5-tetramethyl-1,3,2-dioxaborolan-2-yl)-1H-pyrazole (53 mg, 0.256 mmol), Pd(PPh$_3$)$_4$(13 mg, 0.0116 mmol) and Na$_2$CO$_3$ (49 mg, 0.465 mmol) in 1,4-dioxane (1.5 mL) and water (0.6 mL) at 140° C. for 30 min in the microwave gave the title compound (115 mg, 91%) as pale yellow foam. LCMS (Method A): R$_T$=1.44 min, m/z=539, 541 [M+H]$^+$.

Step 6: 6-Chloro-3-((4-hydroxypiperidin-4-yl)methyl)-7-(3-(1-methyl-1H-pyrazol-5-yl)phenyl)-3H-pyrrolo[2,3-d]pyrimidin-4(7H)-one A solution of tert-butyl 4-((7-(3-bromophenyl)-6-chloro-4-oxo-4,7-dihydro-3H-pyrrolo[2,3-d]pyrimidin-3-yl)methyl)-4-hydroxypiperidine-1-carboxylate (132 mg, 0.245 mmol) in DCM (1 mL) and TFA (0.5 mL) was stirred for 15 min before the reaction was purified using a 2 g Biotage SCX-2 cartridge (pre-equilibrated with, then washed with 1:1 DCM/MeOH, eluted using 1:1 DCM/7 M in NH$_3$ in MeOH). The basic phases were combined, concentrated in vacuo, and the residue was purified by flash chromatography (11 g Biotage KP-NH, 0-100% DCM in cyclohexane, then 0-20% MeOH in DCM) to give the title compound (crude, 121 mg, >100%) as colourless foam. The material was used without further purification. LCMS (Method A): R$_T$=0.73 min, m/z=439, 441 [M+H]$^+$.

Step 7: 6-Chloro-3-((4-hydroxy-1-(1-methylcyclopropanecarbonyl)piperidin-4-yl)methyl)-7-(3-(1-methyl-1H-pyrazol-5-yl)phenyl)-3H-pyrrolo[2,3-d]pyrimidin-4(7H)-one General procedure 4 using 6-chloro-3-((4-hydroxypiperidin-4-yl)methyl)-7-(3-(1-methyl-1H-pyrazol-5-yl)phenyl)-3H-pyrrolo[2,3-d]pyrimidin-4(7H)-one (61 mg, 0.139 mmol), 1-methylcyclopropanecarboxylic acid (15 mg, 0.153 mmol), HATU (58 mg, 0.153 mmol), DIPEA (96 μL, 0.556 mmol) and DCM (2.8 mL) gave the title compound (40 mg, 56%) as a colourless solid after lyophilisation. LCMS (Method B): R$_T$=1.04 min, m/z=521, 523 [M+H]$^+$. $^1$H NMR (500 MHz, DMSO-d$_6$): δ 8.10 (s, 1H), 7.74-7.69 (m, 2H), 7.68 (dt, J=2.1, 1.0 Hz, 1H), 7.56-7.52 (m, 1H), 7.50 (d, J=1.9 Hz, 1H), 6.85 (s, 1H), 6.52 (d, J=1.9 Hz, 1H), 4.91 (s, 1H), 4.02 (s, 2H), 3.98-3.90 (m, 2H), 3.92 (s, 3H), 3.16 (s, 2H), 1.57-1.45 (m, 2H), 1.44-1.36 (m, 2H), 1.21 (s, 3H), 0.80-0.74 (m, 2H), 0.55-0.48 (m, 2H).

Example 209: 6-Chloro-3-((4-hydroxy-1-(1-methyl-cyclopropanecarbonyl)piperidin-4-yl)methyl)-7-methyl-3H-pyrrolo[2,3-d]pyrimidin-4(7H)-one

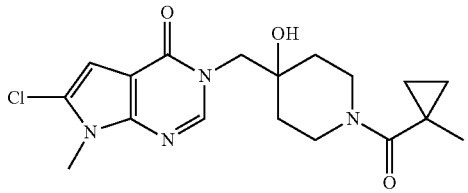 [SMILES: Cn1c(Cl)cc2c(=O)n(CC3(O)CCN(C(=O)C4(C)CC4)CC3)cnc21]

Iodomethane (21.4 mg, 0.151 mmol) was added to a stirred suspension of 6-chloro-3-((4-hydroxy-1-(1-methyl-cyclopropanecarbonyl)piperidin-4-yl)methyl)-3H-pyrrolo[2,3-d]pyrimidin-4(7H)-one (50 mg, 0.137 mmol) and potassium carbonate (22.7 mg, 0.165 mmol) in anhydrous DMF (0.5 mL). After 16 h, the reaction mixture was partitioned between 1:1 brine/water (40 mL) and ethyl acetate (10 mL). After separation, the aqueous phase was extracted using ethyl acetate (3×10 mL). The combined organic phase was washed using 1:1 brine/water (4×10 mL), dried ($Na_2SO_4$), filtered, and the solvents were removed in vacuo. The residue was purified by flash chromatography (0-100% ethyl acetate in cyclohexane, then 0-20% methanol in ethyl acetate). The residue was suspended in acetonitrile (2 mL) and water (10 mL) and freeze-dried to afford the title compound (37.6 mg, 72%). LCMS (Method B): $R_T$=0.85 min, m/z=379 [M+H]$^+$. $^1$H NMR (500 MHz, DMSO-$d_6$): δ 8.15 (s, 1H), 6.61 (s, 1H), 4.92 (s, 1H), 4.00 (s, 2H), 3.93 (dt, 2H), 3.66 (s, 3H), 3.01-3.26 (m, 2H), 1.42-1.56 (m, 2H), 1.32-1.42 (m, 2H), 1.20 (s, 3H), 0.70-0.80 (m, 2H), 0.44-0.56 (m, 2H).

Example 210: 6-Chloro-3-((1-(2-cyclopropyloxazole-5-carbonyl)-4-hydroxypiperidin-4-yl)methyl)-7-(3-(1-methyl-1H-pyrazol-5-yl)phenyl)-3H-pyrrolo[2,3-d]pyrimidin-4(7H)-one

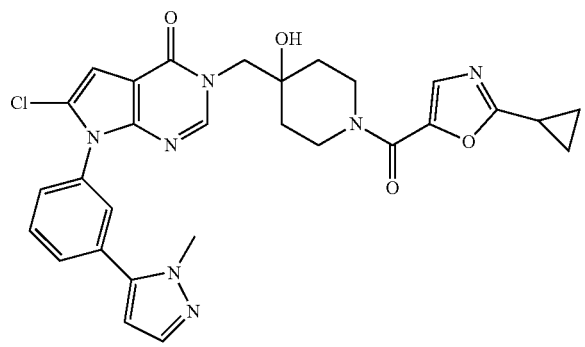 [SMILES: Cn1nccc1-c1cccc(-n2c(Cl)cc3c(=O)n(CC4(O)CCN(C(=O)c5cnc(C6CC6)o5)CC4)cnc32)c1]

General procedure 4 using 6-chloro-3-((4-hydroxypiperidin-4-yl)methyl)-7-(3-(1-methyl-1H-pyrazol-5-yl)phenyl)-3H-pyrrolo[2,3-d]pyrimidin-4(7H)-one (60 mg, 0.137 mmol), 2-cyclopropyloxazole-5-carboxylic acid (23 mg, 0.150 mmol), HATU (57 mg, 0.150 mmol), DIPEA (95 µL, 0.547 mmol) and DCM (2.8 mL) gave the title compound (43 mg, 55%) as a colourless solid after lyophilisation. LCMS (Method B): $R_T$=1.04 min, m/z=574, 576 [M+H]$^+$. $^1$H NMR (500 MHz, DMSO-$d_6$): δ 8.11 (s, 1H), 7.74-7.66 (m, 3H), 7.57-7.52 (m, 1H), 7.52-7.47 (m, 2H), 6.85 (s, 1H), 6.52 (d, J=1.9 Hz, 1H), 5.01 (s, 1H), 4.10-3.95 (br. s, 2H), 4.04 (s, 2H), 3.92 (s, 3H), 3.50-3.01 (br. S, 2H (signal overlaps with HDO)) 2.17 (tt, J=8.3, 4.9 Hz, 1H), 1.66-1.53 (m, 2H), 1.50-1.42 (m, 2H), 1.11-1.05 (m, 2H), 1.02-0.94 (m, 2H).

Example 211: 6-Chloro-3-((1-(2-cyclopropyloxazole-5-carbonyl)-4-hydroxypiperidin-4-yl)methyl)-7-(3-(1-methyl-1H-pyrazol-4-yl)phenyl)-3H-pyrrolo[2,3-d]pyrimidin-4(7H)-one

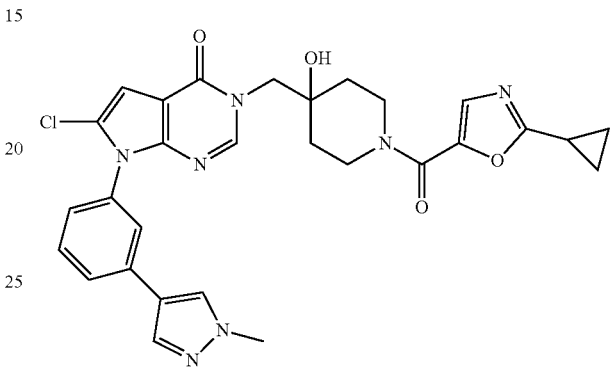

Step 1: tert-Butyl 4-((6-chloro-7-(3-(1-methyl-1H-pyrazol-4-yl)phenyl)-4-oxo-4,7-dihydro-3H-pyrrolo[2,3-d]pyrimidin-3-yl)methyl)-4-hydroxypiperidine-1-carboxylate General procedure 5 using tert-butyl 4-((7-(3-bromophenyl)-6-chloro-4-oxo-4,7-dihydro-3H-pyrrolo[2,3-d]pyrimidin-3-yl)methyl)-4-hydroxypiperidine-1-carboxylate (128 mg, 0.238 mmol), 1-methyl-4-(4,4,5,5-tetramethyl-1,3,2-dioxaborolan-2-yl)-1H-pyrazole (55 mg, 0.262 mmol), Pd(PPh$_3$)$_4$(14 mg, 0.0119 mmol), and Na$_2$CO$_3$ (50 mg, 0.476 mmol), in 1,4-dioxane (1.75 mL) and water (0.7 mL) at 140° C. for 30 min in the microwave gave the title compound (131 mg, 102%) as pale yellow foam. This material was used without further purification. LCMS (Method B): $R_T$=1.02 min, m/z=481, 483, 485 [M-butene+H]$^+$.

Step 2: 6-Chloro-3-((4-hydroxypiperidin-4-yl)methyl)-7-(3-(1-methyl-1H-pyrazol-4-yl)phenyl)-3H-pyrrolo[2,3-d]pyrimidin-4(7H)-one A solution of tert-butyl 4-((6-chloro-7-(3-(1-methyl-1H-pyrazol-4-yl)phenyl)-4-oxo-4,7-dihydro-3H-pyrrolo[2,3-d]pyrimidin-3-yl)methyl)-4-hydroxypiperidine-1-carboxylate (131 mg, 0.243 mmol) in DCM (1 mL) and TFA (0.5 mL) was stirred for 30 min before the reaction was purified using a 5 g Biotage SCX-2 cartridge (pre-equilibrated with, then washed with 1:1 DCM/MeOH, eluted using 1:1 DCM/7 M in NH$_3$ in MeOH). The basic phases were combined, concentrated and the residue was purified by flash chromatography (11 g Biotage KP-NH, 0-100% DCM in cyclohexane, then 0-20% MeOH in DCM) to give the title compound (91 mg, 85%) as pale yellow gum. LCMS (Method B): $R_T$=0.71 min, m/z=439, 441 [M+H]$^+$.

Step 3: 6-Chloro-3-((1-(2-cyclopropyloxazole-5-carbonyl)-4-hydroxypiperidin-4-yl)methy)-7-(3-(1-methyl-1H-pyrazol-4-yl)phenyl)-3H-pyrrolo[2,3-d]pyrimidin-4(7H)-one General procedure 4 using 6-chloro-3-((4-hydroxypiperidin-4-yl)methyl)-7-(3-(1-methyl-1H-pyrazol-4-yl)phenyl)-3H-pyrrolo[2,3-d]pyrimidin-4(7H)-one (42 mg, 0.0957 mmol), 2-cyclopropyloxazole-5-carboxylic acid (16 mg, 0.105 mmol), HATU (40 mg, 0.105 mmol), DIPEA (63 µL, 0.364 mmol) and DCM (1.9 mL) gave the title compound (24 mg, 43%) as a colourless solid after lyophilisation. LCMS (Method B): $R_T$=1.02 min, m/z=574, 576 [M+H]$^+$. $^1$H NMR (500 MHz, DMSO-d$_6$): δ 8.24 (s, 1H), 8.09 (s, 1H), 7.95 (d, J=0.7 Hz, 1H), 7.75 (dt, J=7.9, 1.3 Hz, 1H), 7.67-7.64 (m, 1H), 7.56 (t, J=7.8 Hz, 1H), 7.50 (s, 1H), 7.24 (ddd, J=7.9, 2.1, 1.0 Hz, 1H), 6.82 (s, 1H), 5.02 (s, 1H), 4.10-3.91 (br. s, 2H), 4.04 (s, 2H), 3.86 (s, 3H), 3.60-2.97 (br. s, 2H (signal overlaps with HDO)), 2.17 (tt, J=8.3, 4.9 Hz, 1H), 1.66-1.52 (m, 2H), 1.50-1.41 (m, 2H), 1.13-1.05 (m, 2H), 1.02-0.95 (m, 2H).

Example 212: 6-Chloro-3-((4-hydroxy-1-(1-methylcyclopropanecarbonyl)piperidin-4-yl)methyl)-7-(3-(1-methyl-1H-pyrazol-4-yl)phenyl)-3H-pyrrolo[2,3-d]pyrimidin-4(7H)-one

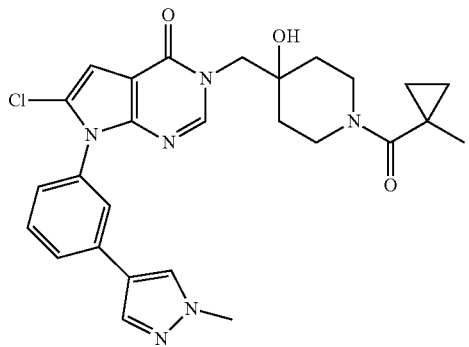 [SMILES: Cn1cc(-c2cccc(-n3c(Cl)cc4c(=O)n(CC5(O)CCN(C(=O)C6(C)CC6)CC5)cnc43)c2)cn1]

General procedure 4 using 6-chloro-3-((4-hydroxypiperidin-4-yl)methyl)-7-(3-(1-methyl-1H-pyrazol-4-yl)phenyl)-3H-pyrrolo[2,3-d]pyrimidin-4(7H)-one (49 mg, 0.112 mmol), 1-methylcyclopropanecarboxylic acid (12 mg, 0.123 mmol), HATU (47 mg, 0.123 mmol), DIPEA (78 µL, 0.447 mmol) and DCM (2.2 mL) gave the title compound (27 mg, 47%) as a colourless solid after lyophilisation. LCMS (Method B): $R_T$=1.02 min, m/z=521, 523 [M+H]$^+$. $^1$H NMR (500 MHz, DMSO-d$_6$): δ 8.24 (d, J=0.8 Hz, 1H), 8.09 (s, 1H), 7.95 (d, J=0.8 Hz, 1H), 7.75 (dt, J=7.9, 1.3 Hz, 1H), 7.65 (t, J=1.9 Hz, 1H), 7.56 (t, J=7.8 Hz, 1H), 7.24 (ddd, J=7.8, 2.1, 1.0 Hz, 1H), 6.83 (s, 1H), 4.93 (s, 1H), 4.02 (s, 2H), 3.95 (dt, J=12.3, 3.8 Hz, 2H), 3.86 (s, 3H), 3.16 (s, 2H), 1.60-1.47 (m, 2H), 1.43-1.36 (m, 2H), 1.21 (s, 3H), 0.80-0.74 (m, 2H), 0.55-0.49 (m, 2H).

Example 213: 7-(3-Bromophenyl)-6-chloro-3-((1-(2-cyclopropyloxazole-5-carbonyl)-4-hydroxypiperidin-4-yl)methyl)-3H-pyrrolo[2,3-d]pyrimidin-4(7H)-one

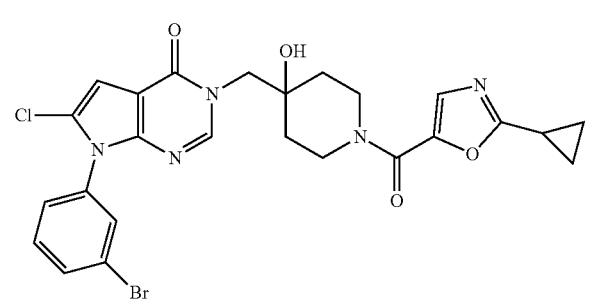 [SMILES: O=C(c1cnc(C2CC2)o1)N1CCC(O)(Cn2cnc3c(cc(Cl)n3-c3cccc(Br)c3)c2=O)CC1]

Step 1: 7-(3-Bromophenyl)-6-chloro-3-((4-hydroxypiperidin-4-yl)methyl)-3H-pyrrolo[2,3-d]pyrimidin-4(7H)-one A solution of tert-butyl 4-((7-(3-bromophenyl)-6-chloro-4-oxo-4,7-dihydro-3H-pyrrolo[2,3-d]pyrimidin-3-yl)methyl)-4-hydroxypiperidine-1-carboxylate (61 mg, 0.113 mmol) in DCM (1 mL) and TFA (0.5 mL) was stirred for 30 min before the reaction was purified using a 2 g Biotage SCX-2 cartridge (pre-equilibrated with, then washed with 1:1 DCM/MeOH, eluted using 1:1 DCM/7 M in NH$_3$ in MeOH). The basic phases were combined, concentrated in vacuo and the residue was dried in vacuo to give the title compound (46 mg, 92%) as a pale yellow solid. LCMS (Method B): $R_T$=0.82 min, m/z=437, 439 [M+H]$^+$.

Step 2: 7-(3-Bromophenyl)-6-chloro-3-((1-(2-cyclopropyloxazole-5-carbonyl)-4-hydroxypiperidin-4-yl)methyl)-3H-pyrrolo[2,3-d]pyrimidin-4(7H)-one General procedure 4 using 7-(3-bromophenyl)-6-chloro-3-((4-hydroxypiperidin-4-yl)methyl)-3H-pyrrolo[2,3-d]pyrimidin-4(7H)-one (24 mg, 0.0458 mmol), 2-cyclopropyloxazole-5-carboxylic acid (9 mg, 0.0603 mmol), HATU (23 mg, 0.0603 mmol), DIPEA (38 µL, 0.219 mmol) and DCM (1.1 mL) gave the title compound (16 mg, 50%) as a colourless solid after lyophilisation. LCMS (Method B): $R_T$=1.21 min, m/z=572, 574 [M+H]$^+$. $^1$H NMR (500 MHz, DMSO-d$_6$): δ 8.11 (s, 1H), 7.82-7.74 (m, 2H), 7.59-7.54 (m, 1H), 7.53-7.50 (m, 1H), 7.50 (s, 1H), 6.83 (s, 1H), 5.01 (s, 1H), 4.11-3.88 (br. s, 2H), 4.04 (s, 2H), 3.46-3.06 (br. s, 2H (signal overlaps with HDO)), 2.17 (tt, J=8.3, 4.9 Hz, 1H), 1.66-1.52 (m, 2H), 1.50-1.40 (m, 2H), 1.12-1.05 (m, 2H), 1.01-0.94 (m, 2H).

Example 214: 7-(3-Bromophenyl)-6-chloro-3-((4-hydroxy-1-(1-methylcyclopropanecarbonyl)piperidin-4-yl)methyl)-3H-pyrrolo[2,3-d]pyrimidin-4(7H)-one

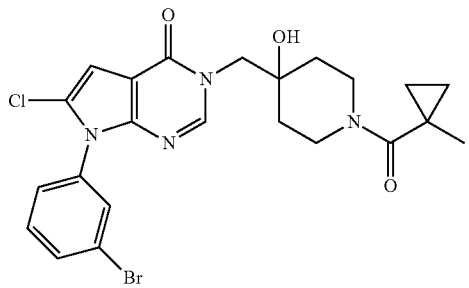 [SMILES: CC1(C(=O)N2CCC(O)(Cn3cnc4c(cc(Cl)n4-c4cccc(Br)c4)c3=O)CC2)CC1]

General procedure 4 using 7-(3-bromophenyl)-6-chloro-3-((4-hydroxypiperidin-4-yl)methyl)-3H-pyrrolo[2,3-d]pyrimidin-4(7H)-one (22 mg, 0.0503 mmol), 1-methylcyclopropanecarboxylic acid (5.5 mg, 0.0553 mmol), HATU (21 mg, 0.0553 mmol), DIPEA (35 µL, 0.201 mmol) and DCM (1 mL) gave the title compound (11 mg, 43%) as a colourless solid after lyophilisation. LCMS (Method B): $R_T$=1.21 min, m/z=519, 521 [M+H]$^+$. $^1$H NMR (500 MHz, DMSO-d$_6$): δ 8.11 (s, 1H), 7.81-7.74 (m, 2H), 7.60-7.54 (m, 1H), 7.51 (ddd, J=8.0, 1.9, 1.2 Hz, 1H), 6.84 (s, 1H), 4.92 (s, 1H), 4.02 (s, 2H), 3.99-3.91 (m, 2H), 3.16 (s, 2H), 1.58-1.45 (m, 2H), 1.43-1.36 (m, 2H), 1.21 (s, 3H), 0.80-0.74 (m, 2H), 0.55-0.48 (m, 2H).

Example 215: 6-Chloro-3-((1-(2-cyclopropyloxazole-5-carbonyl)-4-hydroxypiperidin-4-yl)methyl)-7-phenyl-3H-pyrrolo[2,3-d]pyrimidin-4(7H)-one

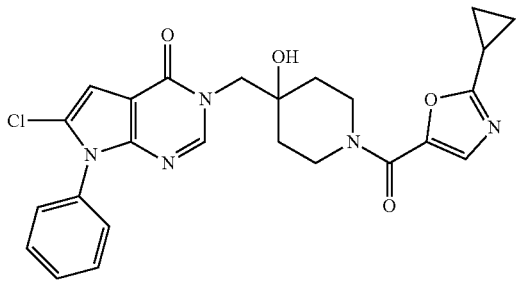 [SMILES: O=C(c1cnc(C2CC2)o1)N1CCC(O)(Cn2cnc3c(cc(Cl)n3-c3ccccc3)c2=O)CC1]

Step 1: 4,6-Dichloro-7-phenyl-7H-pyrrolo[2,3-d]pyrimidine

A mixture of 4,6-dichloro-7H-pyrrolo[2,3-d]pyrimidine (188 mg, 1 mmol), phenylboronic acid (420 mg, 3 mmol), Cu(OAc)$_2$ (363 mg, 2 mmol) and 1,10-phenanthroline (360 mg, 2 mmol) in DMF (10 mL) was stirred for 16 h before the reaction was quenched by the addition of saturated NH$_4$Cl$_{(aq)}$ (300 mL). The resulting mixture was extracted with EtOAc (3×50 mL), the combined organic phases were washed with brine and passed through a Biotage phase separator, concentrated in vacuo and the residue was purified by flash chromatography (24 g GraceResolv silica, 0-100% EtOAc in cyclohexane) to give the title compound (128 mg, 48%) as pale beige solid. LCMS (Method B): $R_T$=1.51 min, m/z=264, 266 [M+H]$^+$.

Step 2: 6-Chloro-7-phenyl-3H-pyrrolo[2,3-d]pyrimidin-4(7H)-one 4,6-Dichloro-7-phenyl-7H-pyrrolo[2,3-d]pyrimidine (125 mg, 0.473 mmol), 1 M HCl$_{(aq)}$ (2 mL, 2 mmol) and 1,4-dioxane (2 mL) were heated at 120° C. using microwave irradiation for 2 h. After cooling, the reaction mixture was diluted with water (5 mL) and the resultant precipitate was isolated by filtration. The material was dried overnight in a vacuum oven at 50° C. to give the title compound (77 mg, 66%) as a light pink solid. LCMS (Method B): $R_T$=0.91 min, m/z=246, 248 [M+H]$^+$.

Step 3: tert-Butyl 4-((6-chloro-4-oxo-7-phenyl-4,7-dihydro-3H-pyrrolo[2,3-d]pyrimidin-3-yl)methyl)-4-hydroxypiperidine-1-carboxylate General procedure 1 using Epoxide 1 (134 mg, 0.627 mmol), 6-chloro-7-phenyl-3H-pyrrolo[2,3-d]pyrimidin-4(7H)-one (77 mg, 0.313 mmol), Cs$_2$CO$_3$ (112 mg, 0.345 mmol) and DMF (1 mL) gave the title compound (125 mg, 86%) as a beige solid. LCMS (Method B): $R_T$=1.32 min, m/z=403, 405 [M-butene+H]$^+$.

Step 4: 6-Chloro-3-((4-hydroxypiperidin-4-yl)methy)-7-phenyl-3H-pyrrolo[2,3-d]pyrimidin-4(7H)-one tert-Butyl 4-((6-chloro-4-oxo-7-phenyl-4,7-dihydro-3H-pyrrolo[2,3-d]pyrimidin-3-yl)methyl)-4-hydroxypiperidine-1-carboxylate (125 mg, 0.272 mmol) was stirred in DCM (2 mL) and TFA (2 mL) for 15 min before the reaction was purified using a 5 g Biotage SCX-2 cartridge (pre-equilibrated with, then washed with 4:1 DCM/MeOH, eluted using 4:1 DCM/7 M in NH$_3$ in MeOH). The basic phases were combined and concentrated to give the title compound (90 mg, 92%) as light beige solid. LCMS (Method B): $R_T$=0.70 min, m/z=359, 361 [M+H]$^+$.

Step 5: 6-Chloro-3-((1-(2-cyclopropyloxazole-5-carbonyl)-4-hydroxypiperidin-4-yl)methy)-7-phenyl-3H-pyrrolo[2,3-d]pyrimidin-4(7H)-one General procedure 4 using 6-chloro-3-((4-hydroxypiperidin-4-yl)methyl)-7-phenyl-3H-pyrrolo[2,3-d]pyrimidin-4(7H)-one (45 mg, 0.125 mmol), 2-cyclopropyloxazole-5-carboxylic acid (21 mg, 0.138 mmol), HATU (57 mg, 0.150 mmol), DIPEA (66 µL, 0.376 mmol) and DCM (1.5 mL) gave the title compound (47 mg, 76%) as a colourless solid after lyophilisation. LCMS (Method B): $R_T$=1.07 min, m/z=494, 496 [M+H]$^+$. $^1$H NMR (500 MHz, DMSO-d$_6$): δ 8.09 (s, 1H), 7.63-7.53 (m, 3H), 7.49 (s, 1H), 7.48-7.44 (m, 2H), 6.82 (s, 1H), 5.00 (s, 1H), 4.13-3.87 (m, 4H), 3.60-2.97 (br. s, 2H (signal overlaps with HDO)), 2.21-2.13 (m, 1H), 1.98-1.51 (m, 2H), 1.51-1.41 (m, 2H), 1.13-1.04 (m, 2H), 1.02-0.95 (m, 2H).

Example 216: 6-Chloro-3-((4-hydroxy-1-(1-methyl-1H-pyrazole-4-carbonyl)piperidin-4-yl)methyl)-7-phenyl-3H-pyrrolo[2,3-d]pyrimidin-4(7H)-one

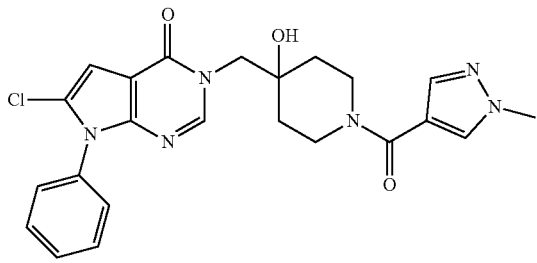 [SMILES: Cn1cc(C(=O)N2CCC(O)(Cn3cnc4c(cc(Cl)n4-c4ccccc4)c3=O)CC2)cn1]

General procedure 4 using 6-chloro-3-((4-hydroxypiperidin-4-yl)methyl)-7-phenyl-3H-pyrrolo[2,3-d]pyrimidin-4(7H)-one (45 mg, 0.125 mmol), 1-methyl-1H-pyrazole-4-carboxylic acid (17 mg, 0.138 mmol), HATU (57 mg, 0.150 mmol), DIPEA (66 µL, 0.376 mmol) and DCM (1.5 mL) gave the title compound (24 mg, 41%) as a colourless solid after lyophilisation. LCMS (Method B): $R_T$=1.07 min, m/z=467, 469 [M+H]$^+$. $^1$H NMR (500 MHz, DMSO-d$_6$): δ 8.08 (s, 1H), 8.02 (s, 1H), 7.64-7.53 (m, 4H), 7.48-7.42 (m, 2H), 6.81 (s, 1H), 4.95 (s, 1H), 4.17-3.78 (m, 7H), 3.48-2.98 (br. s, 2H (signal overlaps with HDO)), 1.61-1.52 (m, 2H), 1.46-1.38 (m, 2H).

Example 217: 6-Chloro-3-((1-(2-cyclopropyloxazole-5-carbonyl)-4-hydroxypiperidin-4-yl)methyl)-7-(3-cyclopropylphenyl)-3H-pyrrolo[2,3-d]pyrimidin-4(7H)-one

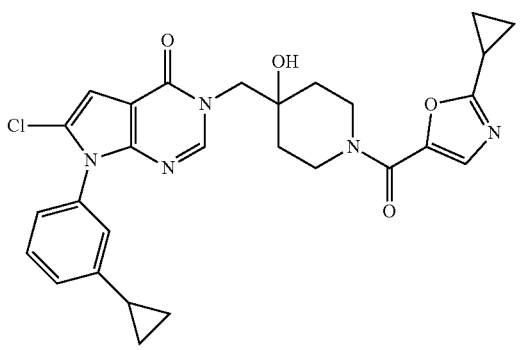 [SMILES: O=C(c1cnc(C2CC2)o1)N1CCC(O)(Cn2cnc3c(cc(Cl)n3-c3cccc(C4CC4)c3)c2=O)CC1]

Step 1: 4,6-Dichloro-7-(3-cyclopropylphenyl)-7H-pyrrolo[2,3-d]pyrimidine

A mixture of 4,6-dichloro-7H-pyrrolo[2,3-d]pyrimidine (387 mg, 2.06 mmol), (3-cyclopropylphenyl)boronic acid (1 g, 6.17 mmol), Cu(OAc)$_2$ (748 mg, 4.12 mmol) and 1,10-phenanthroline (742 mg, 4.12 mmol) in DMF (20 mL) was stirred for 16 h before the reaction was quenched by the addition of saturated NH$_4$Cl$_{(aq)}$ (400 mL). The resulting mixture was extracted with EtOAc (3×75 mL), the combined organic phases were washed with brine and passed through a phase separator, concentrated in vacuo, and the residue was purified by flash chromatography (40 g GraceResolv silica, 0-100% EtOAc in cyclohexane) to give the title compound (210 mg, 34%) as pale beige solid. LCMS (Method B): $R_T$=1.61 min, m/z=304, 306 [M+H]$^+$.

Step 2: 6-Chloro-7-(3-cyclopropylphenyl)-3H-pyrrolo[2,3-d]pyrimidin-4(7H)-one 4,6-Dichloro-7-(3-cyclopropylphenyl)-7H-pyrrolo[2,3-d]pyrimidine (210 mg, 0.690 mmol), 1 M HCl$_{(aq)}$ (3 mL, 3 mmol) and 1,4-dioxane (2 mL) were heated in a microwave at 120° C. for 2 h. The reaction mixture was diluted with water (5 mL) and the resultant precipitate was isolated by filtration. The precipitate was dried overnight in a vacuum oven at 50° C. to give the title compound (172 mg, 87%) as a light pink solid. LCMS (Method B): $R_T$=1.13 min, m/z=286, 288 [M+H]$^+$.

Step 3: tert-Butyl 4-((6-chloro-7-(3-cyclopropylphenyl)-4-oxo-4,7-dihydro-3H-pyrrolo[2,3-d]pyrimidin-3-yl)methyl)-4-hydroxypiperidine-1-carboxylate General procedure 1 using Epoxide 1 (254 mg, 1.19 mmol), 6-chloro-7-(3-cyclopropylphenyl)-3H-pyrrolo[2,3-d]pyrimidin-4(7H)-one (170 mg, 0.595 mmol), Cs$_2$CO$_3$ (213 mg, 0.655 mmol) and DMF (2 mL) gave the title compound (320 mg, quant.) as a beige solid. LCMS (Method B): $R_T$=1.49 min, m/z=443, 445 [M-butene+H]$^+$.

Step 4: 6-Chloro-7-(3-cyclopropylpheny)-3-((4-hydroxypiperidin-4-yl)methy)-3H-pyrrolo[2,3-d]pyrimidin-4(7H)-one tert-Butyl 4-((6-chloro-7-(3-cyclopropylphenyl)-4-oxo-4,7-dihydro-3H-pyrrolo[2,3-d]pyrimidin-3-yl)methyl)-4-hydroxypiperidine-1-carboxylate (320 mg, 0.601 mmol) was stirred in DCM (3 mL) and TFA (3 mL) for 15 min before the reaction was purified using a 5 g Biotage SCX-2 cartridge (pre-equilibrated with, then washed with 4:1 DCM/MeOH, eluted using 4:1 DCM/7 M in NH$_3$ in MeOH). The basic phases were combined and concentrated in vacuo to give the title compound (190 mg, 79%) as light beige solid. LCMS (Method B): $R_T$=0.84 min, m/z=399, 401 [M+H]$^+$.

Step 5: 6-Chloro-3-((1-(2-cyclopropyloxazole-5-carbonyl)-4-hydroxypiperidin-4-yl)methy)-7-(3-cyclopropylphenyl)-3H-pyrrolo[2,3-d]pyrimidin-4(7H)-one General procedure 4 using 6-chloro-7-(3-cyclopropylphenyl)-3-((4-hydroxypiperidin-4-yl)methyl)-3H-pyrrolo[2,3-d]pyrimidin-4(7H)-one (45 mg, 0.113 mmol), 2-cyclopropyloxazole-5-carboxylic acid (19 mg, 0.124 mmol), HATU (52 mg, 0.135 mmol), DIPEA (59 µL, 0.338 mmol) and DCM (1.5 mL) gave the title compound (42 mg, 69%) as a colourless solid after lyophilisation. LCMS (Method B): $R_T$=1.25 min, m/z=534, 536 [M+H]$^+$. $^1$H NMR (500 MHz, DMSO-d$_6$): δ 8.08 (s, 1H), 7.50 (s, 1H), 7.45 (t, 1H), 7.23 (d, 1H), 7.18 (d, 1H), 7.16 (t, 1H), 6.79 (s, 1H), 5.01 (s, 1H), 4.14-3.84 (m, 4H), 3.50-3.03 (br. s, 2H (signal overlaps with HDO)), 2.20-2.12 (m, 1H), 2.05-1.97 (m, 1H), 1.66-1.52 (m, 2H), 1.52-1.39 (m, 2H), 1.11-1.05 (m, 2H), 1.04-0.93 (m, 4H), 0.79-0.69 (m, 2H).

Example 218: 6-Chloro-7-(3-cyclopropylphenyl)-3-((4-hydroxy-1-(1-methylcyclopropanecarbonyl)piperidin-4-yl)methyl)-3H-pyrrolo[2,3-d]pyrimidin-4(7H)-one

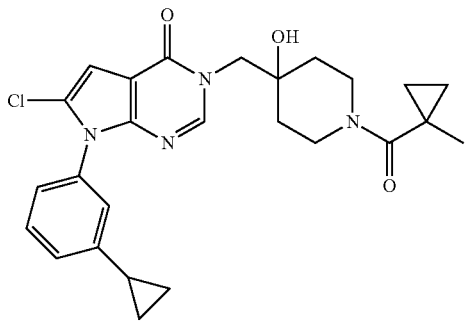 [SMILES: CC1(C(=O)N2CCC(O)(Cn3cnc4c(cc(Cl)n4-c4cccc(C5CC5)c4)c3=O)CC2)CC1]

General procedure 4 using 6-chloro-7-(3-cyclopropylphenyl)-3-((4-hydroxypiperidin-4-yl)methyl)-3H-pyrrolo[2,3-d]pyrimidin-4(7H)-one (45 mg, 0.113 mmol), 1-methylcyclopropanecarboxylic acid (12 mg, 0.124 mmol), HATU (52 mg, 0.135 mmol), DIPEA (59 µL, 0.338 mmol) and DCM (1.5 mL) gave the title compound (39 mg, 72%) as a colourless solid after lyophilisation. LCMS (Method B): $R_T$=1.25 min, m/z=481, 483 [M+H]$^+$. $^1$H NMR (500 MHz, DMSO-d$_6$): δ 8.08 (s, 1H), 7.45 (t, 1H), 7.23 (d, 1H), 7.18 (d, 1H), 7.16 (t, 1H), 6.79 (s, 1H), 4.92 (s, 1H), 4.01 (s, 2H), 3.95 (dt, 2H), 3.26-3.02 (m, 2H), 2.06-1.98 (m, 1H), 1.56-1.45 (m, 2H), 1.44-1.34 (m, 2H), 1.21 (s, 3H), 1.04-0.98 (m, 2H), 0.81-0.69 (m, 4H), 0.47-0.56 (m, 2H).

Example 219: 6-Chloro-7-(3-cyclopropylphenyl)-3-((4-hydroxy-1-(1-methyl-1H-pyrazole-4-carbonyl)piperidin-4-yl)methyl)-3H-pyrrolo[2,3-d]pyrimidin-4(7H)-one

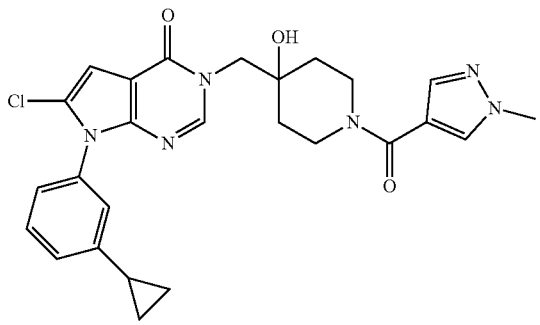 [SMILES: Cn1cc(C(=O)N2CCC(O)(Cn3cnc4c(cc(Cl)n4-c4cccc(C5CC5)c4)c3=O)CC2)cn1]

General procedure 4 using 6-chloro-7-(3-cyclopropylphenyl)-3-((4-hydroxypiperidin-4-yl)methyl)-3H-pyrrolo[2,3-d]pyrimidin-4(7H)-one (45 mg, 0.113 mmol), 1-methyl-1H-pyrazole-4-carboxylic acid (16 mg, 0.124 mmol), HATU (52 mg, 0.135 mmol), DIPEA (59 µL, 0.338 mmol) and DCM (1.5 mL) gave the title compound (24 mg, 42%) as a colourless solid after lyophilisation. LCMS (Method B): $R_T$=1.11 min, m/z=507, 509 [M+H]$^+$. $^1$H NMR (500 MHz, DMSO-d$_6$): δ 8.08 (s, 1H), 8.02 (s, 1H), 7.62 (s, 1H), 7.45 (t, 1H), 7.23 (d, 1H), 7.18 (d, 1H), 7.16 (t, 1H), 6.79 (s, 1H), 4.96 (s, 1H), 4.13-3.87 (m, 4H), 3.84 (s, 3H), 3.45-3.02 (m, 2H), 2.05-1.98 (m, 1H), 1.61-1.51 (m, 2H), 1.45-1.37 (m, 2H), 1.06-0.95 (m, 2H), 0.79-0.69 (m, 2H).

Example 220: 6-Chloro-7-(4-cyclopropylphenyl)-3-((4-hydroxy-1-(1-methylcyclopropanecarbonyl)piperidin-4-yl)methyl)-3H-pyrrolo[2,3-d]pyrimidin-4(7H)-one

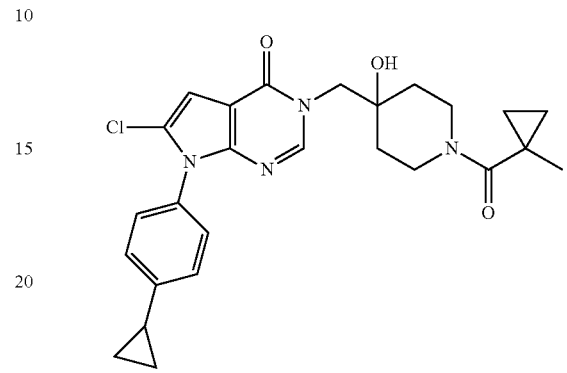

Step 1: 4,6-Dichloro-7-(4-cyclopropylphenyl)-7H-pyrrolo[2,3-d]pyrimidine

A mixture of 4,6-dichloro-7H-pyrrolo[2,3-d]pyrimidine (387 mg, 2.06 mmol), (4-cyclopropylphenyl)boronic acid (1 g, 6.17 mmol), Cu(OAc)$_2$ (748 mg, 4.12 mmol) and 1,10-phenanthroline (742 mg, 4.12 mmol) was stirred in DMF (40 mL) for 20 h before the reaction was quenched by the addition of saturated NH$_4$Cl$_{(aq)}$ (400 mL) and water (200 mL). The resulting mixture was extracted with EtOAc (3×200 mL), the combined organic phases were washed with water (250 mL), passed through a phase separator, concentrated in vacuo, and the residue purified by flash chromatography (100 g Biotage KP-Sil, 0-40% EtOAc in cyclohexane) to give the title compound (281 mg, 45%) as colourless solid. LCMS (Method B): $R_T$=1.62 min, m/z=304, 306 [M+H]$^+$.

Step 2: 6-Chloro-7-(4-cyclopropylphenyl)-3H-pyrrolo[2,3-d]pyrimidin-4(7H)-one A suspension of 4,6-dichloro-7-(4-cyclopropylphenyl)-7H-pyrrolo[2,3-d]pyrimidine (277 mg, 0.911 mmol) in 1 M HCl$_{(aq)}$ (1.8 mL, 1.8 mmol) and 1,4-dioxane (3 mL) was heated at 120° C. using microwave irradiation for 90 min. The reaction mixture was concentrated and the residue dried in a vacuum oven at 50° C. to give the title compound (259 mg, 99%) as a light pinkish orange solid. LCMS (Method B): $R_T$=1.17 min, m/z=286, 288 [M+H]$^+$.

Step 3: tert-Butyl 4-((6-chloro-7-(4-cyclopropylphenyl)-4-oxo-4,7-dihydro-3H-pyrrolo[2,3-d]pyrimidin-3-yl)methyl)-4-hydroxypiperidine-1-carboxylate General procedure 1 using Epoxide 1 (381 mg, 1.78 mmol), 6-chloro-7-(4-cyclopropylphenyl)-3H-pyrrolo[2,3-d]pyrimidin-4(7H)-one (255 mg, 0.892 mmol), Cs$_2$CO3 (320 mg, 0.982 mmol) and DMF (3 mL) gave the title compound (360 mg, 80%) as a beige foam. LCMS (Method B): $R_T$=1.49 min, m/z=443, 445 [M-butene+H]$^+$.

Step 4: 6-Chloro-7-(4-cyclopropylpheny)-3-((4-hydroxypiperidin-4-yl)methy)-3H-pyrrolo[2,3-d]pyrimidin-4(7H)-one A solution of tert-butyl 4-((6-chloro-7-(4-cyclopropyl-phenyl)-4-oxo-4,7-dihydro-3H-pyrrolo[2,3-d]pyrimidine-3-yl)methyl)-4-hydroxypiperidine-1-carboxylate (360 mg, 0.721 mmol) in DCM (2 mL) and TFA (1 mL) was stirred for 30 min before the reaction was purified using a 5 g Biotage SCX-2 cartridge (pre-equilibrated with, then washed with 1:1 DCM/MeOH, eluted using 1:1 DCM/7 M in $NH_3$ in MeOH). The basic phases were combined, concentrated in vacuo and the residue was purified by flash chromatography (28 g Biotage KP-NH, 0-100% DCM in cyclohexane, then 0-20% MeOH in DCM) to give the title compound (290 mg, 100%) as beige foam. LCMS (Method B): $R_T$=0.85 min, m/z=399, 401 $[M+H]^+$.

Step 5: 6-Chloro-7-(4-cyclopropylphenyl)-3-((4-hydroxy-1-(1-methylcyclopropanecarbonyl)piperidin-4-yl)methyl)-3H-pyrrolo[2,3-d]pyrimidin-4(7H)-one General procedure 4 using 6-chloro-7-(4-cyclopropylphenyl)-3-((4-hydroxypiperidin-4-yl)methyl)-3H-pyrrolo[2,3-d]pyrimidin-4(7H)-one (40 mg, 0.100 mmol), 1-methylcyclopropanecarboxylic acid (11 mg, 0.110 mmol), HATU (46 mg, 0.120 mmol), DIPEA (53 µL, 0.301 mmol) and DCM (1 mL) gave the title compound (25 mg, 52%) as a colourless solid after lyophilisation. LCMS (Method B): $R_T$=1.26 min, m/z=481, 483 $[M+H]^+$. $^1$H NMR (500 MHz, DMSO-$d_6$): δ 8.06 (s, 1H), 7.28 (m, 4H), 6.79 (s, 1H), 4.91 (s, 1H), 4.00 (s, 2H), 3.94 (dt, 2H), 3.26-3.05 (m, 2H), 2.07-2.00 (m, 1H), 1.55-1.45 (m, 2H), 1.48-1.40 (m, 2H), 1.20 (s, 3H), 1.06-1.00 (m, 2H), 0.80-0.74 (m, 4H), 0.54-0.49 (m, 2H).

Example 221: 6-Chloro-3-((1-(2-cyclopropyloxazole-5-carbonyl)-4-hydroxypiperidin-4-yl)methyl)-7-(4-cyclopropylphenyl)-3H-pyrrolo[2,3-d]pyrimidin-4(7H)-one

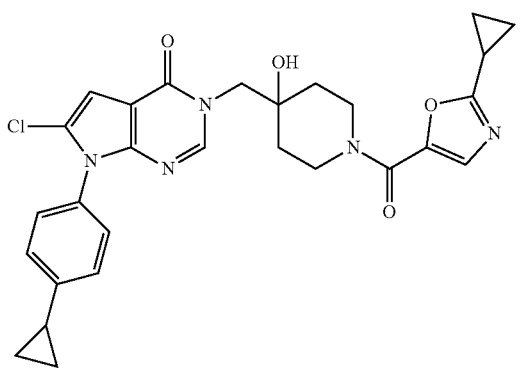 [SMILES: O=C(c1cnc(C2CC2)o1)N1CCC(O)(Cn2cnc3c(cc(Cl)n3-c3ccc(C4CC4)cc3)c2=O)CC1]

General procedure 4 using 6-chloro-7-(4-cyclopropylphenyl)-3-((4-hydroxypiperidin-4-yl)methyl)-3H-pyrrolo[2,3-d]pyrimidin-4(7H)-one (40 mg, 0.100 mmol), 2-cyclopropyloxazole-5-carboxylic acid (17 mg, 0.110 mmol), HATU (46 mg, 0.120 mmol), DIPEA (52 µL, 0.301 mmol) and DCM (1 mL) gave the title compound (27 mg, 50%) as a colourless solid after lyophilisation. LCMS (Method B): $R_T$=1.25 min, m/z=534, 536 $[M+H]^+$. $^1$H NMR (500 MHz, DMSO-$d_6$): δ 8.07 (s, 1H), 7.49 (s, 1H), 7.28 (m, 4H), 6.78 (s, 1H), 5.00 (s, 1H), 4.12-3.90 (m, 4H), 3.49-3.03 (br. s, 2H signal overlaps with HDO)), 2.20-2.13 (m, 1H), 2.07-1.99 (m, 1H), 1.65-1.53 (m, 2H), 1.48-1.40 (m, 2H), 1.11-1.06 (m, 2H), 1.06-1.01 (m, 2H), 1.00-0.95 (m, 2H), 0.79-0.74 (m, 2H).

Example 222: 6-Bromo-3-((1-(2-cyclopropyloxazole-5-carbonyl)-4-hydroxypiperidin-4-yl)methyl)-7-phenyl-3H-pyrrolo[2,3-d]pyrimidin-4(7H)-one

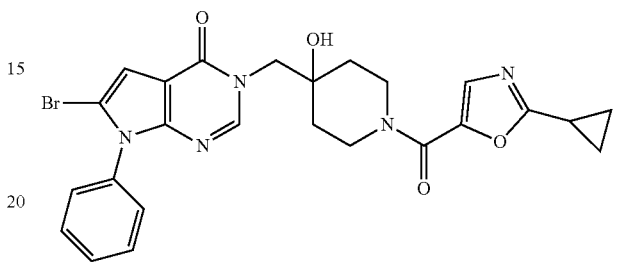

Step 1: 6-Bromo-4-chloro-7-phenyl-7H-pyrrolo[2,3-d]pyrimidine

A mixture of 6-bromo-4-chloro-7H-pyrrolo[2,3-d]pyrimidine (232 mg, 1 mmol), $PhB(OH)_2$ (365 mg, 3 mmol), $Cu(OAc)_2$ (363 mg, 2 mmol) and 1,10-phenanthroline (360 mg, 2 mmol) was stirred in DMF (20 mL) for 16 h before the reaction was diluted with saturated $NH_4Cl(aq)$ (200 mL) and water (200 mL). The resulting mixture was extracted with EtOAc (3×50 mL), the combined organic phases were passed through a phase separator, concentrated in vacuo, and the residue was purified by flash chromatography (40 g GraceResolv silica, 0-60% EtOAc in cyclohexane) to give the title compound (170 mg, 55%) as colourless solid. LCMS (Method B): $R_T$=1.42 min, m/z=308, 310, 312 $[M+H]^+$.

Step 2: 6-Bromo-7-phenyl-3H-pyrrolo[2,3-d]pyrimidin-4(7H)-one

A solution of 6-bromo-4-chloro-7-phenyl-7H-pyrrolo[2,3-d]pyrimidine (170 mg, 0.551 mmol) in 4 M $NaOH_{(aq)}$ (1 mL, 4 mmol) and 1,4-dioxane (2 mL) was heated at reflux. After 16 h, the reaction mixture was allowed to cool to RT and the pH was adjusted to ~pH 2 by the addition of 1 M $HCl_{(aq)}$. The precipitate was isolated by filtration and dried at 50° C. in a vacuum oven to give the title compound (crude, 178 mg, >100%) as a brown solid that was used in the next step without further purification. $^1$H NMR (500 MHz, DMSO-$d_6$: δ 12.14 (br. s, 1H), 7.84 (s, 1H), 7.60-7.50 (m, 3H), 7.43-7.38 (m, 2H), 6.85 (s, 1H).

Step 3: tert-Butyl 4-((6-bromo-4-oxo-7-phenyl-4,7-dihydro-3H-pyrrolo[2,3-d]pyrimidin-3-yl)methyl)-4-hydroxypiperidine-1-carboxylate General procedure 1 using Epoxide 1 (175 mg, 0.603 mmol), 6-bromo-7-phenyl-3H-pyrrolo[2,3-d]pyrimidin-4 (7H)-one (106 mg, 0.365 mmol), $Cs_2CO_3$ (216 mg, 0.663 mmol) and DMF (2 mL) gave the title compound (192 mg, 63%) as a beige solid. LCMS (Method B): $R_T$=1.33 min, m/z=447, 449 [M-butene+H]$^+$.

Step 4: 6-Bromo-3-((4-hydroxypiperidin-4-yl)methy)-7-phenyl-3H-pyrrolo[2,3-d]pyrimidin-4(7H)-one A solution of tert-butyl 4-((6-bromo-4-oxo-7-phenyl-4,7-dihydro-3H-pyrrolo[2,3-d]pyrimidin-3-yl)methyl)-4-hydroxypiperidine-1-carboxylate (131 mg, 0.243 mmol) in DCM (4 mL) and TFA (2 mL) was stirred for 10 min before the reaction was purified using a 5 g Biotage SCX-2 cartridge (pre-equilibrated with, then washed with 1:1 DCM/MeOH, eluted using 1:1 DCM/7 M in NH$_3$ in MeOH). The basic phases were combined, concentrated in vacuo and the residue purified by flash chromatography (11 g Biotage KP-NH, 0-100% DCM in cyclohexane, then 0-30% MeOH in DCM) to give the title compound (120 mg, 78%) as a beige foam. LCMS (Method B): R$_T$=0.71 min, m/z=403, 405 [M+H]$^+$.

Step 5: 6-Bromo-3-((1-(2-cyclopropyloxazole-5-carbonyl)-4-hydroxypiperidin-4-yl)methy)-7-phenyl-3H-pyrrolo[2,3-d]pyrimidin-4(7H)-one General procedure 4 using 6-bromo-3-((4-hydroxypiperidin-4-yl)methyl)-7-phenyl-3H-pyrrolo[2,3-d]pyrimidin-4(7H)-one (30 mg, 0.0744 mmol), 2-cyclopropyloxazole-5-carboxylic acid (12.5 mg, 0.0818 mmol), HATU (31 mg, 0.0818 mmol), DIPEA (52 µL, 0.298 mmol) and DCM (1.5 mL) gave the title compound (37 mg, 93%) as a colourless solid after lyophilisation. LCMS (Method B): R$_T$=1.07 min, m/z=538, 540 [M+H]$^+$. $^1$H NMR (500 MHz, DMSO-d$_6$): δ 8.06 (s, 1H), 7.63-7.52 (m, 3H), 7.49 (s, 1H), 7.46-7.39 (m, 2H), 6.89 (s, 1H), 5.00 (s, 1H), 4.09-3.92 (m, 2H), 4.03 (s, 2H), 3.56-3.00 (m, 2H (signal overlaps with HDO)), 2.17 (tt, J=8.3, 4.9 Hz, 1H), 1.68-1.55 (m, 2H), 1.49-1.42 (m, 2H), 1.13-1.04 (m, 2H), 1.02-0.94 (m, 2H).

Example 223: 6-Bromo-3-((4-hydroxy-1-(1-methylcyclopropanecarbonyl)piperidin-4-yl)methyl)-7-phenyl-3H-pyrrolo[2,3-d]pyrimidin-4(7H)-one

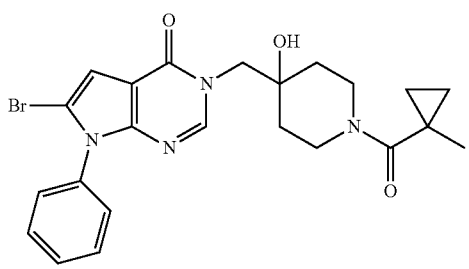 [SMILES: CC1(C(=O)N2CCC(O)(Cn3cnc4c(cc(Br)n4-c4ccccc4)c3=O)CC2)CC1]

General procedure 4 using 6-bromo-3-((4-hydroxypiperidin-4-yl)methyl)-7-phenyl-3H-pyrrolo[2,3-d]pyrimidin-4(7H)-one (30 mg, 0.0744 mmol), 1-methylcyclopropanecarboxylic acid (8.2 mg, 0.0818 mmol), HATU (31 mg, 0.0818 mmol), DIPEA (52 µL, 0.298 mmol) and DCM (1.5 mL) gave the title compound (24 mg, 66%) as a colourless solid after lyophilisation. LCMS (Method B): R$_T$=1.08 min, m/z=485, 487 [M+H]$^+$. $^1$H NMR (500 MHz, DMSO-d$_6$): δ 8.05 (s, 1H), 7.63-7.52 (m, 3H), 7.45-7.39 (m, 2H), 6.90 (s, 1H), 4.91 (s, 1H), 4.01 (s, 2H), 3.95 (dt, J=13.3, 4.2 Hz, 2H), 3.15 (s, 2H), 1.56-1.45 (m, 2H), 1.43-1.36 (m, 2H), 1.21 (s, 3H), 0.80-0.74 (m, 2H), 0.55-0.48 (m, 2H).

Example 224: 3-((1-(2-Cyclopropyloxazole-5-carbonyl)-4-hydroxypiperidin-4-yl)methyl)-6-iodo-7-phenyl-3H-pyrrolo[2,3-d]pyrimidin-4(7H)-one

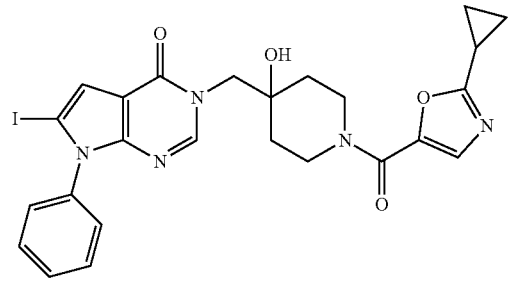 [SMILES: O=C(c1cnc(C2CC2)o1)N1CCC(O)(Cn2cnc3c(cc(I)n3-c3ccccc3)c2=O)CC1]

Step 1: 4-Chloro-6-iodo-7-phenyl-7H-pyrrolo[2,3-d]pyrimidine

A mixture of 4-chloro-6-iodo-7H-pyrrolo[2,3-d]pyrimidine (400 mg, 1.43 mmol), phenylboronic acid (524 mg, 4.29 mmol), copper(II) acetate (520 mg, 2.86 mmol) and 1,10-phenanthroline (516 mg, 2.86 mmol) in anhydrous dimethylformamide (16 mL) was stirred for 16 h. The reaction mixture was partitioned between saturated ammonium chloride (80 mL), water (80 mL) and ethyl acetate (80 mL). The separated aqueous phase was extracted with ethyl acetate (3×80 mL). The combined organic phase was washed with 1:1 brine/water (4×80 mL), dried (Na$_2$SO$_4$), filtered, and concentrated in vacuo. The residue was purified by flash chromatography (0-30% EtOAc in cyclohexane) to afford the title compound (207 mg, 41%). LCMS (Method B): R$_T$=1.42 min, m/z=356 [M+H]$^+$.

Step 2: 6-Iodo-7-phenyl-3H-pyrrolo[2,3-d]pyrimidin-4(7H)-one

Sodium hydroxide, 4M (84.4 mg, 2.11 mmol) (0.53 mL) was added to a stirred solution of 4-chloro-6-iodo-7-phenyl-7H-pyrrolo[2,3-d]pyrimidine (50 mg, 0.141 mmol) in 1,4-dioxane (1 mL). The solution was heated to 100° C. After 16 h, the reaction mixture was cooled and the solvents were removed in vacuo. Water (3 mL) was added and the pH was adjusted by dropwise addition of 2M hydrochloric acid to ca. pH 4. The solid was collected by filtration and dried under vacuum. The material was dissolved in DCM and the solvents were removed in vacuo to afford the title compound (44.2 mg, 93%) which was used without further purification. LCMS (Method B): R$_T$=0.93 min, m/z=338 [M+H]$^+$.

Step 3: tert-Butyl 4-hydroxy-4-((6-iodo-4-oxo-7-phenyl-4,7-dihydro-3H-pyrrolo[2,3-d]pyrimidin-3-yl)methyl)piperidine-1-carboxylate tert-Butyl 1-oxa-6-azaspiro[2.5]octane-6-carboxylate (33.6 mg, 0.157 mmol) was added to a stirred solution of 6-iodo-7-phenyl-3H-pyrrolo[2,3-d]pyrimidin-4(7H)-one (44.2 mg, 0.131 mmol) and cesium carbonate (128 mg, 0.393 mmol) in DMF (1 mL). The solution was heated to 80° C. and stirred for 16 h. After cooling, the mixture was partitioned between 1:1 brine/water (10 mL) and ethyl acetate (10 mL). The separated aqueous phase was extracted with ethyl acetate (3×5 mL). The combined ethyl acetate fractions were washed with 1:1 brine/water (4×5 mL), dried (Na$_2$SO$_4$), filtered, and reduced in vacuo. The residue was purified by flash chromatography (0-100% EtOAc in cyclohexane) to afford the title compound (41.5 mg, 58%). LCMS (Method B): R$_T$=1.33 min, m/z=495 [M-butene+H]$^+$.

Step 4: 3-((4-Hydroxypiperidin-4-yl)methyl)-6-iodo-7-phenyl-3H-pyrrolo[2,3-d]pyrimidin-4(7H)-one Trifluoroacetic acid (0.5 mL) was added to a stirred solution of tert-butyl 4-hydroxy-4-((6-iodo-4-oxo-7-phenyl-4,7-dihydro-3H-pyrrolo[2,3-d]pyrimidin-3-yl)methyl)piperidine-1-carboxylate (41.5 mg, 0.0754 mmol) in DCM (2 mL) and the solution was stirred for 15 min. An SCX-2 silica cartridge (5 g) was pre-equilibrated using 20% v/v methanol in DCM (50 mL) and loaded using DCM (3×1 mL) to transfer the reaction mixture. After 5 mins, the column was flushed using 20% v/v methanol in DCM (50 mL) followed by 20% v/v (7M ammonia in methanol) in DCM (25 mL). The ammonia containing fraction was concentrated in vacuo to afford the title compound (32.7 mg, 96%). LCMS (Method B): R$_T$=0.72 min, m/z=451 [M+H]$^+$.

Step 5: 3-((1-(2-Cyclopropyloxazole-5-carbonyl)-4-hydroxypiperidin-4-yl)methyl)-6-iodo-7-phenyl-3H-pyrrolo[2,3-d]pyrimidin-4(7H)-one To a stirred solution of 3-((4-hydroxypiperidin-4-yl)methyl)-6-iodo-7-phenyl-3H-pyrrolo[2,3-d]pyrimidin-4(7H)-one (16.4 mg, 0.0364 mmol), 2-cyclopropyloxazole-5-carboxylic acid (5.6 mg, 0.0364 mmol) and HATU (16.6 mg, 0.0437 mmol) in anhydrous DCM (1 mL) was added DIPEA (9.4 mg, 0.0728 mmol). After 30 min, the reaction mixture was washed with saturated sodium bicarbonate (aq) solution (0.5 mL). The separated aqueous phase was extracted with DCM (3×0.5 mL). The combined DCMf reactions were dried (phase separator) and purified by flash chromatography (0-100% EtOAc in cyclohexane, then 0-8% methanol in EtOAc). The residue was purified by flash chromatography (0-4% methanol in DCM). The residue was suspended in acetonitrile (1 mL) and water (10 mL) and freeze-dried to afford the title compound (16.7 mg, 78%). LCMS (Method B): R$_T$=1.08 min, m/z=586 [M+H]$^+$. $^1$H NMR (500 MHz, DMSO-d$_6$): δ 7.99 (s, 1H), 7.53-7.61 (m, 3H), 7.49 (s, 1H), 7.37 (dd, 2H), 6.99 (s, 1H), 4.99 (s, 1H), 3.90-4.10 (m, 4H), 3.32-3.50 (m, 1H), 3.07-3.26 (m, 2H), 2.12-2.20 (m, 1H), 1.53-1.65 (m, 2H), 1.40-1.49 (m, 2H), 1.069-1.12 (m, 2H), 0.95-1.00 (m, 2H).

Example 225: 6-Chloro-3-((4-hydroxy-1-(1-methylcyclopropanecarbonyl)piperidin-4-yl)methyl)-7-(3-(4-(trifluoromethyl)-1H-pyrazol-1-yl)phenyl)-3H-pyrrolo[2,3-d]pyrimidin-4(7H)-one

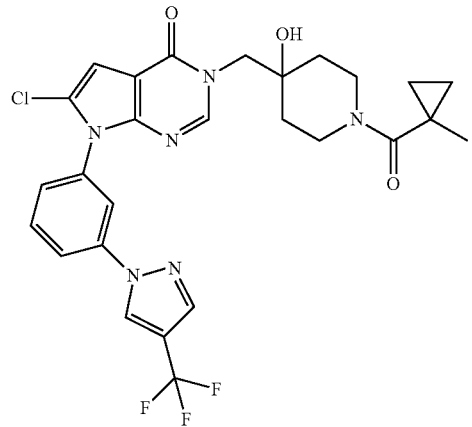 [SMILES: CC1(C(=O)N2CCC(O)(Cn3cnc4c(cc(Cl)n4-c4cccc(-n5cc(C(F)(F)F)cn5)c4)c3=O)CC2)CC1]

Step 1: tert-Butyl 4-((6-chloro-4-oxo-7-(3-(4-(trifluoromethyl)-1H-pyrazol-1-yl)phenyl)-4,7-dihydro-3H-pyrrolo[2,3-d]pyrimidin-3-yl)methyl)-4-hydroxypiperidine-1-carboxylate A suspension of tert-butyl 4-((7-(3-bromophenyl)-6-chloro-4-oxo-4,7-dihydro-3H-pyrrolo[2,3-d]pyrimidin-3-yl)methyl)-4-hydroxypiperidine-1-carboxylate (50 mg, 0.0930 mmol), 4-(trifluoromethyl)-1H-pyrazole (15 mg, 0.112 mmol), CuI (18 mg, 0.186 mmol), trans-N,N'-dimethylcyclohexane-1,2-diamine (26 mg, 0.186 mmol) and K$_2$CO$_3$ (51 mg, 0.372 mmol) in DMF (1 mL) in a sealed reaction tube was degassed with N$_2$ and heated at 110° C. for 4 h. The mixture was allowed to cool to RT, diluted with saturated NH$_4$Cl$_{(aq)}$ (15 mL) and the resulting mixture was extracted using DCM (3×10 mL). The combined organic phases were concentrated in vacuo and the residue was purified by flash chromatography (12 g GraceResolv silica, 0-100% EtOAc in cyclohexane) to give the title compound (51 mg, 92%) as a colourless solid. LCMS (Method B): R$_T$=1.50 min, m/z=537, 539 [M-butene+H]$^+$.

Step 2: 6-Chloro-3-((4-hydroxypiperidin-4-yl)methyl)-7-(3-(4-(trifluoromethyl)-1H-pyrazol-1-yl)phenyl)-3H-pyrrolo[2,3-d]pyrimidin-4(7H)-one A solution of tert-butyl 4-((6-chloro-4-oxo-7-(3-(4-(trifluoromethyl)-1H-pyrazol-1-yl)phenyl)-4,7-dihydro-3H-pyrrolo[2,3-d]pyrimidin-3-yl)methyl)-4-hydroxypiperidine-1-carboxylate (51 mg, 0.0860 mmol) in DCM (1 mL) and TFA (0.5 mL) was stirred for 10 min before the reaction was purified using a 2 g Biotage SCX-2 cartridge (pre-equilibrated with, then washed with 1:1 DCM/MeOH, eluted using 1:1 DCM/7 M in NH$_3$ in MeOH). The basic phases were combined, concentrated and the residue was purified by flash chromatography (11 g Biotage KP-NH, 0-100% DCM in cyclohexane, then 0-30% MeOH in DCM) to give the title compound (35 mg, 82%) as a glassy solid. LCMS (Method B): R$_T$=0.91 min, m/z=493, 495 [M+H]$^+$.

Step 3: 6-Chloro-3-((4-hydroxy-1-(1-methylcyclopropanecarbonyl)piperidin-4-yl)methyl)-7-(3-(4-(trifluoromethyl)-1H-pyrazol-1-yl)phenyl)-3H-pyrrolo[2,3-d]pyrimidin-4(7H)-one General procedure 4 using 6-chloro-3-((4-hydroxypiperidin-4-yl)methyl)-7-(3-(4-(trifluoromethyl)-1H-pyrazol-1-yl)phenyl)-3H-pyrrolo[2,3-d]pyrimidin-4(7H)-one (35 mg, 0.0710 mmol), 1-methylcyclopropanecarboxylic acid (8 mg, 0.0781 mmol), HATU (30 mg, 0.781 mmol), DIPEA (50 µL, 0.284 mmol) and DCM (1.5 mL) after preparative HPLC (Method A) gave the title compound (16 mg, 40%) as a colourless solid after lyophilisation. LCMS (Method A): $R_T$=1.49 min, m/z=575, 577 [M+H]$^+$. $^1$H NMR (500 MHz, DMSO-d$_6$): δ 9.31 (s, 1H), 8.27 (s, 1H), 8.14-8.10 (m, 2H), 8.08 (t, J=2.1 Hz, 1H), 7.78 (t, J=8.1 Hz, 1H), 7.53 (ddd, J=7.9, 2.0, 0.9 Hz, 1H), 6.88 (s, 1H), 4.92 (s, 1H), 4.02 (s, 2H), 3.95 (dt, J=13.3, 4.2 Hz, 2H), 3.16 (s, 2H), 1.59-1.48 (m, 2H), 1.43-1.36 (m, 2H), 1.21 (s, 3H), 0.80-0.74 (m, 2H), 0.55-0.49 (m, 2H).

Example 226: 6-Chloro-3-((4-hydroxy-1-(1-methylcyclopropanecarbonyl)piperidin-4-yl)methyl)-7-(3-morpholinophenyl)-3H-pyrrolo[2,3-d]pyrimidin-4(7H)-one

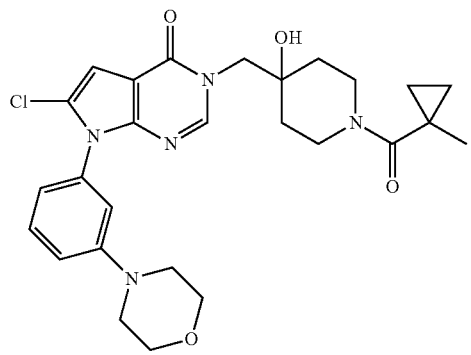 [SMILES: CC1(C(=O)N2CCC(O)(Cn3cnc4c(cc(Cl)n4-c4cccc(N5CCOCC5)c4)c3=O)CC2)CC1]

A mixture of Intermediate F (142 mg, 0.389 mmol), (3-morpholinophenyl)boronic acid (241 mg, 1.17 mmol), Cu(OAc)$_2$ (141 mg, 0.778 mmol) and 1,10-phenanthroline (140 mg, 0.778 mmol) was stirred in DMF (3.9 mL) for 18 h at RT before the reaction was diluted with NH$_4$OH (50 mL) and water (50 mL). The resulting mixture was extracted with DCM (5×30 mL) using a phase separator, the combined organic phases were concentrated in vacuo and the residue was purified by flash chromatography (28 g KP-NH, 0-100% EtOAc in cyclohexane, then 0-15% MeOH in EtOAc; then 40 g GraceResolv silica, 0-15% MeOH in DCM) to give the title compound (70 mg, 34%) as a pale pink solid after lyophilisation. LCMS (Method A): $R_T$=1.18 min, m/z=526, 528 [M+H]$^+$. $^1$H NMR (500 MHz, DMSO-d$_6$): δ 8.07 (s, 1H), 7.41 (t, J=8.1 Hz, 1H), 7.10 (ddd, J=8.6, 2.6, 0.9 Hz, 1H), 6.96 (t, J=2.2 Hz, 1H), 6.82 (ddd, J=7.7, 1.9, 0.8 Hz, 1H), 6.78 (s, 1H), 4.92 (s, 1H), 4.01 (s, 2H), 3.95 (dt, J=13.2, 4.2 Hz, 2H), 3.77-3.71 (m, 4H), 3.27-3.04 (m, 6H), 1.56-1.47 (m, 2H), 1.42-1.36 (m, 2H), 1.21 (s, 3H), 0.80-0.74 (m, 2H), 0.55-0.48 (m, 2H).

Example 227: 6-Chloro-7-(3-(4-fluoro-1H-pyrazol-1-yl)phenyl)-3-((4-hydroxy-1-(1-methylcyclopropanecarbonyl)piperidin-4-yl)methyl)-3H-pyrrolo[2,3-d]pyrimidin-4(7H)-one

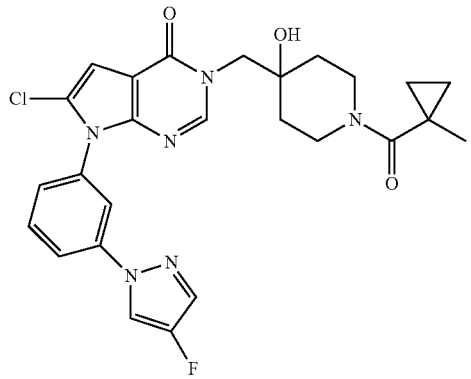 [SMILES: CC1(C(=O)N2CCC(O)(Cn3cnc4c(cc(Cl)n4-c4cccc(-n5cc(F)cn5)c4)c3=O)CC2)CC1]

Step 1: tert-Butyl 4-((6-chloro-7-(3-(4-fluoro-1H-pyrazol-1-yl)phenyl)-4-oxo-4,7-dihydro-3H-pyrrolo[2,3-d]pyrimidin-3-yl)methyl)-4-hydroxypiperidine-1-carboxylate tert-Butyl 4-((7-(3-bromophenyl)-6-chloro-4-oxo-4,7-dihydro-3H-pyrrolo[2,3-d]pyrimidin-3-yl)methyl)-4-hydroxypiperidine-1-carboxylate (50 mg, 0.093 mmol), 4-fluoro-1H-pyrazole (10 mg, 0.112 mmol), CuI (18 mg, 0.186 mmol), trans-N,N'-dimethylcyclohexane-1,2-diamine (26 mg, 0.186 mmol) and K$_2$CO$_3$ (51 mg, 0.372 mmol) in DMF (1 mL) in a sealed reaction tube was degassed with N$_2$ and heated at 110° C. for 4 h. The reaction mixture was allowed to cool to RT, diluted with saturated NH$_4$Cl$_{(aq)}$ (15 mL) and the resulting mixture was extracted with DCM (3×10 mL) using a phase separator. The combined organic phases were concentrated in vacuo and the residue was purified by flash chromatography (12 g GraceResolv silica, 0-100% EtOAc in cyclohexane) to give the title compound (50 mg, 99%) as a colourless solid. LCMS (Method A): $R_T$=1.62 min, m/z=543, 545 [M+H]$^+$.

Step 2: 6-Chloro-7-(3-(4-fluoro-1H-pyrazol-1-yl)phenyl)-3-((4-hydroxypiperidin-4-yl)methyl)-3H-pyrrolo[2,3-d]pyrimidin-4(7H)-one A solution of tert-butyl 4-((6-chloro-7-(3-(4-fluoro-1H-pyrazol-1-yl)phenyl)-4-oxo-4,7-dihydro-3H-pyrrolo[2,3-d]pyrimidin-3-yl)methyl)-4-hydroxypiperidine-1-carboxylate (50 mg, 0.0921 mmol) in DCM (1 mL) and TFA (0.5 mL) was stirred for 10 min before the reaction was purified using a 2 g Biotage SCX-2 cartridge (pre-equilibrated with, then washed with 1:1 DCM/MeOH, eluted using 1:1 DCM/7 M in NH$_3$ in MeOH). The basic phases were combined and concentrated in vacuo to give the title compound (crude, 49 mg, >100%) as a glassy solid that was used without further purification. LCMS (Method A): $R_T$=0.84 min, m/z=443, 445 [M+H]$^+$.

Step 3: 6-Chloro-7-(3-(4-fluoro-1H-pyrazol-1-yl)phenyl)-3-((4-hydroxy-1-(1-methylcyclopropanecarbonyl)piperidin-4-yl)methyl)-3H-pyrrolo[2,3-d]pyrimidin-4(7H)-one General procedure 4 using 6-chloro-7-(3-(4-fluoro-1H-pyrazol-1-yl)phenyl)-3-((4-hydroxypiperidin-4-yl)methyl)-

3H-pyrrolo[2,3-d]pyrimidin-4(7H)-one (41 mg, 0.0926 mmol), 1-methylcyclopropanecarboxylic acid (10 mg, 0.102 mmol), HATU (39 mg, 0.102 mmol), DIPEA (64 μL, 0.370 mmol) and DCM (1.8 mL) gave the title compound (28 mg, 58%) as a colourless solid after lyophilisation. LCMS (Method A): $R_T$=1.32 min, m/z=525, 527 [M+H]$^+$. $^1$H NMR (500 MHz, DMSO-d$_6$): δ 8.81 (d, J=4.4 Hz, 1H), 8.11 (s, 1H), 8.01 (ddd, J=8.3, 2.3, 0.9 Hz, 1H), 7.94 (t, J=2.1 Hz, 1H), 7.90 (d, J=4.1 Hz, 1H), 7.73 (t, J=8.1 Hz, 1H), 7.43 (ddd, J=7.9, 2.0, 0.9 Hz, 1H), 6.86 (s, 1H), 4.93 (s, 1H), 4.02 (s, 2H), 3.95 (dt, J=13.2, 4.2 Hz, 2H), 3.16 (s, 2H), 1.59-1.46 (m, 2H), 1.44-1.36 (m, 2H), 1.21 (s, 3H), 0.80-0.74 (m, 2H), 0.55-0.49 (m, 2H).

Example 228: 6-Chloro-7-(4-chlorophenyl)-3-((1-(2-cyclopropyloxazole-5-carbonyl)-4-hydroxypiperidin-4-yl)methyl)-3H-pyrrolo[2,3-d]pyrimidin-4(7H)-one

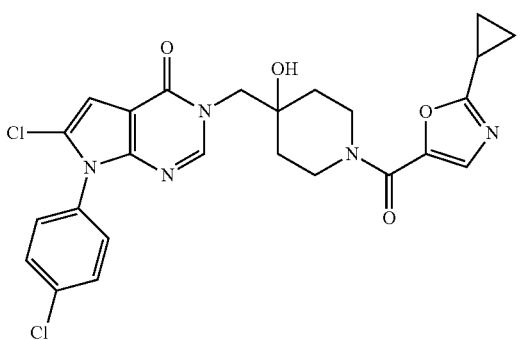 [SMILES: O=C(c1cnc(C2CC2)o1)N1CCC(O)(Cn2cnc3c(cc(Cl)n3-c3ccc(Cl)cc3)c2=O)CC1]

Step 1: 4,6-Dichloro-7-(4-chlorophenyl)-7H-pyrrolo[2,3-d]pyrimidine

A mixture of 4,6-dichloro-7H-pyrrolo[2,3-d]pyrimidine (300 mg, 1.60 mmol), (4-chlorophenyl)boronic acid (499 mg, 3.19 mmol), Cu(OAc)$_2$ (580 mg, 3.19 mmol) in DMF (10 mL) was added pyridine (1 mL, 12.8 mmol) and stirred for 16 h before the reaction was quenched by the addition of saturated NH$_4$Cl$_{(aq)}$ (300 mL). The resulting mixture was extracted with EtOAc (3×50 mL), the combined organic phases were washed with brine, dried (phase separator), concentrated in vacuo, and the residue was purified by flash chromatography (24 g GraceResolv silica, 0-100% EtOAc in cyclohexane) to give the title compound (100 mg, 21%) as pale beige solid. LCMS (Method B): $R_T$=1.74 min, m/z=298, 300, 302 [M+H]$^+$.

Step 2: 6-Chloro-7-(4-chlorophenyl)-3H-pyrrolo[2,3-d]pyrimidin-4(7H)-one 4,6-Dichloro-7-(4-chlorophenyl)-7H-pyrrolo[2,3-d]pyrimidine (100 mg, 0.335 mmol), 1 M HCl$_{(aq)}$ (2 mL, 2 mmol) and 1,4-dioxane (2 mL) were heated in a microwave at 120° C. for 1.5 h. The reaction was diluted with water (5 mL) and the precipitate was isolated by filtration. The material was dried overnight in a vacuum oven at 50° C. to give the title compound (57 mg, 61%) as a pale pink solid. LCMS (Method B): $R_T$=1.06 min, m/z=280, 282 [M+H]$^+$.

Step 3: tert-Butyl 4-((6-chloro-7-(4-chlorophenyl)-4-oxo-4,7-dihydro-3H-pyrrolo[2,3-d]pyrimidin-3-yl)methyl)-4-hydroxypiperidine-1-carboxylate General procedure 1 using Epoxide 1 (85 mg, 0.400 mmol), 6-chloro-7-(4-chlorophenyl)-3H-pyrrolo[2,3-d]pyrimidin-4(7H)-one (56 mg, 0.200 mmol), Cs$_2$CO$_3$ (72 mg, 0.220 mmol) and DMF (1 mL) gave the title compound (80 mg, 81%) as a beige solid. LCMS (Method B): $R_T$=1.43 min, m/z=437, 439 [M-butene+H]$^+$.

Step 4: 6-Chloro-7-(4-chlorophenyl)-3-((4-hydroxypiperidin-4-yl)methyl)-3H-pyrrolo[2,3-d]pyrimidin-4(7H)-one tert-Butyl 4-((6-chloro-7-(4-chlorophenyl)-4-oxo-4,7-dihydro-3H-pyrrolo[2,3-d]pyrimidin-3-yl)methyl)-4-hydroxypiperidine-1-carboxylate (80 mg, 0.162 mmol) was stirred in DCM (1 mL) and TFA (1 mL) for 15 min before the reaction was purified using a 5 g Biotage SCX-2 cartridge (pre-equilibrated with, then washed with 4:1 DCM/MeOH, eluted using 4:1 DCM/7 M in NH$_3$ in MeOH). The basic phases were combined and concentrated in vacuo to give the title compound (70 mg, quant.) as a light beige solid. LCMS (Method B): $R_T$=0.80 min, m/z=393, 395 [M+H]$^+$.

Step 5: 6-Chloro-7-(4-chlorophenyl)-3-((1-(2-cyclopropyloxazole-5-carbonyl)-4-hydroxypiperidin-4-yl)methyl)-3H-pyrrolo[2,3-d]pyrimidin-4(7H)-one General procedure 4 using 6-chloro-7-(4-chlorophenyl)-3-((4-hydroxypiperidin-4-yl)methyl)-3H-pyrrolo[2,3-d]pyrimidin-4(7H)-one (35 mg, 0.089 mmol), 2-cyclopropyloxazole-5-carboxylic acid (15 mg, 0.098 mmol), HATU (41 mg, 0.107 mmol), DIPEA (47 μL, 0.277 mmol) and DCM (1 mL) gave the title compound (26 mg, 55%) as a colourless solid after lyophilisation. LCMS (Method A): $R_T$=1.35 min, m/z=528, 530 [M+H]$^+$. $^1$H NMR (500 MHz, DMSO-d$_6$): δ 8.10 (s, 1H), 7.69-7.64 (m, 2H), 7.54-7.50 (m, 2H), 7.49 (s, 1H), 6.83 (s, 1H), 4.99 (s, 1H), 4.13-3.87 (m, 4H), 3.63-2.94 (br. s, 2H (signal overlaps with HDO)), 2.20-2.13 (m, 1H), 1.67-1.51 (m, 2H), 1.51-1.40 (m, 2H), 1.15-1.03 (m, 2H), 1.03-0.93 (m, 2H).

Example 229: 6-Chloro-7-(4-chlorophenyl)-3-((4-hydroxy-1-(1-methyl-1H-pyrazole-4-carbonyl)piperidin-4-yl)methyl)-3H-pyrrolo[2,3-d]pyrimidin-4(7H)-one

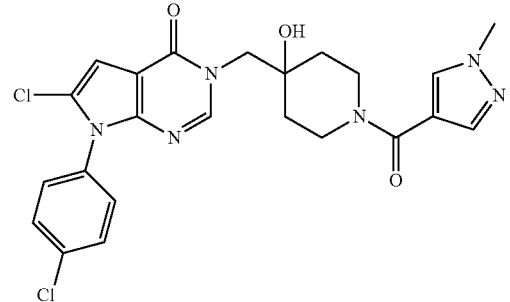 [SMILES: Cn1cc(C(=O)N2CCC(O)(Cn3cnc4c(cc(Cl)n4-c4ccc(Cl)cc4)c3=O)CC2)cn1]

General procedure 4 using 6-chloro-7-(4-chlorophenyl)-3-((4-hydroxypiperidin-4-yl)methyl)-3H-pyrrolo[2,3-d]pyrimidin-4(7H)-one or (35 mg, 0.089 mmol), 1-methyl-1H-pyrazole-4-carboxylic acid (12 mg, 0.098 mmol), HATU (41 mg, 0.107 mmol), DIPEA (47 μL, 0.277 mmol) and DCM (1 mL) gave the title compound (26 mg, 55%) as a colourless solid after lyophilisation. LCMS (Method A): $R_T$=1.18 min, m/z=501, 503 [M+H]$^+$. $^1$H NMR (500 MHz, DMSO-d$_6$): δ

8.10 (s, 1H), 8.02 (s, 1H), 7.69-7.65 (m, 2H), 7.62 (s, 1H), 7.55-7.50 (m, 2H), 6.83 (s, 1H), 4.95 (s, 1H), 4.17-3.75 (m, 7H), 3.63-2.97 (br. s, 2H (signal overlaps with HDO)), 1.62-1.49 (m, 2H), 1.47-1.36 (m, 2H).

Example 230: 6-Chloro-3-((1-(2-cyclopropyloxazole-5-carbonyl)-4-hydroxypiperidin-4-yl)methyl)-7-(4-fluoro-3-(1-methyl-1H-pyrazol-5-yl)phenyl)-3H-pyrrolo[2,3-d]pyrimidin-4(7H)-one

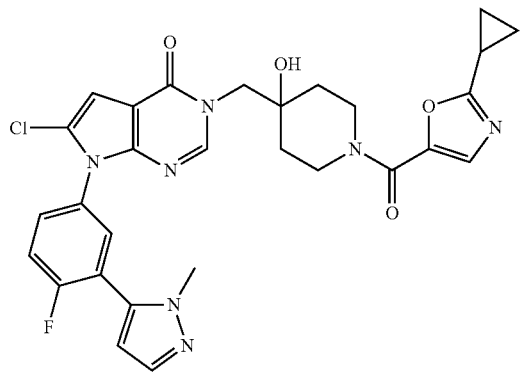 [SMILES: Cn1nccc1-c1cc(-n2c(Cl)cc3c(=O)n(CC4(O)CCN(C(=O)c5cnc(C6CC6)o5)CC4)cnc32)ccc1F]

Step 1: 7-(3-Bromo-4-fluorophenyl)-4-chloro-5H-pyrrolo[2,3-d]pyrimidin-6(7H)-one A mixture of methyl 2-(4,6-dichloropyrimidin-5-yl)acetate (884 mg, 4 mmol) and 3-bromo-4-fluoroaniline (760 mg, 4 mmol) in EtOH (8 mL) was heated at 120° C. using microwave irradiation. After 2 h, the reaction mixture was concentrated in vacuo and saturated NaHCO$_{3(aq)}$ (75 mL) was added to the residue. The resulting mixture was extracted using DCM (3×50 mL), the combined organic phases were concentrated in vacuo and the residue was purified by flash chromatography (80 g GraceResolv silica, 0-40% EtOAc in cyclohexane) to give ethyl 2-(4-((3-bromo-4-fluorophenyl)amino)-6-chloropyrimidin-5-yl)acetate (344 mg, 23%) as a colourless solid (LCMS (Method B): R$_T$=1.38 min, m/z=388, 390, 392 [M+H]$^+$) and the title compound (369 mg, 26%) as a beige solid (LCMS (Method B): R$_T$=1.18 min, m/z=342, 344, 346 [M+H]$^+$). A solution of ethyl 2-(4-((3-bromo-4-fluorophenyl)amino)-6-chloropyrimidin-5-yl)acetate (344 mg, 0.885 mmol) and p-TSA (34 mg, 0.177 mmol) in toluene (9 mL) was heated at reflux for 75 min before the reaction mixture was concentrated in vacuo and the residue was purified by flash chromatography (40 g GraceResolv silica, 0-30% EtOAc in cyclohexane) to give the title compound (285 mg, 94%) as a colourless solid. LCMS (Method B): R$_T$=1.19 min, m/z=342, 344, 346 [M+H]$^+$.

Step 2: 7-(3-Bromo-4-fluorophenyl)-4,6-dichloro-7H-pyrrolo[2,3-d]pyrimidine

Water (103 µL, 5.72 mmol) was added to a mixture of 7-(3-bromo-4-fluorophenyl)-4-chloro-5H-pyrrolo[2,3-d]pyrimidin-6(7H)-one (654 mg, 1.91 mmol), POCl$_3$ (1.07 mL, 11.4 mmol) and PhNEt$_2$ (456 µL, 2.86 mmol) in a reaction vial. Once the effervescence had subsided, the vial was capped and the mixture was heated at 115° C. for 1.5 h. Once the reaction had cooled to RT, it was diluted with DCM (~2 mL) and was poured on to ice (~5 g). Once the ice had melted, saturated NaHCO$_{3(aq)}$ (75 mL) and DCM (200 mL) were added and the mixture was stirred for 1 h. The resulting mixture was extracted with DCM (3×50 mL). The combined organic phases were concentrated in vacuo and the residue was purified by flash chromatography (80 g GraceResolv silica, 0-40% EtOAc in cyclohexane) to give the title compound (358 mg, 51%) as a colourless solid. LCMS (Method B): R$_T$=1.55 min, m/z=360, 362, 364 [M+H]$^+$.

Step 3: 7-(3-Bromo-4-fluorophenyl)-6-chloro-3H-pyrrolo[2,3-d]pyrimidin-4(7H)-one A suspension of 7-(3-bromo-4-fluorophenyl)-4,6-dichloro-7H-pyrrolo[2,3-d]pyrimidine (347 mg, 0.961 mmol) in 2 M HCl$_{(aq)}$ (1.92 mL, 3.84 mmol) and 1,4-dioxane (3.8 mL) was heated at 120° C. using microwave irradiation for 1.5. Further 1,4-dioxane (1.8 mL) was added and the reaction was heated at 120° C. using microwave irradiation for 1.5 h. The reaction mixture was concentrated in vacuo and the residue was dried in a vacuum oven at 50° C. to give the title compound (325 mg, 98%) as a beige solid. LCMS (Method B): R$_T$=1.09 min, m/z=342, 344, 346 [M+H]$^+$.

Step 4: tert-Butyl 4-((7-(3-bromo-4-fluorophenyl)-6-chloro-4-oxo-4,7-dihydro-3H-pyrrolo[2,3-d]pyrimidin-3-yl)methyl)-4-hydroxypiperidine-1-carboxylate General procedure 1 using Epoxide 1 (402 mg, 1.88 mmol), 7-(3-bromo-4-fluorophenyl)-6-chloro-3H-pyrrolo[2,3-d]pyrimidin-4(7H)-one (323 mg, 0.942 mmol), Cs$_2$CO$_3$ (338 mg, 1.04 mmol) and DMF (9 mL) gave the title compound (446 mg, 85%) as a beige foam. LCMS (Method B): R$_T$=1.46 min, m/z=499, 501, 503 [M-butene+H]$^+$.

Step 5: tert-Butyl 4-((6-chloro-7-(4-fluoro-3-(1-methyl-1H-pyrazol-5-yl)phenyl)-4-oxo-4,7-dihydro-3H-pyrrolo[2,3-d]pyrimidin-3-yl)methyl)-4-hydroxypiperidine-1-carboxylate General procedure 5 using tert-butyl 4-((7-(3-bromo-4-fluorophenyl)-6-chloro-4-oxo-4,7-dihydro-3H-pyrrolo[2,3-d]pyrimidin-3-yl)methyl)-4-hydroxypiperidine-1-carboxylate (150 mg, 0.270 mmol), 1-methyl-5-(4,4,5,5-tetramethyl-1,3,2-dioxaborolan-2-yl)-1H-pyrazole (124 mg, 0.594 mmol), Pd(PPh$_3$)$_4$ (31 mg, 0.027 mmol) and Na$_2$CO$_3$ (86 mg, 0.810 mmol) in 1,4-dioxane (1.5 mL) and water (0.6 mL) at 140° C. for 1 h in the microwave gave the title compound (122 mg, 81%) as pale yellow foam. LCMS (Method A): R$_T$=1.46 min, m/z=501, 503 [M-butene+H]$^+$.

Step 6: 6-Chloro-7-(4-fluoro-3-(1-methyl-1H-pyrazol-5-yl)phenyl)-3-((4-hydroxypiperidin-4-yl)methyl)-3H-pyrrolo[2,3-d]pyrimidin-4(7H)-one A solution of tert-butyl 4-((6-chloro-7-(4-fluoro-3-(1-methyl-1H-pyrazol-5-yl)phenyl)-4-oxo-4,7-dihydro-3H-pyrrolo[2,3-d]pyrimidin-3-yl)methyl)-4-hydroxypiperidine-1-carboxylate (120 mg, 0.215 mmol) in DCM (2 mL) and TFA (2 mL) was stirred for 15 min before the reaction was purified using a 5 g Biotage SCX-2 cartridge (pre-equilibrated with, then washed with 4:1 DCM/MeOH, eluted using 4:1 DCM/7 M in NH₃ in MeOH). The basic phases were combined and concentrated in vacuo to give the title compound (85 mg, 86%) as a light beige solid. LCMS (Method A): $R_T$=0.76 min, m/z=457, 459 [M+H]⁺.

Step 7: 6-Chloro-3-((1-(2-cyclopropyloxazole-5-carbonyl)-4-hydroxypiperidin-4-yl)methy)-7-(4-fluoro-3-(1-methyl-1H-pyrazol-5-yl)phenyl)-3H-pyrrolo[2,3-d]pyrimidin-4(7H)-one General procedure 4 using 6-chloro-7-(4-fluoro-3-(1-methyl-1H-pyrazol-5-yl)phenyl)-3-((4-hydroxypiperidin-4-yl)methyl)-3H-pyrrolo[2,3-d]pyrimidin-4(7H)-one (40 mg, 0.088 mmol), 2-cyclopropyloxazole-5-carboxylic acid (15 mg, 0.096 mmol), HATU (40 mg, 0.105 mmol), DIPEA (46 µL, 0.263 mmol) and DCM (1 mL) gave the title compound (33 mg, 63%) as a colourless solid after lyophilisation. LCMS (Method A): $R_T$=1.17 min, m/z=592, 594 [M+H]⁺. ¹H NMR (500 MHz, DMSO-d₆): δ 8.12 (s, 1H), 7.73-7.69 (m, 1H), 7.69-7.60 (m, 2H), 7.57-7.54 (m, 1H), 7.49 (s, 1H), 6.84 (s, 1H), 6.51 (s, 1H), 5.00 (s, 1H), 4.13-3.87 (m, 4H), 3.82 (s, 3H), 3.60-2.96 (br. s, 2H (signal overlaps with HDO)), 2.20-2.13 (m, 1H), 1.69-1.51 (m, 2H), 1.51-1.39 (m, 2H), 1.14-1.03 (m, 2H), 1.13-0.94 (m, 2H).

Example 231: 6-Chloro-7-(4-fluoro-3-(1-methyl-1H-pyrazol-5-yl)phenyl)-3-((4-hydroxy-1-(1-methyl-cyclopropanecarbonyl)piperidin-4-yl)methyl)-3H-pyrrolo[2,3-d]pyrimidin-4(7H)-one

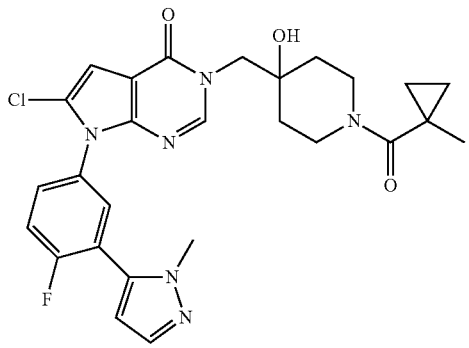 [SMILES: Cn1nccc1-c1cc(-n2c(Cl)cc3c(=O)n(CC4(O)CCN(C(=O)C5(C)CC5)CC4)cnc32)ccc1F]

General procedure 4 using 6-chloro-7-(4-fluoro-3-(1-methyl-1H-pyrazol-5-yl)phenyl)-3-((4-hydroxypiperidin-4-yl)methyl)-3H-pyrrolo[2,3-d]pyrimidin-4(7H)-one (40 mg, 0.088 mmol), 1-methylcyclopropanecarboxylic acid (11 mg, 0.108 mmol), HATU (40 mg, 0.105 mmol), DIPEA (46 µL, 0.263 mmol) and DCM (1 mL) gave the title compound (23 mg, 43%) as a colourless solid after lyophilisation. LCMS (Method A): $R_T$=1.17 min, m/z=539, 541 [M+H]⁺. ¹H NMR (500 MHz, DMSO-d₆): δ 8.11 (s, 1H), 7.69-7.69 (m, 1H), 7.69-7.60 (m, 2H), 7.57-7.54 (m, 1H), 6.85 (s, 1H), 6.53-6.49 (m, 1H), 4.91 (s, 1H), 4.02 (s, 2H), 3.94 (dt, 2H), 3.82 (s, 3H), 3.28-2.97 (br. s, 2H), 1.59-1.45 (m, 2H), 1.44-1.34 (m, 2H), 1.20 (s, 3H), 0.81-0.72 (m, 2H), 0.57-0.47 (m, 2H).

Example 232: 6-Chloro-3-((1-(2-cyclopropyloxazole-5-carbonyl)-4-hydroxypiperidin-4-yl)methyl)-7-(4-fluoro-3-(1-methyl-1H-pyrazol-4-yl)phenyl)-3H-pyrrolo[2,3-d]pyrimidin-4(7H)-one

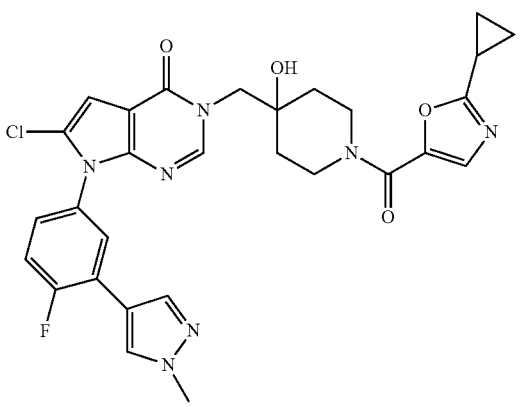 [SMILES: Cn1cc(-c2cc(-n3c(Cl)cc4c(=O)n(CC5(O)CCN(C(=O)c6cnc(C7CC7)o6)CC5)cnc43)ccc2F)cn1]

Step 1: tert-Butyl 4-((6-chloro-7-(4-fluoro-3-(1-methyl-1H-pyrazol-4-yl)phenyl)-4-oxo-4,7-dihydro-3H-pyrrolo[2,3-d]pyrimidin-3-yl)methyl)-4-hydroxypiperidine-1-carboxylate General procedure 5 using tert-butyl 4-((7-(3-bromo-4-fluorophenyl)-6-chloro-4-oxo-4,7-dihydro-3H-pyrrolo[2,3-d]pyrimidin-3-yl)methyl)-4-hydroxypiperidine-1-carboxylate (150 mg, 0.270 mmol), 1-methyl-4-(4,4,5,5-tetramethyl-1,3,2-dioxaborolan-2-yl)-1H-pyrazole (124 mg, 0.594 mmol), Pd(PPh₃)₄ (31 mg, 0.027 mmol) and Na₂CO₃ (86 mg, 0.810 mmol) in 1,4-dioxane (1.5 mL) and water (0.6 mL) at 140° C. for 40 min in the microwave gave the title compound (142 mg, 94%) as a beige solid. LCMS (Method A): $R_T$=1.47 min, m/z=501, 503 [M-butene+H]⁺.

Step 2: 6-Chloro-7-(4-fluoro-3-(1-methyl-1H-pyrazol-4-yl)phenyl)-3-((4-hydroxypiperidin-4-yl)methyl)-3H-pyrrolo[2,3-d]pyrimidin-4(7H)-one A solution of tert-butyl 4-((6-chloro-7-(4-fluoro-3-(1-methyl-1H-pyrazol-4-yl)phenyl)-4-oxo-4,7-dihydro-3H-pyrrolo[2,3-d]pyrimidin-3-yl)methyl)-4-hydroxypiperidine-1-carboxylate (140 mg, 0.251 mmol) in DCM (2 mL) and TFA (2 mL) was stirred for 1 h before the reaction was purified using a 5 g Biotage SCX-2 cartridge (pre-equilibrated with, then washed with 4:1 DCM/MeOH, eluted using 4:1 DCM/7 M in NH₃ in MeOH). The basic phases were combined and concentrated in vacuo to give the title compound (92 mg, 81%) as a light beige solid. LCMS (Method A): $R_T$=0.78 min, m/z=457, 459 [M+H]⁺.

Step 3: 6-Chloro-3-((1-(2-cyclopropyloxazole-5-carbonyl)-4-hydroxypiperidin-4-yl)methy)-7-(4-fluoro-3-(1-methyl-1H-pyrazol-4-yl)phenyl)-3H-pyrrolo[2,3-d]pyrimidin-4(7H)-one General procedure 4 using 6-chloro-7-(4-fluoro-3-(1-methyl-1H-pyrazol-4-yl)phenyl)-3-((4-hydroxypiperidin-4-yl)methyl)-3H-pyrrolo[2,3-d]pyrimidin-4(7H)-one or (45 mg, 0.098 mmol), 2-cyclopropyloxazole-5-carboxylic acid (17 mg, 0.108 mmol), HATU (45 mg, 0.118 mmol), DIPEA (52 µL, 0.295 mmol) and DCM (1 mL). Further purification by preparative HPLC (Method A) gave the title compound (19 mg, 32%) as a colourless solid after lyophilisation. LCMS (Method A): $R_T$=1.18 min, m/z=592, 594 [M+H]$^+$. $^1$H NMR (500 MHz, DMSO-d$_6$): δ 8.24 (d, 1H), 8.12 (s, 1H), 7.97 (s, 1H), 7.86 (dd, 1H), 7.52-7.44 (m, 2H), 7.35-7.30 m, 1H), 6.83 (s, 1H), 5.02 (s, 1H), 4.11-3.92 (m, 4H), 3.90 (s, 3H), 3.62-2.99 (br. s, 2H (signal overlaps with HDO)), 2.20-2.14 (m, 1H), 1.66-1.54 (m, 2H), 1.49-1.41 (m, 2H), 1.12-1.04 (m, 2H), 1.03-0.95 (m, 2H).

Example 233: 6-Chloro-7-(4-fluoro-3-(1-methyl-1H-pyrazol-4-yl)phenyl)-3-((4-hydroxy-1-(1-methyl-cyclopropanecarbonyl)piperidin-4-yl)methyl)-3H-pyrrolo[2,3-d]pyrimidin-4(7H)-one

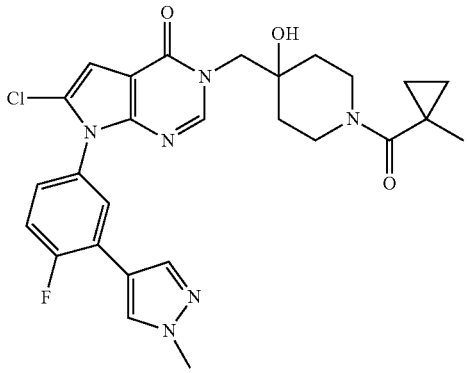 [SMILES: Cn1cc(-c2cc(-n3c(Cl)cc4c(=O)n(CC5(O)CCN(C(=O)C6(C)CC6)CC5)cnc43)ccc2F)cn1]

General procedure 4 using 6-chloro-7-(4-fluoro-3-(1-methyl-1H-pyrazol-4-yl)phenyl)-3-((4-hydroxypiperidin-4-yl)methyl)-3H-pyrrolo[2,3-d]pyrimidin-4(7H)-one (45 mg, 0.098 mmol), 1-methylcyclopropanecarboxylic acid (11 mg, 0.108 mmol), HATU (45 mg, 0.118 mmol), DIPEA (52 μL, 0.295 mmol) and DCM (1 mL) gave the title compound (21 mg, 39%) as a colourless solid after lyophilisation. LCMS (Method A): $R_T$=1.18 min, m/z=539, 541 [M+H]$^+$. $^1$H NMR (500 MHz, DMSO-d$_6$): δ 8.24 (d, 1H), 8.10 (s, 1H), 7.97 (s, 1H), 7.86 (dd, 1H), 7.51-7.45 (m, 1H), 7.35-7.30 (m, 1H), 6.83 (s, 1H), 4.92 (s, 1H), 4.02 (s, 2H), 3.99-3.92 (m, 2H), 3.90 (s, 3H), 3.27-2.99 (br. s, 2H), 1.57-1.45 (m, 2H), 1.45-1.35 (m, 2H), 1.21 (s, 3H), 0.81-0.72 (m, 2H), 0.57-0.47 (m, 2H).

Example 234: 3-((4-Hydroxy-1-(1-methylcyclopropanecarbonyl)piperidin-4-yl)methyl)-4-oxo-7-phenyl-4,7-dihydro-3H-pyrrolo[2,3-d]pyrimidine-6-carbonitrile

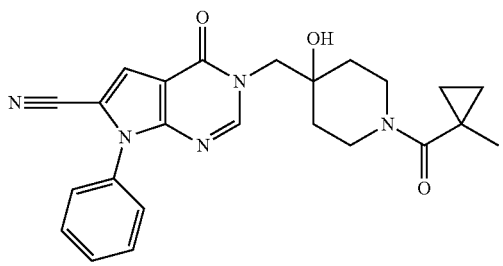 [SMILES: CC1(C(=O)N2CCC(O)(Cn3cnc4c(cc(C#N)n4-c4ccccc4)c3=O)CC2)CC1]

A suspension of 6-bromo-3-((4-hydroxy-1-(1-methylcyclopropanecarbonyl)piperidin-4-yl)methyl)-7-phenyl-3H-pyrrolo[2,3-d]pyrimidin-4(7H)-one (27 mg, 0.0556 mmol), Zn(CN)$_2$ (6.5 mg, 0.0556 mmol), dppf (6.2 mg, 0.0111 mmol), Pd$_2$(dba)$_3$ (5.1 mg, 0.0056 mmol) and Zn (0.7 mg, 0.0111 mmol) in 100:1 dilute AcOH in DMF (275 μL in 1 L)/water (0.5 mL) in sealed reaction tube was degassed by bubbling N$_2$ through the reaction mixture for 20 min before being heated at 100° C. for 19 h. Further Zn(CN)$_2$ (6.5 mg, 0.0556 mmol), dppf (6.2 mg, 0.0111 mmol), Pd$_2$(dba)$_3$ (5.1 mg, 0.0056 mmol) and Zn (0.7 mg, 0.0111 mmol) were added and the reaction stirred for 1 h at 100° C. The reaction was cooled to RT, diluted with water (20 mL) and the mixture extracted with DCM (3×5 mL) using a phase separator. The combined organic phases were concentrated and the residue purified by flash chromatography (12 g GraceResolv silica, 0-100% EtOAc in cyclohexane, then 0-15% MeOH in EtOAc; then 12 g GraceResolv silica, 0-10% MeOH in DCM) and preparative HPLC (Method A) to give the title compound (7 mg, 29%) as a colourless solid after lyophilisation. LCMS (Method A): $R_T$=1.11 min, m/z=432 [M+H]$^+$. $^1$H NMR (500 MHz, DMSO-d$_6$) δ 8.25 (s, 1H), 7.77 (s, 1H), 7.67-7.54 (m, 5H), 4.93 (s, 1H), 4.02 (s, 2H), 3.95 (dt, J=13.6, 3.9 Hz, 2H), 3.15 (s, 2H), 1.56-1.47 (m, 2H), 1.43-1.36 (m, 2H), 1.21 (s, 3H), 0.81-0.72 (m, 2H), 0.56-0.47 (m, 2H).

Example 235: 7-(Benzo[d][1,3]dioxol-5-yl-2,2-d$_2$)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one

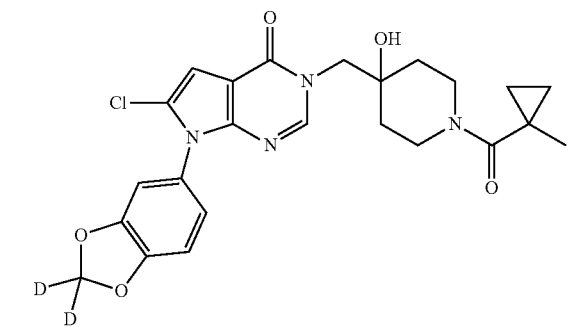 [SMILES: [2H]C1([2H])Oc2ccc(-n3c(Cl)cc4c(=O)n(CC5(O)CCN(C(=O)C6(C)CC6)CC5)cnc43)cc2O1]

Step 1: 5-Bromobenzo[d][1,3]dioxole-2,2-d$_2$

A suspension of 4-bromobenzene-1,2-diol (690 mg, 3.65 mmol) in deuterium oxide (2 mL) and THF (2 mL) was stirred for 20 h before the volatiles were removed in vacuo and the residue was dried in a vacuum oven at 50° C. to give a brownish yellow solid. This was repeated before the solid was stirred in CD$_3$OD (2 mL) and deuterium oxide (2 mL) for 3 days. The volatiles were removed in vacuo and the residue was dried in a vacuum oven at 60° C. to give a brownish grey solid. $^1$H NMR indicated ~60% H to D exchange. A solution of this material and dibromomethane-d$_2$ (2.21 mL, 31.4 mmol) in NMP (2 mL) was slowly added dropwise via syringe to a suspension of potassium carbonate (870 mg, 6.29 mmol) in NMP (6 mL) at 110° C. in a 100 mL 3-necked RBF under a N$_2$ atmosphere. After 90 min, the reaction mixture was allowed to cool to RT, diluted with water (60 mL) and the resulting mixture was extracted with EtOAc (3×20 mL). The combined organic phases were washed with water (2×20 mL) and brine (20 mL). The organic phase was passed through a Biotage phase separator, concentrated in vacuo and the residue was purified by flash chromatography (GraceResolv silica 40 g cartridge, 100% cyclohexane) to give the title compound (486 mg, 76%) as colourless oil. $^1$H NMR (500 MHz, CDCl$_3$): δ 6.98-6.91 (m, 2H), 6.72-6.65 (m, 1H).

Step 2: (Benzo[d][1,3]dioxol-5-yl-2,2-d$_2$)boronic Acid

To a stirred solution of 5-bromobenzo[d][1,3]dioxole-2, 2-d$_2$ (486 mg, 2.39 mmol) in THF (4.8 mL) at 0° C. was added dropwise isopropylmagnesium chloride lithium chloride complex (1.09 M in THF, 2.64 mL, 2.87 mmol). After 25 min, the ice bath was removed and the reaction was allowed to warm to RT. After 1 h, 1,4-dioxane (5 mL) was added. After a further 1 h, there was no significant reaction and therefore, further isopropylmagnesium chloride lithium chloride complex (1.09 M in THF, 2.64 mL, 2.87 mmol) was added. After 16 h, triisopropyl borate (0.67 mL, 2.87 mmol) was added. After a further 1 h, 2 M HCl$_{(aq)}$ was added and the resulting suspension was stirred for 23 h. Water (30 mL) was added to the resulting yellow solution and the mixture was extracted with DCM (3×20 mL) using a Biotage phase separator. The combined organic phases were concentrated in vacuo and the residue was dried in a vacuum oven at 50° C. to give title compound (258 mg, 64%) as a yellow semi-solid. This material was used in the next step without further purification.

Step 3: 7-(Benzo[d][1,3]dioxol-5-yl-2,2-d$_2$)-4,6-dichloro-7H-pyrrolo[2,3-d]pyrimidine A suspension of 4,6-dichloro-7H-pyrrolo[2,3-d]pyrimidine (96 mg, 0.511 mmol), (benzo[d][1,3]dioxol-5-yl-2,2-d$_2$)boronic acid (257 mg, 1.53 mmol), 1,10-phenanthroline (184 mg, 1.02 mmol) and copper(II) acetate (185 mg, 1.02 mmol) in DMF (10 mL) was stirred at RT for 3 days before being quenched by the addition of saturated NH$_4$Cl$_{(aq)}$ (150 mL). The resulting mixture was diluted with water (350 mL) and extracted with EtOAc (3×100 mL). The combined organic phases were washed with brine (300 mL) and passed through a Biotage phase separator. The resulting purple solution was concentrated in vacuo and the residue was purified by flash chromatography (GraceResolv silica 40 g cartridge, 0% then 10% EtOAc in cyclohexane (isocratic)) to give the title compound (85 mg, 53%) as light peach solid. LCMS (Method A): R$_T$=1.63 min, m/z=310, 312 [M+H]$^+$. $^1$H NMR (500 MHz, CDCl$_3$): δ 8.62 (s, 1H), 6.97 (d, J=8.1 Hz, 1H), 6.89-6.82 (m, 2H), 6.71 (s, 1H).

Step 4: 7-(Benzo[d][1,3]dioxol-5-yl-2,2-d$_2$)-6-chloro-3,7-dihydro-4H-pyrrolo[2,3-d]pyrimidin-4-one A suspension of 7-(benzo[d][1,3]dioxol-5-yl-2,2-d$_2$)-4,6-dichloro-7H-pyrrolo[2,3-d]pyrimidine (84 mg, 0.271 mmol) in 2 M HCl$_{(aq)}$ (0.54 mL, 1.08 mmol) and 1,4-dioxane (1.08 mL) was heated under microwave irradiation at 120° C. for 2 h before the mixture was concentrated in vacuo and the residue was dried in a vacuum oven at 50° C. to give the crude title compound (85 mg, >100%) as green/brownish beige heterogeneous looking solid that was used without further purification. LCMS (Method A): R$_T$=1.02 min, m/z=292, 294 [M+H]$^+$. $^1$H NMR (500 MHz, DMSO-d$_6$): δ 12.18-12.08 (m, 1H), 7.86 (d, J=3.8 Hz, 1H), 7.07 (d, J=8.2 Hz, 1H), 7.05 (d, J=2.1 Hz, 1H), 6.89 (dd, J=8.2, 2.1 Hz, 1H), 6.72 (s, 1H).

Step 5: tert-Butyl 4-((7-(benzo[d][1,3]dioxol-5-yl-2, 2-d$_2$)-6-chloro-4-oxo-4,7-dihydro-3H-pyrrolo[2,3-d] pyrimidin-3-yl)methyl)-4-hydroxypiperidine-1-carboxylate General procedure 1 using Epoxide 1 (123 mg, 0.576 mmol), 7-(benzo[d][1,3]dioxol-5-yl-2,2-d$_2$)-6-chloro-3,7-dihydro-4H-pyrrolo[2,3-d]pyrimidin-4-one (84 mg, 0.288 mmol) and cesium carbonate (103 mg, 0.317 mmol) in DMF (1.9 mL) gave the title compound (80 mg, 55%) as a light beige foam. LCMS (Method A): R$_T$=1.50 min, m/z=505, 507 [M+H]$^+$. $^1$H NMR (500 MHz, DMSO-d$_e$): δ 8.07 (s, 1H), 7.08 (d, J=8.2 Hz, 1H), 7.06 (d, J=2.1 Hz, 1H), 6.89 (dd, J=8.2, 2.1 Hz, 1H), 6.75 (s, 1H), 4.85 (s, 1H), 3.99 (s, 2H), 3.70-3.59 (m, 2H), 3.11-2.99 (m, 2H), 1.58-1.19 (m, 4H), 1.39 (s, 9H).

Step 6: 7-(Benzo[d][1,3]dioxol-5-yl-2,2-d$_2$)-6-chloro-3-((4-hydroxypiperidin-4-yl)methyl)-3,7-dihydro-4H-pyrrolo[2,3-d]pyrimidin-4-one A solution of tert-butyl 4-((7-(benzo[d][1,3]dioxol-5-yl-2,2-d$_2$)-6-chloro-4-oxo-4,7-dihydro-3H-pyrrolo[2,3-d]pyrimidin-3-yl)methyl)-4-hydroxypiperidine-1-carboxylate (80 mg, 0.158 mmol) in TFA (0.8 mL) and DCM (1.6 mL) was stirred for 20 min before the reaction mixture was purified using a 2 g Biotage SCX-2 cartridge (pre-equilibrated and washed with 1:1 DCM/MeOH, then eluted using 1:1 DCM/7 M NH$_3$ in MeOH) the basic phase was concentrated in vacuo to give the title compound (52 mg, 81%) as light beige foam. LCMS (Method A): R$_T$=0.79 min, m/z=405, 407 [M+H]$^+$. $^1$H NMR (500 MHz, DMSO-d$_6$): δ 8.07 (s, 1H), 7.08 (d, J=8.2 Hz, 1H), 7.06 (d, J=2.1 Hz, 1H), 6.89 (dd, J=8.2, 2.2 Hz, 1H), 6.74 (s, 1H), 4.59 (s, 1H), 3.95 (s, 2H), 2.75-2.61 (m, 4H), 2.00 (s, 1H), 1.43 (ddd, J=13.9, 9.8, 4.5 Hz, 2H), 1.27 (dt, J=13.0, 3.8 Hz, 2H).

Step 7: 7-(Benzo[d][1,3]dioxol-5-yl-2,2-d$_2$)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one General procedure 4 using 7-(benzo[d][1,3]dioxol-5-yl-2,2-d$_2$)-6-chloro-3-((4-hydroxypiperidin-4-yl)methyl)-3,7-dihydro-4H-pyrrolo[2,3-d]pyrimidin-4-one (43 mg, 0.106 mmol), 1-methylcyclopropane-1-carboxylic acid (12 mg, 0.117 mmol), HATU (44 mg, 0.117 mmol) and DIPEA (74 µL, 0.425 mmol) in DCM (2 mL) gave the title compound (50.9 mg, 97%) as colourless solid after lyophilisation. LCMS (Method B): R$_T$=1.07 min, m/z=487, 489 [M+H]$^+$. $^1$H NMR (500 MHz, DMSO-d$_6$): δ 8.08 (s, 1H), 7.08 (d, J=8.2 Hz, 1H), 7.06 (d, J=2.1 Hz, 1H), 6.90 (dd, J=8.2, 2.2 Hz, 1H), 6.76 (s, 1H), 4.90 (brs, 1H), 4.01 (s, 2H), 3.94 (dt, J=13.3, 4.2 Hz, 2H), 3.23-2.97 (m, 2H), 1.59-1.46 (m, 2H), 1.45-1.34 (m, 2H), 1.21 (s, 3H), 0.81-0.70 (m, 2H), 0.57-0.46 (m, 2H).

Example 236: 7-(Benzo[d][1,3]dioxol-5-yl-2,2-d$_2$)-6-chloro-3-((1-(2-cyclopropyloxazole-5-carbonyl)-4-hydroxypiperidin-4-yl)methyl)-3,7-dihydro-4H-pyrrolo[2,3-d]pyrimidin-4-one

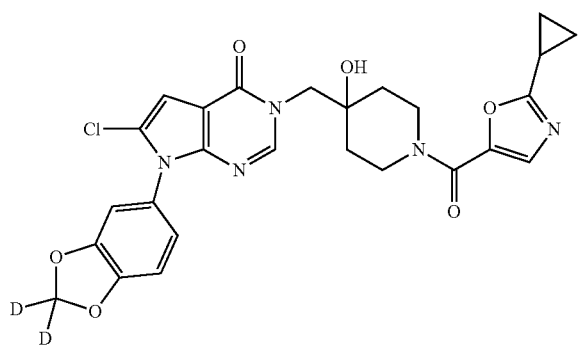 [SMILES: [2H]C1([2H])Oc2ccc(-n3c(Cl)cc4c(=O)n(CC5(O)CCN(C(=O)c6cnc(C7CC7)o6)CC5)cnc43)cc2O1]

General procedure 4 using 7-(benzo[d][1,3]dioxol-5-yl-2,2-d$_2$)-6-chloro-3-((4-hydroxypiperidin-4-yl)methyl)-3,7-dihydro-4H-pyrrolo[2,3-d]pyrimidin-4-one (10 mg, 24.7 µmol), 2-cyclopropyloxazole-5-carboxylic acid (4.2 mg, 27.2 µmol), DIPEA (17 µL, 98.8 µmol) and HATU (10 mg, 27.2 µmol) in DCM (0.5 mL) gave the title compound (11 mg, 81%) as colourless solid after lyophilisation. LCMS (Method B): R$_T$=1.09 min, m/z=540, 542 [M+H]$^+$. $^1$H NMR (500 MHz, DMSO-d$_6$): δ 8.09 (s, 1H), 7.49 (s, 1H), 7.08 (d, J=8.2 Hz, 1H), 7.06 (d, J=2.1 Hz, 1H), 6.90 (dd, J=8.2, 2.1 Hz, 1H), 6.76 (s, 1H), 4.99 (br s, 1H), 4.13-3.89 (m, 2H), 4.03 (s, 2H), 3.49-3.05 (m, 2H (signal overlaps with HDO)), 2.17 (tt, J=8.4, 4.9 Hz, 1H), 1.65-1.54 (m, 2H), 1.50-1.41 (m, 2H), 1.12-1.06 (m, 2H), 1.01-0.94 (m, 2H).

Example 237: 3-(4-(Aminomethyl)phenyl)-6-((4-hydroxy-1-(1-methylcyclopropane-1-carbonyl)piperidin-4-yl)methyl)-2-methyl-2,6-dihydro-7H-pyrazolo[4,3-d]pyrimidin-7-one

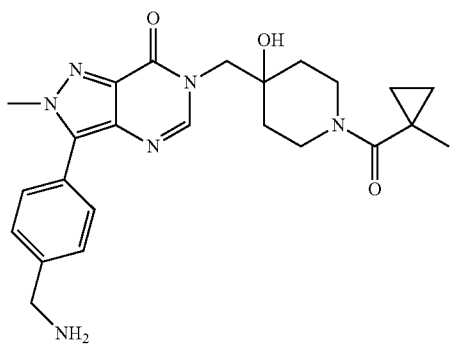

Step 1: 3-Bromo-6-((4-hydroxypiperidin-4-yl)methyl)-2-methyl-2,6-dihydro-7H-pyrazolo[4,3-d]pyrimidin-7-one Intermediate C (10 g, 22.6 mmol) was stirred in DCM (75 mL) and TFA (37.5 mL) for 5 min before the reaction mixture was purified using 2×70 g Biotage SCX-2 cartridges in parallel (pre-equilibrated and washed with 1:1 DCM/MeOH; then eluted using 1:1 DCM/7 M NH$_3$ in MeOH). The basic phases were combined and concentrated in vacuo to give the title compound (7.69 g, 99%) as a colourless foam. LCMS (Method A): R$_T$=0.32 min, m/z=342, 344 [M+H]$^+$.

Step 2: 3-Bromo-6-((4-hydroxy-1-(1-methylcyclopropane-1-carbonyl)piperidin-4-yl)methyl)-2-methyl-2,6-dihydro-7H-pyrazolo[4,3-d]pyrimidin-7-one General procedure 4 using 3-bromo-6-((4-hydroxypiperidin-4-yl)methyl)-2-methyl-2,6-dihydro-7H-pyrazolo[4,3-d]pyrimidin-7-one (342 mg, 1 mmol), 1-methylcyclopropane-1-carboxylic acid (100 mg, 1 mmol), HATU (380 mg, 1 mmol) and DIPEA (0.699 mL, 4 mmol) in DCM (20 mL) gave the title compound (348 mg, 82%) as very pale yellow foam. LCMS (Method A): R$_T$=0.63 min, m/z=424, 426 [M+H]$^+$. $^1$H NMR (500 MHz, DMSO-d$_6$): δ 8.05 (s, 1H), 4.89 (s, 1H), 4.08 (s, 3H), 3.99 (s, 2H), 3.95 (dt, J=13.2, 4.2 Hz, 2H), 3.15 (s, 2H), 1.55-1.45 (m, 2H), 1.45-1.36 (m, 2H), 1.21 (s, 3H), 0.80-0.72 (m, 2H), 0.54-0.47 (m, 2H).

Step 3: tert-Butyl (4-(6-((4-hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzyl)carbamate General procedure 5 using 3-bromo-6-((4-hydroxy-1-(1-methylcyclopropane-1-carbonyl)piperidin-4-yl)methyl)-2-methyl-2,6-dihydro-7H-pyrazolo[4,3-d]pyrimidin-7-one (348 mg, 0.820 mmol), (4-(((tert-butoxycarbonyl)amino)methyl)phenyl)boronic acid (618 mg, 2.46 mmol), K$_3$PO$_4$ (1.04 g, 4.92 mmol), Pd(PPh$_3$)$_4$ (47 mg, 41.0 µmol), 1,4-dioxane (6 mL) and water (2 mL) at 130° C. for 1 h in a microwave gave the title compound (453 mg, 100%) as pale yellow foam. LCMS (Method A): R$_T$=1.06 min, m/z=551 [M+H]$^+$.

Step 4: 3-(4-(Aminomethyl)phenyl)-6-((4-hydroxy-1-(1-methylcyclopropane-1-carbonyl)piperidin-4-yl)methyl)-2-methyl-2,6-dihydro-7H-pyrazolo[4,3-d]pyrimidin-7-one A solution of tert-butyl (4-(6-((4-hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzyl)carbamate (453 mg, 0.823 mmol) in TFA (4 mL) and DCM (8 mL) was stirred for 90 min before the reaction mixture was purified using a 10 g Biotage SCX-2 cartridge (pre-equilibrated and washed with 1:1 DCM/MeOH, then eluted using 1:1 DCM/7 M NH$_3$ in MeOH). The basic phase was concentrated in vacuo and the residue was purified by flash chromatography (GraceResolv silica 40 g cartridge, 0-30% ca. 1% NH$_3$ in MeOH/DCM) to give the title compound (278 mg, 73%) as colourless solid after lyophilisation. LCMS (Method B): R$_T$=0.63 min, m/z=451 [M+H]$^+$. $^1$H NMR (500 MHz, DMSO-d$_6$): δ 8.00 (s, 1H), 7.71-7.60 (m, 2H), 7.56-7.43 (m, 2H), 4.89 (s, 1H), 4.10 (s, 3H), 4.01 (s, 2H), 3.96 (dt, J=13.1, 4.2 Hz, 2H), 3.82 (s, 2H), 3.23-3.08 (m, 2H), 2.40 (br s, 2H (overlaps with DMSO)), 1.59-1.47 (m, 2H), 1.47-1.36 (m, 2H), 1.21 (s, 3H), 0.83-0.72 (m, 2H), 0.58-0.45 (m, 2H).

Example 238: 3-(4-(Aminomethyl)phenyl)-6-((1-(2-cyclopropyloxazole-5-carbonyl)-4-hydroxypiperidin-4-yl)methyl)-2-methyl-2,6-dihydro-7H-pyrazolo[4,3-d]pyrimidin-7-one

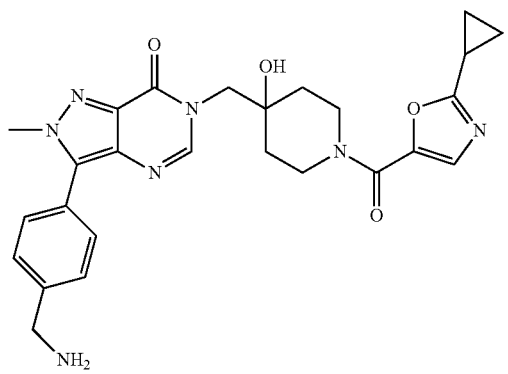 [SMILES: Cn1nc2c(=O)n(CC3(O)CCN(C(=O)c4cnc(C5CC5)o4)CC3)cnc2c1-c1ccc(CN)cc1]

Step 1: 3-Bromo-6-((1-(2-cyclopropyloxazole-5-carbonyl)-4-hydroxypiperidin-4-yl)methyl)-2-methyl-2,6-dihydro-7H-pyrazolo[4,3-d]pyrimidin-7-one General procedure 4 using 3-bromo-6-((4-hydroxypiperidin-4-yl)methyl)-2-methyl-2,6-dihydro-7H-pyrazolo[4,3-d]pyrimidin-7-one (342 mg, 1 mmol) (Example 237, Step 1), 2-cyclopropyloxazole-5-carboxylic acid (153 mg, 1 mmol), HATU (380 mg, 1 mmol) and DIPEA (0.699 mL, 4 mmol) in DCM (20 mL) gave the title compound (287 mg, 60%) as very pale yellow foam. LCMS (Method A): $R_T$=0.67 min, m/z=477, 479 [M+H]$^+$. $^1$H NMR (500 MHz, DMSO-d$_6$): δ 8.06 (s, 1H), 7.48 (s, 1H), 4.98 (s, 1H), 4.08 (s, 3H), 4.06-3.90 (m, 2H), 4.00 (s, 2H), 3.47-3.08 (m, 2H signal overlaps with HDO)), 2.16 (tt, J=8.3, 4.9 Hz, 1H), 1.65-1.53 (m, 2H), 1.51-1.42 (m, 2H), 1.12-1.06 (m, 2H), 1.01-0.95 (m, 2H).

Step 2: tert-Butyl (4-(6-((1-(2-cyclopropyloxazole-5-carbonyl)-4-hydroxypiperidin-4-yl)methyl)-2-methyl-7-oxo-6,7-dihydro-2H-pyrazolo[4,3-d]pyrimidin-3-yl)benzyl)carbamate General procedure 5 using 3-bromo-6-((1-(2-cyclopropyloxazole-5-carbonyl)-4-hydroxypiperidin-4-yl)methyl)-2-methyl-2,6-dihydro-7H-pyrazolo[4,3-d]pyrimidin-7-one (287 mg, 0.601 mmol), (4-(((tert-butoxycarbonyl)amino)methyl)phenyl)boronic acid (453 mg, 1.80 mmol), K$_3$PO$_4$ (766 mg, 3.61 mmol), Pd(PPh$_3$)$_4$ (35 mg, 30.1 µmol), 1,4-dioxane (4.5 mL) and water (1.5 mL) at 130° C. for 1 h in a microwave gave the title compound (334 mg, 92%) as pale yellow foam. LCMS (Method A): $R_T$=1.06 min, m/z=604 [M+H]$^+$.

Step 3: 3-(4-(Aminomethyl)phenyl)-6-((1-(2-cyclopropyloxazole-5-carbonyl)-4-hydroxypiperidin-4-yl)methyl)-2-methyl-2,6-dihydro-7H-pyrazolo[4,3-d]pyrimidin-7-one A solution of tert-butyl (4-(6-((1-(2-cyclopropyloxazole-5-carbonyl)-4-hydroxypiperidin-4-yl)methyl)-2-methyl-7-oxo-6,7-dihydro-2H-pyrazolo[4,3-d]pyrimidin-3-yl)benzyl)carbamate (334 mg, 0.553 mmol) in TFA (3 mL) and DCM (6 mL) was stirred for 90 min before the reaction mixture was purified using a 10 g Biotage SCX-2 cartridge (pre-equilibrated and washed with 1:1 DCM/MeOH, then eluted using 1:1 DCM/7 M NH$_3$ in MeOH). The basic phase was concentrated in vacuo and the residue was purified by flash chromatography (GraceResolv silica 40 g cartridge, 0-30% ca. 1% NH$_3$ in MeOH/DCM) to give the title compound (123 mg, 43%) as colourless solid after lyophilisation. LCMS (Method B): $R_T$=0.66 min, m/z=504 [M+H]$^+$. $^1$H NMR (500 MHz, DMSO-d$_6$): δ 8.00 (s, 1H), 7.70-7.60 (m, 2H), 7.56-7.43 (m, 2H), 7.49 (s, 1H), 4.98 (s, 1H), 4.19-3.85 (m, 2H), 4.10 (s, 3H), 4.03 (s, 2H), 3.81 (s, 2H), 3.55-3.03 (m, 2H signal overlaps with HDO signal)), 2.17 (tt, J=8.3, 4.9 Hz, 1H), 1.97 (br s, 2H), 1.65-1.55 (m, 2H), 1.53-1.44 (m, 2H), 1.15-1.04 (m, 2H), 1.02-0.94 (m, 2H).

Example 239: 6-Chloro-7-(3,4-dimethoxyphenyl)-3-((4-hydroxy-1-(1-methylcyclopropane-1-carbonyl)piperidin-4-yl)methyl)-3,7-dihydro-4H-pyrrolo[2,3-d]pyrimidin-4-one

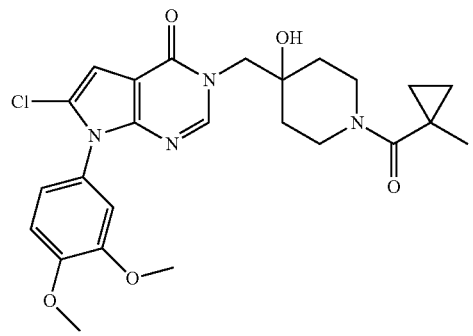 [SMILES: COc1ccc(-n2c(Cl)cc3c(=O)n(CC4(O)CCN(C(=O)C5(C)CC5)CC4)cnc32)cc1OC]

Step 1: 4,6-Dichloro-7-(3,4-dimethoxyphenyl)-7H-pyrrolo[2,3-d]pyrimidine

A suspension of 4,6-dichloro-7H-pyrrolo[2,3-d]pyrimidine (282 mg, 1.50 mmol), (3,4-dimethoxyphenyl)boronic acid (819 mg, 4.50 mmol), 1,10-phenanthroline (541 mg, 3.00 mmol) and copper(II) acetate (545 mg, 3.00 mmol) in DMF (30 mL) was stirred at RT for 87 h and quenched by the addition of saturated NH$_4$Cl$_{(aq)}$ (100 mL). The resulting mixture was diluted with water (200 mL) and extracted with EtOAc (4×50 mL). The combined organic phases were washed with water (100 mL) and brine (100 mL), passed through a Biotage phase separator and concentrated in vacuo. The residue was purified by flash chromatography (GraceResolv silica 40 g cartridge, 0-80% EtOAc in cyclohexane; then GraceResolv silica 40 g cartridge, 0% EtOAc in DCM then 5% EtOAc in DCM (isocratic)) to give the title compound (300 mg, 61%) as a colourless crystalline solid. LCMS (Method A): $R_T$=1.53 min, m/z=324, 326 [M+H]$^+$.
$^1$H NMR (500 MHz, DMSO-d$_6$): δ 8.62 (s, 1H), 7.17-7.13 (m, 2H), 7.06-7.03 (m, 2H), 3.86 (s, 3H), 3.76 (s, 3H).

Step 2: 6-Chloro-7-(3,4-dimethoxyphenyl)-3,7-dihydro-4H-pyrrolo[2,3-d]pyrimidin-4-one A suspension of 4,6-dichloro-7-(3,4-dimethoxyphenyl)-7H-pyrrolo[2,3-d]pyrimidine (300 mg, 0.926 mmol) in 2 M HCl$_{(aq)}$ (1.85 mL, 3.70 mmol) and 1,4-dioxane (3 mL) was heated under microwave irradiation at 120° C. for 2 h before the reaction mixture was concentrated in vacuo and the residue was dried in a vacuum oven at 50° C. to give the title compound (281 mg, 99%) as a beige solid. LCMS (Method A): $R_T$=0.85 min, m/z=306, 308 [M+H]$^+$. $^1$H NMR (500 MHz, DMSO-d$_6$): δ 12.11 (s, 1H), 7.86 (d, J=3.0 Hz, 1H), 7.11 (d, J=8.6 Hz, 1H), 7.03 (d, J=2.5 Hz, 1H), 6.95 (dd, J=8.5, 2.4 Hz, 1H), 6.73 (s, 1H), 3.84 (s, 3H), 3.76 (s, 3H).

Step 3: tert-Butyl 4-((6-chloro-7-(3,4-dimethoxyphenyl)-4-oxo-4,7-dihydro-3H-pyrrolo[2,3-d]pyrimidin-3-yl)methyl)-4-hydroxypiperidine-1-carboxylate General procedure 1 using Epoxide 1 (385 mg, 1.81 mmol), 6-chloro-7-(3,4-dimethoxyphenyl)-3,7-dihydro-4H-pyrrolo[2,3-d]pyrimidin-4-one (276 mg, 0.903 mmol), cesium carbonate (324 mg, 0.993 mmol) and DMF (6 mL) gave the title compound (219 mg, 46%) as pale yellow solid. LCMS (Method A): $R_T$=1.42 min, m/z=519, 521 [M+H]$^+$. $^1$H NMR (500 MHz, DMSO-d$_6$): δ 8.07 (s, 1H), 7.12 (d, J=8.6 Hz, 1H), 7.03 (d, J=2.4 Hz, 1H), 6.96 (dd, J=8.5, 2.4 Hz, 1H), 6.76 (s, 1H), 4.85 (s, 1H), 3.99 (s, 2H), 3.84 (s, 3H), 3.77 (s, 3H), 3.70-3.61 (m, 2H), 3.12-2.97 (m, 2H), 1.47 (ddd, J=13.2, 11.0, 4.5 Hz, 2H), 1.39 (s, 9H), 1.37-1.30 (m, 2H).

Step 4: 6-Chloro-7-(3,4-dimethoxyphenyl)-3-((4-hydroxypiperidin-4-yl)methyl)-3,7-dihydro-4H-pyrrolo[2,3-d]pyrimidin-4-one A solution of tert-butyl 4-((6-chloro-7-(3,4-dimethoxyphenyl)-4-oxo-4,7-dihydro-3H-pyrrolo[2,3-d]pyrimidin-3-yl)methyl)-4-hydroxypiperidine-1-carboxylate (219 mg, 0.422 mmol) in TFA (2 mL) and DCM (4 mL) was stirred for 15 min before the reaction mixture was purified using a 5 g Biotage SCX-2 cartridge (pre-equilibrated and washed with 1:1 DCM/MeOH, then eluted using 1:1 DCM/7 M in NH$_3$ in MeOH). The basic phase was concentrated in vacuo to give the title compound (137 mg, 77%) as colourless solid. LCMS (Method A): $R_T$=0.68 min, m/z=419, 421 [M+H]$^+$. $^1$H NMR (500 MHz, DMSO-d$_6$): δ 8.07 (s, 1H), 7.12 (d, J=8.5 Hz, 1H), 7.03 (d, J=2.4 Hz, 1H), 6.96 (dd, J=8.5, 2.4 Hz, 1H), 6.75 (s, 1H), 4.59 (s, 1H), 3.96 (s, 2H), 3.84 (s, 3H), 3.77 (s, 3H), 2.75-2.62 (m, 4H), 2.03 (s, 1H), 1.43 (ddd, J=13.9, 9.8, 4.5 Hz, 2H), 1.34-1.18 (m, 2H).

Step 5: 6-Chloro-7-(3,4-dimethoxyphenyl)-3-((4-hydroxy-1-(1-methylcyclopropane-1-carbonyl)piperidin-4-yl)methyl)-3,7-dihydro-4H-pyrrolo[2,3-d]pyrimidin-4-one General procedure 4 using 6-chloro-7-(3,4-dimethoxyphenyl)-3-((4-hydroxypiperidin-4-yl)methyl)-3,7-dihydro-4H-pyrrolo[2,3-d]pyrimidin-4-one (70 mg, 0.167 mmol), 1-methylcyclopropane-1-carboxylic acid (18.4 mg, 0.184 mmol), HATU (70 mg, 0.184 mmol) and DIPEA (0.117 mL, 0.669 mmol) in DCM (3.2 mL) gave the title compound (82.4 mg, 97%) as colourless solid after lyophilisation. LCMS (Method A): $R_T$=1.14 min, m/z=501, 503 [M+H]$^+$. $^1$H NMR (500 MHz, DMSO-d$_6$): δ 8.08 (s, 1H), 7.12 (d, J=8.6 Hz, 1H), 7.03 (d, J=2.4 Hz, 1H), 6.96 (dd, J=8.5, 2.4 Hz, 1H), 6.76 (s, 1H), 4.91 (s, 1H), 4.01 (s, 2H), 3.94 (dt, J=13.2, 4.3 Hz, 2H), 3.85 (s, 3H), 3.77 (s, 3H), 3.17 (s, 2H), 1.57-1.47 (m, 2H), 1.43-1.36 (m, 2H), 1.21 (s, 3H), 0.81-0.73 (m, 2H), 0.56-0.48 (m, 2H).

Example 240: 6-Chloro-3-((1-(2-cyclopropyloxazole-5-carbonyl)-4-hydroxypiperidin-4-yl)methyl)-7-(3,4-dimethoxyphenyl)-3,7-dihydro-4H-pyrrolo[2,3-d]pyrimidin-4-one

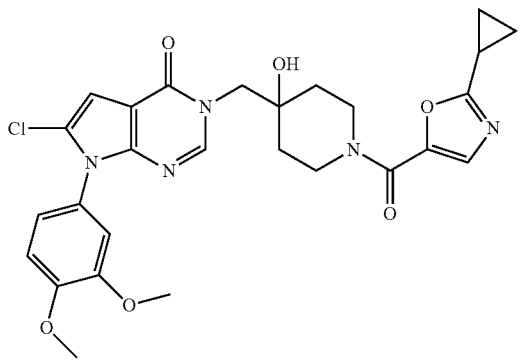 [SMILES: COc1ccc(-n2c(Cl)cc3c(=O)n(CC4(O)CCN(C(=O)c5cnc(C6CC6)o5)CC4)cnc32)cc1OC]

General procedure 4 using 6-chloro-7-(3,4-dimethoxyphenyl)-3-((4-hydroxypiperidin-4-yl)methyl)-3,7-dihydro-4H-pyrrolo[2,3-d]pyrimidin-4-one (70 mg, 0.167 mmol) (Example 239, Step 4), 2-cyclopropyloxazole-5-carboxylic acid (28.2 mg, 0.184 mmol), HATU (70 mg, 0.184 mmol) and DIPEA (0.117 mL, 0.669 mmol) in DCM (3.2 mL) gave the title compound (92.5 mg, 98%) as colourless solid after lyophilisation. LCMS (Method A): $R_T$=1.14 min, m/z=554, 556 [M+H]$^+$. $^1$H NMR (500 MHz, DMSO-d$_6$): δ 8.08 (s, 1H), 7.49 (s, 1H), 7.12 (d, J=8.6 Hz, 1H), 7.04 (d, J=2.4 Hz, 1H), 6.96 (dd, J=8.5, 2.4 Hz, 1H), 6.76 (s, 1H), 5.00 (s, 1H), 4.11-3.91 (m, 2H), 4.03 (s, 2H), 3.85 (s, 3H), 3.77 (s, 3H), 3.50-3.10 (m, 2H (signal overlaps with HDO)), 2.17 (tt, J=8.4, 4.9 Hz, 1H), 1.65-1.55 (m, 2H), 1.50-1.42 (m, 2H), 1.12-1.05 (m, 2H), 1.01-0.94 (m, 2H).

Example 241: 7-(4-(Aminomethyl)phenyl)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one

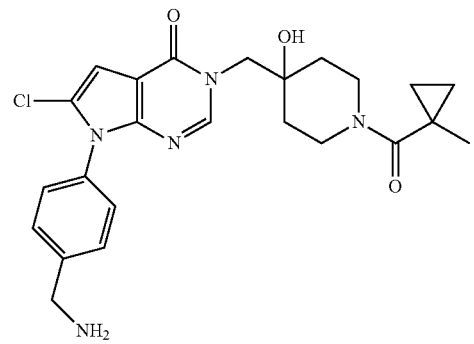 [SMILES: CC1(C(=O)N2CCC(O)(Cn3cnc4c(cc(Cl)n4-c4ccc(CN)cc4)c3=O)CC2)CC1]

Step 1: 1-(1-Methylcyclopropane-1-carbonyl)piperidin-4-one

4 M HCl in 1,4-dioxane (7.5 mL, 30.0 mmol) was added to a solution of tert-butyl 4-oxopiperidine-1-carboxylate (598 mg, 3.00 mmol) in 1,4-dioxane (15 mL) and after 20 h, the reaction was concentrated in vacuo and the residue was dried in a vacuum oven at 50° C. To this material was added 1-methylcyclopropane-1-carboxylic acid (300 mg, 3.00 mmol), HATU (1.14 g, 3.00 mmol), DCM (60 mL) and DIPEA (2.10 mL, 12.0 mmol). The reaction was stirred for 1 h 45 min, diluted with saturated $NaHCO_{3(aq)}$ (60 mL) and the resulting mixture was extracted with DCM (3×30 mL) using a Biotage phase separator. The combined organic phases were concentrated in vacuo and the residue was purified by flash chromatography (Biotage KP-NH 28 g cartridge, 0-100% EtOAc in cyclohexane) to give title compound (328 mg, 60%) as a colourless oil that solidified upon standing. LCMS (Method A): $R_T$=0.42 min, m/z=182 [M+H]$^+$. $^1$H NMR (500 MHz, DMSO-d): δ 3.80 (t, J=6.3 Hz, 4H), 2.38 (t, J=6.3 Hz, 4H), 1.27 (s, 3H), 0.89-0.84 (m, 2H), 0.59-0.53 (m, 2H).

Step 2: (1-Methylcyclopropyl) (1-oxa-6-azaspiro [2.5]octan-6-yl)methanone

A 60% dispersion of sodium hydride in mineral oil (109 mg, 2.71 mmol) was added to a stirred suspension of trimethylsulfonium iodide (554 mg, 2.71 mmol) in DMF (4.5 mL) at RT. After 1 h, a solution of 1-(1-methylcyclopropane-1-carbonyl)piperidin-4-one (328 mg, 1.81 mmol) in DMF (4.5 mL) was added dropwise. After 16 h, the reaction was diluted with 1:1 water/saturated $NH_4Cl_{(aq)}$ (40 mL) and was extracted with EtOAc (3×20 mL). The combined organic phases were washed with water (20 mL) and brine (20 mL) before being passed through a Biotage phase separator. The resulting solution was concentrated in vacuo and the residue was purified by flash chromatography (GraceResolv silica 24 g cartridge, 0-100% EtOAc in cyclohexane) to give the title compound (136 mg, 38%) as pale yellow oil. LCMS (Method A): $R_T$=0.61 min, m/z=196 [M+H]$^+$. $^1$H NMR (500 MHz, DMSO-d): δ 3.79-3.66 (m, 2H), 3.63-3.43 (m, 2H), 2.68 (s, 2H), 1.69 (ddd, J=13.1, 8.6, 4.2 Hz, 2H), 1.43 (ddd, J=13.3, 6.5, 3.8 Hz, 2H), 1.23 (s, 3H), 0.86-0.75 (m, 2H), 0.60-0.48 (m, 2H).

Step 3: tert-Butyl (4-(4,6-dichloro-7H-pyrrolo[2,3-d]pyrimidin-7-yl)benzyl)carbamate A suspension of 4,6-dichloro-7H-pyrrolo[2,3-d]pyrimidine (940 mg, 5.00 mmol), (4-(((tert-butoxycarbonyl)amino)methyl)phenyl)boronic acid (3.77 g, 15.0 mmol), 1,10-phenanthroline (1.80 g, 10.0 mmol) and copper(II) acetate (1.82 g, 10.0 mmol) in DMF (100 mL) was stirred at RT for 19 h before being quenched by the addition of saturated $NH_4Cl_{(aq)}$ (150 mL). The resulting mixture was diluted with water (600 mL) and extracted with EtOAc (3×150 mL). The combined organic phases were washed with water (150 mL) and brine (150 mL), passed through a Biotage phase separator and concentrated in vacuo. The residue was dry loaded onto silica and purified by flash chromatography (Biotage KP-Sil 100 g cartridge, 0-15% EtOAc in cyclohexane) to give a mixture of starting material, product and what is presumed to be homocoupled boronic acid. This material was dry loaded on to silica and purified by flash chromatography (Biotage KP-Sil 100 g cartridge, 0-20% EtOAc in DCM) to give a 1.5:1 mixture of starting material and product (1.06 g). This colourless solid was suspended in cyclohexane (~200 mL) and the resulting mixture stirred for 20 min before being filtered. The filtrate was concentrated in vacuo to give the title compound (263 mg, 13%) as a colourless solid. LCMS (Method A): $R_T$=1.71 min, m/z=393, 395 [M+H]$^+$. $^1$H NMR (500 MHz, DMSO-d$_6$): δ 8.61 (s, 1H), 7.53-7.44 (m, 5H), 7.08 (s, 1H), 4.25 (d, J=6.2 Hz, 2H), 1.42 (s, 9H).

Step 4: tert-Butyl (4-(6-chloro-4-oxo-3,4-dihydro-7H-pyrrolo[2,3-d]pyrimidin-7-yl)benzyl)carbamate Acetate A mixture of tert-butyl (4-(4,6-dichloro-7H-pyrrolo[2,3-d]pyrimidin-7-yl)benzyl)carbamate (260 mg, 0.661 mmol), 4 M $NaOH_{(aq)}$ (0.165 mL, 0.661 mmol) and 1,4-dioxane (2.6 mL) was heated at reflux. After 20.5 h, 4 M $NaOH_{(aq)}$ (0.165 mL, 0.661 mmol), water (0.5 mL) and 1,4-dioxane (2.6 mL) were added. After 5.5 h, further 4 M $NaOH_{(aq)}$ (0.3 mL, 1.2 mmol), 1,4-dioxane (2 mL) and water (0.5 mL) were added. After 20 h, further 4 M NaOH (0.3 mL, 1.2 mmol) was added. After 6 h, further 4 M NaOH (1.5 mL, 6 mmol) was added. After a further 17.5 h, the reaction mixture was cooled to RT and diluted with water (10 mL). The pH of the resulting mixture was adjusted to ~pH 4 by the addition of AcOH and the mixture was extracted with DCM (3×40 mL) using a Biotage phase separator. The combined organic phases were concentrated in vacuo and the residue was dried in a vacuum oven at 50° C. to give the title compound (247 mg, 85%) as a brown solid. LCMS (Method A): $R_T$=1.21 min, m/z=375, 377 [M-acetate]$^+$. $^1$H NMR (500 MHz, DMSO-d$_6$): δ 12.23-11.71 (br m, 2H), 7.85 (s, 1H), 7.53-7.33 (m, 5H), 6.76 (s, 1H), 4.23 (d, J=6.3 Hz, 2H), 1.91 (s, 3H), 1.41 (s, 9H).

Step 5: tert-Butyl (4-(6-chloro-3-((4-hydroxy-1-(1-methylcyclopropane-1-carbonyl)piperidin-4-yl)methyl)-4-oxo-3,4-dihydro-7H-pyrrolo[2,3-d]pyrimidin-7-yl)benzyl)carbamate General procedure 1 using (1-methylcyclopropyl)(1-oxa-6-azaspiro[2.5]octan-6-yl)methanone (29 mg, 0.150 mmol), tert-butyl (4-(6-chloro-4-oxo-3,4-dihydro-7H-pyrrolo[2,3-d]pyrimidin-7-yl)benzyl)carbamate acetate (65 mg, 0.150 mmol), cesium carbonate (107 mg, 0.329 mmol) and DMF (1 mL) gave the title compound (50.9 mg, 59%) as a yellow solid. LCMS (Method A): $R_T$=1.35 min, m/z=570, 572 [M+H]$^+$.

Step 6: 7-(4-(Aminomethyl)phenyl)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one A solution of tert-butyl (4-(6-chloro-3-((4-hydroxy-1-(1-methylcyclopropane-1-carbonyl)piperidin-4-yl)methyl)-4-oxo-3,4-dihydro-7H-pyrrolo[2,3-d]pyrimidin-7-yl)benzyl)carbamate (50.9 mg, 89.3 µmol) in TFA (0.5 mL) and DCM (1 mL) was stirred at RT for 25 min before the reaction mixture purified using a 2 g Biotage SCX-2 cartridge (pre-equilibrated and washed with 1:1 DCM/MeOH, then eluted using 1:1 DCM/7 M in NH$_3$ in MeOH). The basic phase was concentrated in vacuo and the residue was purified by flash chromatography (Biotage KP-NH 11 g cartridge, 0-10% MeOH in DCM) to give the title compound (31.2 mg, 73%) as colourless solid after lyophilisation. LCMS (Method A): $R_T$=0.61 min, m/z=470, 472 [M+H]$^+$. $^1$H NMR (500 MHz, DMSO-d$_6$): δ 8.07 (s, 1H), 7.55-7.44 (m, 2H), 7.40-7.32 (m, 2H), 6.79 (s, 1H), 4.90 (s, 1H), 4.01 (s, 2H), 3.95 (dt, J=13.2, 4.2 Hz, 2H), 3.82 (s, 2H), 3.22-3.06

(m, 2H), 2.28 (br s, 2H), 1.58-1.46 (m, 2H), 1.46-1.34 (m, 2H), 1.21 (s, 3H), 0.81-0.71 (m, 2H), 0.57-0.47 (m, 2H).

Example 242: 7-(4-(Aminomethyl)phenyl)-6-chloro-3-((1-(2-cyclopropyloxazole-5-carbonyl)-4-hydroxypiperidin-4-yl)methyl)-3,7-dihydro-4H-pyrrolo[2,3-d]pyrimidin-4-one

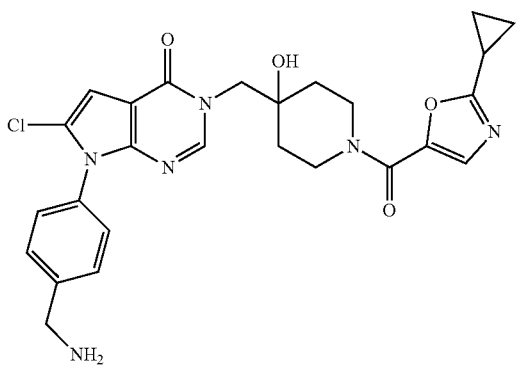 [SMILES: NCc1ccc(-n2c(Cl)cc3c(=O)n(CC4(O)CCN(C(=O)c5cnc(C6CC6)o5)CC4)cnc32)cc1]

Step 1:
1-(2-Cyclopropyloxazole-5-carbonyl)piperidin-4-one

4 M HCl in 1,4-dioxane (7.5 mL, 30.0 mmol) was added to a stirred solution of tert-butyl 4-oxopiperidine-1-carboxylate (598 mg, 3.00 mmol) in 1,4-dioxane (15 mL) and after 20 h, the reaction was concentrated in vacuo and the residue dried in a vacuum oven at 50° C. To this material was added 2-cyclopropyloxazole-5-carboxylic acid (459 mg, 3.00 mmol), HATU (1.14 g, 3.00 mmol), DCM (60 mL) and DIPEA (2.10 mL, 12.0 mmol). After 1 h 45 min, the reaction mixture was diluted with saturated NaHCO$_{3(aq)}$ (60 mL) and the resulting biphasic mixture was extracted with DCM (3×30 mL) using a Biotage phase separator. The combined organic phases were concentrated in vacuo and the residue was purified by flash chromatography (Biotage KP-NH 28 g cartridge, 0-100% EtOAc in cyclohexane) to give title compound (280 mg, 39%) as a colourless oil that solidified upon standing. LCMS (Method A): R$_T$=0.49 min, m/z=235 [M+H]$^+$. $^1$H NMR (500 MHz, DMSO-d$_6$): δ 7.59 (s, 1H), 3.97-3.82 (m, 4H), 2.49-2.45 (m, 4H (signal overlaps with DMSO)), 2.19 (tt, J=8.3, 4.9 Hz, 1H), 1.14-1.07 (m, 2H), 1.04-0.96 (m, 2H).

Step 2: (2-Cyclopropyloxazole-5-yl) (1-oxa-6-azaspiro[2.5]octan-6-yl)methanone

A 60% dispersion of sodium hydride in mineral oil (72 mg, 1.79 mmol) was added to a stirred suspension of trimethylsulfonium iodide (366 mg, 1.79 mmol) in DMF (4 mL) at RT. After 1 h, a solution of 1-(2-cyclopropyloxazole-5-carbonyl)piperidin-4-one (280 mg, 1.12 mmol) in DMF (4 mL) was added dropwise. After 16 h, the reaction was diluted with 1:1 water/saturated NH$_4$Cl$_{(aq)}$ (40 mL) and was extracted using EtOAc (3×20 mL). The combined organic phases were washed with water (20 mL) and brine (20 mL) before being passed through a Biotage phase separator. The resulting solution was concentrated in vacuo and the residue was purified by flash chromatography (GraceResolv silica 24 g cartridge, 0-100% EtOAc in cyclohexane) to give the title compound (86 mg, 28%) as pale yellow oil. LCMS (Method A): R$_T$=0.67 min, m/z=249 [M+H]$^+$. $^1$H NMR (500 MHz, DMSO-d$_6$): δ 7.53 (s, 1H), 3.83 (ddd, J=13.3, 6.5, 4.3 Hz, 2H), 3.72-3.54 (m, 2H), 2.70 (s, 2H), 2.18 (tt, J=8.3, 4.9 Hz, 1H), 1.78 (ddd, J=13.2, 8.7, 4.2 Hz, 2H), 1.49 (ddd, J=13.5, 6.5, 3.9 Hz, 2H), 1.14-1.06 (m, 2H), 1.03-0.96 (m, 2H).

Step 3: tert-Butyl (4-(6-chloro-3-((1-(2-cyclopropyloxazole-5-carbonyl)-4-hydroxypiperidin-4-yl)methyl)-4-oxo-3,4-dihydro-7H-pyrrolo[2,3-d]pyrimidin-7-yl)benzyl)carbamate General procedure 1 using (2-cyclopropyloxazole-5-yl)(1-oxa-6-azaspiro[2.5]octan-6-yl)methanone (37 mg, 0.150 mmol), tert-butyl (4-(6-chloro-4-oxo-3,4-dihydro-7H-pyrrolo[2,3-d]pyrimidin-7-yl)benzyl)carbamate acetate (65 mg, 0.150 mmol) (Example 241, Step 4), cesium carbonate (107 mg, 0.329 mmol) and DMF (1 mL) gave the title compound (47.8 mg, 51%) as a yellow solid. LCMS (Method A): R$_T$=1.34 min, m/z=623, 625 [M+H]$^+$.

Step 4: 7-(4-(Aminomethyl)phenyl)-6-chloro-3-((1-(2-cyclopropyloxazole-5-carbonyl)-4-hydroxypiperidin-4-yl)methyl)-3,7-dihydro-4H-pyrrolo[2,3-d]pyrimidin-4-one A solution of tert-butyl (4-(6-chloro-3-((1-(2-cyclopropyloxazole-5-carbonyl)-4-hydroxypiperidin-4-yl)methyl)-4-oxo-3,4-dihydro-7H-pyrrolo[2,3-d]pyrimidin-7-yl)benzyl)carbamate (47.8 mg, 76.7 µmol) in TFA (0.5 mL) and DCM (1 mL) was stirred at RT for 30 min before the reaction mixture was purified using a 2 g Biotage SCX-2 cartridge (pre-equilibrated and washed with 1:1 DCM/MeOH, then eluted using 1:1 DCM/7 M in NH$_3$ in MeOH). The basic phase was concentrated in vacuo and the residue was purified by flash chromatography (Biotage KP-NH 11 g cartridge, 0-10% MeOH in DCM) to give the title compound (29.8 mg, 72%) as colourless solid after lyophilisation. LCMS (Method A): R$_T$=0.65 min, m/z=523, 523 [M+H]$^+$. $^1$H NMR (500 MHz, DMSO-d$_6$): δ 8.08 (s, 1H), 7.57-7.43 (m, 2H), 7.49 (s, 1H), 7.41-7.33 (m, 2H), 6.79 (s, 1H), 4.99 (s, 1H), 4.11-3.88 (m, 2H), 4.03 (s, 2H), 3.83 (s, 2H), 3.48-3.12 (m, 2H (signal overlaps with HDO)), 2.57 (br s, 2H (signal overlaps with DMSO)), 2.17 (tt, J=8.3, 4.9 Hz, 1H), 1.65-1.54 (m, 2H), 1.50-1.41 (m, 2H), 1.13-1.04 (m, 2H), 1.02-0.93 (m, 2H).

Example 243: (R)-4-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic Acid

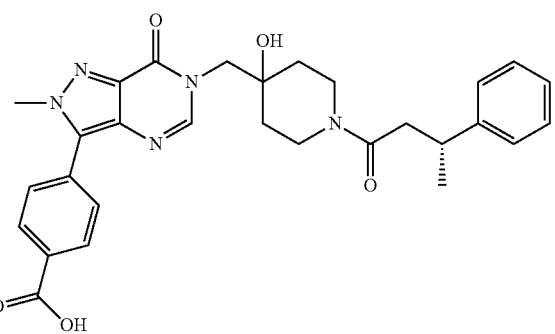

Step 1: tert-Butyl (R)-4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzoate General procedure 5 using Intermediate B (44 mg, 0.090 mmol), (4-(tert-butoxycarbonyl)phenyl)boronic acid (60 mg, 0.270 mmol), K$_3$PO$_4$ (115 mg, 0.541 mmol), Pd(PPh$_3$)$_4$(5.2 mg, 4.5 µmol), 1,4-dioxane (0.5 mL) and water (0.2 mL) in a microwave at 120° C. for 30 min gave the title compound (45 mg, 85%) as a colourless solid. LCMS (Method A): R$_T$=1.53 min, m/z=586 [M+H]$^+$.

Step 2: (R)-4-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic Acid A solution of tert-butyl (R)-4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzoate (45 mg, 0.077 mmol) in DCM (1 mL) and TFA (0.2 mL) was stirred at RT for 4 h. The reaction mixture was concentrated in vacuo and purification of the residue by flash chromatography (GraceResolv silica 12 g, 0-30% ca. 0.1% formic acid in MeOH/DCM) gave the title compound (29.7 mg, 71%) as a colourless solid after lyophilisation. LCMS (Method A): R$_T$=1.06 min, m/z=530 [M+H]$^+$. $^1$H NMR (500 MHz, DMSO-d$_6$): δ 13.14 (s, 1H), 8.15-8.09 (m, 2H), 8.02 (d, J=12.2 Hz, 1H), 7.91-7.85 (m, 2H), 7.26 (dd, J=7.5, 5.6 Hz, 4H), 7.16 (ddt, J=9.7, 6.4, 2.5 Hz, 1H), 4.86 (d, J=5.2 Hz, 1H), 4.16 (s, 3H), 4.08-3.87 (m, 3H), 3.65 (s, 1H), 3.27-3.13 (m, 2H), 2.88 (t, J=11.5 Hz, 1H), 2.62-2.53 (m, 2H), 1.47-1.23 (m, 4H), 1.21 (d, J=6.9 Hz, 3H).

Example 244: (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic Acid

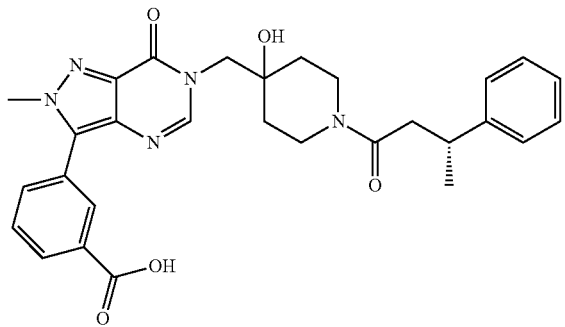 [SMILES: C[C@H](CC(=O)N1CCC(O)(Cn2cnc3c(-c4cccc(C(=O)O)c4)n(C)nc3c2=O)CC1)c1ccccc1]

Step 1: tert-Butyl (R)-3-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzoate General procedure 5 using Intermediate B (40 mg, 0.082 mmol), (3-(tert-butoxycarbonyl)phenyl)boronic acid (55 mg, 0.246 mmol), K$_3$PO$_4$ (104 mg, 0.491 mmol), Pd(PPh$_3$)$_4$(4.73 mg, 4.1 µmol), 1,4-dioxane (0.5 mL) and water (0.2 mL) in a microwave at 120° C. for 15 min gave the title compound (41 mg, 85%) as a pale yellow solid. LCMS (Method A): R$_T$=1.60 min, m/z=586 [M+H]$^+$.

Step 2: (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic Acid A solution of tert-butyl (R)-3-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzoate (41 mg) in DCM (1 mL) and TFA (0.2 mL) was stirred at RT for 2 h. The reaction mixture was concentrated in vacuo and purification of the residue by flash chromatography (GraceResolv silica 12 g, 0-30% ca. 0.1% formic acid in MeOH/DCM) gave the title compound (31.5 mg, 84%) as a colourless solid after lyophilisation. LCMS (Method A): R$_T$=1.13 min, m/z=530 [M+H]$^+$. $^1$H NMR (500 MHz, DMSO-d$_6$): δ 13.19 (s, 1H), 8.27 (s, 1H), 8.07 (dt, J=7.9, 1.4 Hz, 1H), 8.05-7.95 (m, 2H), 7.72 (t, J=7.8 Hz, 1H), 7.26 (dd, J=7.5, 5.6 Hz, 4H), 7.16 (dq, J=6.3, 3.3, 2.5 Hz, 1H), 4.86 (s, 1H), 4.13 (s, 3H), 4.08-3.87 (m, 3H), 3.65 (s, 1H), 3.28-3.13 (m, 3H), 2.93-2.83 (m, 1H), 2.62-2.56 (m, 1H), 1.33 (dddd, J=44.1, 28.7, 10.6, 4.0 Hz, 4H), 1.21 (d, J=7.0 Hz, 3H).

Example 245: 4-(6-((4-Hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzoic Acid

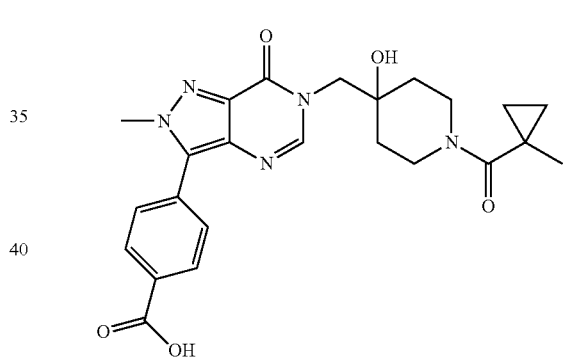

Step 1: tert-Butyl 4-hydroxy-4-((3-(4-(methoxycarbonyl)phenyl)-2-methyl-7-oxo-2,7-dihydro-6H-pyrazolo[4,3-d]pyrimidin-6-yl)methyl)piperidine-1-carboxylate General procedure 5 using Intermediate C (300 mg, 0.678 mmol), (4-(methoxycarbonyl)phenyl)boronic acid (366 mg, 2.04 mmol), K$_3$PO$_4$ (863 mg, 4.07 mmol), Pd(PPh$_3$)$_4$(39.2 mg, 33.9 µmol), 1,4-dioxane (2.25 mL) and water (0.9 mL) in a microwave at 130° C. for 30 min gave the title compound (240 mg, 71%) as a colourless solid. LCMS (Method A): R$_T$=1.22 min, m/z=498 [M+H]$^+$.

Step 2: Methyl 4-(6-((4-hydroxypiperidin-4-yl)methyl)-2-methyl-7-oxo-6,7-dihydro-2H-pyrazolo[4,3-d]pyrimidin-3-yl)benzoate General procedure 2 using tert-butyl 4-hydroxy-4-((3-(4-(methoxycarbonyl)phenyl)-2-methyl-7-oxo-2,7-dihydro-6H-pyrazolo[4,3-d]pyrimidin-6-yl)methyl)piperidine-1-carboxylate (240 mg, 0.482 mmol), DCM (4 mL) and TFA (2 mL) stirred at RT for 20 min gave the title compound (170 mg, 88%) as a colourless solid. LCMS (Method A): $R_T$=0.46 min, m/z=398 [M+H]$^+$.

Step 3: Methyl 4-(6-((4-hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzoate General procedure 4 using methyl 4-(6-((4-hydroxypiperidin-4-yl)methyl)-2-methyl-7-oxo-6,7-dihydro-2H-pyrazolo[4,3-d]pyrimidin-3-yl)benzoate (55 mg, 0.138 mmol), 1-methylcyclopropane-1-carboxylic acid (15.2 mg, 0.152 mmol), HATU (63.1 mg, 0.166 mmol), DIPEA (72.5 µL, 0.415 mmol) and DCM (2 mL) stirred at RT for 1 h gave the title compound (60 mg, 90%) as a colourless solid. LCMS (Method A): $R_T$=0.93 min, m/z=480 [M+H]$^+$.

Step 4: 4-(6-((4-Hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzoic acid A mixture of methyl 4-(6-((4-hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzoate (20 mg, 41.7 µmol) and lithium hydroxide (1.2 mg, 50.0 µmol) in THF (0.25 mL) and water (0.125 mL) was stirred for 1 h at 50° C. The reaction mixture was diluted with water, acidified by addition of 2 M HCl$_{(aq)}$ and extracted using EtOAc (×3). The combined organic phases were passed through a Biotage phase separator, concentrated in vacuo and the crude material was purified by flash chromatography (Grace Resolv 4 g, 0-30% ca. 0.1% formic acid in MeOH/DCM) to give the title compound (9.9 mg, 50%) as a colourless solid. LCMS (Method A): $R_T$=0.60 min, m/z=466 [M+H]$^+$. $^1$H NMR (500 MHz, DMSO-d$_6$): δ 13.17 (s, 1H), 8.12 (d, J=8.1 Hz, 2H), 8.05 (d, J=2.9 Hz, 1H), 7.88 (d, J=8.1 Hz, 2H), 4.90 (s, 1H), 4.16 (d, J=2.9 Hz, 3H), 4.02 (s, 2H), 3.96 (dt, J=13.3, 4.0 Hz, 2H), 3.15 (s, 2H), 1.52 (s, 2H), 1.43 (d, J=13.2 Hz, 2H), 1.21 (d, J=2.9 Hz, 3H), 0.77 (s, 2H), 0.52 (s, 2H).

Measurement of USP7 Inhibitory Activity

USP7 activity was monitored in a fluorescence polarisation (FP) homogeneous assay using the isopeptide ubiquitin-Lys-TAMRA substrate (U-558, Boston Biochem). Full-length USP7 was purchased from Boston Biochem (His6-USP7FL, E-519). Unless otherwise stated, all other reagents were purchased from Sigma-Aldrich. Enzymatic reactions were conducted in black flat-bottom polystyrene 384-well plates (Nunc) and 15 µL total volume. USP7 (2.5 nM, 5 µL) was incubated in assay buffer (50 mM HEPES (pH 7.2), 150 mM NaCl, 0.5 mM EDTA, 5 mM DTT, 0.05% BSA (w/v), 0.05% CHAPS) in the presence or absence of inhibitor (5 µl). Inhibitors were stored as 10 mM DMSO stocks in an inert environment (low humidity, dark, low oxygen, room temperature) using a Storage Pod System and serial dilutions were prepared in buffer just prior to the assay (from 200 to 0.1 µM, 8 dp curve). Following incubation at room temperature for 30 min, the enzymatic reactions were initiated by dispensing the Ub substrate (250 nM, 5 µL). FP was measured every 15 min over a period of 1.5 h (within the linear range of the assay) using a Synergy 4 plate reader (BioTek) exciting at 530 nm and measuring the amount of parallel and perpendicular light at 575 nm. The FP signal was subsequently normalised to the control without compound present. Data were plotted and fitted, and the concentrations resulting in 50% inhibition (IC$_{50}$) were calculated using the non-linear regression curve fitting model using GraphPad (Prism). IC$_{50}$ values for the inhibitors of the invention are compiled in Table 1 above and represent the average of at least duplicate experiments.

Proliferation Assay

LNCaP cells from ATCC, were seeded in 96 well plate format (typically 2500 cells/well) in their growth media (RPMI, Life Technologies #52400-025+10% Fetal Calf Serum, Life Technologies #10500-064) and treated after 24 h with increasing concentration of compound from 0 to 30 µM. Cell viability was assessed after 168 h by CellTiter-Glo® as recommended by the manufacturer's instructions (Promega). Analysis and EC$_{50}$ values were derived using GraphPadPrism.

Target Engagement Assay

A target engagement assay was conducted to demonstrate inhibition of USP7 by the exemplified compounds in cells by competition with ubiquitin vinyl sulfone (Ub-VS) substrate. HCT116 cells were treated with vehicle (DMSO) or compound at various concentrations for 2 h and subsequently lysed on ice and homogenised. The Ub-VS probe was then added to the cell lysate and incubated on ice for 10 min. Samples were analysed by western blotting probing for USP7.

Representative results for this assay (from Example 29) are shown in FIG. 1. Further data for other examples are presented below:

p53, p21 and MDM2 Protein Levels p53 stabilisation, p21 induction and MDM2 decrease following treatment with Example 29 was demonstrated in 2 cell lines (HCT116 cells and SJSA-1 cells) (FIGS. 2A and 2B respectively). Cells were treated with vehicle (DMSO) or Example 29 for 24 h, lysed in RIPA buffer and samples subsequently analysed by western blotting probing for USP7, p53, p21 and MDM2. A dose-dependent p53 stabilisation, p21 induction and concomitant decrease in MDM2 levels was observed in both cell lines.

Selectivity for Deubiquitylating Enzymes (DUBs)

Biochemical and cellular assays were conducted demonstrating the selectivity of the compounds of the invention for USP7 over other USPs, as well as broader classes of deubiquitylating enzymes (DUBs).

FIG. 3A shows selectivity as assessed against a panel of 38 DUBs (DUBprofiler™ Ubiquigent, Dundee) for representative Example 29. Screening was performed at a fixed concentration of 100 µM and levels of activity determined.

FIGS. 3B and 3C show the results of cellular assays for selectivity. In FIG. 3B, HCT116 cells were treated with vehicle (DMSO) or compound (as indicated, in µM) for 2 h and subsequently lysed on ice and homogenised. The HA-UbVS probe was then added to the cell lysate and incubated on ice for 10 min. Samples were analysed by western blotting probing for HA. + and − signs represent the presence or absence of Ub-VS. Labelled HA-UbVS USP7 is indicated by the red arrow. The data presented are for Example 29 and are representative of data for other compounds of the invention. For FIG. 3C, the same method was applied as for FIG. 3B using Ub-VS and probing the samples for USP4, USP47, USP11 and USP30. Compound concentrations are shown in µM (as indicated).

As the closest related DUB to USP7, USP47 was used as a stringent test for selectivity. USP4, USP11 and USP30 were used as general, non-relative representative members of the DUB family. + and − signs represent the presence or absence of Ub-VS. It is surprising how selective the compounds of the invention are, as the overall homology between DUBs would lead to an expectation of cross-reactivity.

Anti-Proliferative Effect of USP7 Inhibitor Example 29

FIG. 4 shows a representative clonogenic assay for compound Example 29 in HCT116 cells. Cells were treated for 7 days with increasing concentration of compound as indicated. Further data from the above assays for other exemplified compounds are presented below:

Example 27: $EC_{50}$ in 50-100 nM Range in Target Engagement

Example 30: $EC_{50}$ in 50-100 nM Range in Target Engagement

Kinetic Solubility Assay
Assay Procedure

Samples were prepared by adding 4 μL of the 10 mM compound DMSO stock solutions into 196 μL of PBS buffer pH 7.4 in the 96 well filter plates, yielding a compound concentration of 200 μM and 2% DMSO. The PBS buffer pH7.4 was prepared by Genentech media lab. Filter plates were sealed with aluminum sealing film and shaken at RT at 1000 rpm. After 24 h, the solutions were filtered into a clean 96 well plates utilizing a vacuum manifold. After filtration, some precipitate was often observed at the bottom of the filtration plate wells. Most of the precipitates appeared to be crystalline under a polarizing light microscope. The filtrate samples were diluted by a factor of 2 using PBS pH7.4 buffer and were transferred to a 384-well plate for analysis by UHPLC-CLND (CLND: chemiluminescence nitrogen detector). 5 μL of each sample was injected twice into the UHPLC-CLND for two repeat analysis.

Data Processing and Solubility Determination

Samples were detected and analyzed using UV 254 nm and CLND. UV 254 nm is used primarily to confirm the sample purity but in rare cases, is also used to quantify the concentration of compounds with no nitrogens, where additional work was done to create a compound specific calibration curve. The identification of CLND target peaks of each compound were confirmed by LCMS. Sample quantification was accomplished by CLND peak intensity, the calibration curve, and the number of nitrogen contained in the compound. One calibration curve of caffeine was used for solubility quantitative determination. A fresh calibration curve was created for every batch. The number of nitrogens in a compound used for this quantification needs to be corrected for the actual configuration of the nitrogen in the compound. [Literature reference: Lin et al., J. Pharm. Biomed. Anal., 2016, 122, p126-140].

The invention claimed is:
1. A compound of formula (I):

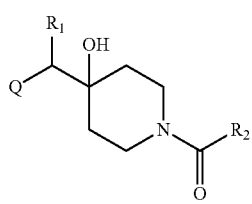

(I)

or a pharmaceutically acceptable salt, tautomer, stereoisomer or N-oxide derivative thereof, wherein:

$R_1$ is H, OH or an optionally substituted alkyl group;
$R_2$ is an optionally substituted C1-C6 alkyl, optionally substituted C2-C6 alkenyl, optionally substituted C2-C6 alkynyl, optionally substituted C3-C6 cycloalkyl, optionally substituted C4-C6 alkylcycloalkyl, optionally substituted C4-C6 aryl, optionally substituted C3-C6 heteroaryl, optionally substituted C4-C8 aryloxy, optionally substituted C7-C10 arylalkyl or optionally substituted C5-C10 heteroarylalkyl group; and
Q is selected from the group consisting of:

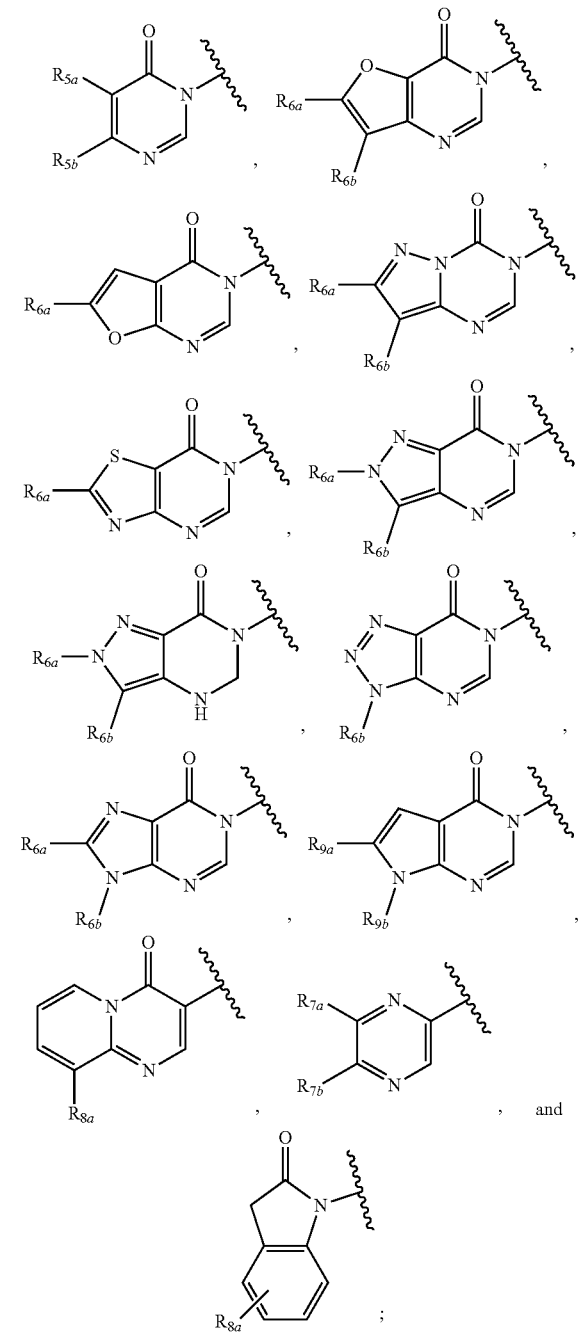

wherein:
$R_{5a}$ is H, halo, optionally substituted C1-C6 alkyl, or optionally substituted amino;

R$_{5b}$ is H, halo, optionally substituted C1-C6 alkyl, optionally substituted C2-C6 alkynyl, benzyl, optionally monosubstituted C3-C6 heteroaryl, optionally substituted C3-C6 heterocycloalkyl, optionally substituted C1-C6 alkoxy, NR'R", or R$^a$NR'R", wherein R$^a$ is C1-C6 alkyl or C2-C6 alkenyl; and wherein R' and R" are each independently selected from H, oxo-substituted C1-C6 alkyl, hydroxy-substituted C1-C6 alkyl, optionally substituted C1-C6 alkoxy, optionally substituted C3-C6 cycloalkyl, optionally substituted C1-C7 alkylamine, optionally substituted C2-C7 alkenylamine, optionally substituted C3-C10 heterocycloalkyl, optionally substituted C4-C10 aryl, optionally substituted C3-C10 heteroaryl, optionally substituted C5-C10 alkylaryl, optionally substituted C4-C10 alkylheterocycloalkyl, and C4-C6 alkylheteroaryl, or wherein R' and R" together form an optionally substituted C3-C8 heterocycloalkyl including the N to which they are attached;

R$_{6a}$ is H, optionally substituted C1-C6 alkyl, optionally substituted amino, optionally substituted C4-C6 aryl, optionally substituted C1-C6 sulfide, optionally substituted C1-C6 sulfonyl, or optionally substituted amino;

R$_{6b}$ is H, cyano, halo, optionally substituted C1-C6 alkyl, optionally substituted C2-C6 alkenyl, optionally substituted C2-C6 alkynyl, optionally substituted C3-C6 cycloalkyl, optionally substituted C4-C6 cycloalkenyl, optionally substituted C2-C6 ynol, optionally substituted C4-C6 aryl, optionally substituted C3-C6 heteroaryl, optionally substituted amino;

R$_{7a}$ is H;

R$_{7b}$ is H or optionally substituted C4-C6 aryl;

or wherein R$_{7a}$ and R$_{7b}$ together form an optionally substituted C1-C6 aryl group together with the carbons to which they are attached;

R$_{8a}$ is H or is optionally substituted C4-C6 aryl;

R$_{9a}$ is Cl, F, Br, I, or cyano; and

R$_{9b}$ is H, optionally substituted C1-C6 alkyl, optionally substituted C4-C6 aryl, optionally substituted C3-C8 heteroaryl, C1-C6 alkoxy.

2. The compound according to claim 1 wherein the optional substituents are independently selected from OH, F, Cl, Br, I, CN, C1-C6 alkyl, CF$_3$, CHF$_2$, CH$_2$F, CH$_2$OH, COOH, C(O)CH$_3$, CH2NHC(O)OCH$_2$CH$_3$, C2-C6 alkenyl, C2-C6 alkynyl, C3-C6 cycloalkyl, C1-C6 alkoxy, amino, C1-C6 alkylamine, C5-C6 aryl, C3-C6 heteroaryl, benzyl, oxo and amide, or two adjacent substituents may together constitute a ring.

3. The compound according to claim 1 wherein Q is:

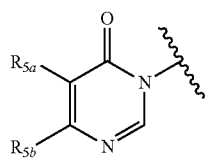

and:

R$_{5a}$ is H,

R$_{5b}$ is selected from optionally methyl- or ethylamine-substituted pyrazole, and NR'R", wherein R' and R" are each independently selected from H, methyl, cyclohexylamine, optionally methyl-, fluoro-, or fluorophenyl-substituted C2-C7 ethylamine, optionally substituted phenyl or wherein R' and R" together form an optionally substituted C3-C8 heterocycloalkyl including the N to which they are attached.

4. The compound of claim 3 wherein R' is H and R" is ethylpyrollidine optionally substituted with methyl, fluoro, or fluorophenyl.

5. The compound according to claim 1 wherein Q is:

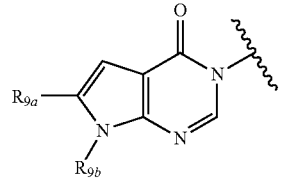

and

R$_{9a}$ Cl, F, Br, I, or cyano;

R$_{9b}$ is H, optionally substituted C1-C6 alkyl, optionally substituted C4-C6 aryl;

wherein the optional substituents are selected from F, Cl, Br, methoxy, OH, CH2OH, C1-C6 alkylamine, cyclopropane, dioxolane, methylpyrazole optionally substituted with fluoro, and morpholine.

6. The compound according to claim 5, wherein R$_{9a}$ is Cl, Br, I, or cyano and R$_{9b}$ is phenyl optionally substituted with F, Cl, Br, methoxy, OH, C1-C6 alkylamine, cyclopropane, dioxolane, methylpyrazole.

7. The compound according to claim 1 wherein Q is:

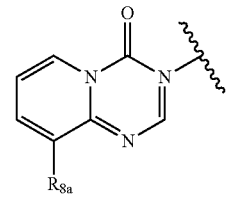

and

R$_{8a}$ is H or phenyl; and optionally wherein R1 is OH.

8. The compound according to claim 1 wherein Q is:

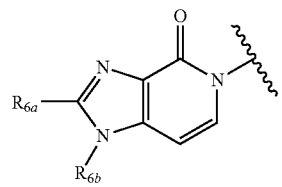

and

R$_{6a}$ is H, or C1-C6 alkyl;

R$_{6b}$ is H, or optionally substituted C4-C6 aryl;

wherein the optional substituent is selected from C1-C6 alkylamine.

9. The compound according to claim 8 wherein R$_{6a}$ is H, or methyl and R$_{6b}$ is H, or phenyl optionally substituted with CH2NH2 or CH(CH3)NH2.

10. The compound according to claim 1 wherein Q is:

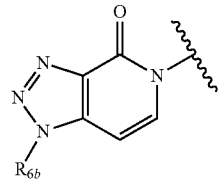

and

R$_{6b}$ is H, or C4-C6 aryl, optionally wherein R$_{6b}$ is phenyl.

11. The compound according to claim 1 wherein Q is:

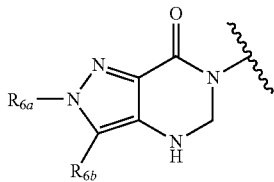

and

R$_{6a}$ is H or C1-C6 alkyl, optionally wherein R$_{6a}$ is methyl;
R$_{6b}$ is H, or C1-C6 alkyl, optionally wherein R$_{6b}$ is propyl.

12. The compound according to claim 1 wherein Q is:

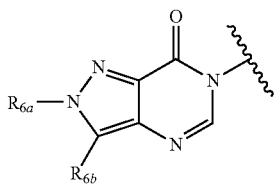

and

R$_{6a}$ is H or C1-C6 alkyl;

R$_{6b}$ is H, halo, optionally substituted C2-C6 alkenyl, optionally substituted C2-C6 alkynyl, optionally substituted C3-C6 cycloalkyl, optionally substituted C4-C6 aryl, optionally substituted C3-C6 heteroaryl;

wherein the optional substituents are independently selected from F, CN, OH, CH2OH, amide, NH2, C1-C6 alkylamine, C3-C6 cycloalkylamine, CF3, COOH, methylmorpholine, CH(CF3)NH2, CH(CHF2)NH2, CH2NHC(O)OCH2CH3.

13. The compound according to claim 12, wherein R$_{6a}$ is H, methyl or ethyl; R$_{6b}$ is H, Br, optionally substituted propenyl, ethynyl, optionally substituted propynyl, optionally substituted pentynyl, optionally substituted cyclohexane, optionally substituted phenyl, pyrazole, pyridine;

wherein the optional substituents are independently selected from F, CN, OH, CH2OH, amide, NH2, C1-C6 alkylamine, C3-C6 cycloalkylamine, CF3, CH(CF3)NH2, CH(CHF2)NH2.

14. The compound according to claim 12, wherein R$_{6a}$ is methyl and R$_{6b}$ is phenyl optionally substituted with one or more of F, CN, OH, CH2OH, NH2, CH2NH2, CH2CH2NH2, CH(CH3)NH2, amide, cyclopropylamine, and cyclobutylamine.

15. The compound according to claim 1, wherein Q is:

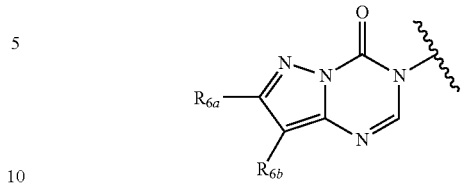

and

R$_{6a}$ is H or C1-C6 alkyl;
R$_{6b}$ is C4-C6 aryl, optionally phenyl.

16. The compound according to claim 1 wherein R$_2$ is CH2CR$^b$R$^c$R$^d$ and wherein no more than one of R$^b$, R$^c$ and R$^d$ are hydrogen.

17. The compound according to claim 1 wherein R$_2$ is optionally substituted C3-C5 heteroaryl, optionally substituted C3-C6 cycloalkyl, optionally substituted C4-C6 alkylcycloalkyl, optionally substituted C5-C10 arylalkyl or optionally substituted C5-C10 heteroarylalkyl group, wherein each optional substituent is independently selected from OH, F, methyl, CF$_3$, CHF$_2$, CH$_2$F, CH$_2$OH, C1-C4 alkoxy, and C3-C4 cycloalkyl.

18. The compound according to claim 17, wherein R$_2$ is optionally substituted ethylphenyl, wherein the ethyl group is optionally substituted with methyl, methyl, CF$_3$, CHF$_2$, or CH$_2$F and the phenyl group is optionally substituted with F.

19. The compound according to claim 17, wherein when R$_2$ has the structure CH2CR$^b$R$^c$R$^d$, no more than one of R$^b$, R$^c$ and R$^d$ is hydrogen.

20. The compound according to claim 17, wherein the R$_2$ is oxazole optionally substituted with cyclopropane, or pyrazole optionally substituted with methyl.

21. The compound of claim 1 selected from the group consisting of:

(R)-6-Chloro-3-((4-hydroxy-1-(3-phenylbutanoyl)piperidin-4-yl)methyl)pyrimidin-4(3H)-one (R)-3-((4-Hydroxy-1-(3-phenylbutanoyl)piperidin-4-yl)methyl)-6-(pyridin-4-yl)pyrimidin-4(3H)-one (R)-3-((4-Hydroxy-1-(3-phenylbutanoyl)piperidin-4-yl)methyl)-6-(1H-pyrazol-5-yl)pyrimidin-4(3H)-one (R)-3-((4-Hydroxy-1-(3-phenylbutanoyl)piperidin-4-yl)methyl)-6-(phenylamino)pyrimidin-4(3H)-one (R)-6-Amino-3-((4-hydroxy-1-(3-phenylbutanoyl)piperidin-4-yl)methyl)pyrimidin-4(3H)-one (R)-6-((2-(Dimethylamino)ethyl)amino)-3-((4-hydroxy-1-(3-phenylbutanoyl)piperidin-4-yl)methyl)pyrimidin-4(3H)-one (R)-6-((2-(Dimethylamino)ethyl)(methyl)amino)-3-((4-hydroxy-1-(3-phenylbutanoyl)piperidin-4-yl)methyl)pyrimidin-4(3H)-one (R)-3-((4-Hydroxy-1-(3-phenylbutanoyl)piperidin-4-yl)methyl)-6-(4-methylpiperazin-1-yl)pyrimidin-4(3H)-one (R)-3-((4-Hydroxy-1-(3-phenylbutanoyl)piperidin-4-yl)methyl)-6-methoxypyrimidin-4(3H)-one (R)-6-(2-(Dimethylamino)ethoxy)-3-((4-hydroxy-1-(3-phenylbutanoyl)piperidin-4-yl)methyl)pyrimidin-4(3H)-one (R)-3-((4-Hydroxy-1-(3-phenylbutanoyl)piperidin-4-yl)methyl)-6-((2-(pyrrolidin-1-yl)ethyl)amino)pyrimidin-4(3H)-one 6-((S)-3-Aminopyrrolidin-1-yl)-3-((4-hydroxy-1-((R)-3-phenylbutanoyl)piperidin-4-yl)methyl)pyrimidin-4(3H)-one (R)-6-(3-Aminoazetidin-1-yl)-3-((4-hydroxy-1-(3-phenylbutanoyl)piperidin-4-yl)methyl)pyrimidin-4(3H)-one (R)-5-Amino-6-chloro-3-((4-hydroxy-1-(3-phenylbutanoyl)piperidin-4-yl)methyl)pyrimidin-4(3H)-one (R)-1-((4-Hydroxy-1-(3-phenylbutanoyl)piperidin-4-yl)methyl)-9-methyl-1H-purin-6(9H)-one (R)-1-((4-Hydroxy-1-(3-phenylbutanoyl)piperidin-4-yl)methyl)-9-methyl-8-phenyl-1H-purin-6(9H)-one (R)-1-((4-Hydroxy-1-(3-phenylbutanoyl)piperidin-4-yl)methyl)-9-phenyl-1H-purin-6(9H)-one (R)-3-((4-Hydroxy-1-(3-phenylbutanoyl)piperidin-4-yl)methyl)-4H-pyrido[1,2-a]pyrimidin-4-one (R)-3-((4-Hydroxy-1-(3-phenylbutanoyl)piperidin-4-yl)methyl)-9-phenyl-4H-pyrido[1,2-a]pyrimidin-4-one (R)-6-((4-Hydroxy-1-(3-phenylbutanoyl)piperidin-4-yl)methyl)-2-methyl-2H-pyrazolo[4,3-d]pyrimidin-7(6H)-one (R)-3-Bromo-6-((4-hydroxy-1-(3-phenylbutanoyl)piperidin-4-yl)methyl)-2-methyl-2H-pyrazolo[4,3-d]pyrimidin-7(6H)-one (R)-3-Ethynyl-6-((4-hydroxy-1-(3-phenylbutanoyl)piperidin-4-yl)methyl)-2-methyl-2H-pyrazolo[4,3-d]pyrimidin-7(6H)-one (R)-6-((4-Hydroxy-1-(3-phenylbutanoyl)piperidin-4-yl)methyl)-2-methyl-3-(trifluoromethyl)-2H-pyrazolo[4,3-d]pyrimidin-7(6H)-one (R)-6-((4-Hydroxy-1-(3-phenylbutanoyl)piperidin-4-yl)methyl)-3-(3-hydroxy-3-methyl but-1-yn-1-yl)-2-methyl-2H-pyrazolo[4,3-d]pyrimidin-7(6H)-one (R)-6-((4-Hydroxy-1-(3-phenylbutanoyl)piperidin-4-yl)methyl)-2-methyl-3-(1H-pyrazol-5-yl)-2H-pyrazolo[4,3-d]pyrimidin-7(6H)-one (R)-6-((4-Hydroxy-1-(3-phenylbutanoyl)piperidin-4-yl)methyl)-2-methyl-3-(pyridin-4-yl)-2H-pyrazolo[4,3-d]pyrimidin-7(6H)-one (R)-6-((4-Hydroxy-1-(3-phenylbutanoyl)piperidin-4-yl)methyl)-2-methyl-3-phenyl-2H-pyrazolo[4,3-d]pyrimidin-7(6H)-one (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzamide (R)-3-(3-Aminophenyl)-6-((4-hydroxy-1-(3-phenylbutanoyl)piperidin-4-yl)methyl)-2-methyl-2H-pyrazolo[4,3-d]pyrimidin-7(6H)-one (R)-3-(4-(Aminomethyl)phenyl)-6-((4-hydroxy-1-(3-phenylbutanoyl)piperidin-4-yl)methyl)-2-methyl-2H-pyrazolo[4,3-d]pyrimidin-7(6H)-one (R)-6-((4-Hydroxy-1-(3-phenylbutanoyl)piperidin-4-yl)methyl)-3-(3-hydroxyprop-1-yn-1-yl)-2-methyl-2H-pyrazolo[4,3-d]pyrimidin-7(6H)-one (R)-6-((4-Hydroxy-1-(3-phenylbutanoyl)piperidin-4-yl)methyl)-2-methyl-3-(prop-1-en-2-yl)-2H-pyrazolo[4,3-d]pyrimidin-7(6H)-one (R)-6-((4-Hydroxy-1-(3-phenylbutanoyl)piperidin-4-yl)methyl)-3-isopropyl-2-methyl-2H-pyrazolo[4,3-d]pyrimidin-7(6H)-one (R)-6-((4-Hydroxy-1-(3-phenylbutanoyl)piperidin-4-yl)methyl)-3-isopropyl-2-methyl-5,6-dihydro-2H-pyrazolo[4,3-d]pyrimidin-7(4H)-one (R)-6-((1-(3,4-Dimethylpent-4-enoyl)-4-hydroxypiperidin-4-yl)methyl)-2-methyl-3-phenyl-2H-pyrazolo[4,3-d]pyrimidin-7(6H)-one (R)-6-((4-Hydroxy-1-(4-methyl-3-(trifluoromethyl) pent-4-enoyl)piperidin-4-yl)methyl)-2-methyl-3-phenyl-2H-pyrazolo[4,3-d]pyrimidin-7(6H)-one (R)-6-((4-Hydroxy-1-(4,4,4-trifluoro-3-phenylbutanoyl)piperidin-4-yl)methyl)-2-methyl-3-phenyl-2H-pyrazolo[4,3-d]pyrimidin-7(6H)-one 6-((4-Hydroxy-1-(3-phenylpropanoyl)piperidin-4-yl)methyl)-2-methyl-2H-pyrazolo[4,3-d]pyrimidin-7(6H)-one 6-((4-Hydroxy-1-(3-phenylpropanoyl)piperidin-4-yl)methyl)-2-methyl-3-(trifluoromethyl)-2H-pyrazolo[4,3-d]pyrimidin-7(6H)-one (R)-3-((4-Hydroxy-1-(3-phenylbutanoyl)piperidin-4-yl)methyl)-6-(1-methyl-1H-pyrazol-4-yl)pyrimidin-4(3H)-one (R)-3-((4-Hydroxy-1-(3-phenylbutanoyl)piperidin-4-yl)methyl)-6-(1-isobutyl-1H-pyrazol-4-yl)pyrimidin-4(3H)-one 3-((4-Hydroxy-1-((R)-3-phenylbutanoyl)piperidin-4-yl)methyl)-6-((1,2,3,4-tetrahydro-1,4-epiminonaphthalen-6-yl)amino)pyrimidin-4(3H)-one (R)-6-((4-Hydroxy-1-(3-phenylbutanoyl)piperidin-4-yl)methyl)-2-methyl-3-(phenylamino)-2H-pyrazolo[4,3-d]pyrimidin-7(6H)-one (R)-6-Chloro-3-((4-hydroxy-1-(3-phenylbutanoyl)piperidin-4-yl)methyl)-5-methylpyrimidin-4(3H)-one (R)-5-Bromo-3-((4-hydroxy-1-(3-phenylbutanoyl)piperidin-4-yl)methyl)-6-((2-(pyrrolidin-1-yl)ethyl)amino)pyrimidin-4(3H)-one (R)-3-(4-(Aminomethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one 6-((S)-3-Aminopiperidin-1-yl)-3-((4-hydroxy-1-((R)-3-phenylbutanoyl)piperidin-4-yl)methyl)pyrimidin-4(3H)-one (R)-6-(4-Aminopiperidin-1-yl)-3-((4-hydroxy-1-(3-phenylbutanoyl)piperidin-4-yl)methyl)pyrimidin-4(3H)-one (R)-3-((4-Hydroxy-1-(3-phenylbutanoyl)piperidin-4-yl)methyl)-6-(2,8-diazaspiro[4.5]decan-8-yl)pyrimidin-4(3H)-one 6-((S)-3-(Dimethylamino)piperidin-1-yl)-3-((4-hydroxy-1-((R)-3-phenylbutanoyl)piperidin-4-yl)methyl)pyrimidin-4(3H)-one (R,E)-3-((4-Hydroxy-1-(3-phenylbutanoyl)piperidin-4-yl)methyl)-6-(3-(pyrrolidin-1-yl) prop-1-en-1-yl)pyrimidin-4(3H)-one (R)-3-((4-Hydroxy-1-(3-phenylbutanoyl)piperidin-4-yl)methyl)-6-((2-(piperidin-1-yl)ethyl)amino)pyrimidin-4(3H)-one (R,S)-3-(4-(Aminomethyl)phenyl)-6-((4-hydroxy-1-(4-methoxy-3-phenylbutanoyl)piperidin-4-yl)methyl)-2-methyl-2H-pyrazolo[4,3-d]pyrimidin-7(6H)-one (R)-6-(1-(2-(Dimethylamino)ethyl)-1H-pyrazol-4-yl)-3-((4-hydroxy-1-(3-phenylbutanoyl)piperidin-4-yl)methyl)pyrimidin-4(3H)-one 6-((E)-3-((R)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one 6-((E)-3-((S)-3-Aminopyrrolidin-1-yl)prop-1-en-1-yl)-3-((4-hydroxy-1-((R)-3-phenylbutanoyl)piperidin-4-yl)methyl)pyrimidin-4(3H)-one 3-((4-Hydroxy-1-((R)-3-phenylbutanoyl)piperidin-4-yl)methyl)-6-(((S)-1-phenyl-3-(pyrrolidin-1-yl) propan-2-yl)amino)pyrimidin-4(3H)-one 3-((4-Hydroxy-1-((R)-3-phenylbutanoyl)piperidin-4-yl)methyl)-6-(((R)-2-(pyrrolidin-1-yl)propyl)amino)pyrimidin-4(3H)-one 3-((4-Hydroxy-1-((R)-3-phenylbutanoyl)piperidin-4-yl)methyl)-6-(((S)-2-(pyrrolidin-1-yl)propyl)amino)pyrimidin-4(3H)-one 3-((4-Hydroxy-1-((R)-3-phenylbutanoyl)piperidin-4-yl)methyl)-6-(((R)-1-(pyrrolidin-1-yl)propan-2-yl)amino)pyrimidin-4(3H)-one 3-((4-Hydroxy-1-((R)-3-phenylbutanoyl)piperidin-4-yl)methyl)-6-(((S)-1-(pyrrolidin-1-yl)propan-2-yl)amino)pyrimidin-4(3H)-one 6-((S)-3-(Dimethylamino)pyrrolidin-1-yl)-3-((4-hydroxy-1-((R)-3-phenylbutanoyl)piperidin-4-yl)methyl)pyrimidin-4(3H)-one rac-6-(((±-trans-1,2)-2-Aminocyclohexyl)amino)-3-((4-hydroxy-1-((R)-3-phenylbutanoyl)piperidin-4-yl)methyl)pyrimidin-4(3H)-one 6-(((±-cis-1,2)-2-Aminocyclohexyl)amino)-3-((4-hydroxy-1-((R)-3-phenylbutanoyl)piperidin-4-yl)methyl)pyrimidin-4(3H)-one 3-((4-Hydroxy-1-((R)-3-phenylbutanoyl)piperidin-4-yl)methyl)-6-((((R)-1-methylpyrrolidin-2-yl)methyl)amino)pyrimidin-4(3H)-one 3-((4-Hydroxy-1-((R)-3-phenylbutanoyl)piperidin-4-yl)methyl)-6-((((S)-1-methylpyrrolidin-2-yl)methyl)amino)pyrimidin-4(3H)-one (R)-3-((4-Hydroxy-1-(3-phenylbutanoyl)piperidin-4-yl)methyl)pyrimidin-4(3H)-one (R)-9-(4-(Aminomethyl)phenyl)-1-((4-hydroxy-1-(3-phenylbutanoyl)piperidin-4-yl)methyl)-1H-purin-6(9H)-one 3-((4-Hydroxy-1-((R)-3-phenylbutanoyl)piperidin-4-yl)methyl)-6-((2-((S)-2-methylpyrrolidin-1-yl)ethyl)amino)pyrimidin-4(3H)-one 3-((4-Hydroxy-1-((R)-3-phenylbutanoyl)piperidin-4-yl)methyl)-6-((2-((R)-2-(methoxymethyl)pyrrolidin-1-yl)ethyl)amino)pyrimidin-4(3H)-one 3-((4-Hydroxy-1-((R)-3-phenylbutanoyl)piperidin-4-yl)methyl)-6-((2-((S)-3-methylpyrrolidin-1-yl)ethyl)amino)pyrimidin-4(3H)-one (R)-9-(4-(Aminomethyl)phenyl)-1-((4-hydroxy-1-(3-phenylbutanoyl)piperidin-4-yl)methyl)-8-methyl-1H-purin-6(9H)-one 6-((2-((R)-3-Fluoropyrrolidin-1-yl)ethyl)amino)-3-((4-hydroxy-1-((R)-3-phenylbutanoyl)piperidin-4-yl)methyl)pyrimidin-4(3H)-one 6-((2-((S)-3-Fluoropyrrolidin-1-yl)ethyl)amino)-3-((4-hydroxy-1-((R)-3-phenylbutanoyl)piperidin-4-yl)methyl)pyrimidin-4(3H)-one 3-(4-((R)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one 3-(4-((S)-1-Aminoethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one (R)-9-(4-(Aminomethyl)phenyl)-1-((4-hydroxy-1-(4,4,4-trifluoro-3-phenylbutanoyl)piperidin-4-yl)methyl)-1H-purin-6(9H)-one (R)-9-(4-(Aminomethyl)phenyl)-1-((4-hydroxy-1-(4,4,4-trifluoro-3-phenylbutanoyl)piperidin-4-yl)methyl)-8-methyl-1H-purin-6(9H)-one (R)-3-(4-((Dimethylamino)methyl)phenyl)-6-((4-hydroxy-1-(4,4,4-trifluoro-3-phenylbutanoyl)piperidin-4-yl)methyl)-2-methyl-2H-pyrazlo[4,3-d]pyrimidin-7(6H)-one (R)-3-(4-(Aminomethyl)phenyl)-6-((1-(4,4-difluoro-3-phenylbutanoyl)-4-hydroxypiperidin-4-yl)methyl)-2-methyl-2H-pyrazolo[4,3-d]pyrimidin-7(6H)-one (R)-3-((4-Hydroxy-1-(3-phenylbutanoyl)piperidin-4-yl)methyl)-6-isopropylpyrimidin-4(3H)-one (R)-3-(4-(Aminomethyl)-3-fluorophenyl)-6-((4-hydroxy-1-(4,4,4-trifluoro-3-phenylbutanoyl)piperidin-4-yl)methyl)-2-methyl-2H-pyrazlo[4,3-d]pyrimidin-7(6H)-one (R)-6-((4-Hydroxy-1-(4,4,4-trifluoro-3-phenylbutanoyl)piperidin-4-yl)methyl)-2-methyl-3-(4-((methylamino)methyl)phenyl)-2H-pyrazolo[4,3-d]pyrimidin-7(6H)-one (R)-3-(4-(Aminomethyl)phenyl)-6-((1-(3-(3,5-difluorophenyl)-4,4,4-trifluorobutanoyl)-4-hydroxypiperidin-4-yl)methyl)-2-methyl-2H-pyrazolo[4,3-d]pyrimidin-7(6H)-one (R)-3-(4-(Aminomethyl)phenyl)-6-((4-hydroxy-1-(4,4,4-trifluoro-3-(4-fluorophenyl)butanoyl)piperidin-4-yl)methyl)-2-methyl-2H-pyrazolo[4,3-d]pyrimidin-7(6H)-one (R)-6-((2-(4-Fluoroisoindolin-2-yl)ethyl)amino)-3-((4-hydroxy-1-(3-phenylbutanoyl)piperidin-4-yl)methyl)pyrimidin-4(3H)-one (R)-3-(4-(2-Aminoethyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-(4-(1-Aminocyclobutyl)phenyl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-((1-(4,4-Difluoro-3-phenylbutanoyl)-4-hydroxypiperidin-4-yl)methyl)-6-((2-(pyrrolidin-1-yl)ethyl)amino)pyrimidin-4(3H)-one 6-((4-Hydroxy-1-(3-phenylpropanoyl)piperidin-4-yl)methyl)-2-(methylthio)thiazolo[4,5-d]pyrimidin-7(6H)-one 3-((4-Hydroxy-1-(3-phenylpropanoyl)piperidin-4-yl)methyl)furo[3,2-d]pyrimidin-4(3H)-one 6-((4-Hydroxy-1-(3-phenylpropanoyl)piperidin-4-yl)methyl)-2-(methylsulfonyl)thiazolo[4,5-d]pyrimidin-7(6H)-one 6-((4-Hydroxy-1-(3-phenylpropanoyl)piperidin-4-yl)methyl)-2-(methylamino)thiazolo[4,5-d]pyrimidin-7(6H)-one 3-((4-Hydroxy-1-(3-phenylpropanoyl)piperidin-4-yl)methyl)furo[2,3-d]pyrimidin-4(3H)-one 6-((4-Hydroxy-1-(3-phenylpropanoyl)piperidin-4-yl)methyl)-2-methyl-3-(trifluoromethyl)-2H-pyrazolo[4,3-d]pyrimidin-7(6H)-one (R)-1-((4-Hydroxy-1-(3-phenylbutanoyl)piperidin-4-yl)methyl)-9-methyl-8-(trifluoromethyl)-1H-purin-6(9H)-one 3-(2-Fluorophenyl)-6-((4-hydroxy-1-((R)-3-phenylbutanoyl)piperidin-4-yl)methyl)-2-methyl-2H-pyrazolo[4,3-d]pyrimidin-7(6H)-one (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzonitrile 3-(2-Aminophenyl)-6-((4-hydroxy-1-((R)-3-phenylbutanoyl)piperidin-4-yl)methyl)-2-methyl-2H-pyrazolo[4,3-d]pyrimidin-7(6H)-one (R)-3-((4-Hydroxy-1-(3-phenylbutanoyl)piperidin-4-yl)methyl)-6-morpholinopyrimidin-4(3H)-one 3-(Hydroxy(4-hydroxy-1-((R)-3-phenylbutanoyl)piperidin-4-yl)methyl)-4H-pyrido[1,2-a]pyrimidin-4-one (R)-1-((4-Hydroxy-1-(3-phenylbutanoyl)piperidin-4-yl)methyl)-[4,5'-bipyrimidin]-6(1H)-one (R)-3-((4-Hydroxy-1-(3-phenylbutanoyl)piperidin-4-yl)methyl)-6-((2-hydroxyethyl)amino)pyrimidin-4(3H)-one (R)-6-((4-Hydroxy-1-(3-phenylbutanoyl)piperidin-4-yl)methyl)-3-(3-hydroxyphenyl)-2-methyl-2H-pyrazolo[4,3-d]pyrimidin-7(6H)-one 3-(Hydroxy(4-hydroxy-1-((R)-3-phenylbutanoyl)piperidin-4-yl)methyl)-9-phenyl-4H-pyrido[1,2-a]pyrimidin-4-one (R)-4-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzamide (R)-6-((4-Hydroxy-1-(3-phenylbutanoyl)piperidin-4-yl)methyl)-3-(4-(hydroxymethyl)phenyl)-2-methyl-2H-pyrazolo[4,3-d]pyrimidin-7(6H)-one (R)-6-((4-Hydroxy-1-(3-phenylbutanoyl)piperidin-4-yl)methyl)-2-methyl-3-(3-(morpholinomethyl)phenyl)-2H-pyrazolo[4,3-d]pyrimidin-7(6H)-one (R)-3-((4-Hydroxy-1-(3-phenylbutanoyl)piperidin-4-yl)methyl)-6-((2-methoxyethyl)amino)pyrimidin-4(3H)-one 3-((4-Hydroxy-1-((R)-3-phenylbutanoyl)piperidin-4-yl)methyl)-6-(((R)-pyrrolidin-3-yl)amino)pyrimidin-4(3H)-one (R)-3-((4-Hydroxy-1-(3-phenylbutanoyl)piperidin-4-yl)methyl)-5-methyl-6-((2-(pyrrolidin-1-yl)ethyl)amino)pyrimidin-4(3H)-one Benzyl 4-((3-(4-(aminomethyl)phenyl)-2-methyl-7-oxo-2,7-dihydro-6H-pyrazolo[4,3-d]pyrimidin-6-yl)methyl)-4-hydroxypiperidine-1-carboxylate (R)—N-(1-((4-Hydroxy-1-(3-phenylbutanoyl)piperidin-4-yl)methyl)-6-oxo-1,6-dihydropyrimidin-4-yl)-N-(2-(pyrrolidin-1-yl)ethyl)acetamide 3-((4-Hydroxy-1-((R)-3-phenylbutanoyl)piperidin-4-yl)methyl)-6-((2-((R)-2-methylpyrrolidin-1-yl)ethyl)amino)pyrimidin-4(3H)-one (R)-1-(4-Hydroxy-4-((5-phenylpyrazin-2-yl)methyl)piperidin-1-yl)-3-phenylbutan-1-one (R)-3-((4-Hydroxy-1-(3-phenylbutanoyl)piperidin-4-yl)methyl)-6-(phenylethynyl)pyrimidin-4(3H)-one (R)-6-Benzyl-3-((4-hydroxy-1-(3-phenylbutanoyl)piperidin-4-yl)methyl)pyrimidin-4(3H)-one 3-(4-((R)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one 3-(4-((S)-1-Amino-2,2,2-trifluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one (R)-3-(4-(Aminomethyl)phenyl)-2-ethyl-6-((4-hydroxy-1-(3-phenylbutanoyl)piperidin-4-yl)methyl)-2H-pyrazolo[4,3-d]pyrimidin-7(6H)-one (R)-3-((4-Hydroxy-1-(3-phenylbutanoyl)piperidin-4-yl)methyl)-6-(phenyl(2-(pyrrolidin-1-yl)ethyl)amino)pyrimidin-4(3H)-one 3-(4-((S)-1-Amino-2,2-difluoroethyl)phenyl)-6-((4-hydroxy-1-((R)-4,4,4-trifluoro-3-phenylbutanoyl)piperidin-4-yl)methyl)-2-methyl-2H-pyrazolo[4,3-d]pyrimidin-7(6H)-one (R)-3-(4-(Aminomethyl)-3-(trifluoromethyl)phenyl)-6-((4-hydroxy-1-(4,4,4-trifluoro-3-phenylbutanoyl)piperidin-4-yl)methyl)-2-methyl-2H-pyrazlo[4,3-d]pyrimidin-7(6H)-one (R)-3-(4-(1-Aminocyclopropyl)phenyl)-6-((4-hydroxy-1-(4,4,4-trifluoro-3-phenylbutanoyl)piperidin-4-yl)methyl)-2-methyl-2H-pyrazlo[4,3-d]pyrimidin-7(6H)-one (S)-3-(4-(Aminomethyl)phenyl)-6-((4-hydroxy-1-(4,4,4-trifluoro-3-(5-methylthiophen-2-yl) butanoyl)piperidin-4-yl)methyl)-2-methyl-2H-pyrazolo[4,3-d]pyrimidin-7(6H)-one (R)-1-((4-Hydroxy-1-(3-phenylbutanoyl)piperidin-4-yl)methyl)indolin-2-one 3-(4-(Aminomethyl)phenyl)-6-((1-(3,3-dicyclopropylpropanoyl)-4-hydroxypiperidin-4-yl)methyl)-2-methyl-2H-pyrazolo[4,3-d]pyrimidin-7(6H)-one (R)-1-((4-Hydroxy-1-(4,4,4-trifluoro-3-phenylbutanoyl)piperidin-4-yl)methyl)-9-phenyl-1H-purin-6(9H)-one (R)-1-((1-(4,4-Difluoro-3-phenylbutanoyl)-4-hydroxypiperidin-4-yl)methyl)-9-phenyl-1H-purin-6(9H)-one (R)-6-((4-Hydroxy-1-(4,4,4-trifluoro-3-phenylbutanoyl)piperidin-4-yl)methyl)-2-methyl-3-(1-methyl-1,2,3,6-tetrahydropyridin-4-yl)-2H-pyrazolo[4,3-d]pyrimidin-7(6H)-one 6-((1-Acetyl-4-hydroxypiperidin-4-yl)methyl)-2-methyl-3-phenyl-2H-pyrazolo[4,3-d]pyrimidin-7(6H)-one 3-((1-Acetyl-4-hydroxypiperidin-4-yl)methyl)-6-((2-(pyrrolidin-1-yl)ethyl)amino)pyrimidin-4(3H)-one 3-((1-(3,3-Dicyclopropylpropanoyl)-4-hydroxypiperidin-4-yl)methyl)-6-((2-(pyrrolidin-1-yl)ethyl)amino)pyrimidin-4(3H)-one (R)-3-(Cyclohex-1-en-1-yl)-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-3-(3-(Dimethylamino)prop-1-yn-1-yl)-6-((4-hydroxy-1-(4,4,4-trifluoro-3-phenylbutanoyl)piperidin-4-yl)methyl)-2-methyl-2H-pyrazlo[4,3-d]pyrimidin-7(6H)-one (R)-3-Cyclohexyl-6-((4-hydroxy-1-(4,4,4-trifluoro-3-phenylbutanoyl)piperidin-4-yl)methyl)-2-methyl-2H-pyrazolo[4,3-d]pyrimidin-7(6H)-one (R)-6-((4-Hydroxy-1-(4,4,4-trifluoro-3-phenylbutanoyl)piperidin-4-yl)methyl)-2-methyl-3-(4-(morpholinomethyl)phenyl)-2H-pyrazolo[4,3-d]pyrimidin-7(6H)-one 3-(4-(Aminomethyl)phenyl)-6-((1-(3-cyclobutylpropanoyl)-4-hydroxypiperidin-4-yl)methyl)-2-methyl-2H-pyrazolo[4,3-d]pyrimidin-7(6H)-one (R)-3-((4-Hydroxy-1-(3-phenylbutanoyl)piperidin-4-yl)methyl)-8-phenylpyrazolo[1,5-a][1,3,5]triazin-4(3H)-one 3-((4-hydroxy-1-((R)-3-phenylbutanoyl)piperidin-4-yl)methyl)-6-((R)-2-(hydroxymethyl)pyrrolidin-1-yl)pyrimidin-4(3H)-one (R)-3-((4-Hydroxy-1-(3-phenylbutanoyl)piperidin-4-yl)methyl)-6-(3-(methoxymethyl)azetidin-1-yl)pyrimidin-4(3H)-one (R)-3-((4-Hydroxy-1-(3-phenylbutanoyl)piperidin-4-yl)methyl)-6-((2-(isopropylamino)ethyl)amino)pyrimidin-4(3H)-one (R)—N-(2-((1-((4-hydroxy-1-(3-phenylbutanoyl)piperidin-4-yl)methyl)-6-oxo-1,6-dihydropyrimidin-4-yl)amino)ethyl)acetamide (R)-3-((4-Hydroxy-1-(3-phenylbutanoyl)piperidin-4-yl)methyl)-6-(4-hydroxypiperidin-1-yl)pyrimidin-4(3H)-one (R)-3-((4-Hydroxy-1-(3-phenylbutanoyl)piperidin-4-yl)methyl)-6-((2-((4-(trifluoromethyl)pyrimidin-2-yl)amino)ethyl)amino)pyrimidin-4(3H)-one (R)-3-((4-Hydroxy-1-(3-phenylbutanoyl)piperidin-4-yl)methyl)-6-((2-(phenylamino)ethyl)amino)pyrimidin-4(3H)-one tert-butyl ((1-(1-((4-hydroxy-1-((R)-3-phenylbutanoyl)piperidin-4-yl)methyl)-6-oxo-1,6-dihydropyrimidin-4-yl)pyrrolidin-2-yl)methyl)carbamate 4-(1-((4-hydroxy-1-((R)-3-phenylbutanoyl)piperidin-4-yl)methyl)-6-oxo-1,6-dihydropyrimidin-4-yl)-N,N,2-trimethylmorpholine-2-carboxamide 3-((4-hydroxy-1-((R)-3-phenylbutanoyl)piperidin-4-yl)methyl)-6-(3-morpholinopyrrolidin-1-yl)pyrimidin-4(3H)-one 3-((4-hydroxy-1-((R)-3-phenylbutanoyl)piperidin-4-yl)methyl)-6-(3-hydroxy-3-methylpyrrolidin-1-yl)pyrimidin-4(3H)-one 3-((4-hydroxy-1-((R)-3-phenylbutanoyl)piperidin-4-yl)methyl)-6-((tetrahydrofuran-3-yl)amino)pyrimidin-4(3H)-one 3-((4-hydroxy-1-((R)-3-phenylbutanoyl)piperidin-4-yl)methyl)-6-(2-oxa-7-azaspiro[4.4]nonan-7-yl)pyrimidin-4(3H)-one 3-((4-hydroxy-1-((R)-3-phenylbutanoyl)piperidin-4-yl)methyl)-6-(tetrahydro-2H-furo[2,3-c]pyrrol-5(3H)-yl)pyrimidin-4(3H)-one (R)-3-((4-hydroxy-1-(3-phenylbutanoyl)piperidin-4-yl)methyl)-6-(((1-methyl-1H-pyrazol-5-yl)methyl)amino)pyrimidin-4(3H)-one (R)-3-((4-hydroxy-1-(3-phenylbutanoyl)piperidin-4-yl)methyl)-6-((3-methyloxetan-3-yl)amino)pyrimidin-4(3H)-one (R)-6-(4-(1H-pyrazol-5-yl)piperidin-1-yl)-3-((4-hydroxy-1-(3-phenylbutanoyl)piperidin-4-yl)methyl)pyrimidin-4(3H)-one (R)-6-((4-chlorobenzyl)amino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(4-(pyridin-3-ylmethyl)piperazin-1-yl)pyrimidin-4(3H)-one (R)-3-((4-hydroxy-1-(3-phenylbutanoyl)piperidin-4-yl)methyl)-6-(4-(pyridin-2-ylmethyl)piperazin-1-yl)pyrimidin-4(3H)-one (R)-6-(4,4-difluoropiperidin-1-yl)-3-((4-hydroxy-1-(3-phenylbutanoyl)piperidin-4-yl)methyl)pyrimidin-4(3H)-one (R)-2-((1-((4-hydroxy-1-(3-phenylbutanoyl)piperidin-4-yl)methyl)-6-oxo-1,6-dihydropyrimidin-4-yl)amino)-N,N-dimethylacetamide (R)-6-(((2,3-dihydrobenzo[b][1,4]dioxin-6-yl)methyl)amino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(((tetrahydro-2H-pyran-4-yl)methyl)amino)pyrimidin-4(3H)-one (R)—N-(cyclopropylmethyl)-1-(1-((4-hydroxy-1-(3-phenylbutanoyl)piperidin-4-yl)methyl)-6-oxo-1,6-dihydropyrimidin-4-yl)azetidine-3-carboxamide (R)-6-(3-fluoroazetidin-1-yl)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-((2-hydroxyethyl)(methyl)amino)pyrimidin-4(3H)-one (R)-6-(cyclopentylamino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(4-methyl-3-oxopiperazin-1-yl)pyrimidin-4(3H)-one (R)-3-((4-hydroxy-1-(3-phenylbutanoyl)piperidin-4-yl)methyl)-6-(5-oxa-2-azaspiro[3.4]octan-2-yl)pyrimidin-4(3H)-one (R)-6-((1,3-dimethyl-1H-pyrazol-4-yl)amino)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(8-methyl-5-oxa-2,8-diazaspiro[3.5]nonan-2-yl)pyrimidin-4(3H)-one (R)-6-(6-acetyl-2,6-diazaspiro[3.3]heptan-2-yl)-3-((4-hydroxy-1-(3-phenylbutanoyl)piperidin-4-yl)methyl)pyrimidin-4(3H)-one (R)-6-(5,5-difluoro-2-azaspiro[3.3]heptan-2-yl)-3-((4-hydroxy-1-(3-phenylbutanoyl)piperidin-4-yl)methyl)pyrimidin-4(3H)-one (R)-3-((4-hydroxy-1-(3-phenylbutanoyl)piperidin-4-yl)methyl)-6-(7-oxa-2-azaspiro[3.5]nonan-2-yl)pyrimidin-4(3H)-one (R)-3-((4-hydroxy-1-(3-phenylbutanoyl)piperidin-4-yl)methyl)-6-(2-oxa-7-azaspiro[3.5]nonan-7-yl)pyrimidin-4(3H)-one (R)-3-((4-hydroxy-1-(3-phenylbutanoyl)piperidin-4-yl)methyl)-6-(6-oxa-2-azaspiro[3.4]octan-2-yl)pyrimidin-4(3H)-one (R)-3-((4-hydroxy-1-(3-phenylbutanoyl)piperidin-4-yl)methyl)-6-((2-hydroxyethyl)(pyridin-3-ylmethyl)amino)pyrimidin-4(3H)-one (R)-3-((4-hydroxy-1-(3-phenylbutanoyl)piperidin-4-yl)methyl)-6-(5-methyl-2,5-diazaspiro[3.4]octan-2-yl)pyrimidin-4(3H)-one (R)-3-((4-hydroxy-1-(3-phenylbutanoyl)piperidin-4-yl)methyl)-6-(2-oxa-6-azaspiro[3.4]octan-6-yl)pyrimidin-4(3H)-one 3-((4-hydroxy-1-((R)-3-phenylbutanoyl)piperidin-4-yl)methyl)-6-((1R,5S)-3-methyl-3,6-diazabicyclo[3.2.1]octan-6-yl)pyrimidin-4(3H)-one 3-((4-hydroxy-1-((R)-3-phenylbutanoyl)piperidin-4-yl)methyl)-6-((1S,5R)-3-methyl-3,6-diazabicyclo[3.2.1]octan-6-yl)pyrimidin-4(3H)-one (R)-3-(4-(1-Aminocyclobutyl)phenyl)-6-((4-hydroxy-1-(3-phenylbutanoyl)piperidin-4-yl)methyl)-2-methyl-2H-pyrazolo[4,3-d]pyrimidin-7(6H)-one 3-((1-(3-Cyclobutylpropanoyl)-4-hydroxypiperidin-4-yl)methyl)-6-((2-(pyrrolidin-1-yl)ethyl)amino)pyrimidin-4(3H)-one 3-((1-(2,2-Dicyclobutylacetyl)-4-hydroxypiperidin-4-yl)methyl)-6-((2-(pyrrolidin-1-yl)ethyl)amino)pyrimidin-4(3H)-one (R)-6-((4-Hydroxy-1-(3-phenylbutanoyl)piperidin-4-yl)methyl)-3-phenyl-3H-[1,2,3]triazolo[4,5-d]pyrimidin-7(6H)-one 6-((1-(3-Cyclobutylpropanoyl)-4-hydroxypiperidin-4-yl)methyl)-3-phenyl-3H-[1,2,3]triazolo[4,5-d]pyrimidin-7(6H)-one 6-((1-(3,3-Dicyclopropylpropanoyl)-4-hydroxypiperidin-4-yl)methyl)-3-phenyl-3H-[1,2,3]triazolo[4,5-d]pyrimidin-7(6H)-one (R)-1-((4-Hydroxy-1-(3-phenylbutanoyl)piperidin-4-yl)methyl)-8-methyl-9-phenyl-1H-purin-6(9H)-one (R)-1-((4-Hydroxy-1-(4,4,4-trifluoro-3-phenylbutanoyl)piperidin-4-yl)methyl)-8-methyl-9-phenyl-1H-purin-6(9H)-one 1-((1-(3,3-Dicyclopropylpropanoyl)-4-hydroxypiperidin-4-yl)methyl)-8-methyl-9-phenyl-1H-purin-6(9H)-one 6-((4-Hydroxy-1-(1-methylcyclopropanecarbonyl)piperidin-4-yl)methyl)-2-methyl-3-phenyl-2H-pyrazolo[4,3-d]pyrimidin-7(6H)-one 6-((4-Hydroxy-1-(oxazole-5-carbonyl)piperidin-4-yl)methyl)-2-methyl-3-phenyl-2H-pyrazolo[4,3-d]pyrimidin-7(6H)-one 6-((1-(3,3-Dicyclopropylpropanoyl)-4-hydroxypiperidin-4-yl)methyl)-2-methyl-3-phenyl-2H-pyrazolo[4,3-d]pyrimidin-7(6H)-one (R)-Ethyl 4-(6-((4-hydroxy-1-(3-phenylbutanoyl)piperidin-4-yl)methyl)-2-methyl-7-oxo-6,7-dihydro-2H-pyrazolo[4,3-d]pyrimidin-3-yl)benzylcarbamate 1-((1-(2-Cyclopropyloxazole-5-carbonyl)-4-hydroxypiperidin-4-yl)methyl)-8-methyl-9-phenyl-1H-purin-6(9H)-one 6-((1-(2-Cyclopropyloxazole-5-carbonyl)-4-hydroxypiperidin-4-yl)methyl)-2-methyl-3-phenyl-2H-pyrazolo[4,3-d]pyrimidin-7(6H)-one 6-((4-Hydroxy-1-(1-methylcyclopropanecarbonyl)piperidin-4-yl)methyl)-3-phenyl-3H-[1,2,3]triazolo[4,5-d]pyrimidin-7(6H)-one 6-((1-(2-Cyclopropyloxazole-5-carbonyl)-4-hydroxypiperidin-4-yl)methyl)-3-phenyl-3H-[1,2,3]triazolo[4,5-d]pyrimidin-7(6H)-one 7-Cyclopropyl-3-((4-hydroxy-1-(3-phenylpropanoyl)piperidin-4-yl)methyl)thieno[3,2-d]pyrimidin-4(3H)-one 6-Chloro-3-((4-hydroxy-1-(1-methylcyclopropanecarbonyl)piperidin-4-yl)methyl)-7-phenyl-3H-pyrrolo[2,3-d]pyrimidin-4(7H)-one 7-(Benzo[d][1,3]dioxol-5-yl)-6-chloro-3-((4-hydroxy-1-(1-methylcyclopropanecarbonyl)piperidin-4-yl)methyl)-3H-pyrrolo[2,3-d]pyrimidin-4(7H)-one 6-Chloro-7-(4-chlorophenyl)-3-((4-hydroxy-1-(1-methyl-cyclopropanecarbonyl)piperidin-4-yl)methyl)-3H-pyrrolo[2,3-d]pyrimidin-4(7H)-one 6-Chloro-7-(4-fluorophenyl)-3-((4-hydroxy-1-(1-methyl-cyclopropanecarbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-fluorophenyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-fluoro-3-methoxyphenyl)-3H-pyrrolo[2,3-d]pyrimidin-4(7H)-one 6-Chloro-7-(4-fluoro-3-methoxyphenyl)-3-((4-hydroxy-1-(1-methylcyclopropanecarbonyl)piperidin-4-yl)methyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-(1-methyl-1H-pyrazol-5-yl)phenyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-methyl-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(3-(1-methyl-1H-pyrazol-5-yl)phenyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(3-(1-methyl-1H-pyrazol-4-yl)phenyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-(1-methyl-1H-pyrazol-4-yl)phenyl)-3H-pyrrolo[2,3-d]pyrimidin-4(7H)-one 7-(3-Bromophenyl)-6-chloro-3-((1-(2-cyclopropyloxazole-5-carbonyl)-4-hydroxypiperidin-4-yl)methyl)-3H-pyrrolo[2,3-d]pyrimidin-4(7H)-one 7-(3-Bromophenyl)-6-chloro-3-((4-hydroxy-1-(1-methylcyclopropanecarbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-phenyl-3H-pyrrolo[2,3-d]pyrimidin-4(7H)-one 6-Chloro-3-((4-hydroxy-1-(1-methyl-1H-pyrazole-4-carbonyl)piperidin-4-yl)methyl)-7-phenyl-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(3-cyclopropylphenyl)-3H-pyrrolo[2,3-d]pyrimidin-4(7H)-one 6-Chloro-7-(3-cyclopropylphenyl)-3-((4-hydroxy-1-(1-methylcyclopropanecarbonyl)piperidin-4-yl)methyl)-3H-pyrrolo[2,3-d]pyrimidin-4(7H)-one 6-Chloro-7-(3-cyclopropylphenyl)-3-((4-hydroxy-1-(1-methyl-1H-pyrazole-4-carbonyl)piperidin-4-yl)methyl)-3H-pyrrolo[2,3-d]pyrimidin-4(7H)-one 6-Chloro-7-(4-cyclopropylphenyl)-3-((4-hydroxy-1-(1-methylcyclopropanecarbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-cyclopropylphenyl)-3H-pyrrolo[2,3-d]pyrimidin-4(7H)-one 6-Bromo-3-((1-(2-cyclopropyloxazole-5-carbonyl)-4-hydroxypiperidin-4-yl)methyl)-7-phenyl-3H-pyrrolo[2,3-d]pyrimidin-4(7H)-one 6-Bromo-3-((4-hydroxy-1-(1-methylcyclopropanecarbonyl)piperidin-4-yl)methyl)-7-phenyl-3H-pyrrolo[2,3-d]pyrimidin-4(7H)-one 3-((1-(2-Cyclopropyloxazole-5-carbonyl)-4-hydroxypiperidin-4-yl)methyl)-6-iodo-7-phenyl-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-(4-(trifluoromethyl)-1H-pyrazol-1-yl)phenyl)-3H-pyrrolo[2,3-d]pyrimidin-4(7H)-one 6-Chloro-3-((4-hydroxy-1-(1-methylcyclopropanecarbonyl)piperidin-4-yl)methyl)-7-(3-morpholinophenyl)-3H-pyrrolo[2,3-d]pyrimidin-4(7H)-one 6-Chloro-7-(3-(4-fluoro-1H-pyrazol-1-yl)phenyl)-3-((4-hydroxy-1-(1-methylcyclopropanecarbonyl)piperidin-4-yl)methyl)-3H-pyrrolo[2,3-d]pyrimidin-4(7H)-one 6-Chloro-7-(4-chlorophenyl)-3-((1-(2-cyclopropyloxazole-5-carbonyl)-4-hydroxypiperidin-4-yl)methyl)-3H-pyrrolo[2,3-d]pyrimidin-4(7H)-one 6-Chloro-7-(4-chlorophenyl)-3-((4-hydroxy-1-(1-methyl-1H-pyrazole-4-carbonyl)piperidin-4-yl)methyl)-3H-pyrrolo[2,3-d]pyrimidin-4(7H)-one 6-Chloro-3-((1-(2-cyclopropyloxazole-5-carbonyl)-4-hydroxypiperidin-4-yl)methyl)-7-(4-fluoro-3-(1-methyl-1H-pyrazol-5-yl)phenyl)-3H-pyrrolo[2,3-d]pyrimidin-4(7H)-one 3-((4-Hydroxy-1-(1-methylcyclopropanecarbonyl)piperidin-4-yl)methyl)-4-oxo-7-phenyl-4,7-dihydro-3H-pyrrolo[2,3-d]pyrimidine-6-carbonitrile, 7-(Benzo[d][1,3]dioxol-5-yl-2,2-d$_2$)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one 7-(Benzo[d][1,3]dioxol-5-yl-2,2-d$_2$)-6-chloro-3-((1-(2-cyclopropyloxazole-5-carbonyl)-4-hydroxypiperidin-4-yl)methyl)-3,7-dihydro-4H-pyrrolo[2,3-d]pyrimidin-4-one 3-(4-(Aminomethyl)phenyl)-6-((4-hydroxy-1-(1-methyl-cyclopropane-1-carbonyl)piperidin-4-yl)methyl)-2-methyl-2,6-dihydro-7H-pyrazolo[4,3-d]pyrimidin-7-one 3-(4-(Aminomethyl)phenyl)-6-((1-(2-cyclopropyloxazole-5-carbonyl)-4-hydroxypiperidin-4-yl)methyl)-2-methyl-2,6-dihydro-7H-pyrazolo[4,3-d]pyrimidin-7-one 6-Chloro-7-(3,4-dimethoxyphenyl)-3-((4-hydroxy-1-(1-methylcyclopropane-1-carbonyl)piperidin-4-yl)methyl)-3,7-dihydro-4H-pyrrolo[2,3-d]pyrimidin-4-one 6-Chloro-3-((1-(2-cyclopropyloxazole-5-carbonyl)-4-hydroxypiperidin-4-yl)methyl)-7-(3,4-dimethoxyphenyl)-3,7-dihydro-4H-pyrrolo[2,3-d]pyrimidin-4-one 7-(4-(Aminomethyl)phenyl)-6-chloro-3-((4-hydroxy-1-(1-methylcyclopropane-1-carbonyl)piperidin-4-yl)methyl)-3,7-dihydro-4H-pyrrolo[2,3-d]pyrimidin-4-one 7-(4-(Aminomethyl)phenyl)-6-chloro-3-((1-(2-cyclopropyloxazole-5-carbonyl)-4-hydroxypiperidin-4-yl)methyl)-3,7-dihydro-4H-pyrrolo[2,3-d]pyrimidin-4-one (R)-4-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic acid (R)-3-(6-((4-Hydroxy-1-(3-phenylbutanoyl)piperidin-4-yl)methyl)-2-methyl-7-oxo-6,7-dihydro-2H-pyrazolo[4,3-d]pyrimidin-3-yl)benzoic acid 4-(6-((4-Hydroxy-1-(1-methylcyclopropane-1-carbonyl)piperidin-4-yl)methyl)-2-methyl-7-oxo-6,7-dihydro-2H-pyrazolo[4,3-d]pyrimidin-3-yl)benzoic acid or a pharmaceutically acceptable salt, tautomer, isomer, or N-oxide derivative thereof.

22. A pharmaceutical composition comprising a compound according to claim 1 or a pharmaceutically acceptable salt thereof and at least one pharmaceutically acceptable excipient.

* * * * *